United States Patent
Park et al.

(10) Patent No.: US 12,101,998 B2
(45) Date of Patent: Sep. 24, 2024

(54) HETEROCYCLIC COMPOUND AND ORGANIC LIGHT EMITTING DIODE COMPRISING SAME

(71) Applicant: LT MATERIALS CO., LTD., Gyeonggi-do (KR)

(72) Inventors: Min-Ji Park, Osan-si (KR); Yun-Ji Lee, Osan-si (KR); Won-Jang Jeong, Hwaseong-si (KR)

(73) Assignee: LT MATERIALS CO., LTD., Yongin (KR)

( * ) Notice: Subject to any disclaimer, the term of this patent is extended or adjusted under 35 U.S.C. 154(b) by 699 days.

(21) Appl. No.: 17/281,414

(22) PCT Filed: Oct. 31, 2019

(86) PCT No.: PCT/KR2019/014512
§ 371 (c)(1),
(2) Date: Mar. 30, 2021

(87) PCT Pub. No.: WO2020/091433
PCT Pub. Date: May 7, 2020

(65) Prior Publication Data
US 2022/0052269 A1 Feb. 17, 2022

(30) Foreign Application Priority Data

Oct. 31, 2018 (KR) .......... 10-2018-0132222

(51) Int. Cl.
*H10K 85/60* (2023.01)
*C07D 491/147* (2006.01)
(Continued)

(52) U.S. Cl.
CPC ....... *H10K 85/654* (2023.02); *C07D 491/147* (2013.01); *C07D 495/14* (2013.01);
(Continued)

(58) Field of Classification Search
CPC ............. C07D 491/47; C07D 491/048; C07D 495/04; C07D 495/14; H10K 85/654; H10K 85/657; H10K 85/6574; H10K 85/6576
See application file for complete search history.

(56) References Cited

U.S. PATENT DOCUMENTS 4,356,429 A   10/1982  Tang
9,590,194 B2   3/2017  Boudreault et al.
(Continued)

FOREIGN PATENT DOCUMENTS

CN    112778320 A  *  5/2021  ......... C07D 491/048
JP    2005-347160 A    12/2005
(Continued)

OTHER PUBLICATIONS

Machine translation of KR 2016-0026661 (no date) (Year:).*
(Continued)

*Primary Examiner* — Amanda C. Walke
(74) *Attorney, Agent, or Firm* — Birch, Stewart, Kolasch & Birch, LLP

(57) ABSTRACT

The present specification relates to a heterocyclic compound represented by Chemical Formula 1, and an organic light emitting device comprising the same.

12 Claims, 2 Drawing Sheets

(51) Int. Cl.
C07D 495/14 (2006.01)
C07D 519/00 (2006.01)
C09K 11/06 (2006.01)
H10K 50/11 (2023.01)
H10K 50/15 (2023.01)
H10K 50/16 (2023.01)
H10K 50/17 (2023.01)
H10K 50/18 (2023.01)
H10K 101/10 (2023.01)

(52) U.S. Cl.
CPC .......... C07D 519/00 (2013.01); C09K 11/06 (2013.01); H10K 85/615 (2023.02); H10K 85/626 (2023.02); H10K 85/657 (2023.02); H10K 85/6572 (2023.02); C09K 2211/1018 (2013.01); H10K 50/11 (2023.02); H10K 50/15 (2023.02); H10K 50/16 (2023.02); H10K 50/17 (2023.02); H10K 50/171 (2023.02); H10K 50/18 (2023.02); H10K 2101/10 (2023.02)

(56) References Cited

U.S. PATENT DOCUMENTS

| | | | |
|---|---|---|---|
| 9,755,159 | B2 | 9/2017 | Dyatkin et al. |
| 9,876,181 | B2 | 1/2018 | Parham et al. |
| 10,400,003 | B2 | 9/2019 | Hwang et al. |
| 10,734,588 | B2 | 8/2020 | Park et al. |
| 2015/0207082 | A1* | 7/2015 | Dyatkin ............... H10K 85/657 544/216 |
| 2016/0164002 | A1 | 6/2016 | Parham et al. |
| 2018/0240983 | A1 | 6/2018 | Heil et al. |

FOREIGN PATENT DOCUMENTS

| | | |
|---|---|---|
| JP | 2016-169210 A | 9/2016 |
| KR | 10-2015-0088176 A | 7/2015 |
| KR | 10-2015-0096314 A | 8/2015 |
| KR | 10-2015-0136942 A | 12/2015 |
| KR | 10-2016-0026661 A | 3/2016 |
| KR | 10-2016-0038006 A | 4/2016 |
| KR | 10-2017-0041886 A | 4/2017 |
| KR | 10-2018-0056314 A | 5/2018 |
| WO | WO-2018043761 A1 * | 3/2018 ......... C07D 491/048 |

OTHER PUBLICATIONS

Translation of the PCT written opinion (ETWOS) (Year:).*
Liu et al., "Advances in Synthesis and Applications of Thieno [2,3-b] pyridine Derivatives", Chinese Journal of Applied Chemistry, vol. 25, No. 2, Feb. 2008, pp. 125-131, with an English abstract.
International Search Report (PCT/ISA/210) issued in PCT/KR2019/014512 mailed on Feb. 7, 2020.
Kuwabara et al., "Thermally Stable Multilayered Organic Electroluminescent Devices Using Novel Starburst Molecules, 4,4',4"—Tri(N-carbazolyl)triphenylamine (TCTA) and 4,4',4' —Tris(3-methylphenylphenylamino)triphenylamine (m-MTDATA), as Hole-Transport Materials", Advanced Materials, vol. 6, No. 9, 1994, pp. 677-679.
STN Database Registry, "893787-47-8/m", ACS, Jul. 17, 2006, pp. 1-11.

* cited by examiner

【FIG. 1】
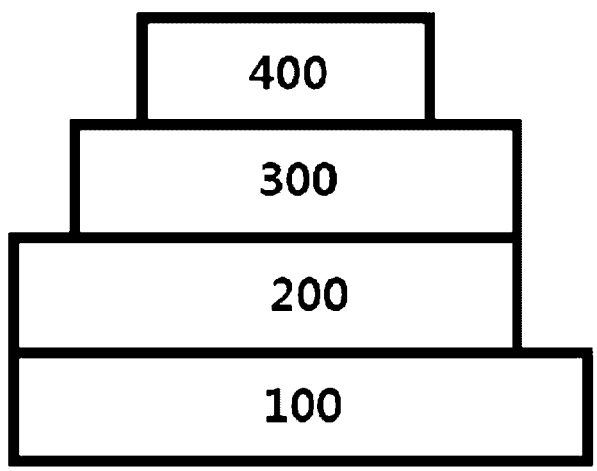
【FIG. 2】
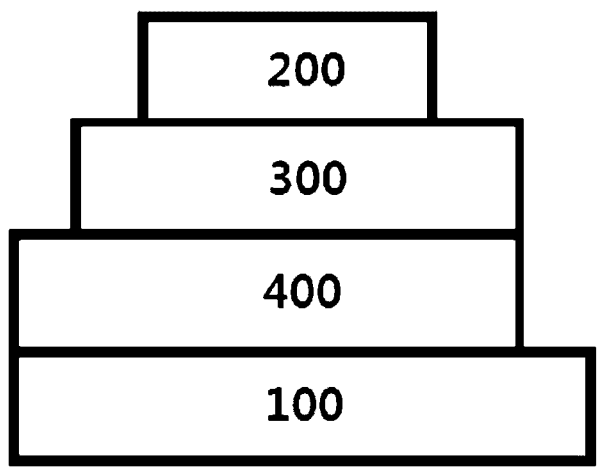

[FIG. 3]
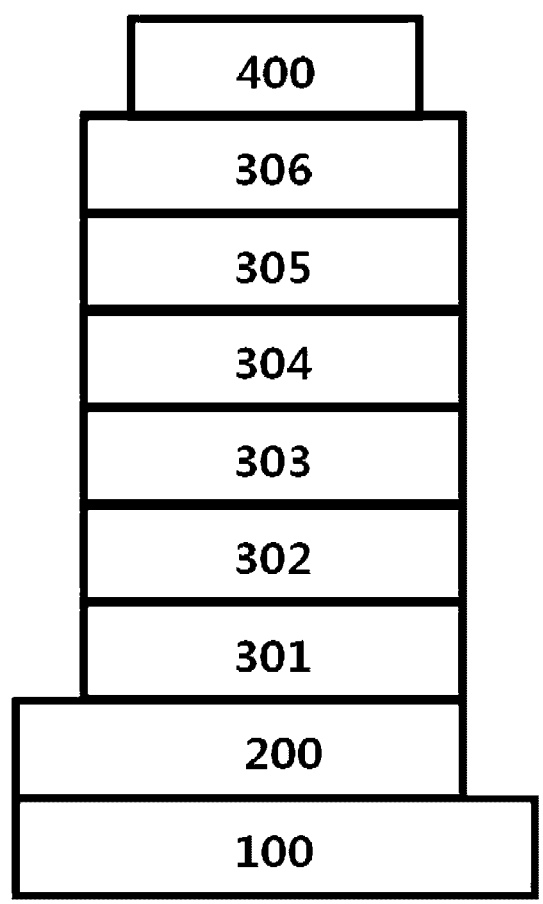

HETEROCYCLIC COMPOUND AND ORGANIC LIGHT EMITTING DIODE COMPRISING SAME

TECHNICAL FIELD

This application claims priority to and the benefits of Korean Patent Application No. 10-2018-0132222, filed with the Korean Intellectual Property Office on Oct. 31, 2018, the entire contents of which are incorporated herein by reference. The present specification relates to a heterocyclic compound, and an organic light emitting device comprising the same.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of foiling a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

PRIOR ART DOCUMENTS

Patent Documents (Patent Document 1) U.S. Pat. No. 4,356,429

DISCLOSURE

Technical Problem

The present disclosure is directed to providing a heterocyclic compound, and an organic light emitting device comprising the same.

Technical Solution

One embodiment of the present application provides a heterocyclic compound represented by the following Chemical Formula 1.

[Chemical Formula 1]

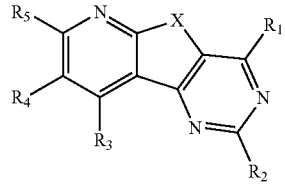

In Chemical Formula 1,

X is O; or S, $R_1$ to $R_5$ are the same as or different from each other, and each independently selected from the group consisting of hydrogen; deuterium; a substituted or unsubstituted alkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group, or two or more groups adjacent to each other bond to each other to form a substituted or unsubstituted aromatic hydrocarbon ring, or a substituted or unsubstituted heteroring, R, R' and R" are the same as or different from each other, and each independently hydrogen; a substituted or unsubstituted alkyl group; a substituted or unsubstituted aryl group; or a substituted or unsubstituted heteroaryl group, at least one of $R_1$, $R_2$ and $R_4$ is represented by -(L)m-(Z)n, at least one of $R_1$, $R_2$ and $R_4$ is a substituted or unsubstituted aryl group, L is a substituted or unsubstituted arylene group; or a substituted or unsubstituted heteroarylene group, Z is selected from the group consisting of hydrogen; a substituted or unsubstituted alkyl group; a substituted or unsubstituted aryl group; a substituted or unsubstituted heteroaryl group; —SiRR'R"; and —P(=O)RR', m is an integer of 1 to 3, n is an integer of 1 to 5, and when m and n are an integer of 2 or greater, substituents in the parentheses are the same as or different from each other.

Another embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound represented by Chemical Formula 1.

Advantageous Effects

A compound described in the present specification can be used as a material of an organic material layer of an organic light emitting device. The compound is capable of performing a role of a hole injection material, a hole transfer material, a light emitting material, an electron transfer material, an electron injection material and the like. Particularly, the compound can be used as an electron transfer layer material or a hole blocking layer material of an organic light emitting device.

When using the compound represented by Chemical Formula 1 in an organic material layer, a device driving voltage can be lowered, light efficiency can be enhanced, and device lifetime properties can be enhanced by thermal stability of the compound.

DESCRIPTION OF DRAWINGS

FIG. 1 to FIG. 3 are diagrams each schematically illustrating a lamination structure of an organic light emitting device according to one embodiment of the present application.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

MODE FOR DISCLOSURE

Herein, the present application will be described in detail.

A term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, the halogen may be fluorine, chlorine, bromine or iodine.

In the present specification, the alkyl group comprises linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group comprises linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenyl-vinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group comprises linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is preferably from 1 to 20. Specific examples thereof may comprise methoxy, ethoxy, n-propoxy, isopropoxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the cycloalkyl group comprises monocyclic or polycyclic having 3 to 60 carbon atoms, and may be further substituted with other substituents. Herein, the polycyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4 methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group comprises O, S, Se, N or Si as a heteroatom, comprises monocyclic or polycyclic having 2 to 60 carbon atoms, and may be further substituted with other substituents. Herein, the polycyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group comprises monocyclic or polycyclic having 6 to 60 carbon atoms, and may be further substituted with other substituents. Herein, the polycyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group comprises a spiro group. The number of carbon atoms of the aryl group may be from 6 to 60, specifically from 6 to 40 and more specifically from 6 to 25. Specific examples of the aryl group may comprise a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the phosphine oxide group is represented by —P(=O)R$_{103}$R$_{104}$, and R$_{103}$ and R$_{104}$ are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the phosphine oxide group may comprise a diphenylphosphine oxide group, a dinaphthylphosphine oxide group and the like, but are not limited thereto.

In the present specification, the silyl group is a substituent comprising Si, having the Si atom directly linked as a radical, and is represented by —SiR$_{105}$R$_{106}$R$_{107}$. R$_{105}$ to R$_{107}$ are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the silyl group may comprise a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the fluorenyl group may be substituted, and adjacent substituents may bond to each other to form a ring.

When the fluorenyl group is substituted, the following structures may be obtained, however, the structure is not limited thereto.

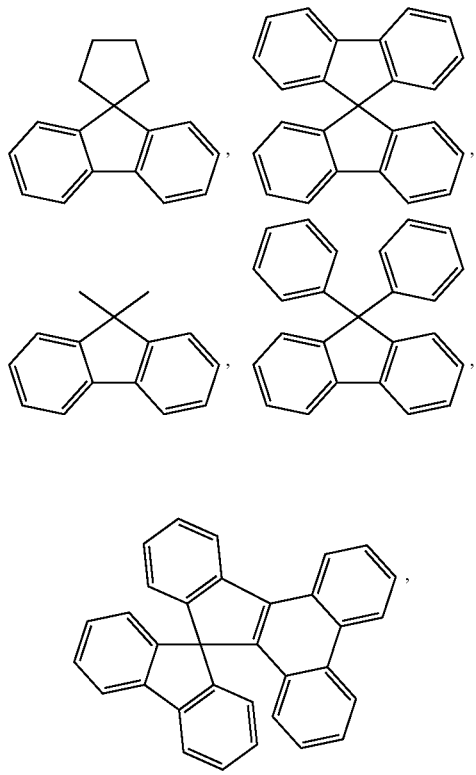

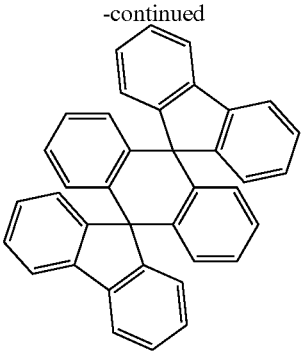

In the present specification, the heteroaryl group comprises O, S, Se, N or Si as a heteroatom, comprises monocyclic or polycyclic having 2 to 60 carbon atoms, and may be further substituted with other substituents. Herein, the polycyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydrodibenzo[b,f]azepine group, a 9,10-dihydroacridinyl group, a phenanthrazinyl group, a phenothiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; —NH$_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means the aryl group having two bonding sites, that is, a divalent group. Descriptions on the aryl group provided above may be applied thereto except for those that are each a divalent. In addition, the heteroarylene group means the heteroaryl group having two bonding sites, that is, a divalent group. Descriptions on the heteroaryl group provided above may be applied thereto except for those that are each a divalent.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, the term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, "substituted or unsubstituted" means being substituted with one or more substituents selected from the group consisting of C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R"; —P(=O)RR'; C1 to C20 alkylamine; C6 to C60 monocyclic or polycyclic arylamine; and C2 to C60 monocyclic or polycyclic heteroarylamine, or being unsubstituted, or being substituted with a substituent linking two or more substituents selected from among the substituents illustrated above, or being unsubstituted.

One embodiment of the present application provides a heterocyclic compound represented by Chemical Formula 1.

In one embodiment of the present application, X may be O; or S.

In one embodiment of the present application, X may be O.

In one embodiment of the present application, X may be S.

In one embodiment of the present application, at least one of $R_1$, $R_2$ and $R_4$ may be represented by -(L)m-(Z)n, and at least one of $R_1$, $R_2$ and $R_4$ may be a substituted or unsubstituted aryl group.

In one embodiment of the present application, $R_1$ may be represented by -(L)m-(Z)n, and $R_2$ and $R_4$ may be a substituted or unsubstituted aryl group.

In one embodiment of the present application, $R_2$ may be represented by -(L)m-(Z)n, and $R_1$ and $R_4$ may be a substituted or unsubstituted aryl group.

In one embodiment of the present application, $R_4$ may be represented by -(L)m-(Z)n, and $R_1$ and $R_2$ may be a substituted or unsubstituted aryl group.

In one embodiment of the present application, $R_1$ may be represented by -(L)m-(Z)n, and $R_4$ may be a substituted or unsubstituted aryl group.

In one embodiment of the present application, $R_1$ may be represented by -(L)m-(Z)n, and $R_2$ may be a substituted or unsubstituted aryl group.

In one embodiment of the present application, $R_2$ may be represented by -(L)m-(Z)n, and $R_4$ may be a substituted or unsubstituted aryl group.

In one embodiment of the present application, $R_2$ may be represented by -(L)m-(Z)n, and $R_1$ may be a substituted or unsubstituted aryl group.

In one embodiment of the present application, $R_4$ may be represented by -(L)m-(Z)n, and $R_1$ may be a substituted or unsubstituted aryl group.

In one embodiment of the present application, $R_4$ may be represented by -(L)m-(Z)n, and $R_2$ may be a substituted or unsubstituted aryl group.

In one embodiment of the present application, Chemical Formula 1 may be represented by any one of the following Chemical Formulae 2 to 4.

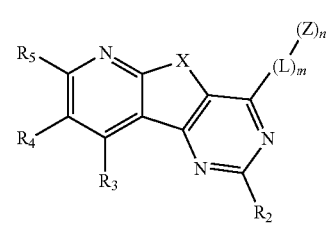

[Chemical Formula 2]

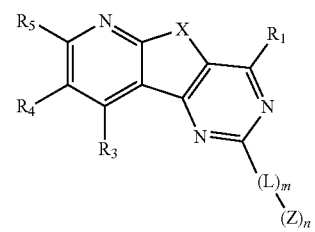

[Chemical Formula 3]

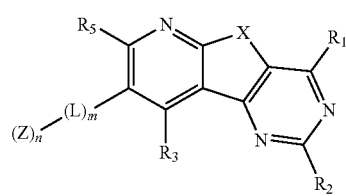

[Chemical Formula 4]

In Chemical Formulae 2 to 4, $R_1$ to $R_5$, L, Z, m, n and X have the same definitions as in Chemical Formula 1.

In one embodiment of the present application, $R_1$ to $R_5$ are the same as or different from each other, and each independently selected from the group consisting of hydrogen; deuterium; a substituted or unsubstituted alkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group, or two or more groups adjacent to each other may bond to each other to form a substituted or unsubstituted aromatic hydrocarbon ring or a substituted or unsubstituted heteroring.

In another embodiment, $R_1$ to $R_5$ are the same as or different from each other, and may be each independently selected from the group consisting of hydrogen; a substituted or unsubstituted alkyl group; a substituted or unsubstituted aryl group; and a substituted or unsubstituted heteroaryl group.

In another embodiment, $R_1$ to $R_5$ are the same as or different from each other, and may be each independently selected from the group consisting of hydrogen; a substituted or unsubstituted C1 to C60 alkyl group; a substituted or unsubstituted C6 to C60 aryl group; and a substituted or unsubstituted C2 to C60 heteroaryl group.

In another embodiment, $R_1$ to $R_5$ are the same as or different from each other, and may be each independently selected from the group consisting of hydrogen; a substituted or unsubstituted C1 to C40 alkyl group; a substituted or unsubstituted C6 to C40 aryl group; and a substituted or unsubstituted C2 to C40 heteroaryl group.

In another embodiment, $R_1$ to $R_5$ are the same as or different from each other, and may be each independently selected from the group consisting of hydrogen; a C6 to C40 aryl group unsubstituted or substituted with one or more substituents selected from the group consisting of a C1 to C40 alkyl group, a C6 to C40 aryl group and a C2 to C40 heteroaryl group; and a C2 to C40 heteroaryl group unsubstituted or substituted with one or more substituents selected from the group consisting of a C1 to C40 alkyl group, a C6 to C40 aryl group and a C2 to C40 heteroaryl group.

In another embodiment, $R_3$ and $R_5$ may be hydrogen.

In one embodiment of the present application, L may be a substituted or unsubstituted arylene group; or a substituted or unsubstituted heteroarylene group.

In another embodiment, L may be a substituted or unsubstituted C6 to C60 arylene group; or a substituted or unsubstituted C2 to C60 heteroarylene group.

In another embodiment, L may be a substituted or unsubstituted C6 to C40 arylene group; or a substituted or unsubstituted C2 to C40 heteroarylene group.

In another embodiment, L may be a C6 to C40 arylene group; or a C2 to C40 heteroarylene group unsubstituted or substituted with a C6 to C40 aryl group.

In another embodiment, L may be a phenylene group; a biphenylene group; a naphthylene group; a phenanthrene group; a triazine group unsubstituted or substituted with a phenyl group; a pyrimidine group unsubstituted or substituted with a phenyl group; or a quinoline group.

In one embodiment of the present application, Z may be selected from the group consisting of hydrogen; a substituted or unsubstituted alkyl group; a substituted or unsubstituted aryl group; a substituted or unsubstituted heteroaryl group; —SiRR'R"; and —P(=O)RR'.

In another embodiment, Z may be selected from the group consisting of hydrogen; a substituted or unsubstituted C1 to C60 alkyl group; a substituted or unsubstituted C6 to C60 aryl group; a substituted or unsubstituted C2 to C60 heteroaryl group; —SiRR'R"; and —P(=O)RR'.

In another embodiment, Z may be selected from the group consisting of hydrogen; a substituted or unsubstituted C6 to C60 aryl group; and a substituted or unsubstituted C2 to C60 heteroaryl group.

In another embodiment, Z may be selected from the group consisting of hydrogen; a C6 to C60 aryl group unsubstituted or substituted with a C2 to C60 heteroaryl group; and a C2 to C60 heteroaryl group unsubstituted or substituted with one or more substituents selected from the group consisting of a C6 to C60 aryl group and a C2 to C60 heteroaryl group.

In another embodiment, Z may be selected from the group consisting of hydrogen; a C6 to C40 aryl group unsubstituted or substituted with a C2 to C40 heteroaryl group; and a C2 to C40 heteroaryl group unsubstituted or substituted with one or more substituents selected from the group consisting of a C6 to C40 aryl group and a C2 to C40 heteroaryl group.

In another embodiment, Z may be a phenyl group unsubstituted or substituted with a pyridine group; a pyridine group unsubstituted or substituted with a pyridine group; a pyrimidine group unsubstituted or substituted with one or more substituents selected from the group consisting of a phenyl group and a biphenyl group; a pyridine group unsubstituted or substituted with one or more substituents selected from the group consisting of a phenyl group and a biphenyl group; a quinoline group unsubstituted or substituted with a pyridine group; a carbazole group; a phenanthroline group; or a pyrido[2',1':2,3]imidazo[4,5-c]isoquinoline group unsubstituted or substituted with a phenyl group.

Particularly, when Z has a heteroaryl-based substituent as above, the molecular weight increases compared to compounds having aryl-based or hydrogen leading to improved thermal properties, and when having heteroaryl-based, HOMO, LUMO or bandgap may be controlled due to the influence of electronic properties, and more superior properties are obtained when used in an organic light emitting device.

In one embodiment of the present application, Z may be substituted again with a C2 to C40 heteroaryl group.

In one embodiment of the present application, Z may be substituted again with a carbazole group.

In one embodiment of the present application, $R_1$ may be represented by -(L)m-(Z)n, $R_4$ may be a substituted or unsubstituted aryl group, and $R_2$ may be hydrogen.

In one embodiment of the present application, $R_1$ may be represented by -(L)m-(Z)n, $R_2$ may be a substituted or unsubstituted aryl group, and $R_4$ may be hydrogen.

In one embodiment of the present application, $R_2$ may be represented by -(L)m-(Z)n, $R_4$ may be a substituted or unsubstituted aryl group, and $R_1$ may be hydrogen.

In one embodiment of the present application, $R_2$ may be represented by -(L)m-(Z)n, $R_1$ may be a substituted or unsubstituted aryl group, and $R_4$ may be hydrogen.

In one embodiment of the present application, $R_4$ may be represented by -(L)m-(Z)n, $R_1$ may be a substituted or unsubstituted aryl group, and $R_2$ may be hydrogen.

In one embodiment of the present application, $R_4$ may be represented by -(L)m-(Z)n, $R_2$ may be a substituted or unsubstituted aryl group, and $R_1$ may be hydrogen.

In the compound of Chemical Formula 1 of the present application, the compound of Chemical Formula 1 of the present application has, compared to when $R_1$, $R_2$ and $R_4$ all have hydrogen, at least one of $R_1$, $R_2$ and $R_4$ being represented by -(L)m-(Z)n and at least one of $R_1$, $R_2$ and $R_4$ having a substituted or unsubstituted aryl group, and as a result, effects of smoothly controlling electron flow may be obtained by resolving the problem of absence of a substituent controlling molecular conjugation.

In one embodiment of the present application, R, R' and R" are the same as or different from each other, and may be each independently hydrogen; a substituted or unsubstituted alkyl group; a substituted or unsubstituted aryl group; or a substituted or unsubstituted heteroaryl group.

In another embodiment, R, R' and R" are the same as or different from each other, and may be each independently a substituted or unsubstituted C1 to C60 alkyl group; or a substituted or unsubstituted C6 to C60 aryl group.

In another embodiment, R, R' and R" are the same as or different from each other, and may be each independently a substituted or unsubstituted C1 to C40 alkyl group; or a substituted or unsubstituted C6 to C40 aryl group.

In another embodiment, R, R' and R" are the same as or different from each other, and may be each independently a C1 to C40 alkyl group; or a C6 to C40 aryl group.

In another embodiment, R, R' and R" are the same as or different from each other, and may be each independently a methyl group; or a phenyl group.

In another embodiment, R, R' and R" may be a phenyl group.

In one embodiment of the present application, Chemical Formula 2 may be represented by any one of the following Chemical Formulae 2-1 to 2-3.

[Chemical Formula 2-1]

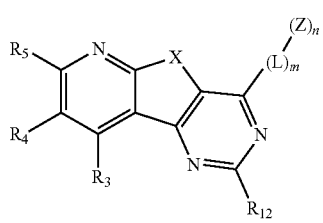

[Chemical Formula 2-2]

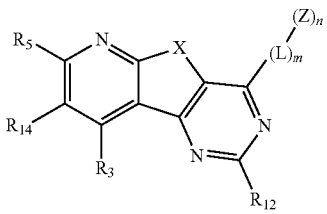

[Chemical Formula 2-3]

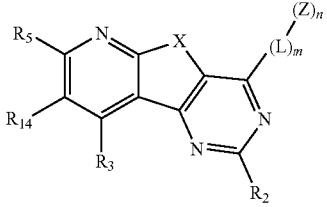

In Chemical Formulae 2-1 to 2-3,

L, Z, m, n and X have the same definitions as in Chemical Formula 2, $R_{12}$ and $R_{14}$ are the same as or different from each other, and each independently a substituted or unsubstituted aryl group, and $R_2$ to $R_5$ are hydrogen.

In one embodiment of the present application, Chemical Formula 3 may be represented by any one of the following Chemical Formulae 3-1 to 3-3.

[Chemical Formula 3-1]

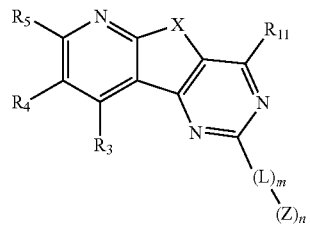

[Chemical Formula 3-2]

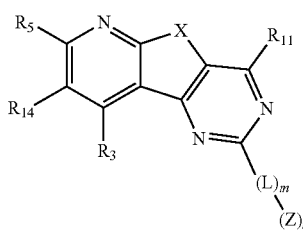

[Chemical Formula 3-3]

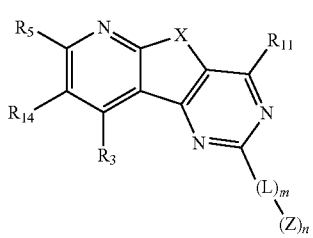

In Chemical Formulae 3-1 to 3-3,

L, Z, m, n and X have the same definitions as in Chemical Formula 3, $R_{11}$ and $R_{14}$ are the same as or different from each other, and each independently a substituted or unsubstituted aryl group, and $R_1$ and $R_3$ to $R_5$ are hydrogen.

In one embodiment of the present application, Chemical Formula 4 may be represented by any one of the following Chemical Formulae 4-1 to 4-3.

[Chemical Formula 4-1]

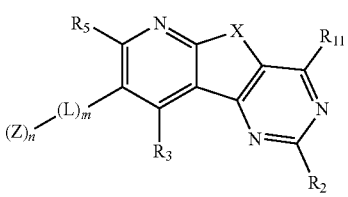

[Chemical Formula 4-2]

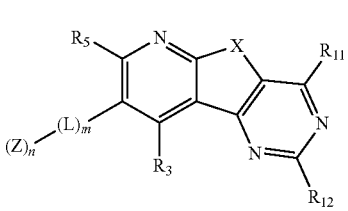

[Chemical Formula 4-3]

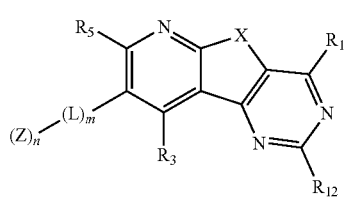

In Chemical Formulae 4-1 to 4-3,

L, Z, m, n and X have the same definitions as in Chemical Formula 4, $R_{11}$ and $R_{12}$ are the same as or different from each other, and each independently a substituted or unsubstituted aryl group, and $R_1$, $R_2$, $R_3$ and $R_5$ are hydrogen.

In one embodiment of the present application, $R_{11}$, $R_{12}$ and $R_{14}$ are the same as or different from each other, and may be each independently a substituted or unsubstituted aryl group.

In another embodiment, $R_{11}$, $R_{12}$ and $R_{14}$ are the same as or different from each other, and may be each independently a substituted or unsubstituted C6 to C60 aryl group.

In another embodiment, $R_{11}$, $R_{12}$ and $R_{14}$ are the same as or different from each other, and may be each independently a substituted or unsubstituted C6 to C40 aryl group.

In another embodiment, $R_{11}$, $R_{12}$ and $R_{14}$ are the same as or different from each other, and may be each independently a C6 to C40 aryl group.

In another embodiment, $R_{11}$, $R_{12}$ and $R_{14}$ are the same as or different from each other, and may be each independently a phenyl group; a biphenyl group; a naphthyl group; or an anthracenyl group.

In the heterocyclic compound provided in one embodiment of the present application, Chemical Formula 1 is represented by any one of the following compounds.

1

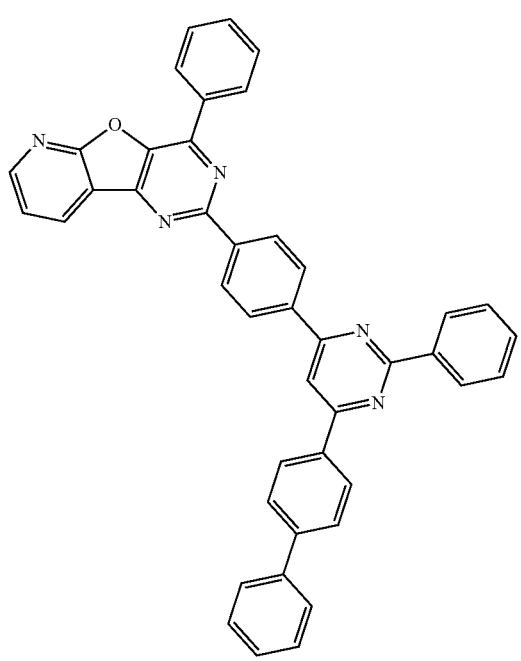

2

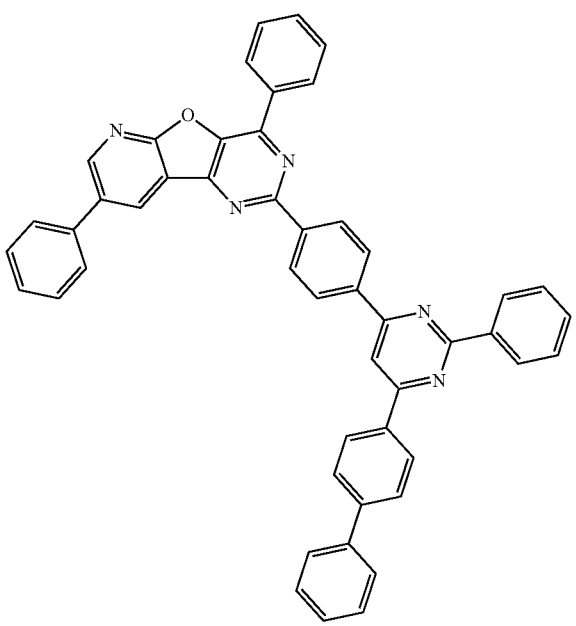

3

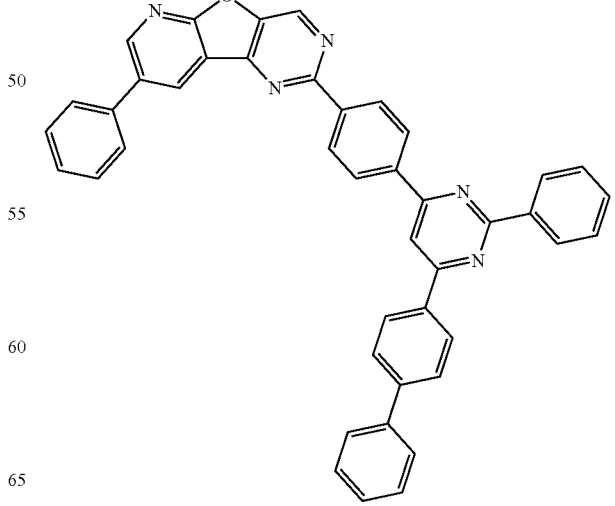

4
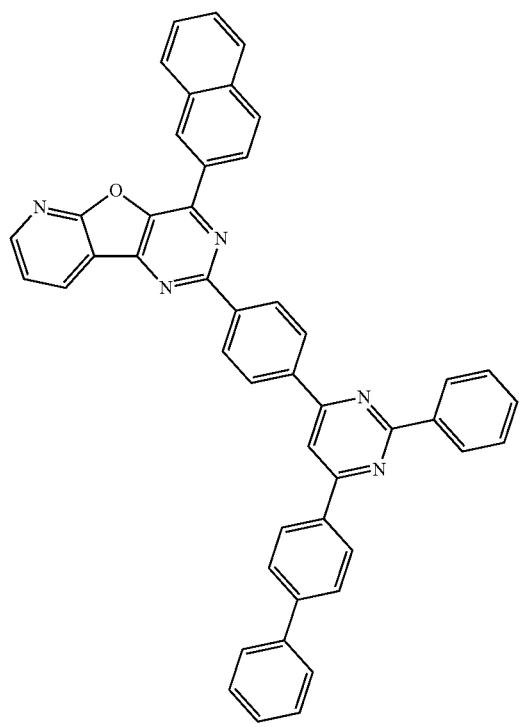
5
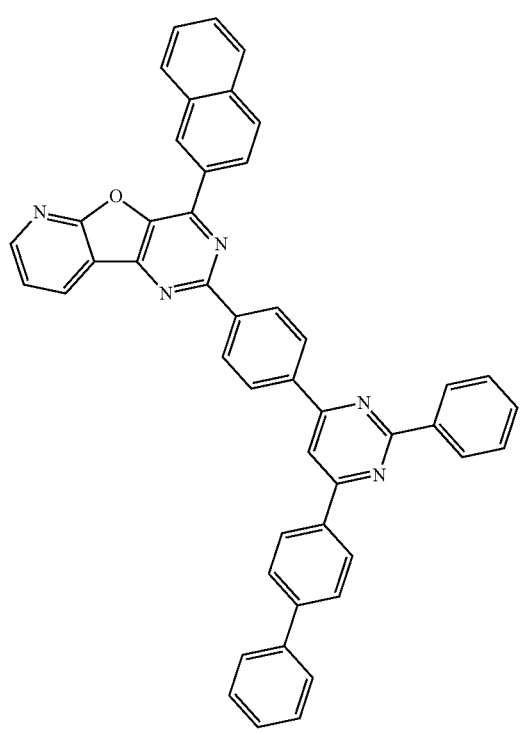
6
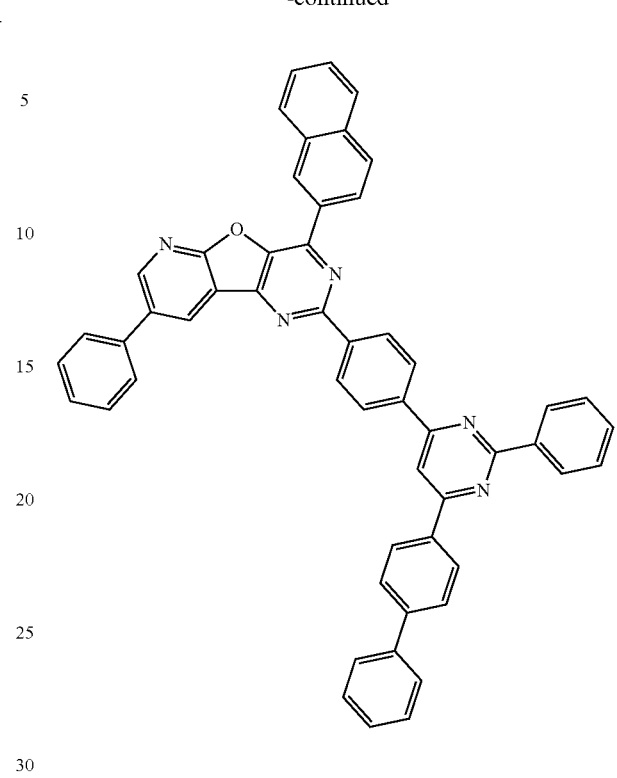
7
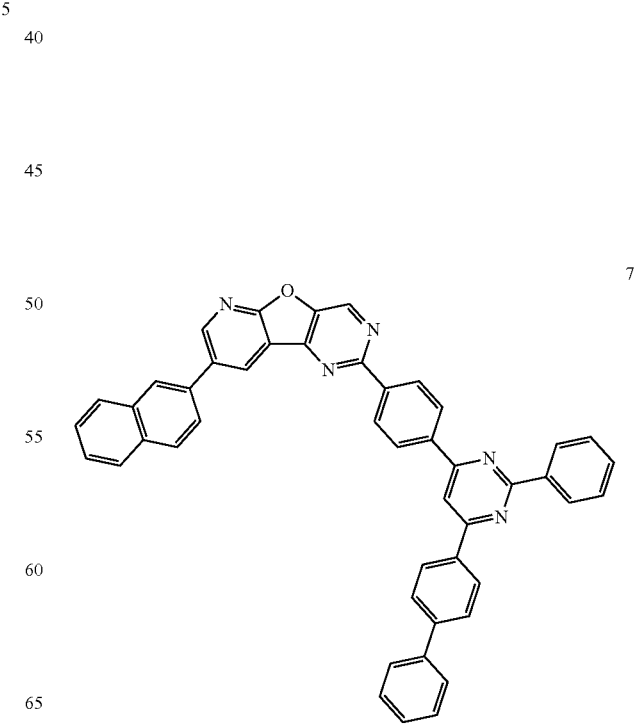

8
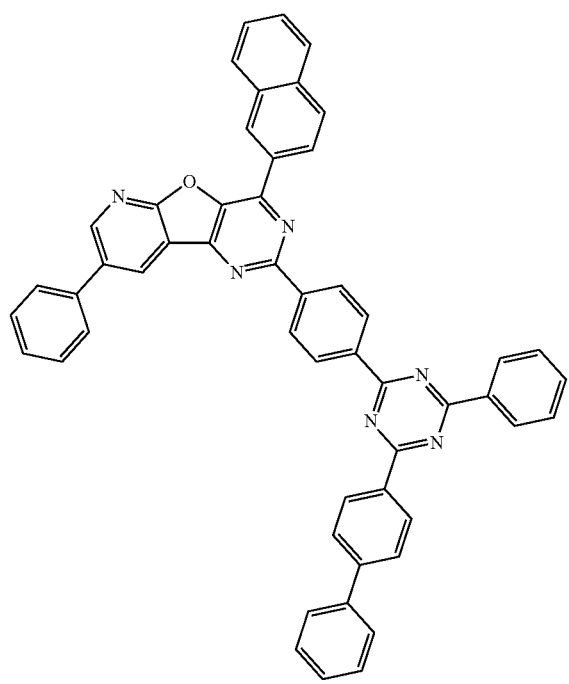
10
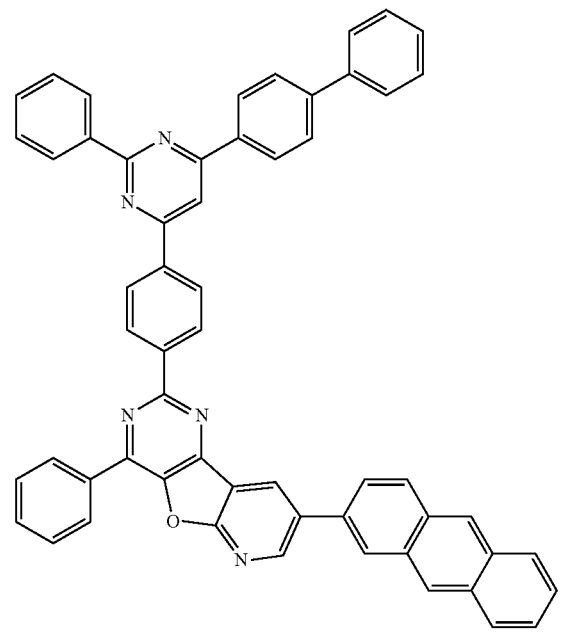
9
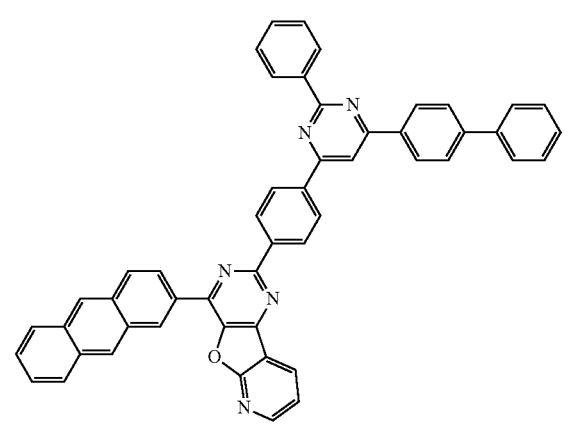
11
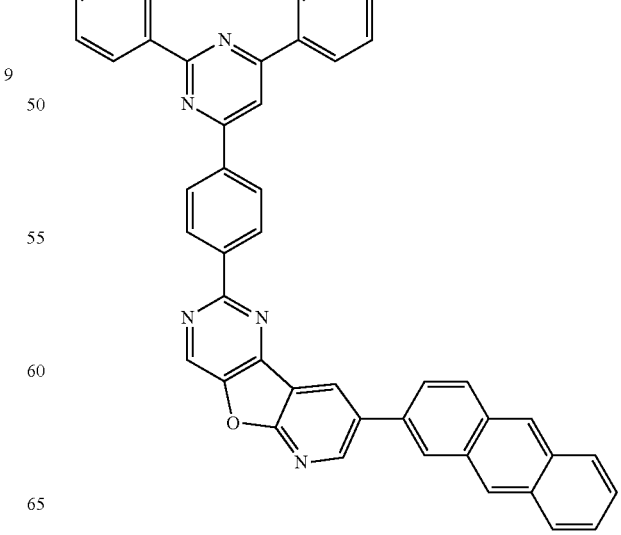

12
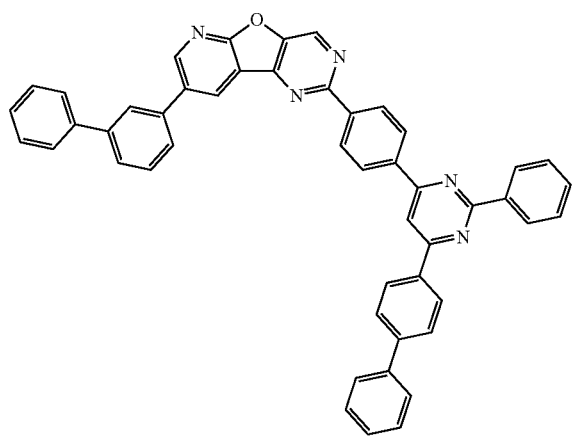
13
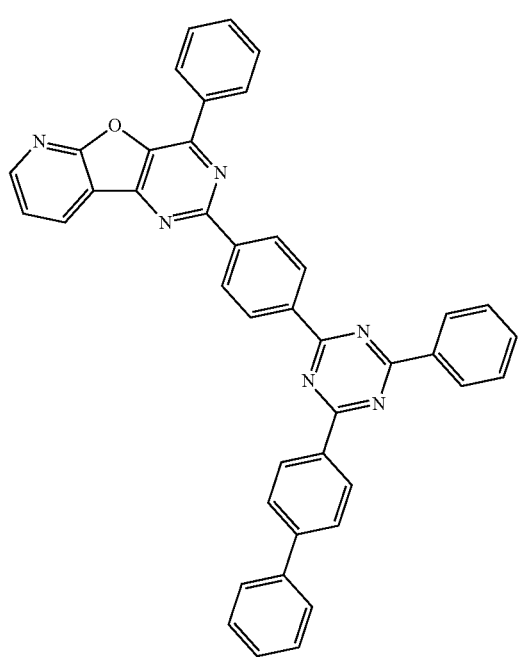
14
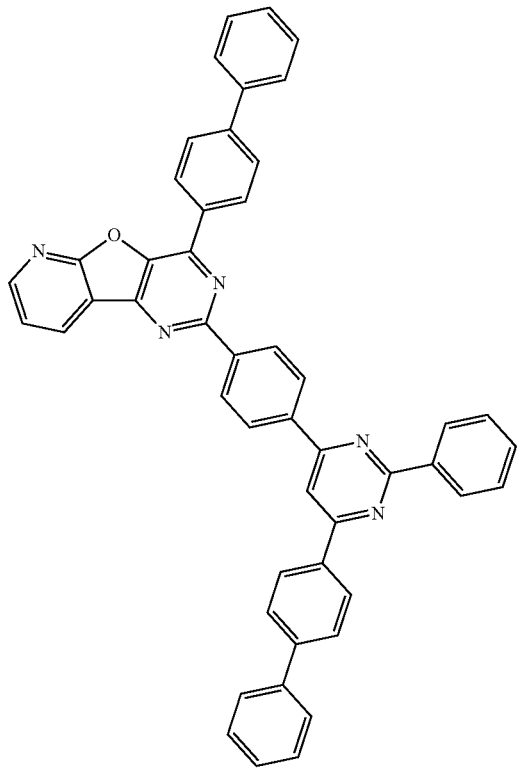
15
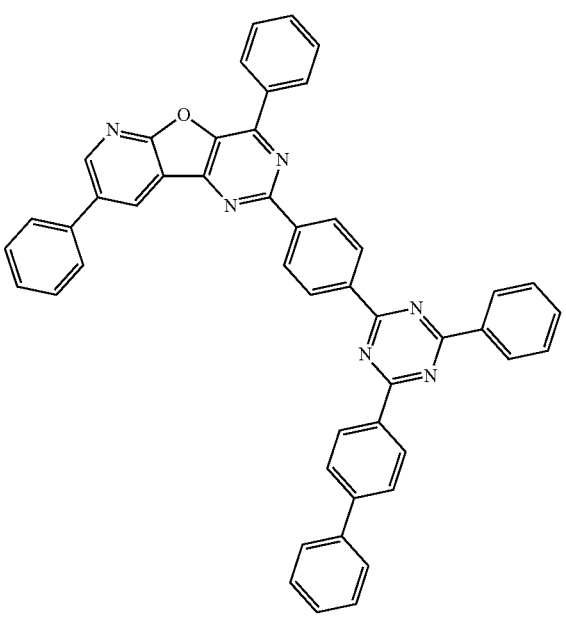

16
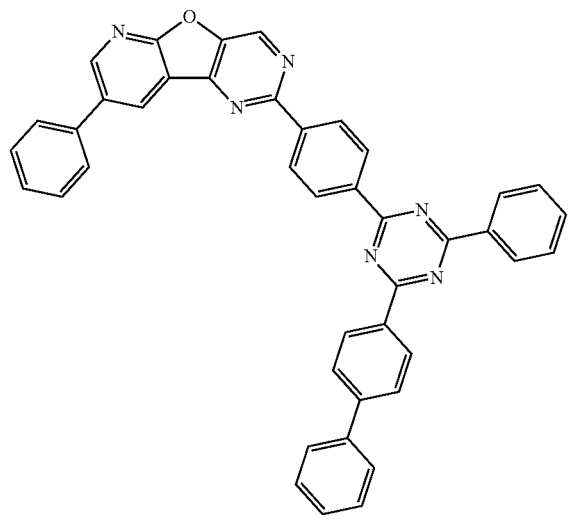
17
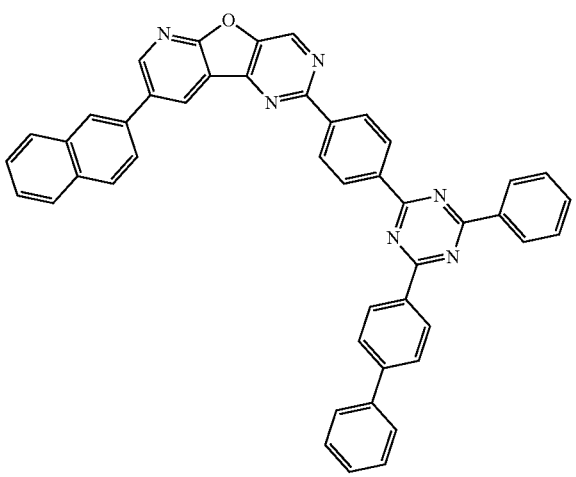
18
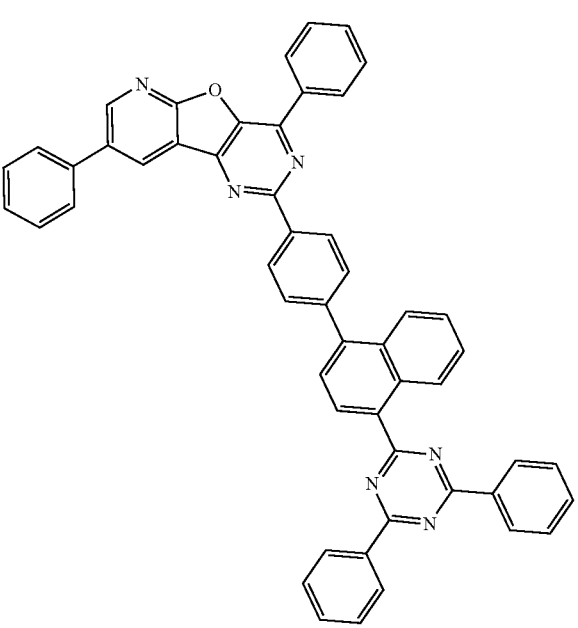
19
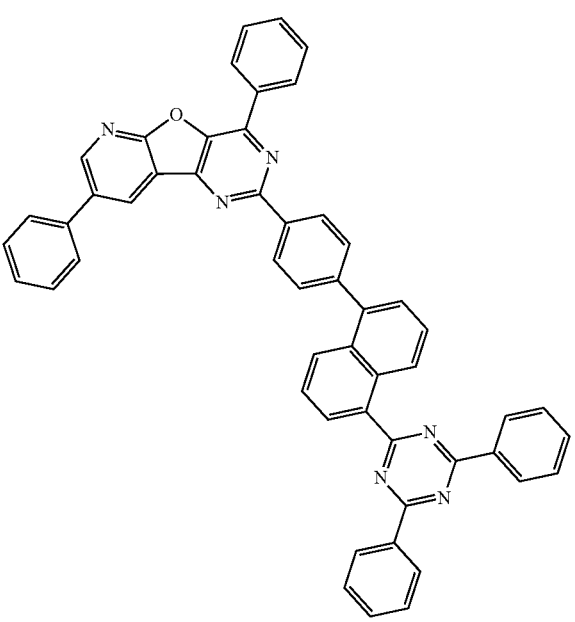
20
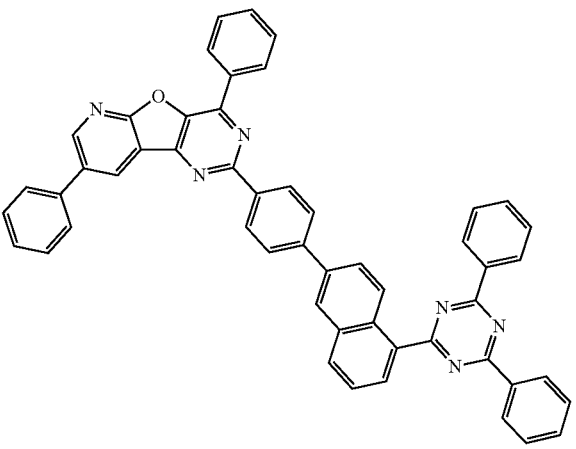

21
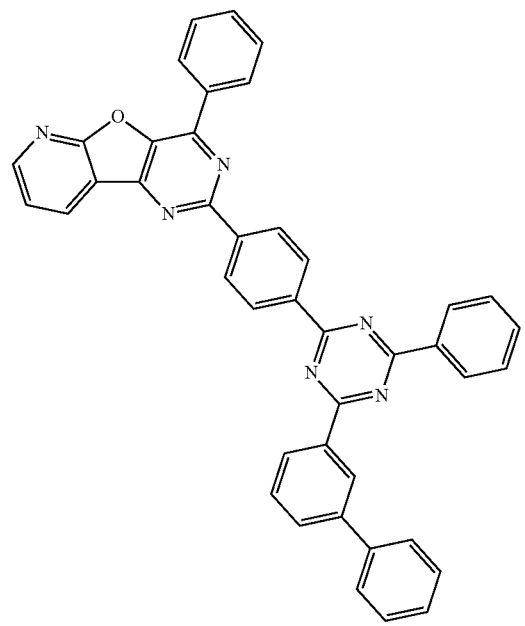
22
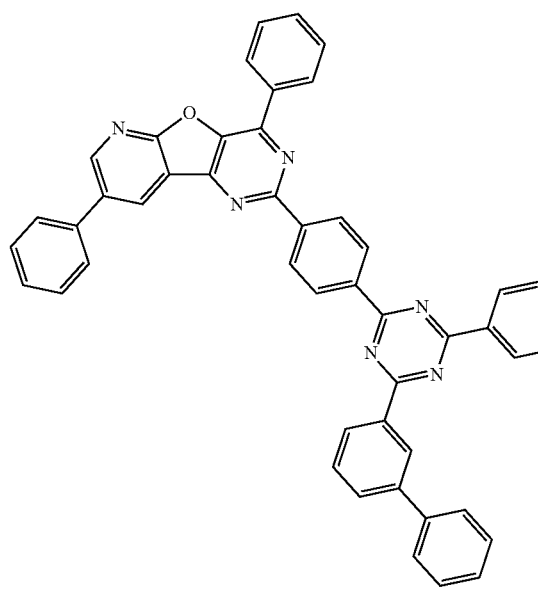
23
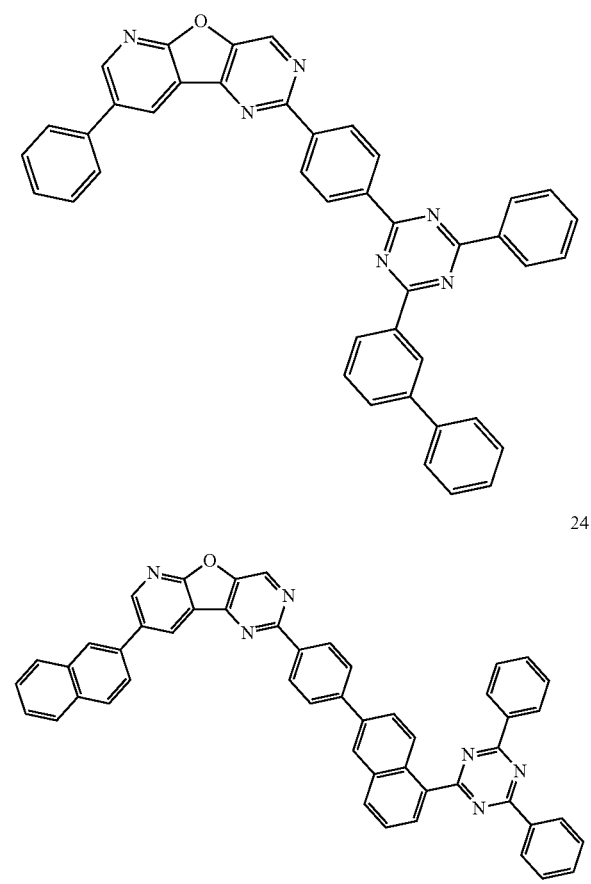
24
25
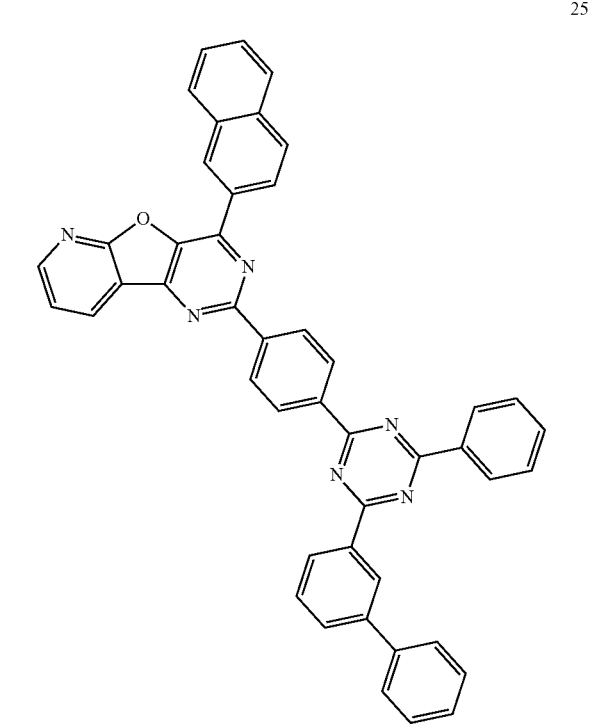

26
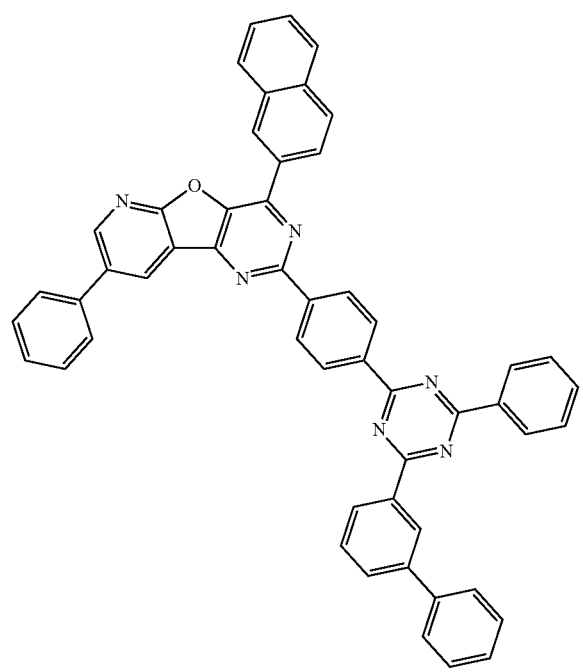
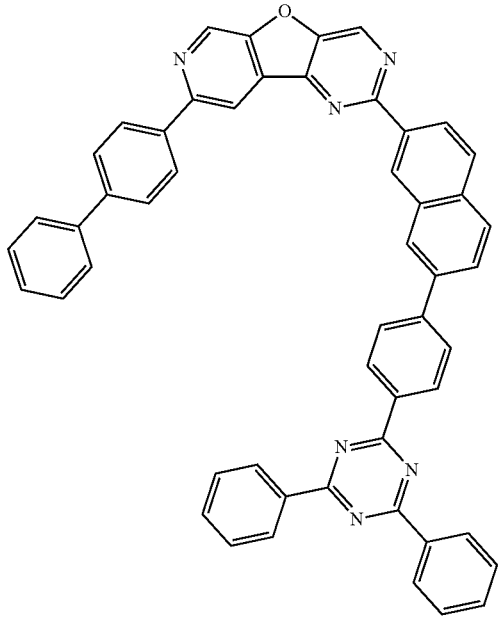
27
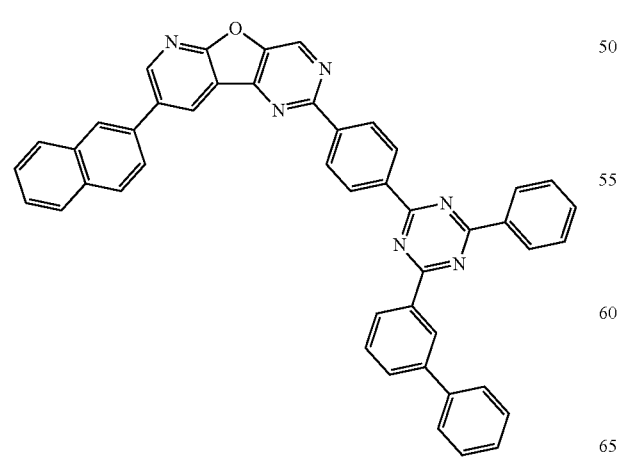
28
29
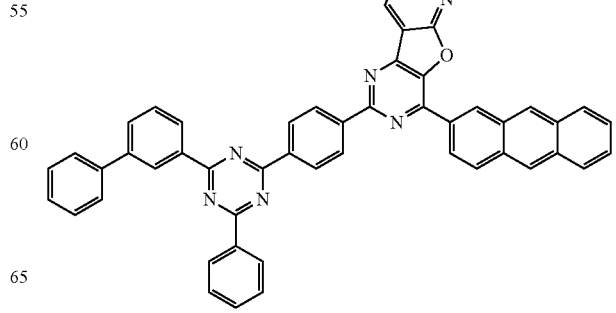

30
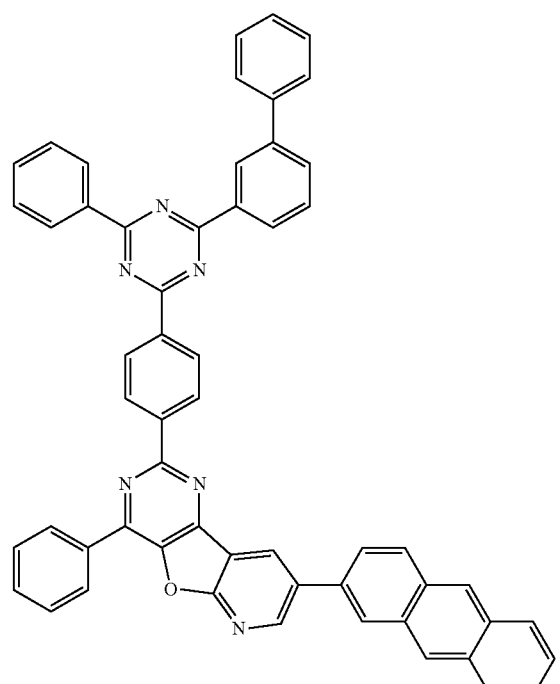
31
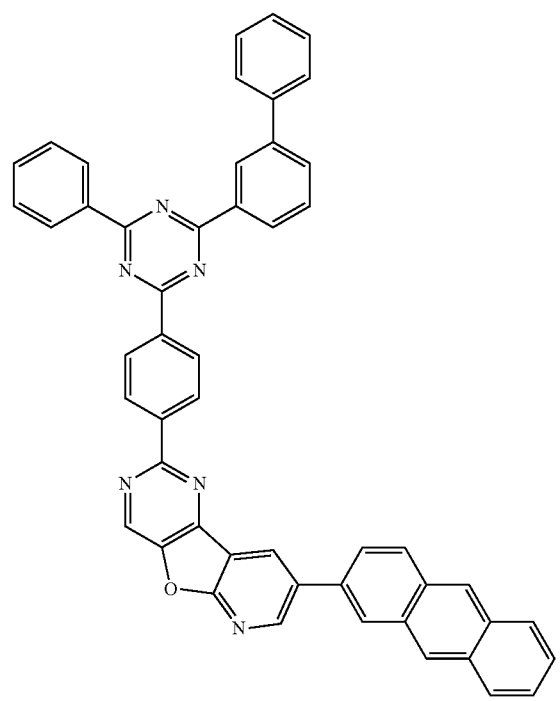
32
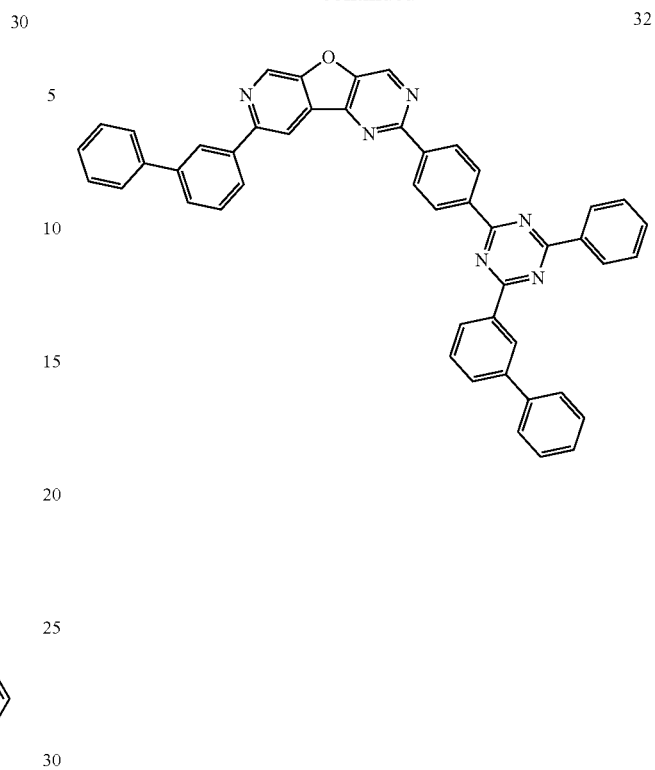
33
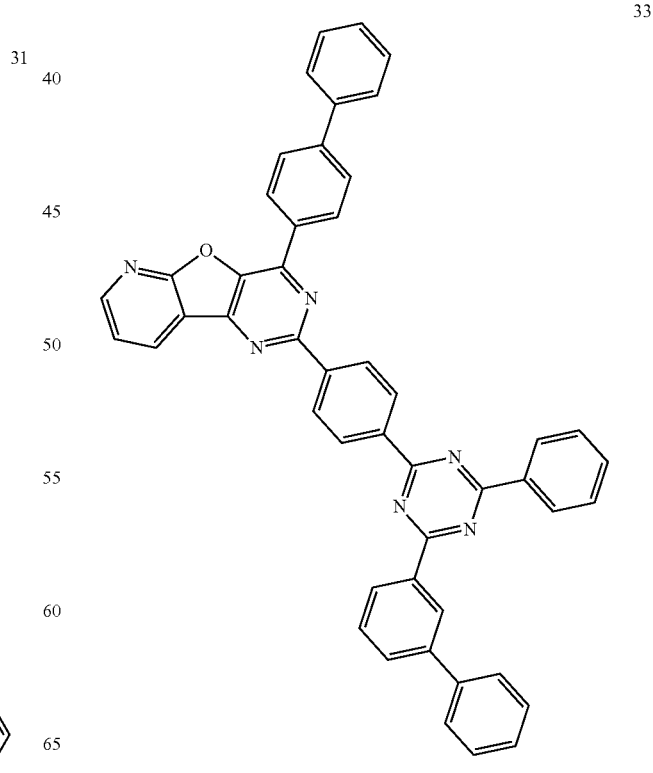

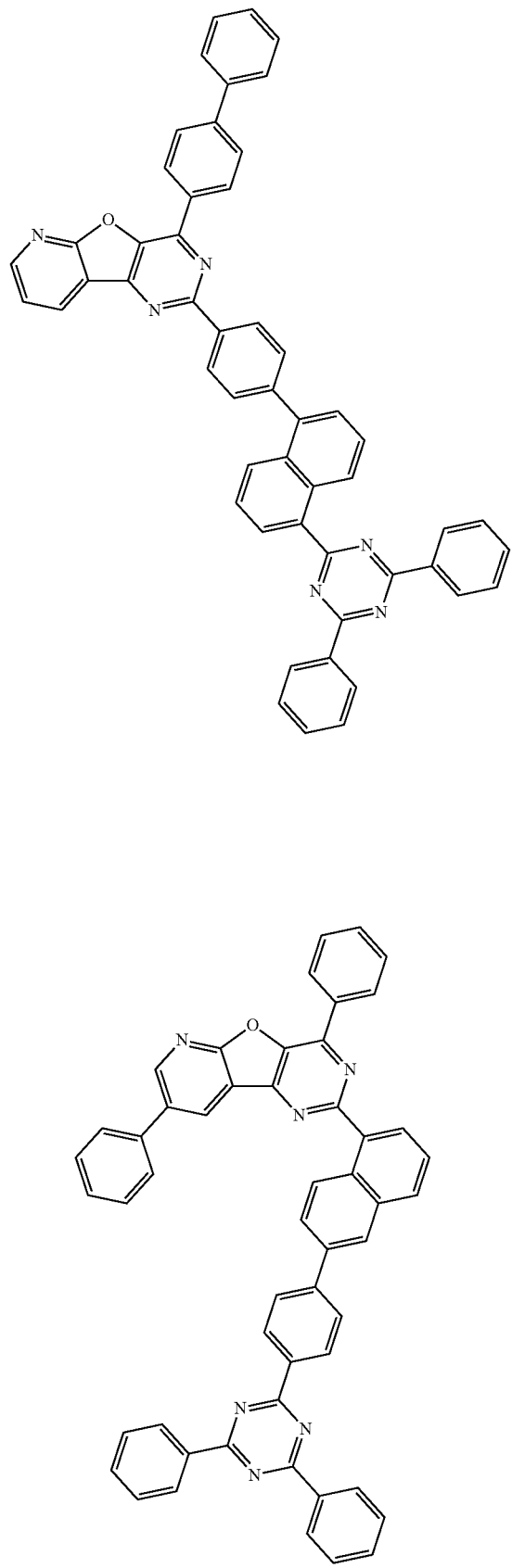
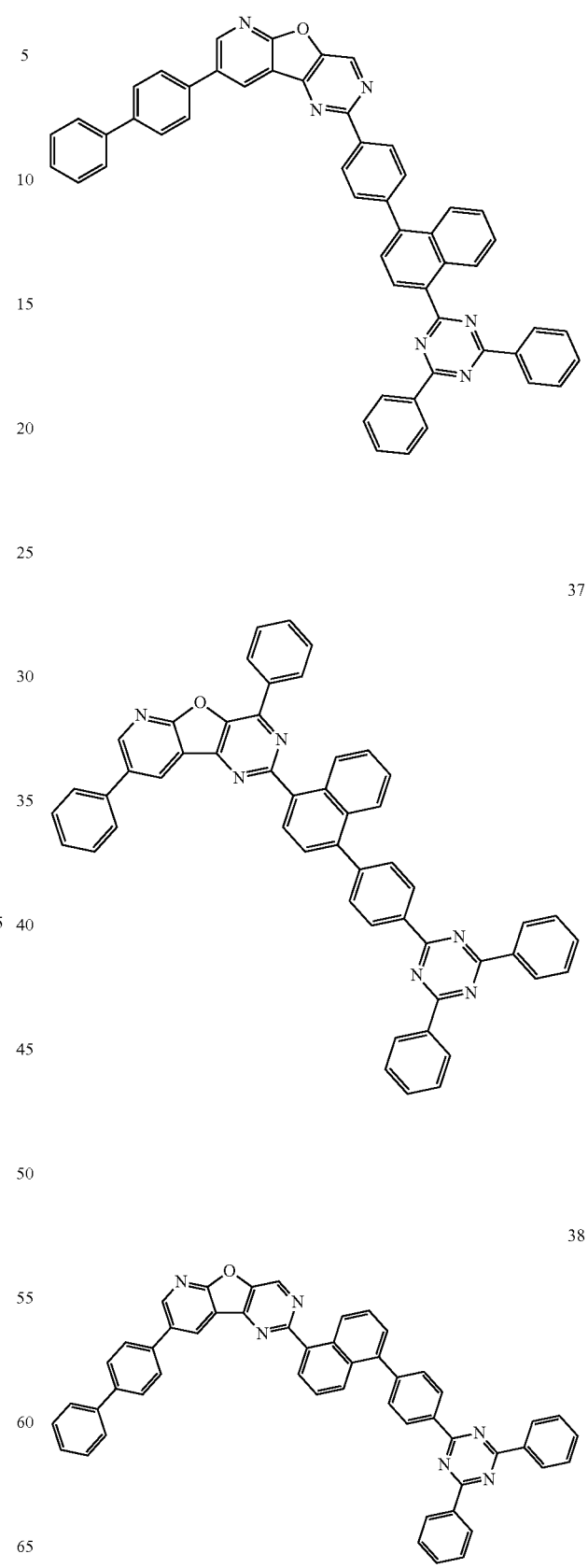

39
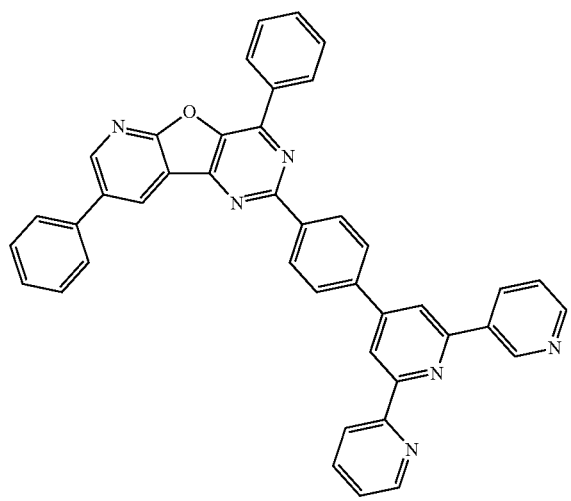
40
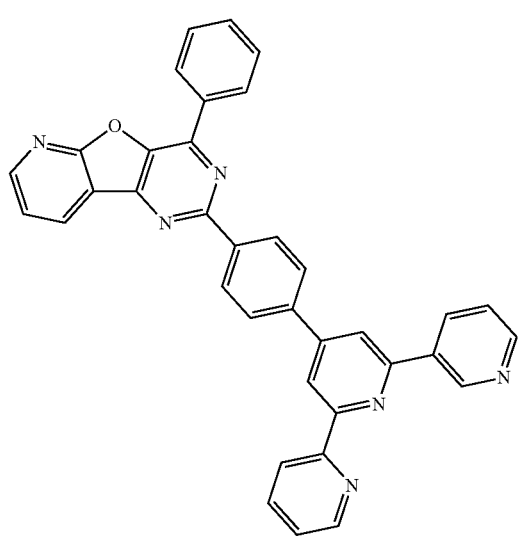
41
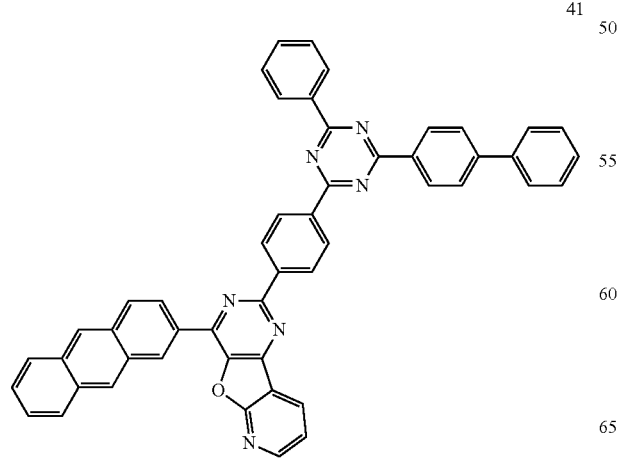
42
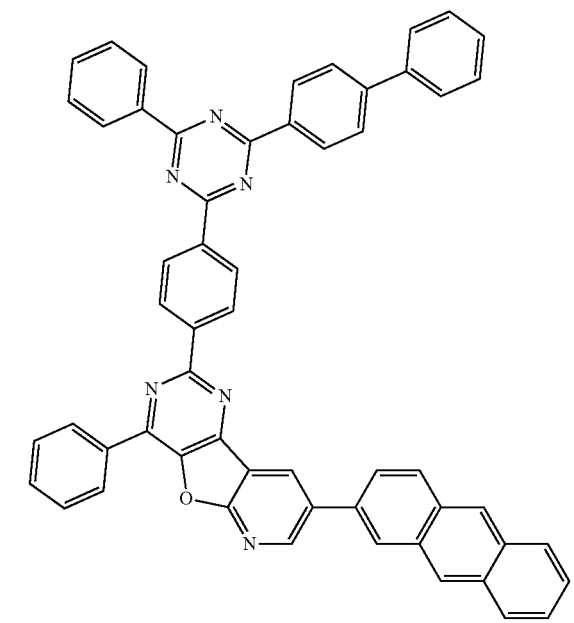
43
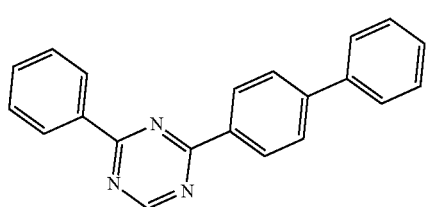
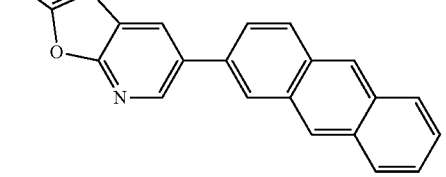
44
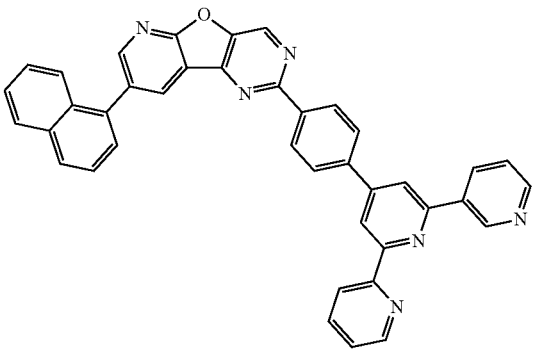

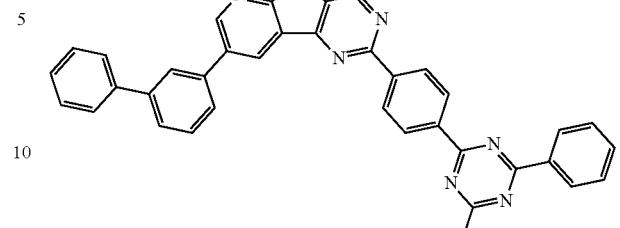
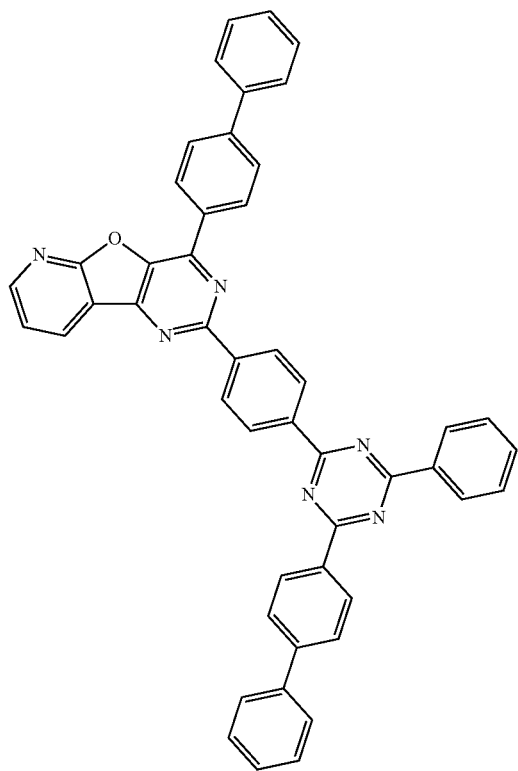
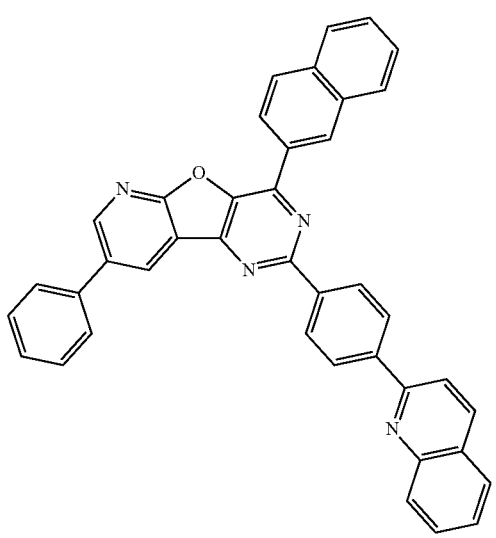
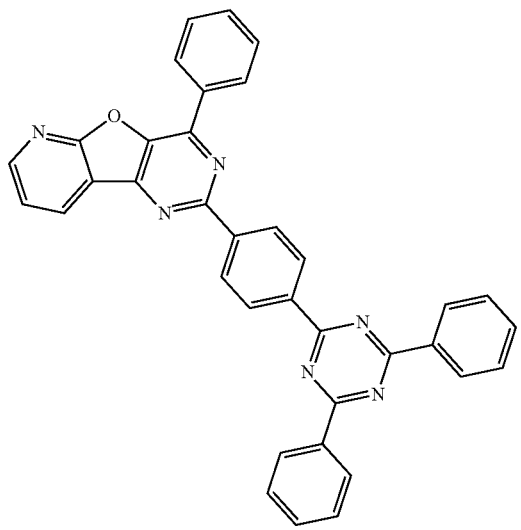

50
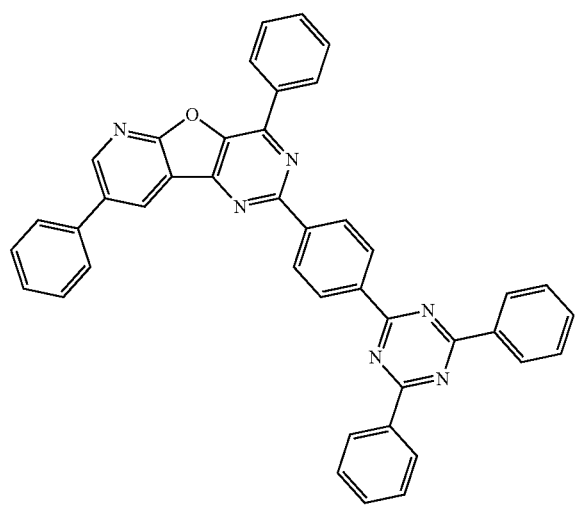
51
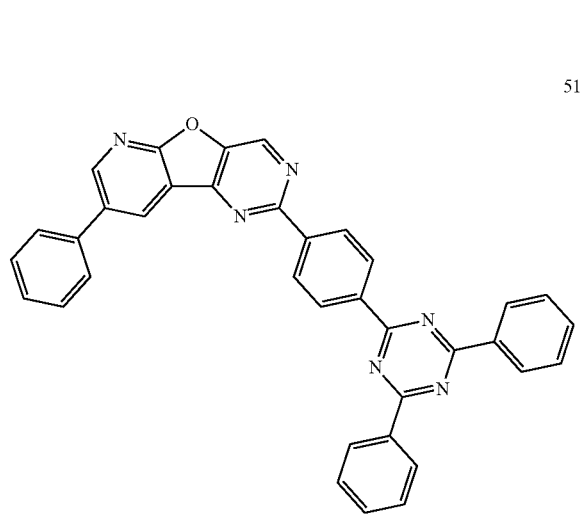
52
53
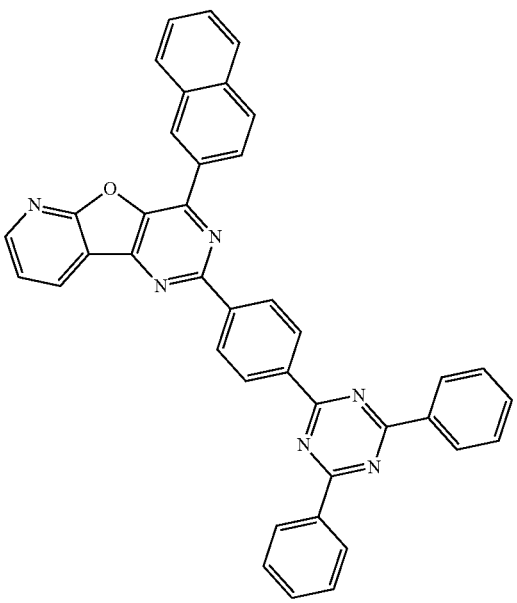
54
55
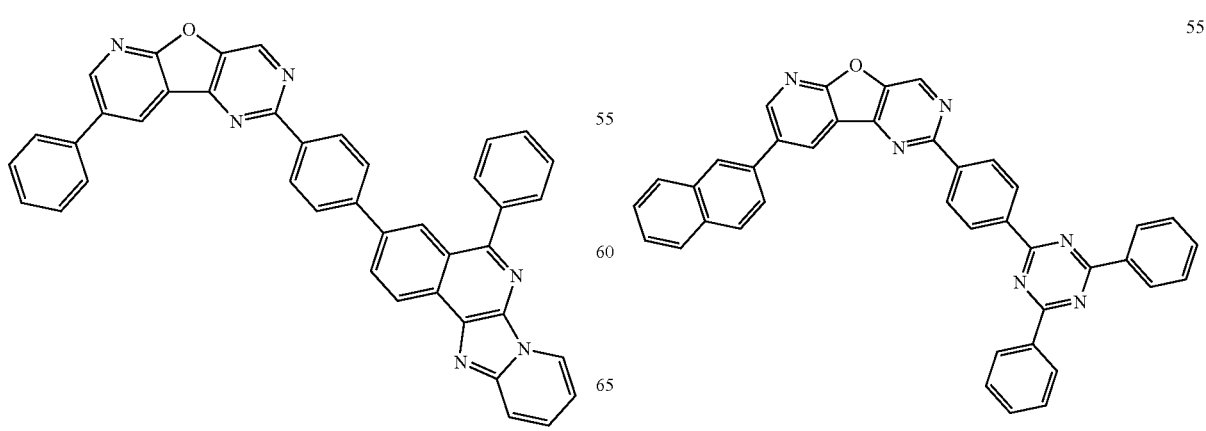

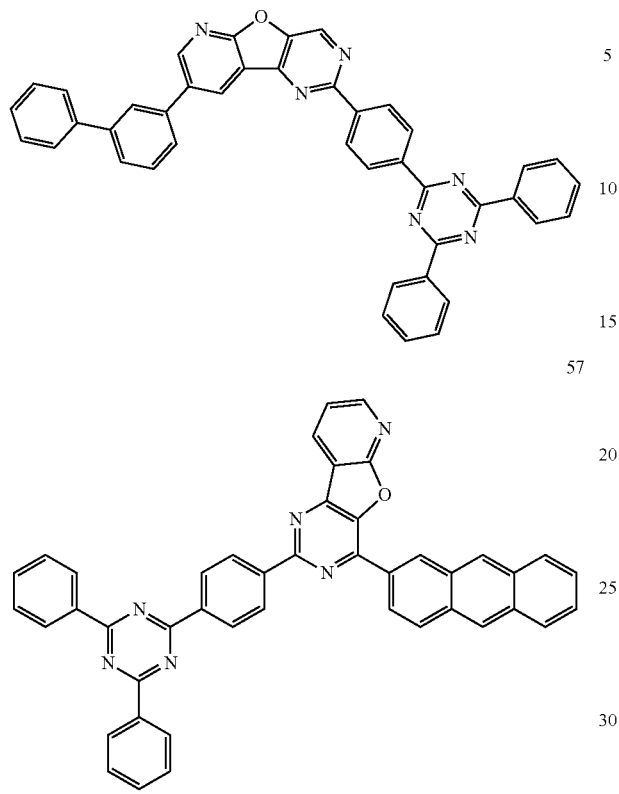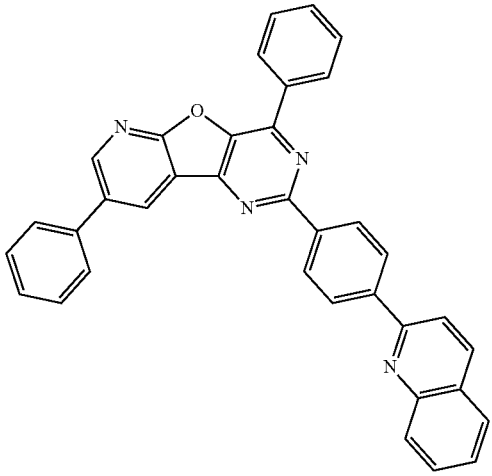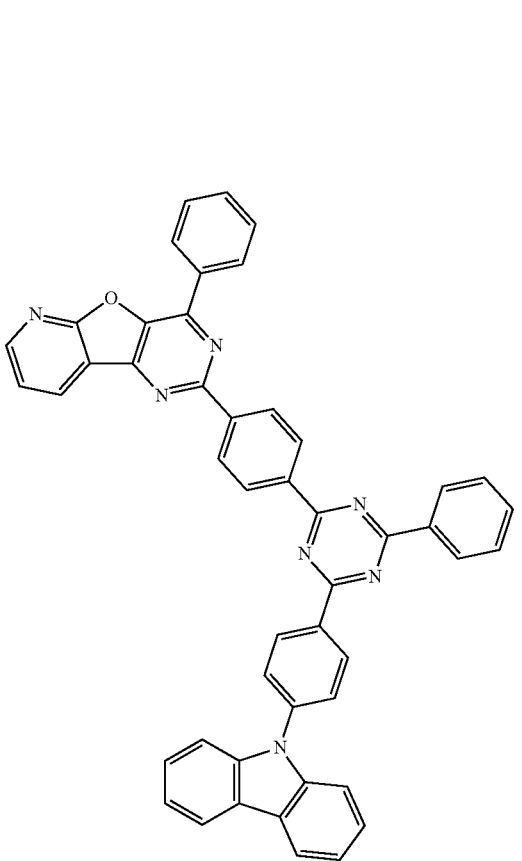

-continued
62
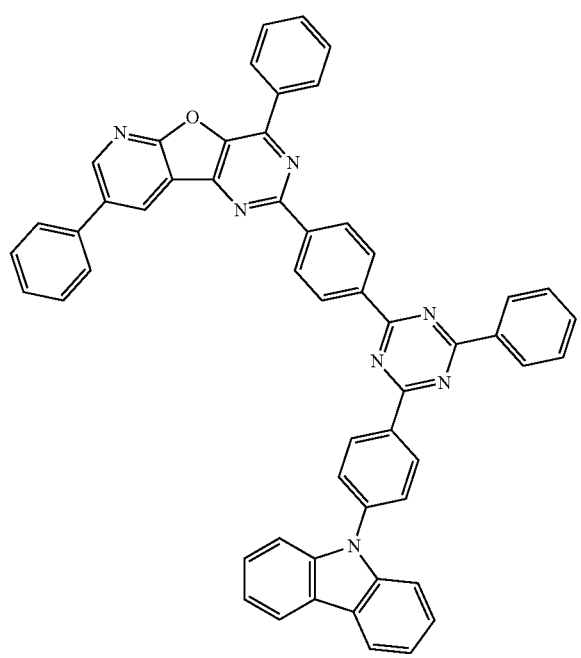
63
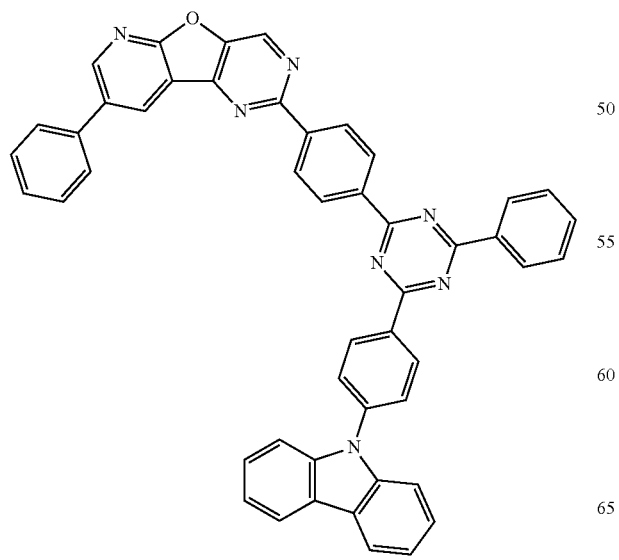
-continued
64
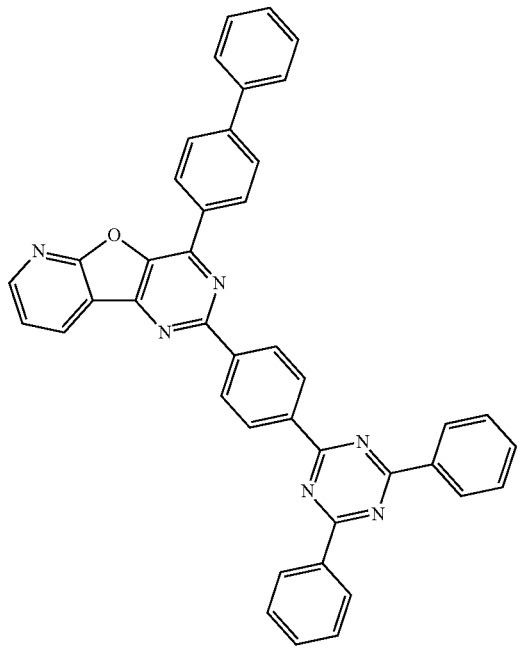
65
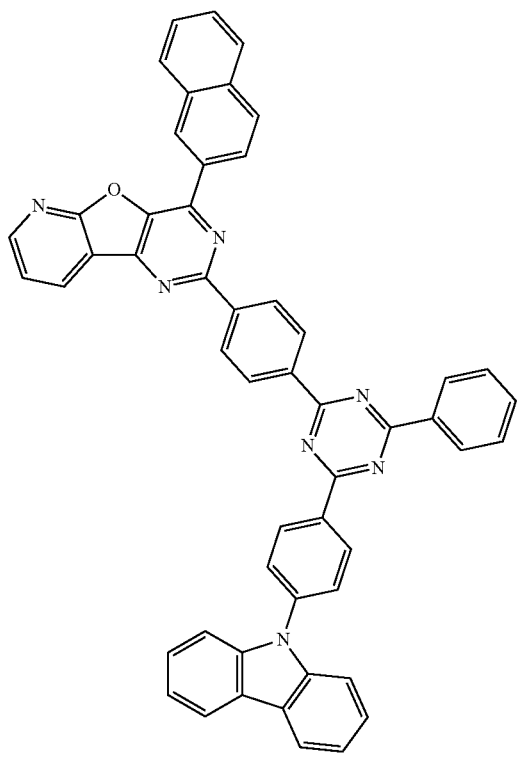

41
-continued
66
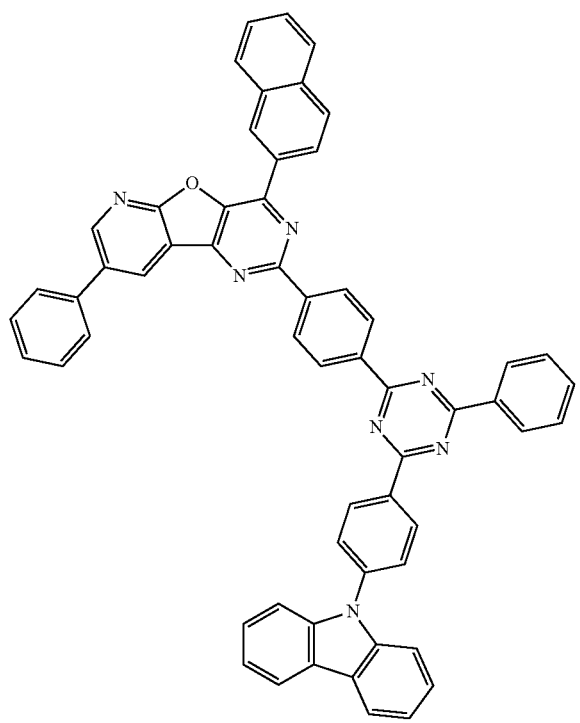
67
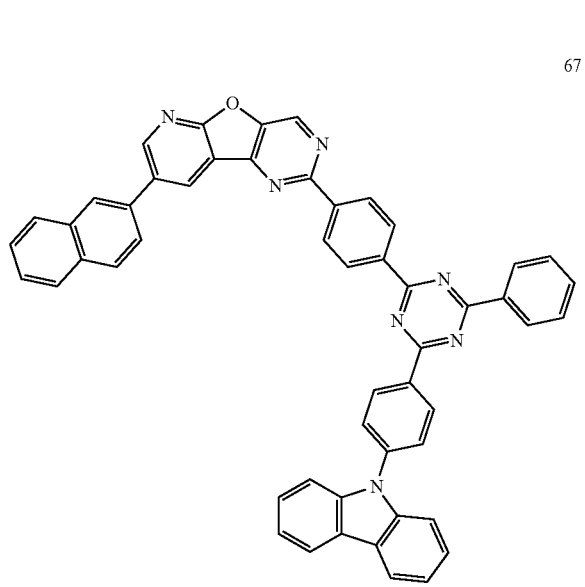
68
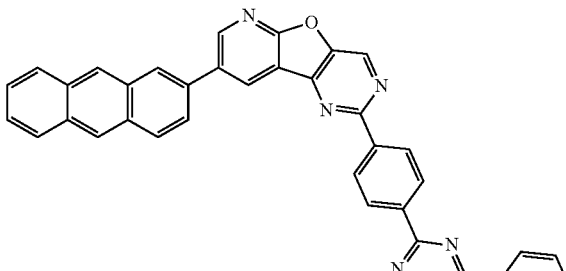
69
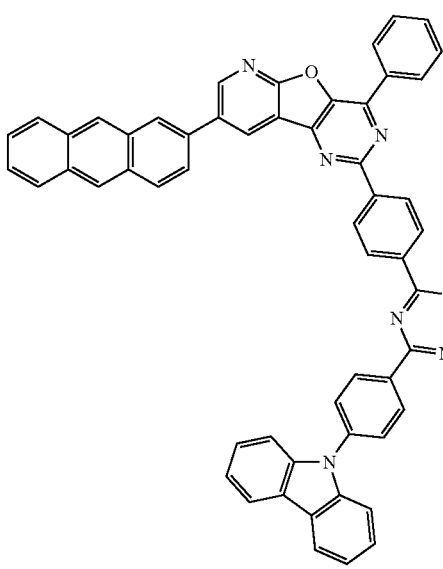
70

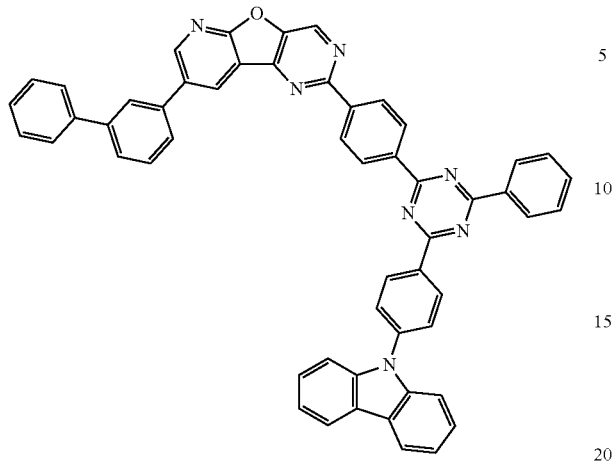
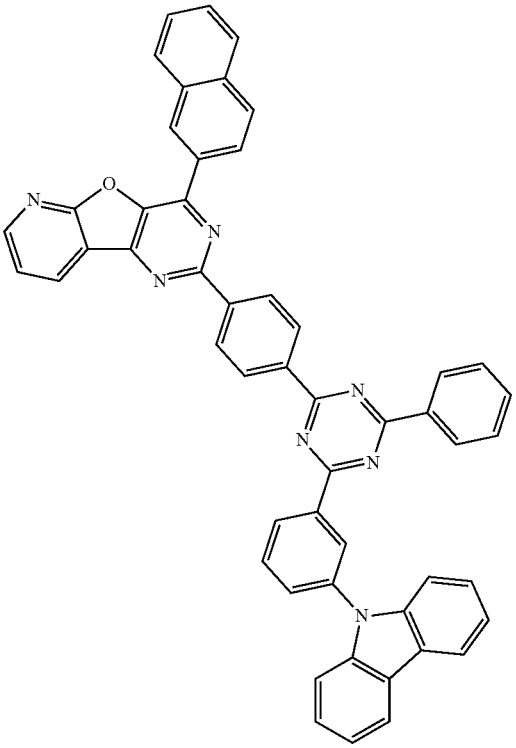
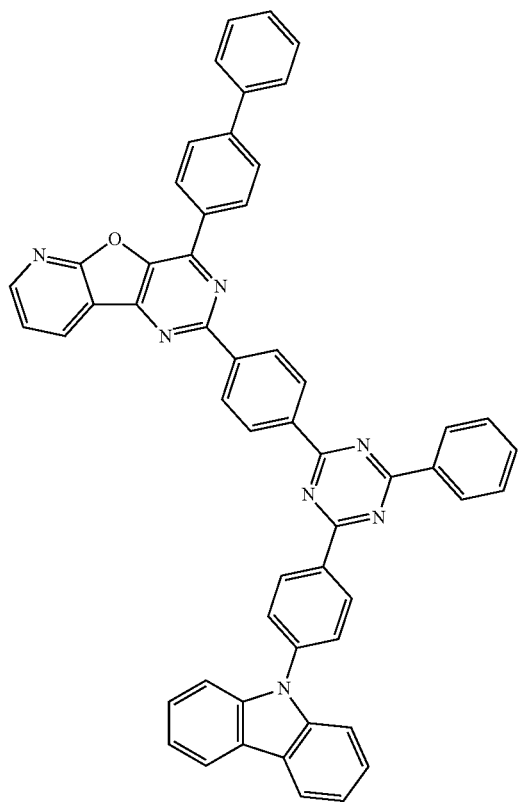
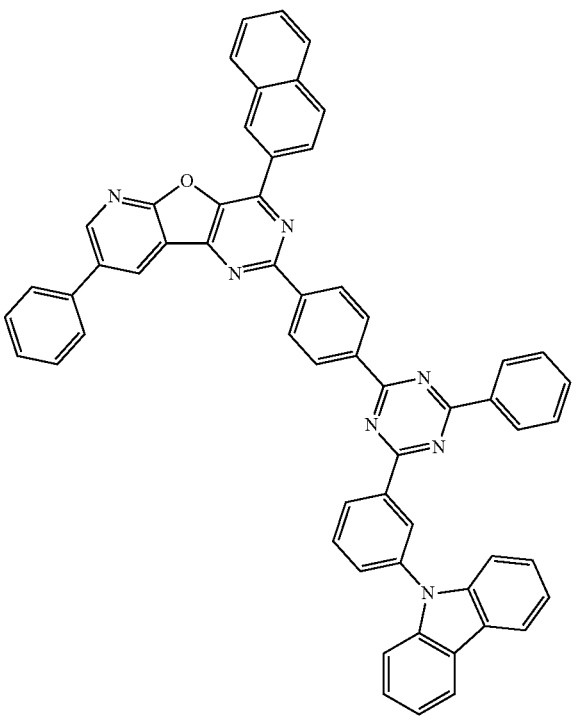

75
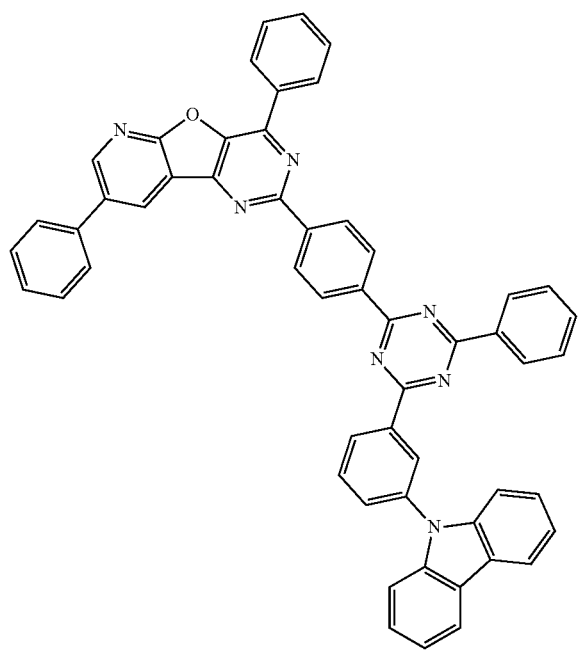
77
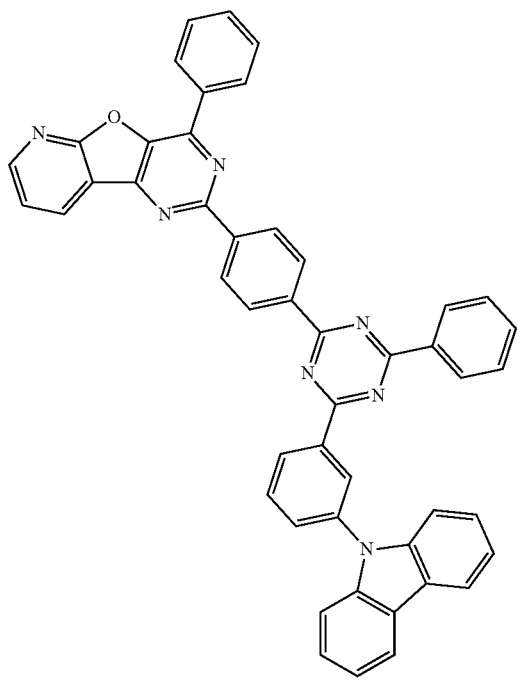
78
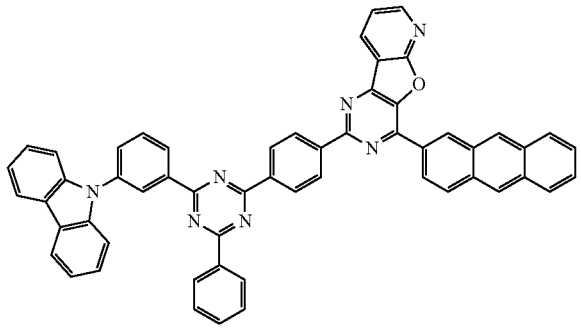
76
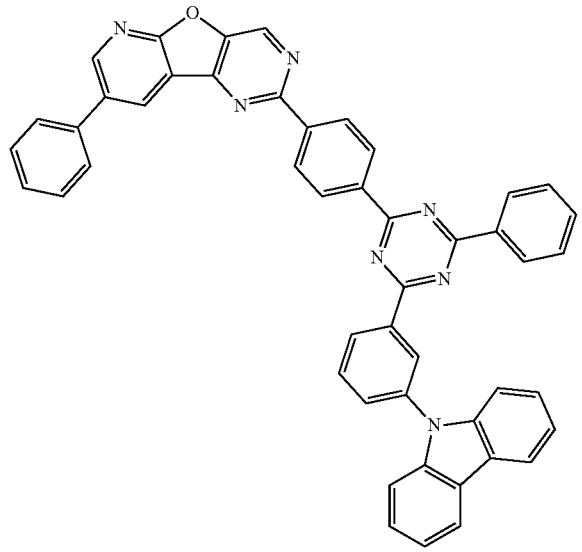
79
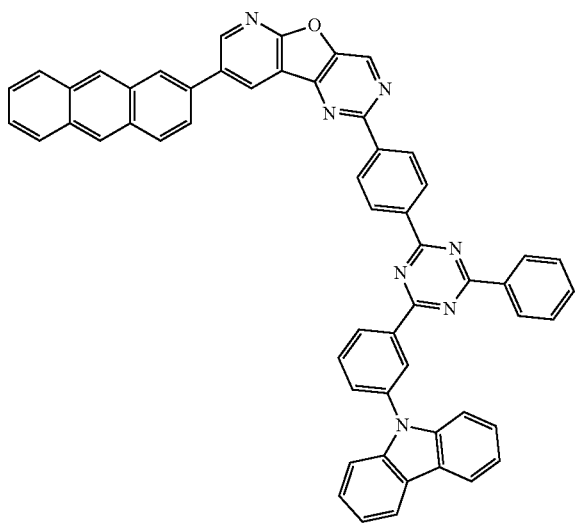

80
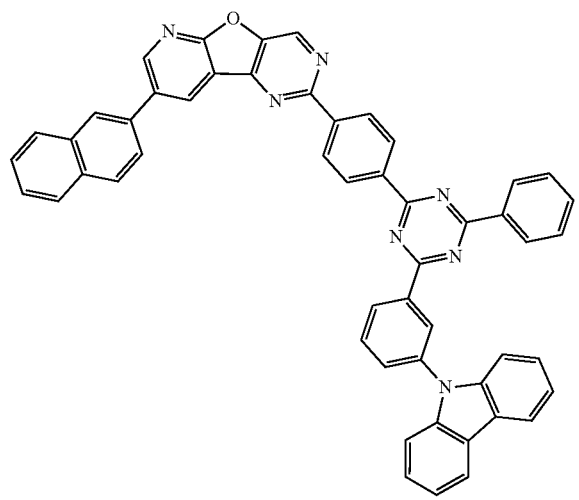
81
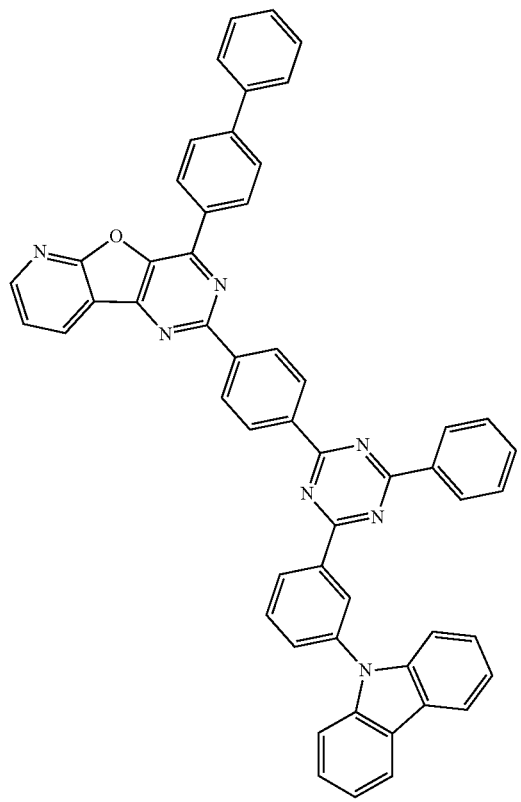
82
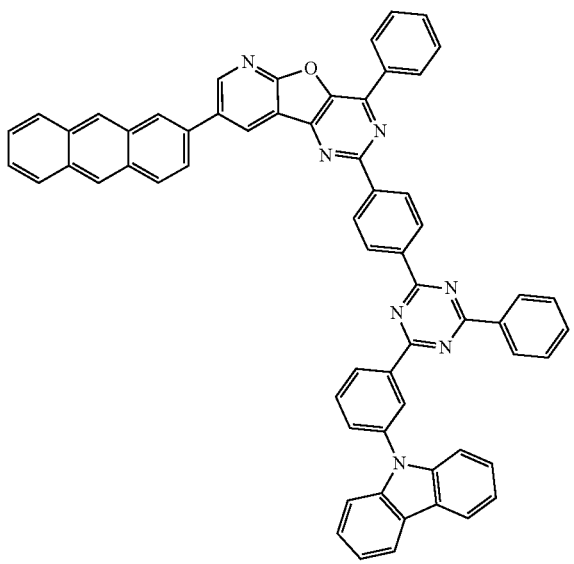
83
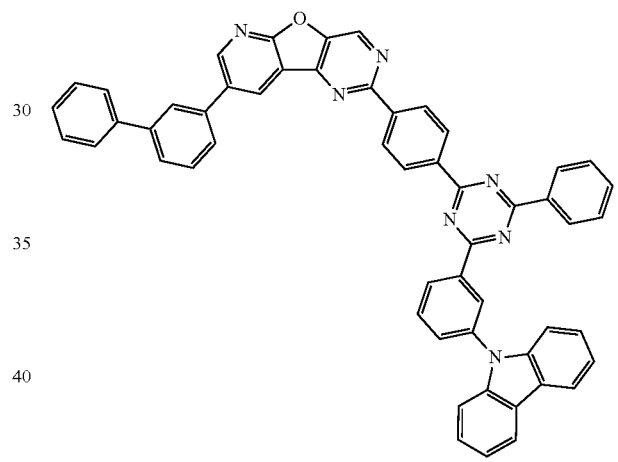
84

85
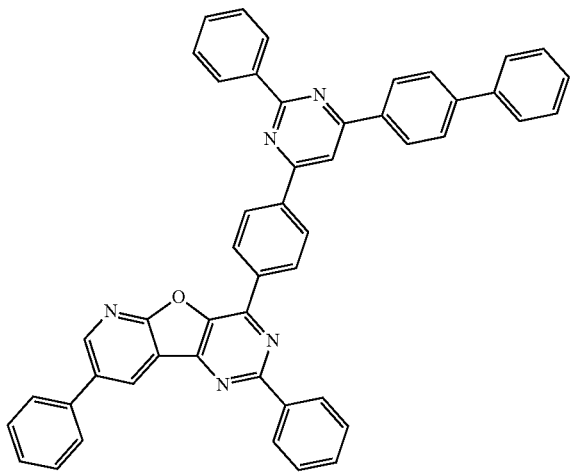
86
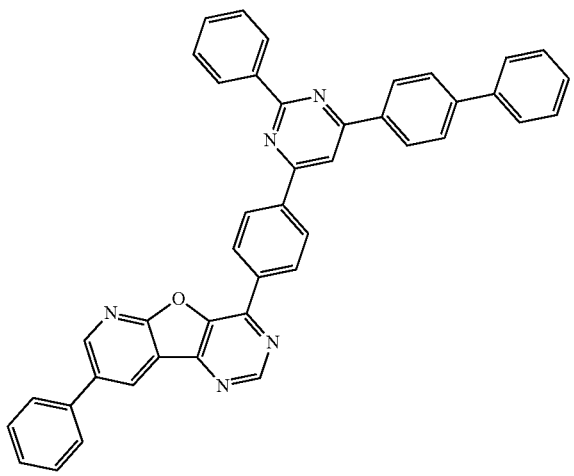
87
88
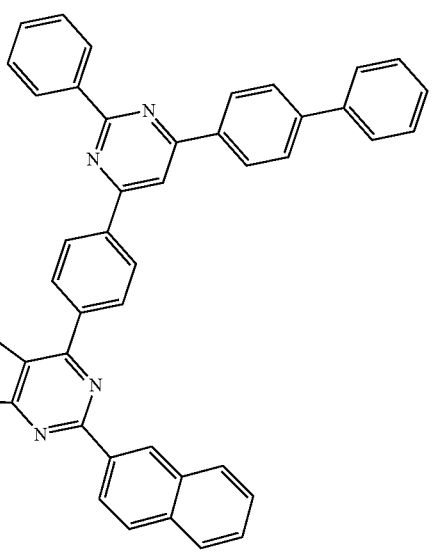
89
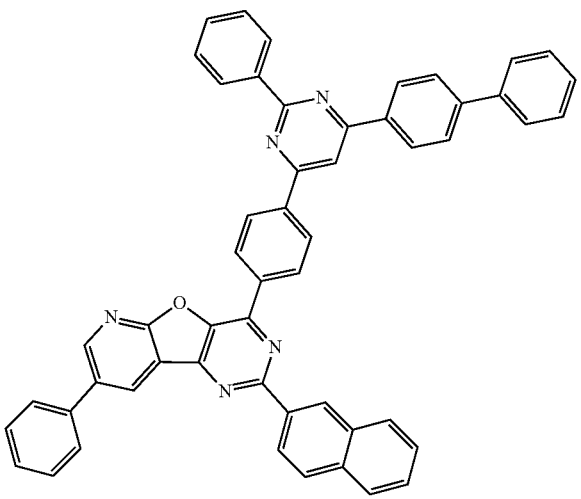
90
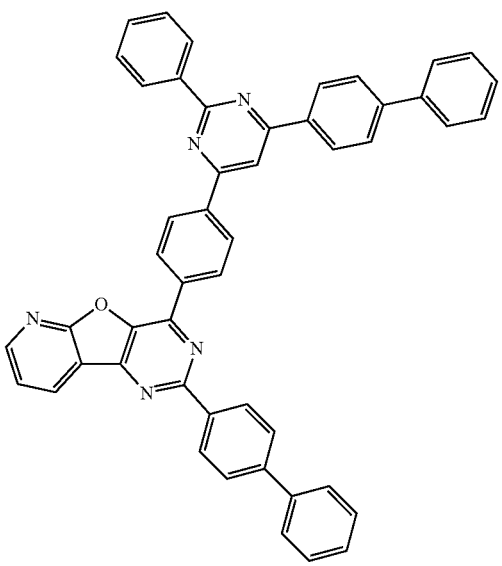

91
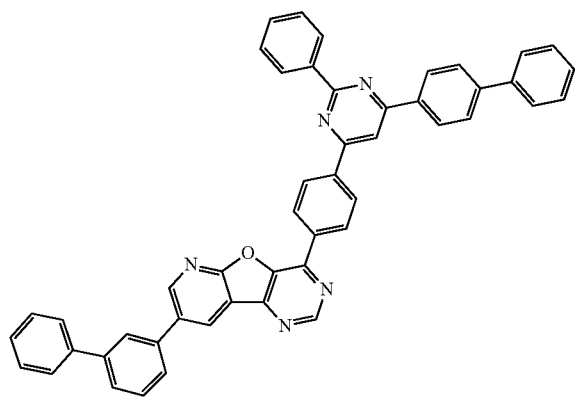
92
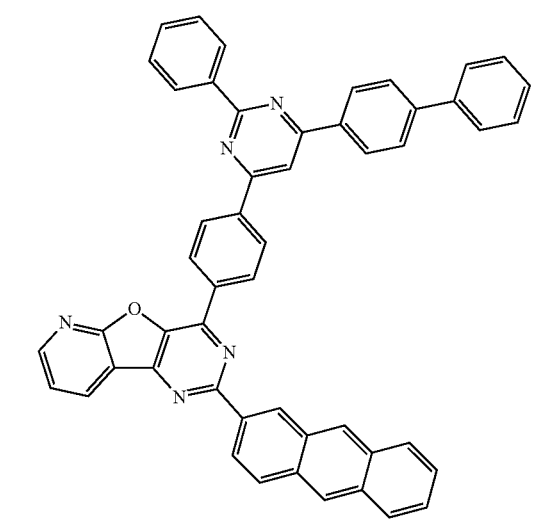
93
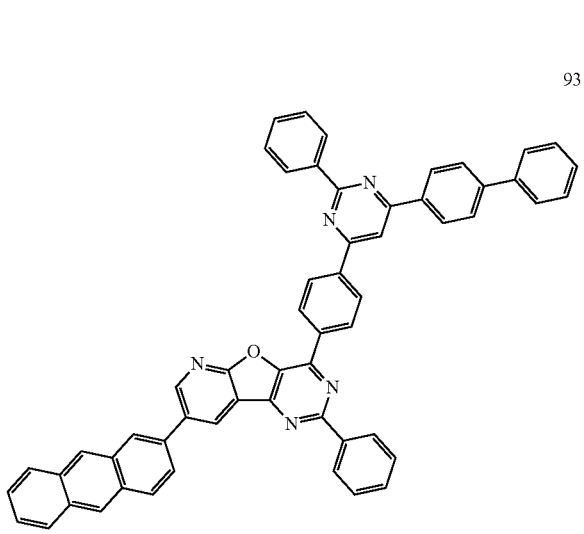
94
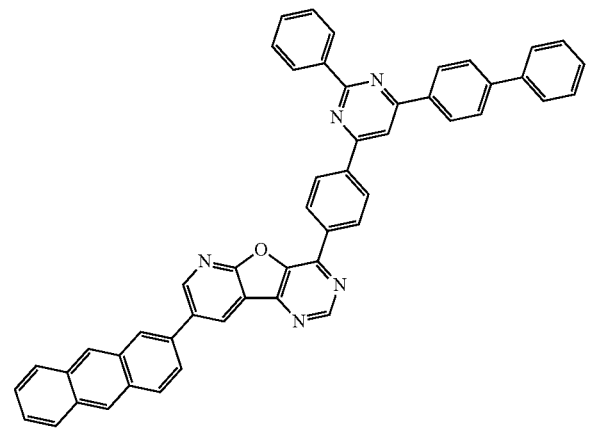
95
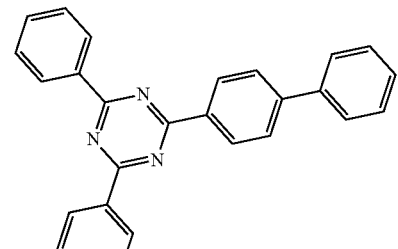
96
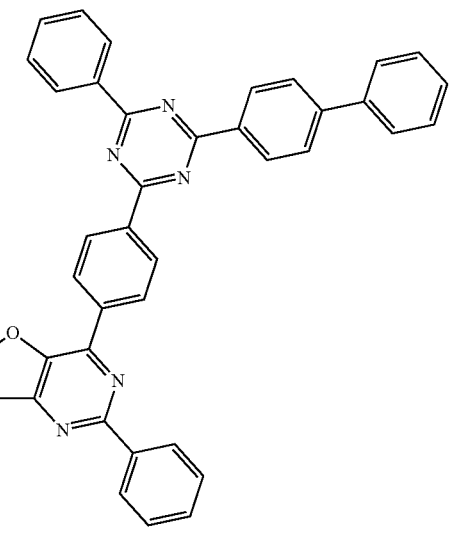

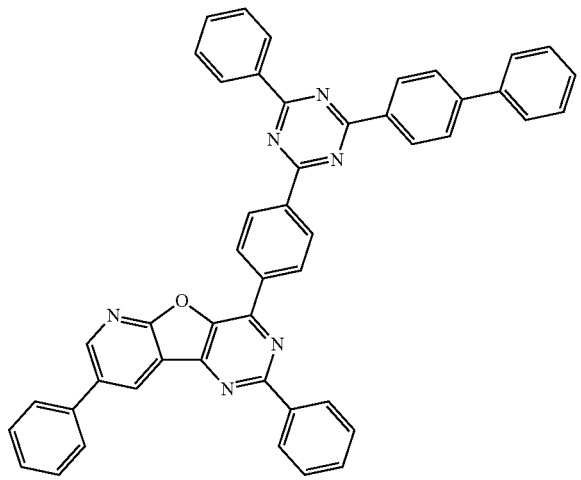
97
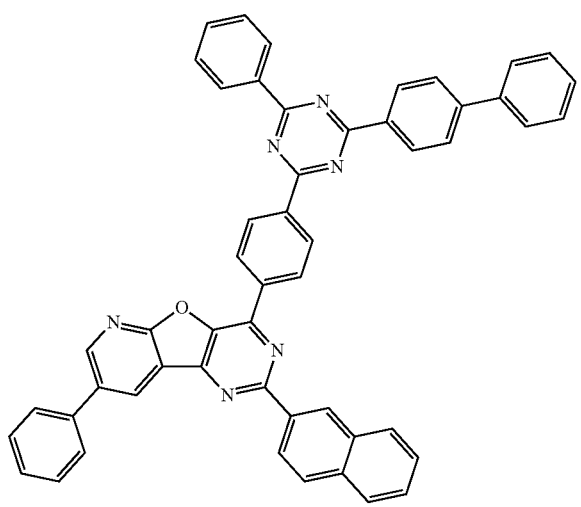
98
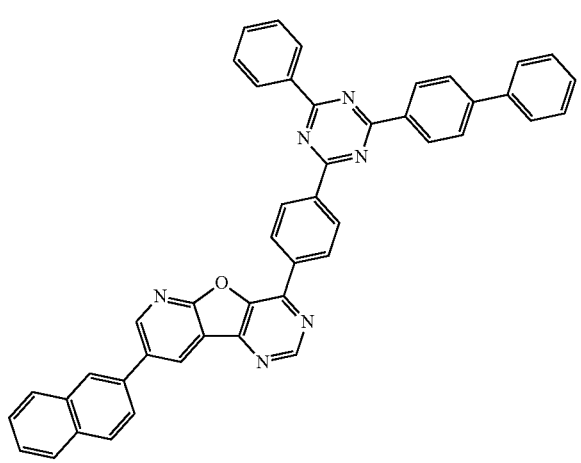
99
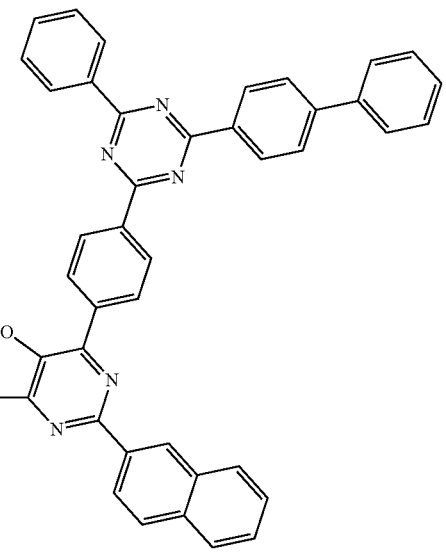
100
101
102

-continued
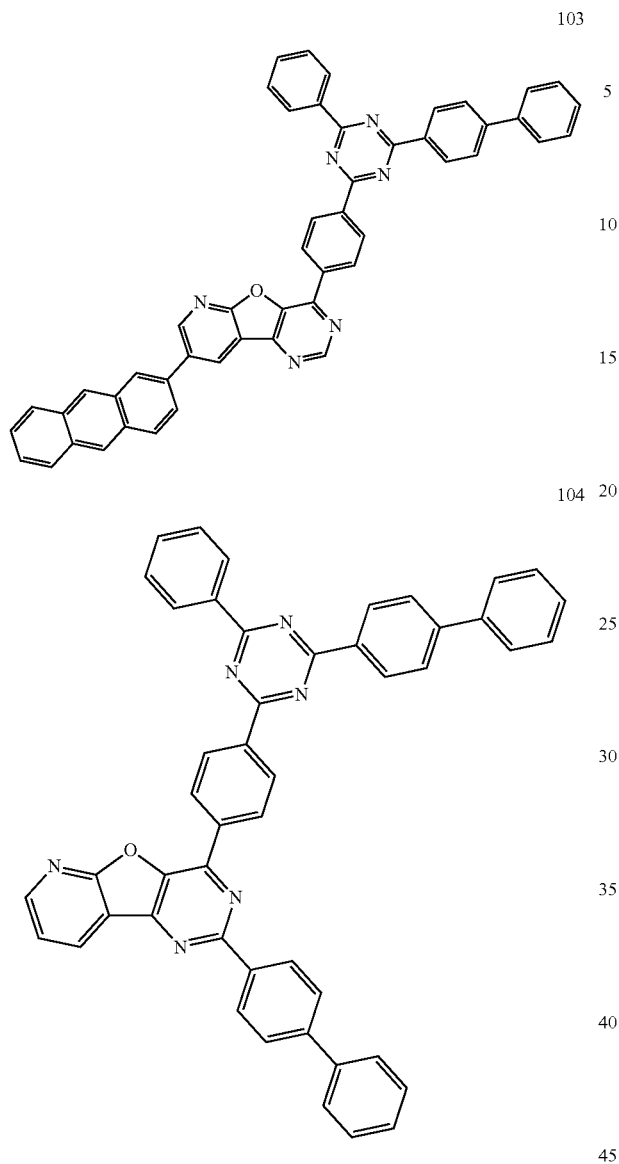
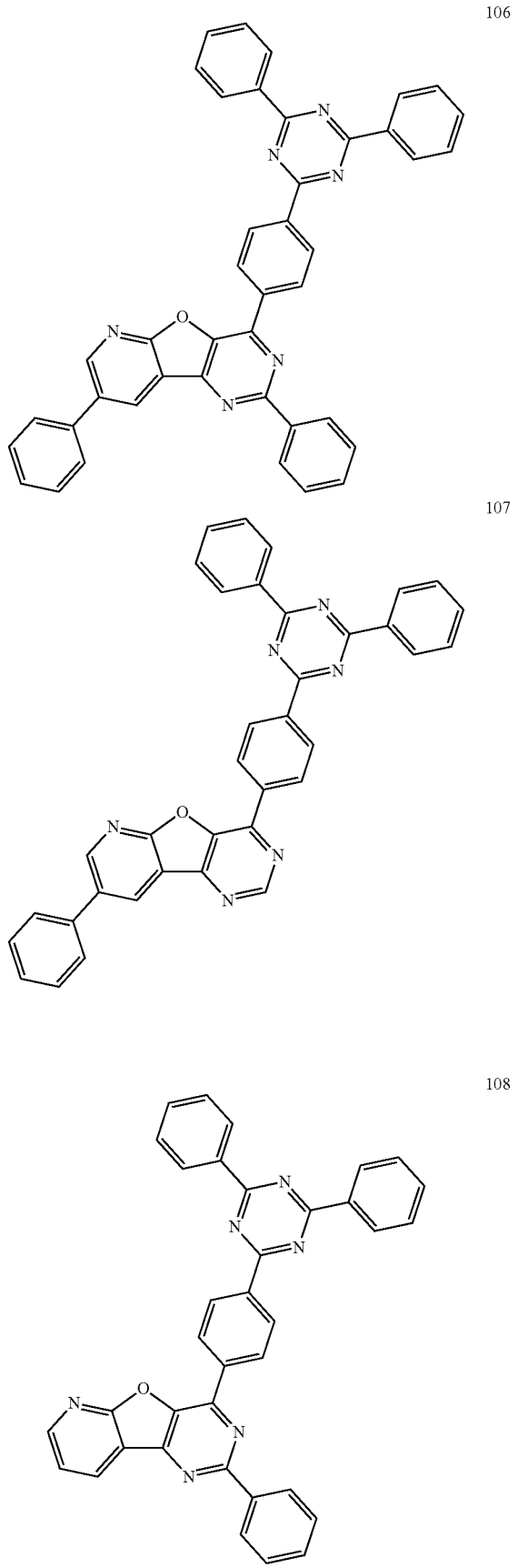

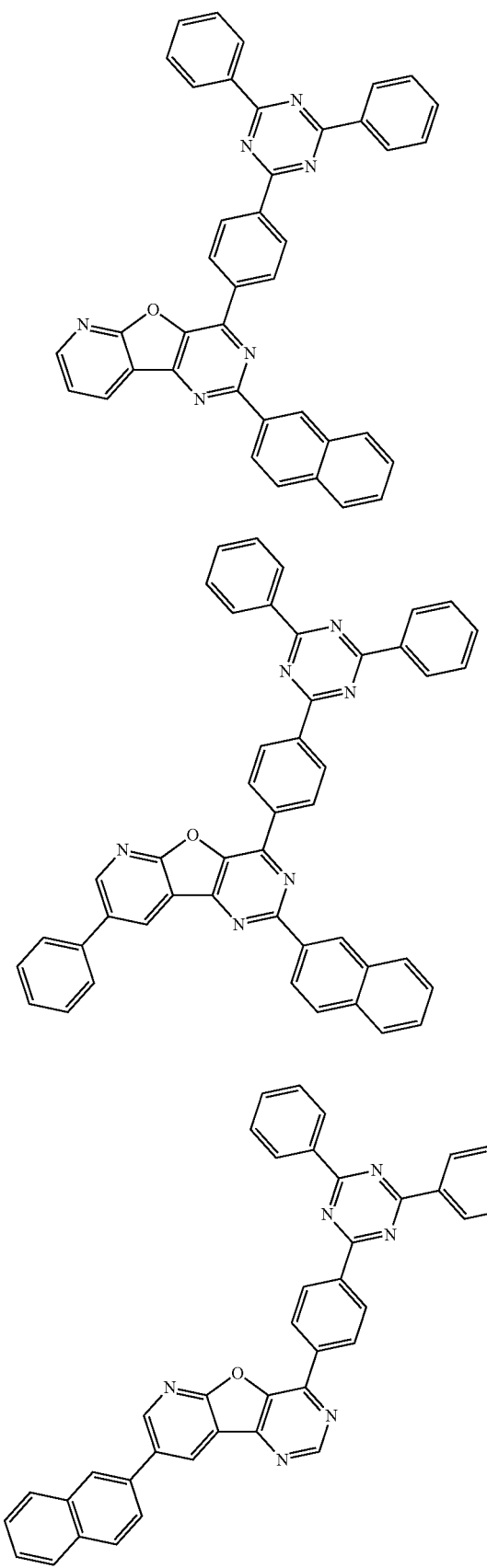
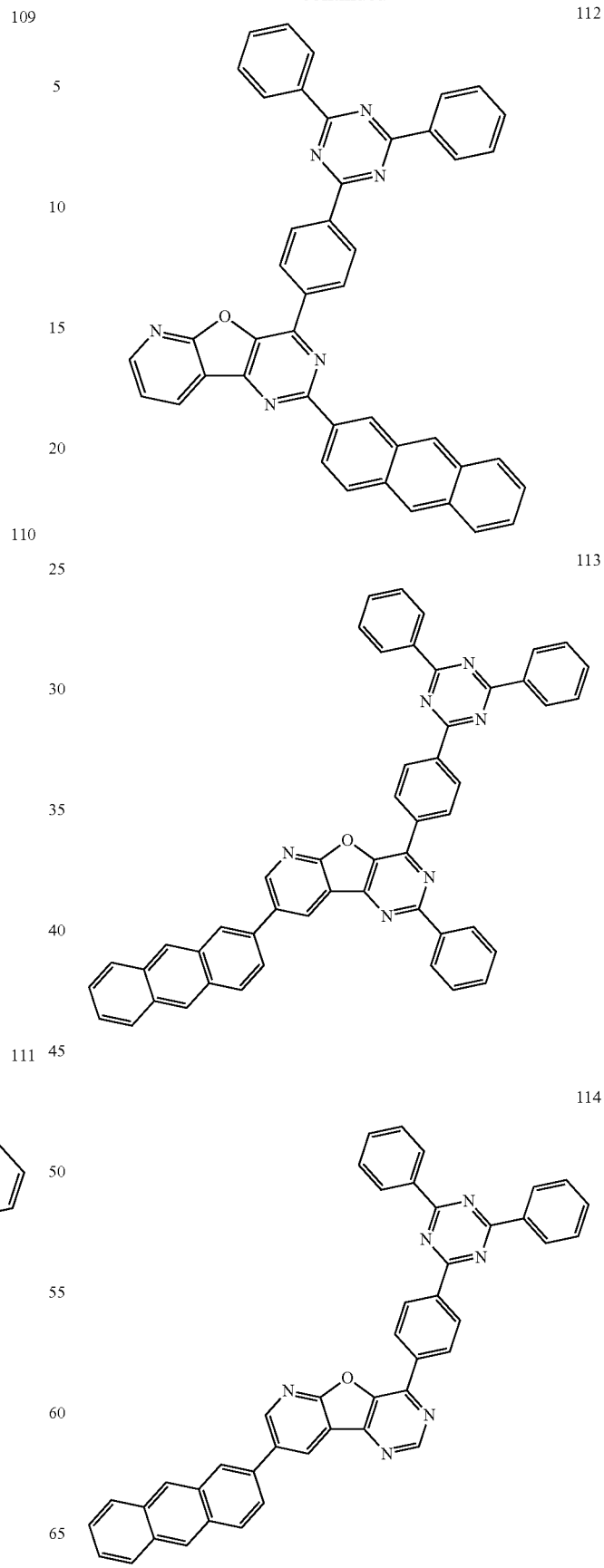

115
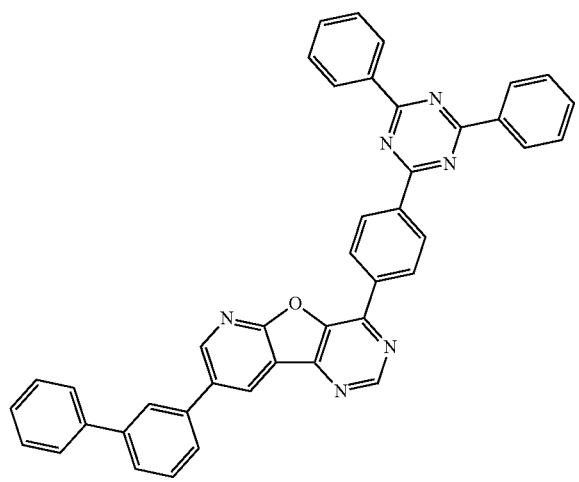
117
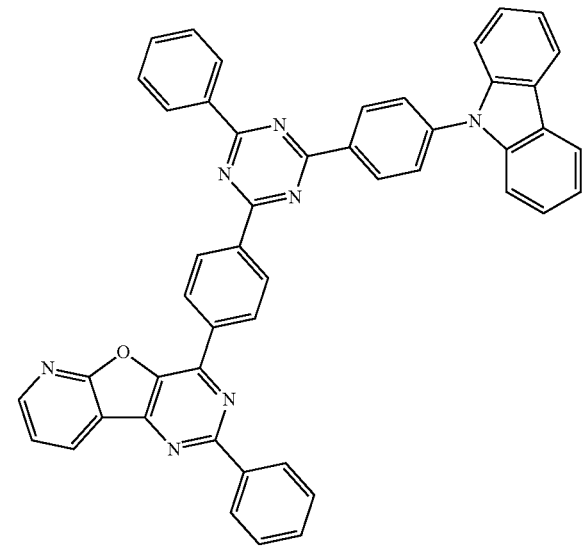
118
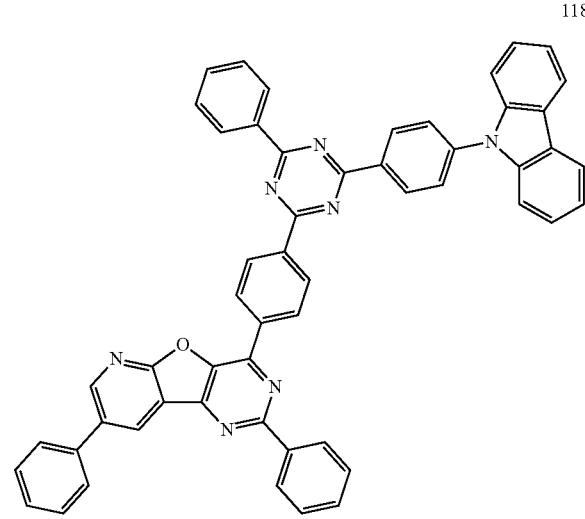
116
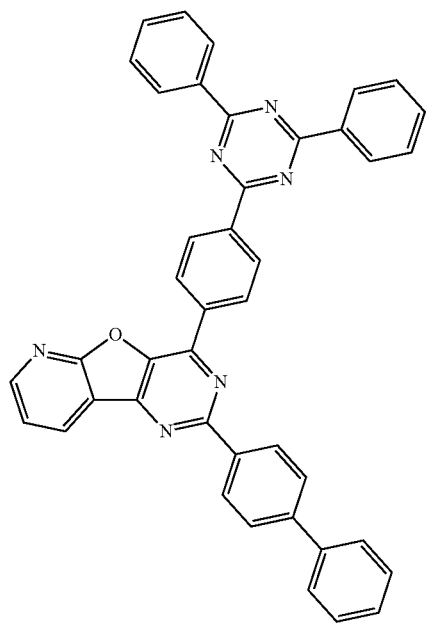
119
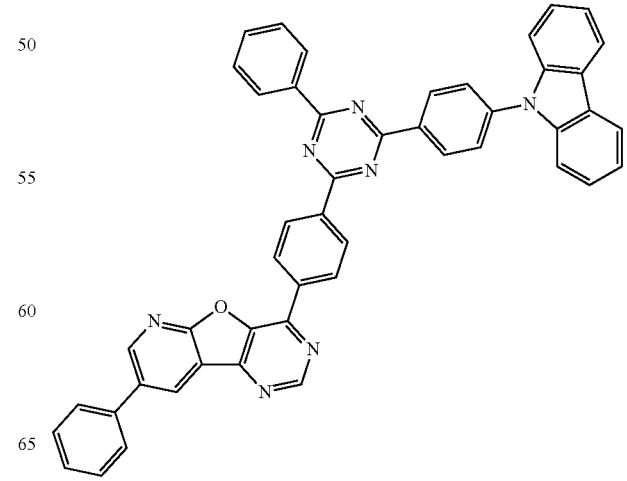

-continued
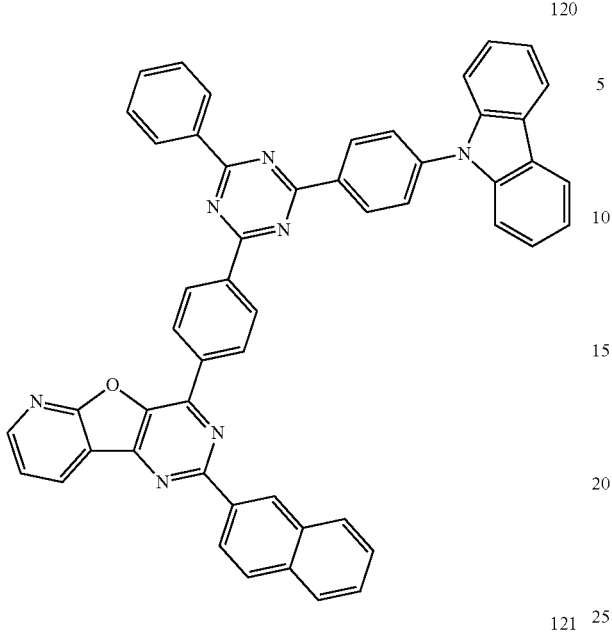
120
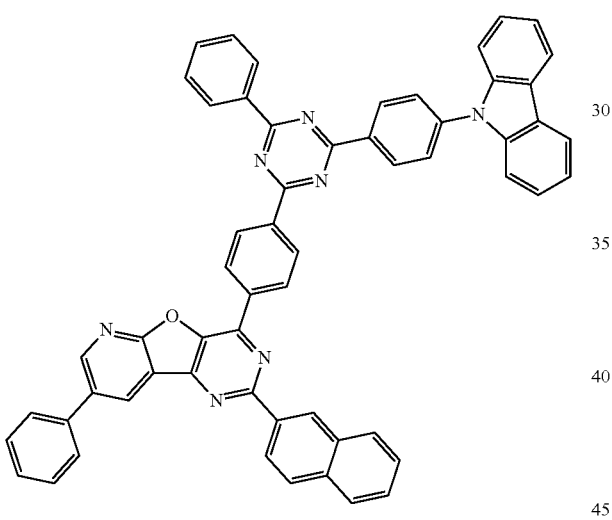
121
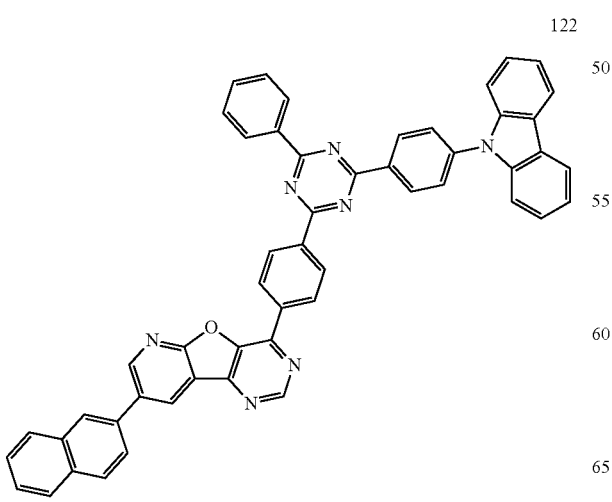
122
-continued
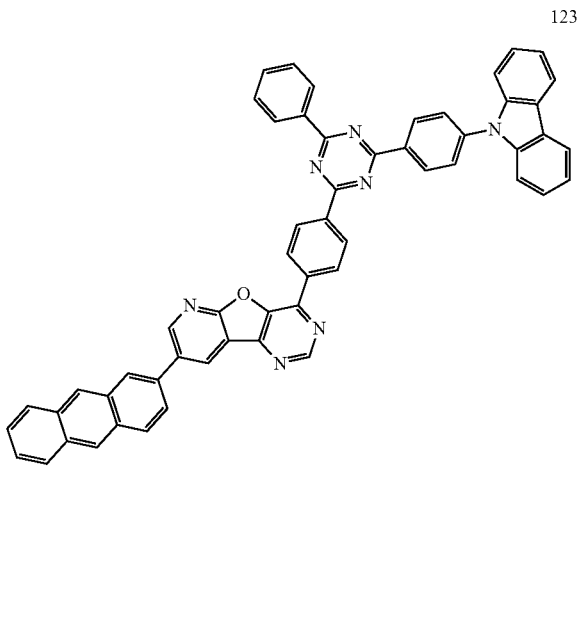
123
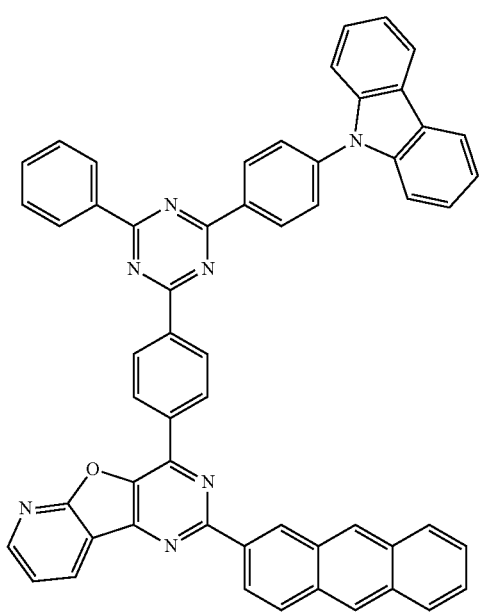
124

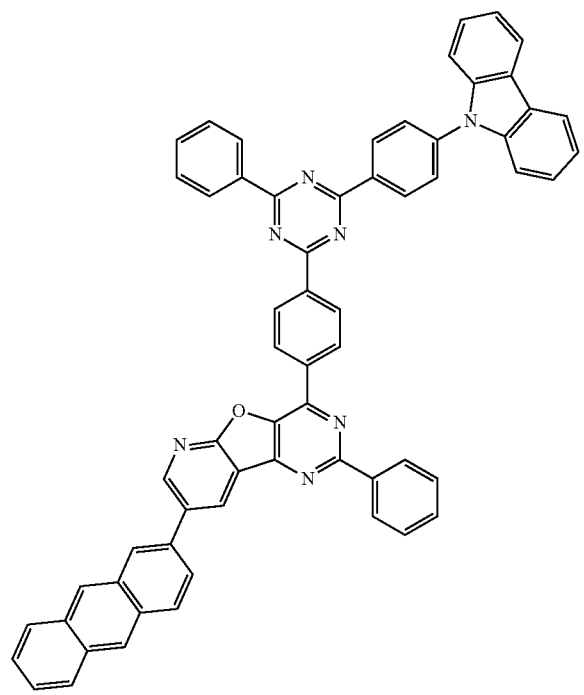
125
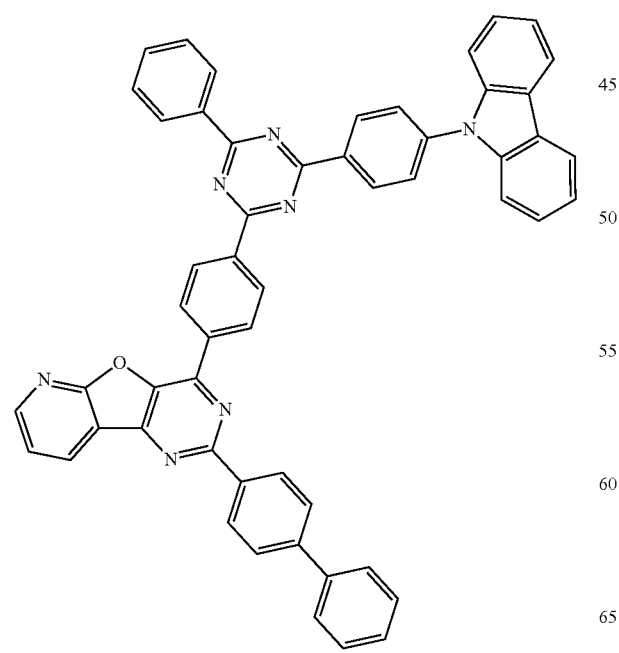
126
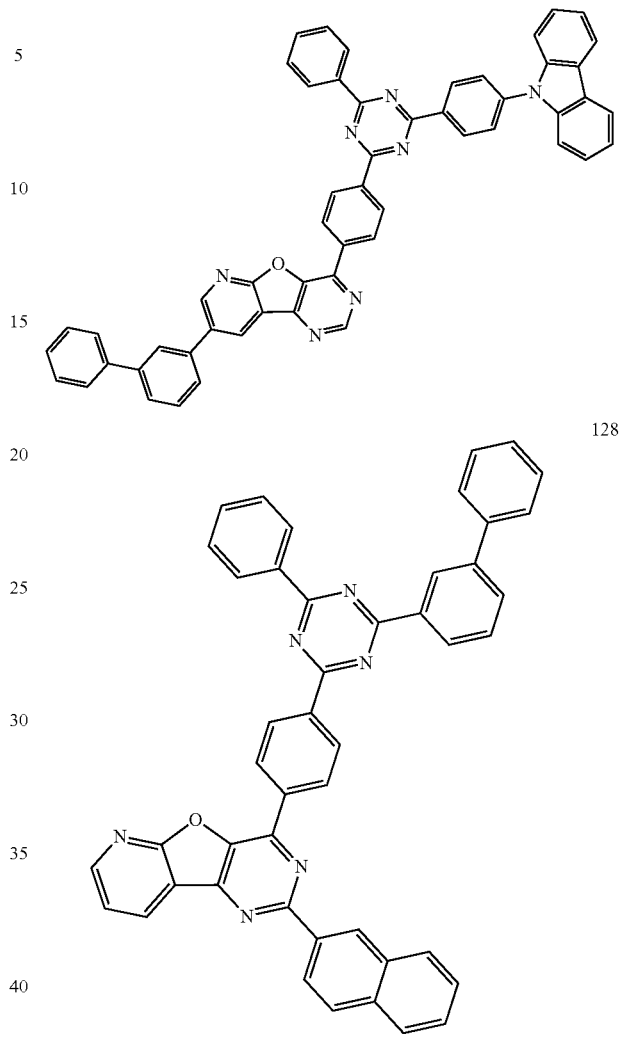
127
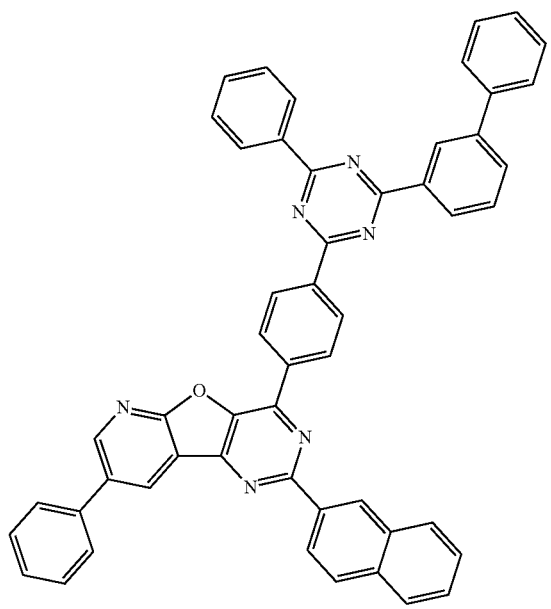
128
129

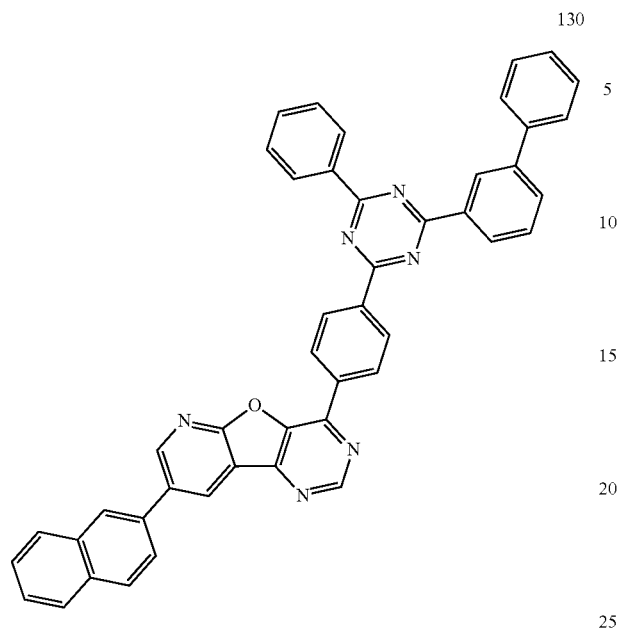
130
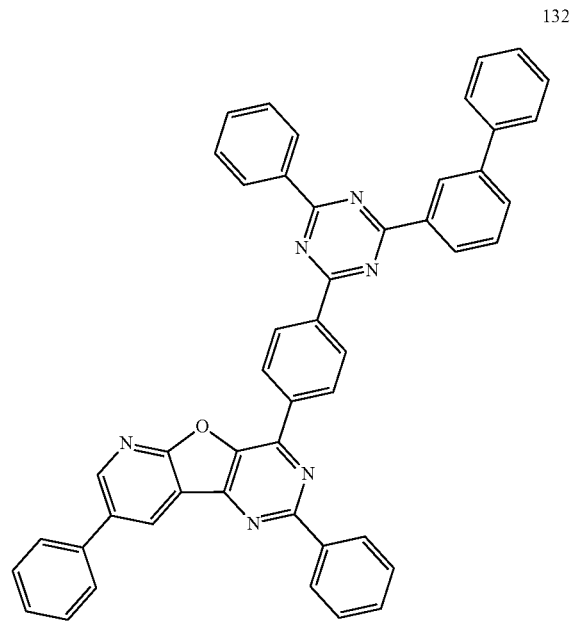
132
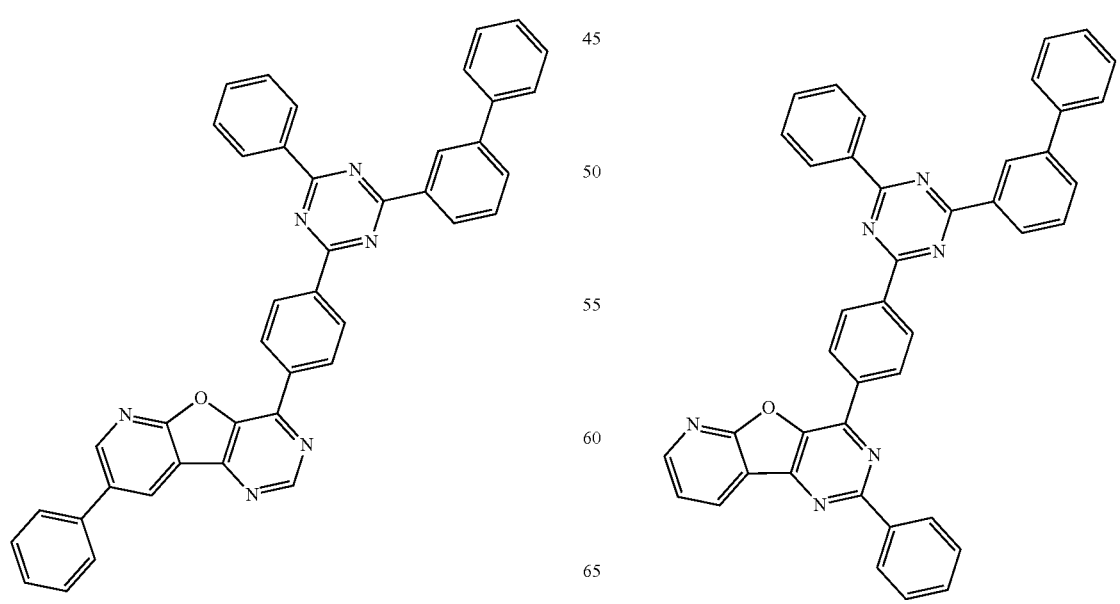
131
133

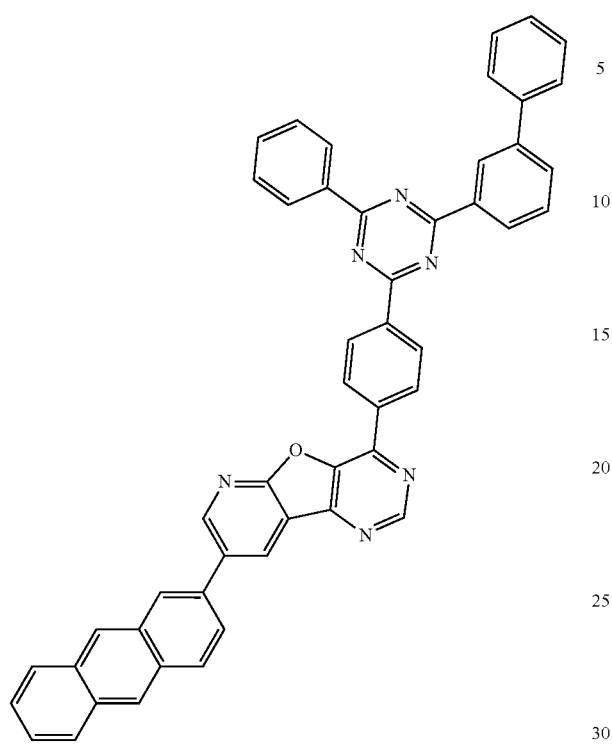
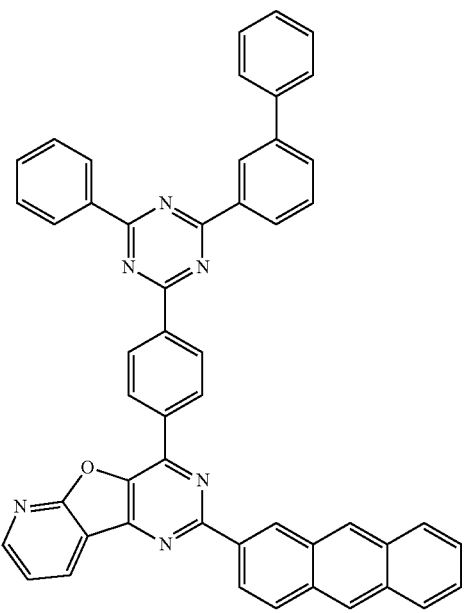
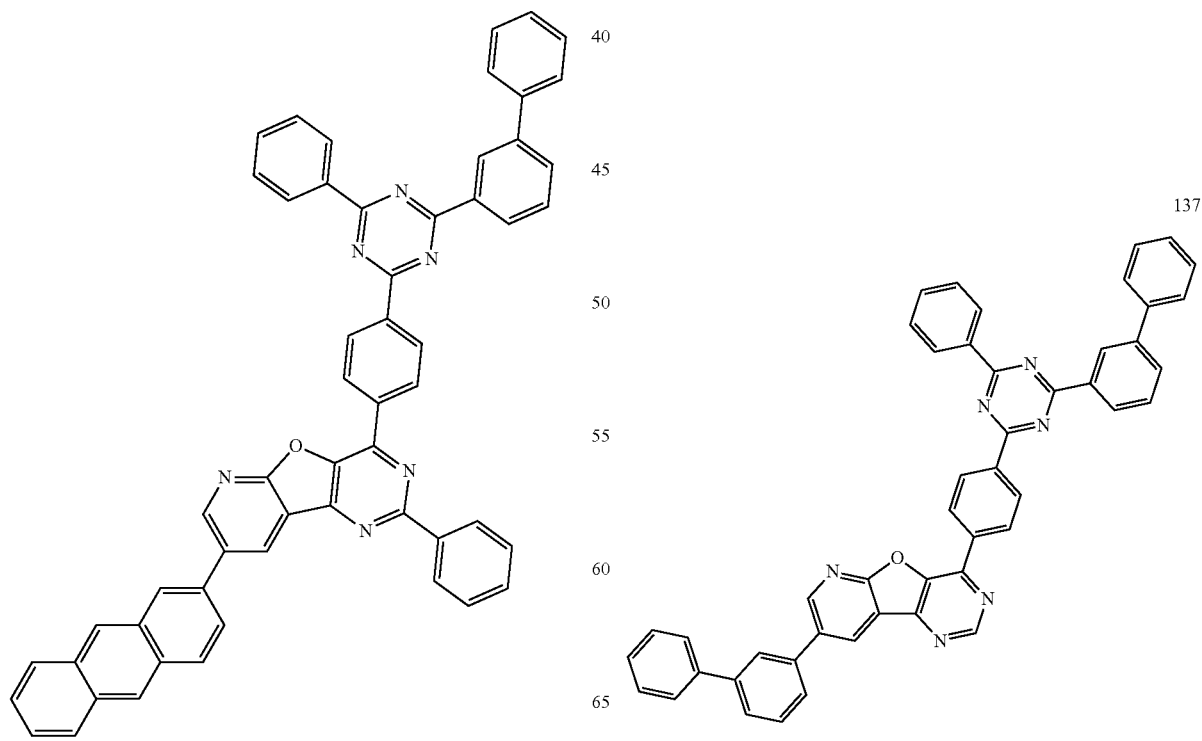

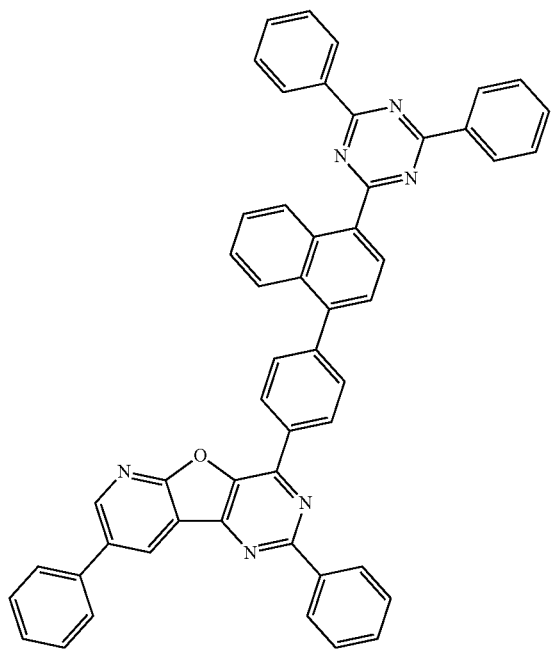
138
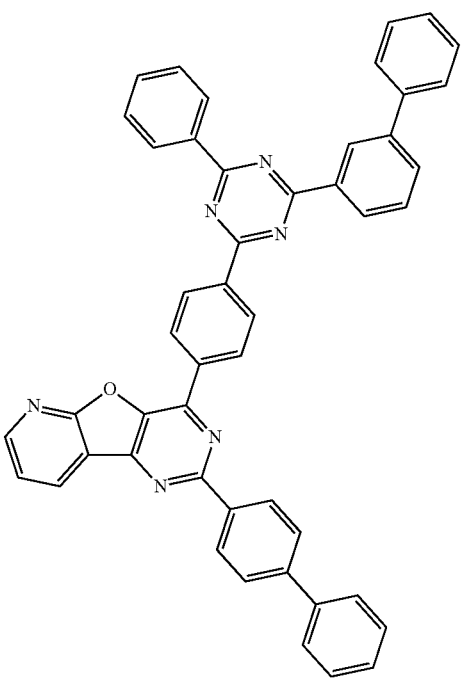
140
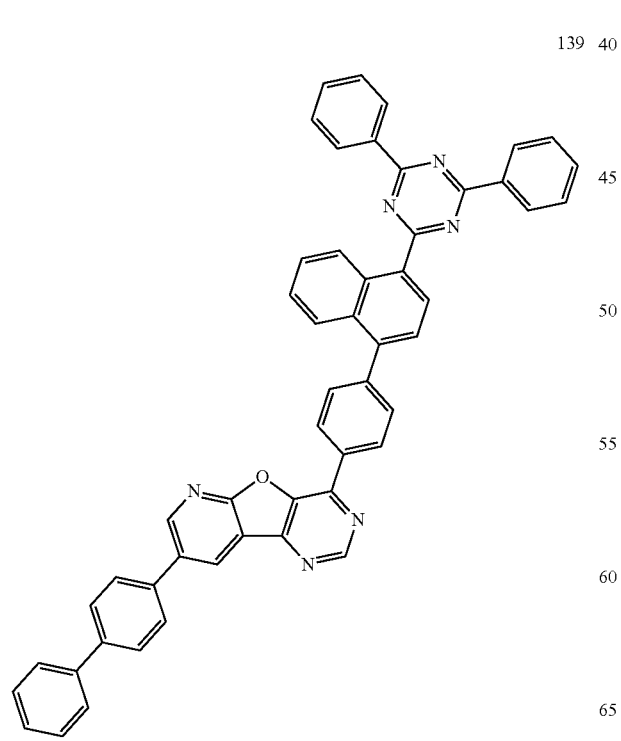
139
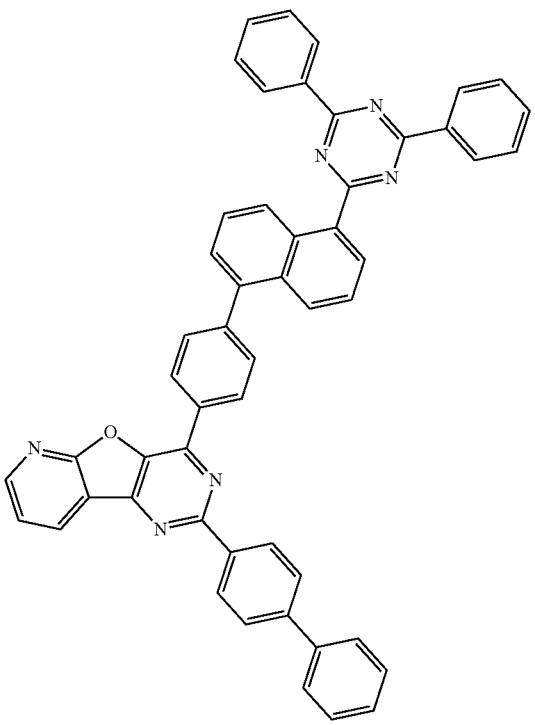
141

142
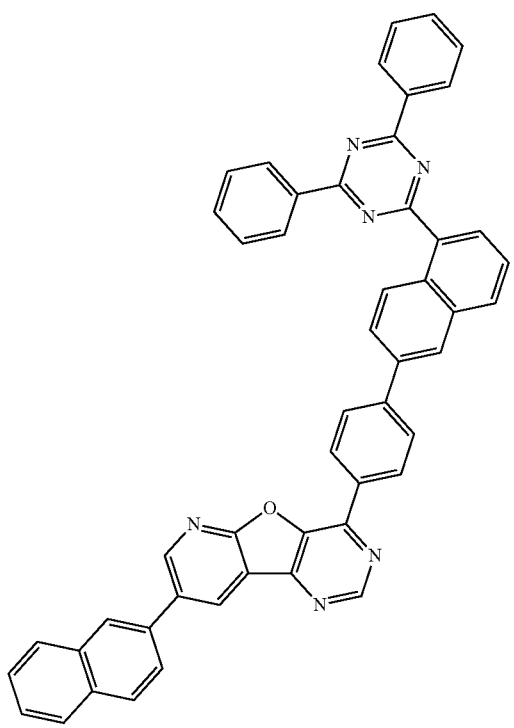
144
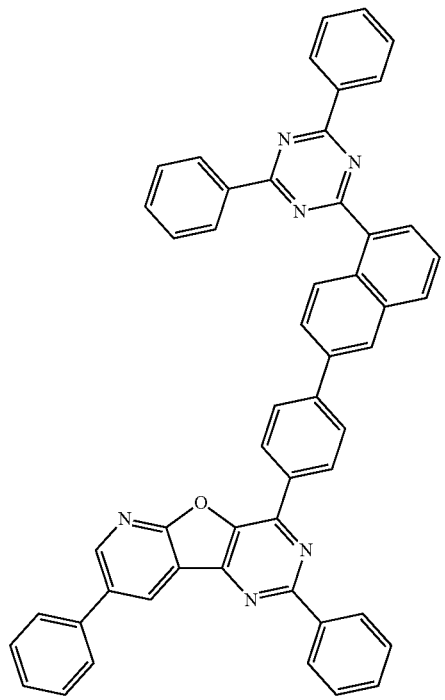
143
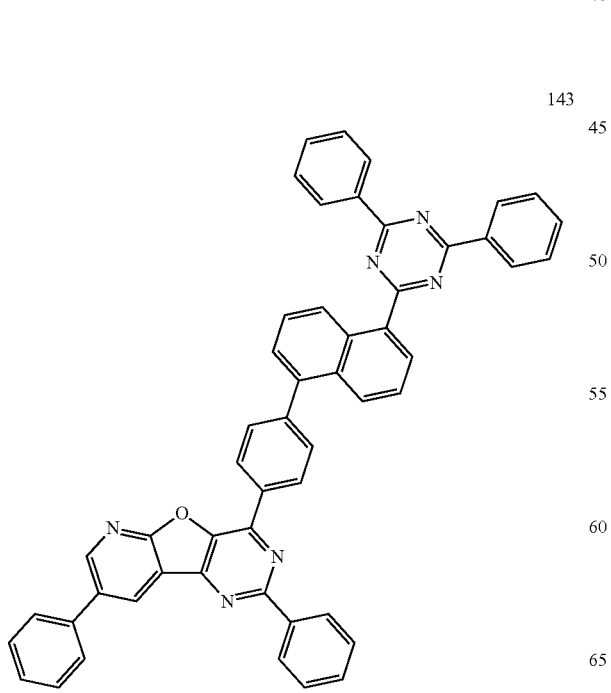
145
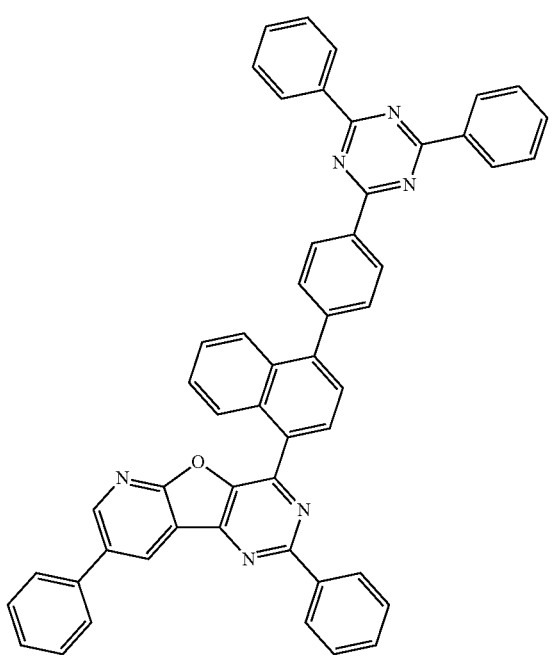

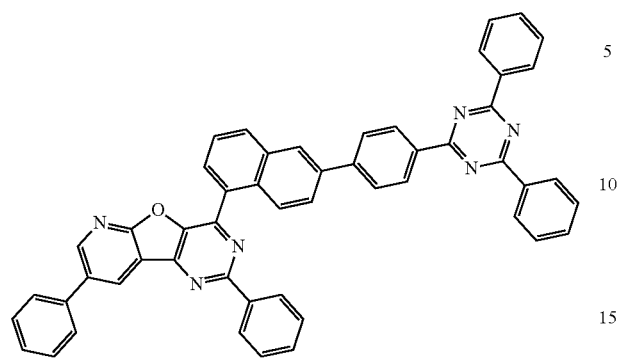
146
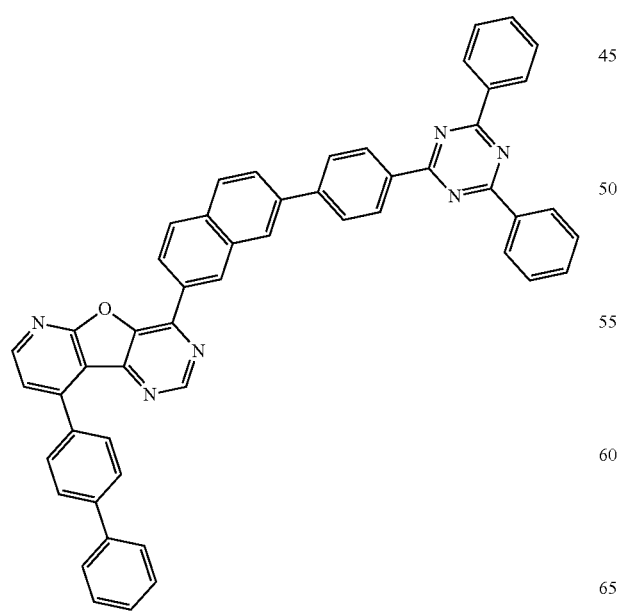
147
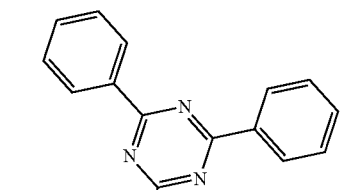
148
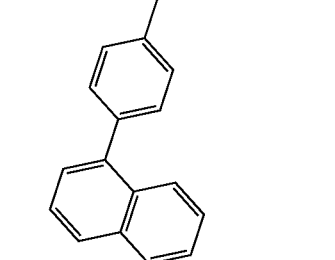
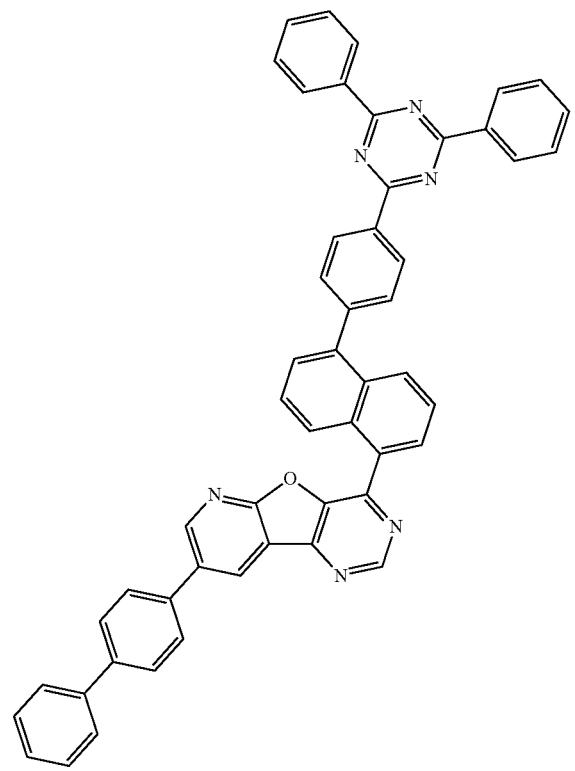
149

150
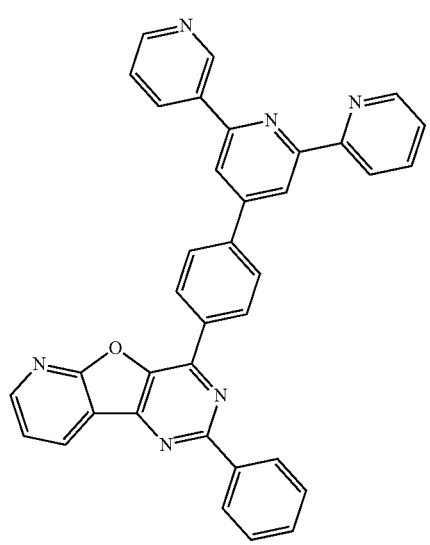
151
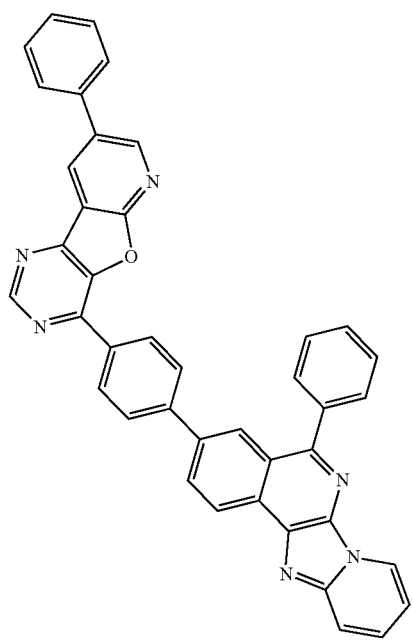
152
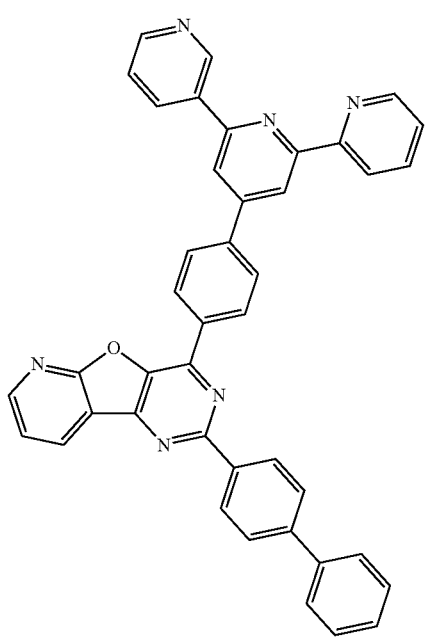
153
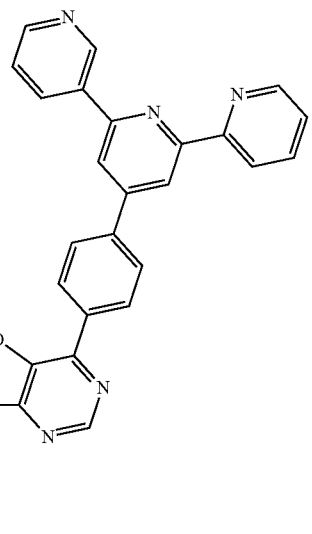

154
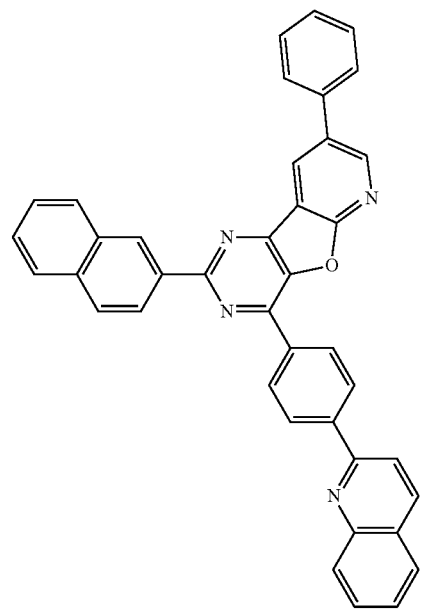
155
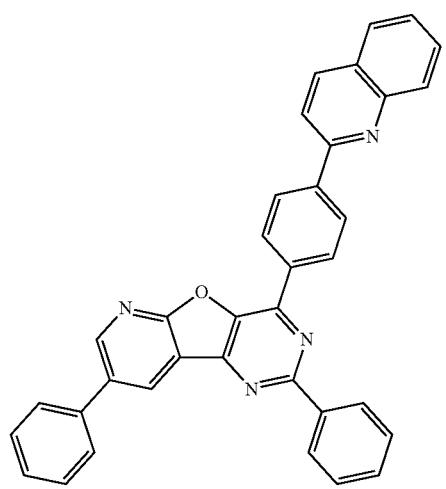
156
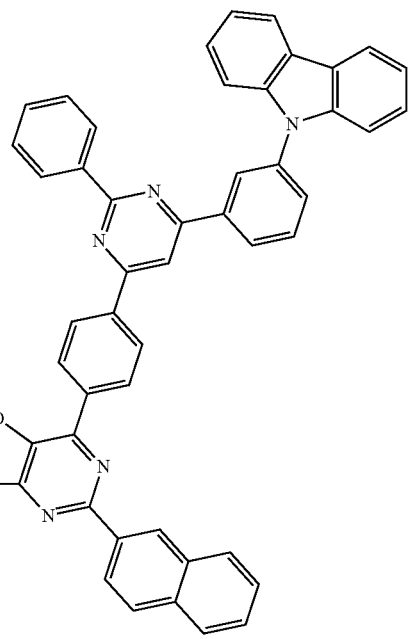
157
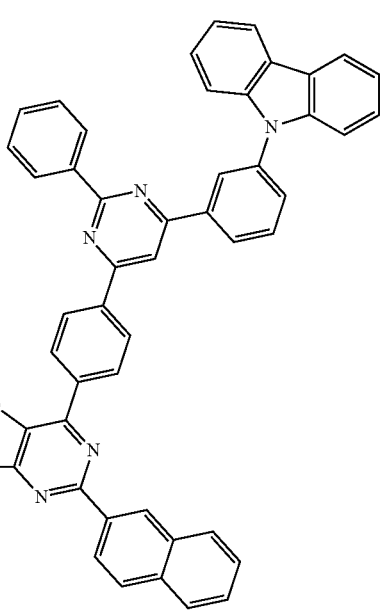

158
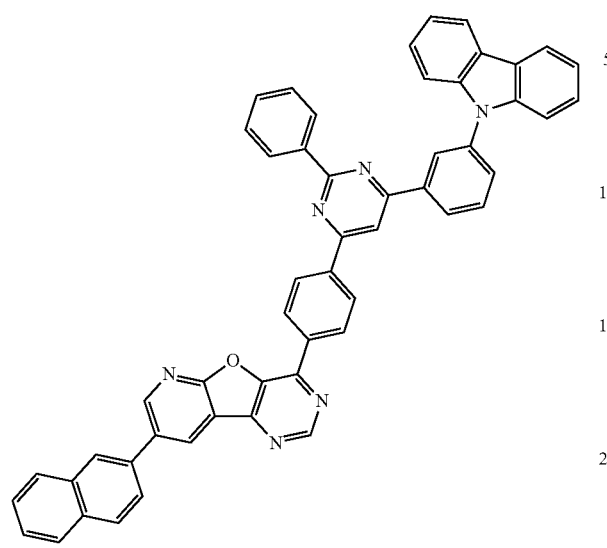
159
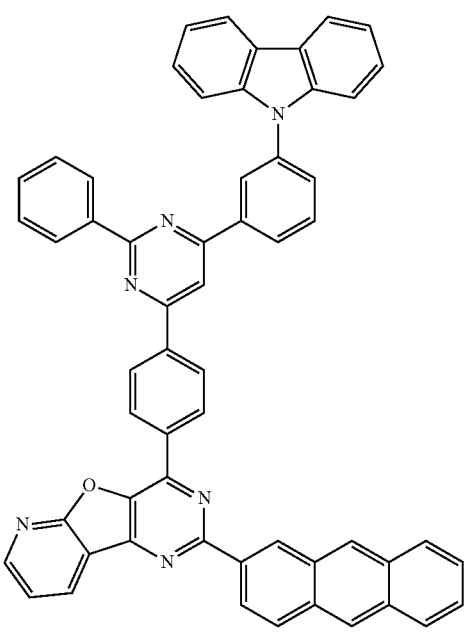
160
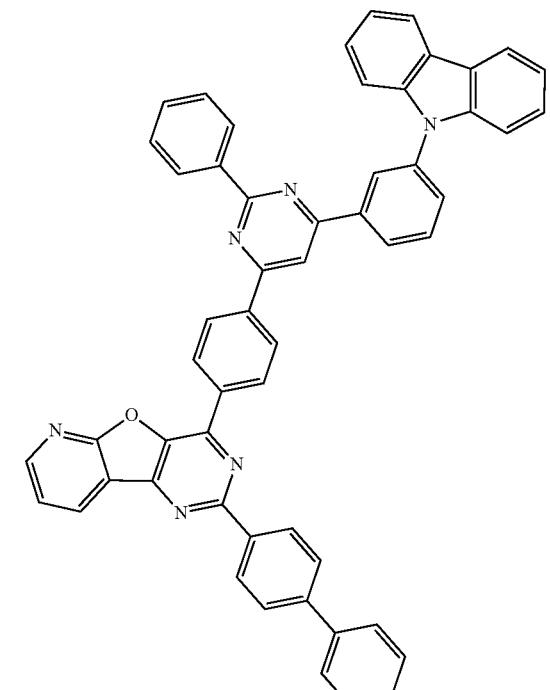
161
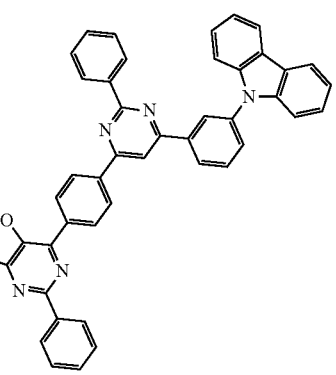
162

163
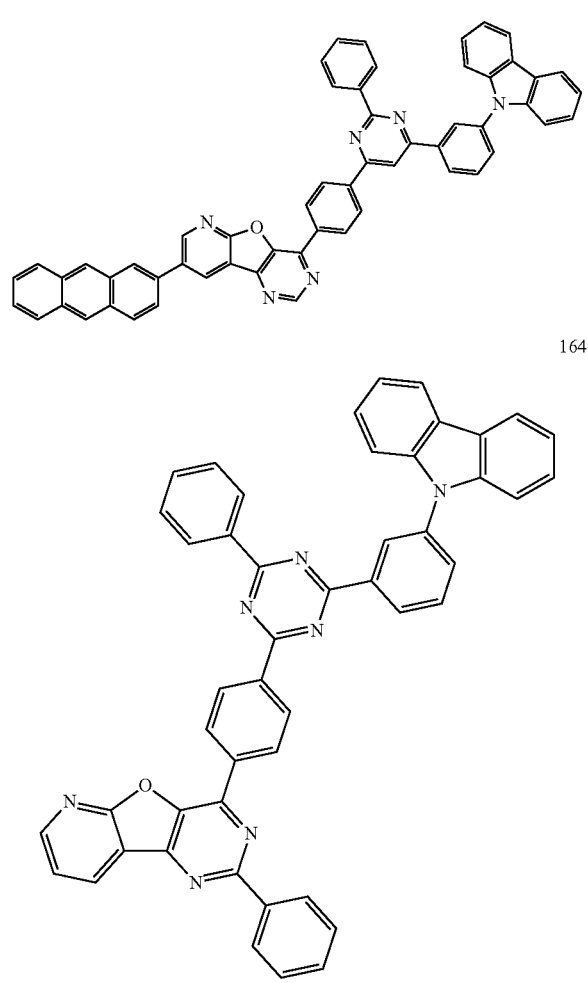
164
165
166
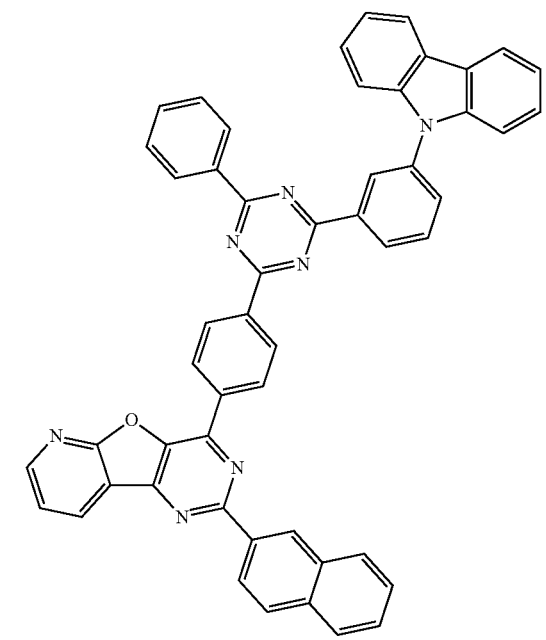
167
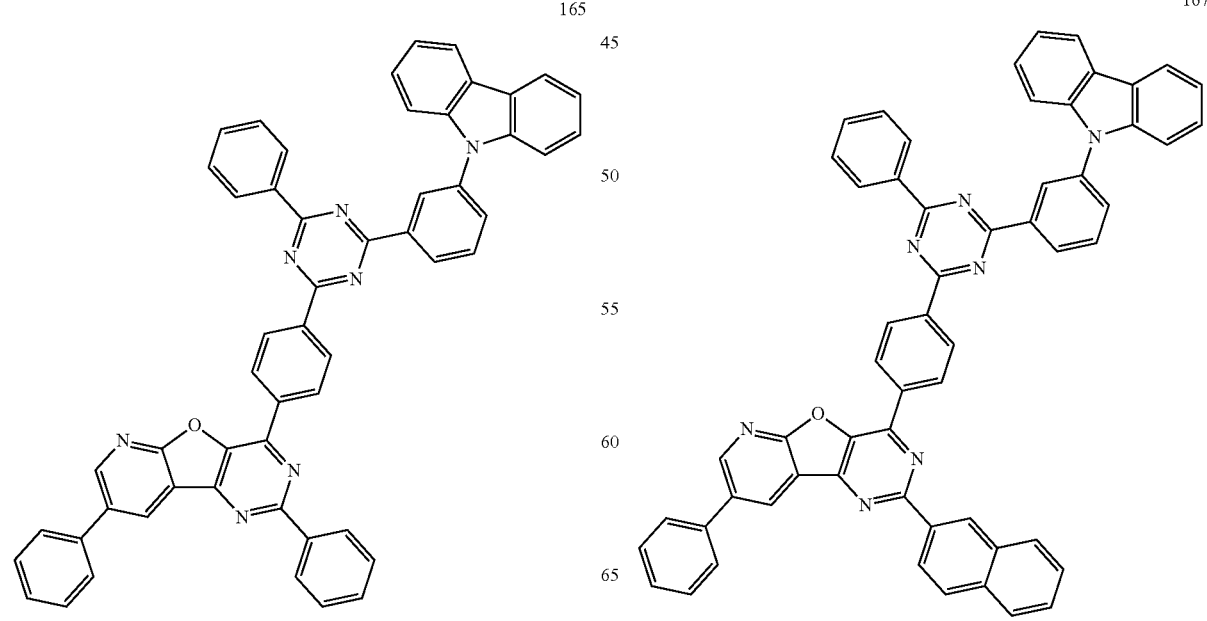

168
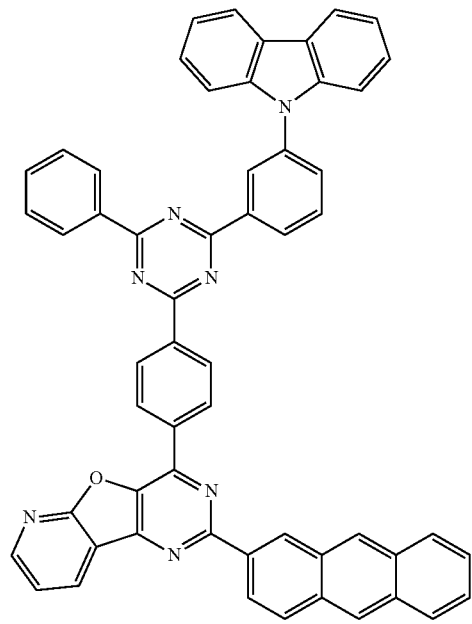
169
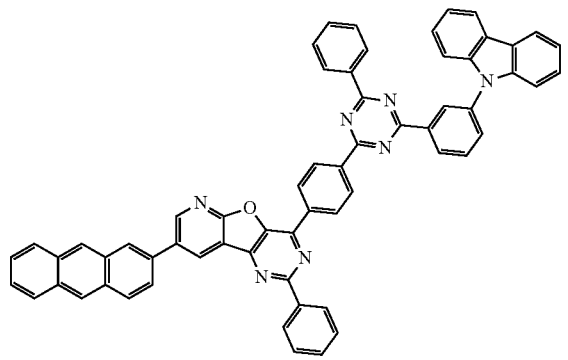
170
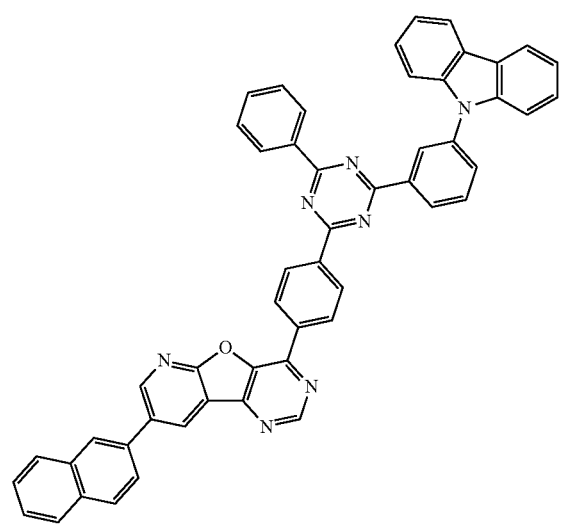
171
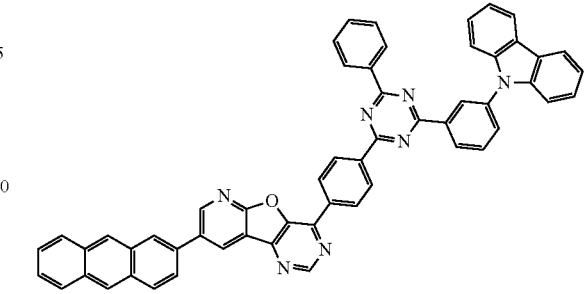
172
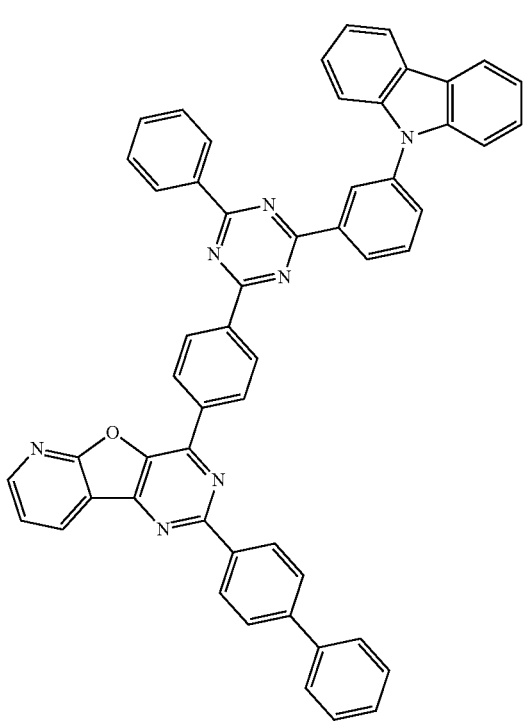
173
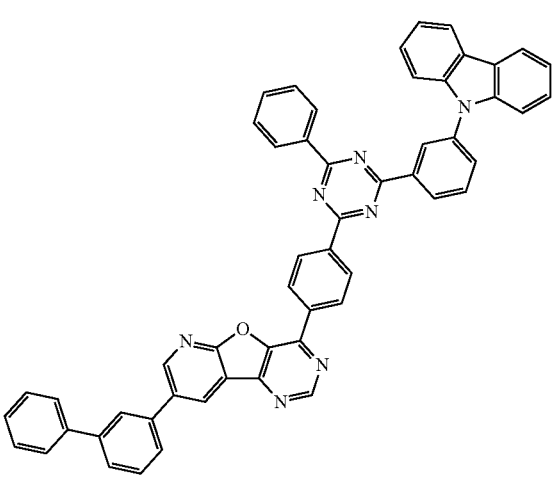

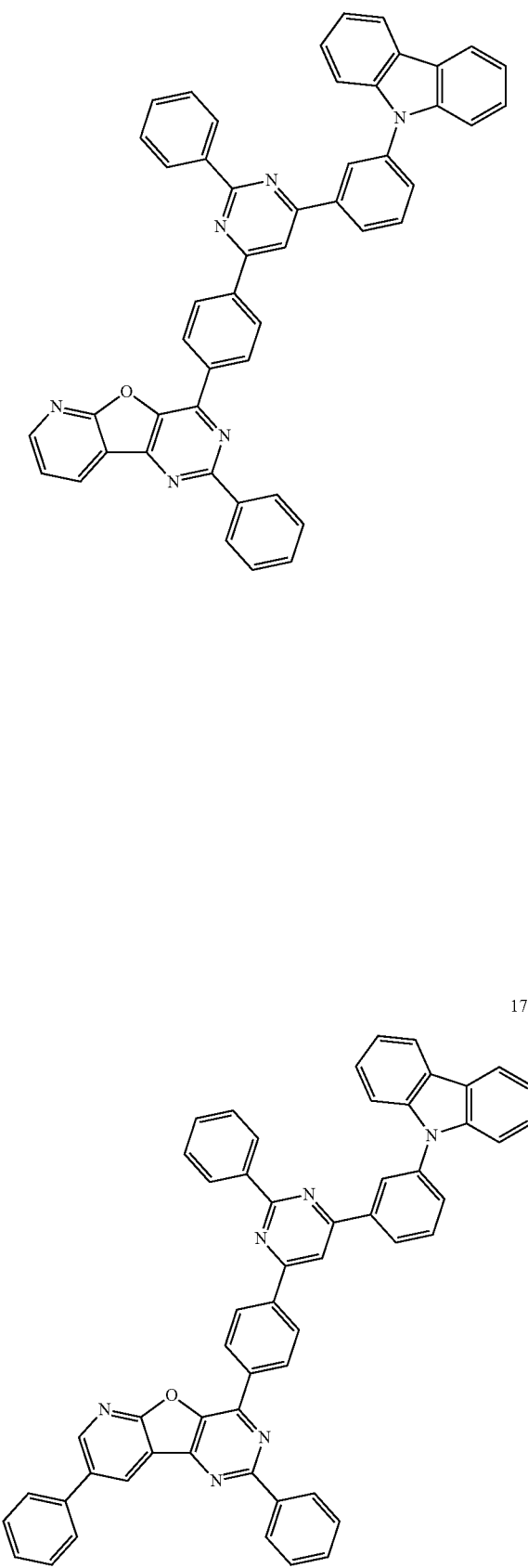
174
175
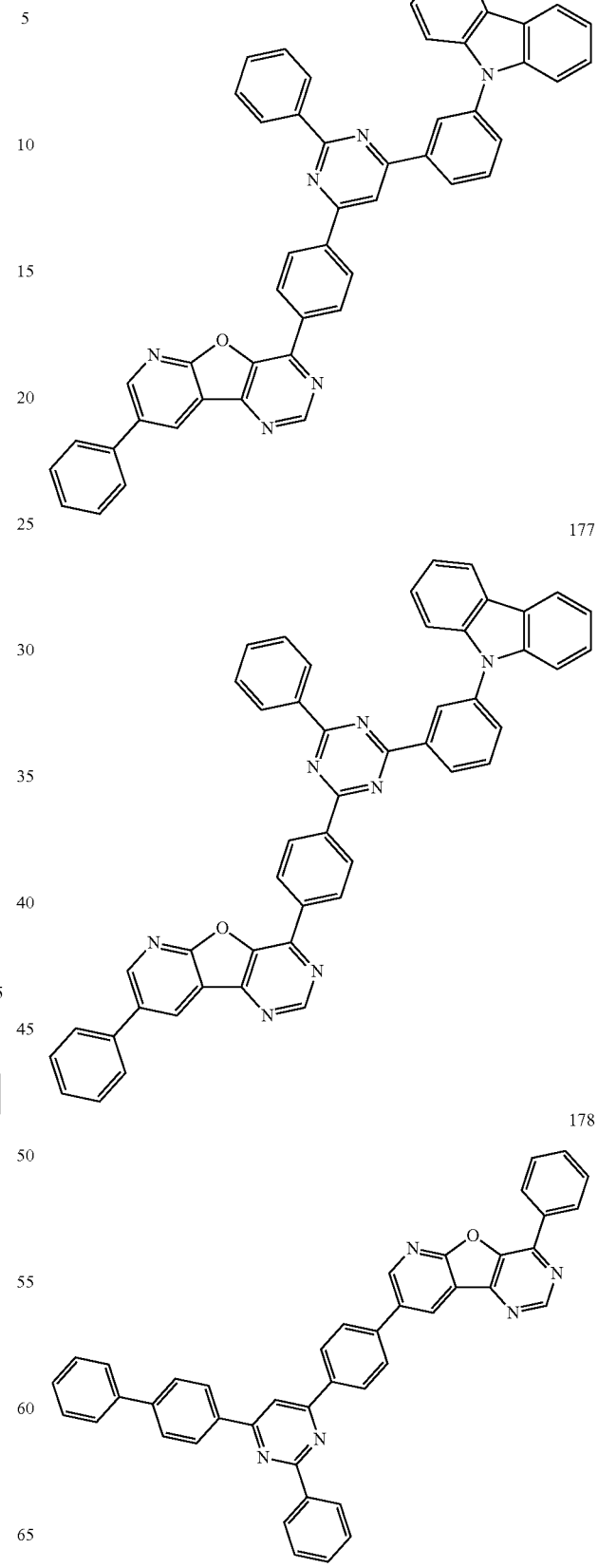
176
177
178

179
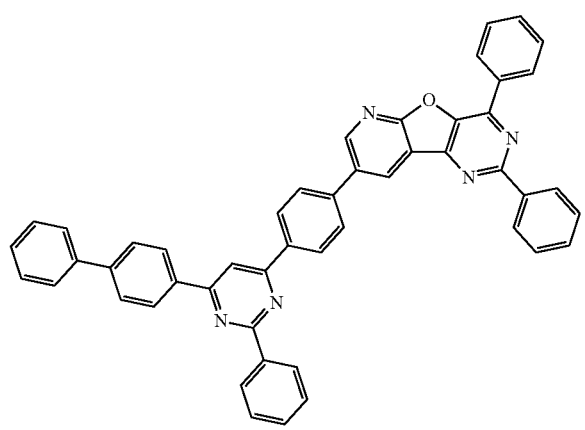
180
181
182
183
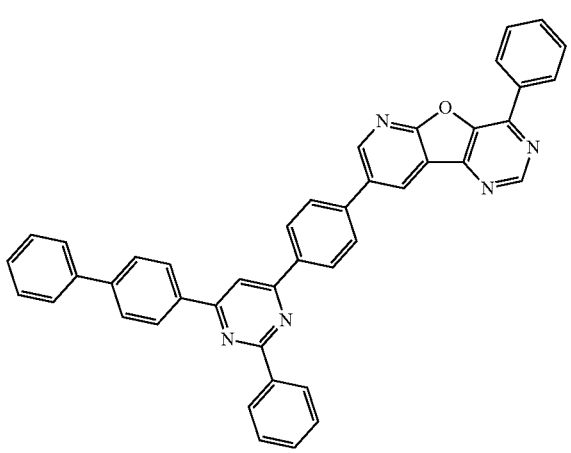
184
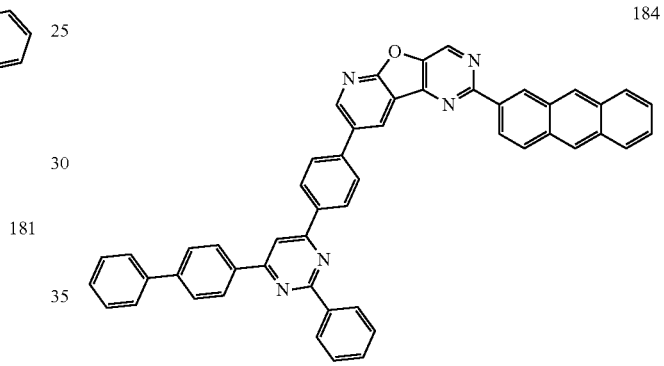
185
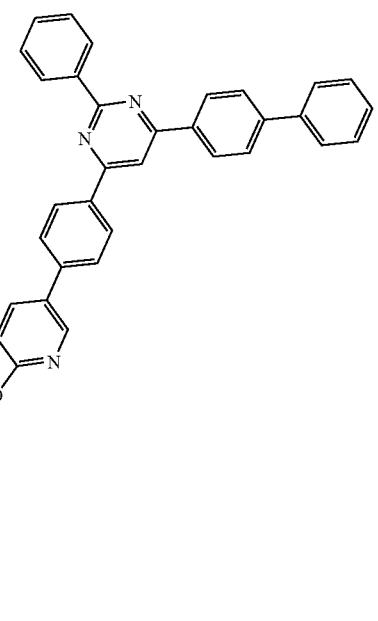

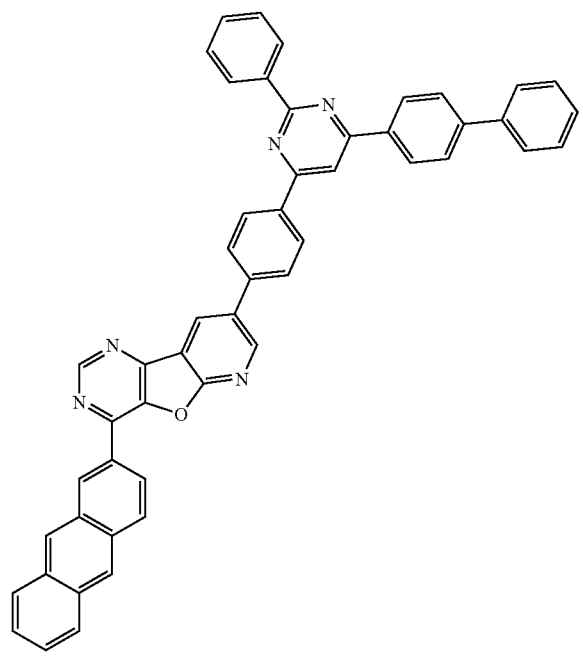
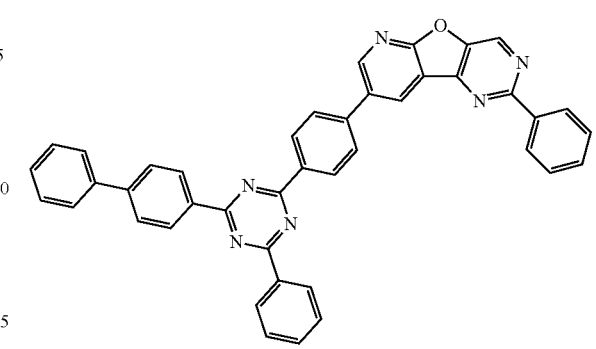
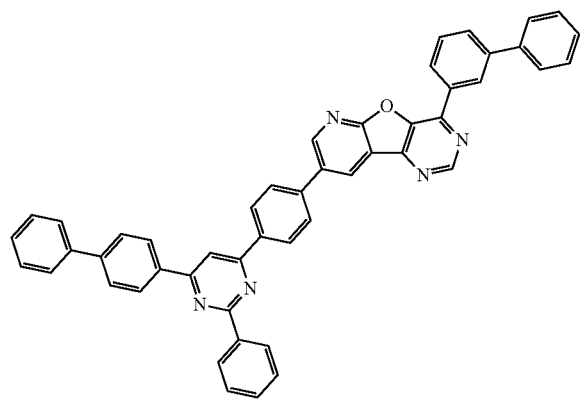
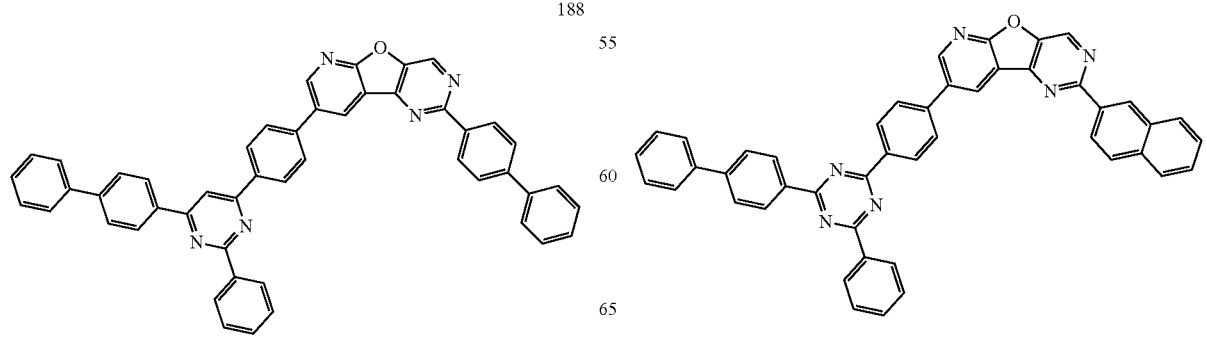

193
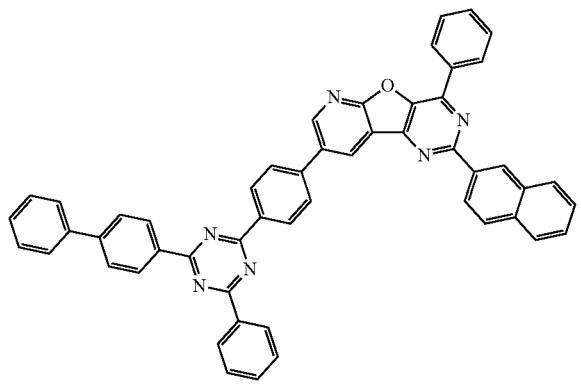
194
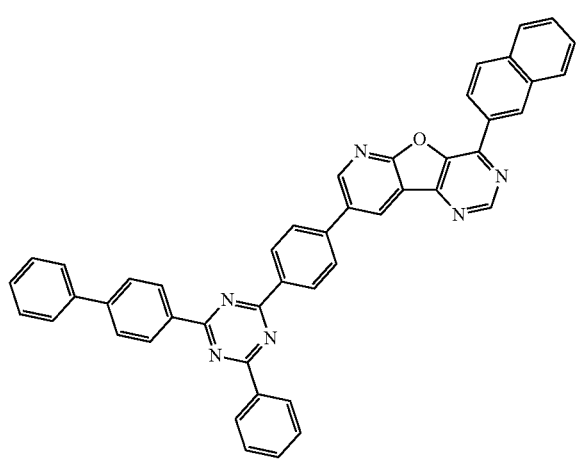
195
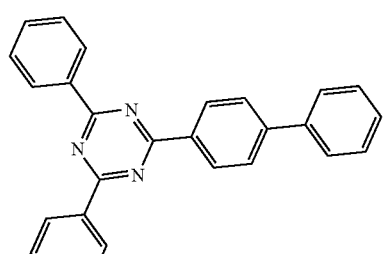
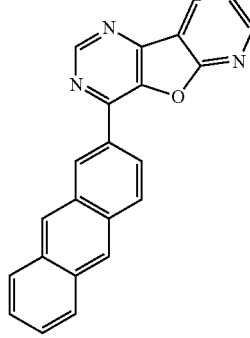
196
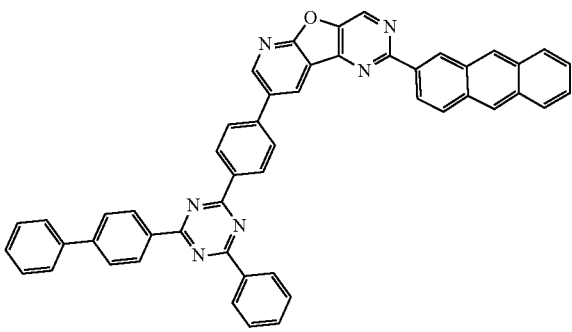
197
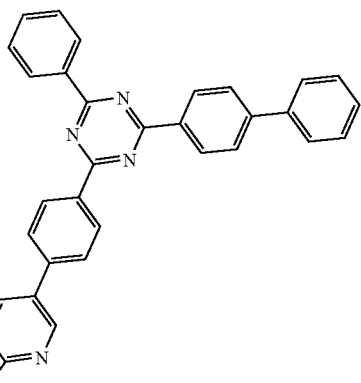
198
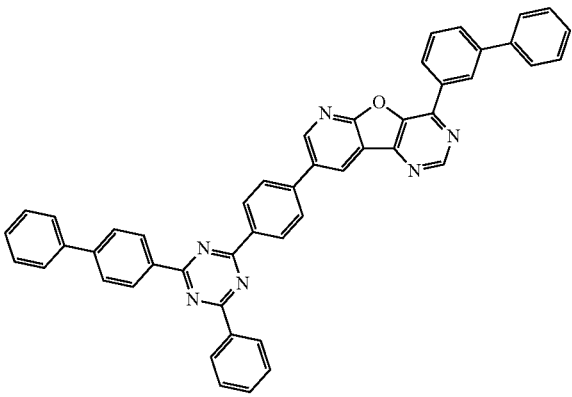

199
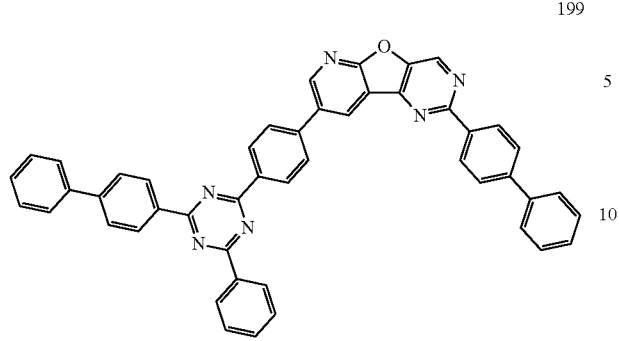
200
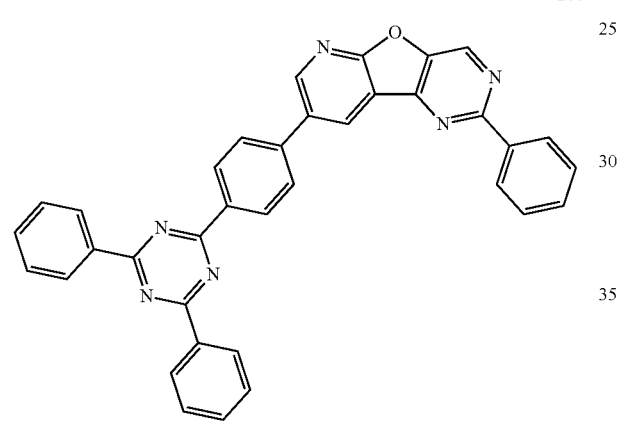
201
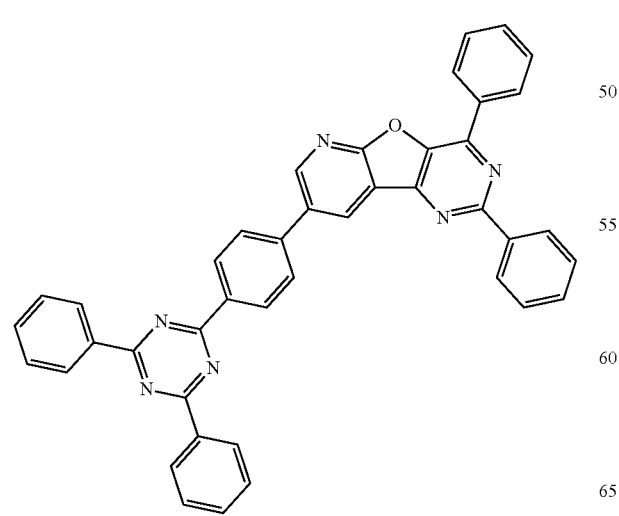
202
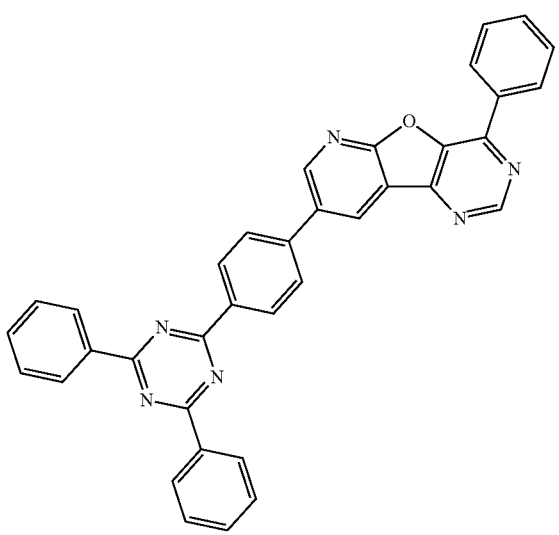
203
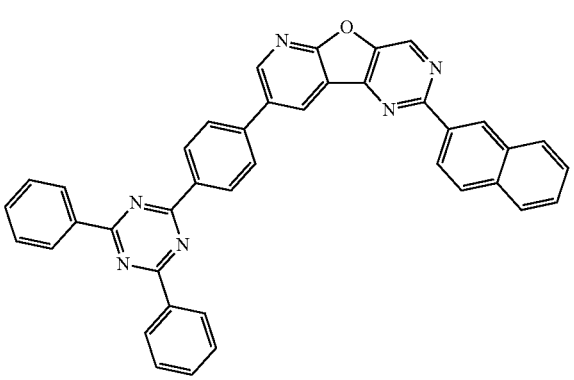
204
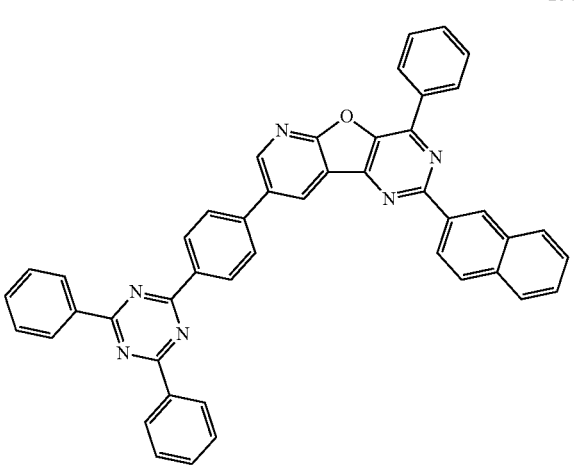

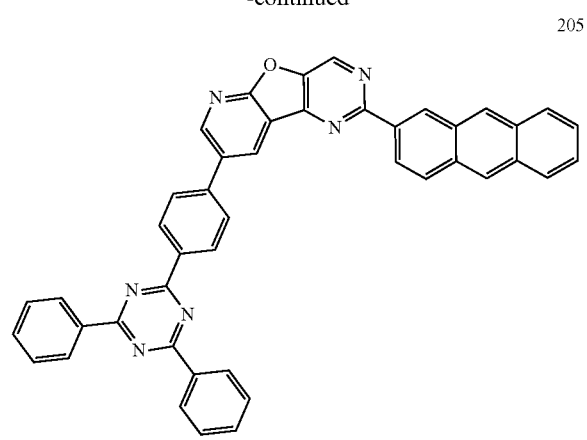
205
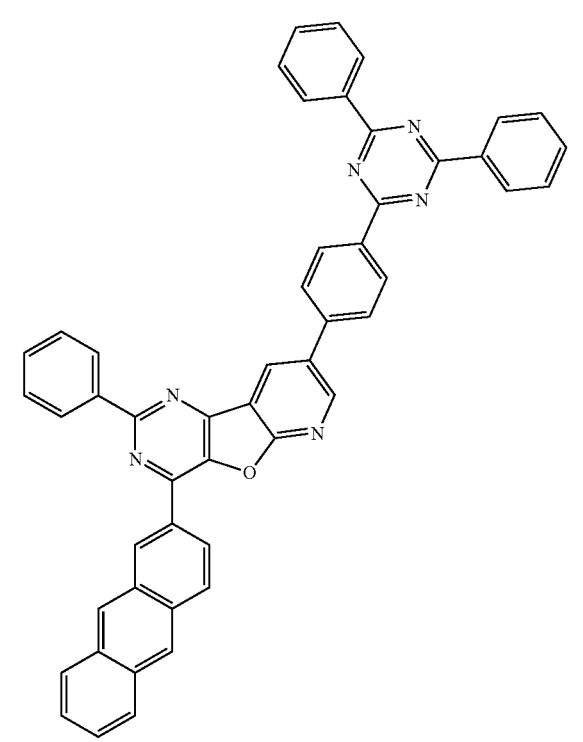
206
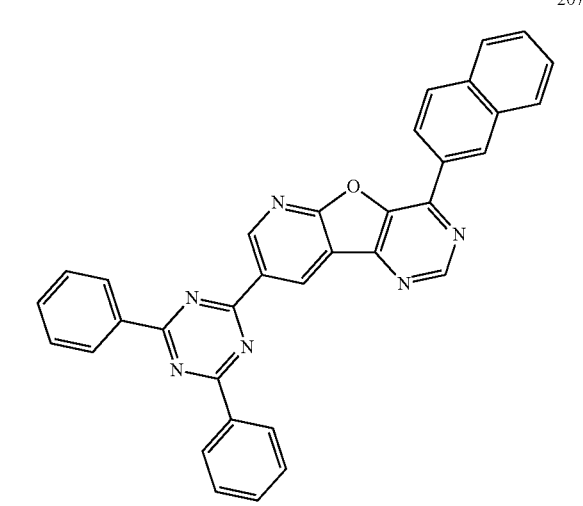
207
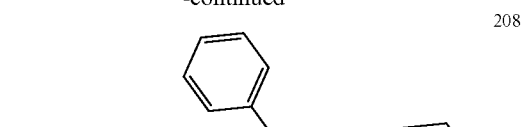
208
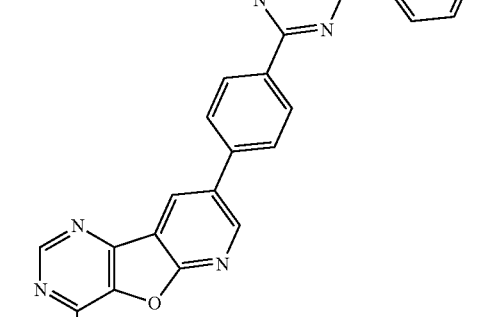
209
210
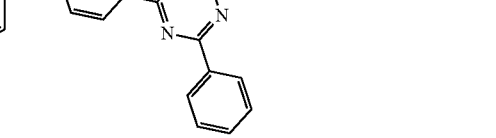

-continued
211
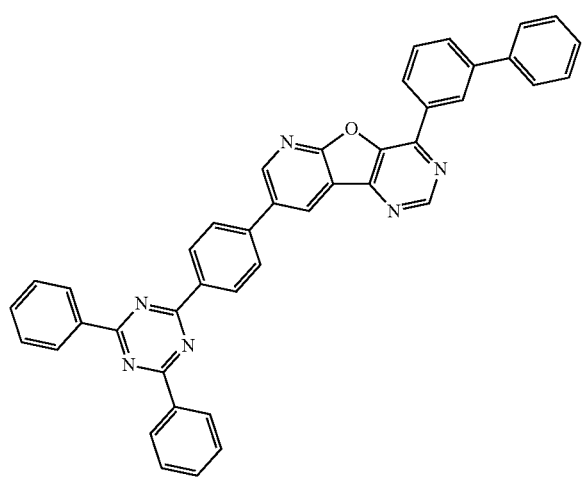
212
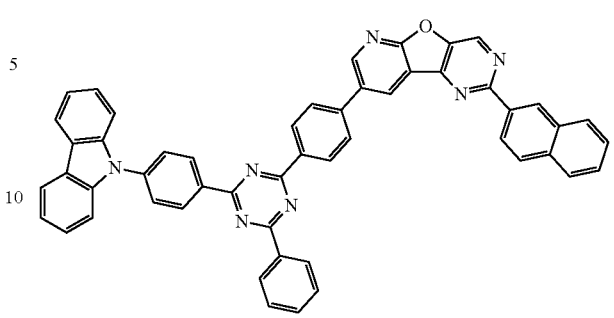
213
214
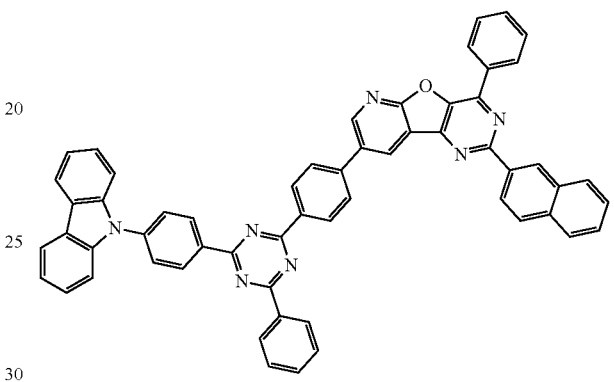
215
216
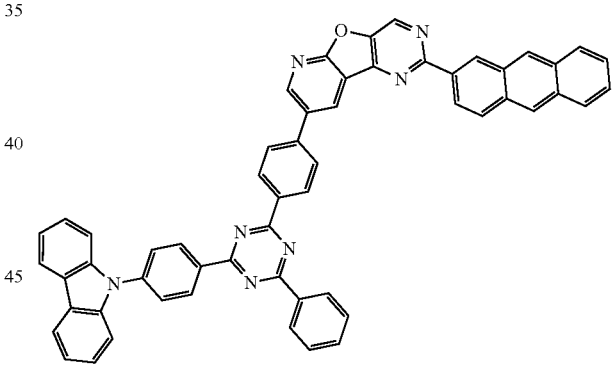
217
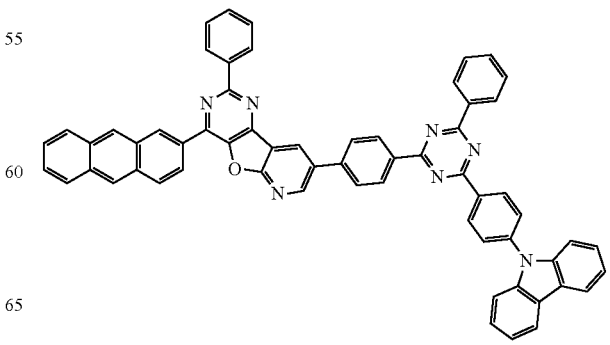

218
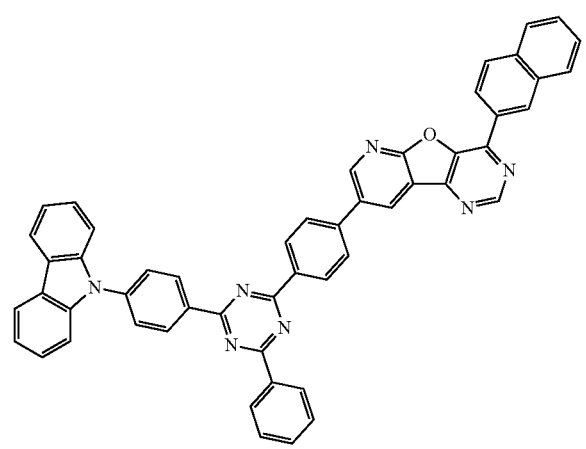
219
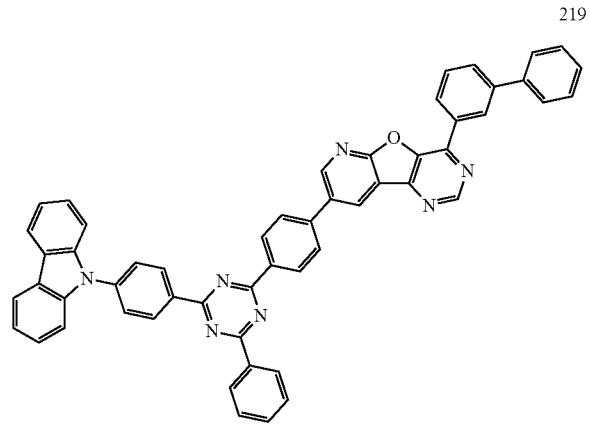
220
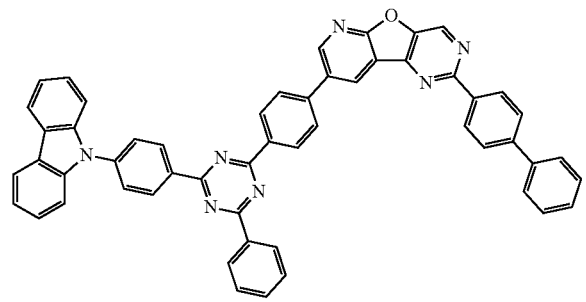
221
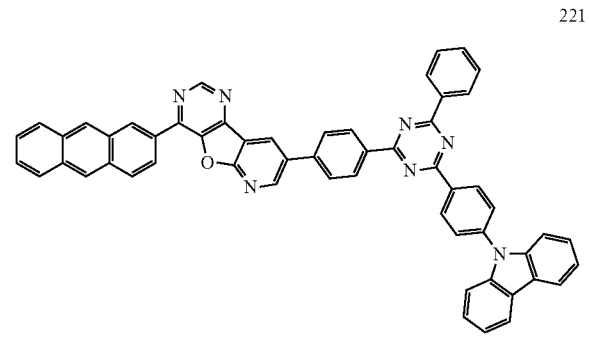
222
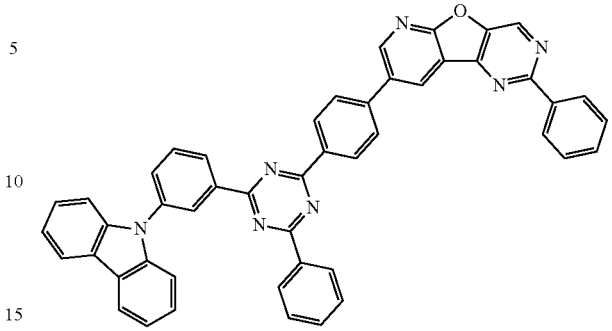
223
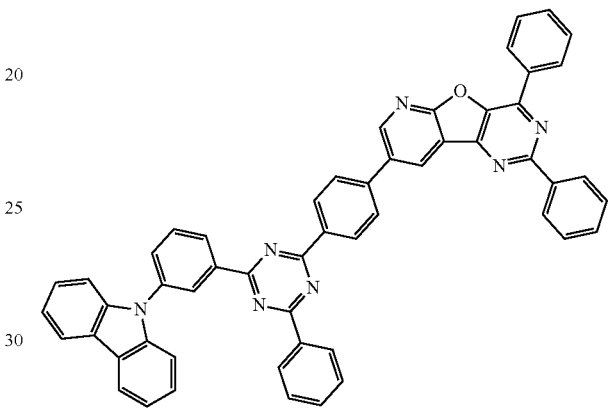
224
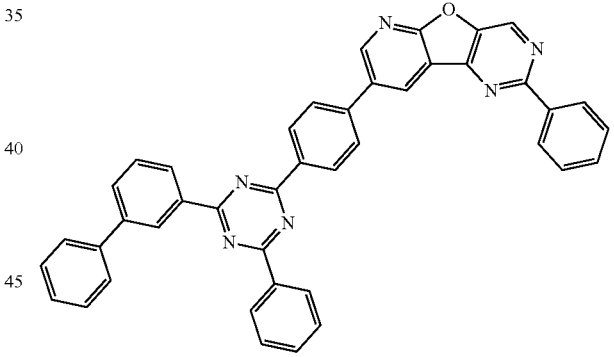
225
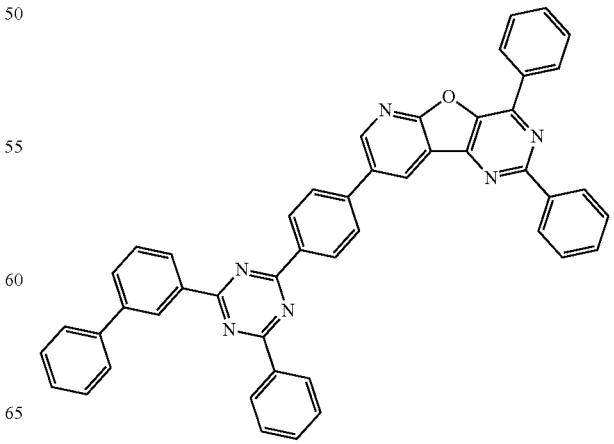

101
-continued
226
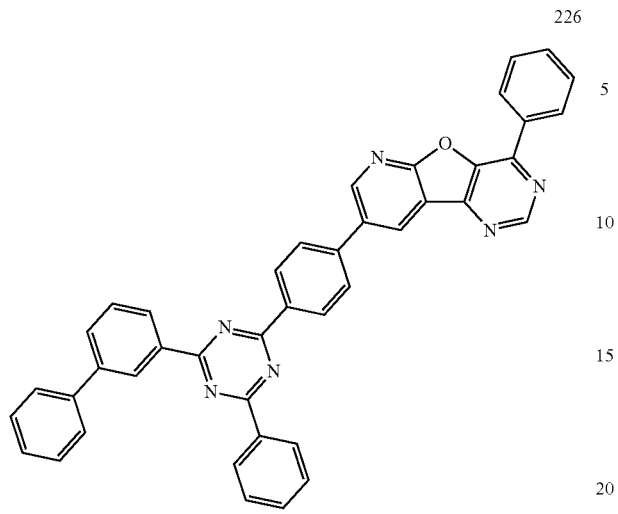
227
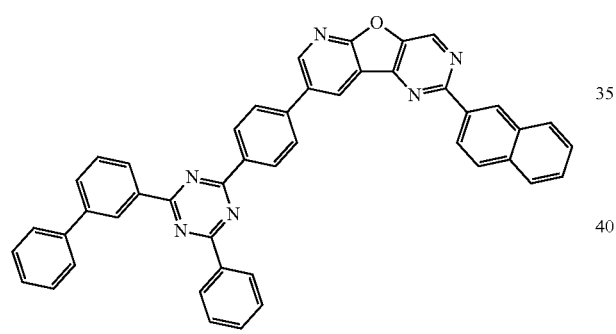
228
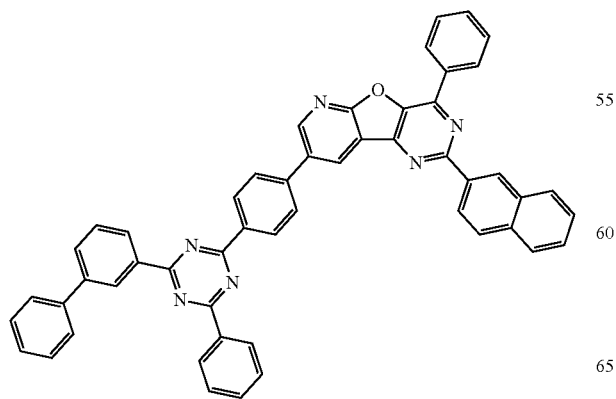
102
-continued
229
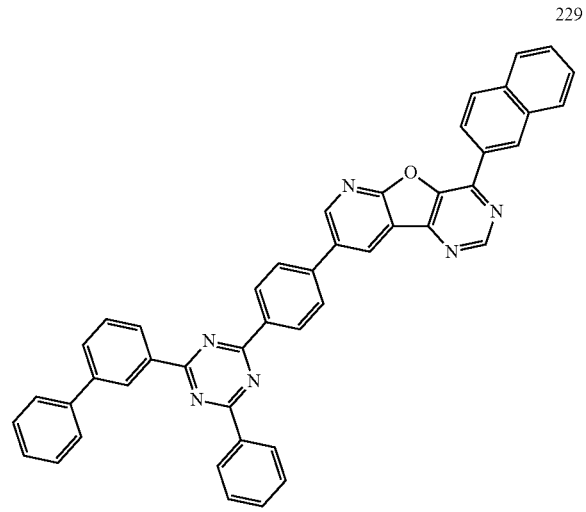
230
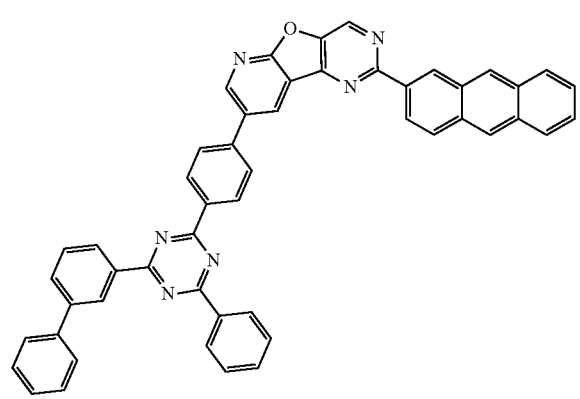

103  
-continued
231
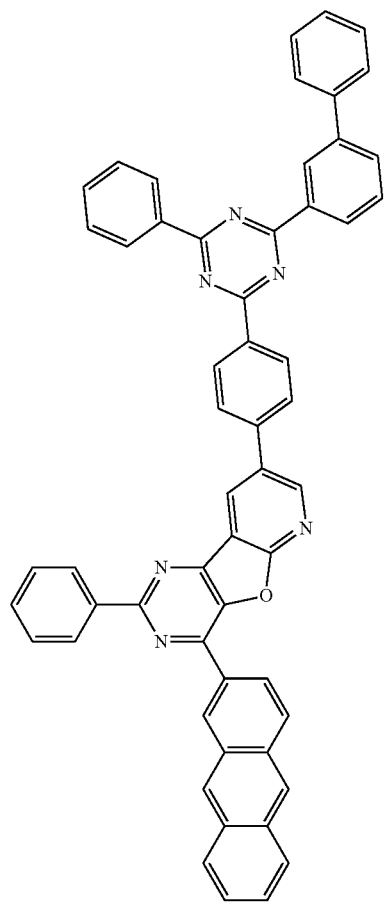
104  
-continued
232
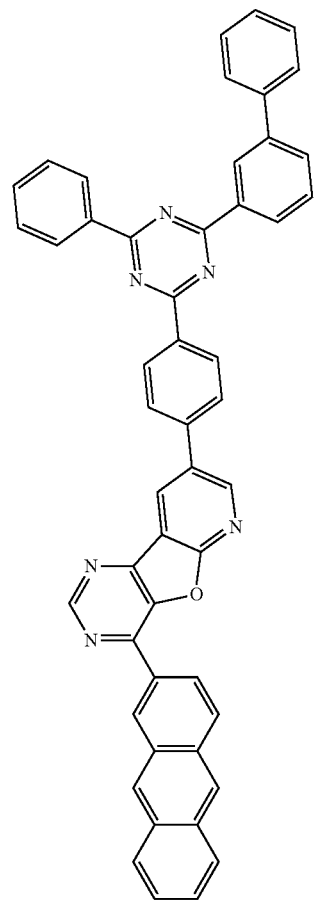
233
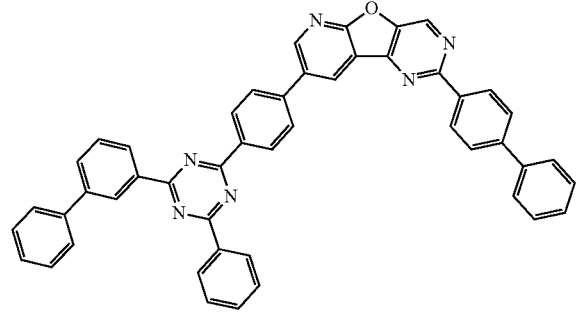

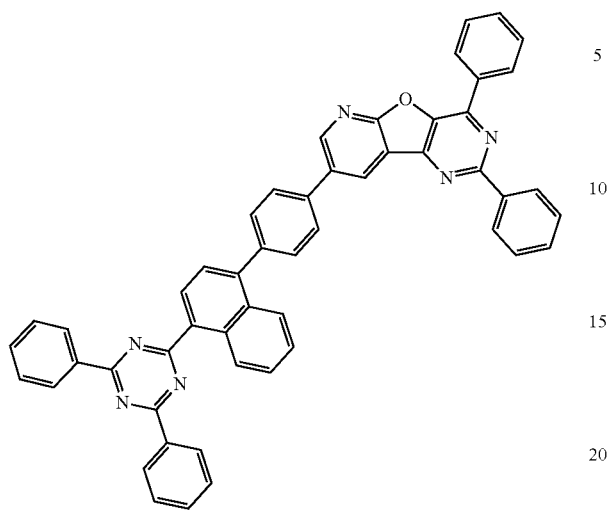
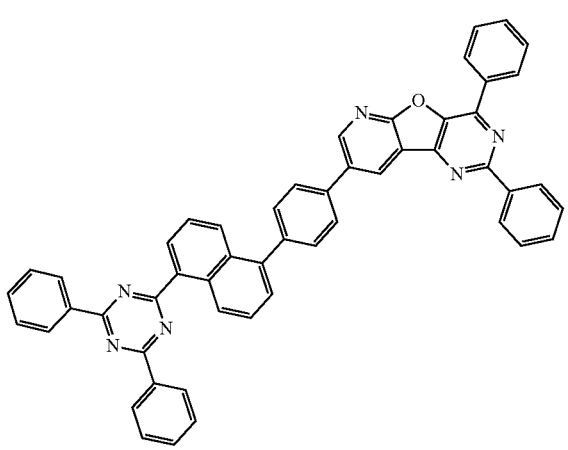
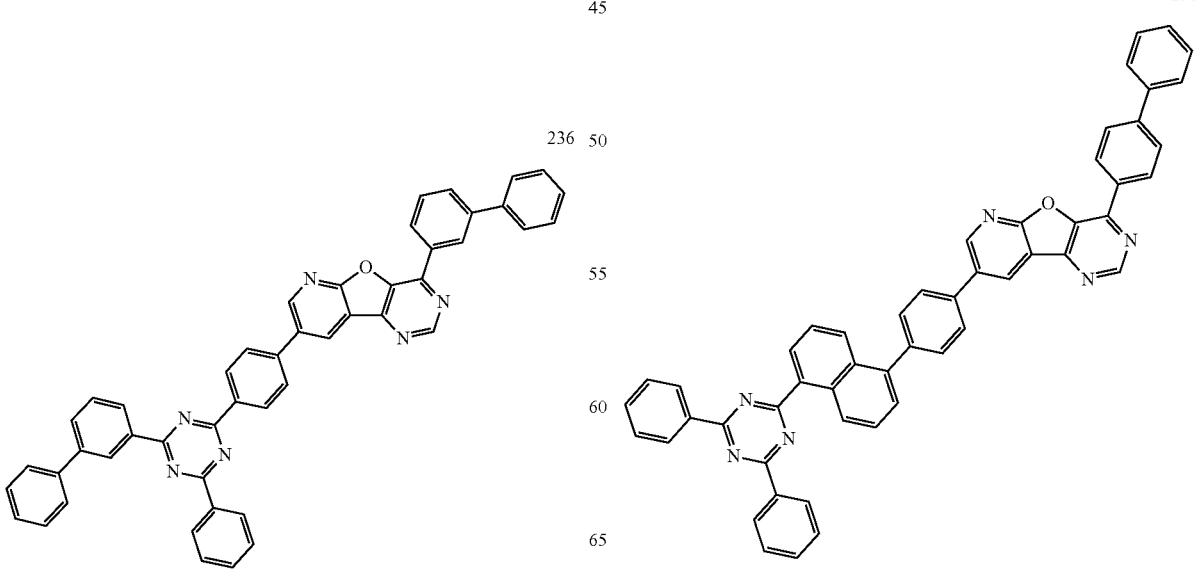
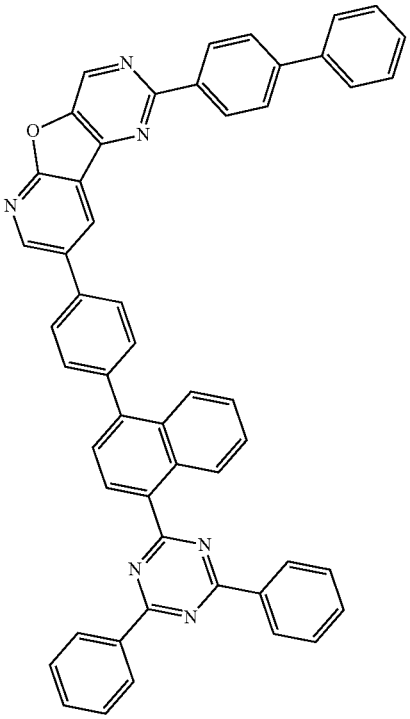

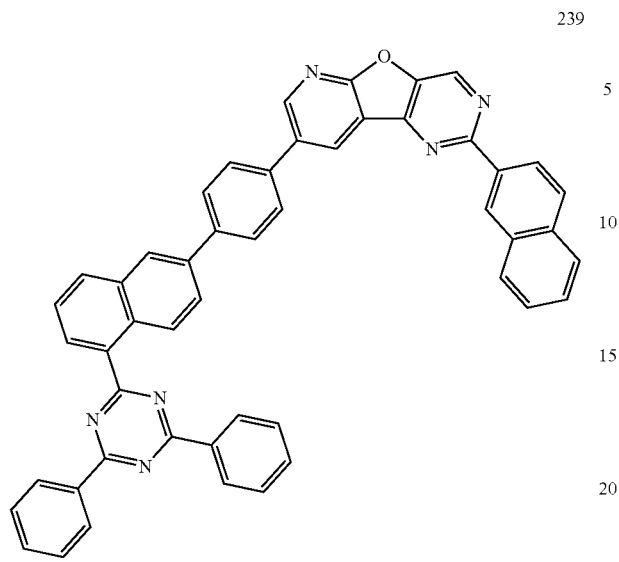
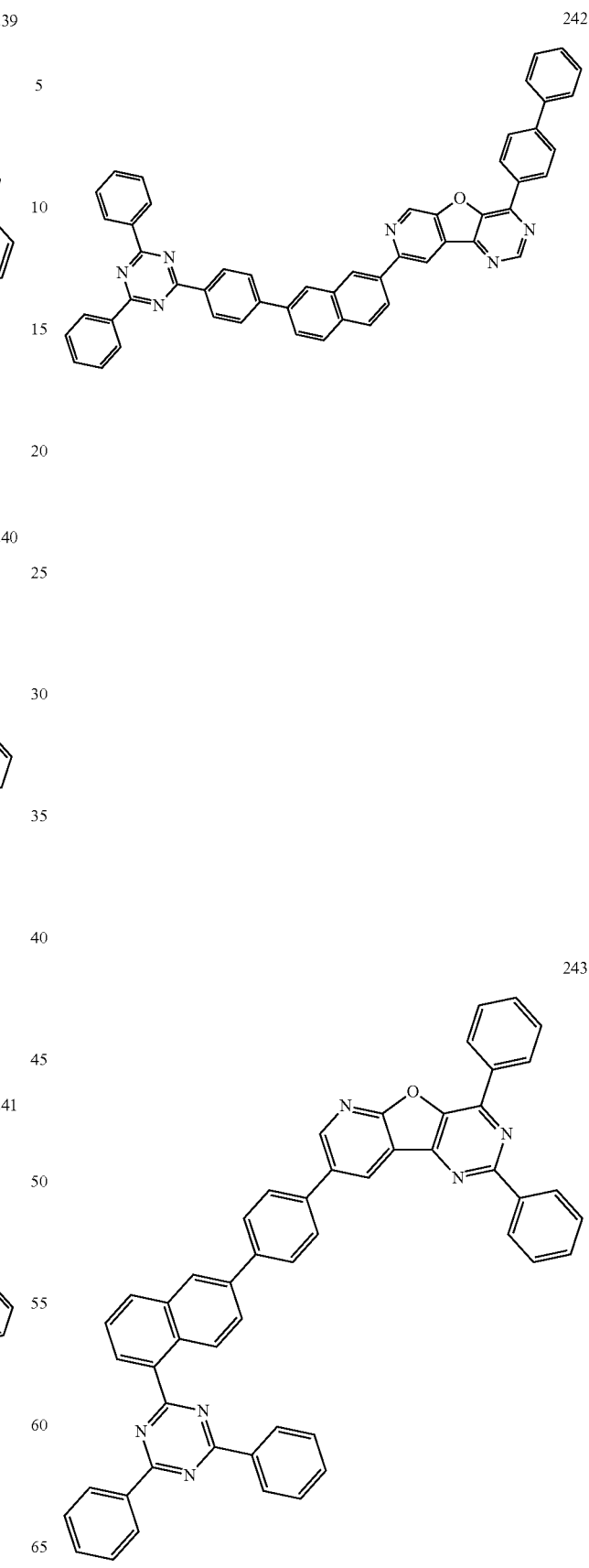

244
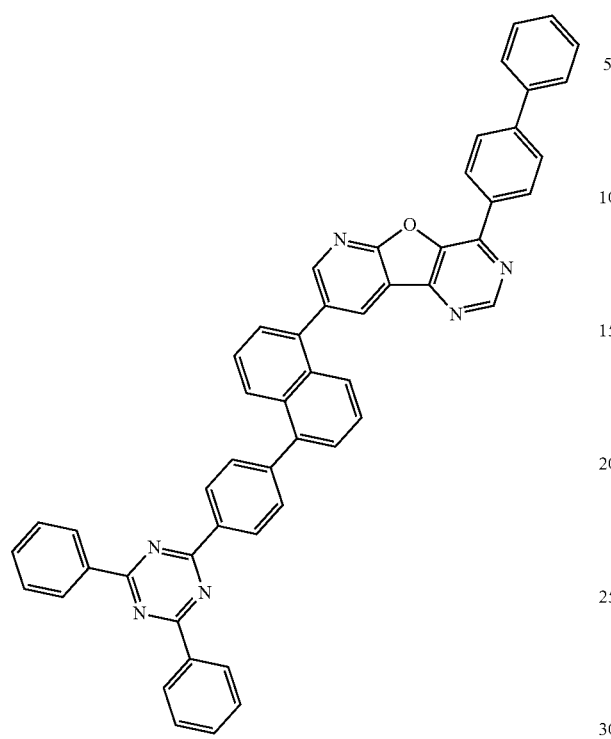
245
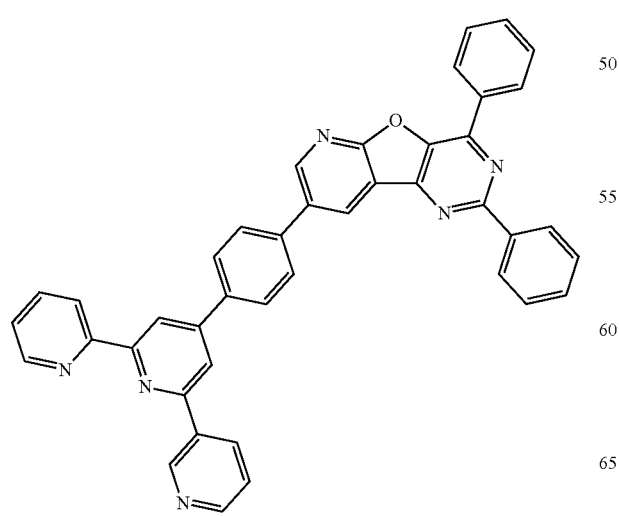
246
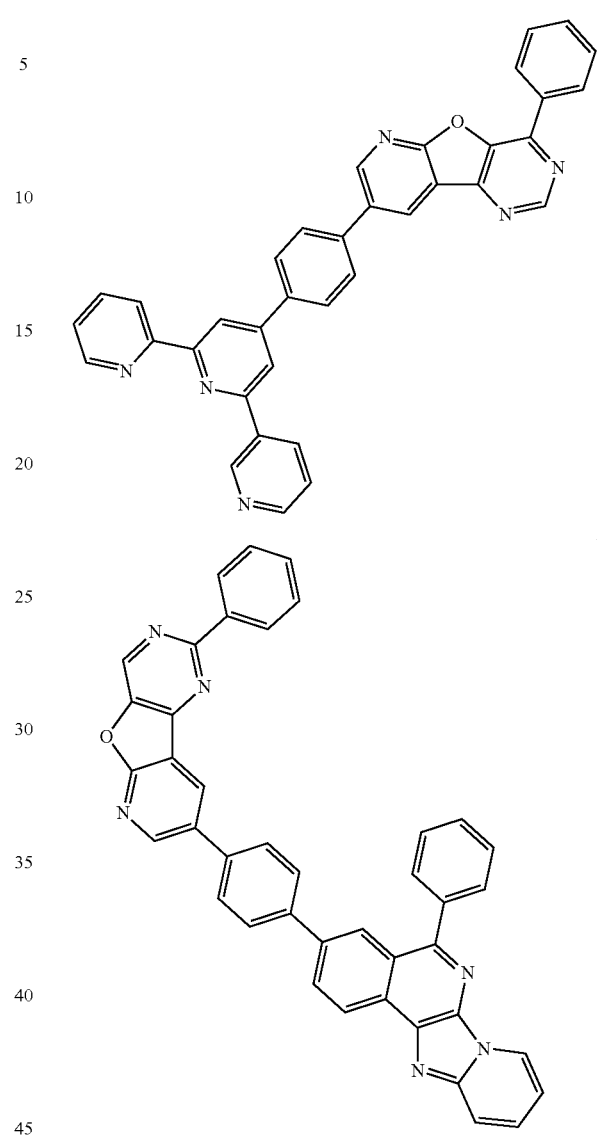
247
248
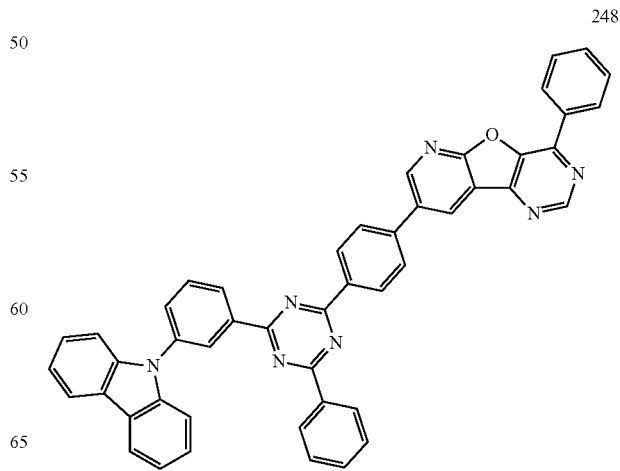

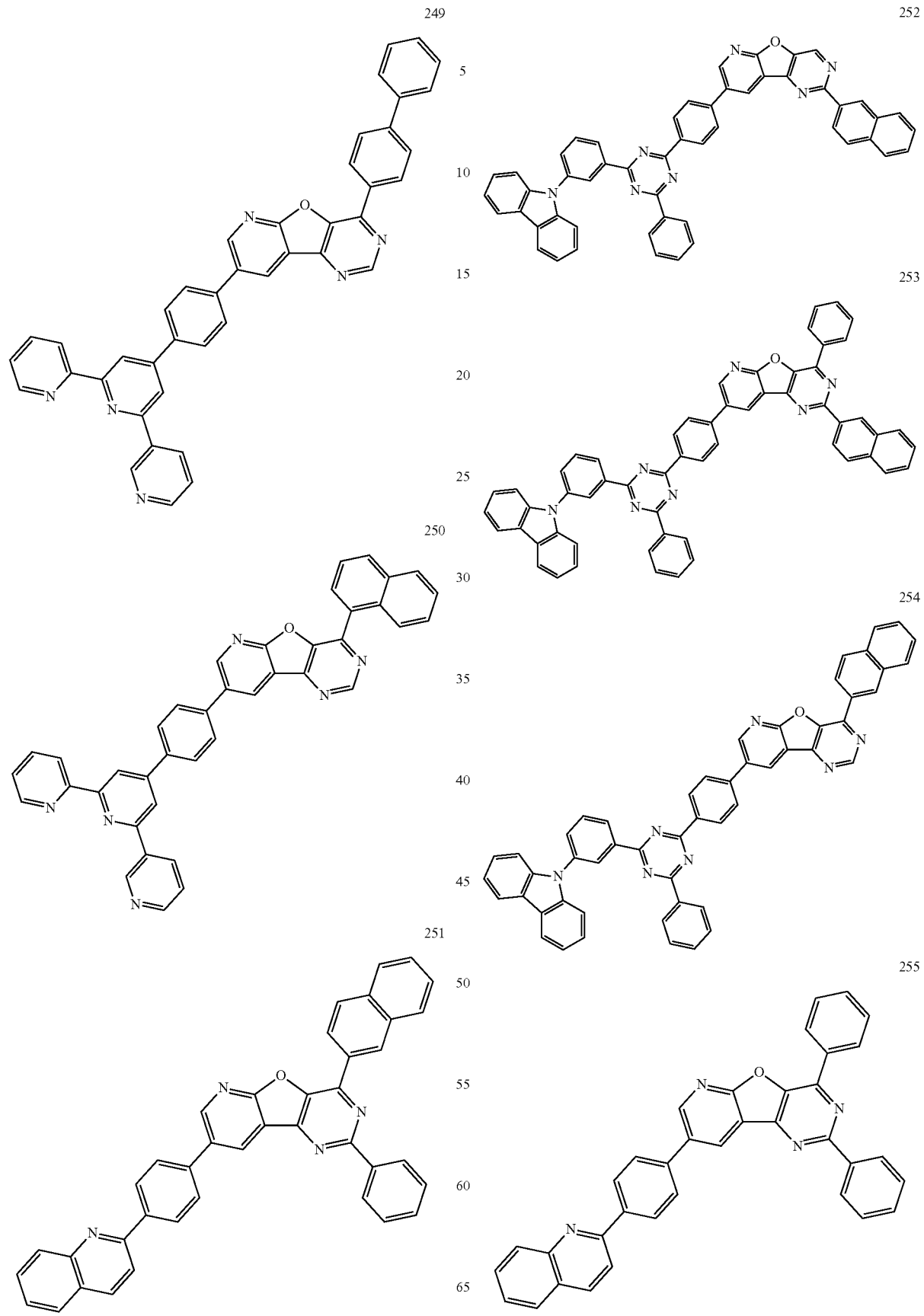

256
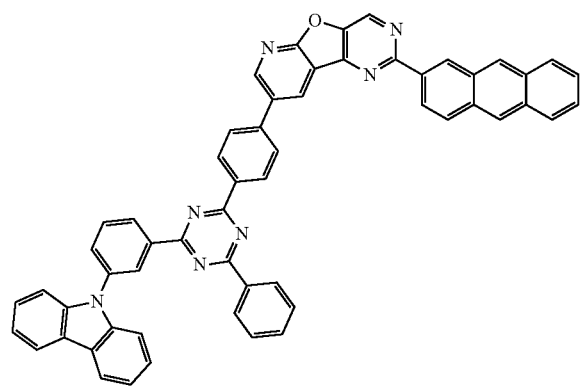
257
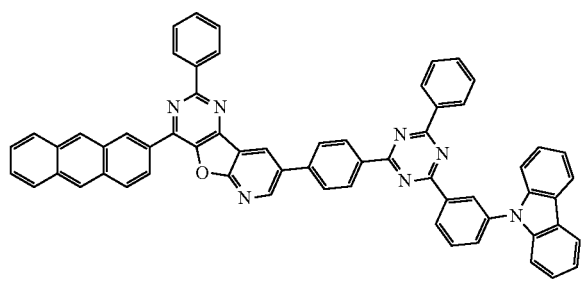
258
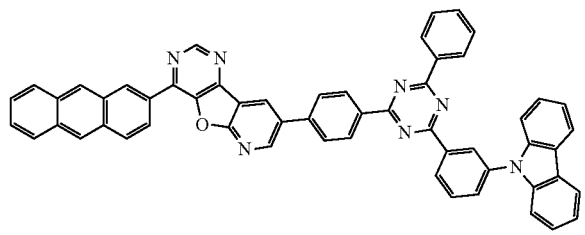
259

260
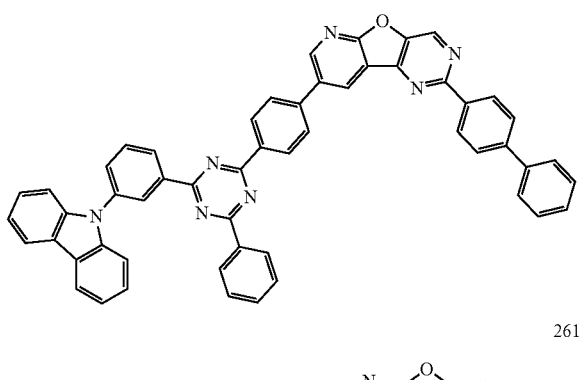
261
262
263

264
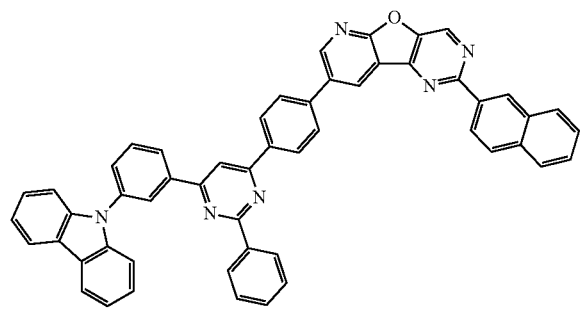
265
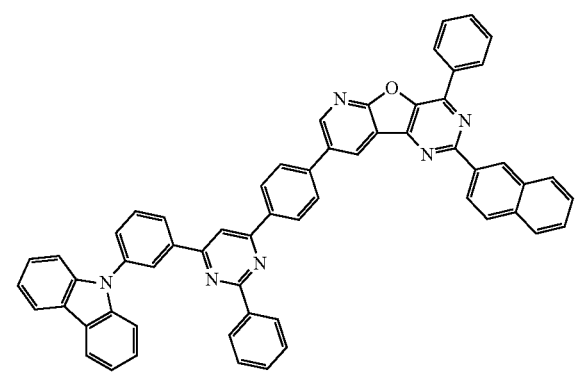
266
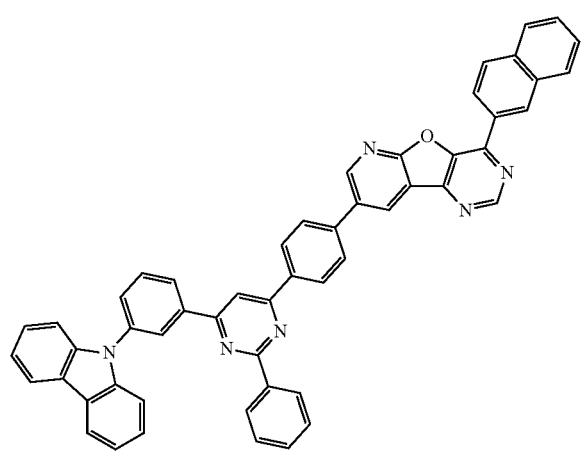
267
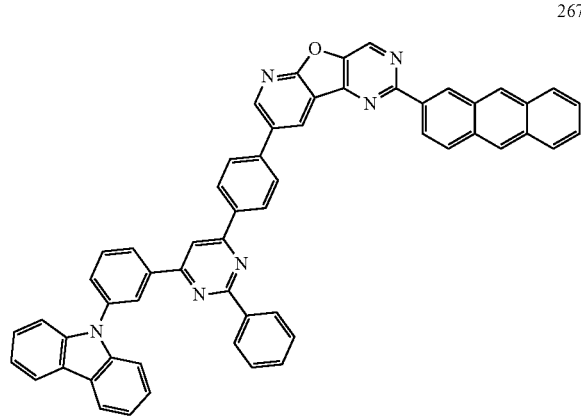
268
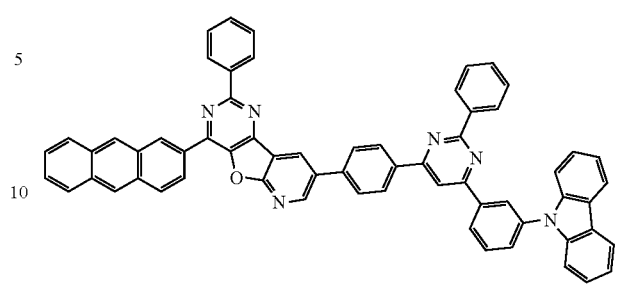
269
270
271
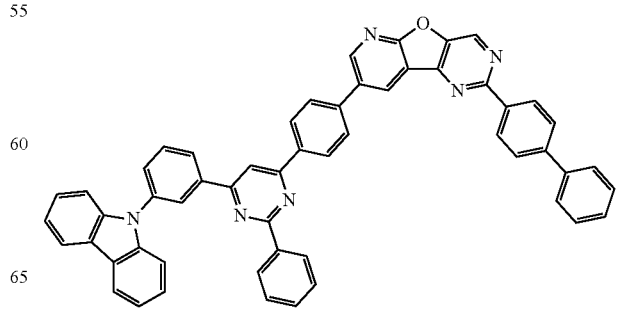

272
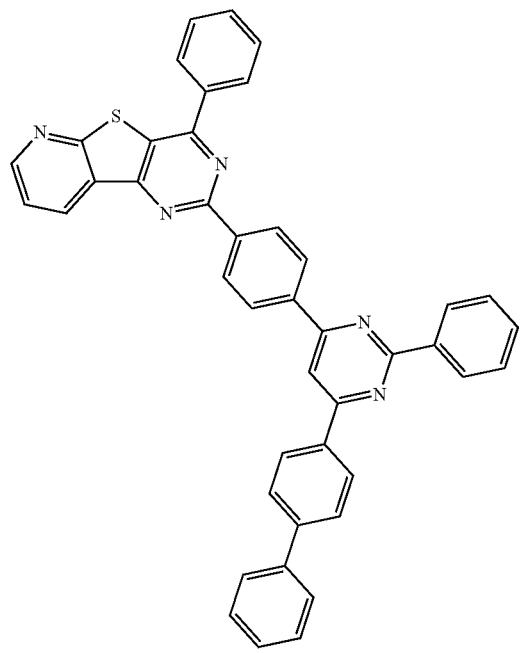
273
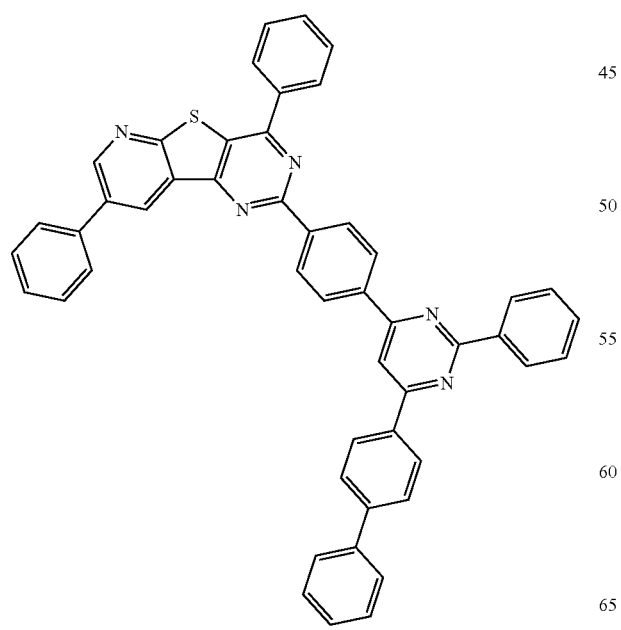
274
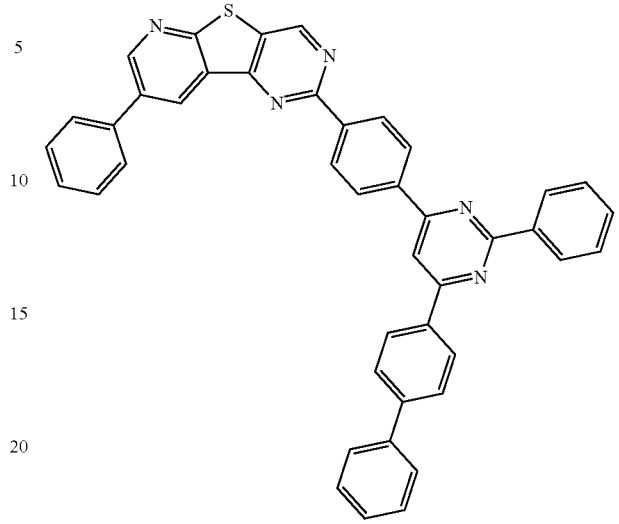
275
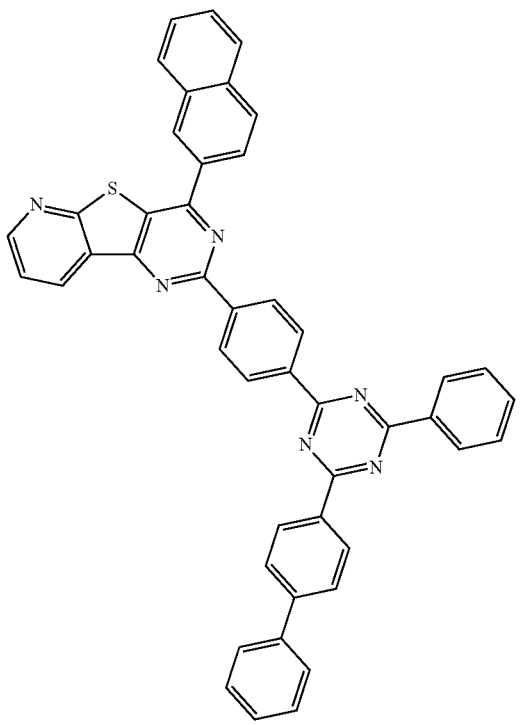

276
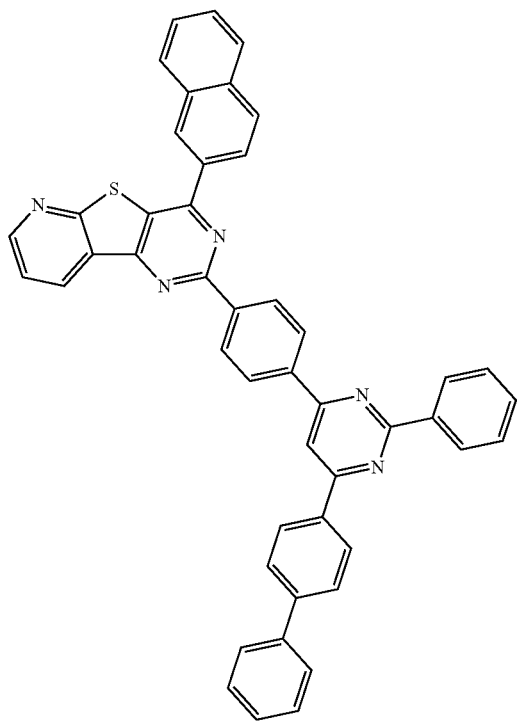
278
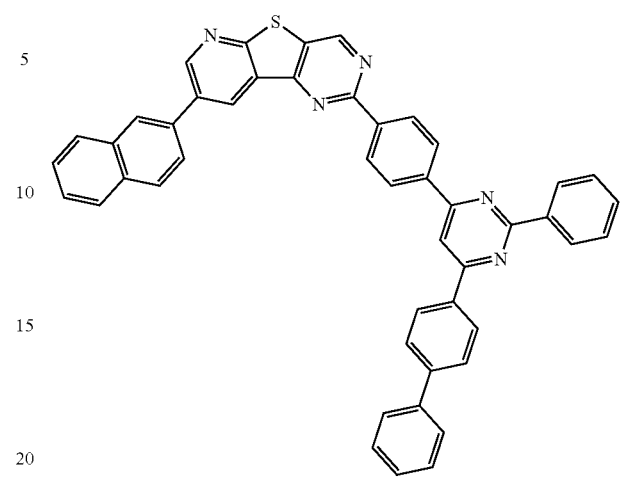
279
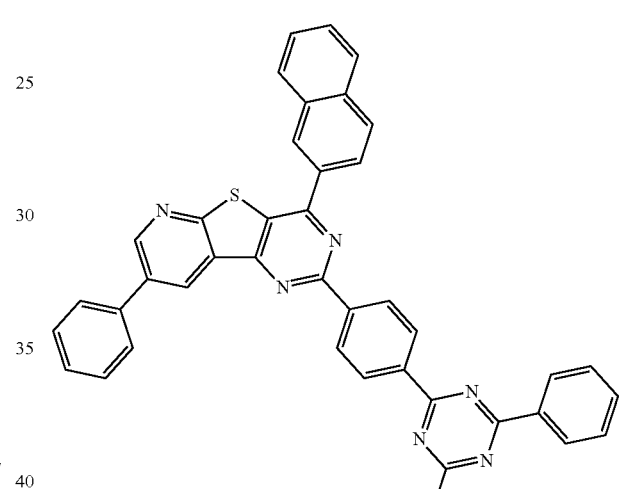
277
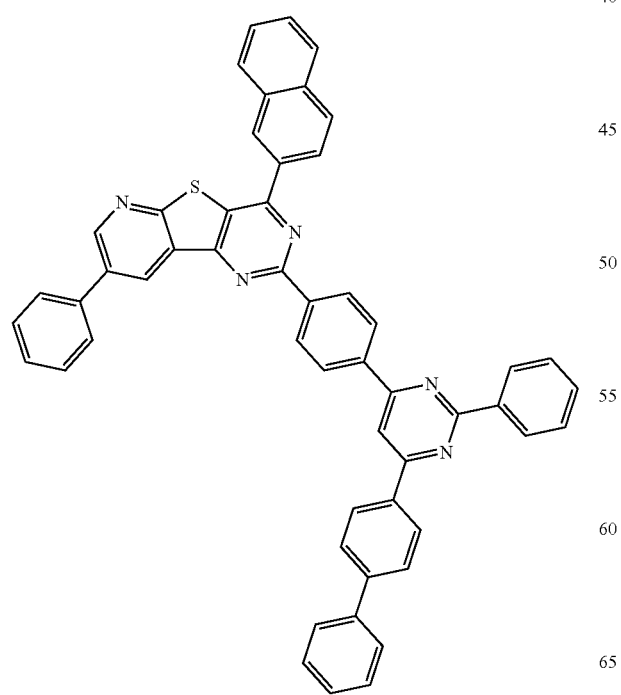
280
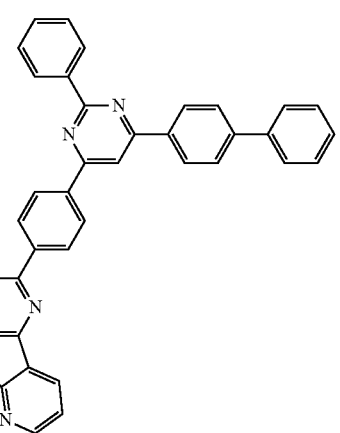

281
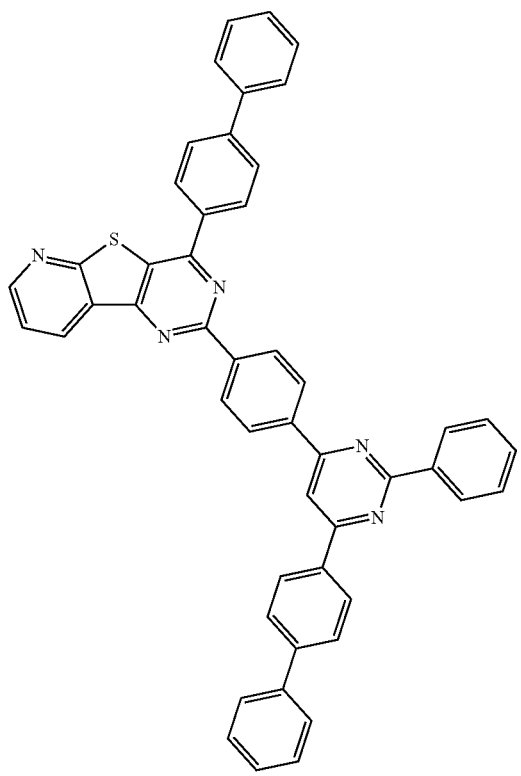
282
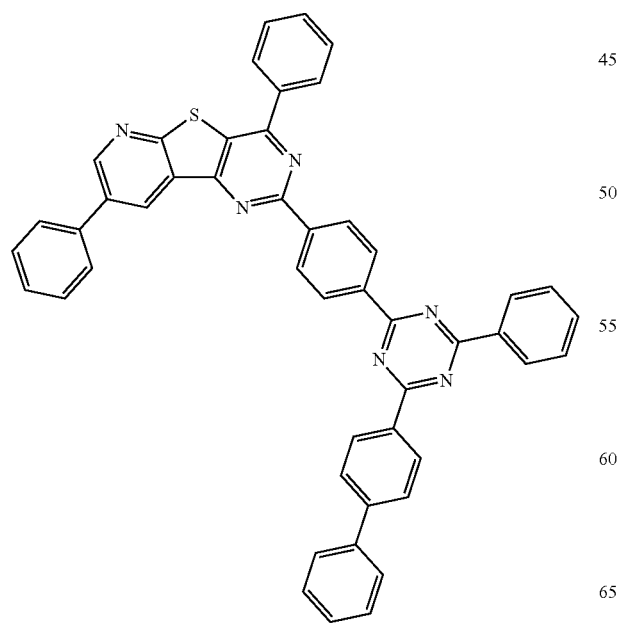
283
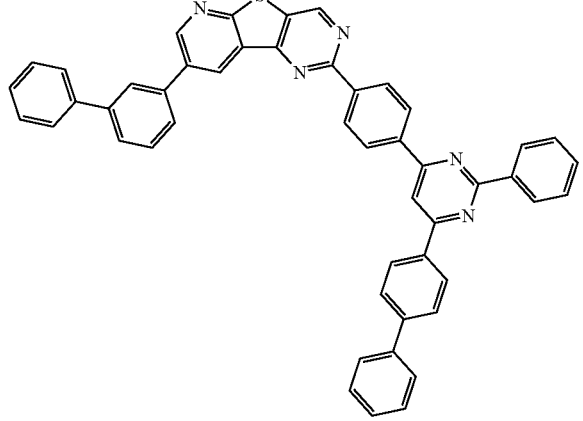
284
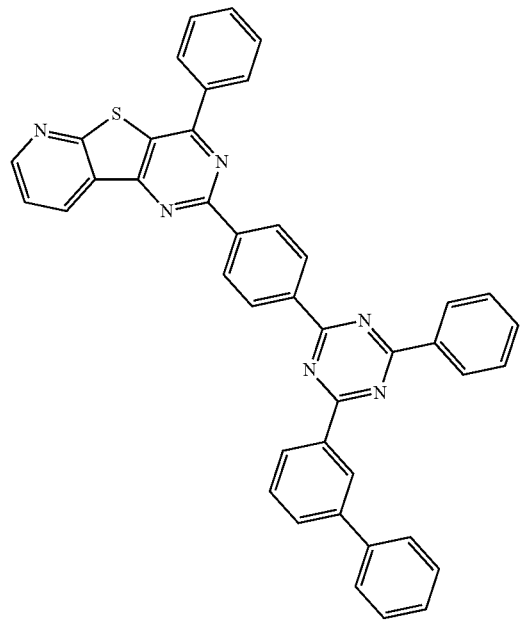

123
-continued
285
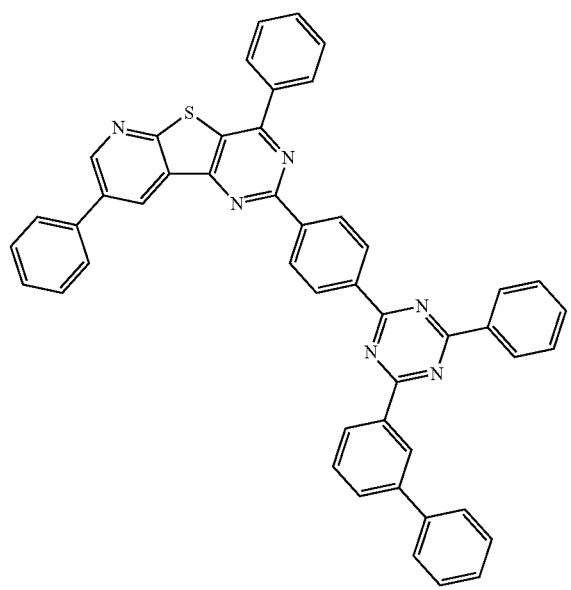
286
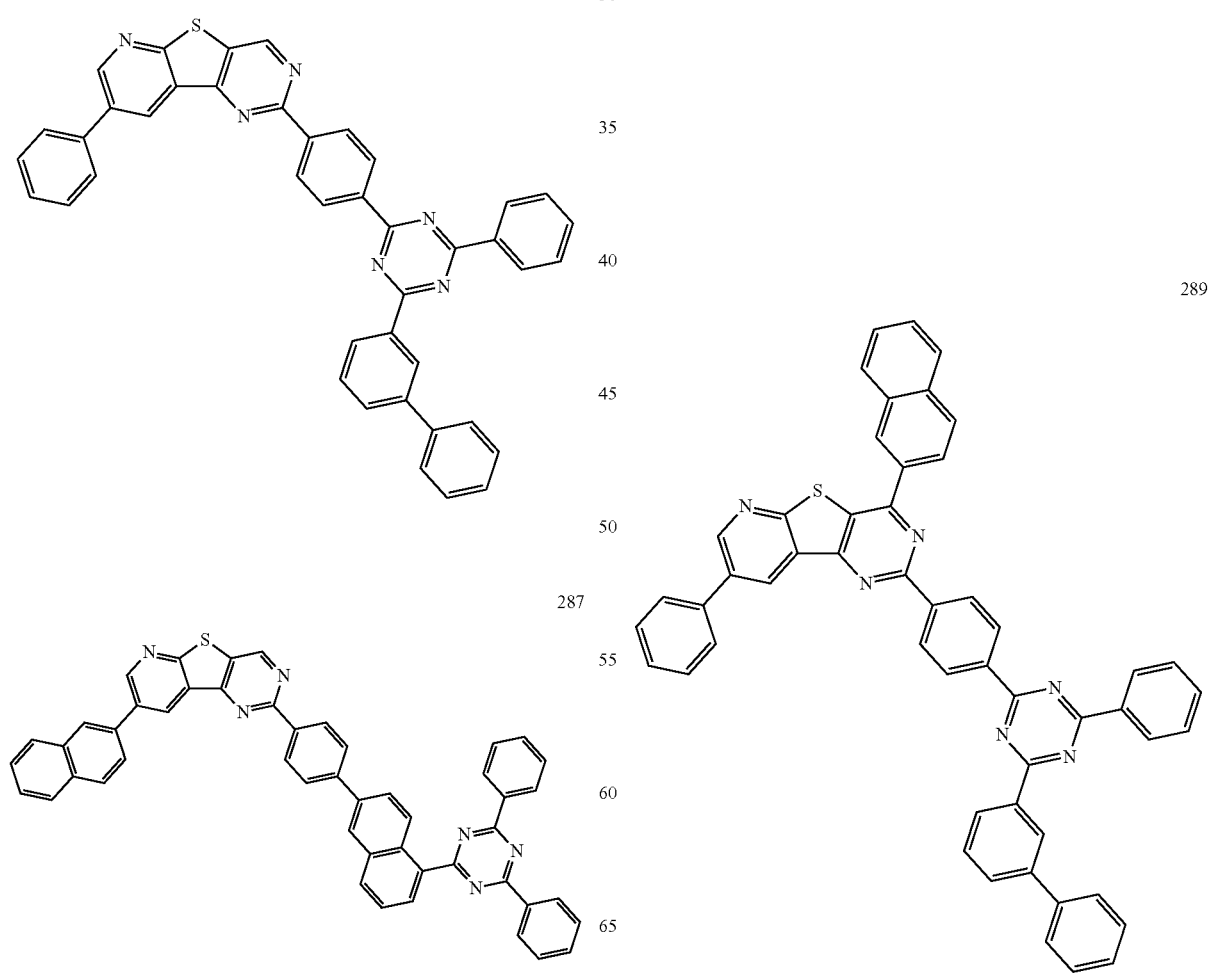
287
124
-continued
288
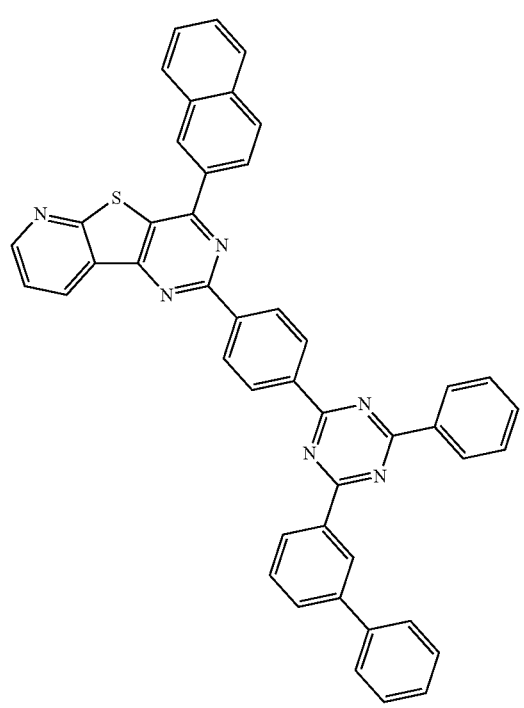
289

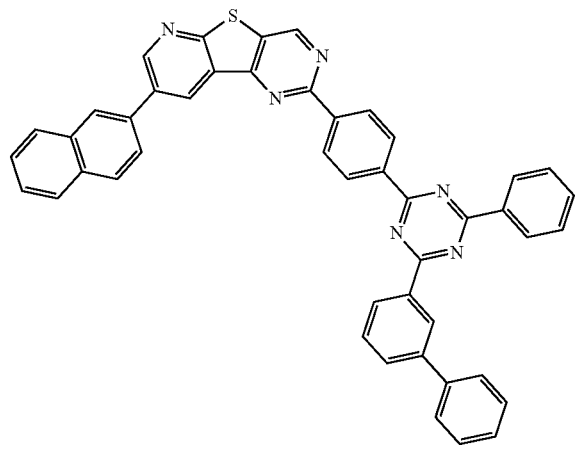
290
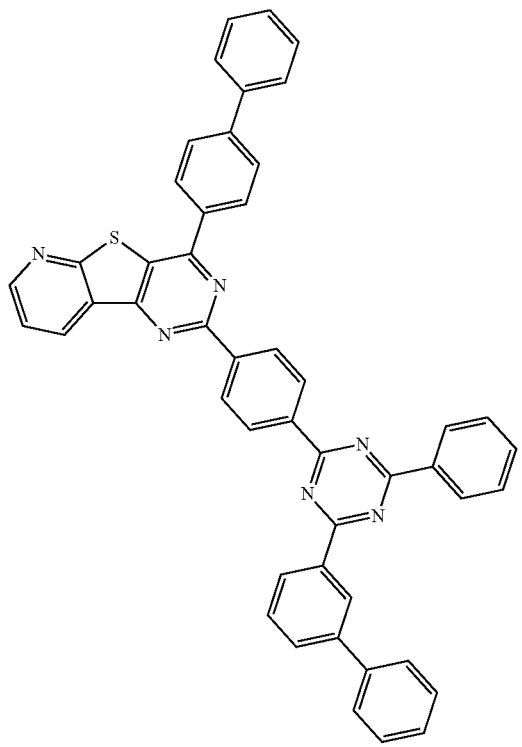
292
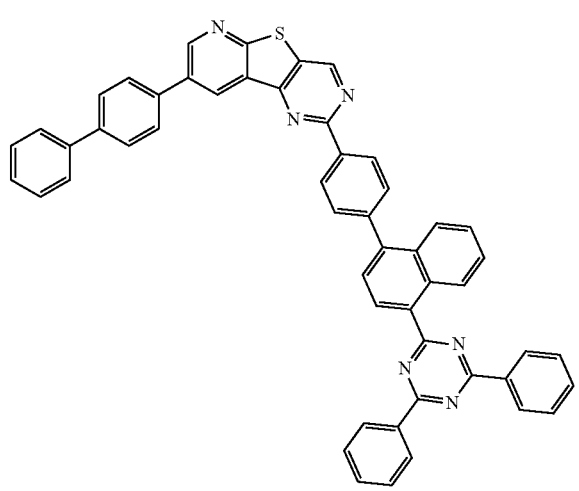
291
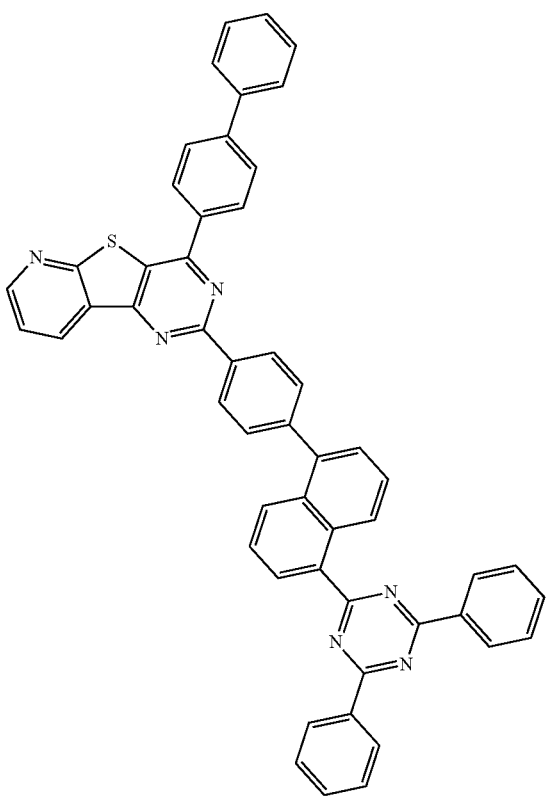
293

127
-continued
294
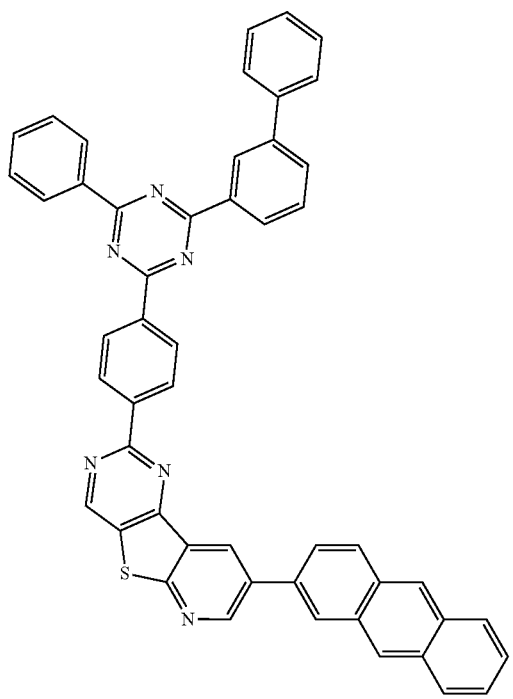
128
-continued
295
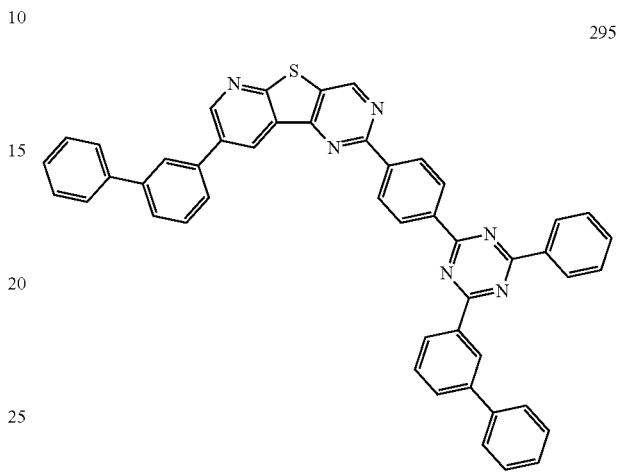
296
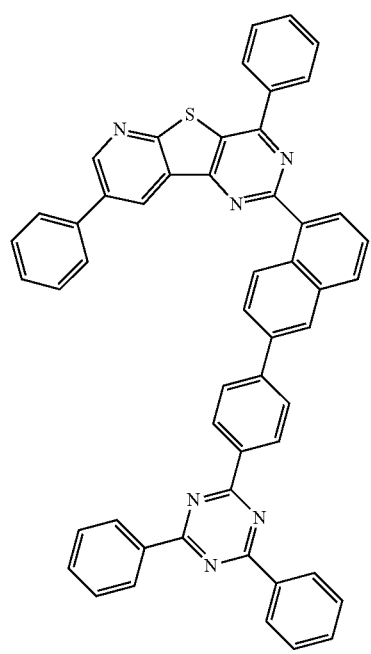

-continued
297
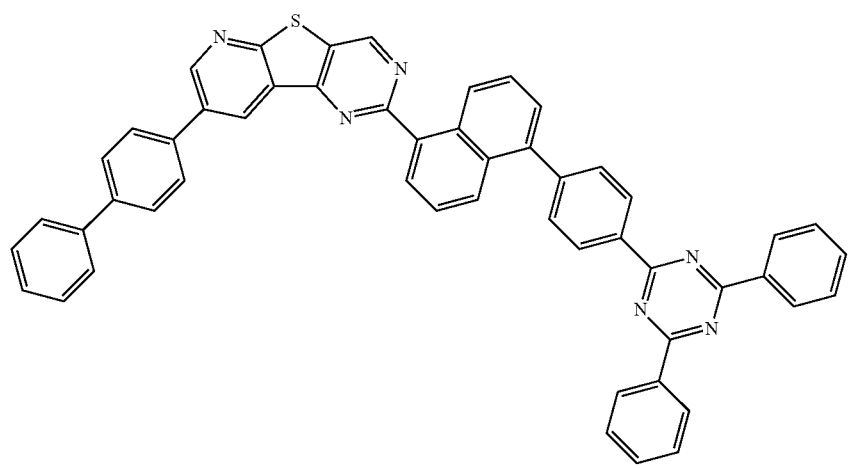
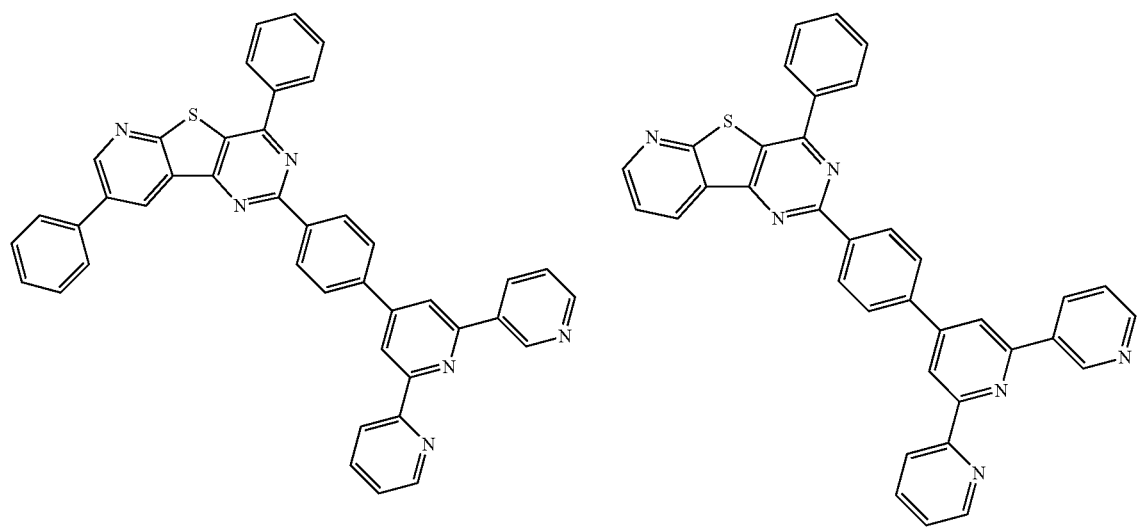

-continued
300
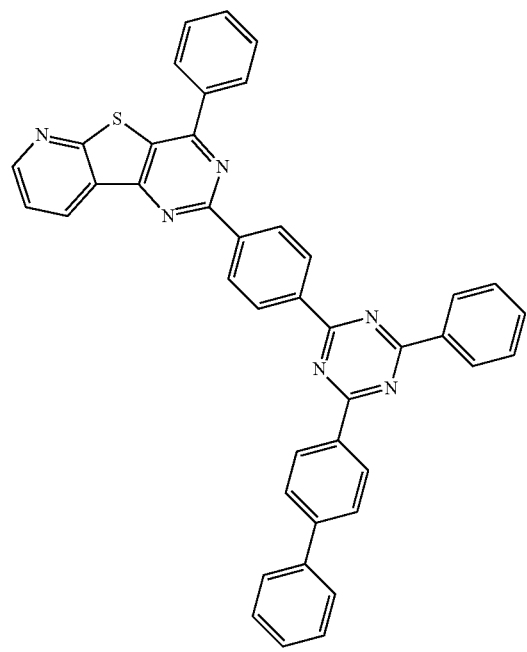 [SMILES: c1ccc(-c2ccc(-c3nc(-c4ccccc4)nc(-c4ccc(-c5nc(-c6ccccc6)c6oc7ncccc7c6n5)cc4)n3)cc2)cc1]
301
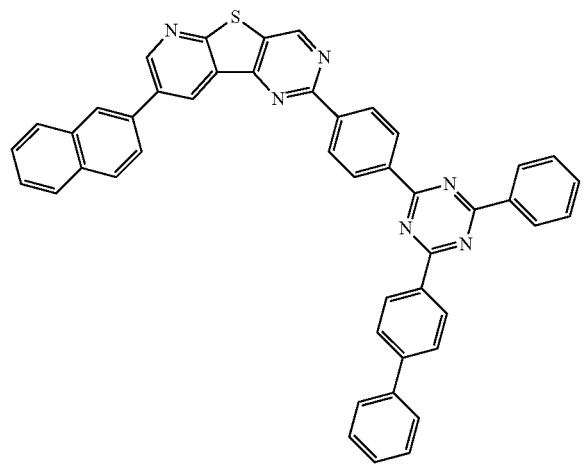
302
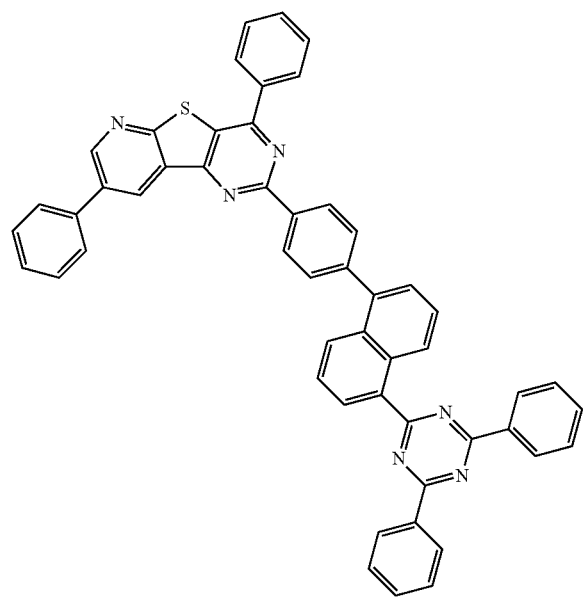
303
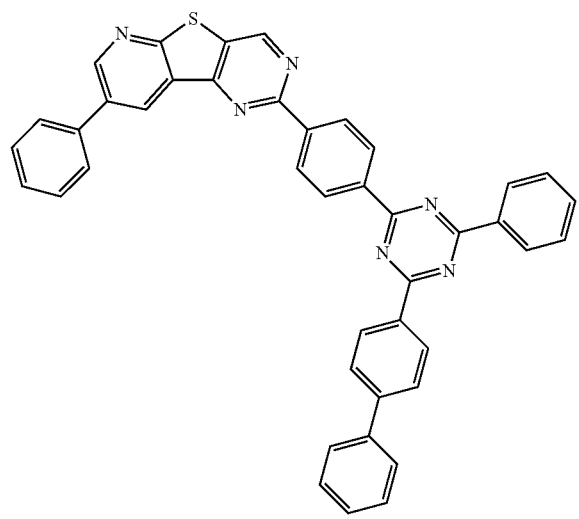

304
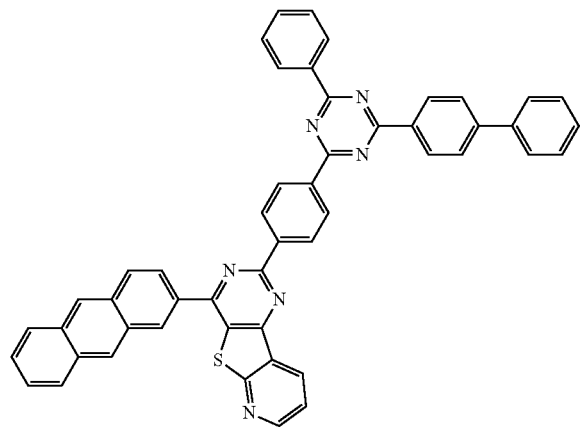
305
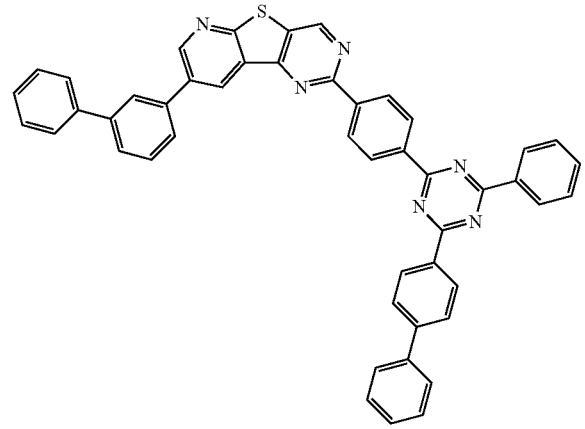
306
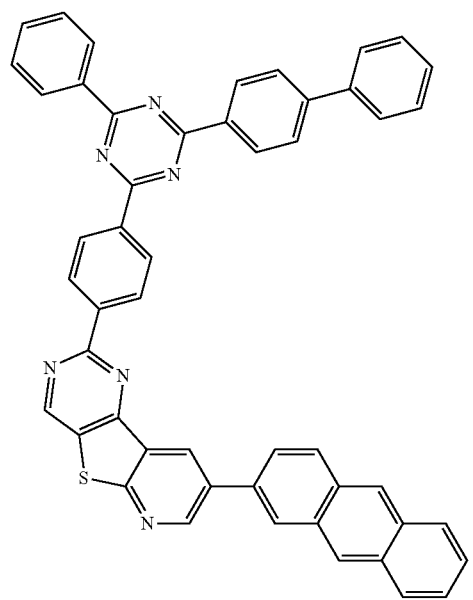
307
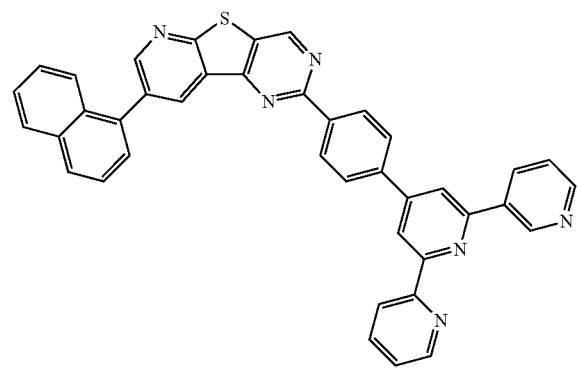

-continued
308
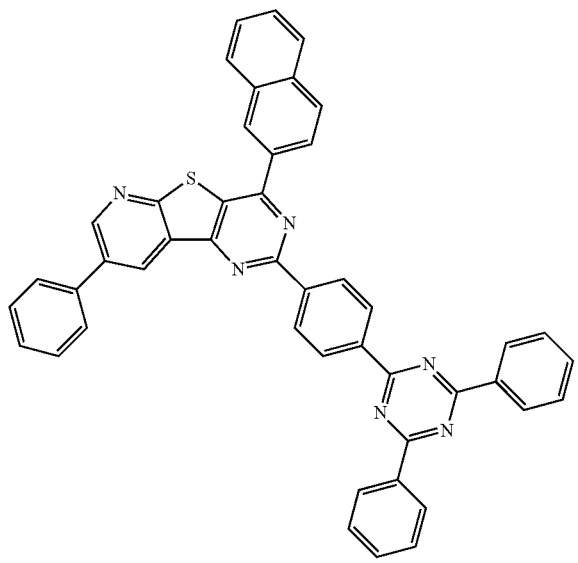
309
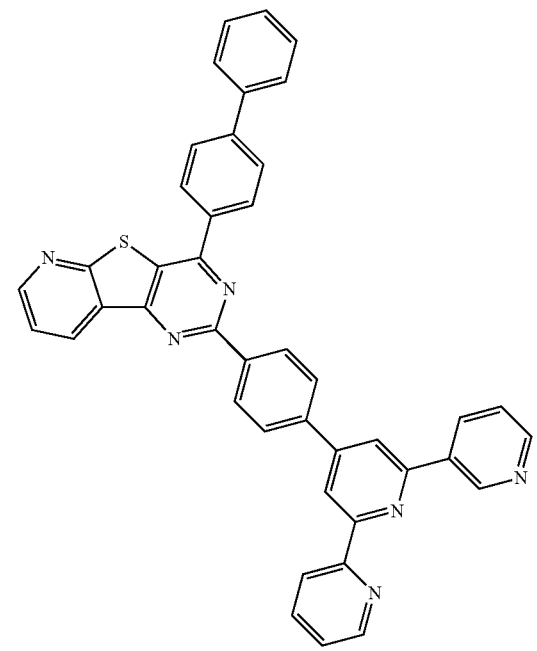
310
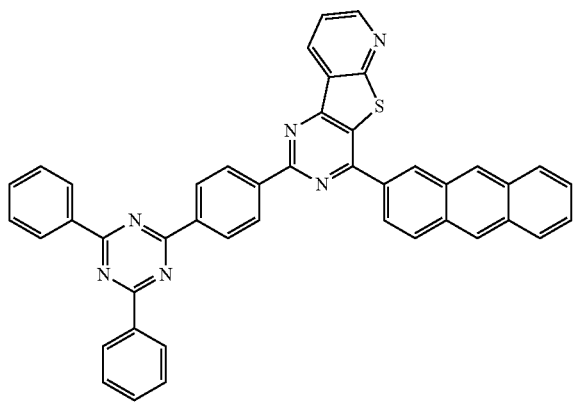
311
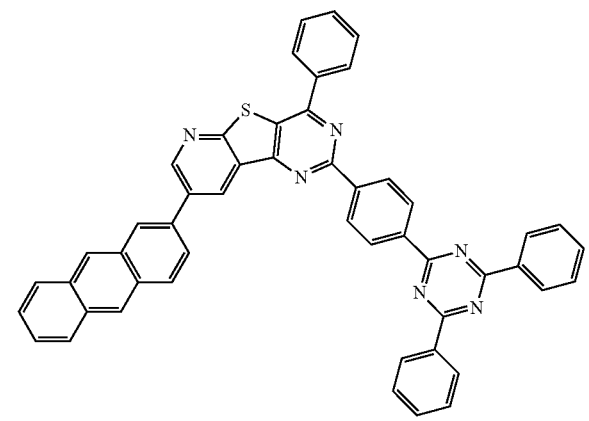
312
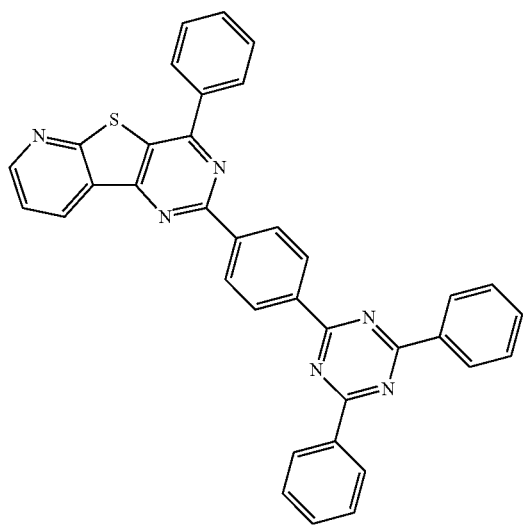 [SMILES: c1ccc(-c2nc(-c3ccccc3)nc(-c3ccc(-c4nc(-c5ccccc5)c5oc6ncccc6c5n4)cc3)n2)cc1]
313
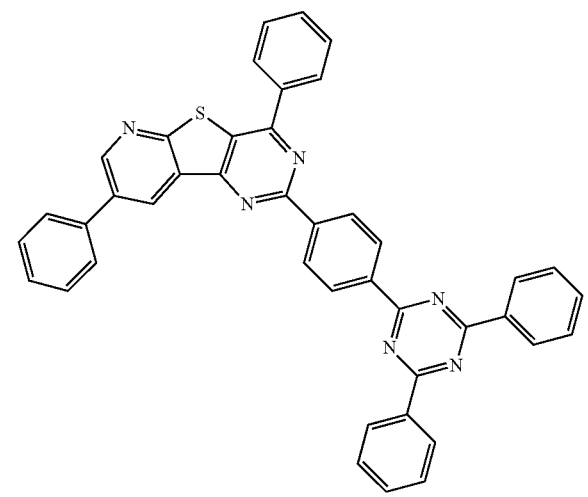 [SMILES: c1ccc(-c2cnc3oc4c(-c5ccccc5)nc(-c5ccc(-c6nc(-c7ccccc7)nc(-c7ccccc7)n6)cc5)nc4c3c2)cc1]

-continued
314
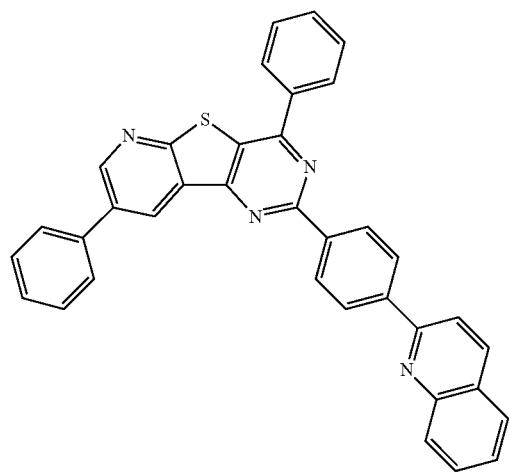 [SMILES: c1ccc(-c2cnc3oc4c(-c5ccccc5)nc(-c5ccc(-c6ccc7ccccc7n6)cc5)nc4c3c2)cc1]
315
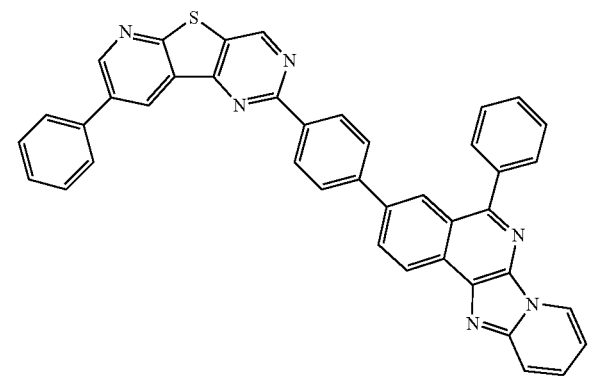
316
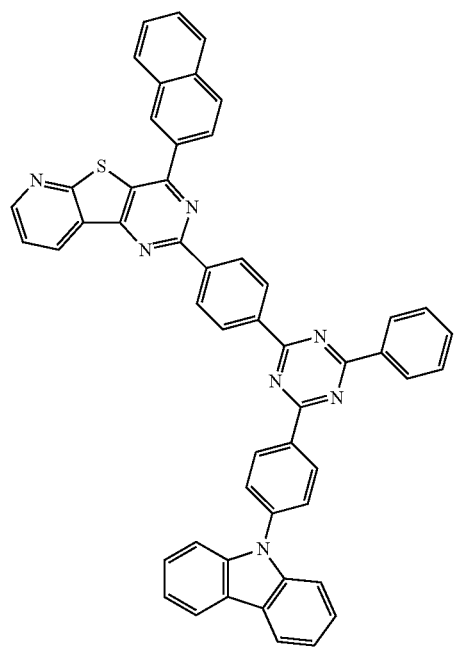
317
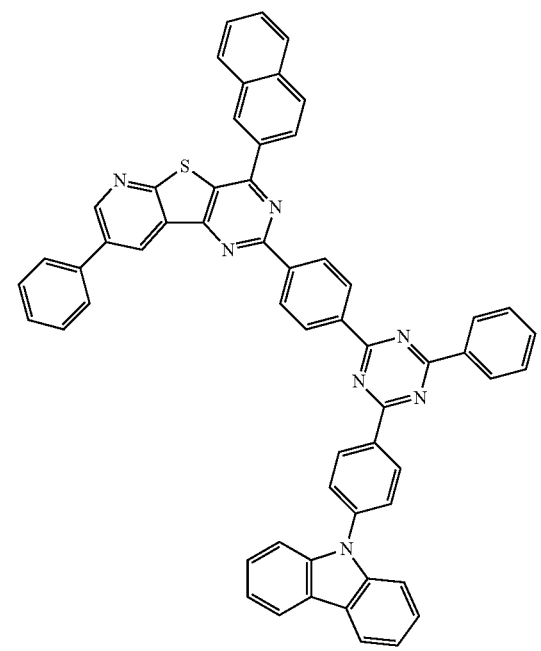 [SMILES: c1ccc(-c2cnc3oc4c(-c5ccc6ccccc6c5)nc(-c5ccc(-c6nc(-c7ccccc7)nc(-c7ccc(-n8c9ccccc9c9ccccc98)cc7)n6)cc5)nc4c3c2)cc1]
318
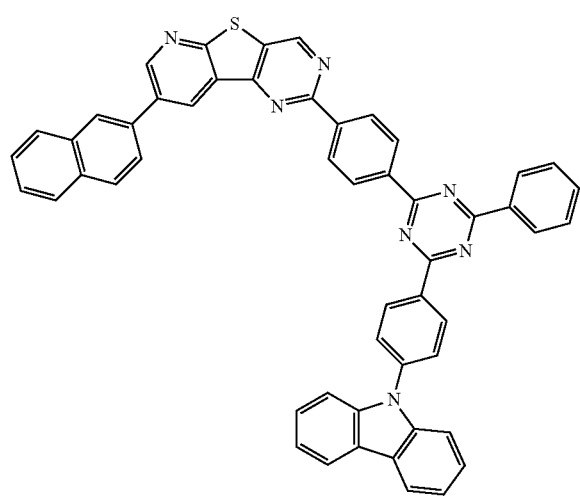
319
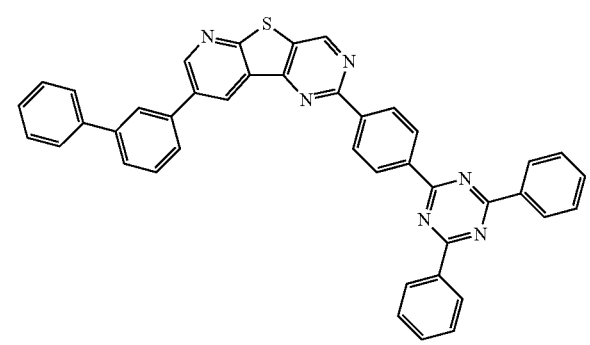

-continued
320
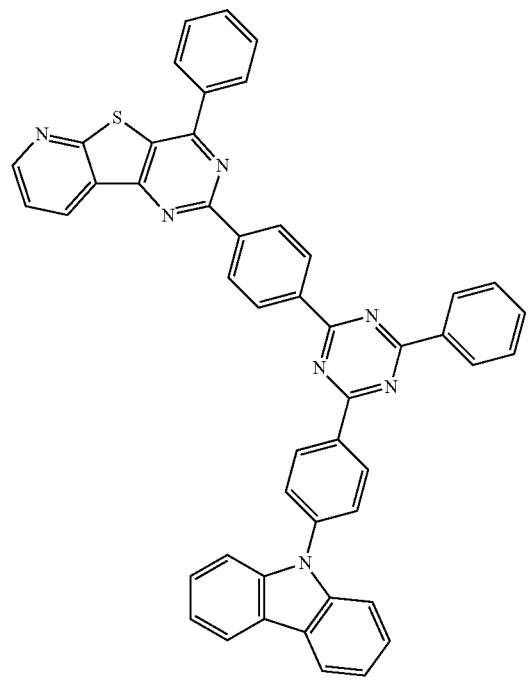
321
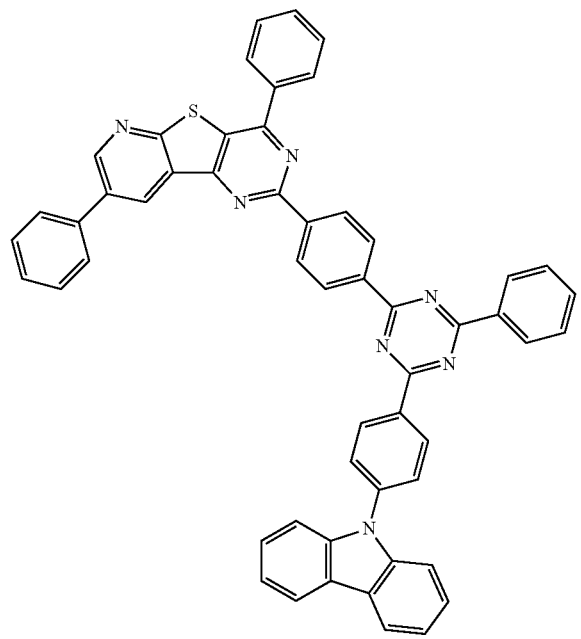 [SMILES: c1ccc(-c2cnc3sc4c(-c5ccccc5)nc(-c5ccc(-c6nc(-c7ccccc7)nc(-c7ccc(-n8c9ccccc9c9ccccc98)cc7)n6)cc5)nc4c3c2)cc1]
322
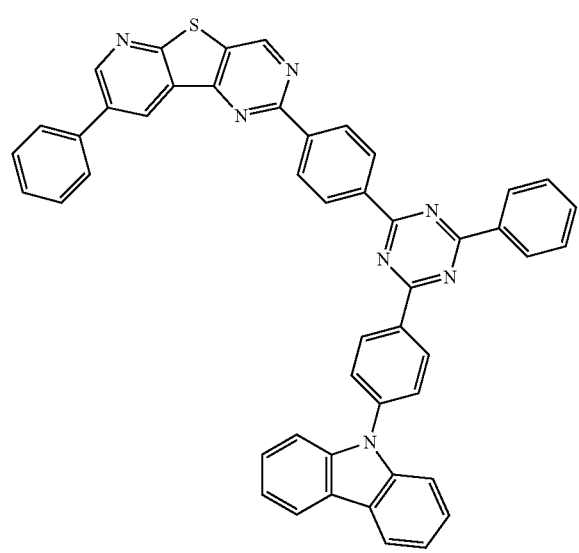
323
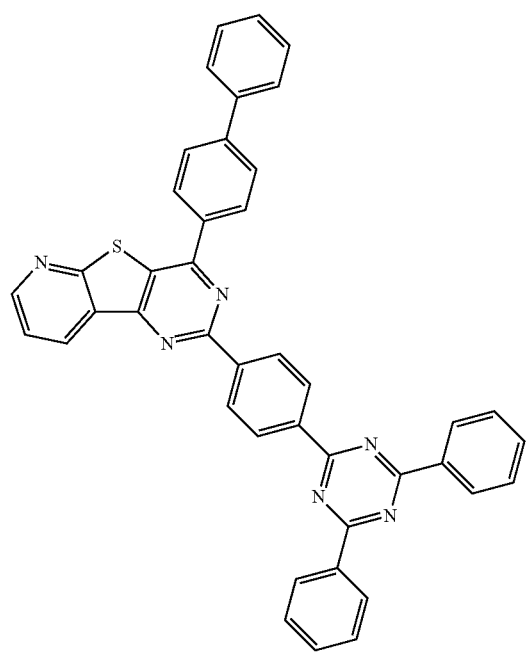

-continued
324
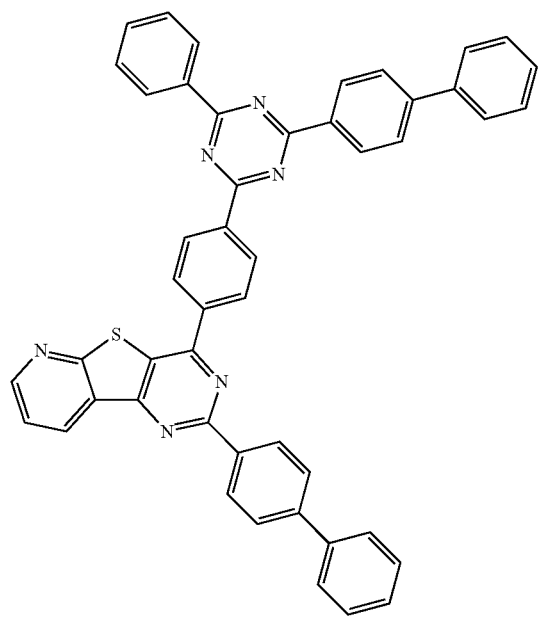
325
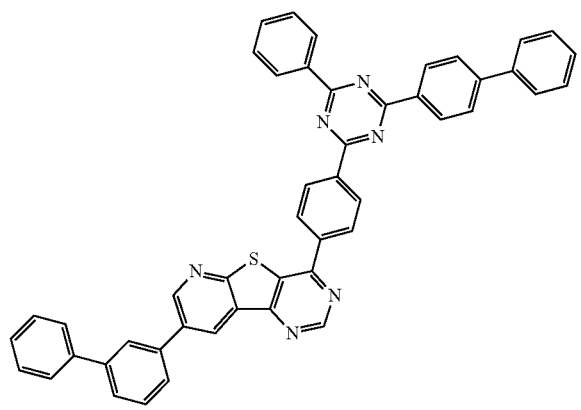
326
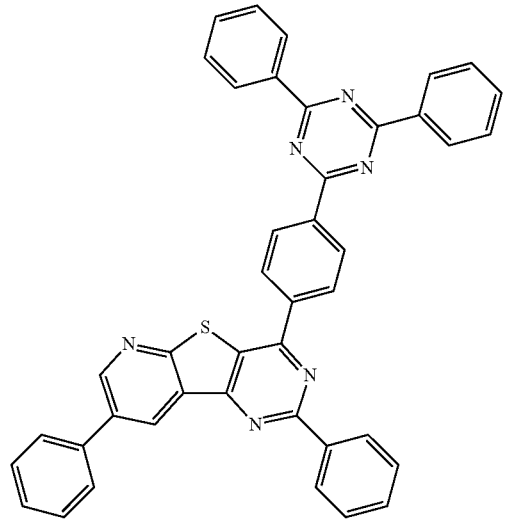
327
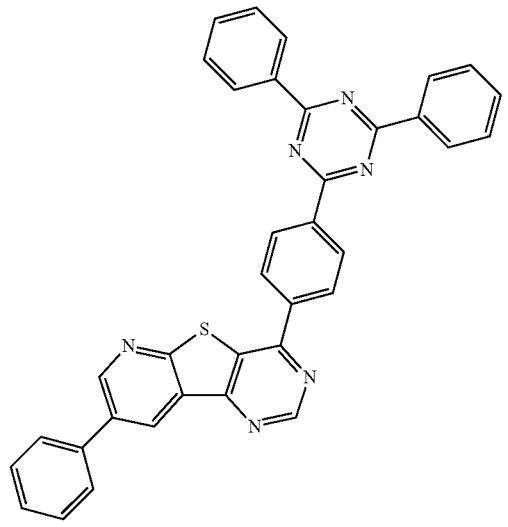

-continued
328
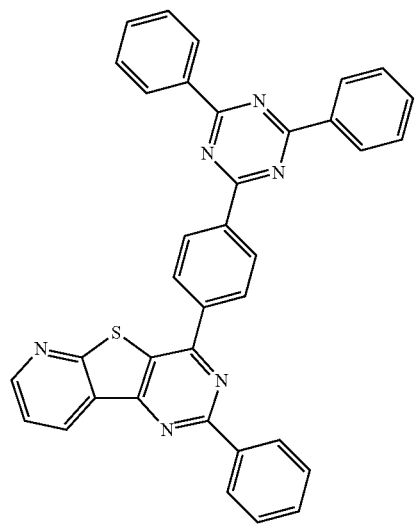
329
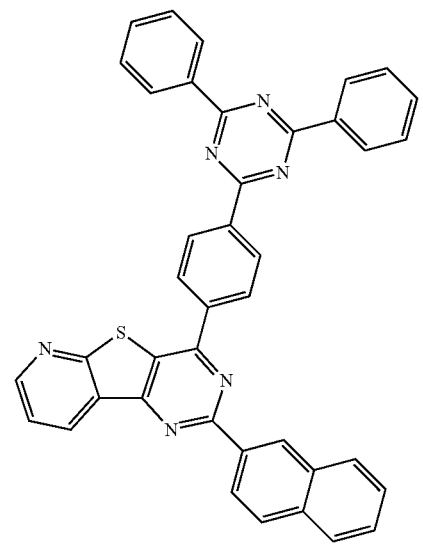
330
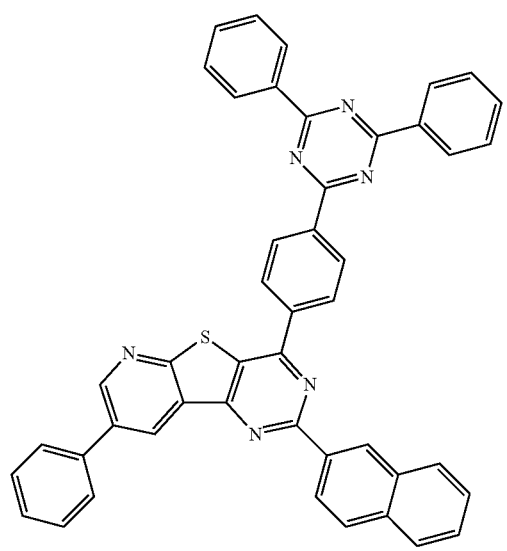
331
332
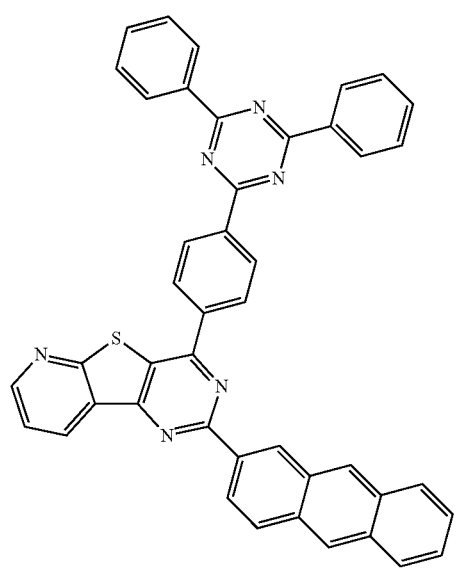
333
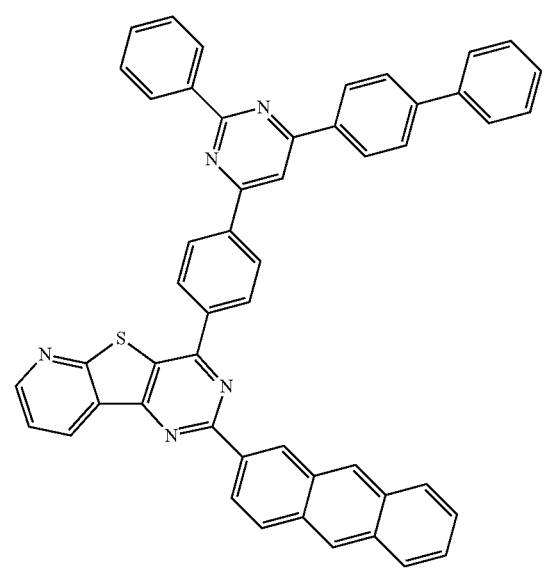

334
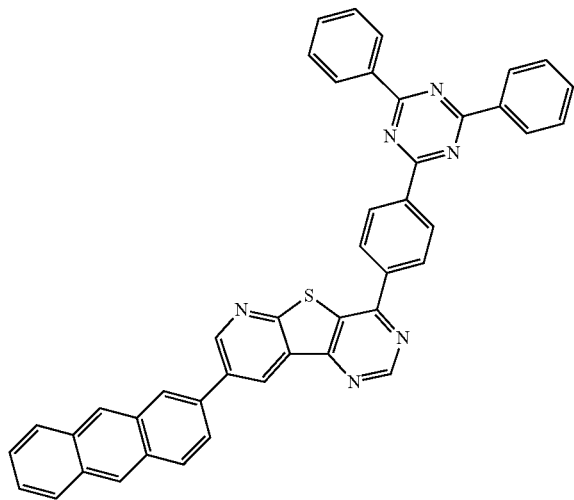
335
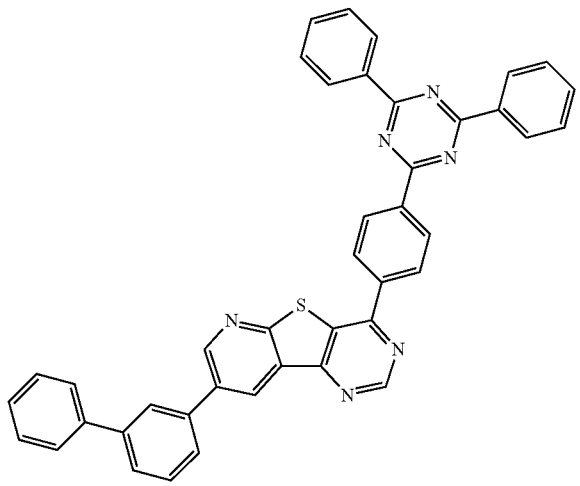
336
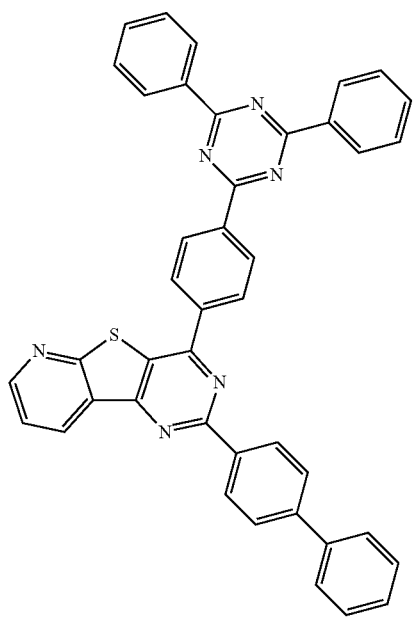
337
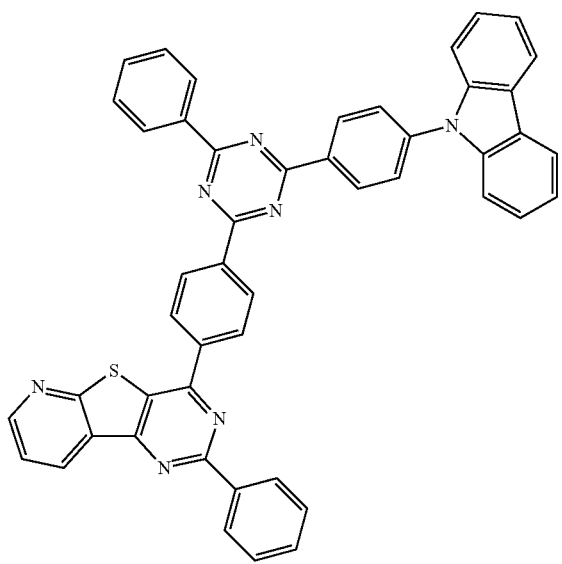

-continued
338
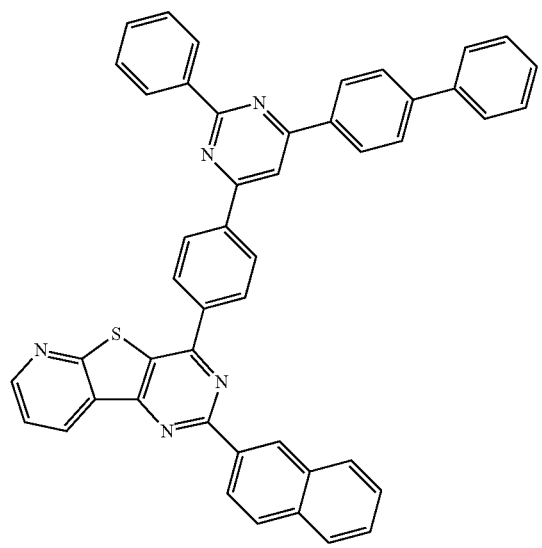 [SMILES: c1ccc(-c2ccc(-c3cc(-c4ccc(-c5nc(-c6ccc7ccccc7c6)nc6c5oc5ncccc56)cc4)nc(-c4ccccc4)n3)cc2)cc1]
339
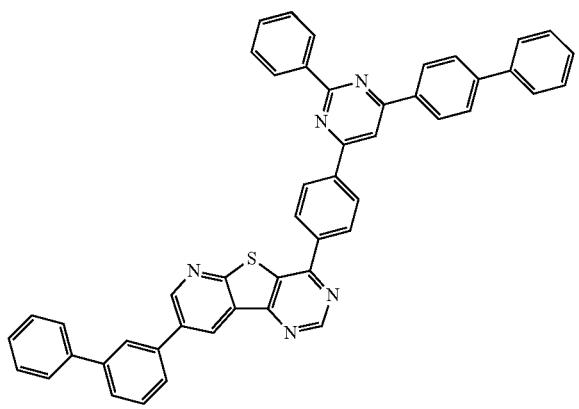
340
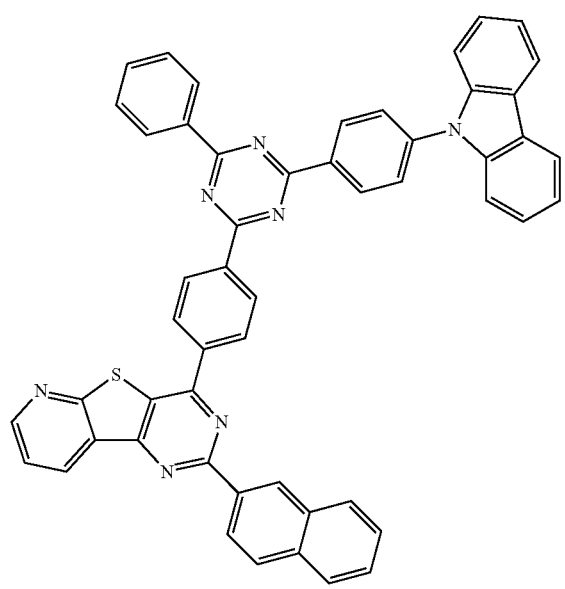
341
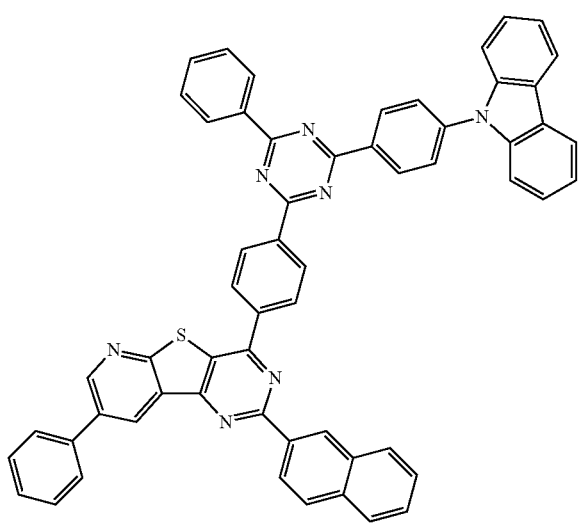
342
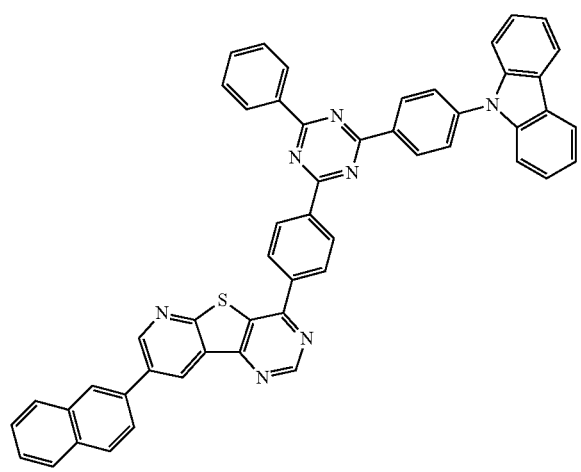
343
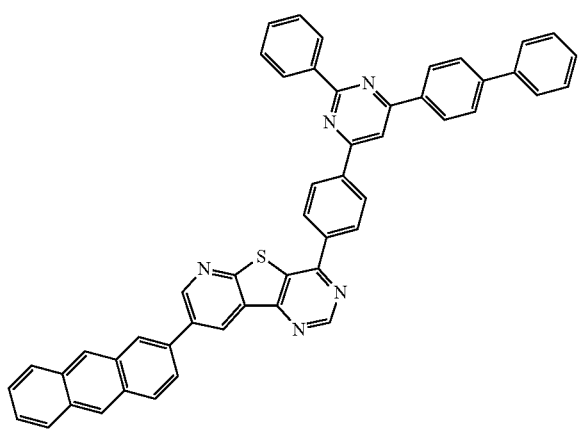

-continued
344
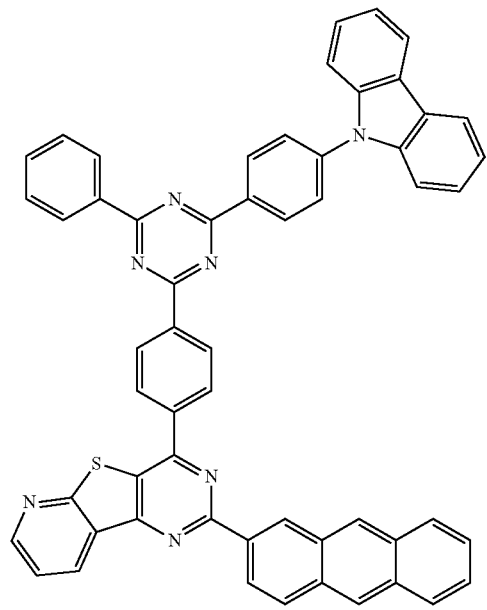
345
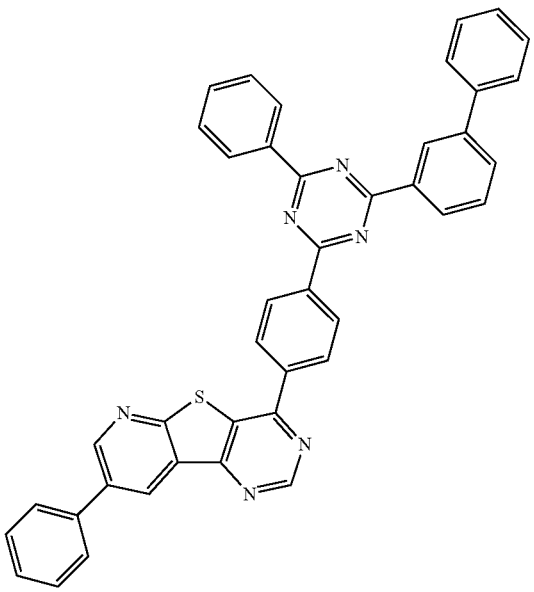
346
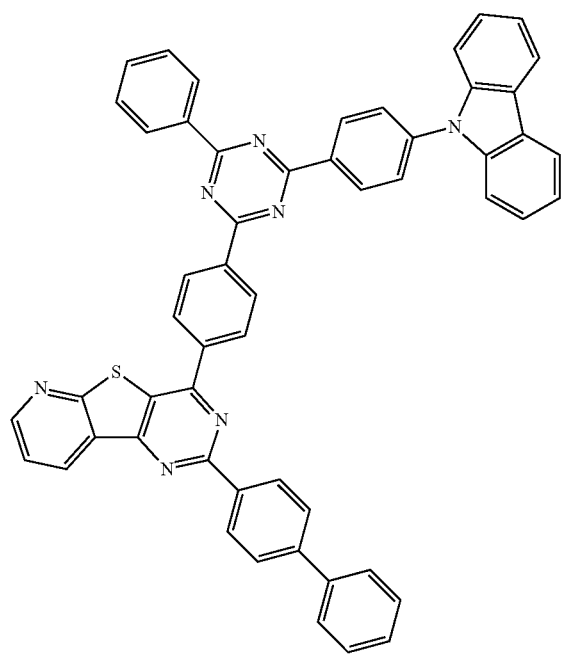
347
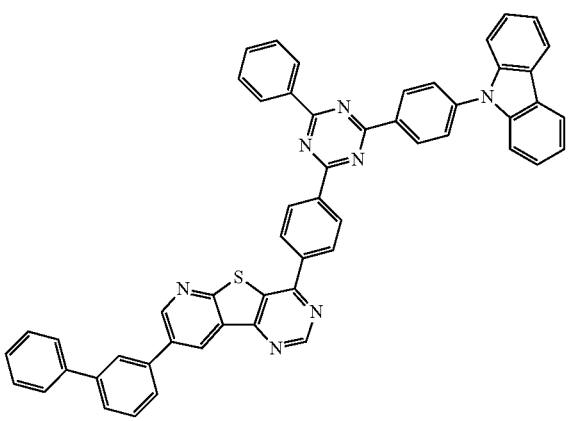

348
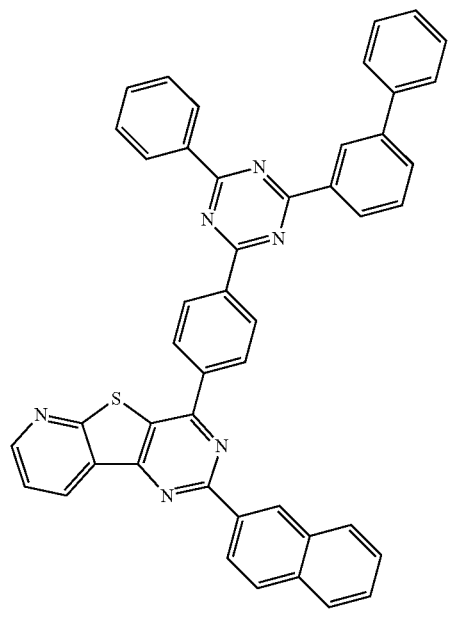 [SMILES: c1ccc(-c2cccc(-c3nc(-c4ccccc4)nc(-c4ccc(-c5nc(-c6ccc7ccccc7c6)nc6c5oc5ncccc56)cc4)n3)c2)cc1]
349
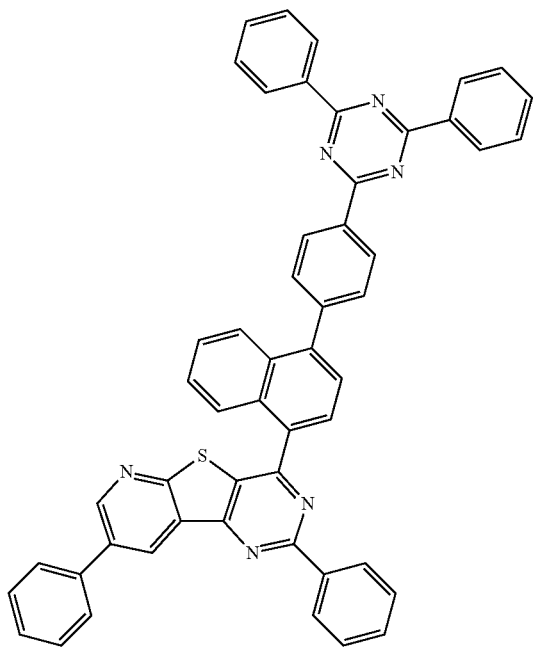
350
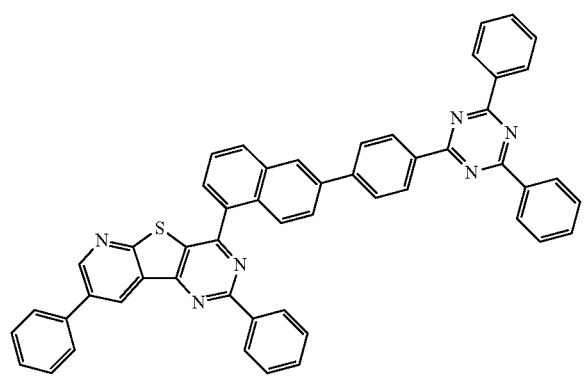
351
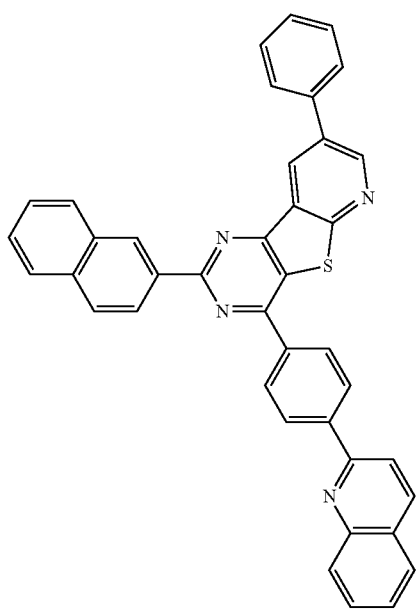

-continued
352
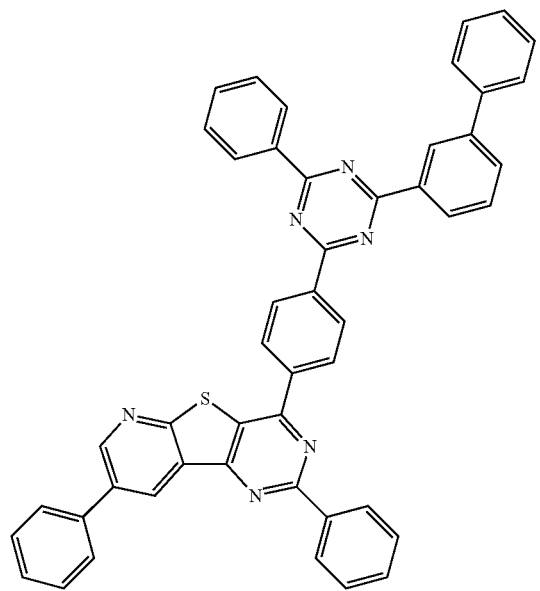
353
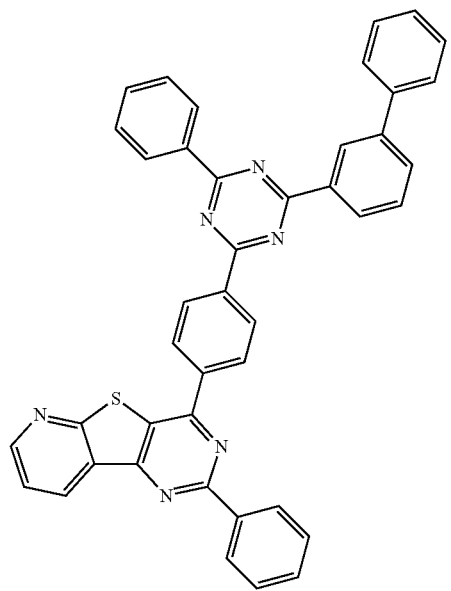
354
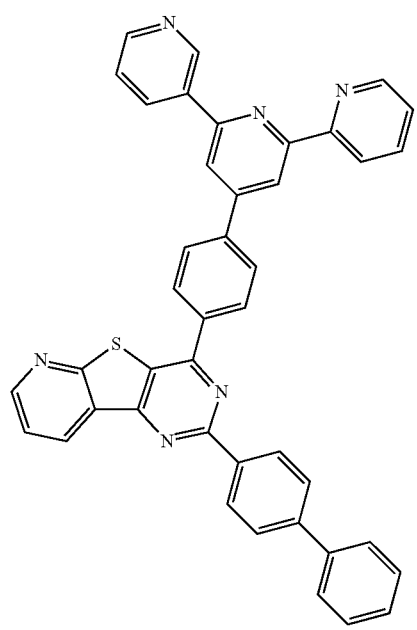
355
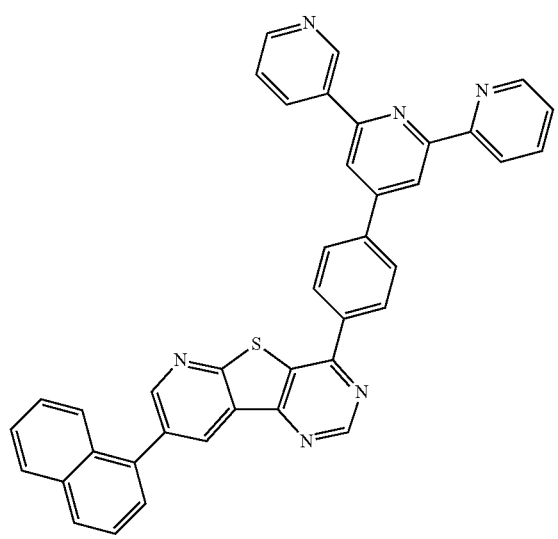

-continued
356
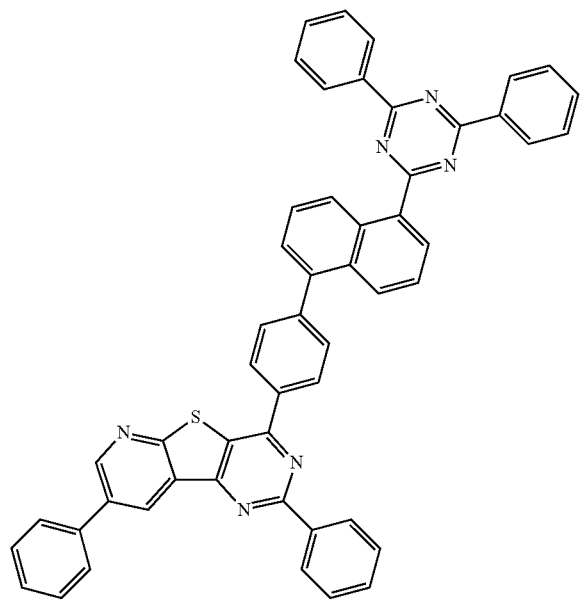
357
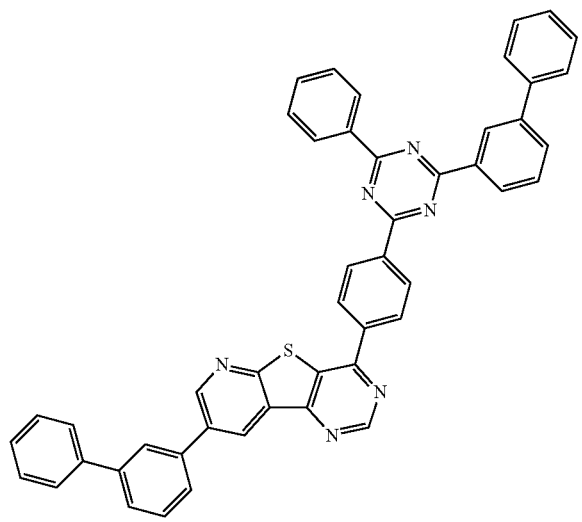
358
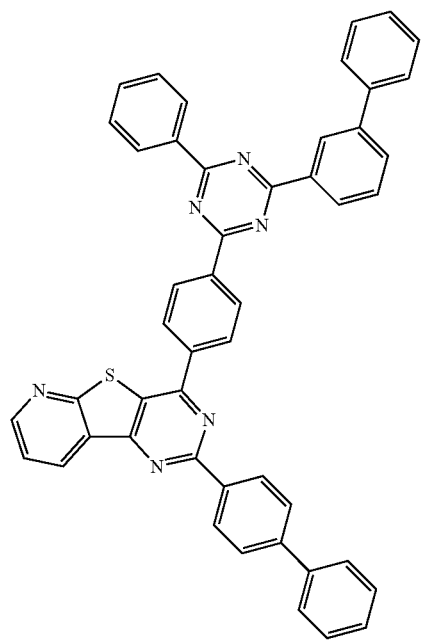 [SMILES: c1ccc(-c2ccc(-c3nc(-c4ccc(-c5nc(-c6ccccc6)nc(-c6cccc(-c7ccccc7)c6)n5)cc4)c4oc5ncccc5c4n3)cc2)cc1]
359
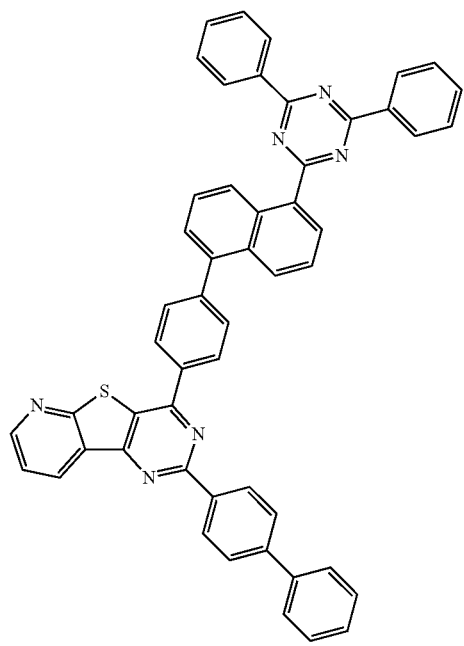

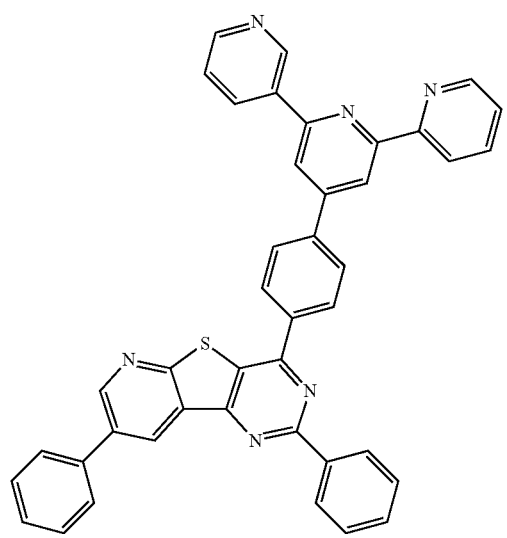

-continued
364
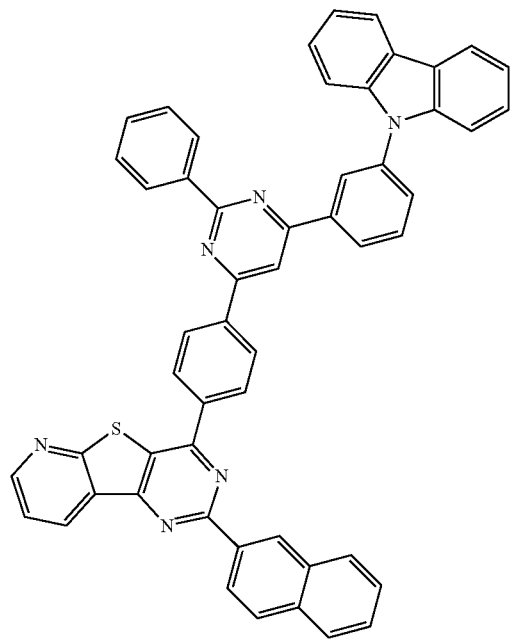 [SMILES: c1ccc(-c2nc(-c3ccc(-c4nc(-c5ccc6ccccc6c5)nc5c4oc4ncccc45)cc3)nc(-c3cccc(-n4c5ccccc5c5ccccc54)c3)n2)cc1]
365
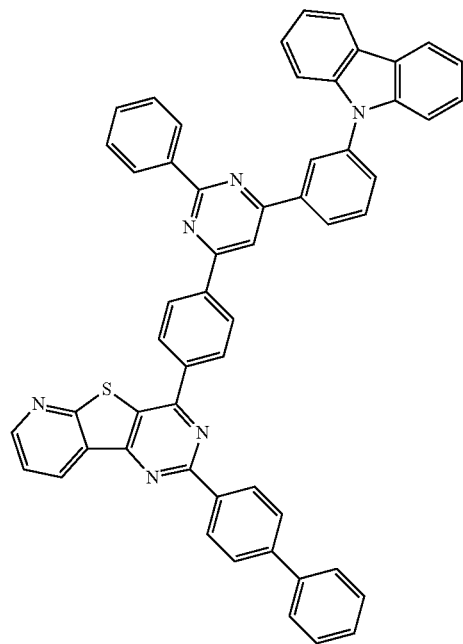 [SMILES: c1ccc(-c2ccc(-c3nc(-c4ccc(-c5nc(-c6ccccc6)nc(-c6cccc(-n7c8ccccc8c8ccccc87)c6)n5)cc4)c4oc5ncccc5c4n3)cc2)cc1]
366
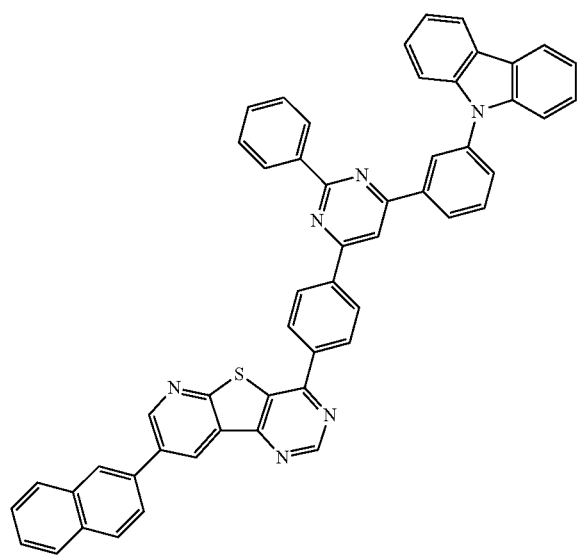
367
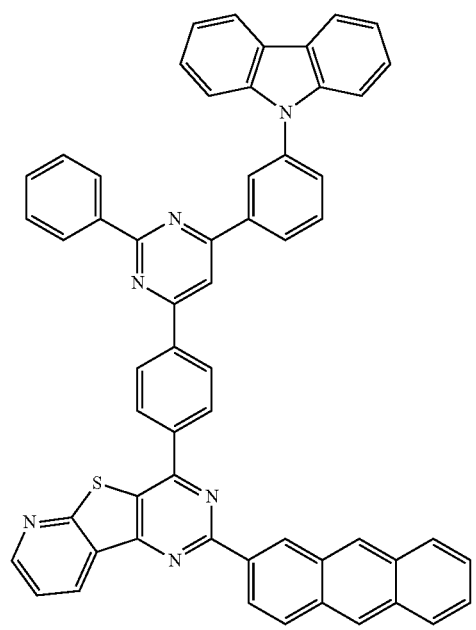

-continued
368
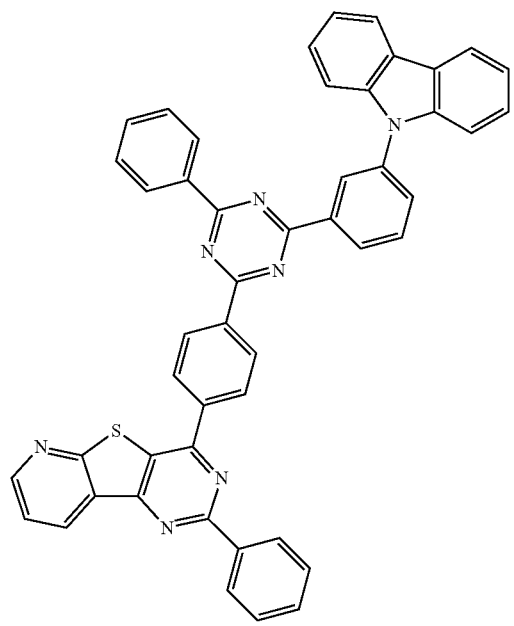 [SMILES: c1ccc(-c2nc(-c3ccc(-c4nc(-c5ccccc5)nc5c4oc4ncccc45)cc3)nc(-c3cccc(-n4c5ccccc5c5ccccc54)c3)n2)cc1]
369
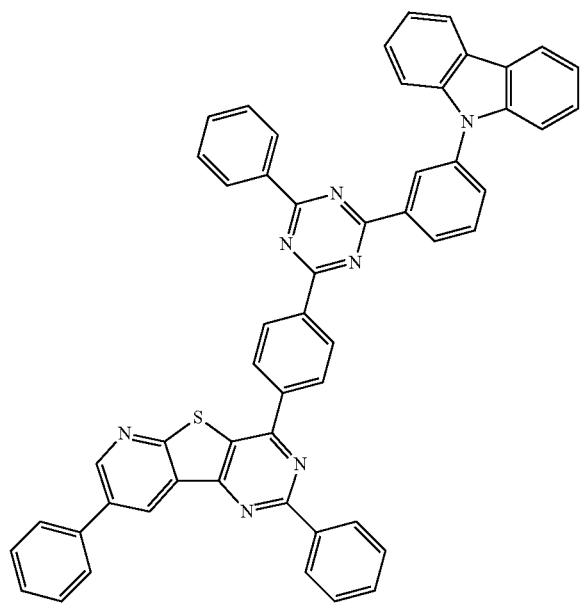
370
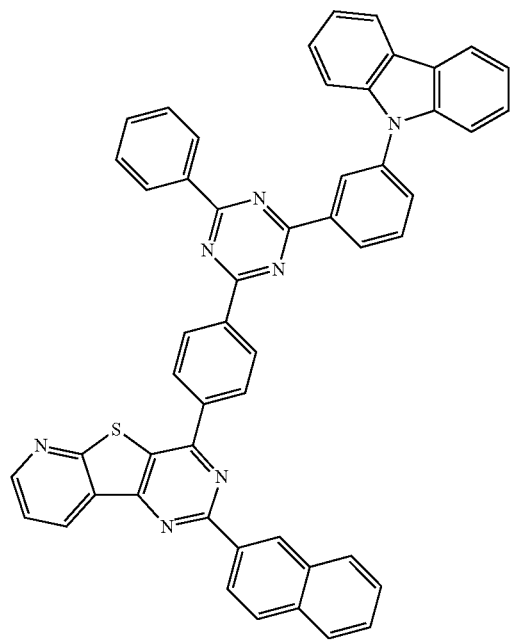
371
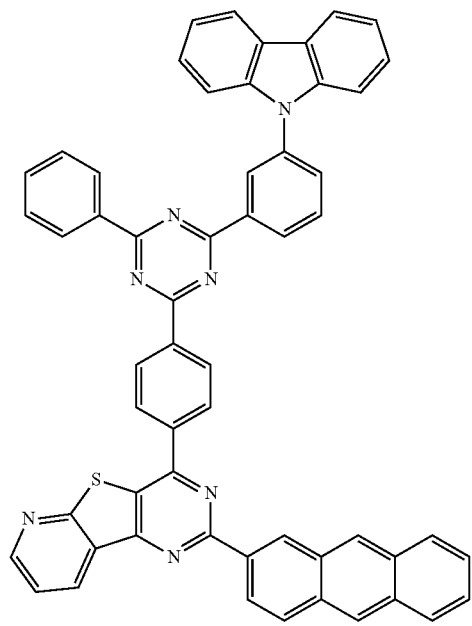 [SMILES: c1ccc(-c2nc(-c3ccc(-c4nc(-c5ccc6cc7ccccc7cc6c5)nc5c4oc4ncccc45)cc3)nc(-c3cccc(-n4c5ccccc5c5ccccc54)c3)n2)cc1]

-continued
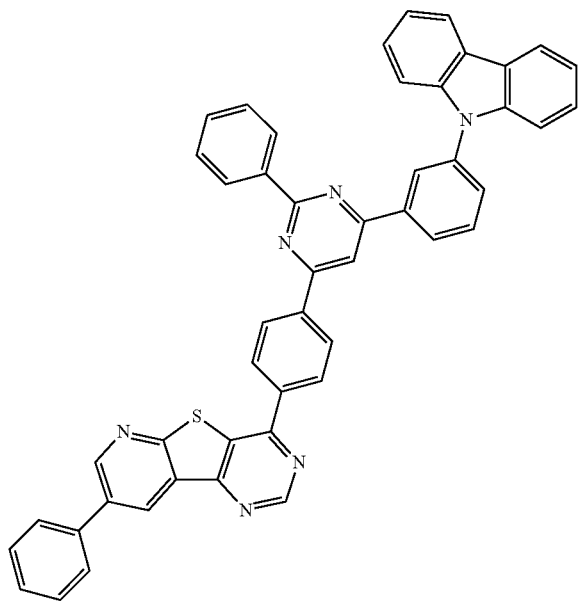
372
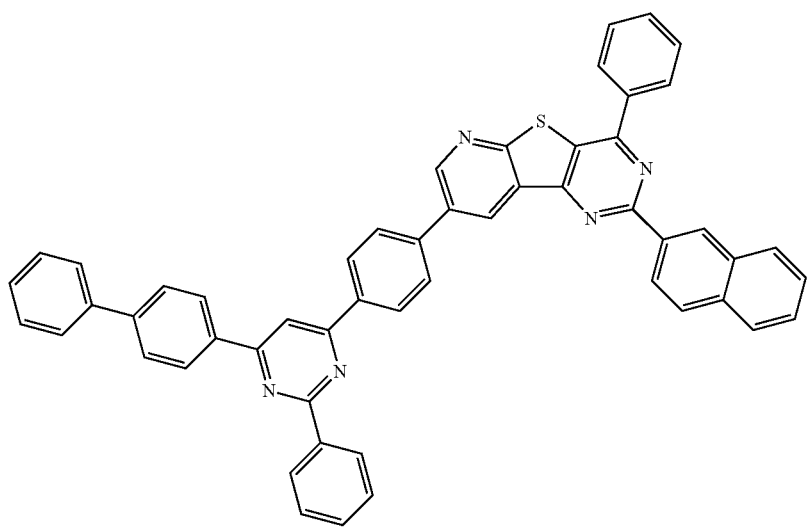
373
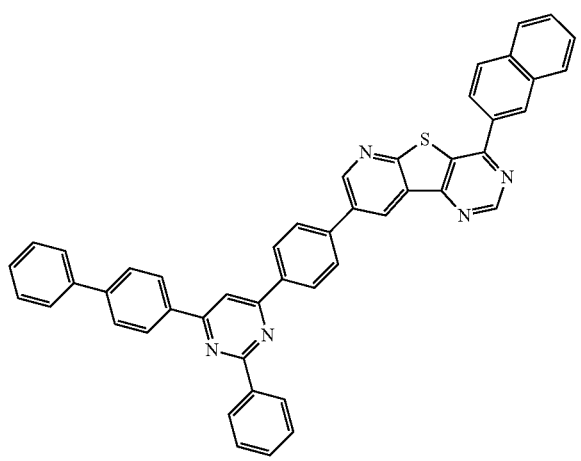
374
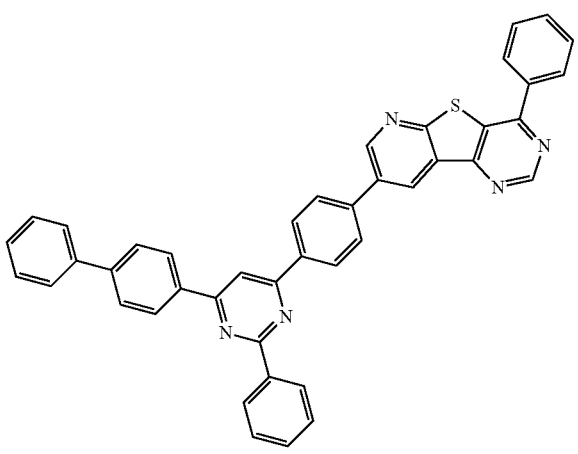
375

-continued
376
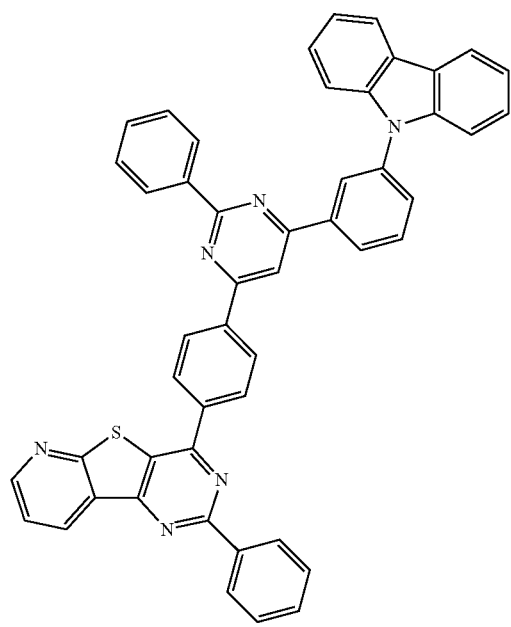
377
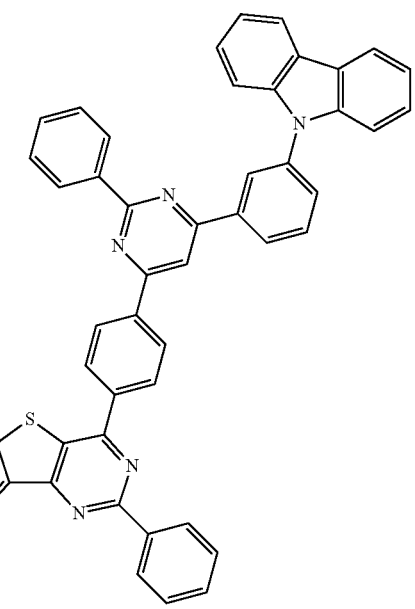
378
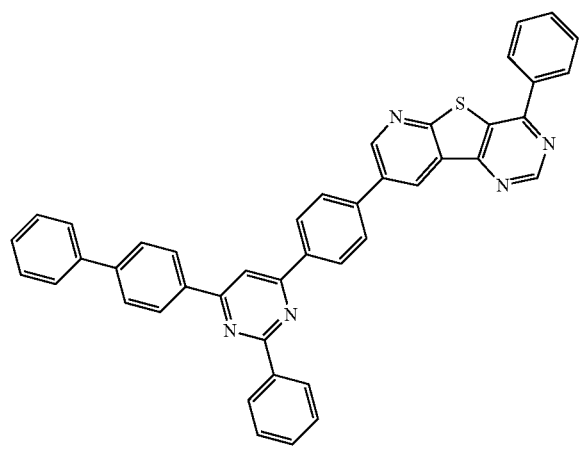
379
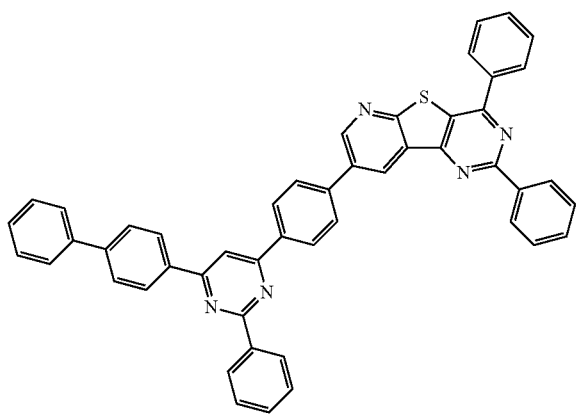 [SMILES: c1ccc(-c2ccc(-c3cc(-c4ccc(-c5cnc6oc7c(-c8ccccc8)nc(-c8ccccc8)nc7c6c5)cc4)nc(-c4ccccc4)n3)cc2)cc1]

-continued
380
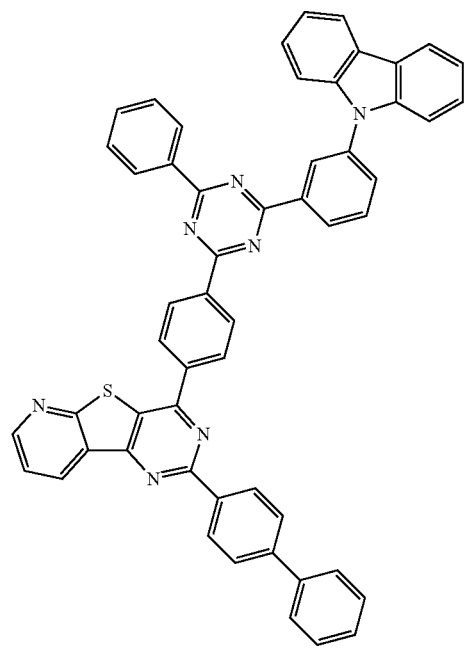
381
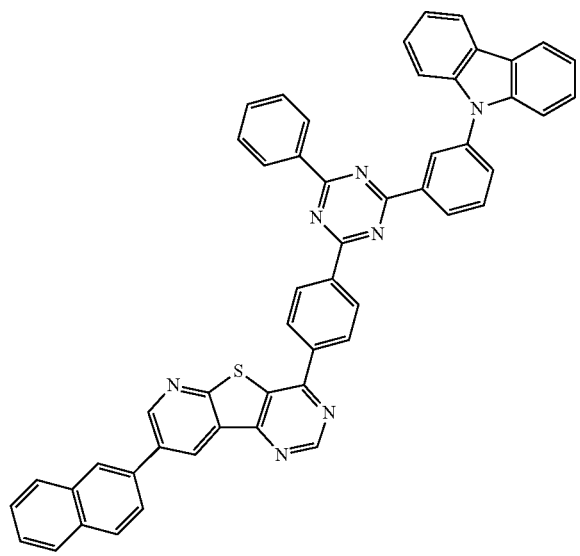
382
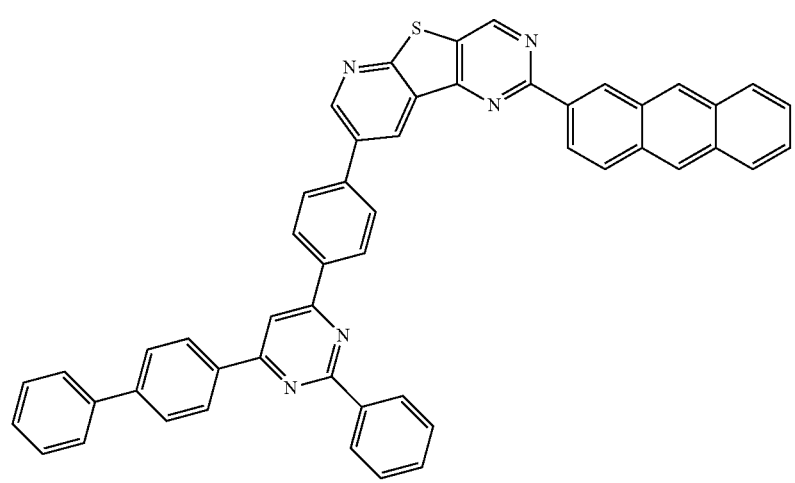

-continued
383
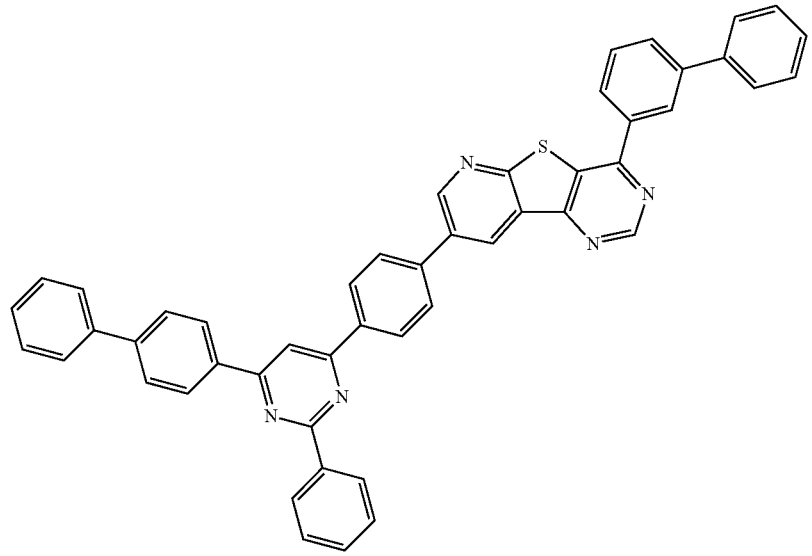
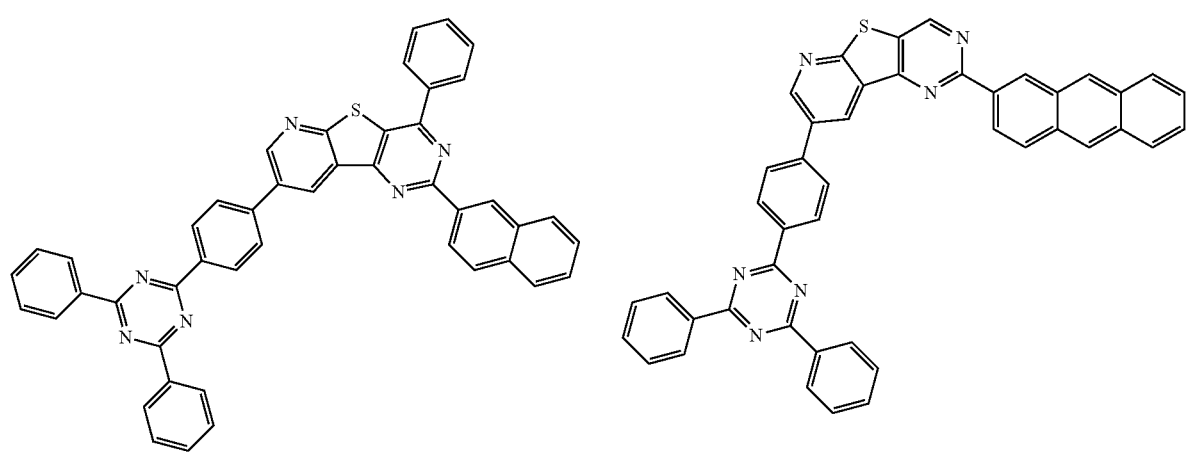

386
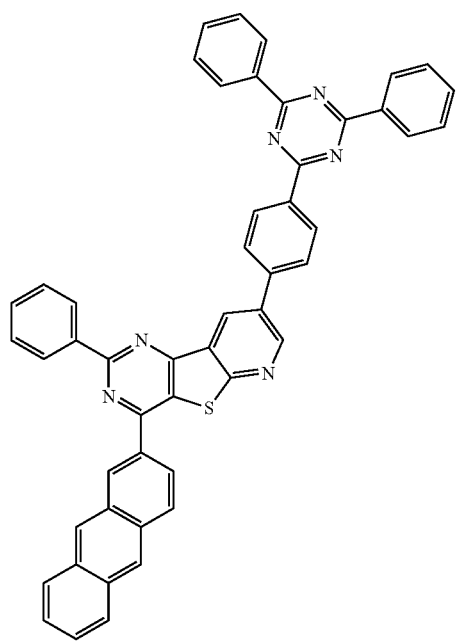
387
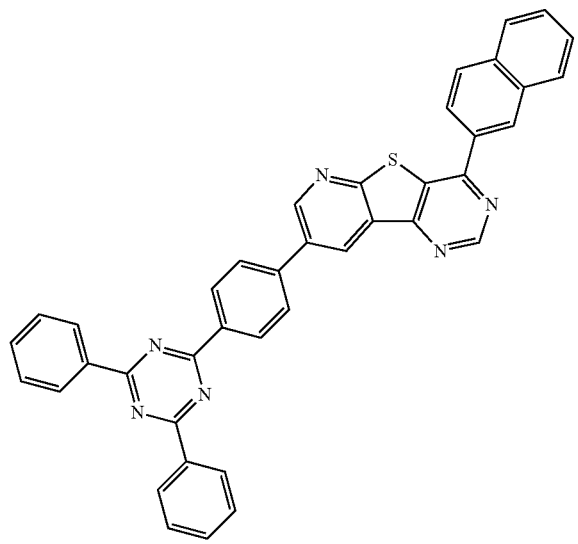
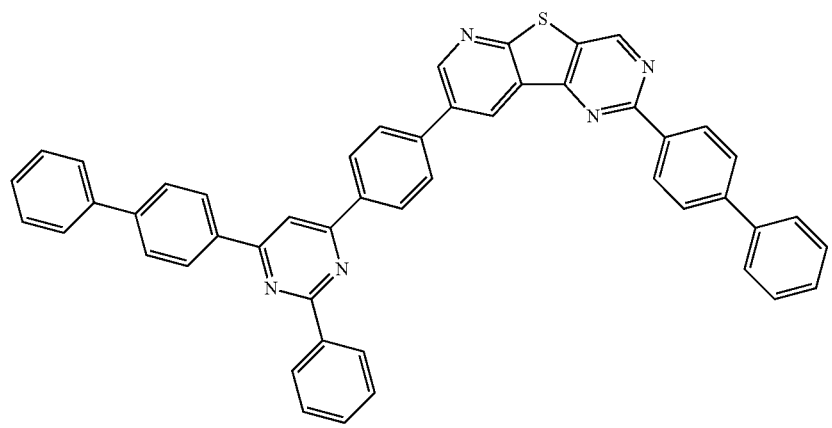
388
389
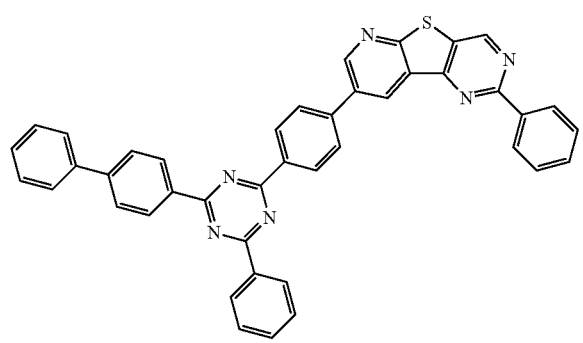
390
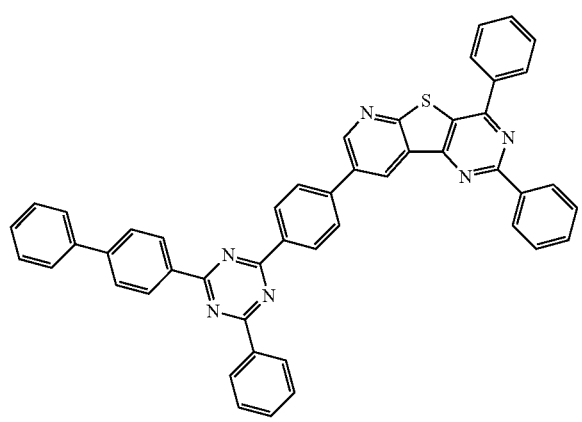 [SMILES: c1ccc(-c2ccc(-c3nc(-c4ccccc4)nc(-c4ccc(-c5cnc6oc7c(-c8ccccc8)nc(-c8ccccc8)nc7c6c5)cc4)n3)cc2)cc1]

-continued
391
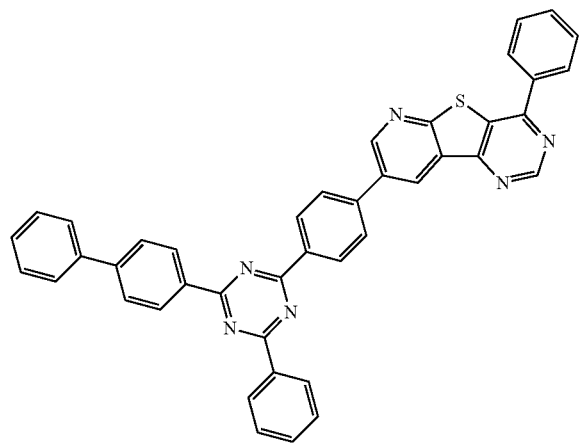
392
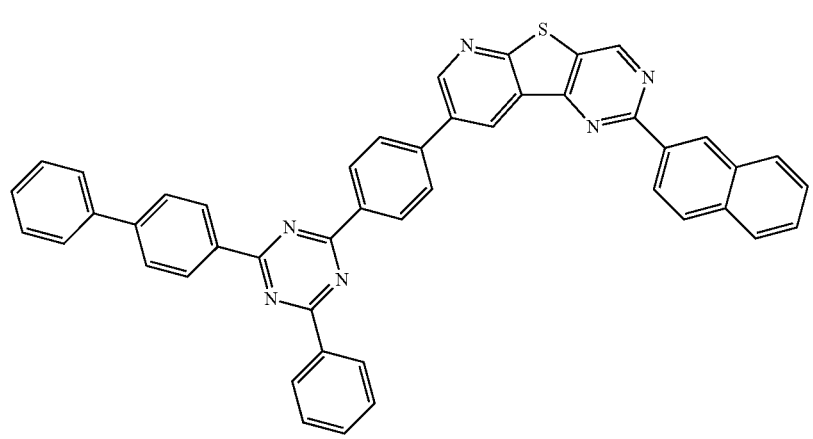
393
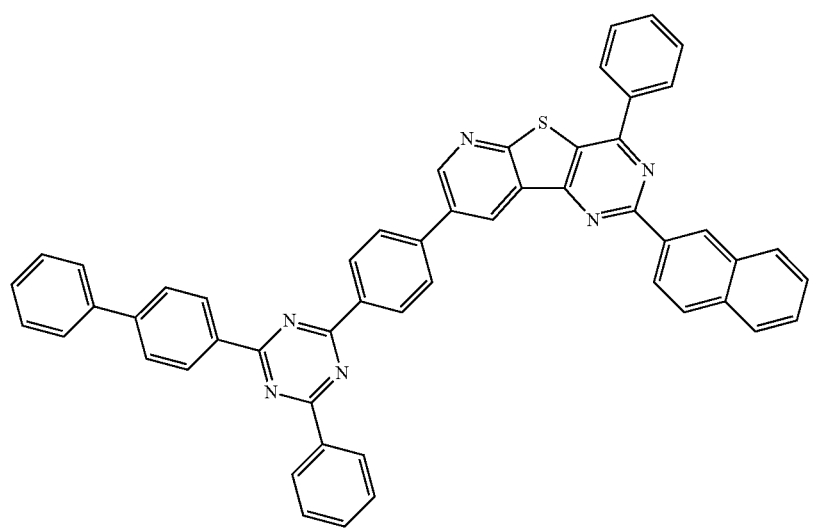 [SMILES: c1ccc(-c2ccc(-c3nc(-c4ccccc4)nc(-c4ccc(-c5cnc6oc7c(-c8ccccc8)nc(-c8ccc9ccccc9c8)nc7c6c5)cc4)n3)cc2)cc1]

-continued
394
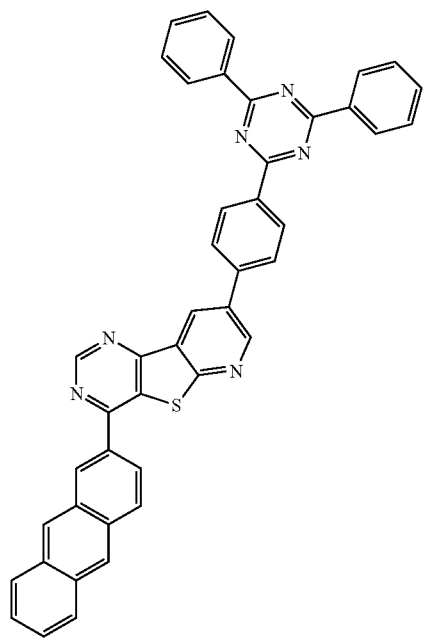
395
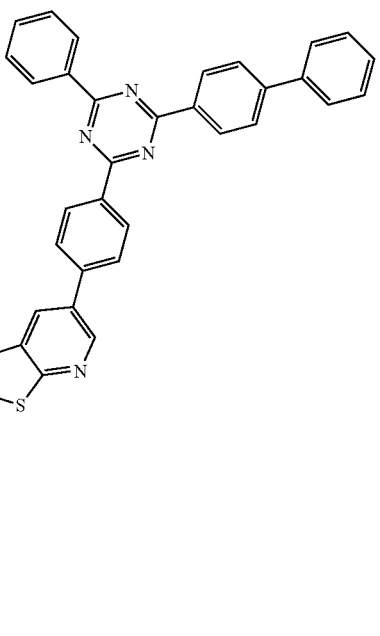
396
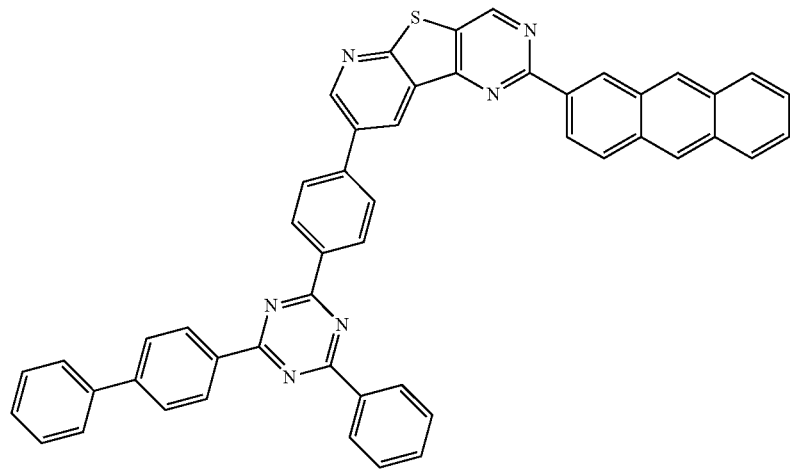
397
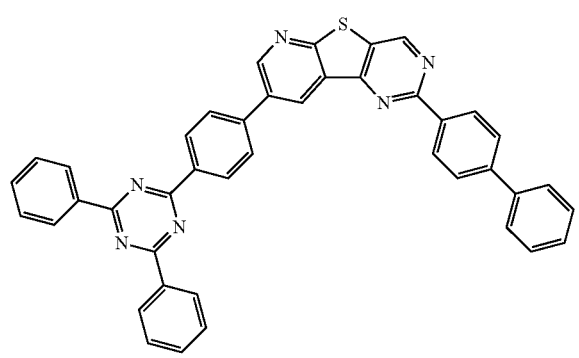

-continued
398
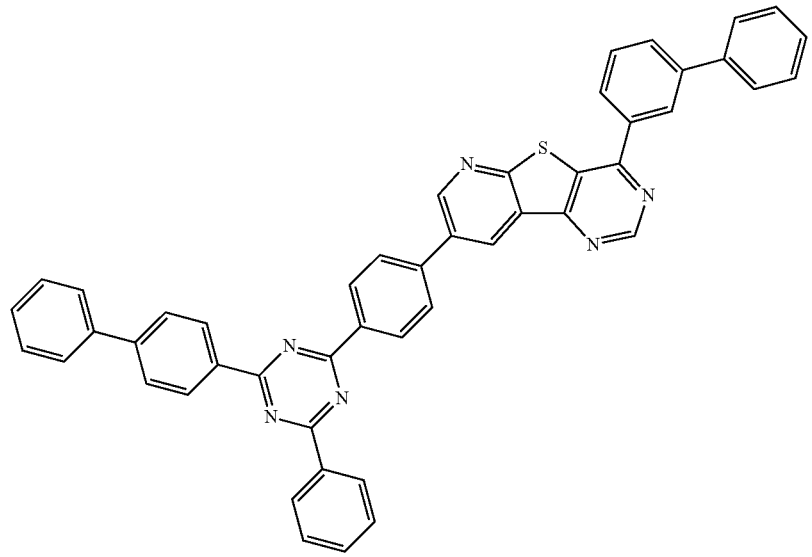
399
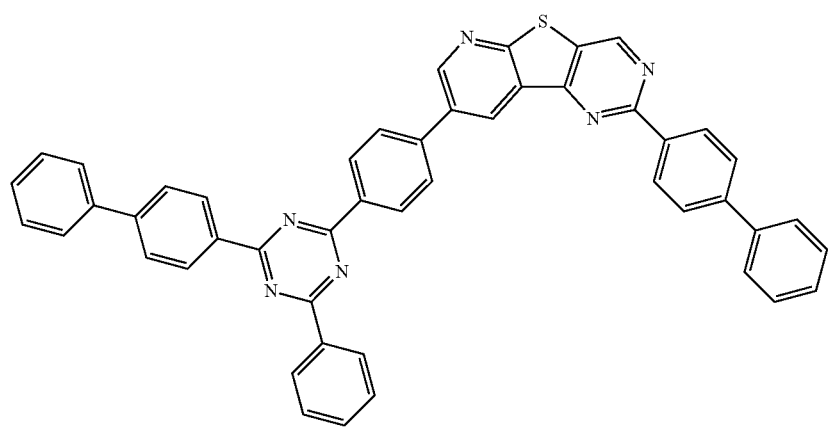
400
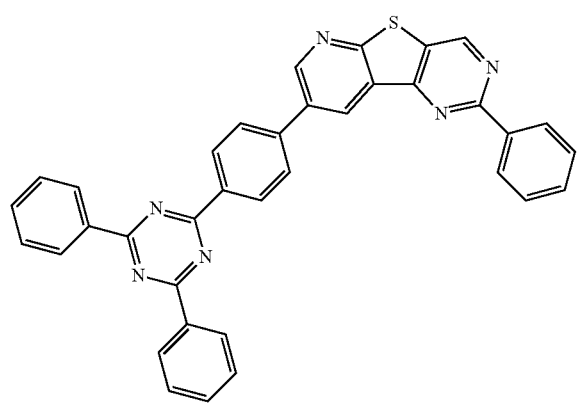
401
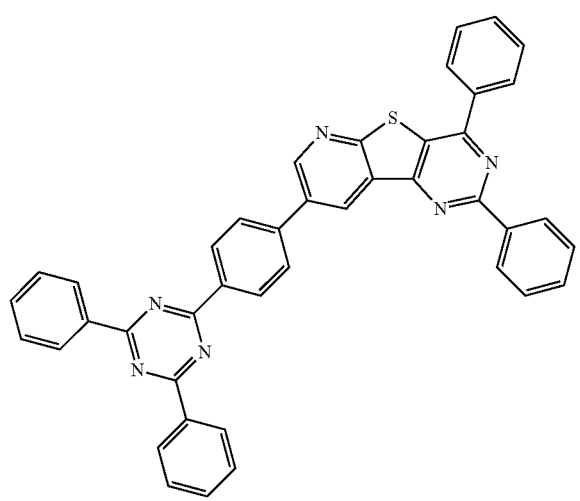 [SMILES: c1ccc(-c2cc(-c3ccc(-c4cnc5oc6c(-c7ccccc7)nc(-c7ccccc7)nc6c5c4)cc3)nc(-c3ccccc3)n2)cc1]

-continued
402
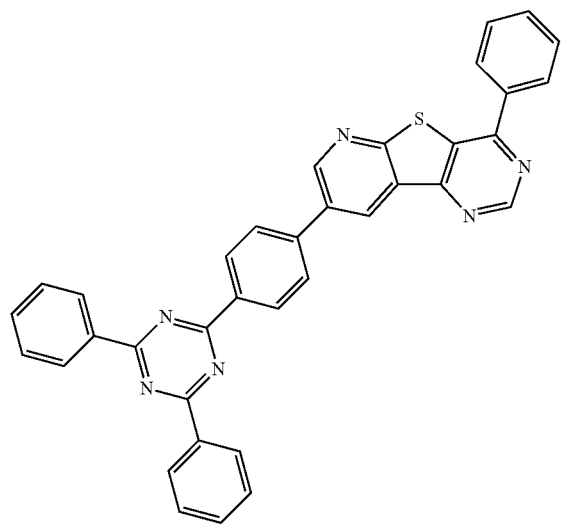
403
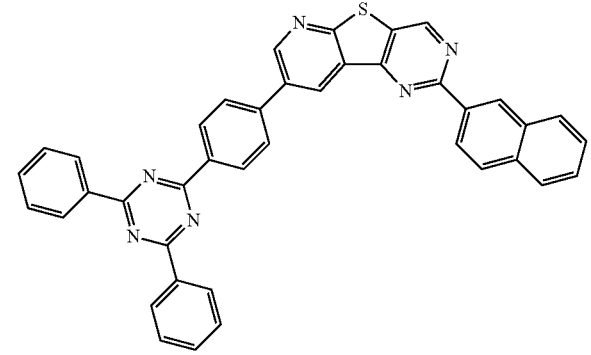
404
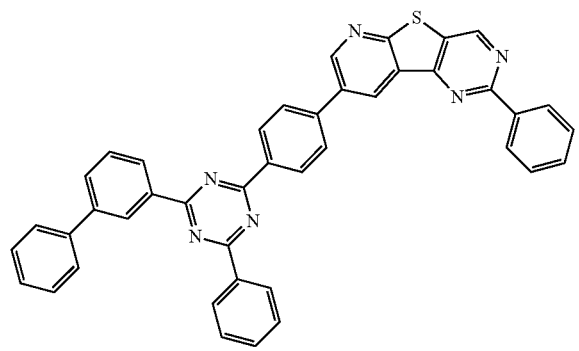
405
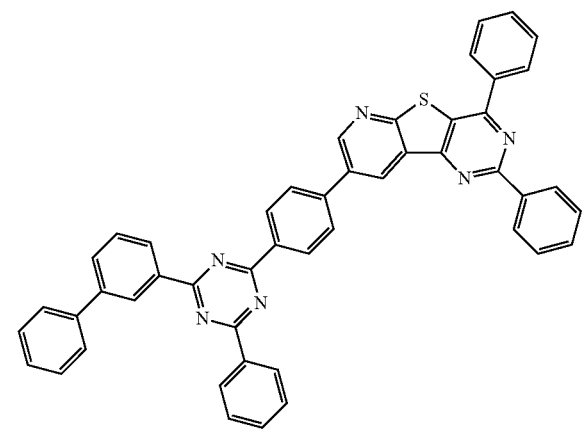
406
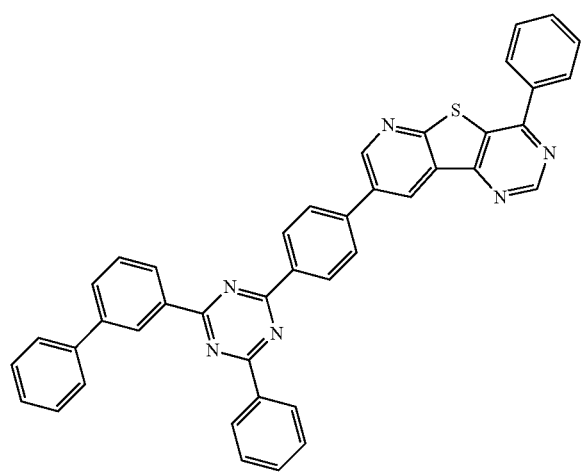
407
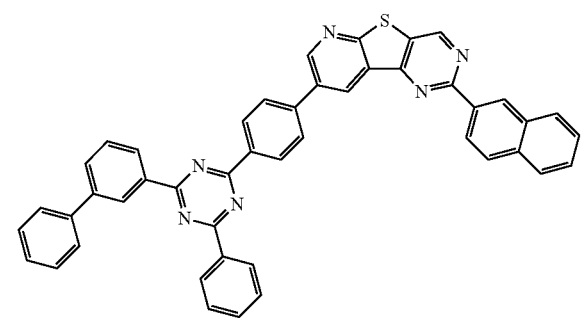

-continued
408
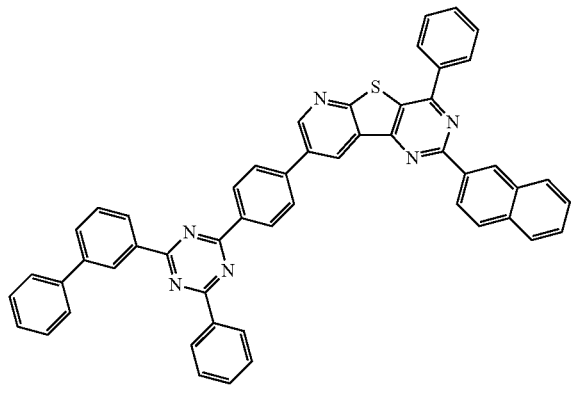
409
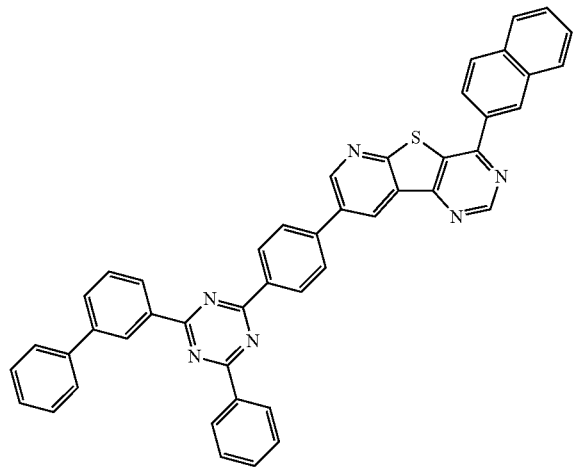
410
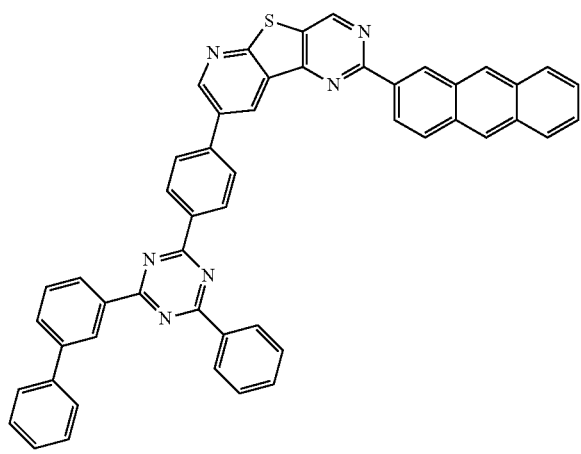
411
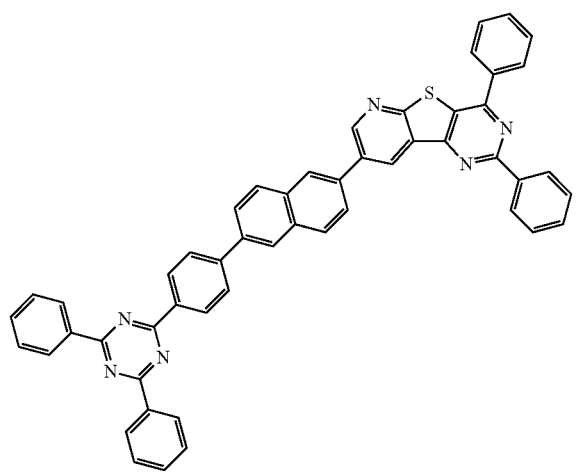
412
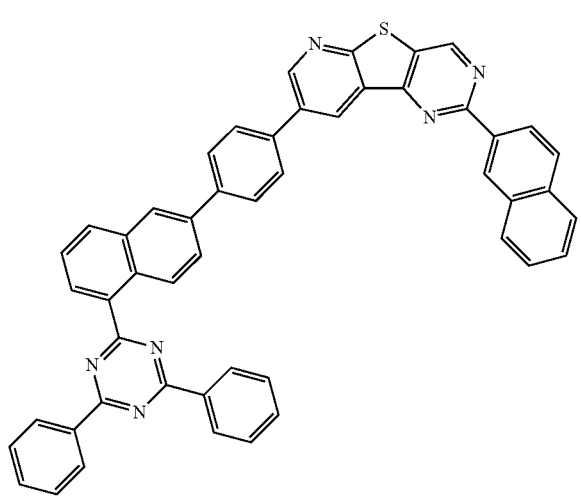

413
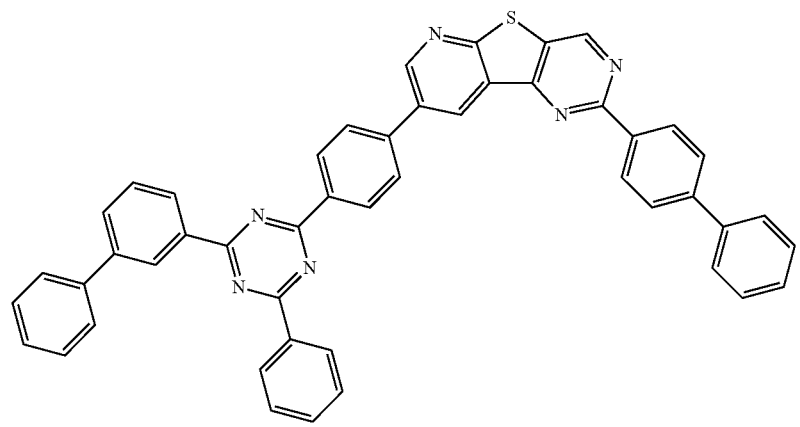
414
415
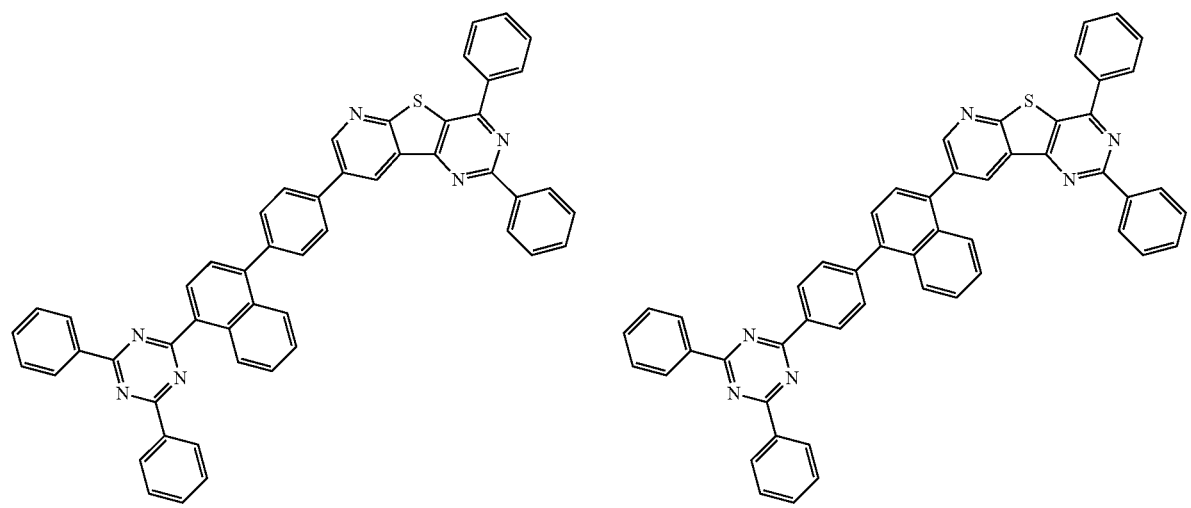
416
417
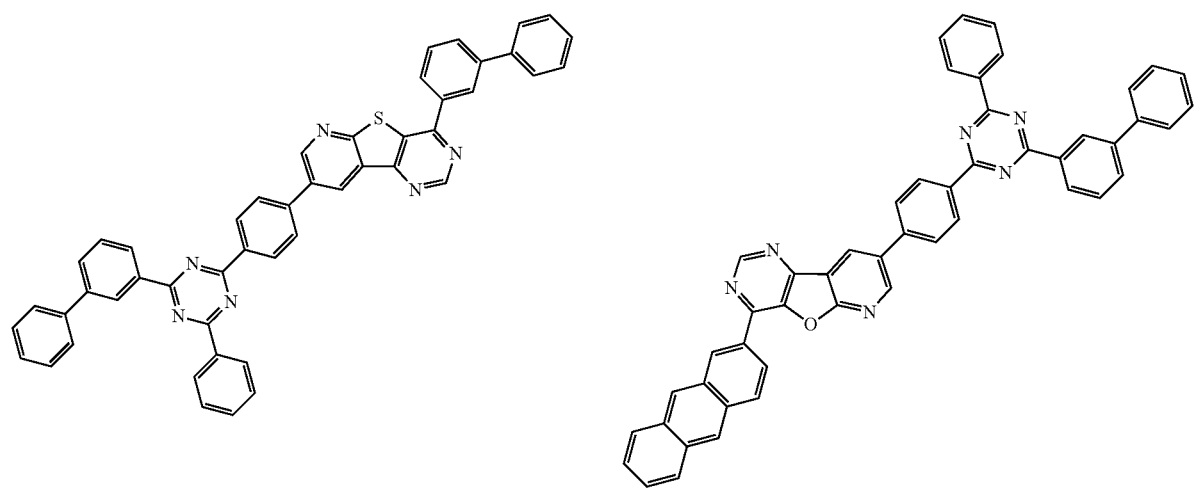

-continued
418
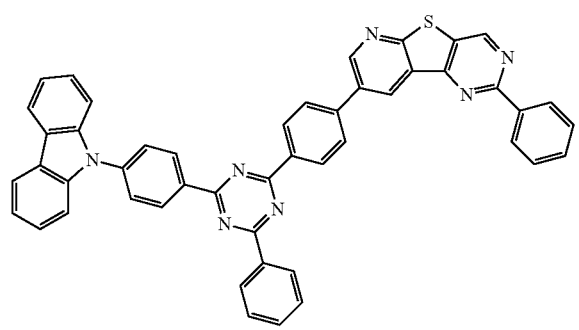
419
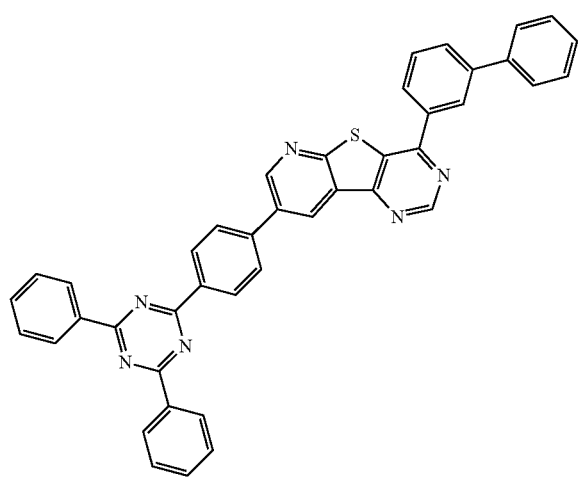
420
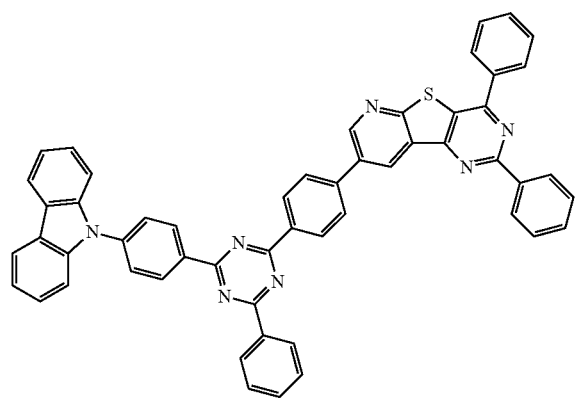 [SMILES: c1ccc(-c2nc(-c3ccc(-c4cnc5oc6c(-c7ccccc7)nc(-c7ccccc7)nc6c5c4)cc3)nc(-c3ccc(-n4c5ccccc5c5ccccc54)cc3)n2)cc1]
421
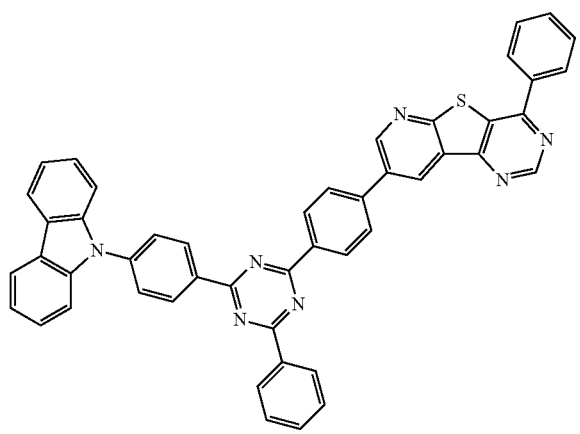
422
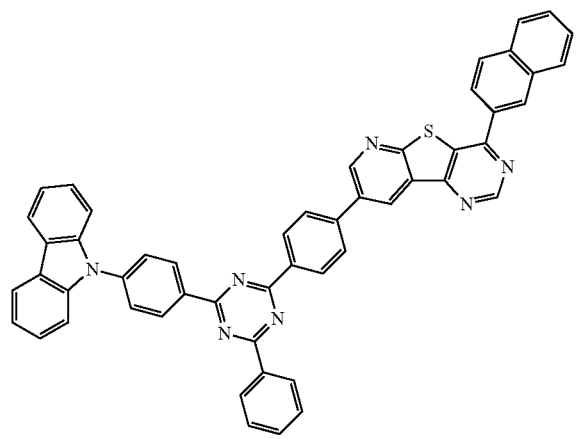

423
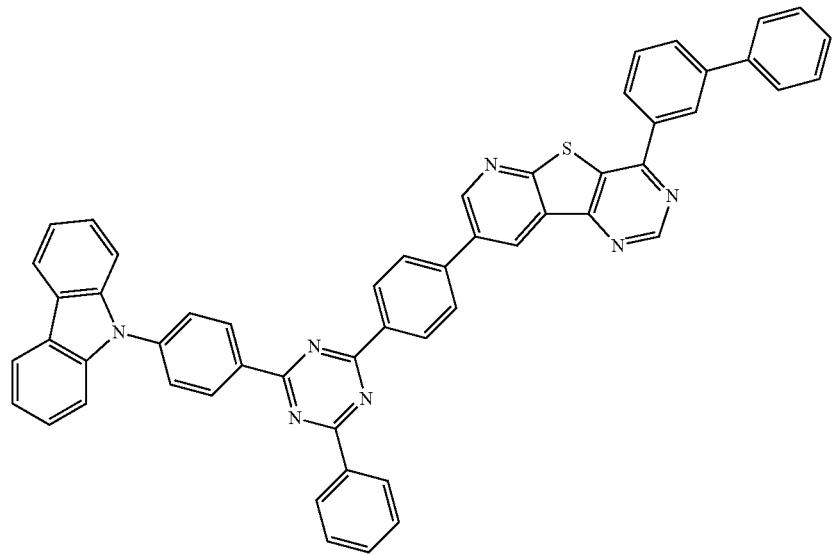
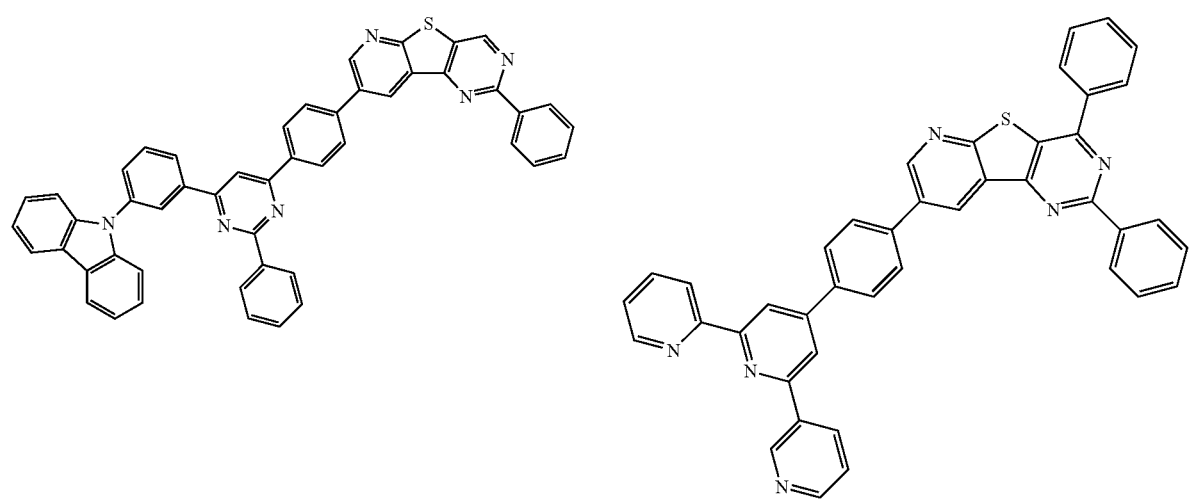

-continued
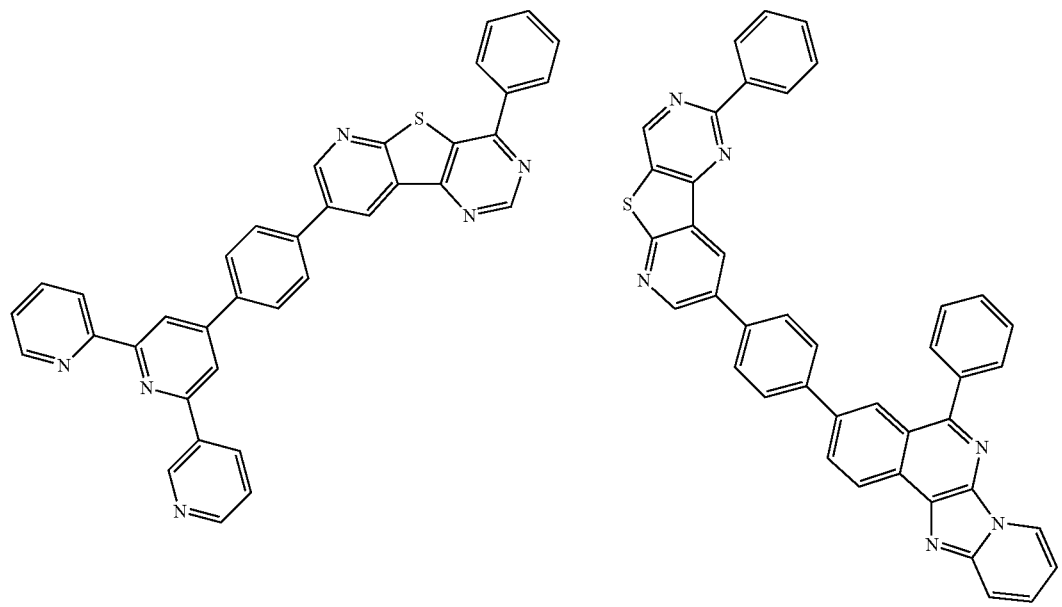
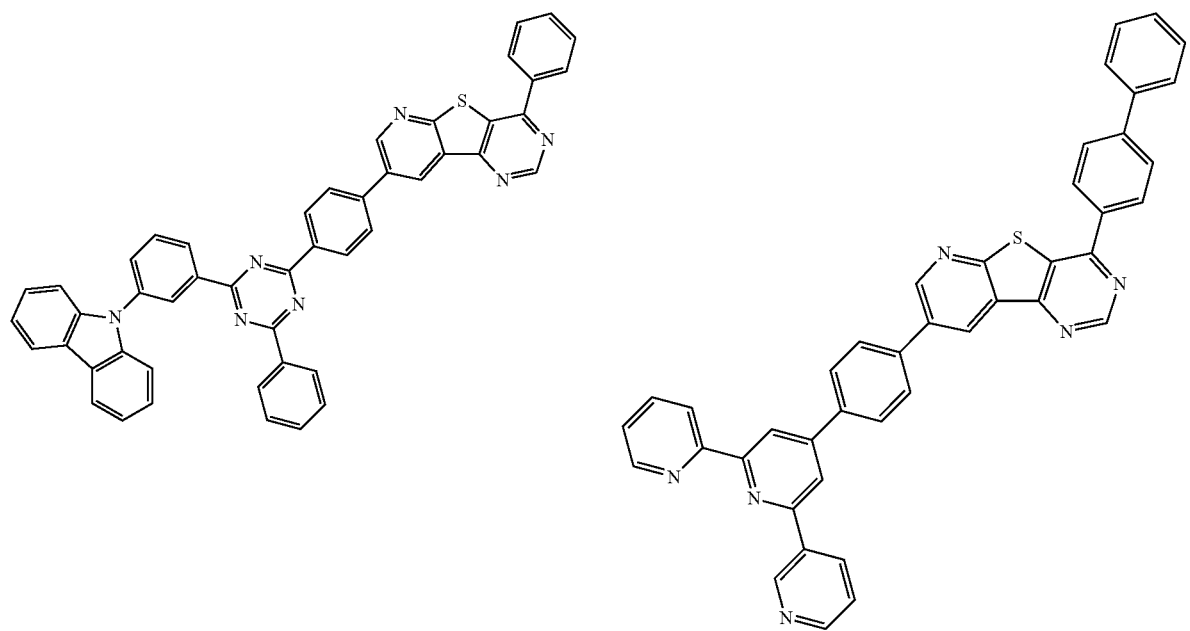

430
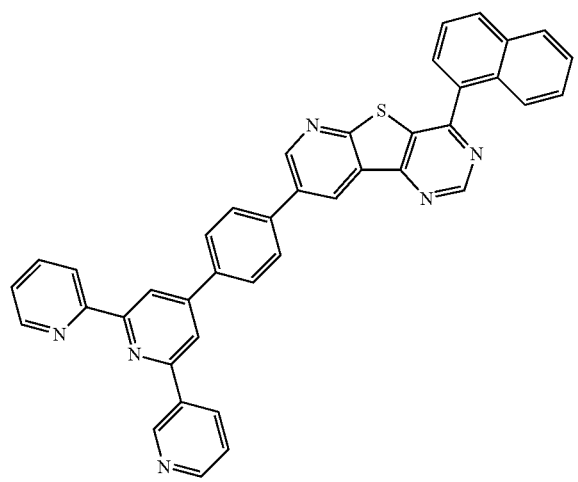
431
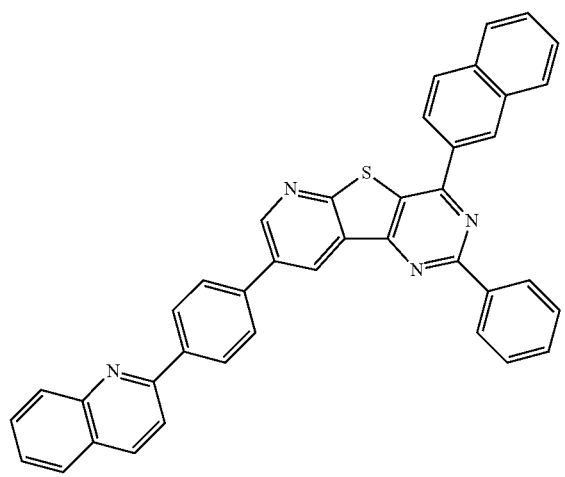
432
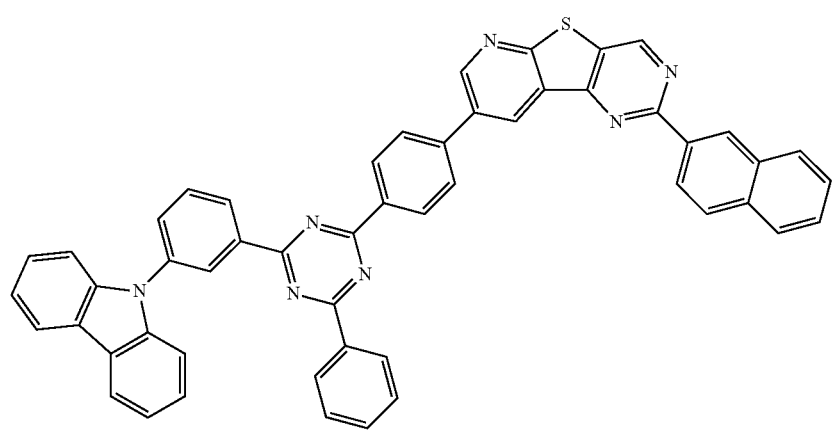
434
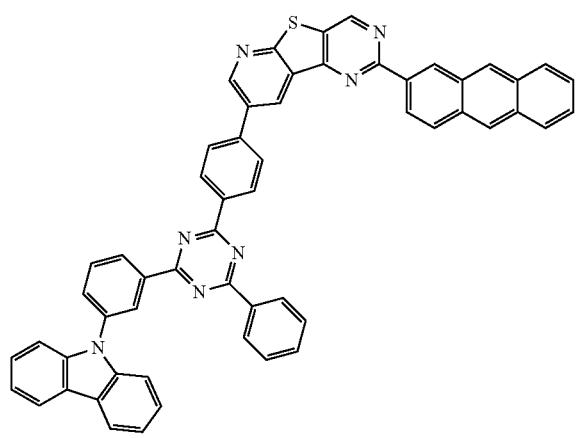
435
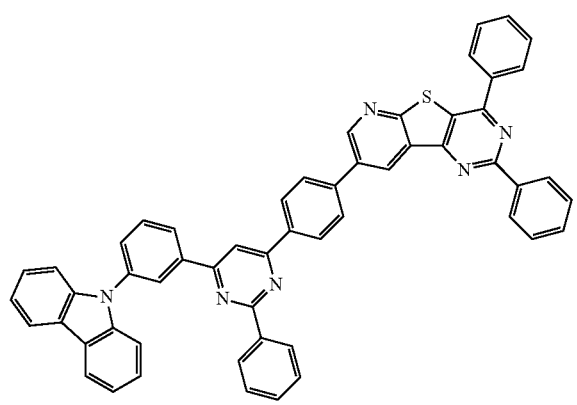

436
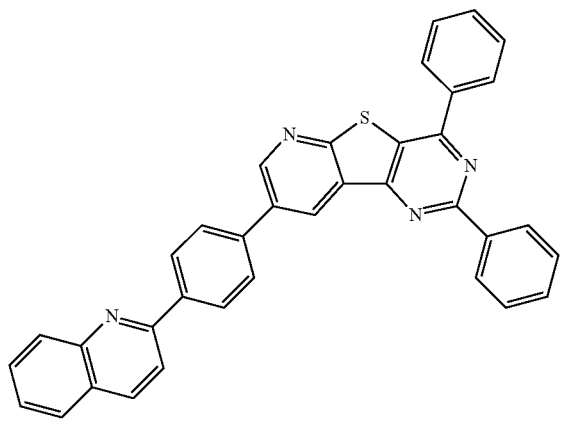
437
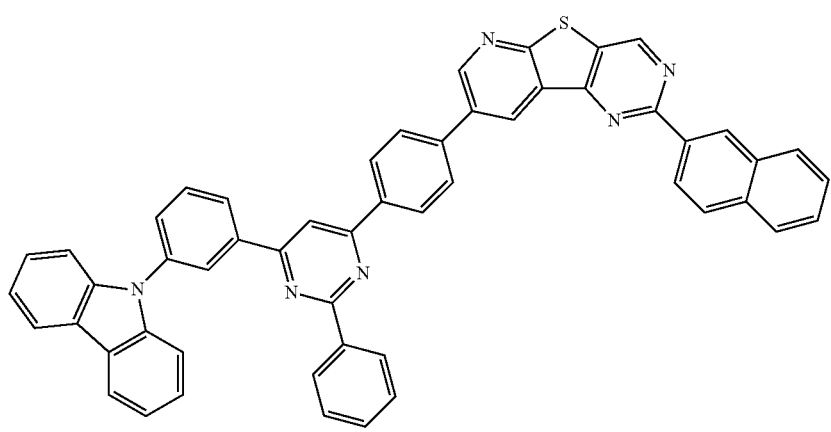
438
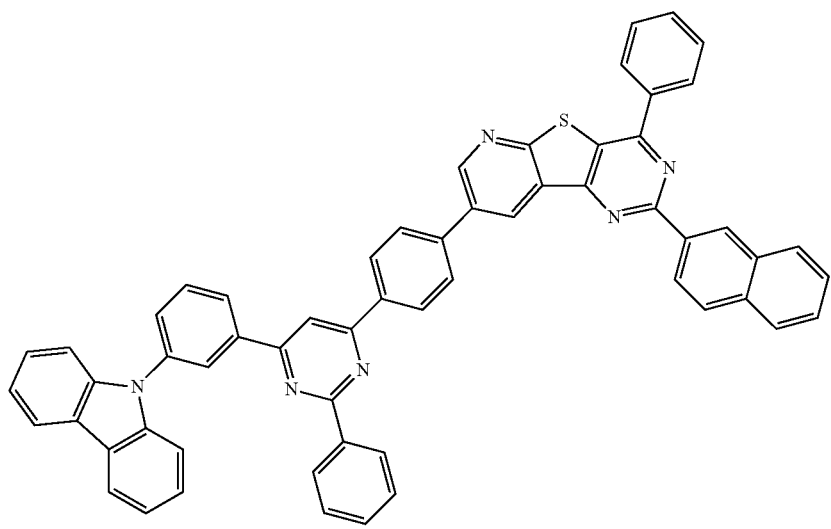 [SMILES: c1ccc(-c2nc(-c3ccc(-c4cnc5oc6c(-c7ccccc7)nc(-c7ccc8ccccc8c7)nc6c5c4)cc3)cc(-c3cccc(-n4c5ccccc5c5ccccc54)c3)n2)cc1]

439
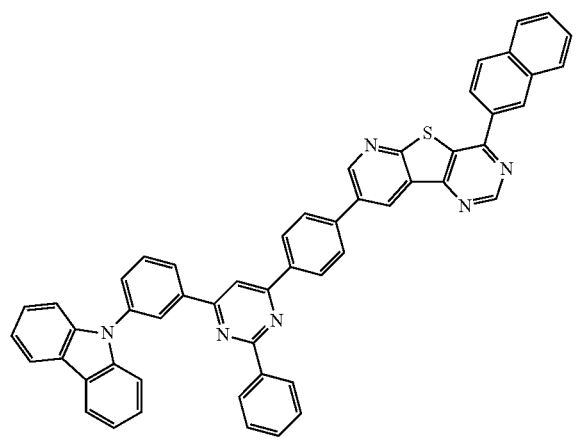
440
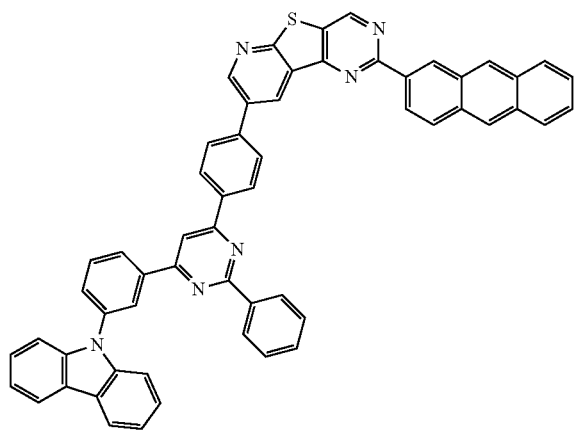
441
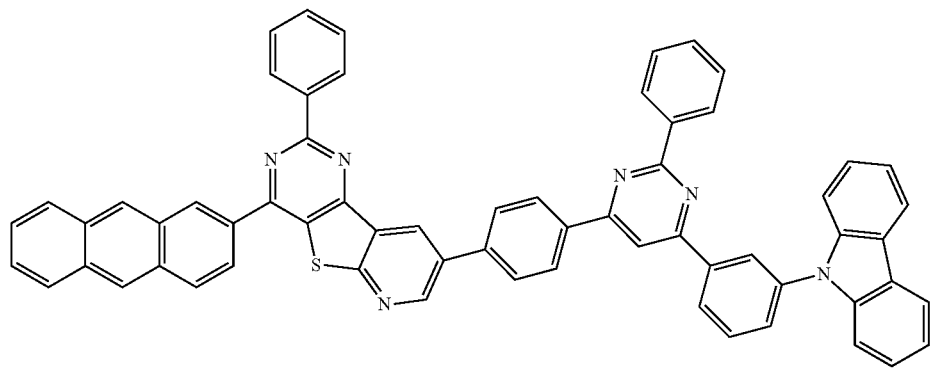
442
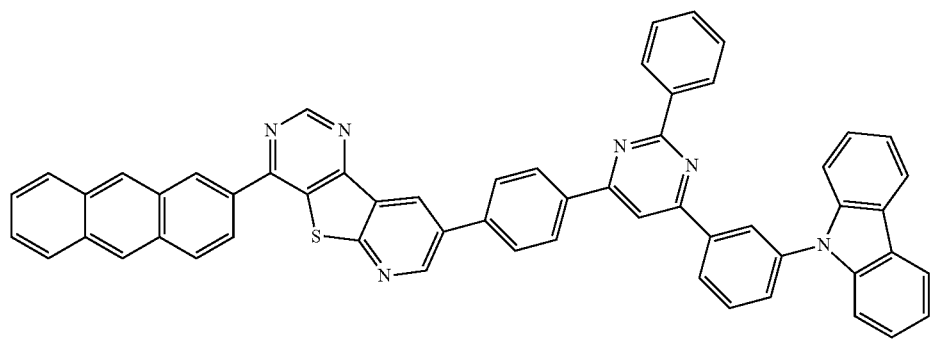

-continued
443
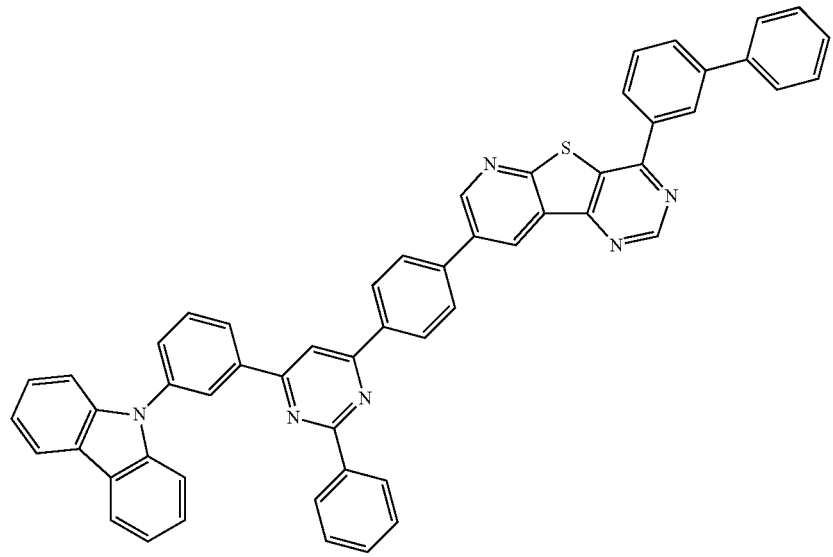
444
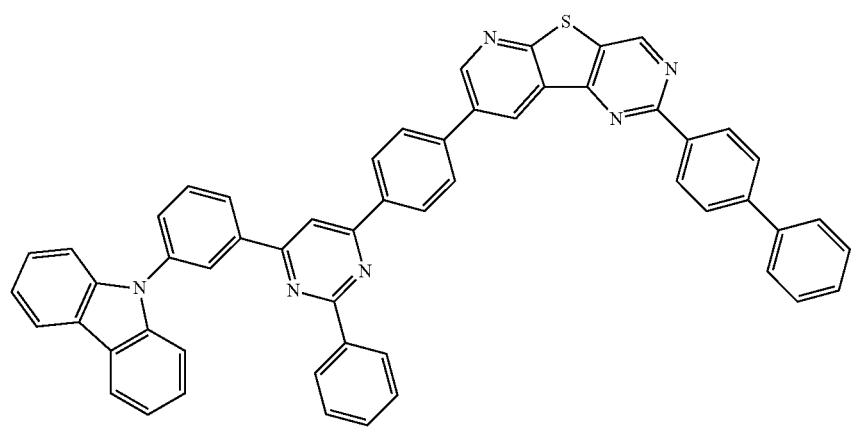
445 446
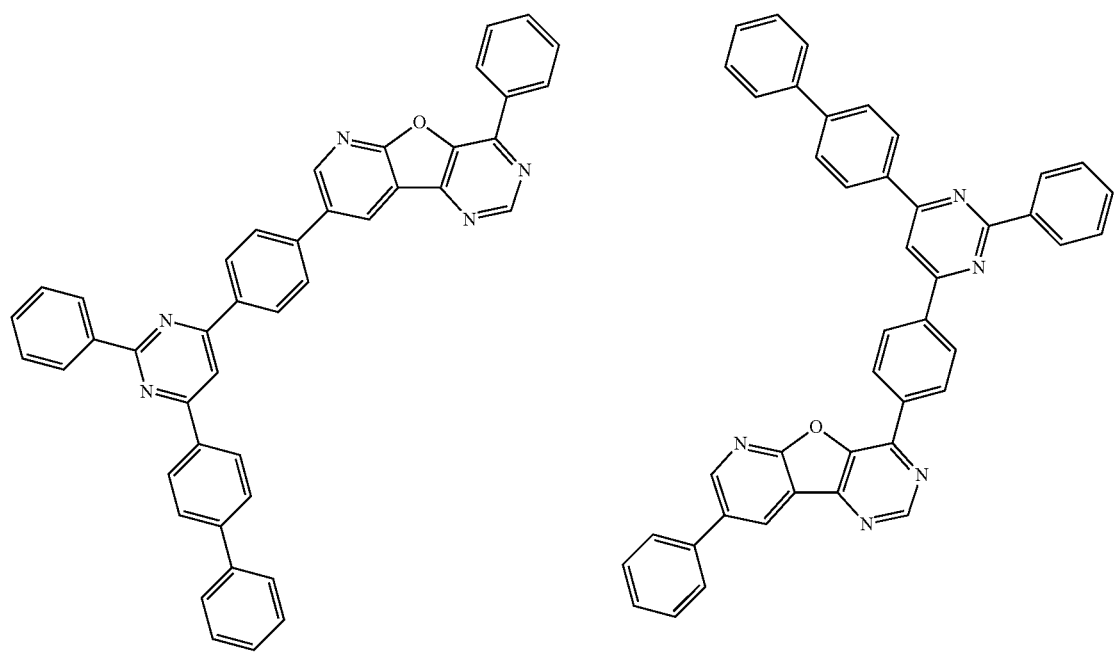

447
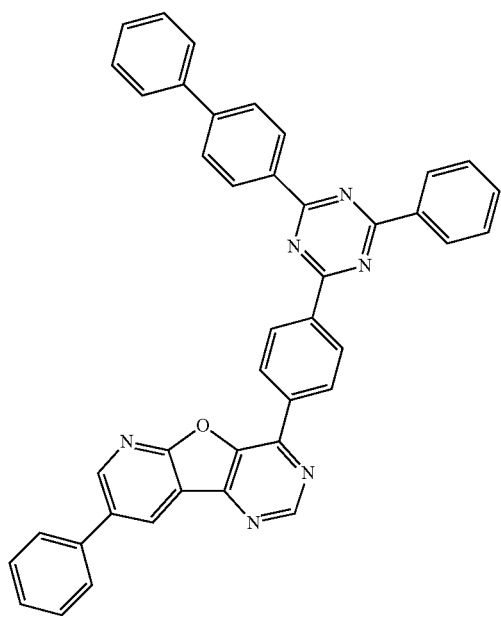
448
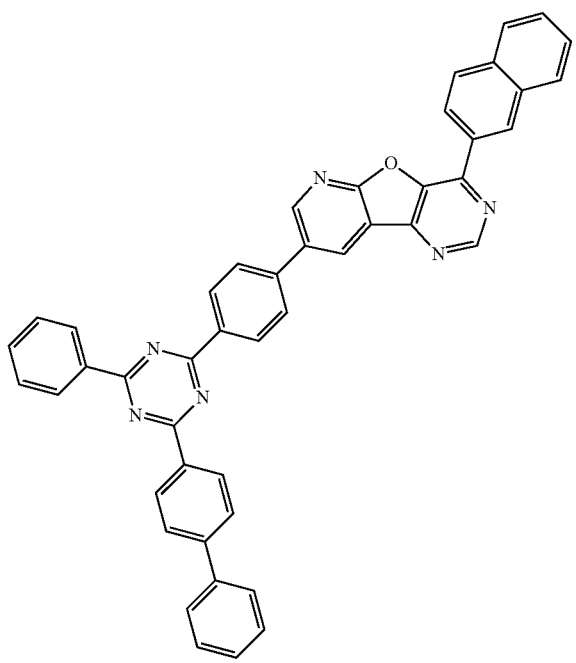
449
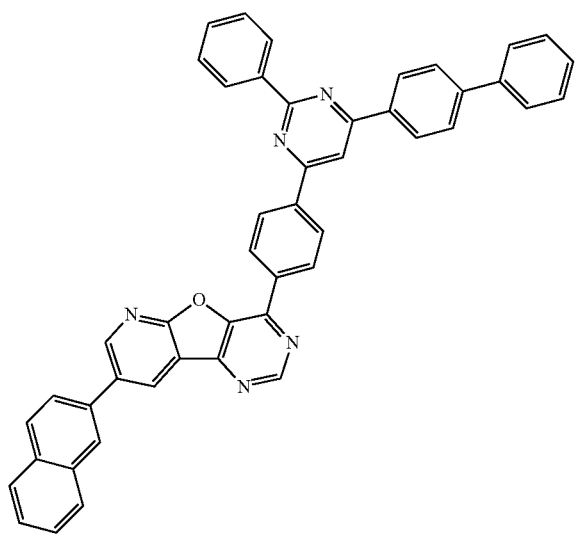
450
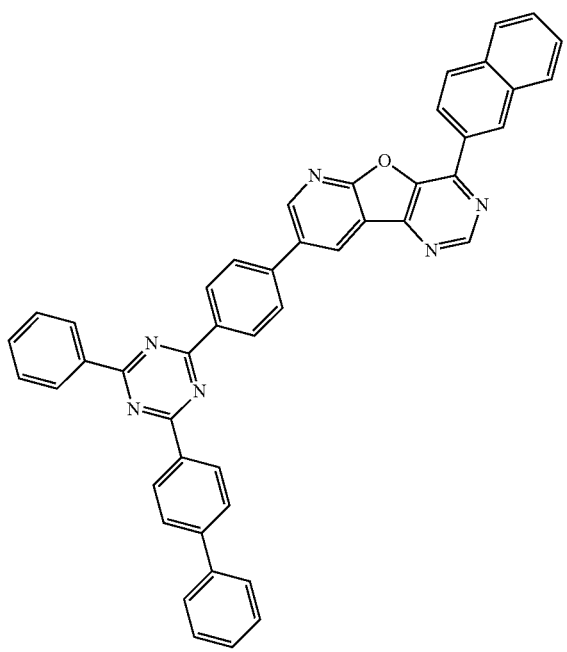

451
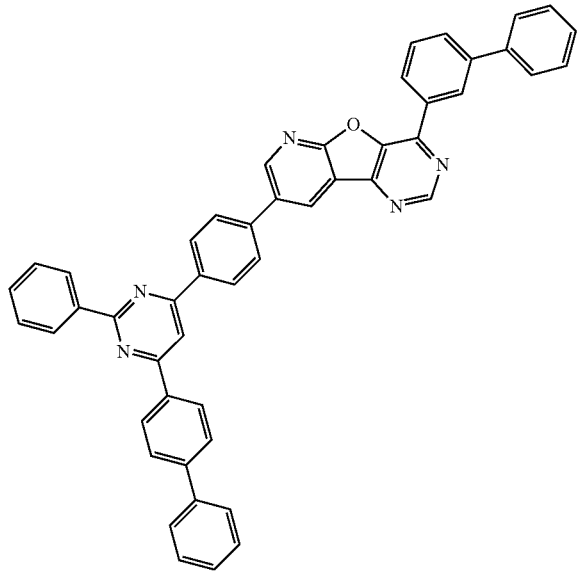
452
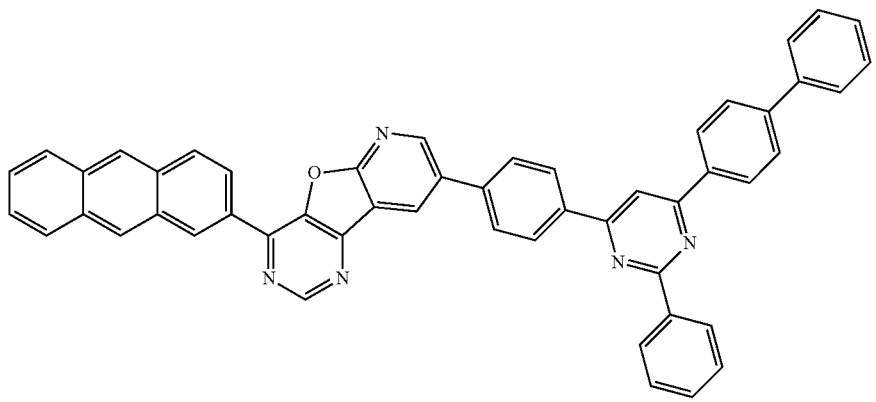
453
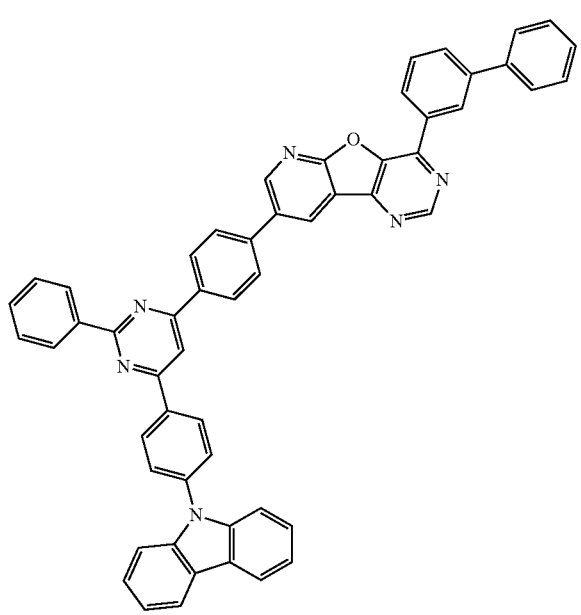
454
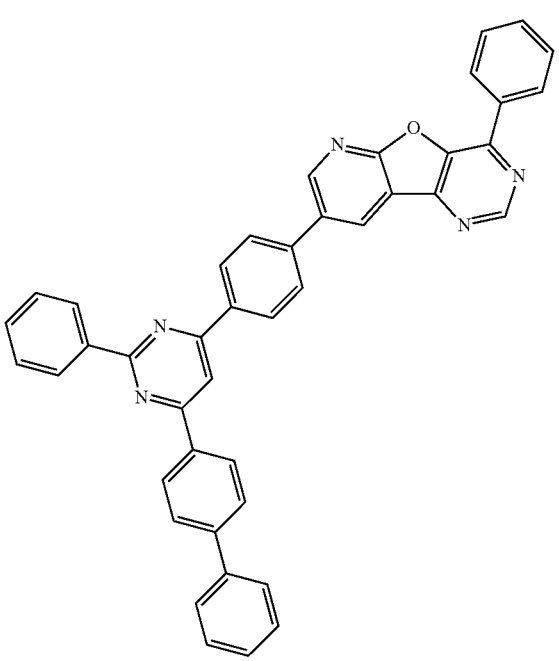

455
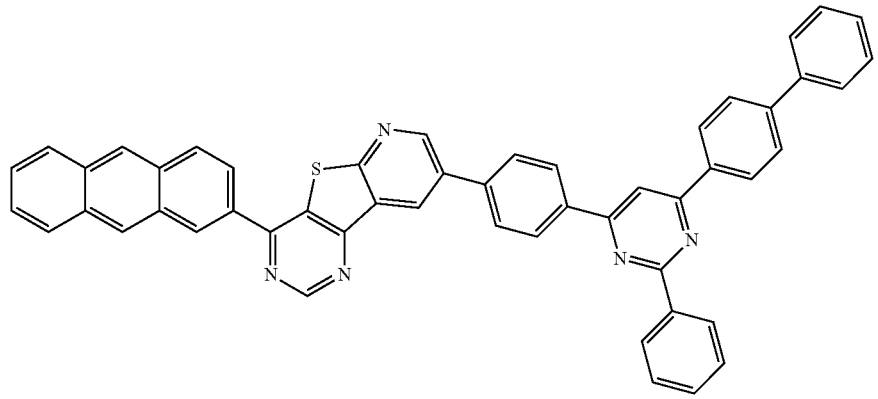
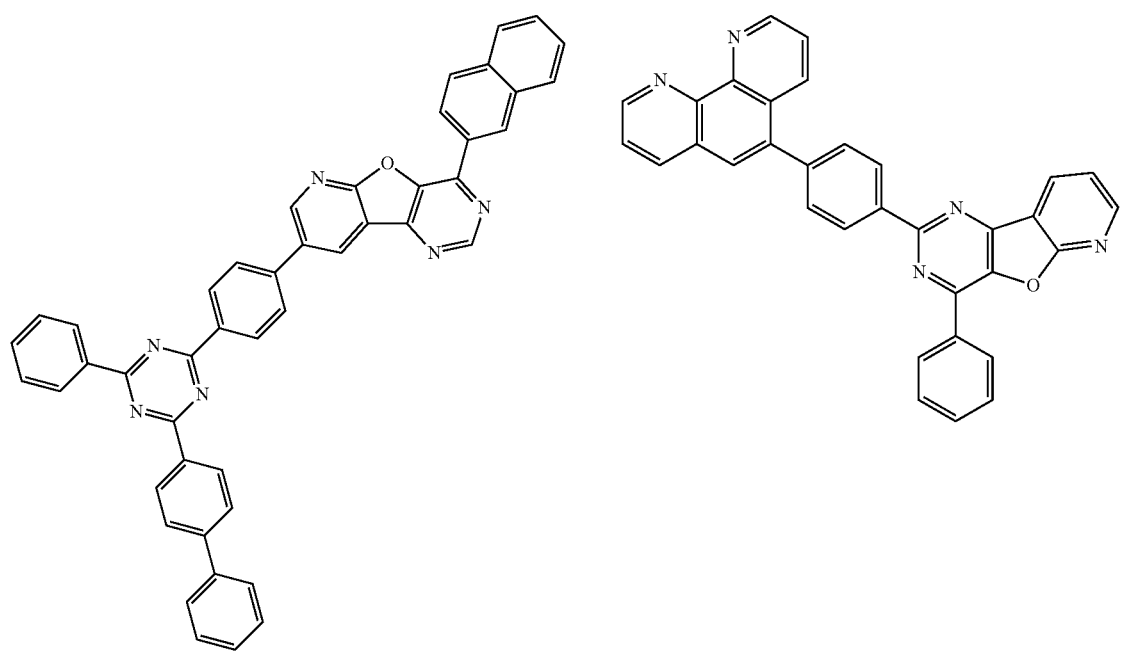
456
457

-continued
458 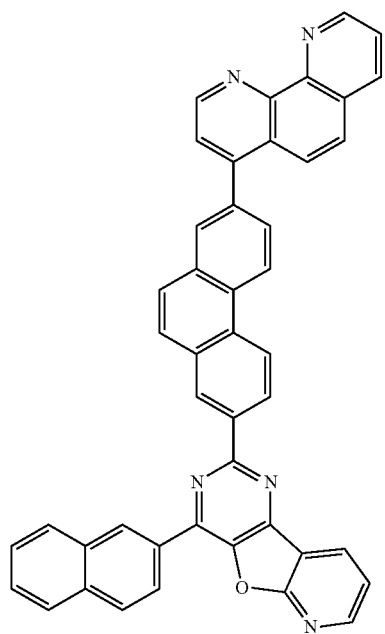
459 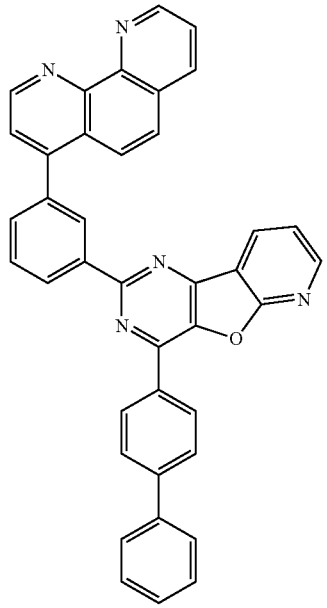
460 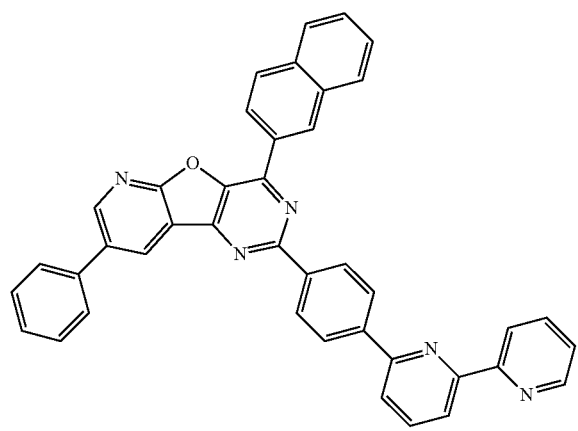
461
462 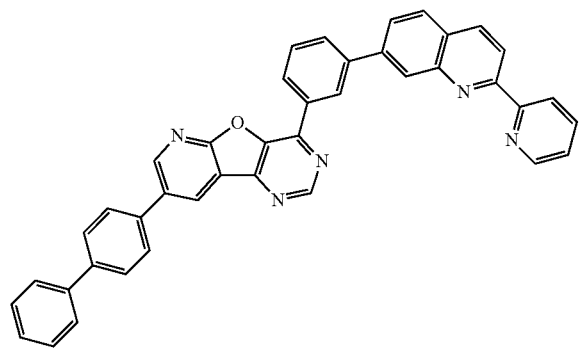
463 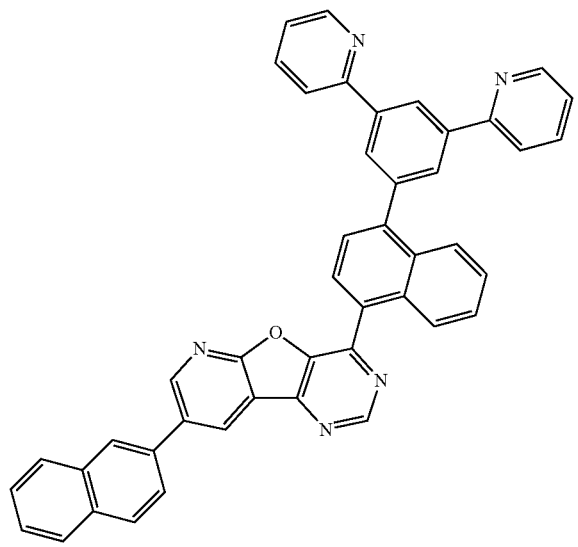

-continued
464
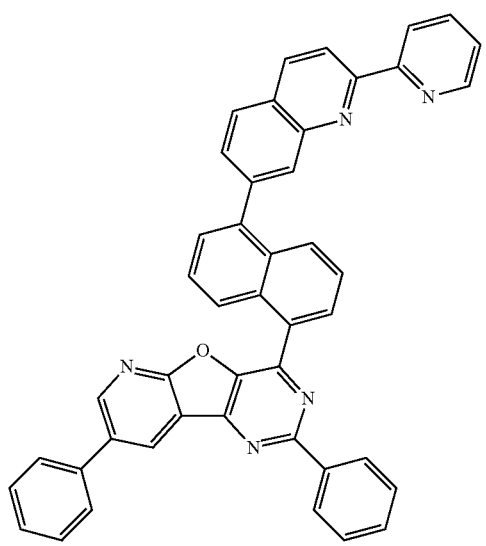
465
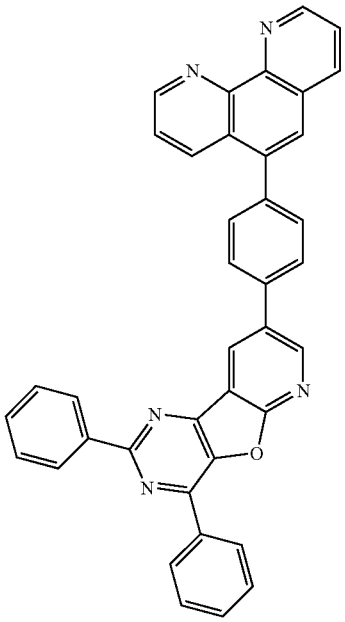
466
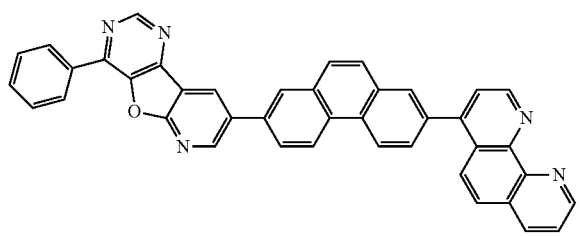
467
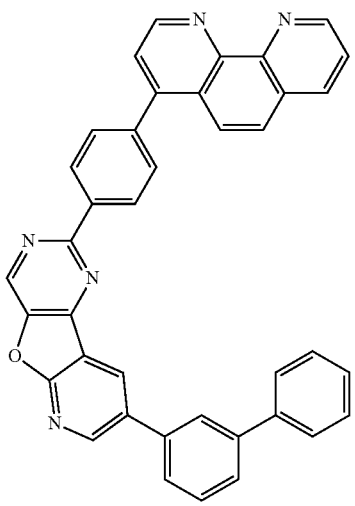
468
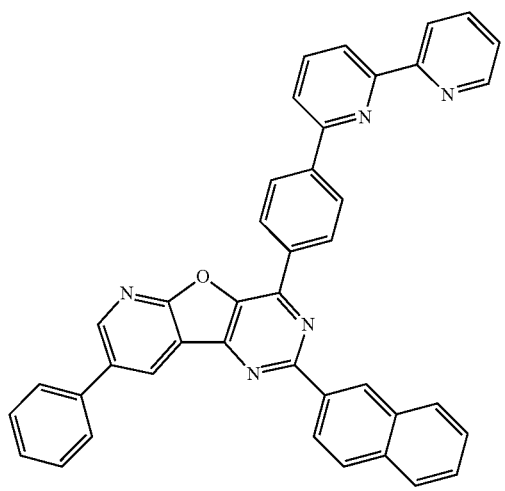
469
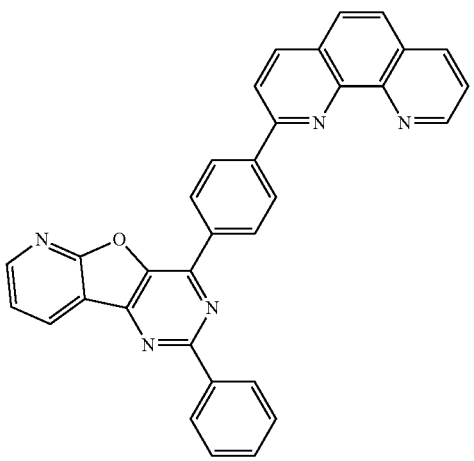

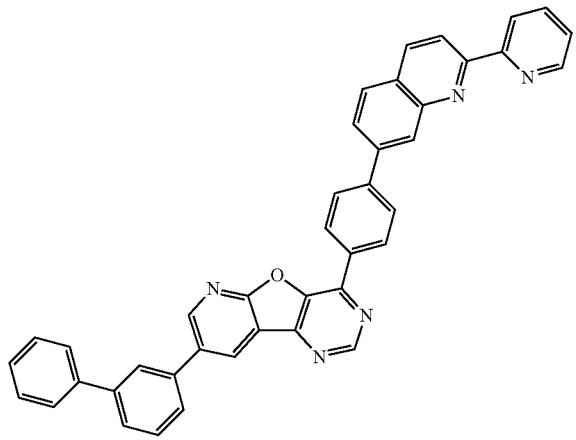

470

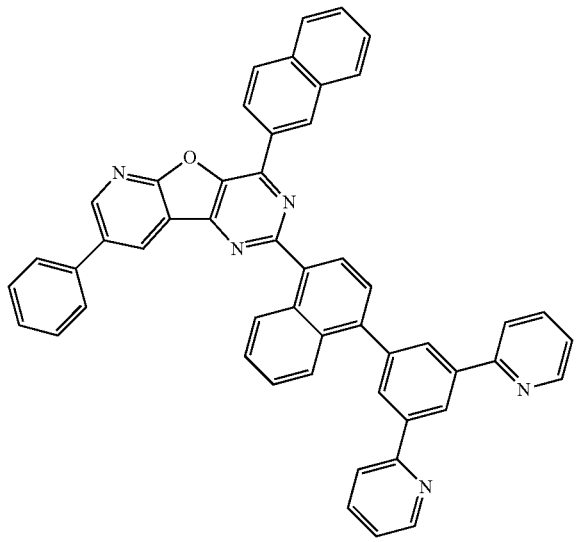

471

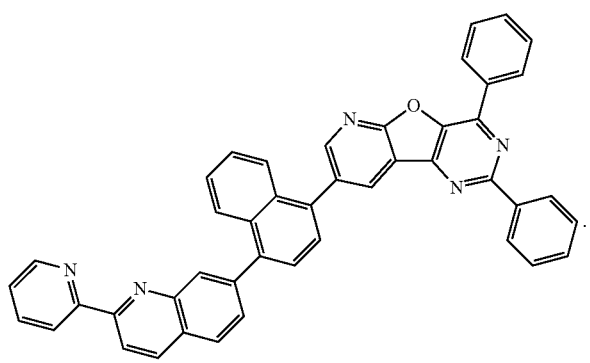

472

In addition, by introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

In addition, one embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound according to Chemical Formula 1.

Specific details on the heterocyclic compound represented by Chemical Formula 1 are the same as the descriptions provided above.

In one embodiment of the present application, the first electrode may be an anode, and the second electrode may be a cathode.

In another embodiment, the first electrode may be a cathode, and the second electrode may be an anode.

In one embodiment of the present application, the organic light emitting device may be a blue organic light emitting device, and the heterocyclic compound according to Chemical Formula 1 may be used as a material of the blue organic light emitting device. For example, the heterocyclic compound according to Chemical Formula 1 may be included in an electron transfer layer of the blue organic light emitting device.

In one embodiment of the present application, the organic light emitting device may be a green organic light emitting device, and the heterocyclic compound according to Chemical Formula 1 may be used as a material of the green organic light emitting device. For example, the heterocyclic compound according to Chemical Formula 1 may be included in an electron transfer layer of the green organic light emitting device.

In one embodiment of the present application, the organic light emitting device may be a red organic light emitting device, and the heterocyclic compound according to Chemical Formula 1 may be used as a material of the red organic light emitting device. For example, the heterocyclic compound according to Chemical Formula 1 may be included in an electron transfer layer of the red organic light emitting device.

The organic light emitting device of the present disclosure may be manufactured using common organic light emitting device manufacturing methods and materials except that one or more organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present disclosure may be formed in a single layer structure, or may also be formed in a multilayer structure in which two or more organic material layers are laminated. For example, the organic light emitting device according to one embodiment of the present disclosure may have a structure comprising a hole injection layer, a hole transfer layer, a light emitting layer, an electron transfer layer, an electron injection layer and the like as the organic material layer. However, the structure of the organic light emitting device is not limited thereto, and may comprise a smaller number of organic material layers.

In the organic light emitting device of the present disclosure, the organic material layer may comprise a light emitting layer, and the light emitting layer may comprise the heterocyclic compound.

In another organic light emitting device, the organic material layer comprises a light emitting layer, the light emitting layer comprises a host material, and the host material may comprise the heterocyclic compound.

As another example, the organic material layer comprising the heterocyclic compound comprises the heterocyclic compound represented by Chemical Formula 1 as a host, and may be used together with an iridium-based dopant.

In the organic light emitting device of the present disclosure, the organic material layer comprises an electron injection layer or an electron transfer layer, and the electron transfer layer or the electron injection layer may comprise the heterocyclic compound.

In the organic light emitting device of the present disclosure, the organic material layer comprises an electron transfer layer, and the electron transfer layer may comprise the heterocyclic compound.

In another organic light emitting device, the organic material layer comprises an electron blocking layer or a hole blocking layer, and the electron blocking layer or the hole blocking layer may comprise the heterocyclic compound.

In the organic light emitting device of the present disclosure, the organic material layer comprises a hole blocking layer, and the hole blocking layer may comprise the heterocyclic compound.

The organic light emitting device of the present disclosure may further comprise one, two or more layers selected from the group consisting of a light emitting layer, a hole injection layer, a hole transfer layer, an electron injection layer, an electron transfer layer, an electron blocking layer and a hole blocking layer.

FIGS. 1 to 3 illustrate a lamination order of electrodes and organic material layers of an organic light emitting device according to one embodiment of the present application. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 comprises a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, other layers except the light emitting layer may not be included, and other necessary functional layers may be further included.

The organic material layer comprising the compound of Chemical Formula 1 may further comprise other materials as necessary.

In the organic light emitting device according to one embodiment of the present application, materials other than the compound of Chemical Formula 1 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having relatively small work function may be used, and metals, metal oxides, conductive polymers or the like may be used. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrene-sulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involving in light emission together may also be used.

When mixing light emitting material hosts, same series hosts may be mixed, or different series hosts may be mixed. For example, any two or more types of materials among n-type host materials or p-type host materials may be selected, and used as a host material of a light emitting layer.

The organic light emitting device according to one embodiment of the present application may be a top-emission type, a bottom-emission type or a dual-emission type depending on the materials used.

The heterocyclic compound according to one embodiment of the present application may also be used in an organic electronic device comprising an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

PREPARATION EXAMPLE

<Preparation Example 1> Preparation of Compound 1

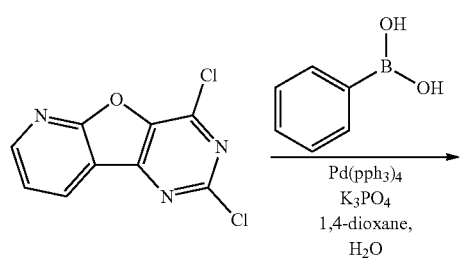

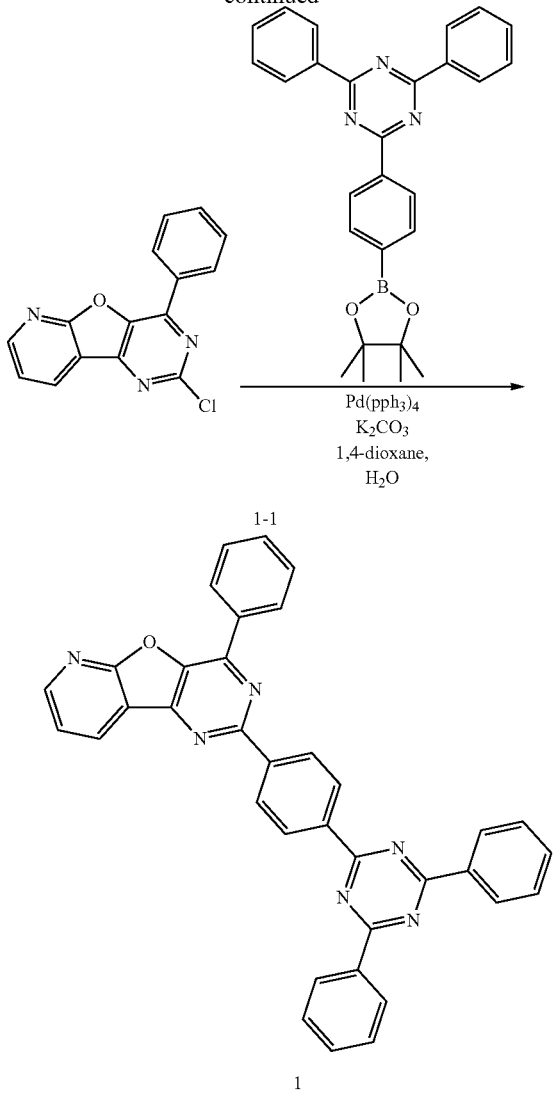

Preparation of Compound 1-1

After dissolving 2,4-dichloropyrido[3',2':4,5]furo[3,2-d]pyrimidine (10 g, 0.042 mol, 1 eq.) and phenylboronic acid (10.25 g, 0.084 mol, 2 eq.) in 1,4-dioxane (100 ml) and $H_2O$ (20 ml), ($N_2$ condition) Pd(PPh$_3$)$_4$ (2.42 g, 0.0021 mol, 0.05 eq.) and K$_3$PO$_4$ (17.8 g, 0.084 mol, 2 eq.) were introduced thereto, and the result was stirred for 3 hours under reflux.

Methylene chloride (MC) was introduced to the reaction solution for dissolution, and the result was extracted with water and the organic layer was dried with anhydrous Na$_2$SO$_4$. The solution was concentrated, dissolved in a small amount of MC, and passed through a MC/hexane column to obtain Compound 1-1 (8.4 g, 56% yield).

Preparation of Compound 1

After dissolving Compound 1-1 (8.4 g, 0.023 mol, 1 eq.) and 2,4-diphenyl-6-(4-(4,4,5,5-tetramethyl-1,3,2-dioxaborolan-2-yl)phenyl)-1,3,5-triazine (10 g, 0.023 mol, 1 eq.) in 1,4-dioxane (100 ml) and $H_2O$ (20 ml), ($N_2$ condition) Pd(PPh$_3$)$_4$ (1.32 g, 0.0012 mol, 0.05 eq.) and K$_2$CO$_3$ (6.3 g, 0.046 mol, 2 eq.) were introduced thereto, and the result was stirred for 12 hours under reflux. Obtained solids were filtered, dissolved in dichlorobenzene (DCB), and then passed through silica gel. The result was MC/MeOH precipitated and then Soxhlet extracted to obtain Compound 1 (9.8 g, 68% yield).

Synthesis of Target Compounds

Target compounds were synthesized in the same manner as in Preparation Example 1 except that Intermediate A of the following Table 1 was used instead of 2,4-dichloropyrido[3',2':4,5]furo[3,2-d]pyrimidine, and Intermediate B of the following Table 1 was used instead of 2,4-diphenyl-6-(4-(4,4,5,5-tetramethyl-1,3,2-dioxaborolan-2-yl)phenyl)-1,3,5-triazine.

TABLE 1

| Compound No. | Intermediate A | Intermediate B | Target compound | Yield |
|---|---|---|---|---|
| 9 | | | | 31% |

TABLE 1-continued
| Compound No. | Intermediate A | Intermediate B | Target compound | Yield |
|---|---|---|---|---|
| 13 | 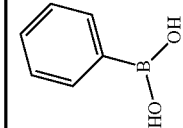 | 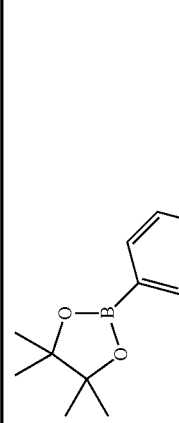 | 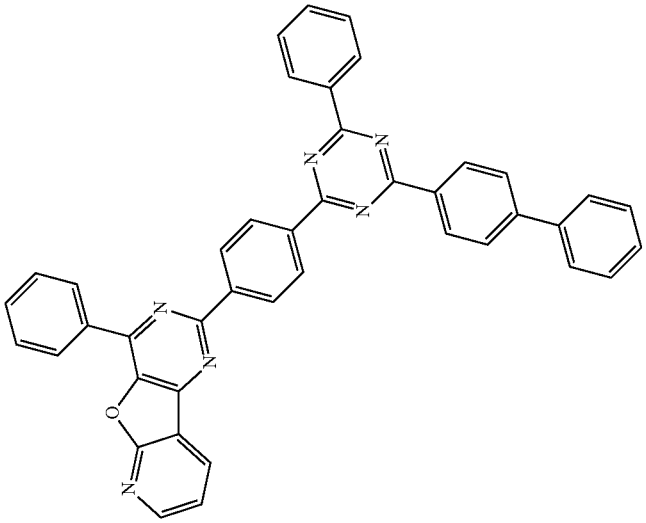 | 25% |

TABLE 1-continued

| Compound No. | Intermediate A | Intermediate B | Target compound | Yield |
|---|---|---|---|---|
| 14 | | | | 28% |

TABLE 1-continued
| Compound No. | Intermediate A | Intermediate B | Target compound | Yield |
|---|---|---|---|---|
| 21 | 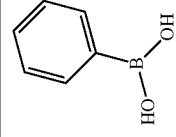 | 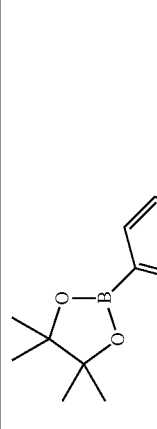 | 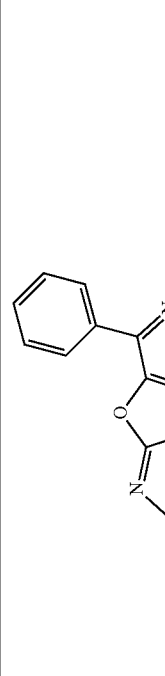 | 32% |

TABLE 1-continued
| Compound No. | Intermediate A | Intermediate B | Target compound | Yield |
|---|---|---|---|---|
| 25 | 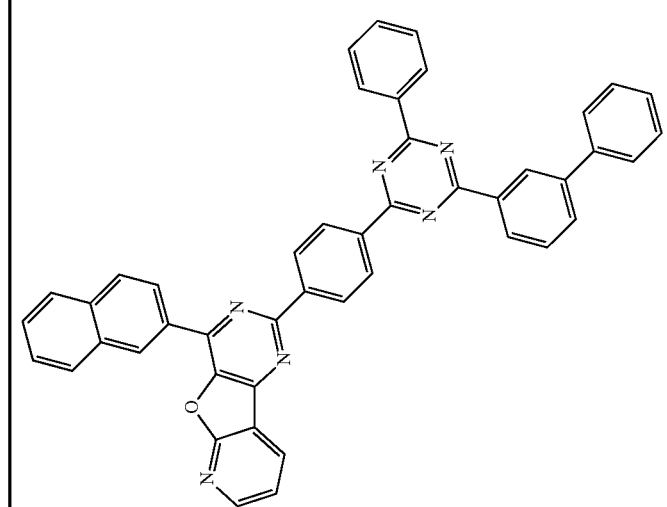 | 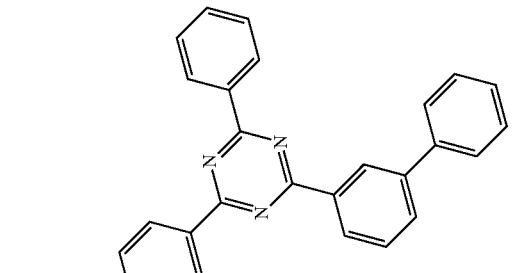 | 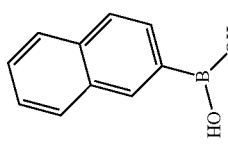 | 35% |

TABLE 1-continued

| Compound No. | Intermediate A | Intermediate B | Target compound | Yield |
|---|---|---|---|---|
| 33 | (4-biphenyl)boronic acid | triazine-phenyl-Bpin intermediate | triazine/furopyridine target compound | 36% |

TABLE 1-continued

| Compound No. | Intermediate A | Intermediate B | Target compound | Yield |
|---|---|---|---|---|
| 41 | (2-naphthaleneboronic acid, anthracene-2-boronic acid structure) | (triazine intermediate with pinacol boronate) | (target compound structure) | 41% |

TABLE 1-continued

| Compound No. | Intermediate A | Intermediate B | Target compound | Yield |
|---|---|---|---|---|
| 45 | [structure] | [structure] | [structure] | 27% |

TABLE 1-continued
| Compound No. | Intermediate A | Intermediate B | Target compound | Yield |
|---|---|---|---|---|
| 49 | 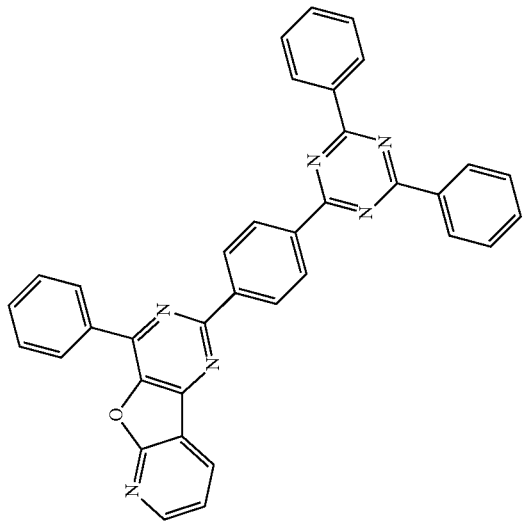 | 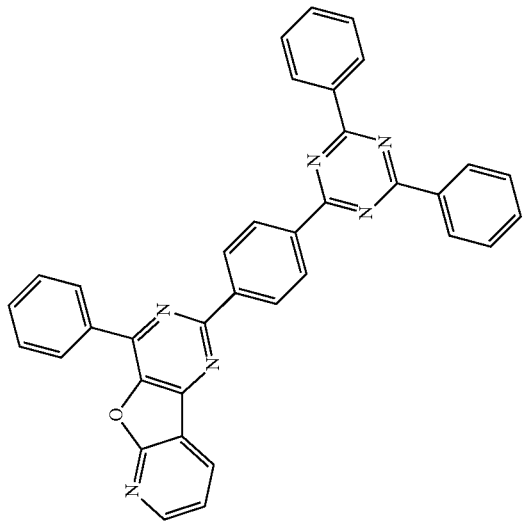 | 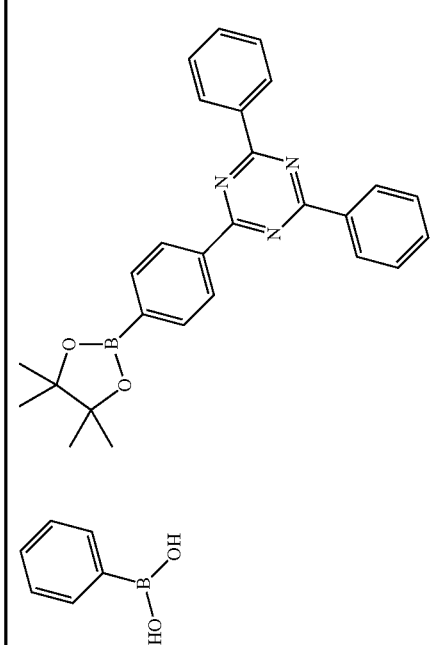 | 24% |

TABLE 1-continued
| Compound No. | Intermediate A | Intermediate B | Target compound | Yield |
|---|---|---|---|---|
| 53 | 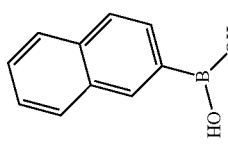 | 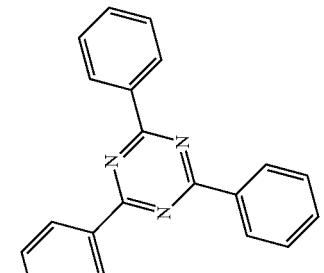 | 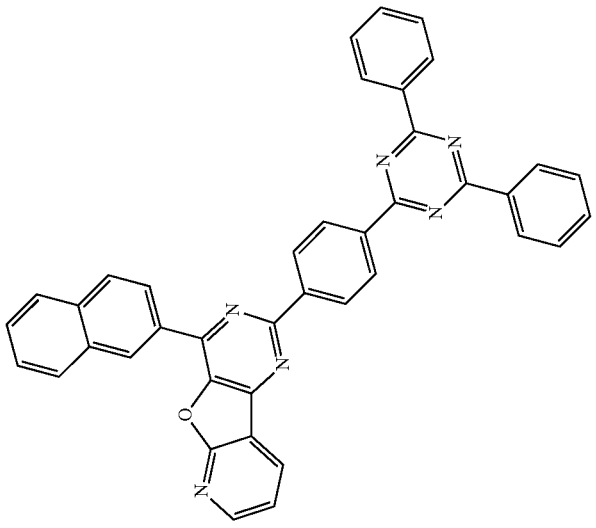 | 29% |

TABLE 1-continued

| Compound No. | Intermediate A | Intermediate B | Target compound | Yield |
|---|---|---|---|---|
| 61 | phenylboronic acid | (intermediate structure) | (target structure) | 30% |

TABLE 1-continued
| Compound No. | Intermediate A | Intermediate B | Target compound | Yield |
|---|---|---|---|---|
| 65 | 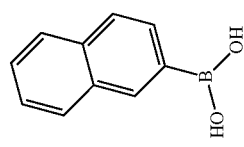 | 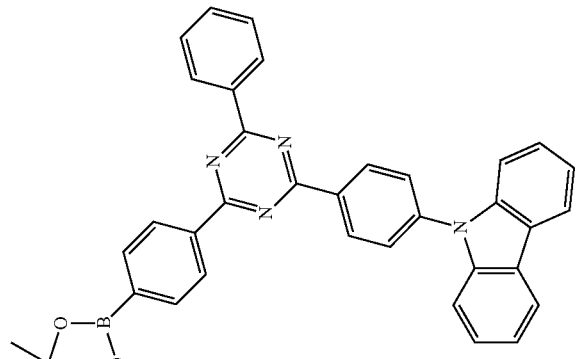 | 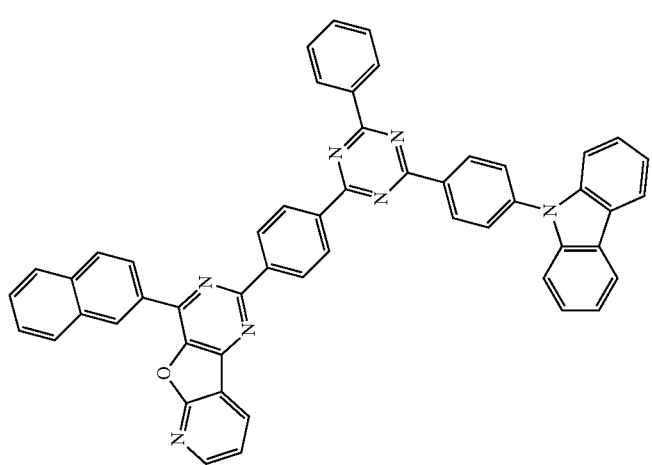 | 21% |

TABLE 1-continued

| Compound No. | Intermediate A | Intermediate B | Target compound | Yield |
|---|---|---|---|---|
| 69 | (structure) | (structure) | (structure) | 22% |

TABLE 1-continued
| Compound No. | Intermediate A | Intermediate B | Target compound | Yield |
|---|---|---|---|---|
| 73 | 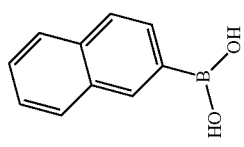 | 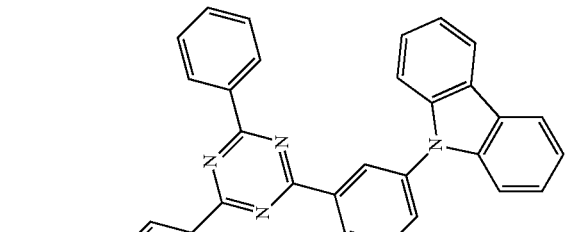 | 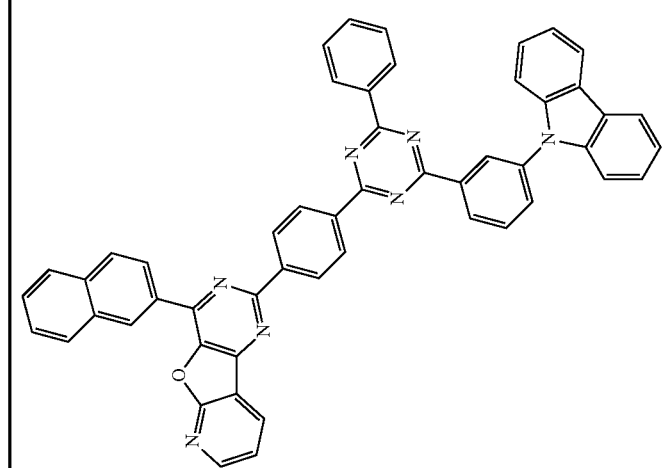 | 28% |

TABLE 1-continued

| Compound No. | Intermediate A | Intermediate B | Target compound | Yield |
|---|---|---|---|---|
| 77 | phenylboronic acid | | | 34% |

TABLE 1-continued

| Compound No. | Intermediate A | Intermediate B | Target compound | Yield |
|---|---|---|---|---|
| 457 | (phenylboronic acid) | (phenanthroline-phenyl-Bpin) | (target structure) | 32% |

TABLE 1-continued
| Compound No. | Intermediate A | Intermediate B | Target compound | Yield |
|---|---|---|---|---|
| 458 | 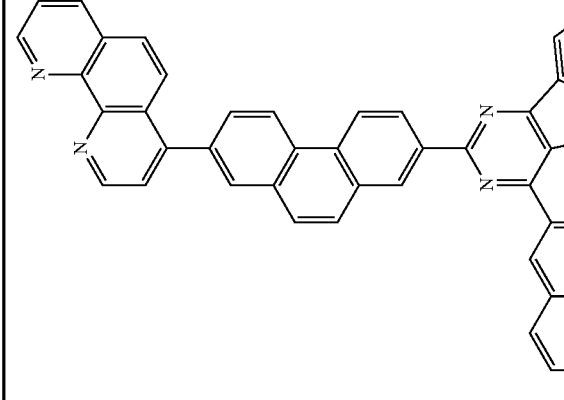 | 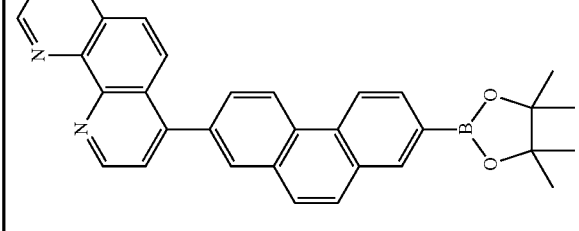 | 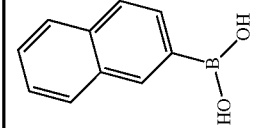 | 28% |

TABLE 1-continued
| Compound No. | Intermediate A | Intermediate B | Target compound | Yield |
|---|---|---|---|---|
| 459 | 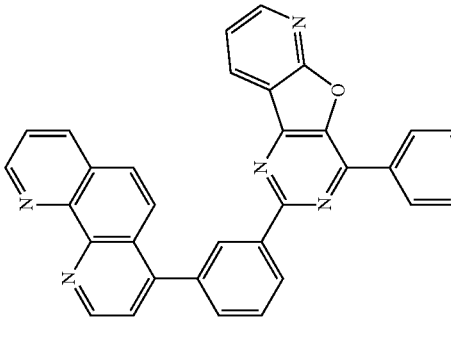 | 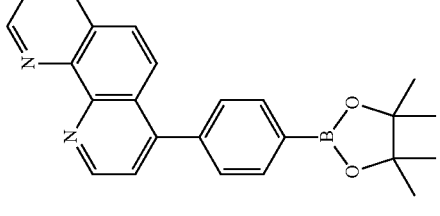 | 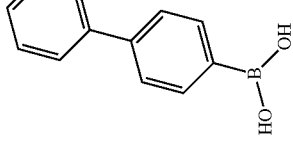 | 29% |

Synthesis of Target Compounds

Target compounds were synthesized in the same manner as in Preparation Example 1 except that 2,4-dichloropyrido[3',2':4,5]thieno[3,2-d]pyrimidine was used instead of 2,4-dichloropyrido[3',2':4,5]furo[3,2-d]pyrimidine, Intermediate A of the following Table 2 was used instead of phenylboronic acid, and Intermediate B of the following Table 2 was used instead of 2,4-diphenyl-6-(4-(4,4,5,5-tetramethyl-1,3,2-dioxaborolan-2-yl)phenyl)-1,3,5-triazine.

TABLE 2

| Compound No. | Intermediate A | Intermediate B | Target compound | Yield |
|---|---|---|---|---|
| 272 | | | | 32% |
| 276 | | | | 28% |

TABLE 2-continued
| Compound No. | Intermediate A | Intermediate B | Target compound | Yield |
|---|---|---|---|---|
| 280 | 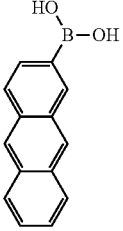 | 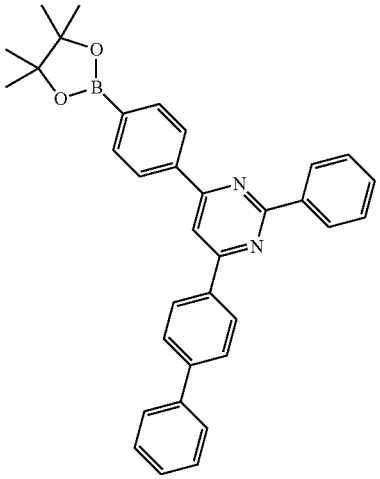 | 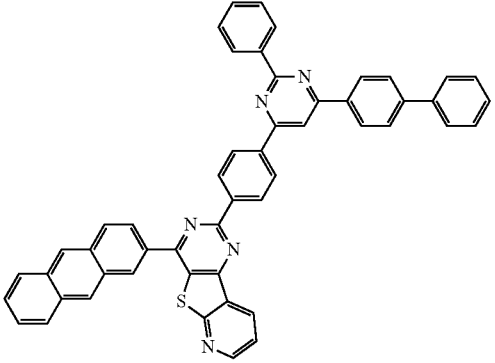 | 29% |
| 284 | 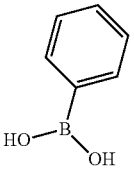 | 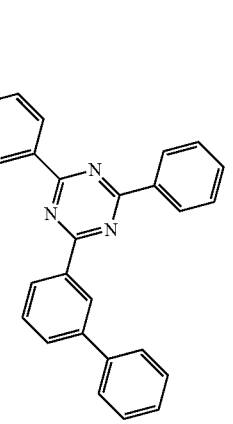 | 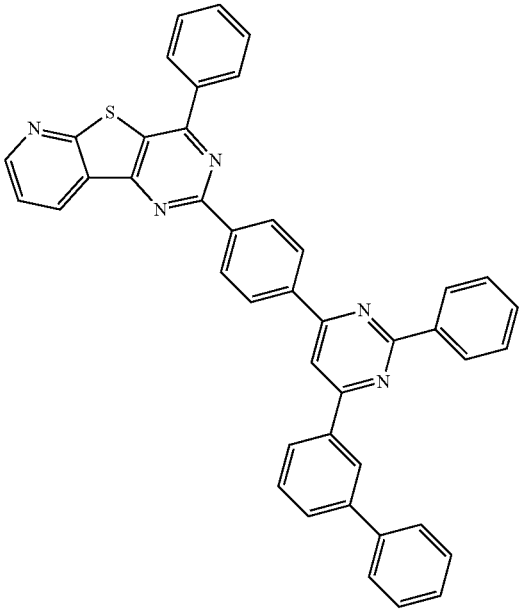 | 30% |

<Preparation Example 2> Synthesis of Compound 6

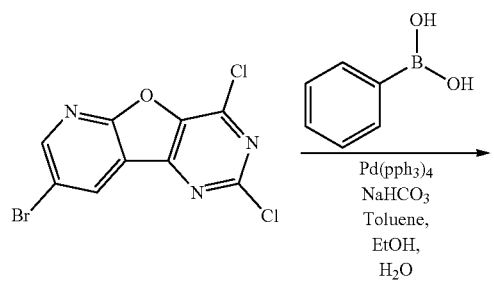

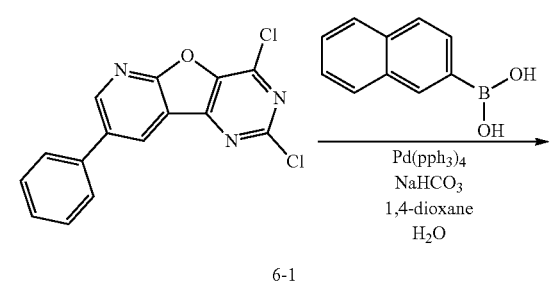

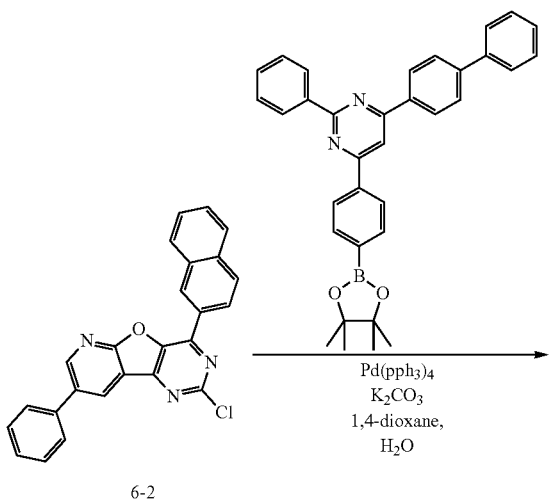

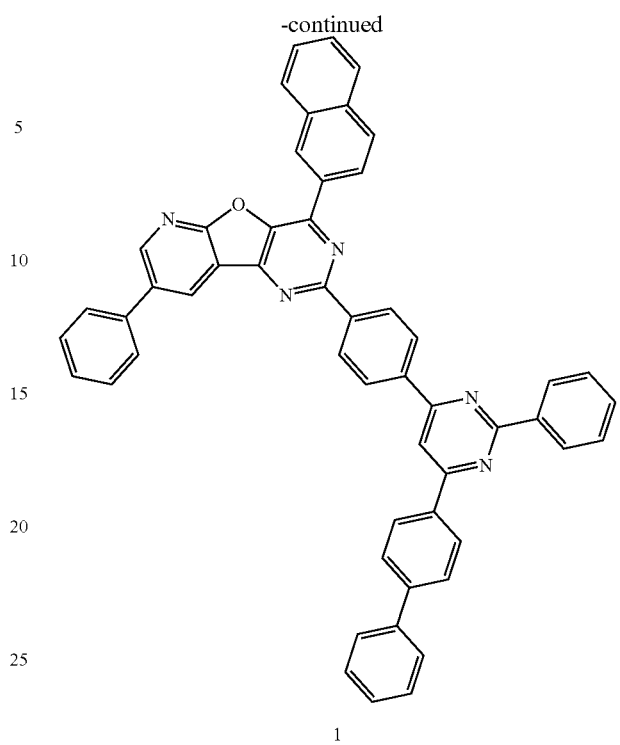

Preparation of Compound 6-1

After dissolving 8-bromo-2,4-dichloropyrido[3',2':4,5]furo[3,2-d]pyrimidine (10 g, 0.031 mol, 1 eq.) and phenylboronic acid (10.25 g, 0.084 mol, 2 eq.) in toluene (Tol) (100 ml), EtOH (20 ml) and $H_2O$ (20 ml), ($N_2$ condition), $Pd(PPh_3)_4$ (1.79 g, 1.55 mmol, 0.05 eq.) and $NaHCO_3$ (5.2 g, 0.062 mmol, 2 eq.) were introduced thereto, and the result was stirred for 2 hours under reflux. MC was introduced to the reaction solution for dissolution, and the result was extracted with water and the organic layer was dried with anhydrous $Na_2SO_4$. The solution was concentrated, dissolved in a small amount of MC, and passed through a MC/hexane column to obtain Compound 6-1 (6.07 g, 62% yield).

Preparation of Compound 6-2

After dissolving Compound 6-1 (6.07 g, 0.019 mol, 1 eq.) and naphthalen-2-ylboronic acid (3.2 g, 0.019 mol, 1 eq.) in Tol (60 ml), EtOH (10 ml) and $H_2O$ (10 ml), ($N_2$ condition) $Pd(PPh_3)_4$ (1.09 g, 0.95 mmol, 0.05 eq.) and $NaHCO_3$ (3.3 g, 0.038 mmol, 2 eq.) were introduced thereto, and the result was stirred for 3 hours under reflux. MC was introduced to the reaction solution for dissolution, and the result was extracted with water and the organic layer was dried with anhydrous $Na_2SO_4$. The solution was concentrated, dissolved in a small amount of MC, and passed through a MC/hexane column to obtain Compound 6-2 (2.7 g, 35% yield).

Preparation of Compound 6

Compound 6 (3.5 g, 71% yield) was obtained in the same manner as in the preparation of Compound 1 of Preparation Example 1 except that 4-([1,1'-biphenyl]-4-yl)-2-phenyl-6-(4-(4,4,5,5-tetramethyl-1,3,2-dioxaborolan-2-yl)phenyl)pyrimidine was used instead of 2,4-diphenyl-6-(4-(4,4,5,5-tetramethyl-1,3,2-dioxaborolan-2-yl)phenyl)-1,3,5-triazine.

Synthesis of Target Compounds

Target compounds were synthesized in the same manner as in Preparation Example 2 except that Compound A of the following Table 3 was used instead of phenylboronic acid, Compound B of the following Table 3 was used instead of naphthalen-2-ylboronic acid, and Compound C of the following Table 3 was used instead of 4-([1,1'-biphenyl]-4-yl)-2-phenyl-6-(4-(4,4,5,5-tetramethyl-1,3,2-dioxaborolan-2-yl)phenyl)pyrimidine.

TABLE 3
| Compound No. | Intermediate A | Intermediate B | Intermediate C | Target compound A | Yield |
|---|---|---|---|---|---|
| 19 | 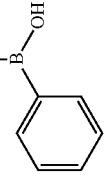 | 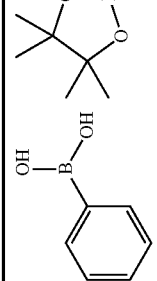 | 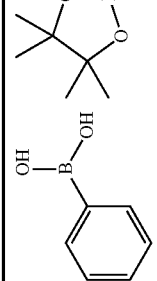 | 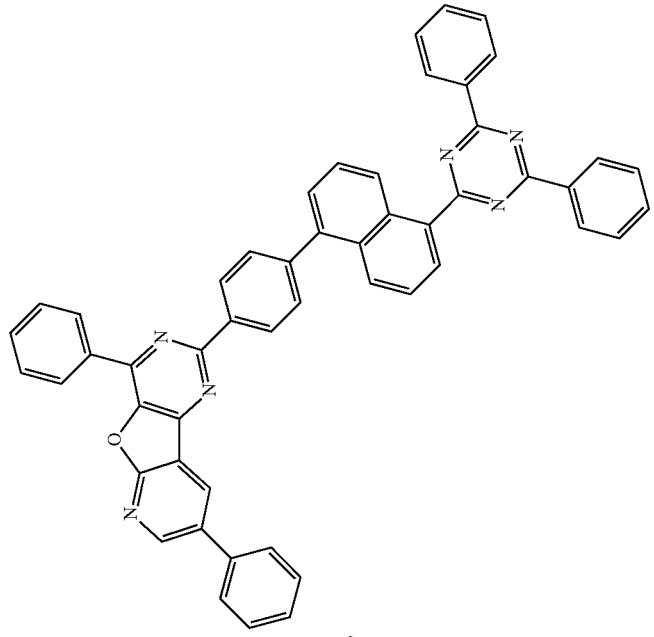 | 31% |

TABLE 3-continued

| Compound No. | Intermediate A | Intermediate B | Intermediate C | Target compound A | Yield |
|---|---|---|---|---|---|
| 50 | phenylboronic acid | phenylboronic acid | 4-(4,6-diphenyl-1,3,5-triazin-2-yl)phenylboronic acid pinacol ester | (triazine-containing benzofuro-pyridine target) | 35% |
| 60 | phenylboronic acid | phenylboronic acid | 4-(quinolin-2-yl)phenylboronic acid pinacol ester | (quinoline-containing benzofuro-pyridine target) | 28% |

TABLE 3-continued

| Compound No. | Intermediate A | Intermediate B | Intermediate C | Target compound A | Yield |
|---|---|---|---|---|---|
| 54 | phenylboronic acid | naphthalen-2-ylboronic acid | [4-(4,6-diphenyl-1,3,5-triazin-2-yl)phenyl]boronic acid pinacol ester | (structure shown) | 34% |

TABLE 3-continued

| Compound No. | Intermediate A | Intermediate B | Intermediate C | Target compound A | Yield |
|---|---|---|---|---|---|
| 62 | (phenylboronic acid) | (phenylboronic acid) | (pinacol boronate-phenyl-triazine-phenyl-carbazole intermediate) | (target compound structure) | 41% |

TABLE 3-continued

| Compound No. | Intermediate A | Intermediate B | Intermediate C | Target compound A | Yield |
|---|---|---|---|---|---|
| 66 | phenylboronic acid | naphthalen-2-ylboronic acid | [structure] | [structure] | 42% |

TABLE 3-continued

| Compound No. | Intermediate A | Intermediate B | Intermediate C | Target compound A | Yield |
|---|---|---|---|---|---|
| 74 | phenylboronic acid | naphthalen-2-ylboronic acid | (see structure) | (see structure) | 38% |

TABLE 3-continued

| Compound No. | Intermediate A | Intermediate B | Intermediate C | Target compound A | Yield |
|---|---|---|---|---|---|
| 75 | diphenylborinic acid (OH-B(Ph)-OH... phenyl) | phenylboronic acid | [triazine-carbazole-pinacol boronate intermediate structure] | [fused pyrido-furo-pyrimidine triazine carbazole target structure] | 36% |

TABLE 3-continued

| Compound No. | Intermediate A | Intermediate B | Intermediate C | Target compound A | Yield |
|---|---|---|---|---|---|
| 460 | phenylboronic acid | naphthalen-2-ylboronic acid | 4-(6-(pyridin-2-yl)pyridin-2-yl)phenyl pinacol boronate | (structure) | 22% |

Synthesis of Target Compounds

Target compounds were synthesized in the same manner as in Preparation Example 2 except that 8-bromo-2,4-dichloropyrido[3',2':4,5]thieno[3,2-d]pyrimidine was used instead of 8-bromo-2,4-dichloropyrido[3',2':4,5]furo[3,2-d]pyrimidine, Compound A of the following Table 4 was used instead of phenylboronic acid, Compound B of the following Table 4 was used instead of naphthalen-2-ylboronic acid, and Compound C of the following Table 4 was used instead of 4-([1,1'-biphenyl]-4-yl)-2-phenyl-6-(4-(4,4,5,5-tetramethyl-1,3,2-dioxaborolan-2-yl)phenyl)pyrimidine.

TABLE 4

| Compound No. | Intermediate A | Intermediate B | Intermediate C | Target compound B | Yield |
|---|---|---|---|---|---|
| 308 | phenylboronic acid | naphthalen-2-ylboronic acid | [4-(4,6-diphenyl-1,3,5-triazin-2-yl)phenyl]boronic acid pinacol ester | (target compound structure) | 21% |

TABLE 4-continued
| Compound No. | Intermediate A | Intermediate B | Intermediate C | Target compound B | Yield |
|---|---|---|---|---|---|
| 313 | 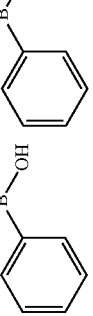 | 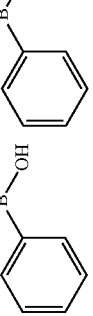 | 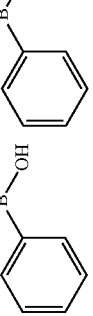 | 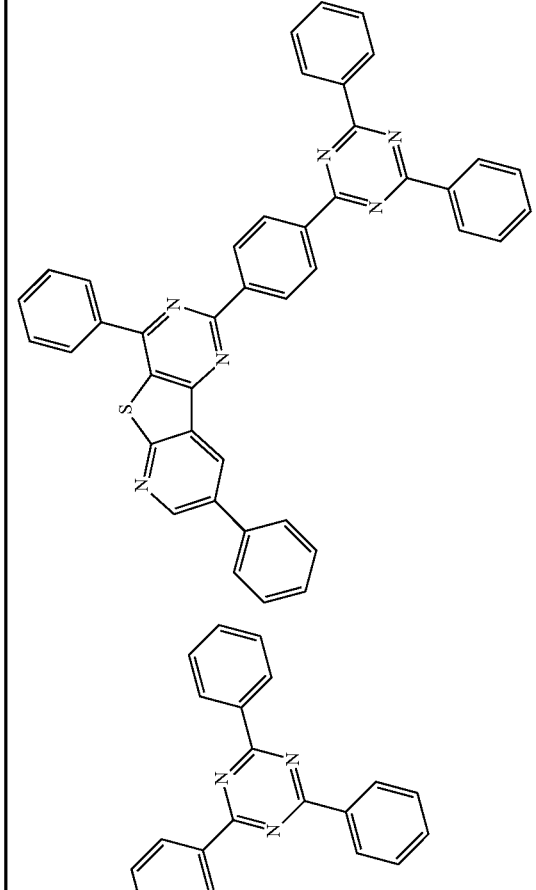 | 29% |

TABLE 4-continued
| Compound No. | Intermediate A | Intermediate B | Intermediate C | Target compound B | Yield |
|---|---|---|---|---|---|
| 321 | 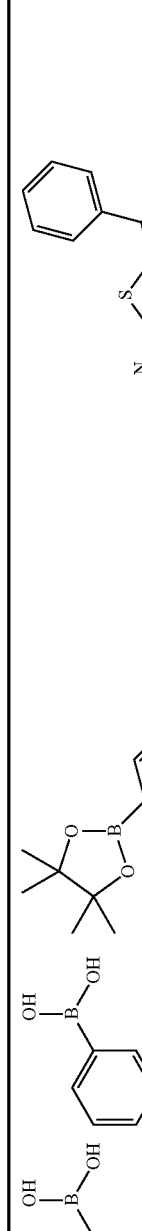 | 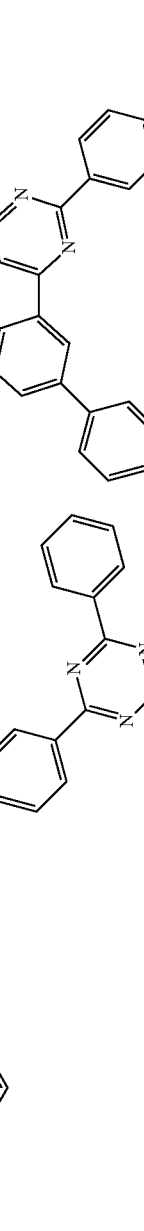 | 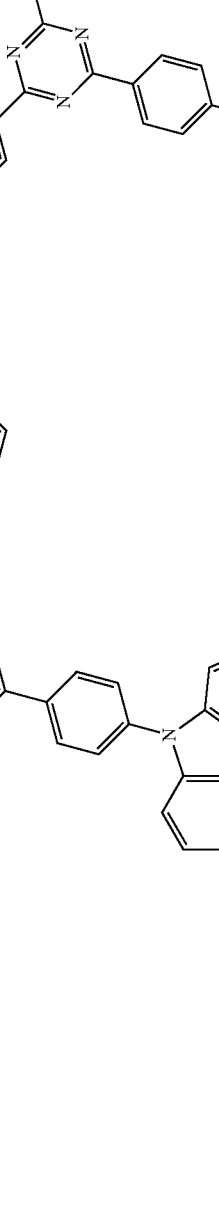 |  | 35% |

<Preparation Example 3> Synthesis of Compound 84

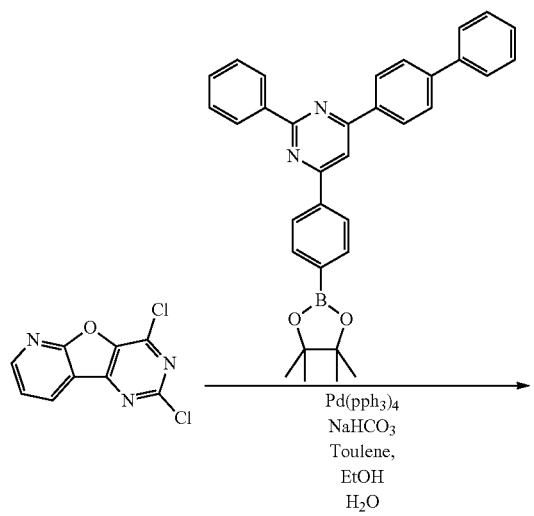

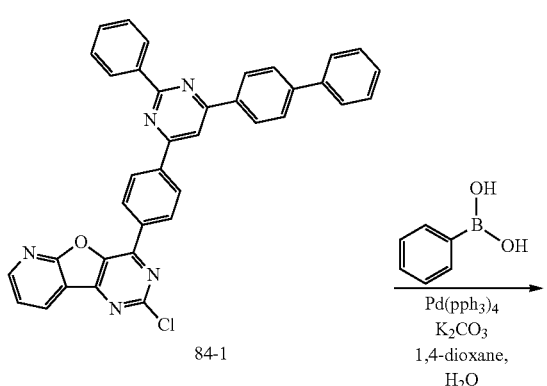

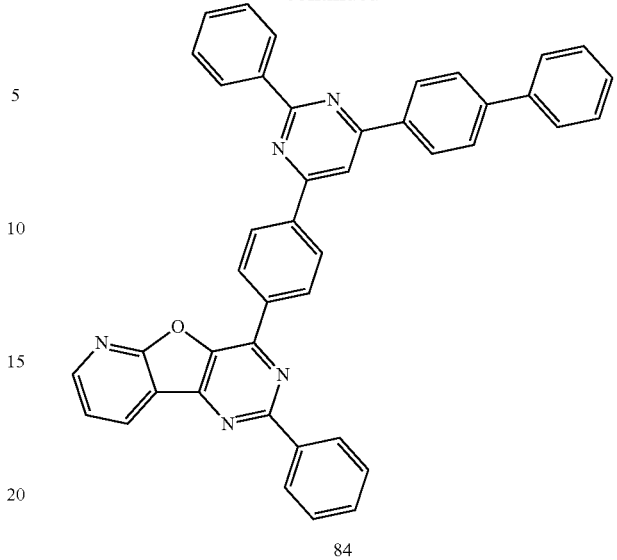

84

Preparation of Compound 84-1

After dissolving 2,4-dichloropyrido[3',2':4,5]furo[3,2-d]pyrimidine (10 g, 0.042 mol, 1 eq.) and 4-([1,1'-biphenyl]-4-yl)-2-phenyl-6-(4-(4,4,5,5-tetramethyl-1,3,2-dioxaborolan-2-yl)phenyl)pyrimidine (21 g, 0.042 mol, 1 eq.) in Tol (100 ml), EtOH (20 ml) and H$_2$O (20 ml), (N$_2$ condition) Pd(PPh$_3$)$_4$ (1.79 g, 1.55 mmol, 0.05 eq.) and NaHCO$_3$ (7.4 g, 0.084 mmol, 2 eq.) were introduced thereto, and the result was stirred for 2 hours under reflux. MC was introduced to the reaction solution for dissolution, and the result was extracted with water and the organic layer was dried with anhydrous Na$_2$SO$_4$. The solution was concentrated, dissolved in a small amount of MC, and passed through a MC/hexane column to obtain Compound 84-1 (7.62 g, 31% yield).

Preparation of Compound 84

After dissolving Compound 84-1 (7.62 g, 0.013 mol, 1 eq.) and phenylboronic acid (3.1 g, 0.026 mol, 2 eq.) in 1,4-dioxane (80 ml) and H$_2$O (20 ml), (N$_2$ condition) Pd(PPh$_3$)$_4$ (1.09 g, 0.65 mmol, 0.05 eq.) and NaHCO$_3$ (2.1 g, 0.026 mmol, 2 eq.) were introduced thereto, and the result was stirred for 12 hours under reflux. The reaction solution was filtered to obtain solids.

The solids were dissolved in dichlorobenzene (DCB), and passed through silica gel. The result was MC/MeOH precipitated and then Soxhlet extracted to obtain Compound 84 (5.3 g, 65% yield).

Synthesis of Target Compounds

Target compounds were synthesized in the same manner as in Preparation Example 3 except that Intermediate A of the following Table 5 was used instead of 4-([1,1'-biphenyl]-4-yl)-2-phenyl-6-(4-(4,4,5,5-tetramethyl-1,3,2-dioxaborolan-2-yl)phenyl)pyrimidine, and Intermediate B of the following Table was used instead of phenylboronic acid.

TABLE 5

| Compound No. | Intermediate A | Intermediate B | Target compound | Yield |
|---|---|---|---|---|
| 88 | | | | 35% |
| 92 | | | | 42% |
| 96 | | | | 37% |

TABLE 5-continued

| Compound No. | Intermediate A | Intermediate B | Target compound | Yield |
|---|---|---|---|---|
| 109 | | | | 21% |
| 128 | | | | 25% |

TABLE 5-continued

| Compound No. | Intermediate A | Intermediate B | Target compound | Yield |
|---|---|---|---|---|
| 133 | | | | 45% |
| 140 | | | | 32% |

TABLE 5-continued

| Compound No. | Intermediate A | Intermediate B | Target compound | Yield |
|---|---|---|---|---|
| 156 | | | | 27% |
| 160 | | | | 21% |

TABLE 5-continued

| Compound No. | Intermediate A | Intermediate B | Target compound | Yield |
|---|---|---|---|---|
| 164 | | | | 19% |
| 168 | | | | 18% |
| 461 | | | | 21% |

TABLE 5-continued
| Compound No. | Intermediate A | Intermediate B | Target compound | Yield |
|---|---|---|---|---|
| 469 | | | | 28% |
<Preparation Example 4> Synthesis of Compound 85
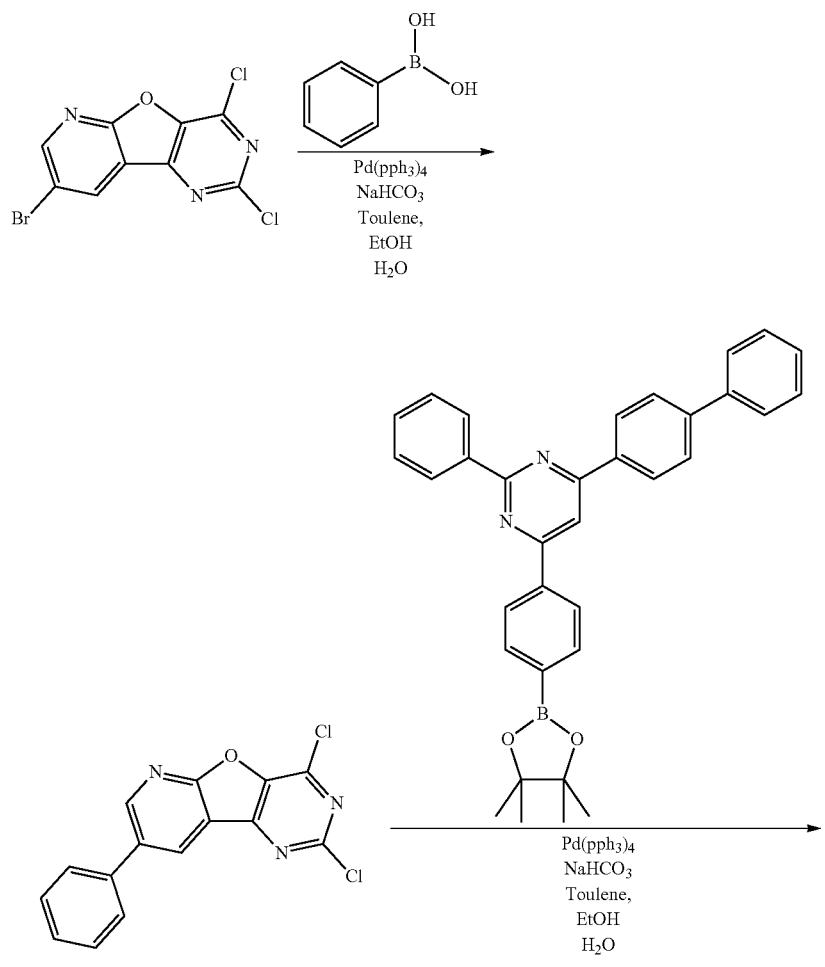
85-1

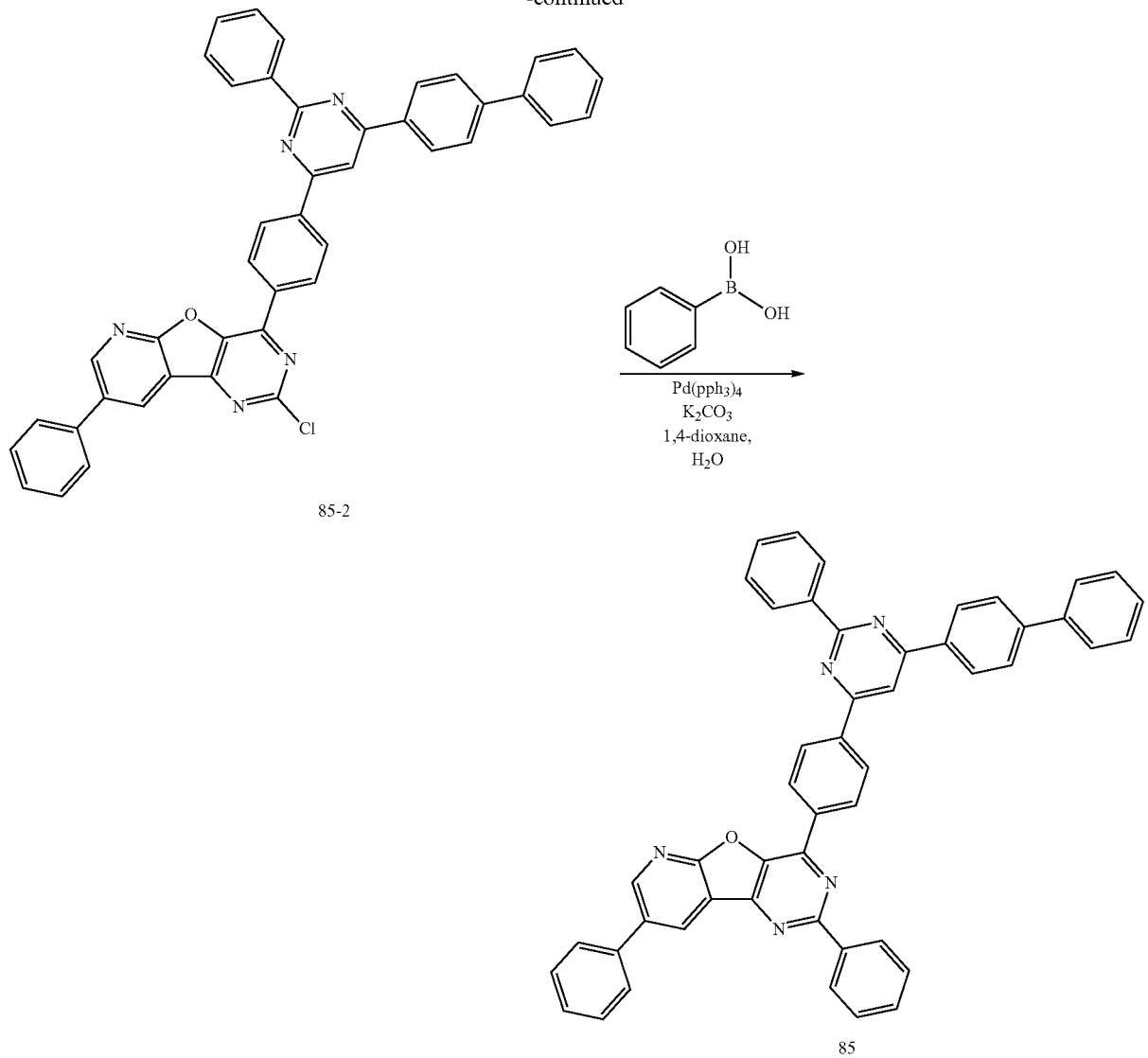

Preparation of Compound 85-1

After dissolving 8-bromo-2,4-dichloropyrido[3',2':4,5]furo[3,2-d]pyrimidine (10 g, 0.031 mol, 1 eq.) and phenylboronic acid (10.25 g, 0.084 mol, 2 eq.) in Tol (100 ml), EtOH (20 ml) and H₂O (20 ml), (N₂ condition) Pd(PPh₃)₄ (1.79 g, 1.55 mmol, 0.05 eq.) and NaHCO₃ (5.2 g, 0.062 mmol, 2 eq.) were introduced thereto, and the result was stirred for 2 hours under reflux. MC was introduced to the reaction solution for dissolution, and the result was extracted with water and the organic layer was dried with anhydrous Na₂SO₄. The solution was concentrated, dissolved in a small amount of MC, and passed through a MC/hexane column to obtain Compound 85-1 (5.68 g, 58% yield).

Preparation of Compound 85-2

After dissolving Compound 85-1 (5.68 g, 0.0179 mol, 1 eq.) and 4-([1,1'-biphenyl]-4-yl)-2-phenyl-6-(4-(4,4,5,5-tetramethyl-1,3,2-dioxaborolan-2-yl)phenyl)pyrimidine (9.16 g, 0.0179 mol, 1 eq.) in Tol (60 ml), EtOH (10 ml) and H₂O (10 ml), (N₂ condition) Pd(PPh₃)₄ (1.03 g, 0.89 mmol, 0.05 eq.) and NaHCO₃ (3.0 g, 0.0358 mmol, 2 eq.) were introduced thereto, and the result was stirred for 3 hours under reflux. The reaction solution was filtered to obtain solids, and the solids were dissolved in 1,2-dichlorobenzene, and then passed through silica gel. The result was MC/MeOH precipitated, and then obtained solids were filtered to obtain Compound 85-2 (6.04 g, 51% yield).

Preparation of Compound 85

Compound 85 (4.18 g 65%, yield) was obtained in the same manner as in the preparation of Compound 1 of Preparation Example 1 except that phenylboronic acid was used instead of 2,4-diphenyl-6-(4-(4,4,5,5-tetramethyl-1,3,2-dioxaborolan-2-yl)phenyl)-1,3,5-triazine.

Synthesis of Target Compounds

Target compounds were synthesized in the same manner as in Preparation Example 4 except that Compound A of the following Table 6 was used instead of phenylboronic acid, Compound B of the following Table 6 was used instead of 4-([1,1'-biphenyl]-4-yl)-2-phenyl-6-(4-(4,4,5,5-tetramethyl-1,3,2-dioxaborolan-2-yl)phenyl)pyrimidine, and Compound C of the following Table 6 was used instead of phenylboronic acid.

TABLE 6

| Compound No. | Compound A | Compound B | Compound C | Target Compound | Yield |
|---|---|---|---|---|---|
| 89 | (phenylboronic acid) | (triazine-phenyl-Bpin compound) | (2-naphthaleneboronic acid) | (target structure) | 34% |

TABLE 6-continued

| Compound No. | Compound A | Compound B | Compound C | Target Compound | Yield |
|---|---|---|---|---|---|
| 93 | | | | | 25% |

TABLE 6-continued

| Compound No. | Compound A | Compound B | Compound C | Target Compound | Yield |
|---|---|---|---|---|---|
| 106 | phenylboronic acid | 4-(4,6-diphenyl-1,3,5-triazin-2-yl)phenylboronic acid pinacol ester | phenylboronic acid | (structure shown) | 36% |

TABLE 6-continued

| Compound No. | Compound A | Compound B | Compound C | Target Compound | Yield |
|---|---|---|---|---|---|
| 110 | phenylboronic acid | 2-[4-(4,6-diphenyl-1,3,5-triazin-2-yl)phenyl]-4,4,5,5-tetramethyl-1,3,2-dioxaborolane | naphthalen-2-ylboronic acid | (structure shown) | 16% |

TABLE 6-continued

| Compound No. | Compound A | Compound B | Compound C | Target Compound | Yield |
|---|---|---|---|---|---|
| 129 | phenylboronic acid | 2-([1,1'-biphenyl]-3-yl)-4-(4-(4,4,5,5-tetramethyl-1,3,2-dioxaborolan-2-yl)phenyl)-6-phenyl-1,3,5-triazine | naphthalen-2-ylboronic acid | (target structure) | 18% |

TABLE 6-continued

| Compound No. | Compound A | Compound B | Compound C | Target Compound | Yield |
|---|---|---|---|---|---|
| 132 | phenylboronic acid | 2-([1,1'-biphenyl]-3-yl)-4-phenyl-6-(4-(4,4,5,5-tetramethyl-1,3,2-dioxaborolan-2-yl)phenyl)-1,3,5-triazine | phenylboronic acid | (see structure) | 21% |

TABLE 6-continued
| Compound No. | Compound A | Compound B | Compound C | Target Compound | Yield |
|---|---|---|---|---|---|
| 138 | 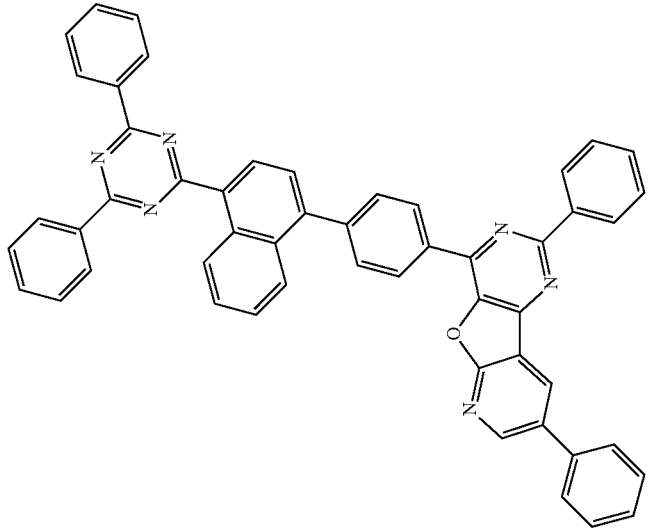 | 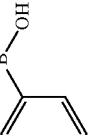 | 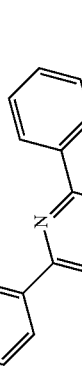 | 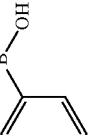 | 18% |

TABLE 6-continued

| Compound No. | Compound A | Compound B | Compound C | Target Compound | Yield |
|---|---|---|---|---|---|
| 143 | phenylboronic acid | [triazine-naphthyl-phenyl-Bpin compound] | phenylboronic acid | [target compound] | 15% |

TABLE 6-continued
| Compound No. | Compound A | Compound B | Compound C | Target Compound | Yield |
|---|---|---|---|---|---|
| 145 | 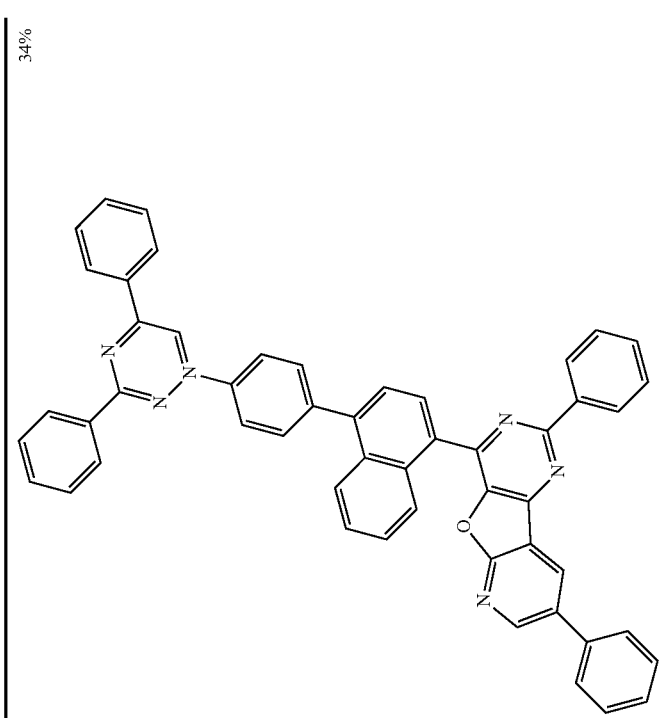 | 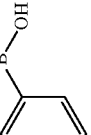 | 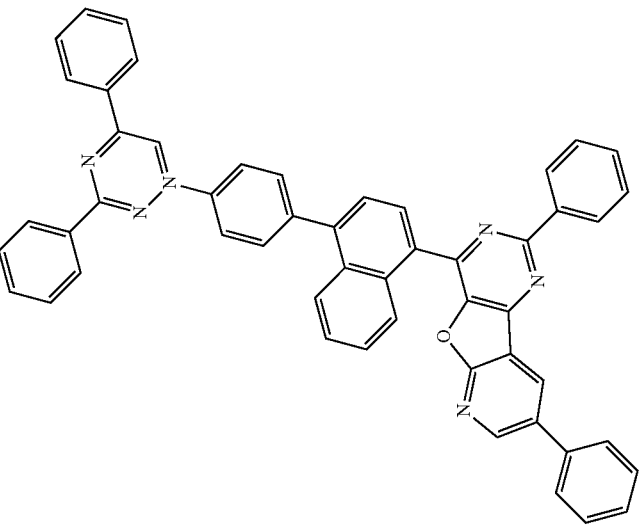 | 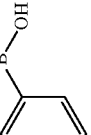 | 34% |

TABLE 6-continued

| Compound No. | Compound A | Compound B | Compound C | Target Compound | Yield |
|---|---|---|---|---|---|
| 165 | phenylboronic acid | carbazole-phenyl-triazine-phenyl-Bpin intermediate | phenylboronic acid | (target structure) | 31% |

TABLE 6-continued
| Compound No. | Compound A | Compound B | Compound C | Target Compound | Yield |
|---|---|---|---|---|---|
| 175 | 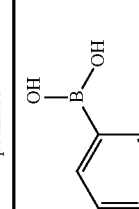 |  | 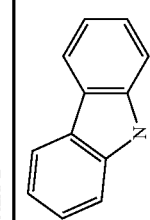 | 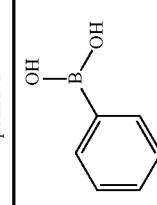 | 35% |

TABLE 6-continued
| Compound No. | Compound A | Compound B | Compound C | Target Compound | Yield |
|---|---|---|---|---|---|
| 464 | 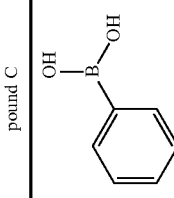 | 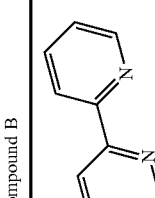 | 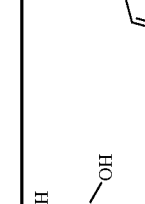 | 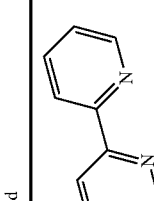 | 32% |

TABLE 6-continued
| Compound No. | Compound A | Compound B | Compound C | Target Compound | Yield |
|---|---|---|---|---|---|
| 468 | 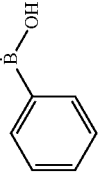 | 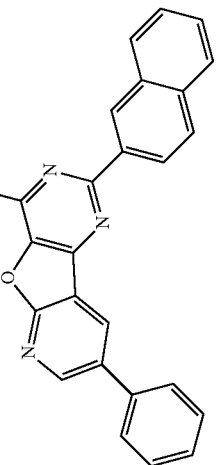 | 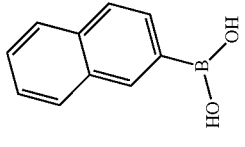 | 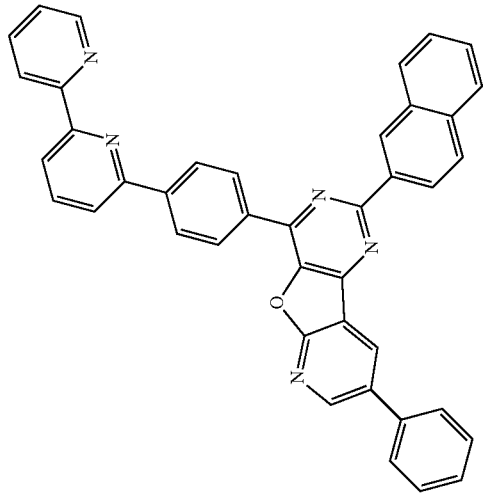 | 28% |

<Preparation Example 5> Synthesis of Compound 193
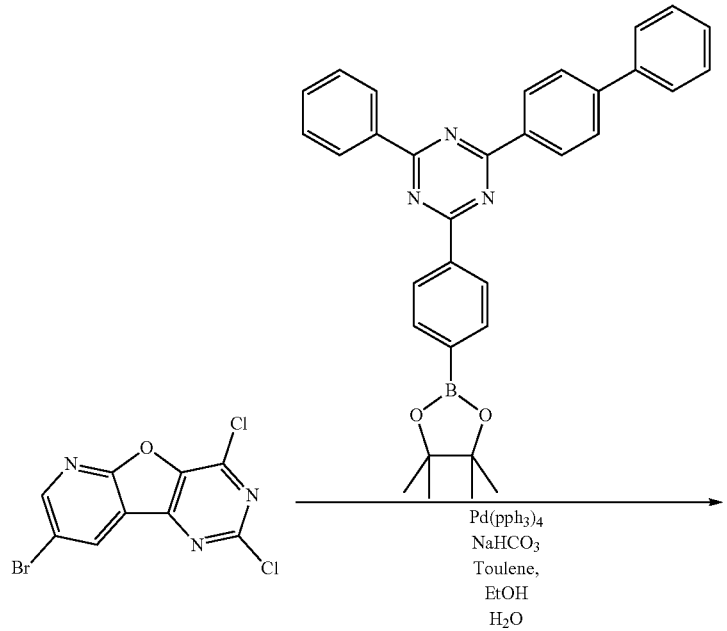
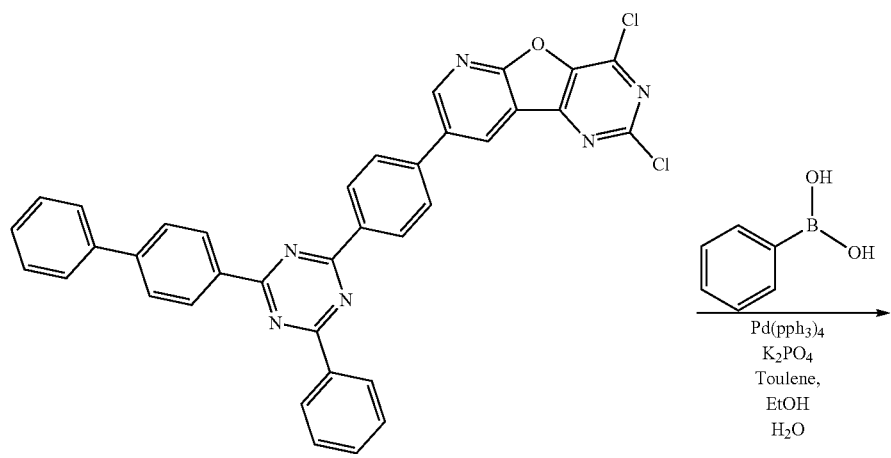
193-1

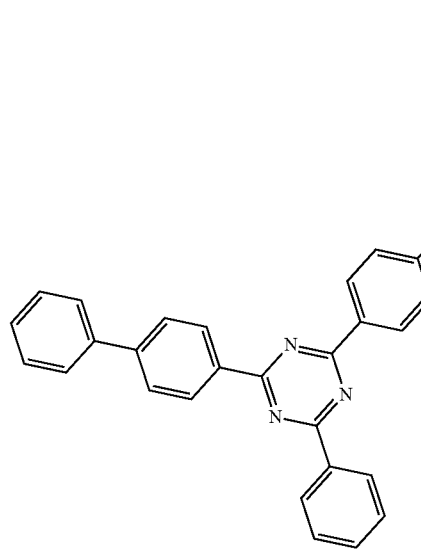
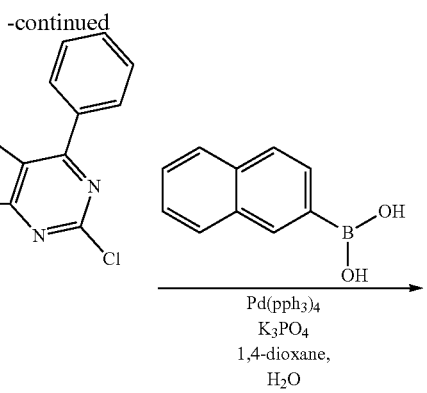

193-2

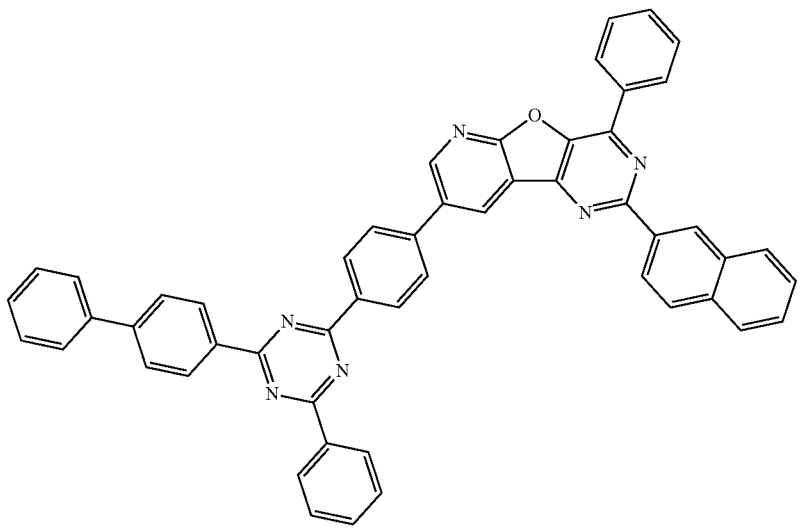

193

Preparation of Compound 193-1

After dissolving 8-bromo-2,4-dichloropyrido[3',2':4,5]furo[3,2-d]pyrimidine (10 g, 0.031 mol, 1 eq.) and 2-([1,1'-biphenyl]-4-yl)-4-phenyl-6-(4-(4,4,5,5-tetramethyl-1,3,2-dioxaborolan-2-yl)phenyl)-1,3,5-triazine (15.8 g, 0.031 mol, 1 eq.) in Tol (100 ml), EtOH (20 ml) and H$_2$O (20 ml), (N$_2$ condition) Pd(PPh$_3$)$_4$ (1.79 g, 1.55 mmol, 0.05 eq.) and NaHCO$_3$ (5.2 g, 0.062 mmol, 2 eq.) were introduced thereto, and the result was stirred for 2 hours under reflux. MC was introduced to the reaction solution for dissolution, and the result was extracted with water and the organic layer was dried with anhydrous Na$_2$SO$_4$. The solution was concentrated, dissolved in a small amount of MC, and passed through a MC/hexane column to obtain Compound 193-1 (6.18 g, 31% yield).

Preparation of Compound 193-2

After dissolving Compound 193-1 (6.18 g, 9.61 mmol, 1 eq.) and phenylboronic acid (1.16 g, 9.61 mmol, 1 eq.) in Tol (60 ml), EtOH (10 ml) and H$_2$O (10 ml), (N$_2$ condition) Pd(PPh$_3$)$_4$ (1.09 g, 0.95 mmol, 0.05 eq.) and NaHCO$_3$ (3.3 g, 0.038 mmol, 2 eq.) were introduced thereto, and the result was stirred for 3 hours under reflux. Produced solids were filtered, dissolved in CB, and passed through silica gel. The result was MC/MeOH precipitated to obtain Compound 193-2 (2.4 g, 34% yield).

Preparation of Compound 193

Compound 193 (2.04 g, 75% yield) was obtained in the same manner as in the preparation of Compound 1 of Preparation Example 1 except that naphthalen-2-ylboronic acid was used instead of 2,4-diphenyl-6-(4-(4,4,5,5-tetramethyl-1,3,2-dioxaborolan-2-yl)phenyl)-1,3,5-triazine.

Synthesis of Target Compounds

Target compounds of the following Table 7 were synthesized in the same manner as in Preparation Example 5 except that Compound A of the following Table 7 was used instead of 2-([1,1'-biphenyl]-4-yl)-4-phenyl-6-(4-(4,4,5,5-tetramethyl-1,3,2-dioxaborolan-2-yl)phenyl)-1,3,5-triazine, Compound B of the following Table 7 was used instead of phenylboronic acid, and Compound C of the following Table 7 was used instead of naphthalen-2-ylboronic acid.

TABLE 7

| Compound No. | Compound A | Compound B | Compound C | Target Compound | Yield |
|---|---|---|---|---|---|
| 179 | (structure) | phenylboronic acid | phenylboronic acid | (structure) | 21% |

TABLE 7-continued
| Compound No. | Compound A | Compound B | Compound C | Target Compound | Yield |
|---|---|---|---|---|---|
| 190 | 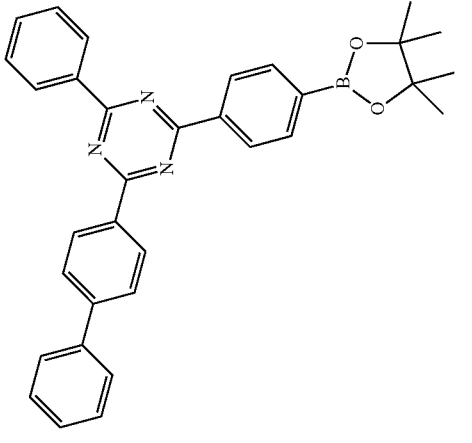 | 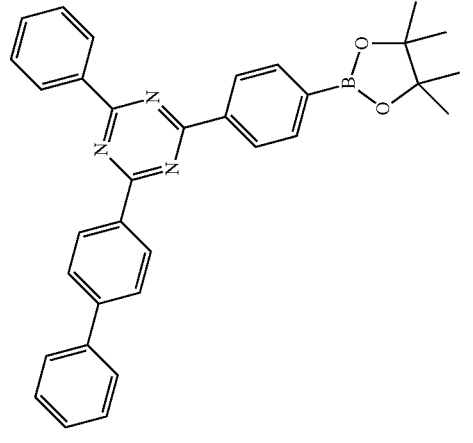 | 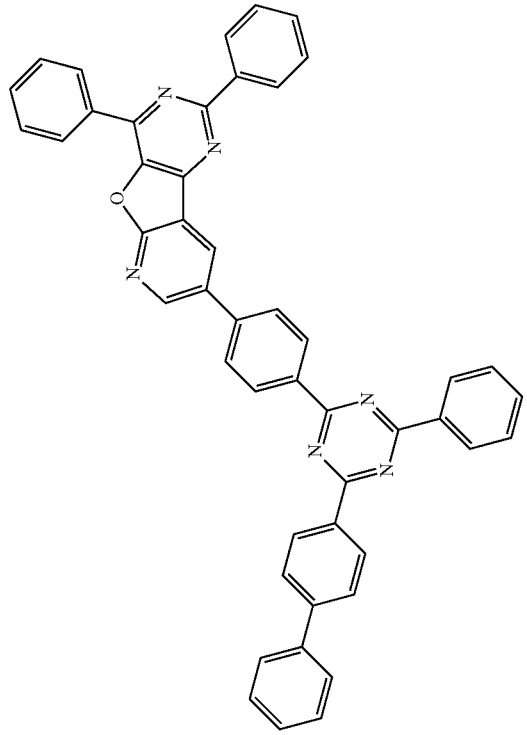 |  | 35% |
| 193 | 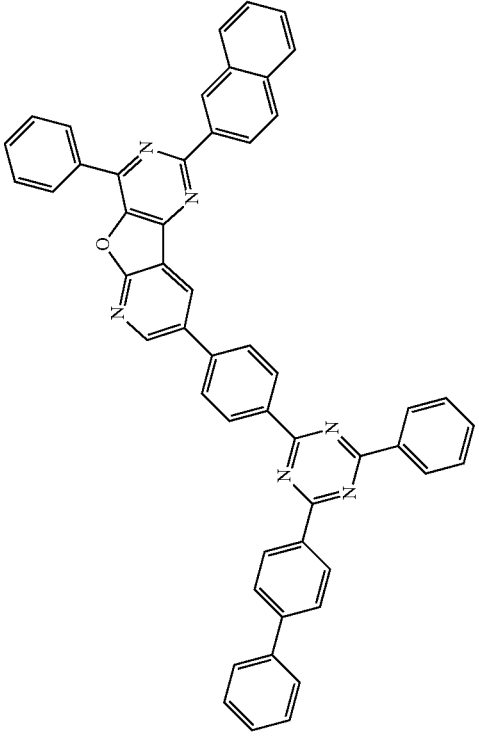 | 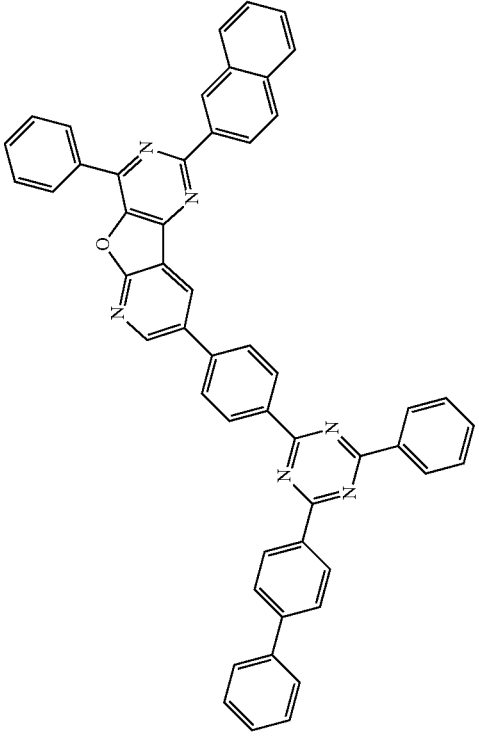 | 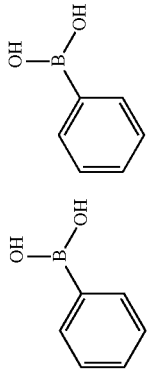 | 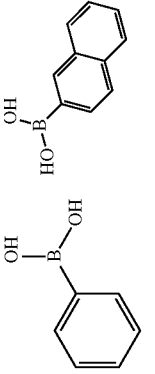 | 24% |

TABLE 7-continued
| Compound No. | Compound A | Compound B | Compound C | Target Compound | Yield |
|---|---|---|---|---|---|
| 197 | 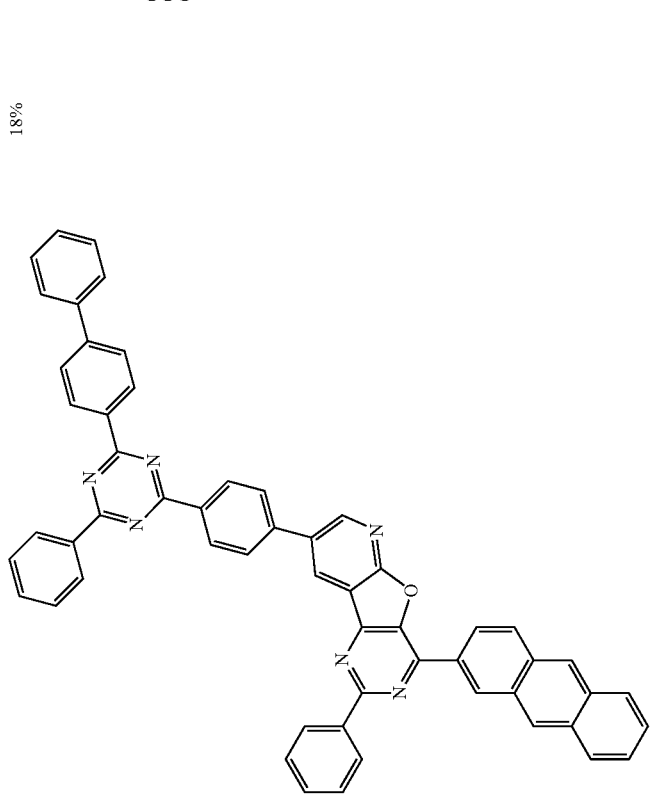 | 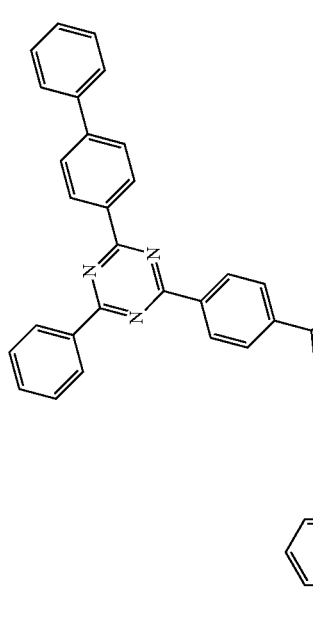 | 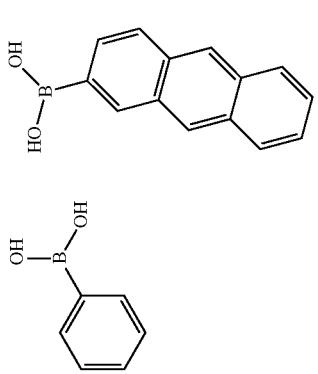 | 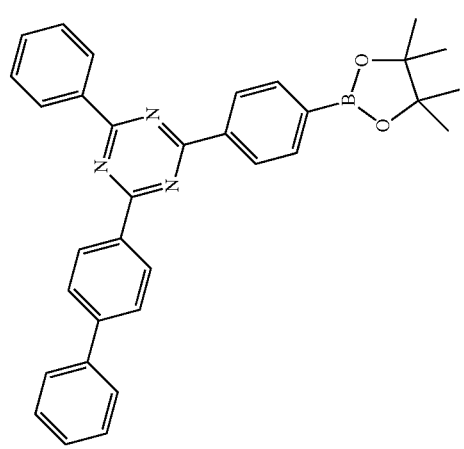 | 18% |

TABLE 7-continued
| Compound No. | Compound A | Compound B | Compound C | Target Compound | Yield |
|---|---|---|---|---|---|
| 201 | 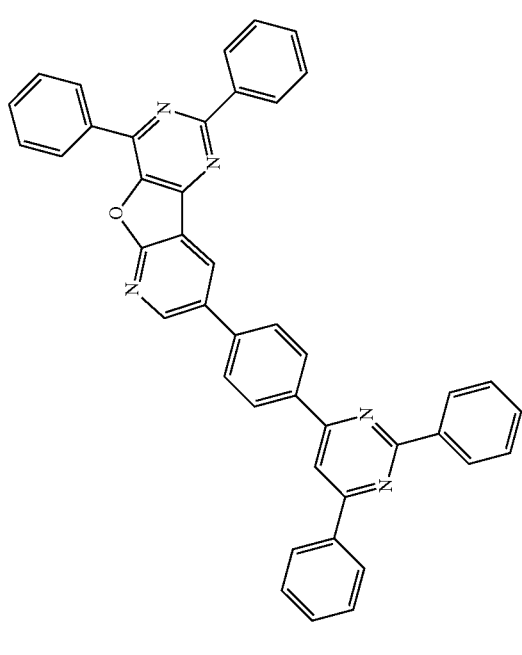 | 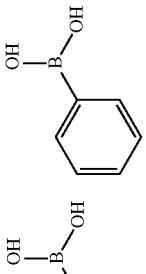 | 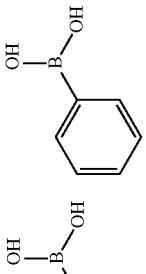 | 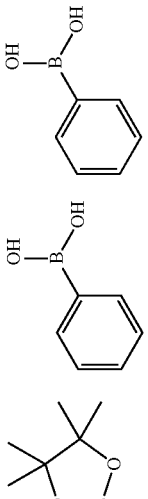 | 19% |

TABLE 7-continued

| Compound No. | Compound A | Compound B | Compound C | Target Compound | Yield |
|---|---|---|---|---|---|
| 204 | | | | | 22% |
| 212 | | | | | 34% |

TABLE 7-continued
| Compound No. | Compound A | Compound B | Compound C | Target Compound | Yield |
|---|---|---|---|---|---|
| 225 | 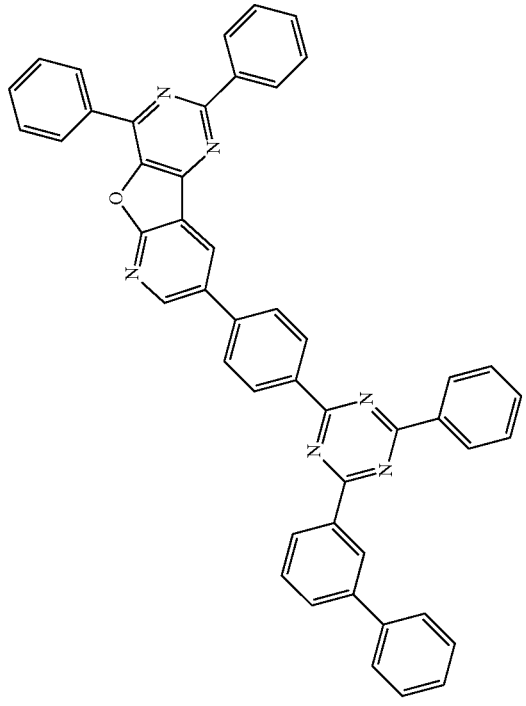 | 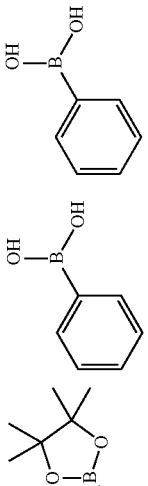 | 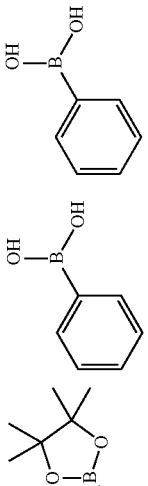 | 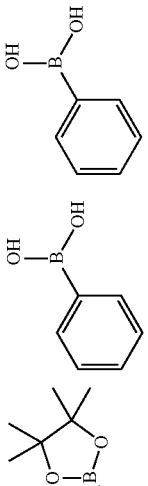 | 31% |

TABLE 7-continued
| Compound No. | Compound A | Compound B | Compound C | Target Compound | Yield |
|---|---|---|---|---|---|
| 240 | 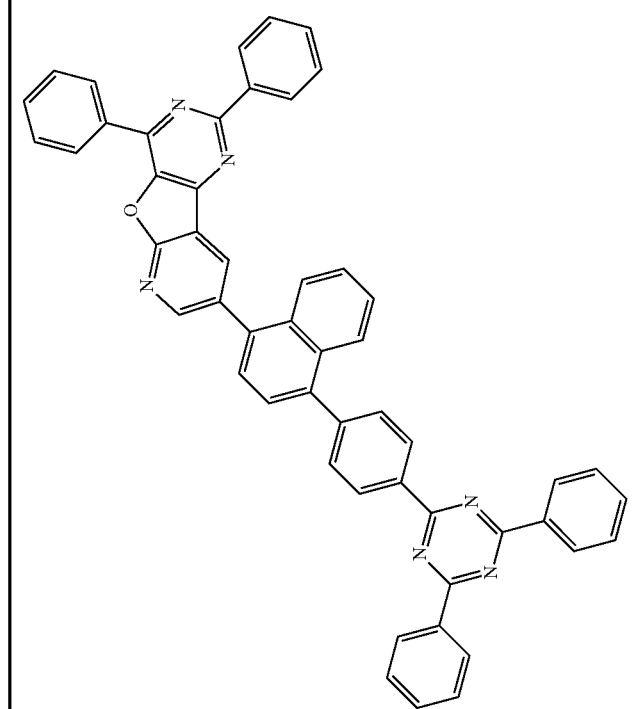 | 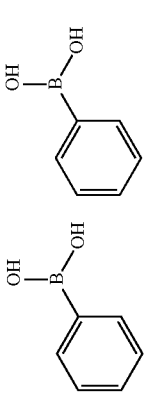 | 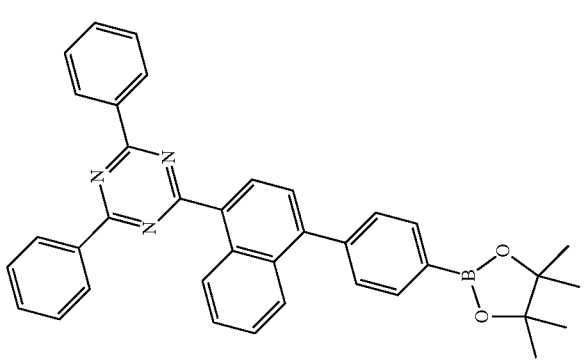 |  | 18% |

TABLE 7-continued

| Compound No. | Compound A | Compound B | Compound C | Target Compound | Yield |
|---|---|---|---|---|---|
| 253 | | | | | 15% |
| 262 | | | | | 21% |

TABLE 7-continued

| Compound No. | Compound A | Compound B | Compound C | Target Compound | Yield |
|---|---|---|---|---|---|
| 265 | | | | | 28% |
| 472 | | | | | 25% |

Compounds other than the compounds described in Preparation Example 1 to Preparation Example 5 and Table 1 to Table 7 were also prepared in the same manner as in the methods described in the preparation examples described above.

The following Table 8 and Table 9 show synthesis identification results for the synthesized compounds, and Table 8 shows measured values of field desorption (FD)-mass spectrometry (FD-MS), and Table 9 shows measured values of 1H NMR (CDCl$_3$, 200 Mz).

TABLE 8

| Compound | FD-MS | Compound | FD-MS |
|---|---|---|---|
| 1 | m/z = 629.71 (C43H27N5O = 629.22) | 138 | m/z = 756.85 (C52H32N6O = 756.26) |
| 6 | m/z = 755.86 (C53H33N5O = 755.27) | 140 | m/z = 706.79 (C48H30N6O = 706.25) |
| 9 | m/z = 729.82 (C51H31N5O = 729.25) | 143 | m/z = 756.85 (C52H32N6O = 756.26) |
| 13 | m/z = 630.70 (C42H26N6O = 630.22) | 145 | m/z = 756.85 (C52H32N6O = 756.26) |
| 14 | m/z = 705.80 (C49H31N5O = 705.25) | 156 | m/z = 768.86 (C53H32N6O = 768.26) |
| 19 | m/z = 756.85 (C52H32N6O = 756.26) | 160 | m/z = 794.90 (C55H34N6O = 794.28) |
| 21 | m/z = 680.75 (C46H28N6O = 680.23) | 164 | m/z = 719.79 (C48H29N7O = 719.24) |
| 25 | m/z = 630.70 (C42H26N6O = 630.22) | 165 | m/z = 795.89 (C54H33N7O = 795.27) |
| 33 | m/z = 706.79 (C48H30N6O = 706.25) | 168 | m/z = 819.91 (C56H33N7O = 819.27) |
| 41 | m/z = 730.81 (C50H30N6O = 730.25) | 175 | m/z = 794.90 (C55H34N6O = 794.28) |
| 45 | m/z = 706.79 (C48H30N6O = 706.25) | 179 | m/z = 705.80 (C49H31N5O = 705.25) |
| 49 | m/z = 554.60 (C36H22N6O = 554.19) | 190 | m/z = 706.79 (C48H30N6O = 706.25) |
| 50 | m/z = 630.70 (C42H26N6O = 630.22) | 193 | m/z = 756.85 (C52H32N6O = 756.26) |
| 53 | m/z = 604.66 (C40H24N6O = 604.20) | 197 | m/z = 806.91 (C56H34N6O = 806.28) |
| 54 | m/z = 680.75 (C46H28N6O = 680.23) | 201 | m/z = 630.70 (C42H26N6O = 630.22) |
| 60 | m/z = 526.59 (C36H22N4O = 526.18) | 204 | m/z = 680.75 (C46H28N6O = 680.23) |
| 61 | m/z = 719.79 (C48H29N7O = 719.24) | 212 | m/z = 795.89 (C54H33N7O = 795.27) |
| 62 | m/z = 795.89 (C54H33N7O = 795.27) | 225 | m/z = 706.79 (C48H30N6O = 706.25) |
| 65 | m/z = 769.85 (C52H31N7O = 769.26) | 240 | m/z = 756.85 (C52H32N6O = 756.26) |
| 66 | m/z = 845.94 (C58H35N7O = 845.29) | 253 | m/z = 845.94 (C58H35N7O = 845.29) |
| 69 | m/z = 819.91 (C56H33N7O = 819.27) | 262 | m/z = 794.90 (C55H34N6O = 794.28) |
| 73 | m/z = 769.85 (C52H31N7O = 769.26) | 265 | m/z = 844.96 (C59H36N6O = 844.30) |
| 74 | m/z = 845.94 (C58H35N7O = 845.29) | 272 | m/z = 645.77 (C43H27N5S = 645.20) |
| 75 | m/z = 795.89 (C54H33N7O = 795.27) | 276 | m/z = 695.83 (C47H29N5S = 695.21) |
| 77 | m/z = 719.79 (C48H29N7O = 719.24) | 280 | m/z = 745.89 (C51H31N5S = 745.23) |
| 84 | m/z = 819.91 (C56H33N7O = 819.27) | 284 | m/z = 646.76 (C42H26N6S = 646.19) |
| 85 | m/z = 705.80 (C49H31N5O = 705.25) | 308 | m/z = 696.82 (C46H28N6S = 696.21) |
| 88 | m/z = 679.77 (C47H29N5O = 679.24) | 313 | m/z = 646.76 (C42H26N6S = 646.19) |
| 89 | m/z = 755.86 (C53H33N5O = 755.27) | 321 | m/z = 811.95 (C54H33N7S = 811.25) |
| 92 | m/z = 729.82 (C51H31N5O = 729.25) | 457 | m/z = 501.54 (C33H19N5O = 501.16) |
| 93 | m/z = 805.92 (C57H35N5O = 805.28) | 458 | m/z = 651.71 (C45H25N5O = 651.21) |
| 96 | m/z = 630.70 (C42H26N6O = 630.22) | 459 | m/z = 577.63 (C39H23N5O = 577.19) |
| 106 | m/z = 630.70 (C42H26N6O = 630.22) | 460 | m/z = 603.67 (C41H25N5O = 603.21) |
| 109 | m/z = 604.66 (C40H24N6O = 604.20) | 461 | m/z = 551.60 (C37H21N5O = 551.17) |
| 110 | m/z = 604.66 (C40H24N6O = 604.20) | 464 | m/z = 653.73 (C45H27N5O = 653.22) |
| 128 | m/z = 680.75 (C46H28N6O = 680.23) | 468 | m/z = 603.67 (C41H25N5O = 603.21) |
| 129 | m/z = 756.85 (C52H32N6O = 756.26) | 469 | m/z = 501.54 (C33H19N5O = 501.16) |
| 132 | m/z = 706.79 (C48H30N6O = 706.25) | 472 | m/z = 653.73 (C45H27N5O = 653.22) |
| 133 | m/z = 630.70 (C42H26N6O = 630.22) | | |

TABLE 9

| Compound | $^1$H NMR (CDCl$_3$, 200 Mz) |
|---|---|
| 1 | δ = 8.51 (m, 1H), 8.43 (m, 1H), 8.28~8.30 (m, 7H), 7.79~7.85 (m, 6H), 7.36~7.51 (m, 12H) |
| 6 | δ = 9.24 (m, 1H), 8.28~8.34 (m, 8H), 7.85~8.00 (m, 9H), 7.41~7.89 (m, 15H) |
| 9 | δ = 8.51 (m, 1H), 8.43 (m, 1H), 8.28~8.31 (m, 9H), 8.13 (m, 1H), 7.85~7.97 (m, 7H), 7.61 (m, 1H), 7.36~7.52 (m, 11H) |
| 13 | δ = 8.51 (m, 1H), 8.43 (m, 1H), 2.28 (m, 2H), 7.79~7.85 (m, 8H), 7.36~7.52 (m, 12H), 7.25 (m, 2H) |
| 14 | δ = 8.51 (m, 1H), 8.43 (m, 1H), 8.28~8.30 (m, 9H), 7.85 (m, 4H), 7.41~7.52 (m, 14H) |
| 19 | δ = 9.24 (m, 1H), 8.51 (m, 2H), 8.42 (m, 1H), 8.28 (m, 3H), 7.95~7.97 (m, 2H), 7.79~7.85 (m, 3H), 7.41~7.61 (m, 16H), 7.25 (m, 2H) |
| 21 | δ = 8.51 (m, 1H), 8.43 (m, 1H), 8.24~8.28 (m, 3H), 7.79~7.85 (m, 6H), 7.70 (m, 1H), 7.367.51 (m, 14H) |
| 25 | δ = 8.51 (m, 1H), 8.43 (m, 1H), 8.24~8.34 (m, 4H), 7.87~8.00 (m, 8H), 7.70 (m, 1H), 7.36~7.59 (m, 13H) |
| 33 | δ = 8.51 (m, 1H), 8.43 (m, 1H), 8.24~8.30 (m, 5H), 7.85 (m, 6H), 7.70 (m, 1H), 7.36~7.57 (m, 16H) |
| 41 | δ = 8.51 (m, 1H), 8.43 (m, 1H), 8.28~8.31 (m, 4H), 8.13 (m, 1H), 7.85~7.91 (m, 9H), 7.61 (m, 1H), 7.36~7.52 (m, 11H) |
| 45 | δ = 8.51 (m, 1H), 8.43 (m, 1H), 8.28~8.30 (m, 4H), 7.85 (m, 8H), 7.41~7.52 (m, 14H), 7.25 (m, 2H) |
| 49 | δ = 8.51 (m, 1H), 8.43 (m, 1H), 8.28 (m, 4H), 7.79~7.85 (m, 6H), 7.41~7.51 (m, 9H) |
| 50 | δ = 8.28 (m, 4H), 7.97 (m, 1H), 7.79~7.85 (m, 6H), 7.41~7.52 (m, 14H) |
| 53 | δ = 8.51 (m, 1H), 8.43 (m, 1H), 8.28~8.34 (m, 5H), 7.85~8.00 (m, 8H), 7.36~7.59 (m, 9H) |
| 54 | δ = 8.28~8.34 (m, 5H), 7.92~8.00 (m, 9H), 7.41~7.59 (m, 13H) |
| 60 | δ = 9.24 (m, 1H), 8.81 (m, 2H), 8.06~8.10 (m, 2H), 7.97~7.98 (m, 2H), 7.88 (m, 2H), 7.78~7.79 (m, 3H), 7.41~7.52 (m, 10H) |
| 61 | δ = 8.51~8.55 (m, 2H), 8.43 (m, 1H), 8.28 (m, 2H), 8.12 (m, 1H), 7.94 (m, 1H), 7.79~7.85 (m, 8H), 7.63~7.68 (m, 3H), 7.29~7.51 (m, 11H) |
| 62 | δ = 9.24 (m, 1H), 8.55 (m, 1H), 8.28 (m, 2H), 8.12 (m, 1H), 7.94~7.97 (m, 2H), 7.79~7.85 (m, 8H), 7.63~7.68 (m, 3H), 7.25~7.52 (m, 13H) |
| 65 | δ = 8.51~8.55 (m, 2H), 8.43 (m, 1H), 8.28~8.34 (m, 3H), 8.12 (m, 1H), 7.79~8.00 (m, 11H), 7.25~7.68 (m, 13H) |
| 66 | δ = 9.24 (m, 1H), 8.55 (m, 1H), 8.28~8.34 (m, 3H), 8.12 (m, 1H), 7.79~8.00 (m, 12H), 7.25~7.68 (m, 17H) |
| 69 | δ = 8.51~8.55 (m, 2H), 8.43 (m, 1H), 8.28~8.31 (m, 4H), 8.12~8.13 (m, 2H), 7.79~7.97 (m, 10H), 7.61~7.68 (m, 4H), 7.25~7.51 (m, 10H) |
| 73 | δ = 8.51~8.55 (m, 2H), 8.43 (m, 1H), 8.28~8.34 (m, 4H), 8.09~8.12 (m, 2H), 7.87~8.00 (m, 9H), 7.35~7.59 (m, 13H) |
| 74 | δ = 9.24 (m, 1H), 8.55 (m, 1H), 8.28~8.34 (m, 4H), 8.09~8.12 (m, 2H), 7.85~8.00 (m, 10H), 7.41~7.59 (m, 17H) |
| 75 | δ = 9.24 (m, 1H), 8.55 (m, 1H), 8.28 (m, 3H), 8.09~8.12 (m, 2H), 7.94~7.97 (m, 2H), 7.79~7.85 (m, 6H), 7.63 (m, 1H), 7.25~7.52 (m, 17H) |

TABLE 9-continued

| Compound | $^1$H NMR (CDCl$_3$, 200 Mz) |
|---|---|
| 77 | δ = 8.51~8.55 (m, 2H), 8.43 (m, 1H), 8.28 (m, 3H), 8.09~8.12 (m, 2H), 7.94 (m, 1H), 7.79~7.85 (m, 6H), 7.63 (m, 1H), 7.36~7.51 (m, 13H) |
| 84 | δ = 8.51 (m, 1H), 8.43 (m, 1H), 8.23~8.90 (m, 11H), 7.85 (m, 2H), 7.36~7.52 (m, 12H) |
| 85 | δ = 9.24 (m, 1H), 8.23~8.30 (m, 11H), 7.97 (m, 1H), 7.85 (m, 2H), 7.41~7.52 (m, 16H) |
| 88 | δ = 9.09 (m, 1H), 8.43~8.51 (m, 3H), 8.23~8.30 (m, 9H), 7.85~8.00 (m, 5H), 7.36~7.52 (m, 11H) |
| 89 | δ = 9.24 (m, 1H), 9.09 (m, 1H), 8.49 (m, 1H), 8.23~8.30 (m, 9H), 7.85~8.00 (m, 6H), 7.41~7.52 (m, 15H) |
| 92 | δ = 8.51 (m, 1H), 8.43 (m, 1H), 8.23~8.31 (m, 11H), 8.13 (m, 1H), 7.85~7.97 (m, 5H), 7.61 (m, 1H), 7.36~7.52 (m, 11H) |
| 93 | δ = 9.24 (m, 1H), 8.28~8.31 (m, 13H), 8.13 (m, 1H), 7.85~7.97 (m, 6H), 7.61 (m, 1H), 7.39~7.52 (m, 13H) |
| 96 | δ = 8.51 (m, 1H), 8.43 (m, 1H), 8.28~8.30 (m, 6H), 7.85 (m, 4H), 7.36~7.52 (m, 12H) |
| 106 | δ = 9.24 (m, 1H), 8.28~8.30 (m, 8H), 7.97 (m, 1H), 7.85 (m, 2H), 7.41~7.52 (m, 14H) |
| 109 | δ = 9.09 (m, 1H), 8.43~8.51 (m, 3H), 8.28~8.30 (m, 6H), 7.85~8.00 (m, 5H), 7.36~7.51 (m, 9H) |
| 110 | δ = 9.24 (m, 1H), 8.49 (m, 1H), 8.28~8.30 (m, 6H), 7.85~8.00 (m, 6H), 7.41~7.59 (m, 13H) |
| 128 | δ = 9.09 (m, 1H), 8.43~8.51 (m, 3H), 8.24~8.30 (m, 5H), 7.85~8.00 (m, 5H), 7.70 (m, 1H), 7.41~7.59 (m, 13H) |
| 129 | δ = 9.24 (m, 1H), 9.09 (m, 1H), 8.49 (m, 1H), 8.24~8.30 (m, 5H), 7.85~8.00 (m, 6H), 7.70 (m, 1H), 7.41~7.59 (m, 17H) |
| 132 | δ = 9.24 (m, 1H), 8.24~8.28 (m, 7H), 7.97 (m, 1H), 7.85 (m, 2H), 7.70 (m, 1H), 7.41~7.52 (m, 18H) |
| 133 | δ = 8.51 (m, 1H), 8.43 (m, 1H), 8.24~8.28 (m, 7H), 7.85 (m, 2H), 7.70 (m, 1H), 7.36~7.52 (m, 14H) |
| 138 | δ = 9.24 (m, 1H), 8.55 (m,1H), 8.28~8.30 (m, 8H), 7.97~8.01 (m, 3H), 7.41~7.52 (m, 16H) |
| 140 | δ = 8.51 (m, 1H), 8.43 (m, 1H), 8.24~8.30 (m, 5H), 7.85 (m, 4H), 7.70 (m, 1H), 7.36~7.52 (m, 16H), 7.25 (m, 2H) |
| 143 | δ = 9.24 (m, 1H), 8.51 (m, 2H), 8.42 (m, 1H), 8.28~8.30 (m, 8H), 7.95~7.97 (m, 2H), 7.41~7.52 (m, 16H), 7.25 (m, 2H) |
| 145 | δ = 9.24 (m, 1H), 8.55 (m, 2H), 8.28 (m, 6H), 7.97~8.01 (m, 3H), 7.85 (m, 2H), 7.41~7.55 (m, ) |
| 156 | δ = 9.09 (m, 1H), 8.43~8.55 (m, 4H), 8.28~8.30 (m, 7H), 8.09~8.12 (m, 2H), 7.98~8.00 (m, 4H), 7.79 (m, 1H), 7.25~7.59 (m, 13H) |
| 160 | δ = 8.55~8.51 (m, 2H), 8.43 (m, 1H), 8.28~8.30 (m, 7H), 8.09~7.12 (m, 2H), 7.94 (m, 1H), 7.79~7.85 (m, 3H), 7.63 (m, 1H), 7.25~7.52 (m, 15H) |
| 164 | δ = 8.51~8.55 (m, 2H), 8.43 (m, 1H), 8.28~8.30 (m, 7H), 8.09~8.12 (m, 2H), 7.94 (m, 1H), 7.85 (m, 2H), 7.63 (m, 1H), 7.25~7.51 (m, 13H) |
| 165 | δ = 9.24 (m, 1H), 8.55 (m, 1H), 8.28~8.30 (m, 7H), 8.09~8.12 (m, 2H), 7.94~7.97 (m, 2H), 7.85 (m, 2H), 7.63 (m, 1H), 7.25~7.52 (m, 17H) |
| 168 | δ = 8.51~8.55 (m, 2H), 8.43 (m, 1H), 8.28~8.30 (m, 7H), 8.09~7.13 (m, 3H), 7.85~7.97 (m, 6H), 7.61~7.63 (m, 2H), 7.25~7.50 (m, 12H) |
| 175 | δ = 9.24 (d, 1H), 8.55 (d, 1H), 8.23~8.30 (m, 9H), 8.09~8.12 (m, 2H), 7.94~7.97 (m, d), 7.79 (d, 1H), 7.63 (d, 1H), 7.25~7.52 (m, 17H) |
| 179 | δ = 9.24 (d, 1H), 8.23~8.30 (m, 9H), 7.97 (d, 1H), 7.79~7.85 (m, 4H), 7.41~7.52 (m, 14H), 7.25 (t, 2H) |
| 190 | δ = 9.24 (d, 1H), 8.28 (m, 4H), 7.97 (d, 1H), 7.79~7.85 (m, 6H), 7.41~7.85 (m, 14H), 7.25 (d, 4H) |
| 193 | δ = 9.24 (d, 1H), 9.09 (t, 1H), 8.49 (t, 1H), 8.28 (m, 2H), 7.79~8.00 (m, 10H), 7.41~7.59 (m, 13H), 7.25 (m, 4H) |
| 197 | δ = 9.24 (d, 1H), 8.28~8.31 (m, 6H), 8.13 (t, 1H), 7.85~7.97 (m, 8H), 7.61 (m, 1H), 7.39~7.52 (m, 13H), 7.25 (m, 4H) |
| 201 | δ = 9.24 (d, 1H), 8.28 (m, 6H), 7.85~7.97 (m, 4H), 7.41~7.51 (m, 12H), 7.25 (m, 2H) |
| 204 | δ = 9.24 (d, 1H), 9.09 (t, 1H), 8.49 (m, 1H), 8.28 (m, 4H), 7.79~8.00 (m, 8H), 7.41~7.59 (m, 8H), 7.25 (m, 2H) |
| 212 | δ = 9.24 (d, 1H), 8.55 (t, 1H), 8.28 (m, 4H), 8.12 (m, 1H), 7.97~7.97 (m, 2H), 7.79~7.85 (m, 6H), 7.63~7.68 (m, 3H), 7.25~7.51 (m, 15H) |
| 225 | δ = 9.24 (d, 1H), 8.24~8.28 (m, 5H), 7.97 (d, 1H), 7.79~7.85 (m, 4H), 7.70 (m, 1H), 7.41~7.52 (m, 16H), 7.25 (m, 2H) |
| 240 | δ = 9.24 (d, 1H), 8.55 (t, 2H), 8.28 (m, 6H), 7.97~8.01 (m, 3H), 7.79~7.85 (m, 4H), 7.41~7.51 (m, 14H), 7.25 (m, 2H) |
| 253 | δ = 9.24 (m, 1H), 9.09 (m, 1H), 8.49~8.55 (m, 2H), 8.28 (m, 3H), 8.09~8.12 (m, 2H), 7.79~8.00 (m, 9H), 7.25~7.59 (m, 17H) |
| 262 | δ = 9.24 (m, 1H), 8.55 (m, 1H), 8.23~8.30 (m, 7H), 8.09~8.12 (m, 1H), 7.94~7.97 (t, 2H), 7.79 (m, 3H), 7.63 (t, 1H), 7.33~7.51 (m, 17H) |
| 265 | δ = 9.24 (d, 1J), 9.09 (t, 1H), 8.498.55 (m, 2H), 8.23~8.30 (m, 5H), 8.09~8.12 (m, 2H), 7.94~8.00 (m, 5H), 7.79 (m, 3H), 7.33~7.59 (m, 17H) |
| 272 | δ = 8.69 (d, 1H), 8.51 (d, 1H), 8.23~8.30 (m, 7H), 7.79~7.85 (m, 6H), 7.36~7.52 (m, 12H) |
| 276 | δ = 8.69 (d, 1H), 8.51 (d, 1H), 8.28~8.34 (m, 8H), 7.85~8.00 (m, 8H), 7.36~7.52 (m, 11H) |
| 280 | δ = 8.69 (d, 1H), 8.51 (d, 1H), 8.28~8.31 (m, 9H), 8.13 (d, 1H), 7.85~7.91 (m, 7H), 7.61 (t, 1H), 7.39~7.52 (m, 11H) |
| 284 | δ = 8.69 (d, 1H), 8.51 (d, 1H), 8.24~8.28 (m, 3H), 7.79~7.85 (m, 6H), 7.70 (d, 1H), 7.36~7.52 (m, 14H) |
| 308 | δ = 9.24 (d, 1H), 8.28~8.34 (m, 5H), 7.85~8.00 (m, 9H), 7.41~7.59 (m, 14H) |
| 313 | δ = 9.24 (d, 1H), 8.28 (m, 4H), 7.97 (d, 1H), 7.79~7.85 (m, 6H), 7.41~7.52 (m, 14H) |
| 321 | δ = 9.24 (d, 1H), 8.55 (m, 1H), 8.28 (m, 2H), 8.12 (m, 1H), 7.94~7.97 (m, 2H), 7.79~7.85 (m, 8H), 7.63~7.68 (m, 3H), 7.25~7.52 (m, 13H) |
| 457 | δ = 8.83 (m, 2H), 8.38~8.51 (m, 4H), 7.79~7.85 (m, 4H), 7.36~7.58 (m, 7H), 7.25 (m, 2H) |
| 458 | δ = 8.99 (m, 2H), 8.83~8.89 (m, 2H), 8.34~8.51 (m, 6H), 7.81~8.10 (m, 8H), 7.71 (m, 2H), 7.58~7.59 (m, 3H), 7.48 (m, 1H), 7.36 (m, 1H) |
| 459 | δ = 8.89 (m, 2H), 8.51 (m, 1H), 8.24~8.43 (m, 5H), 8.06 (m, 1H), 7.81~7.85 (m, 3H), 7.70 (m, 1H), 7.36~7.58 (m, 10H) |
| 460 | δ = 9.24~9.30 (m, 2H), 8.90 (m, 1H), 8.81 (m, 2H), 8.53 (m, 1H), 8.34 (m, 1H), 7.88~7.97 (m, 7H), 7.41~7.70 (m, 9H), 7.14 (m, 1H), 7.00 (m, 1H) |
| 461 | δ = 9.09 (d, 1H), 8.83 (d, 1H), 8.39~8.51 (m, 4H), 8.21~8.26 (m, 2H), 7.92~8.06 (m, 5H), 7.81 (m, 2H), 7.58~7.60 (m, 4H), 7.35~7.36 (m, 2H) |
| 464 | δ = 9.24~9.30 (m, 2H), 8.51~8.53 (m, 3H), 8.27~8.31 (m, 5H), 8.12 (d, 1H), 7.95~8.03 (m, 3H), 7.41~7.70 (m, 11H), 7.14 (m, 1H) |
| 468 | δ = 9.24~9.30 (m, 2H), 9.09 (m, 1H), 8.90 (d, 1H), 8.81 (m, 2H), 8.49~8.53 (m, 2H), 8.33 (m, 2H), 7.92~8.00 (m, 4H), 7.41~7.70 (m, 9H), 7.14 (m, 1H), 7.00 (m, 1H) |
| 469 | δ = 8.81~8.83 (m, 3H), 8.28~8.51 (m, 7H), 8.06~8.10 (m, 2H), 7.81 (m, 1H), 7.35~7.58 (m, 6H) |
| 472 | δ = 9.24~9.30 (m, 2H), 8.53~8.55 (m, 3H), 8.27~8.31 (m, 5H), 8.12 (d, 1H), 7.97~8.03 (m, 4H), 7.70~7.79 (m, 3H), 7.41~7.55 (m, 8H), 7.14 (t, 1H) |

<Experimental Example 1>—Manufacture of Organic Light Emitting Device

1) Manufacture of Organic Light Emitting Device

A transparent indium tin oxide (ITO) electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

Next, an ITO substrate was installed in a substrate folder of a vacuum deposition apparatus, and the following 4,4', 4"-tris(N,N-(2-naphthyl)-phenylamino)triphenylamine (2-TNATA) was deposited on a cell in the vacuum deposition apparatus.

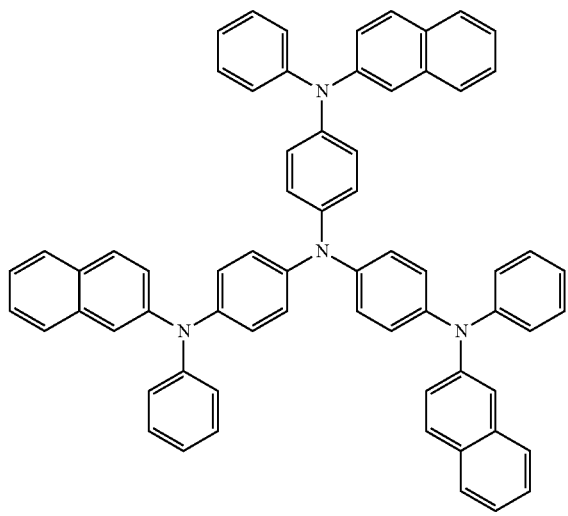

2-TNATA

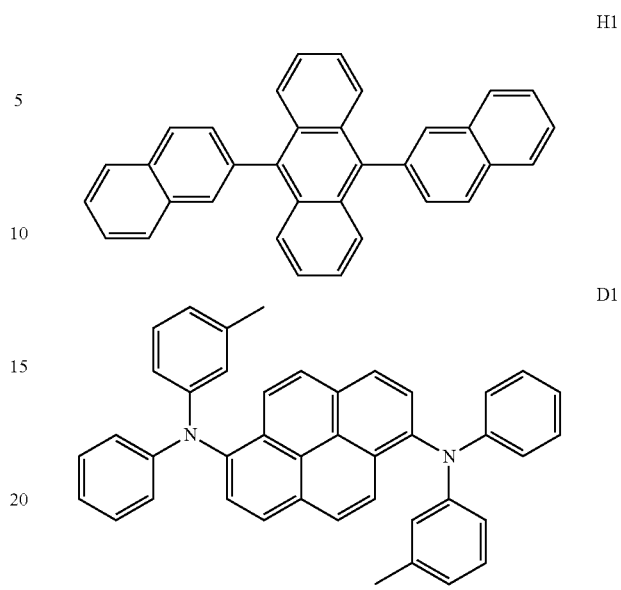

H1

D1

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell of the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

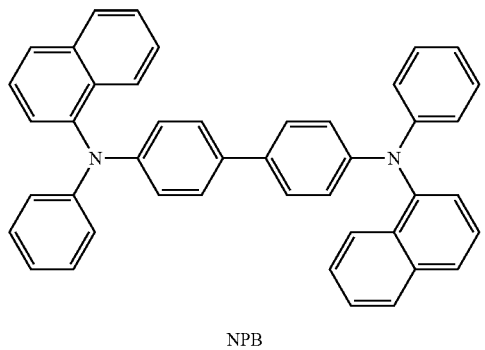 [SMILES: c1ccc(N(c2ccc(-c3ccc(N(c4ccccc4)c4cccc5ccccc45)cc3)cc2)c2cccc3ccccc23)cc1 ; "NPB"]

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

Subsequently, a compound described in the following Table was deposited to a thickness of 300 Å an electron transfer layer.

As an electron injection layer, lithium fluoride (LiF) was deposited to a thickness of 10 Å, and an Al cathode was employed to a thickness of 1,000 Å, and as a result, an OLED was manufactured.

Meanwhile, all the organic compounds required to manufacture the OLED were vacuum sublimation purified under $10^{-6}$ torr to $10^{-8}$ torr by each material to be used in the OLED manufacture.

Results of measuring driving voltage, light emission efficiency, color coordinate (CIE) and lifetime of the blue organic light emitting devices manufactured according to the present disclosure are as shown in the following Table 10.

TABLE 10

| | Compound | Driving Voltage (V) | Light Emission Efficiency (cd/A) | CIE (x, y) | Lifetime (T95) |
|---|---|---|---|---|---|
| Comparative Example 1 | E1 | 5.56 | 5.91 | (0.134, 0.100) | 28 |
| Comparative Example 2 | E2 | 6.10 | 4.52 | (0.132, 0.100) | 18 |
| Comparative Example 3 | E3 | 7.10 | 3.89 | (0.131, 0.100) | 12 |
| Example 1 | 1 | 5.51 | 6.55 | (0.134, 0.101) | 32 |
| Example 2 | 6 | 4.76 | 6.44 | (0.134, 0.102) | 47 |
| Example 3 | 9 | 4.64 | 5.99 | (0.134, 0.101) | 36 |
| Example 4 | 13 | 5.38 | 6.20 | (0.134, 0.103) | 35 |
| Example 5 | 14 | 5.60 | 6.12 | (0.134, 0.102) | 34 |
| Example 6 | 19 | 4.65 | 7.14 | (0.134, 0.101) | 48 |
| Example 7 | 21 | 4.72 | 6.22 | (0.134, 0.102) | 30 |
| Example 8 | 25 | 5.32 | 6.33 | (0.134, 0.101) | 29 |
| Example 9 | 33 | 5.40 | 6.13 | (0.134, 0.101) | 31 |
| Example 10 | 41 | 4.40 | 6.92 | (0.134, 0.100) | 45 |
| Example 11 | 45 | 5.37 | 6.35 | (0.134, 0.101) | 32 |
| Example 12 | 49 | 5.38 | 6.41 | (0.134, 0.100) | 30 |
| Example 13 | 50 | 4.47 | 7.42 | (0.134, 0.100) | 51 |
| Example 14 | 53 | 5.48 | 6.21 | (0.134, 0.100) | 32 |
| Example 15 | 54 | 4.72 | 7.32 | (0.134, 0.100) | 49 |
| Example 16 | 60 | 5.45 | 6.68 | (0.134, 0.100) | 34 |
| Example 17 | 61 | 5.22 | 6.28 | (0.134, 0.102) | 37 |
| Example 18 | 62 | 5.12 | 6.20 | (0.134, 0.101) | 32 |

TABLE 10-continued

| Compound | Driving Voltage (V) | Light Emission Efficiency (cd/A) | CIE (x, y) | Lifetime (T95) |
|---|---|---|---|---|
| Example 19 | 65 | 5.39 | 6.77 | (0.134, 0.102) | 30 |
| Example 20 | 66 | 5.42 | 6.88 | (0.134, 0.100) | 25 |
| Example 21 | 69 | 5.21 | 5.45 | (0.134, 0.103) | 37 |
| Example 22 | 73 | 5.38 | 6.66 | (0.134, 0.100) | 35 |
| Example 23 | 74 | 5.40 | 6.36 | (0.134, 0.102) | 32 |
| Example 24 | 75 | 5.42 | 6.26 | (0.134, 0.101) | 48 |
| Example 25 | 77 | 5.39 | 6.19 | (0.134, 0.100) | 31 |
| Example 26 | 84 | 5.55 | 6.27 | (0.134, 0.102) | 31 |
| Example 27 | 85 | 5.18 | 6.20 | (0.134, 0.103) | 30 |
| Example 28 | 88 | 5.41 | 6.19 | (0.134, 0.100) | 32 |
| Example 29 | 89 | 4.75 | 7.39 | (0.134, 0.103) | 41 |
| Example 30 | 92 | 5.29 | 6.41 | (0.134, 0.102) | 33 |
| Example 31 | 93 | 5.52 | 7.19 | (0.134, 0.101) | 54 |
| Example 32 | 96 | 5.64 | 6.85 | (0.134, 0.100) | 34 |
| Example 33 | 106 | 5.12 | 5.89 | (0.134, 0.102) | 48 |
| Example 34 | 109 | 4.40 | 6.13 | (0.134, 0.103) | 47 |
| Example 35 | 110 | 5.15 | 6.95 | (0.134, 0.100) | 38 |
| Example 36 | 128 | 5.32 | 7.28 | (0.134, 0.103) | 39 |
| Example 37 | 129 | 5.44 | 6.78 | (0.134, 0.102) | 42 |
| Example 38 | 132 | 5.08 | 6.35 | (0.134, 0.103) | 51 |
| Example 39 | 133 | 4.85 | 6.98 | (0.134, 0.101) | 49 |
| Example 40 | 138 | 4.66 | 5.98 | (0.134, 0.100) | 42 |
| Example 41 | 140 | 5.16 | 6.15 | (0.134, 0.102) | 48 |
| Example 42 | 143 | 5.25 | 6.52 | (0.134, 0.102) | 36 |
| Example 43 | 145 | 4.56 | 7.32 | (0.134, 0.103) | 34 |
| Example 44 | 156 | 5.46 | 7.15 | (0.134, 0.102) | 49 |
| Example 45 | 160 | 5.60 | 6.85 | (0.134, 0.102) | 56 |
| Example 46 | 164 | 5.58 | 6.75 | (0.134, 0.101) | 36 |
| Example 47 | 165 | 4.85 | 7.24 | (0.134, 0.100) | 48 |
| Example 48 | 168 | 4.96 | 7.06 | (0.134, 0.102) | 49 |
| Example 49 | 175 | 4.47 | 6.15 | (0.134, 0.103) | 36 |
| Example 50 | 179 | 5.15 | 6.55 | (0.134, 0.101) | 37 |
| Example 51 | 190 | 5.22 | 6.95 | (0.134, 0.100) | 31 |
| Example 52 | 193 | 5.32 | 7.35 | (0.134, 0.102) | 48 |
| Example 53 | 197 | 5.40 | 6.35 | (0.134, 0.102) | 45 |
| Example 54 | 201 | 5.56 | 6.95 | (0.134, 0.103) | 34 |
| Example 55 | 204 | 4.43 | 7.25 | (0.134, 0.101) | 51 |
| Example 56 | 212 | 5.15 | 6.85 | (0.134, 0.102) | 25 |
| Example 57 | 225 | 4.53 | 7.25 | (0.134, 0.100) | 52 |
| Example 58 | 240 | 5.22 | 6.43 | (0.134, 0.102) | 35 |
| Example 59 | 253 | 5.30 | 6.65 | (0.134, 0.103) | 48 |
| Example 60 | 262 | 4.66 | 7.25 | (0.134, 0.103) | 54 |
| Example 61 | 265 | 4.85 | 6.95 | (0.134, 0.100) | 35 |
| Example 62 | 272 | 5.75 | 6.48 | (0.134, 0.100) | 34 |
| Example 63 | 276 | 5.42 | 6.56 | (0.134, 0.102) | 45 |
| Example 64 | 280 | 5.13 | 7.08 | (0.134, 0.102) | 49 |
| Example 65 | 284 | 4.90 | 7.43 | (0.134, 0.101) | 39 |
| Example 66 | 308 | 4.44 | 6.98 | (0.134, 0.102) | 51 |
| Example 67 | 313 | 5.09 | 6.59 | (0.134, 0.101) | 37 |
| Example 68 | 321 | 5.67 | 7.12 | (0.134, 0.102) | 38 |

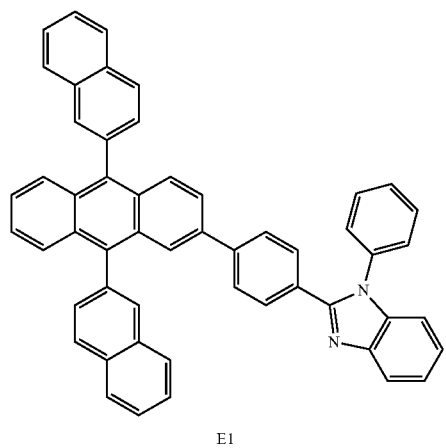 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1]

E1

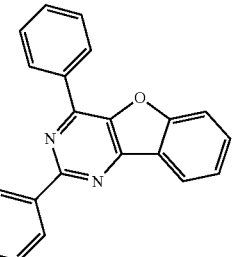

E2

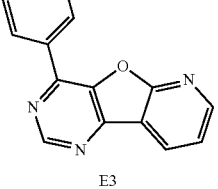

E3

From the results of Table 10, it was seen that the organic electroluminescent device using the electron transfer layer material of the blue organic electroluminescent device of the present disclosure had lower driving voltage and significantly improved light emission efficiency and lifetime compared to Comparative Example 1 to Comparative Example 3.

Such a result is considered to be due to the fact that, when using the disclosed compound having proper length and strength, and flatness as an electron transfer layer, a compound in an excited state is made by receiving electrons under a specific condition, and particularly when a hetero-skeleton site of the compound is formed in an excited state, excited energy moves to a stable state before the excited hetero-skeleton site goes through other reactions, and a relatively stabilized compound is capable of efficiently transferring electrons without the compound being decomposed or destroyed. By the compound of the present disclosure enhancing electron-transfer properties or stability, excellent results were obtained in all aspects of driving, efficiency and lifetime.

<Experimental Example 2>—Manufacture of Organic Light Emitting Device

1) Manufacture of Organic Light Emitting Device

A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

Next, an ITO substrate was installed in a substrate folder of a vacuum deposition apparatus, and the following 4,4', 4"-tris(N,N-(2-naphthyl)-phenylamino)triphenylamine (2-TNATA) was introduced to a cell in the vacuum deposition apparatus.

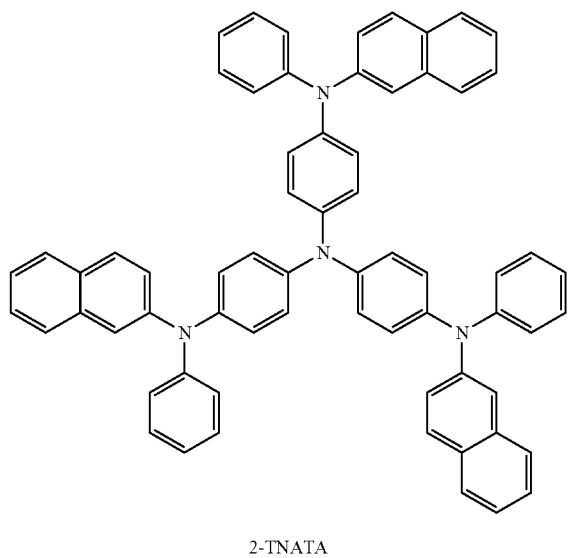 [SMILES: c1ccc(N(c2ccc(N(c3ccc(N(c4ccccc4)c4ccc5ccccc5c4)cc3)c3ccc(N(c4ccccc4)c4ccc5ccccc5c4)cc3)cc2)c2ccc3ccccc3c2)cc1]

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell of the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

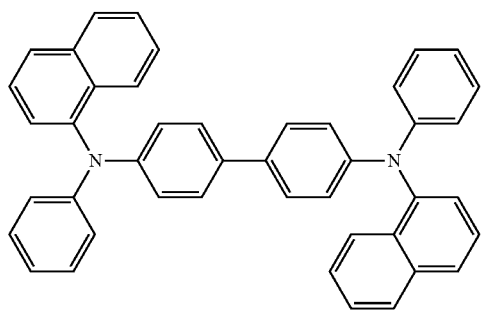

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

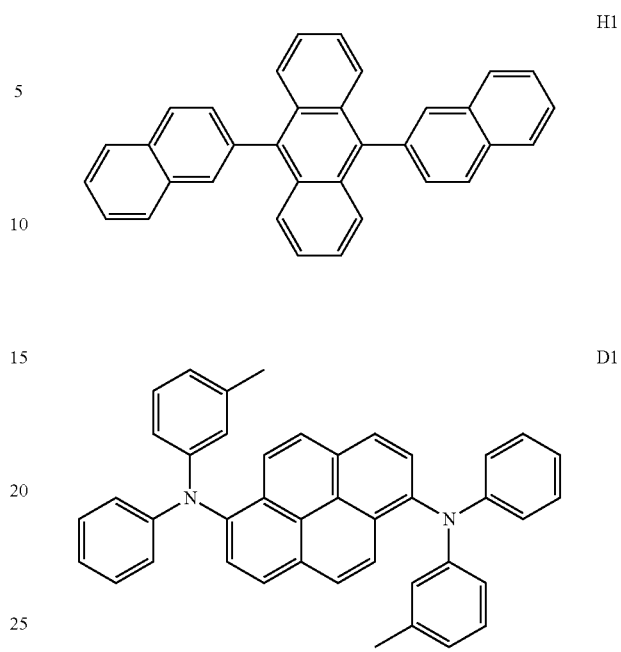

Subsequently, a compound of the following structural formula E1 was deposited to a thickness of 300 Å as an electron transfer layer.

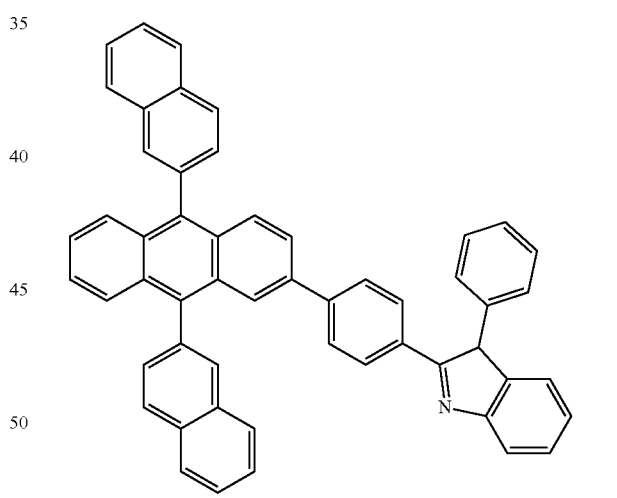

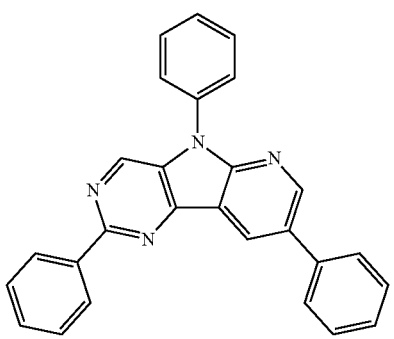

-continued

E5

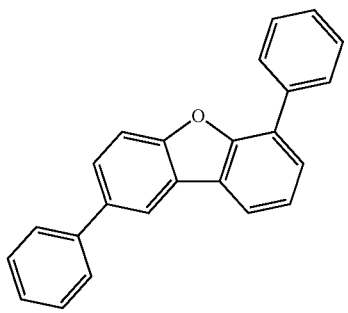

E6

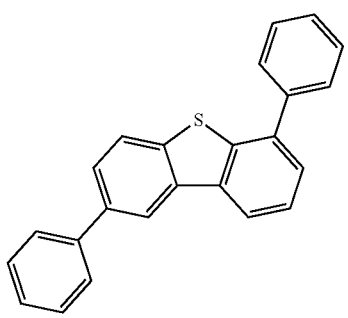

As an electron injection layer, lithium fluoride (LiF) was deposited to a thickness of 10 Å, and an Al cathode was employed to a thickness of 1,000 Å, and as a result, an OLED was manufactured.

Meanwhile, all the organic compounds required to manufacture the OLED were vacuum sublimation purified under $10^{-6}$ torr to $10^{-8}$ torr by each material to be used in the OLED manufacture.

Organic electroluminescent devices were manufactured in the same manner as in Experimental Example 2 except that the electron transfer layer E1 was formed to a thickness of 250 Å, and then a hole blocking layer was formed on the electron transfer layer using each compound presented in the following Table 11 to a thickness of 50 Å.

Results of measuring driving voltage, light emission efficiency, color coordinate (CIE) and lifetime of the blue organic light emitting devices manufactured according to the present disclosure are as shown in the following Table 11.

TABLE 11

| | Compound | Driving Voltage (V) | Light Emission Efficiency (cd/A) | CIE (x, y) | Lifetime (T95) |
|---|---|---|---|---|---|
| Comparative Example 1 | E1 | 5.51 | 5.54 | (0.134, 0.100) | 31 |
| Comparative Example 2 | E4 | 8.10 | 3.58 | (0.131, 0.103) | 25 |
| Comparative Example 3 | E5 | 7.56 | 2.59 | (0.130, 0.102) | 16 |
| Comparative Example 4 | E6 | 6.98 | 3.10 | (0.136, 0.102) | 21 |
| Example 1 | 457 | 4.75 | 6.17 | (0.134, 0.101) | 52 |
| Example 2 | 458 | 5.14 | 6.59 | (0.134, 0.102) | 54 |
| Example 3 | 459 | 5.42 | 5.89 | (0.134, 0.100) | 52 |

TABLE 11-continued

| | Compound | Driving Voltage (V) | Light Emission Efficiency (cd/A) | CIE (x, y) | Lifetime (T95) |
|---|---|---|---|---|---|
| Example 4 | 460 | 4.85 | 6.02 | (0.134, 0.101) | 49 |
| Example 5 | 461 | 5.44 | 5.88 | (0.134, 0.101) | 50 |
| Example 6 | 464 | 5.19 | 6.12 | (0.134, 0.102) | 48 |
| Example 7 | 468 | 4.53 | 6.45 | (0.134, 0.102) | 51 |
| Example 8 | 469 | 5.50 | 6.52 | (0.134, 0.100) | 47 |

From the results of Table 11, it was seen that the organic electroluminescent device using the hole blocking layer material of the blue organic electroluminescent device of the present disclosure had lower driving voltage, and improved light emission efficiency and lifetime compared to Comparative Example 1 to Comparative Example 4.

Particularly, when at least one of R1 to R3 has a heteroaryl-based substituent in the compound of Chemical Formula 1 according to the present application, the molecular weight was improved compared to when R1 to R3 are all substituted by aryl-based substituents leading to favorable thermal properties, and improved interfacial properties were obtained due to an increased Tg value, and an enhancement in the performance was able to be expected when used in the organic light emitting device by the effect of strengthening electron properties than hole properties and an adjustment in the energy level obtained therefrom.

In addition, in the compound of Chemical Formula 1 of the present application, the compound of Chemical Formula 1 of the present application has, compared to when R1, R2 and R4 are all hydrogen, at least one of $R_1$, $R_2$ and $R_4$ being represented by -(L)m-(Z)n and at least one of $R_1$, $R_2$ and $R_4$ having a substituted or unsubstituted aryl group, and as a result, effects of smoothly controlling electron flow was obtained by resolving the problem of absence of a substituent controlling molecular conjugation.

The invention claimed is:

1. A heterocyclic compound represented by the following Chemical Formula 1:

[Chemical Formula 1]

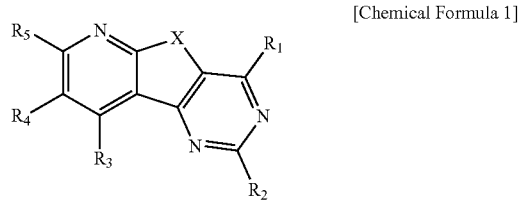

wherein, in Chemical Formula 1,
X is O; or S;
R3 and R5 are the same as or different from each other, and each independently selected from the group consisting of hydrogen; and deuterium,
R1, R2 and R4 are the same as or different from each other, and each independently selected from the group consisting of hydrogen; deuterium; a substituted or unsubstituted aryl group; and a substituted or unsubstituted heteroaryl group;
at least one of $R_1$, $R_2$ and $R_4$ is represented by -(L)m-(Z)n;
at least one of $R_1$, $R_2$ and $R_4$ is a substituted or unsubstituted aryl group;

L is a substituted or unsubstituted arylene group; or a substituted or unsubstituted heteroarylene group;

Z is selected from the group consisting of hydrogen; a substituted or unsubstituted aryl group; and a substituted or unsubstituted heteroaryl group;

m is an integer of 1 to 3;

n is an integer of 1 to 5; and when m and n are an integer of 2 or greater, substituents in the parentheses are the same as or different from each other, wherein the "substituted or unsubstituted" means being substituted with one or more substituents selected from C6 to C60 monocyclic or polycyclic aryl; C2 to C60 monocyclic or polycyclic heteroaryl; or being unsubstituted, or being substituted with a substituent linking two or more substituents selected from among the substituents illustrated above, or being unsubstituted.

2. The heterocyclic compound of claim 1, wherein Chemical Formula 1 is represented by any one of the following Chemical Formulae 2 to 4:

[Chemical Formula 2]

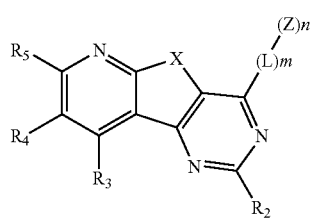

[Chemical Formula 3]

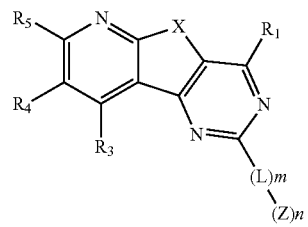

[Chemical Formula 4]

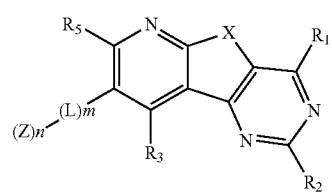

in Chemical Formulae 2 to 4, $R_1$ to $R_5$, L, Z, m, n and X have the same definitions as in Chemical Formula 1.

3. The heterocyclic compound of claim 1, wherein $R_3$ and $R_5$ are hydrogen.

4. The heterocyclic compound of claim 1, wherein L is a substituted or unsubstituted C6 to C60 arylene group; or a substituted or unsubstituted C2 to C60 heteroarylene group.

5. The heterocyclic compound of claim 1, wherein Z is selected from the group consisting of hydrogen; a substituted or unsubstituted C6 to C60 aryl group; and a substituted or unsubstituted C2 to C60 heteroaryl group.

6. The heterocyclic compound of claim 1, wherein Chemical Formula 1 is represented by any one of the following compounds:

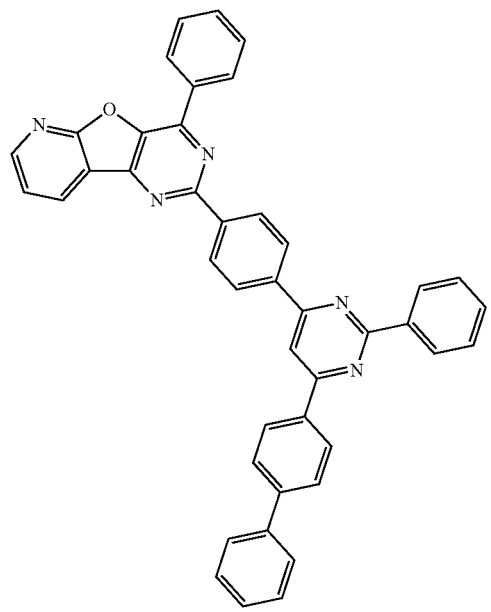

1

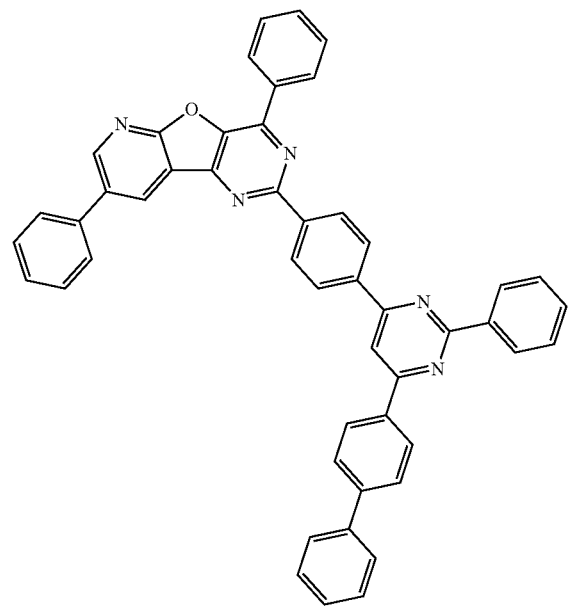

2

-continued
3
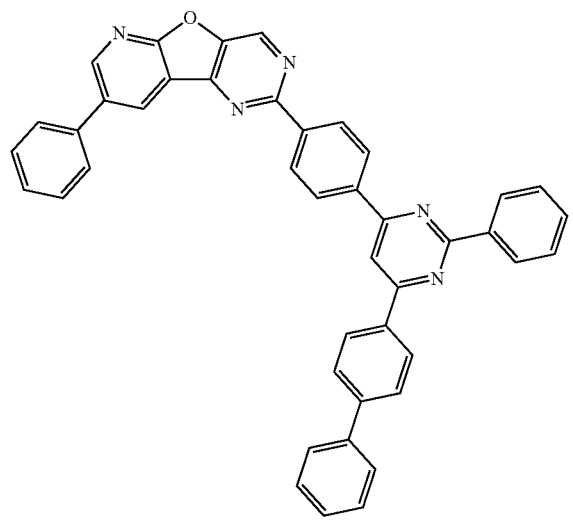
4
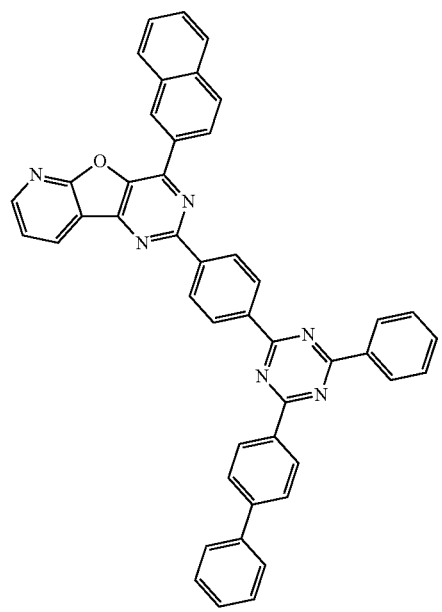
5
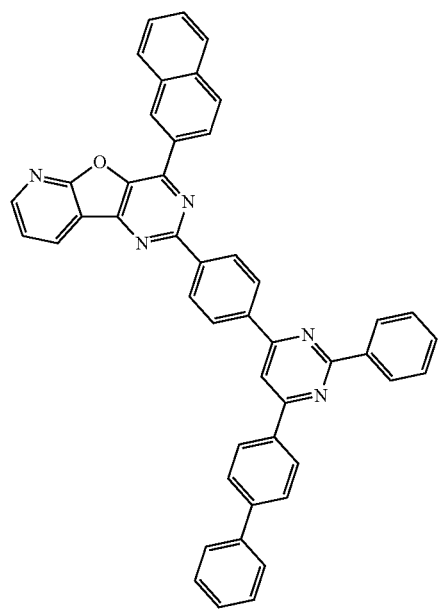
6
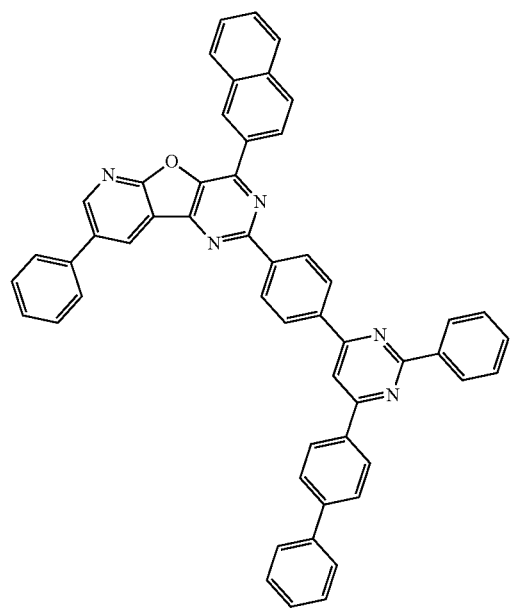

-continued
7
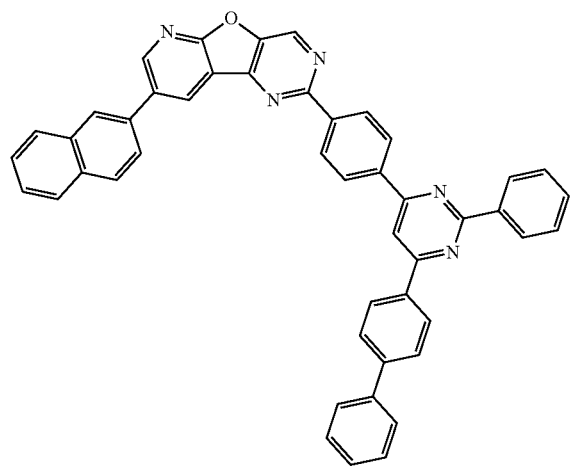
8
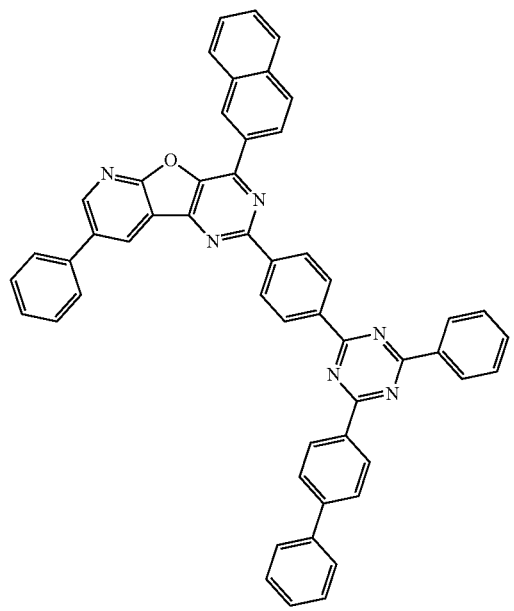
9
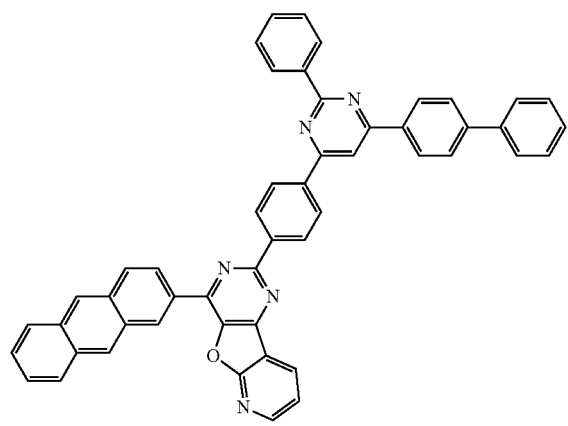
10
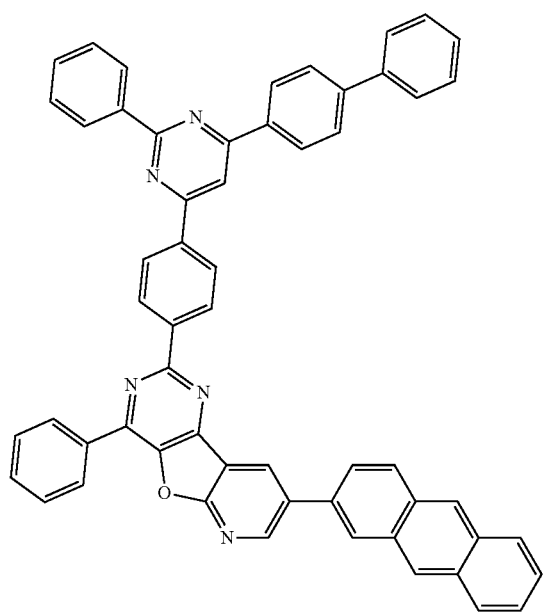

-continued
11
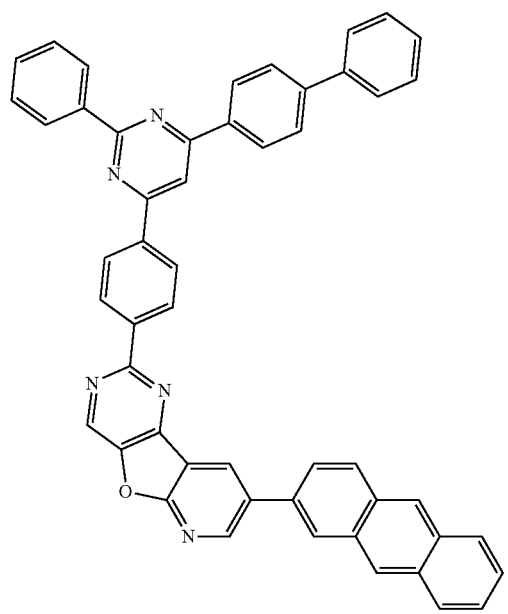
12
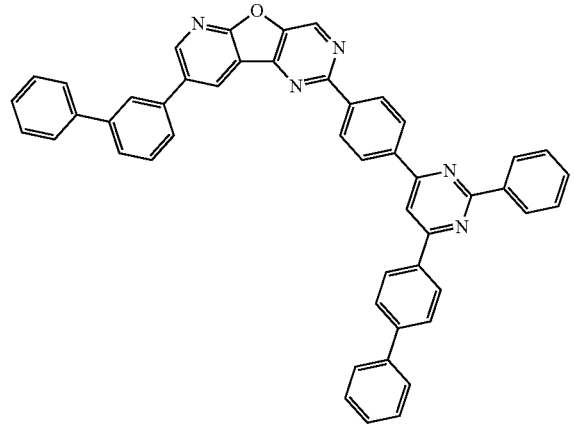
13
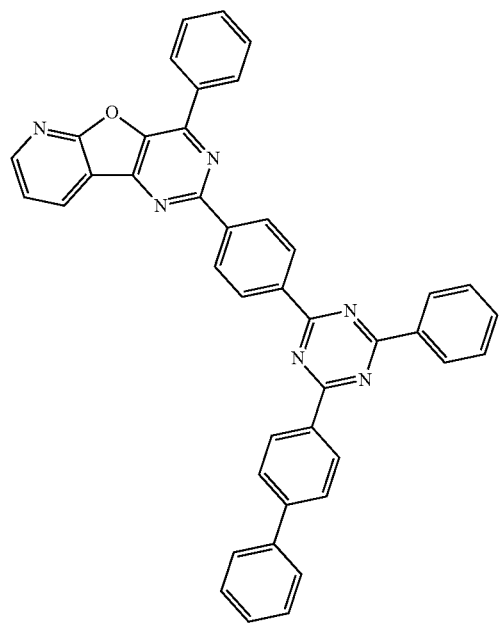
14
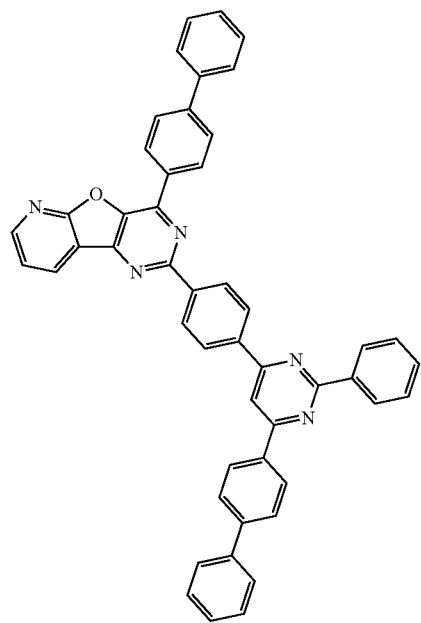

369 | 370
-continued
15 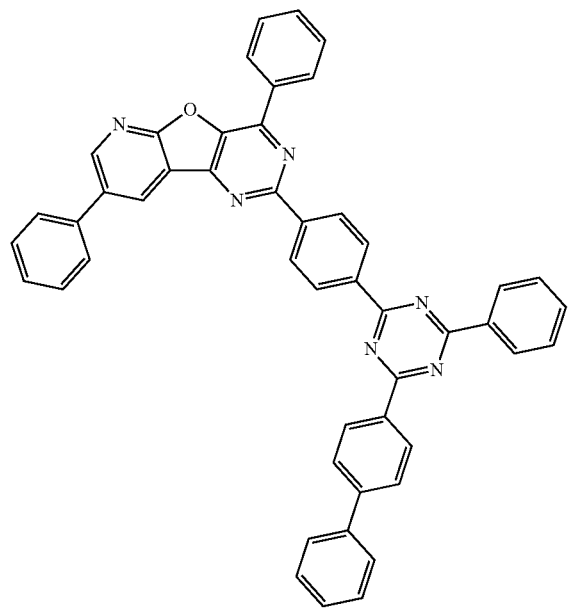 16 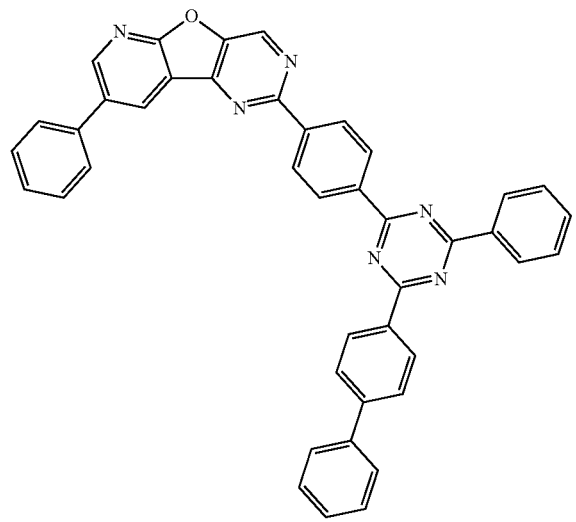
17 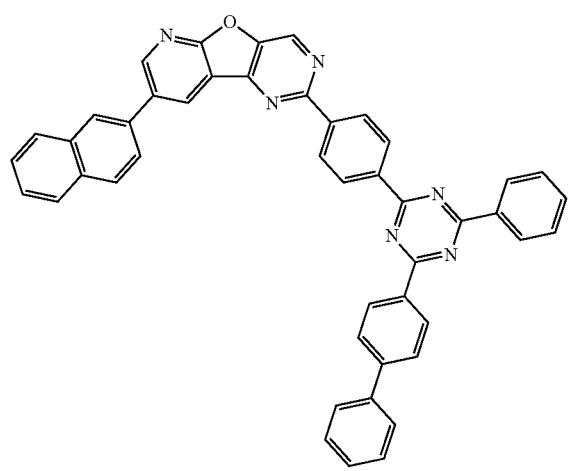 18 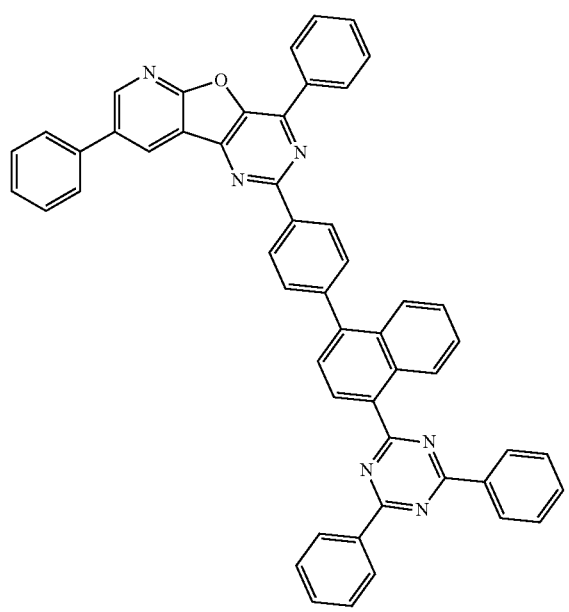

-continued
19
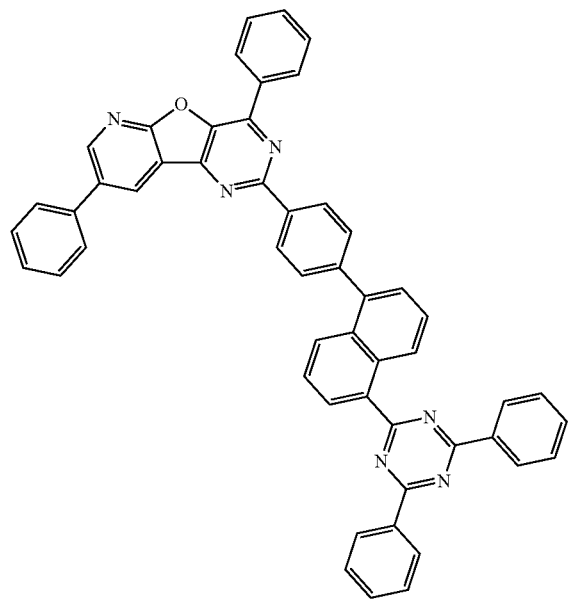
20
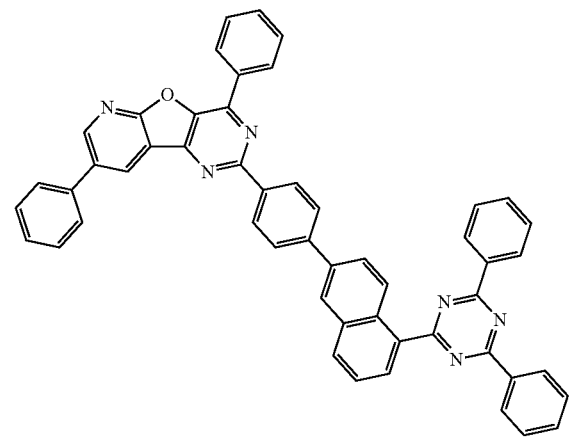
21
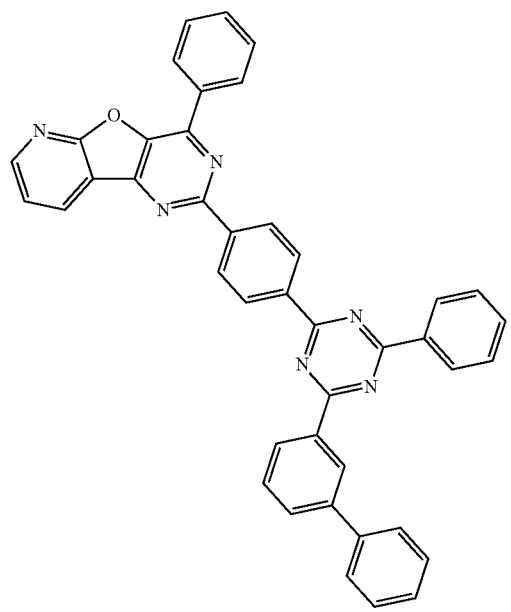
22
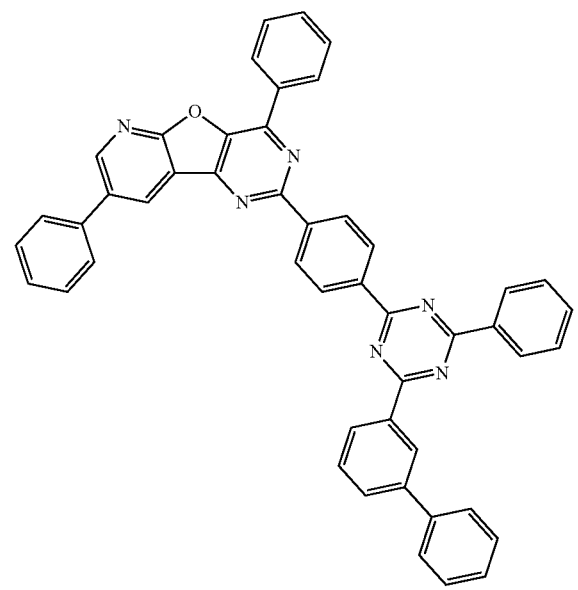

373
374
23
24
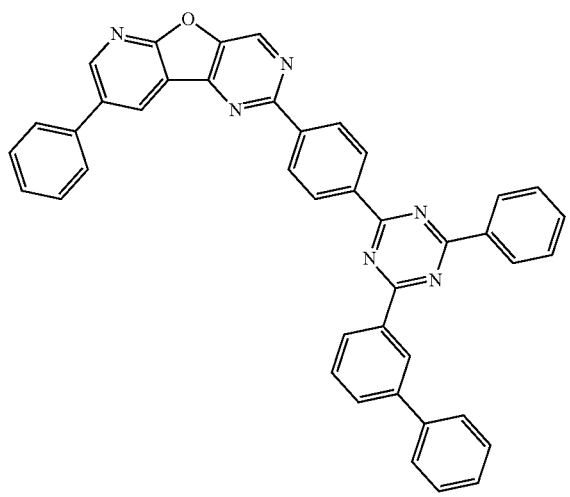
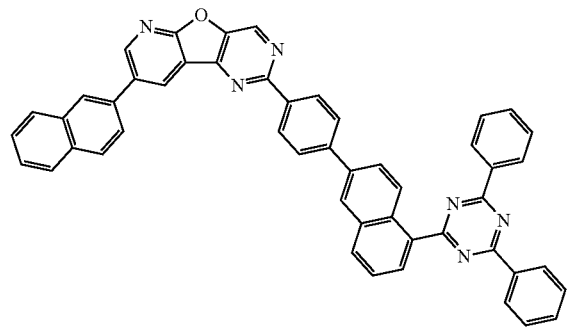
25
26
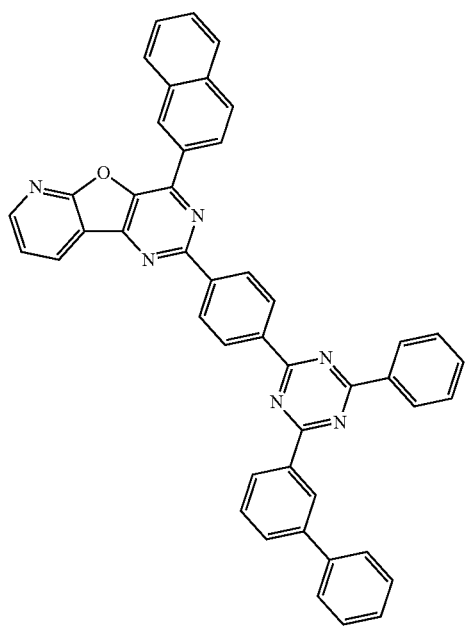
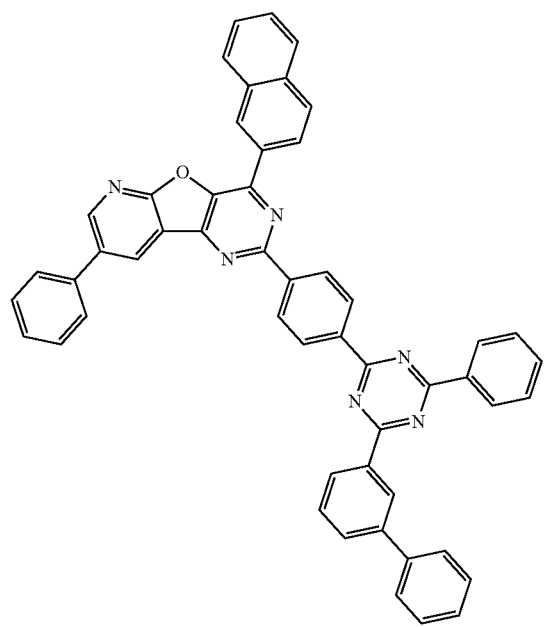

-continued
27
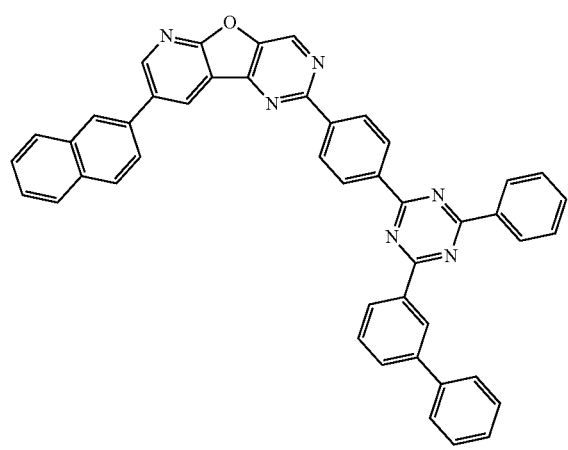
28
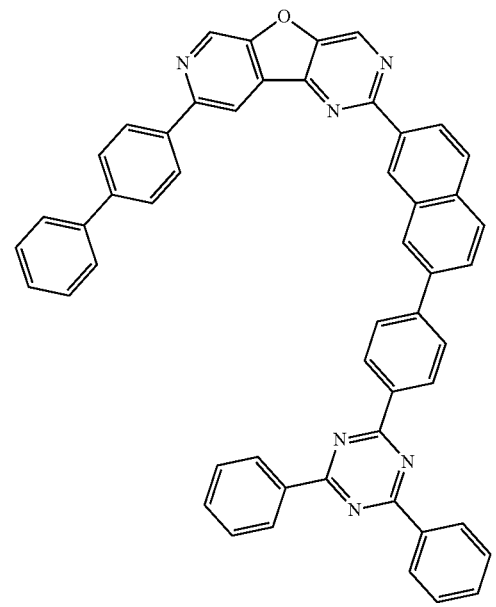
29
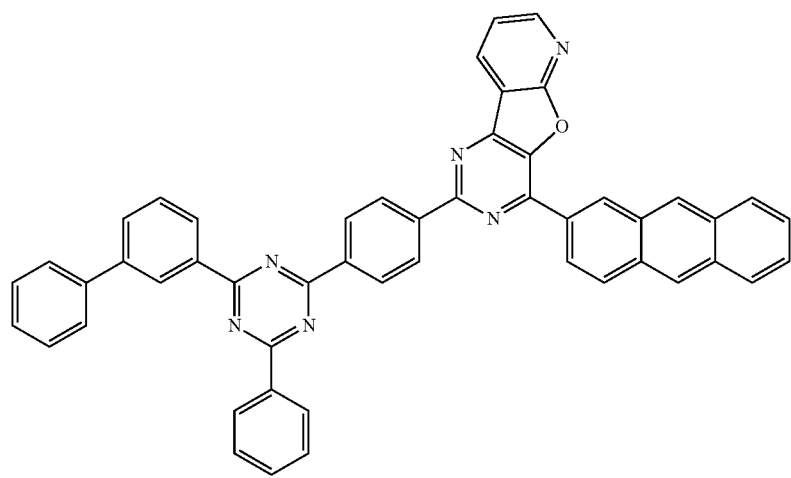

-continued
377
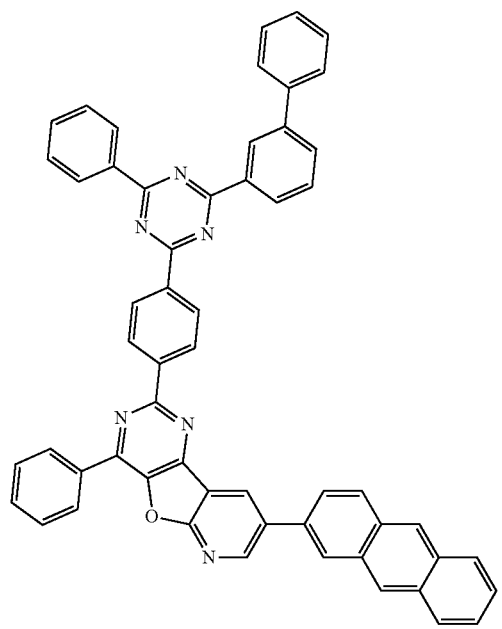
378
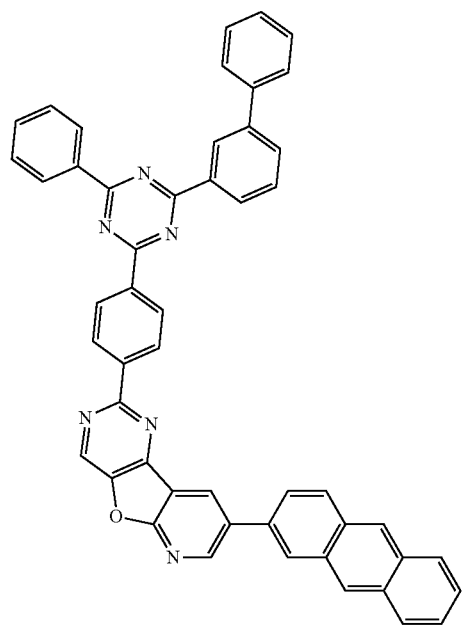
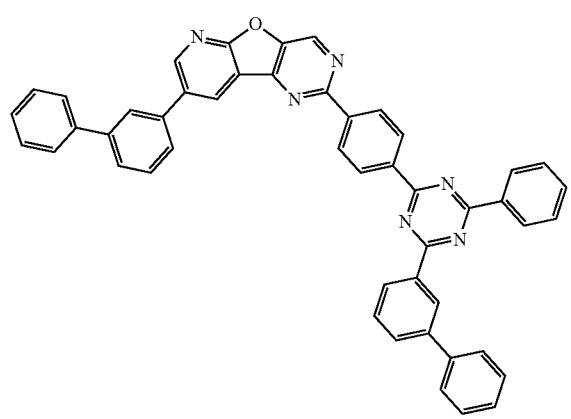
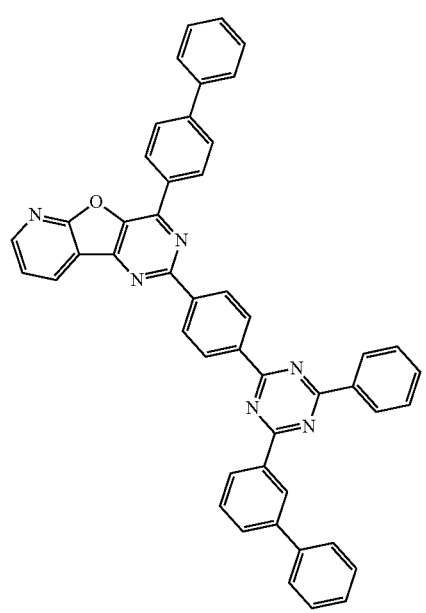

-continued
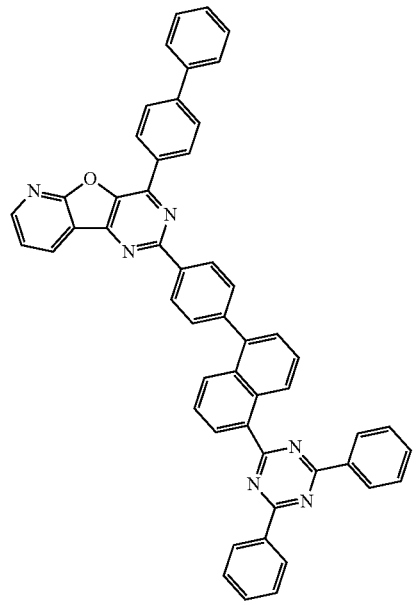
34
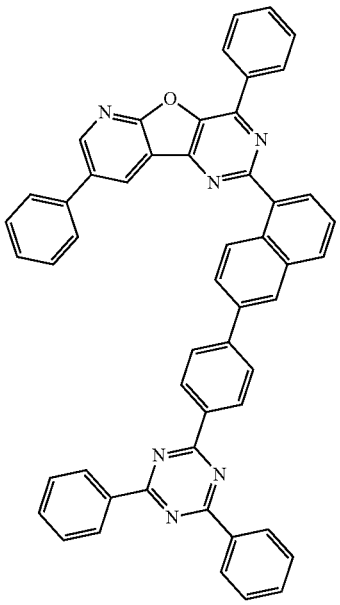
35
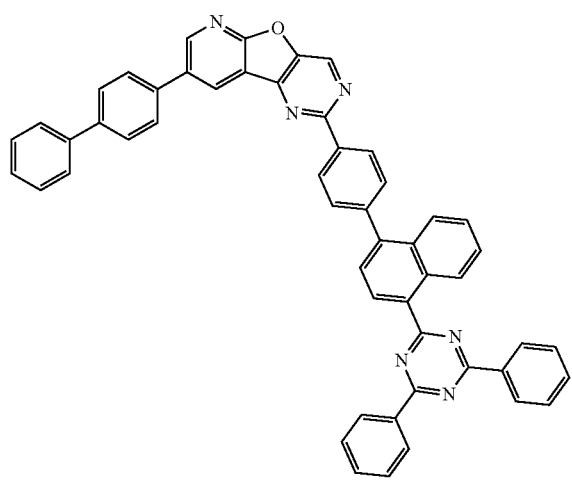
36
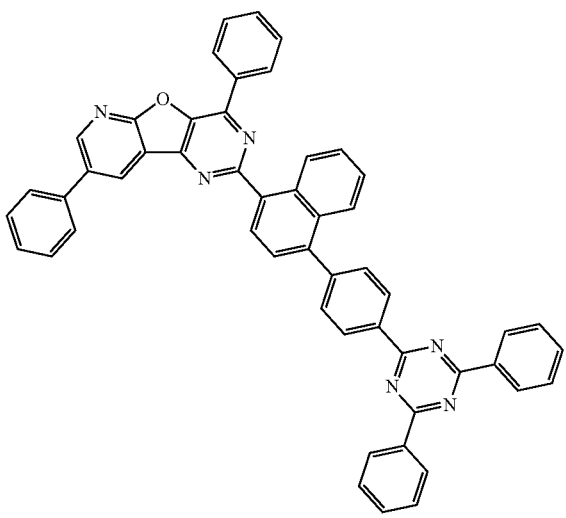
37
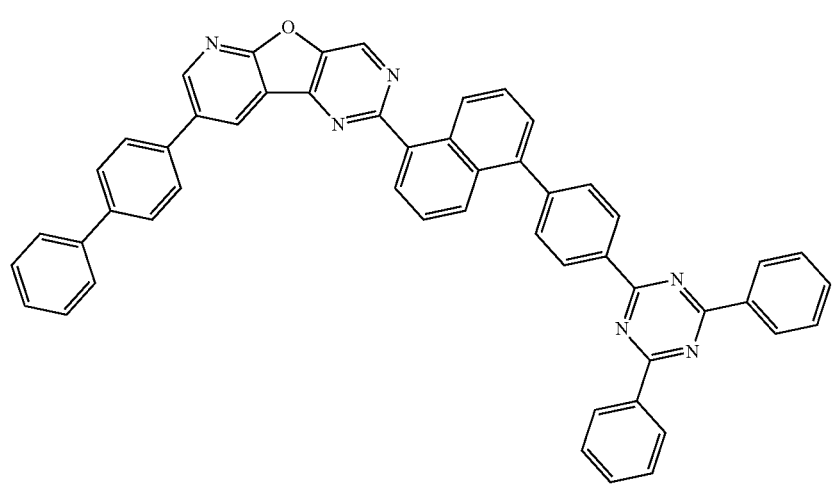
38

-continued
381
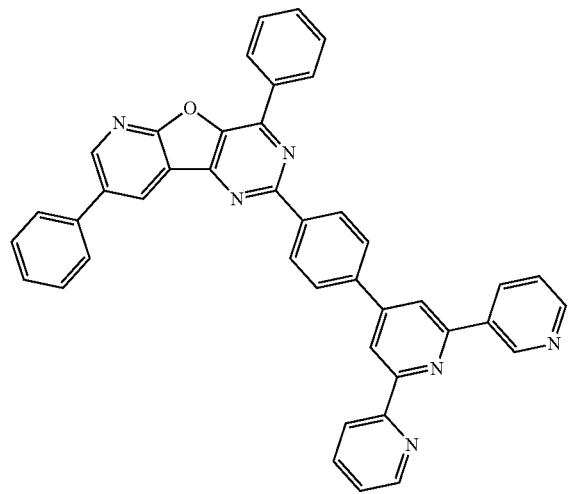
382
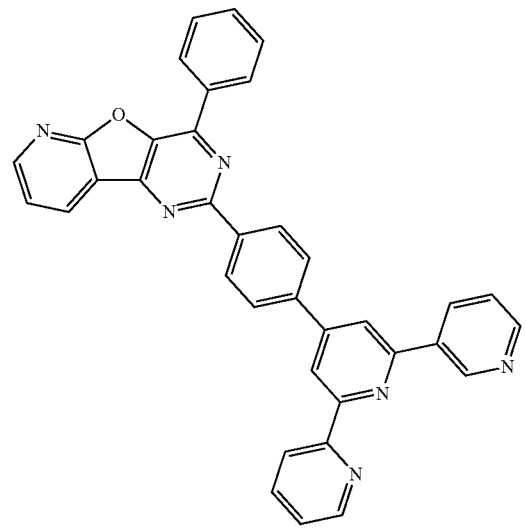
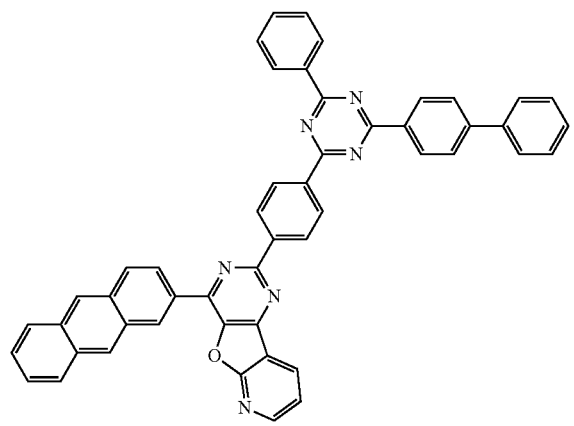
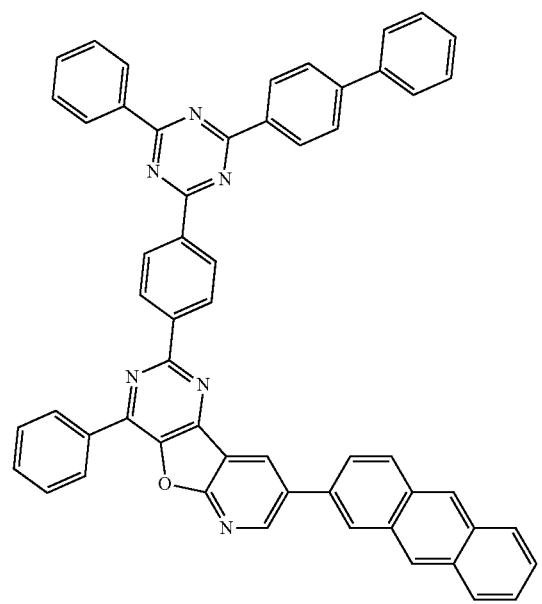

43
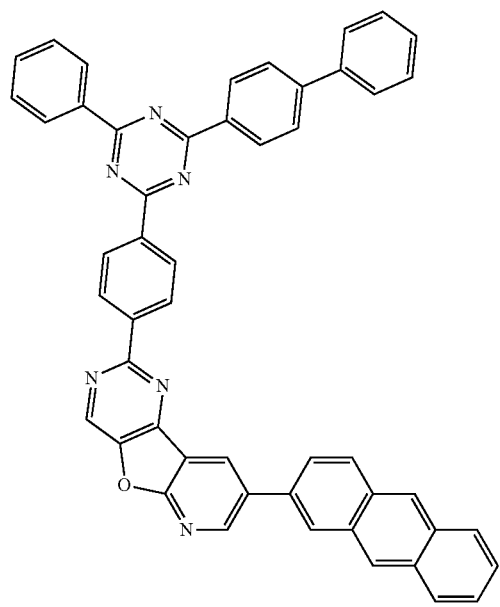
44
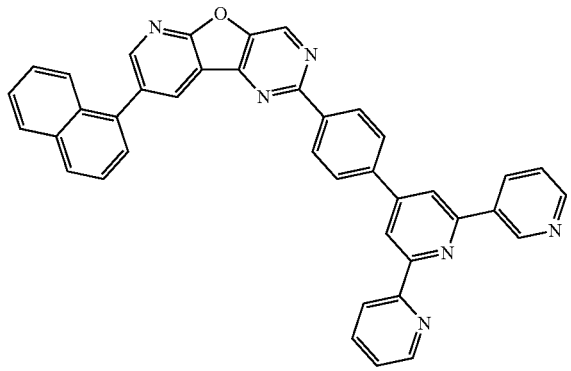
45
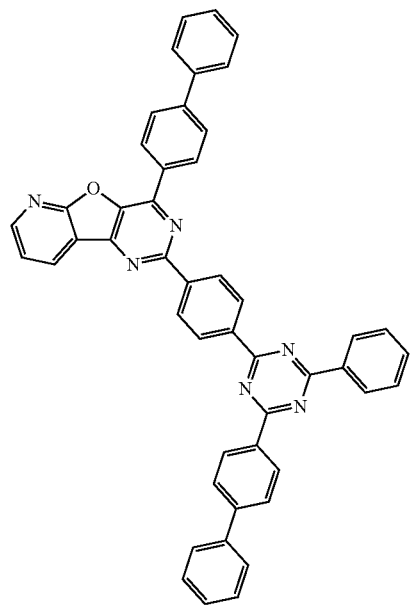
46
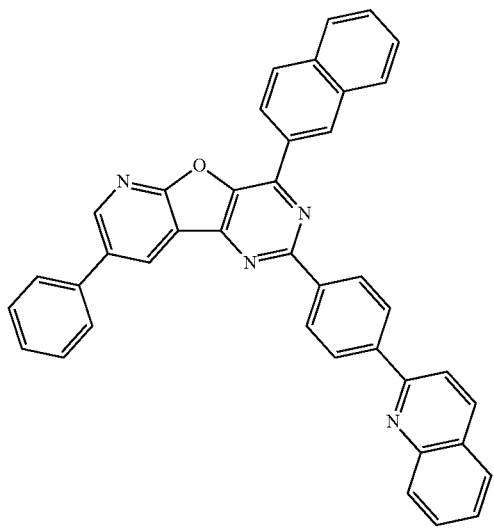

-continued
47
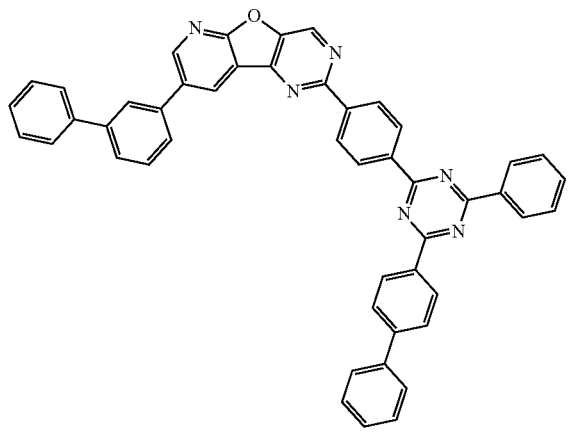
48
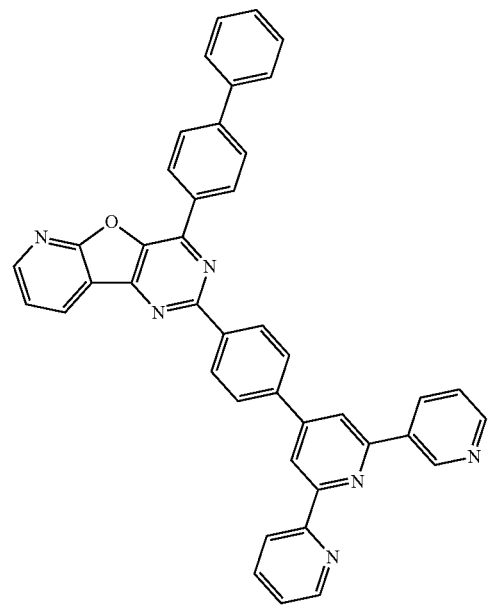
49
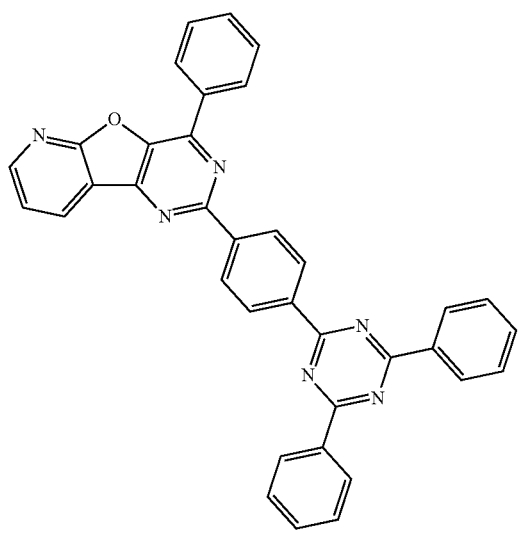
50
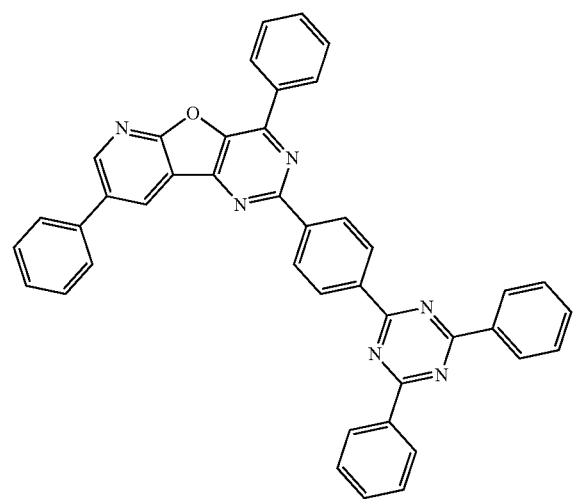
51
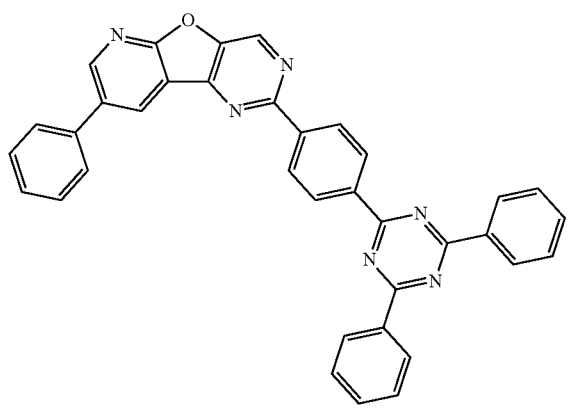
52
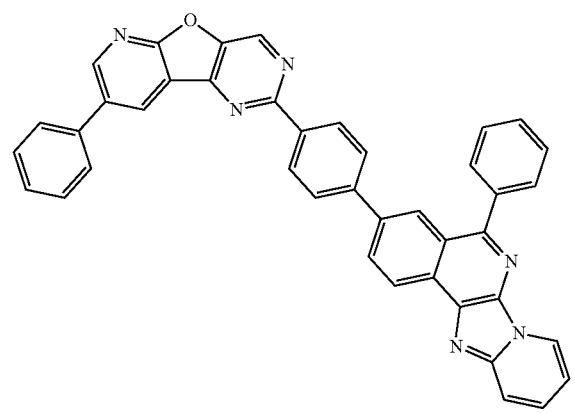

-continued
53
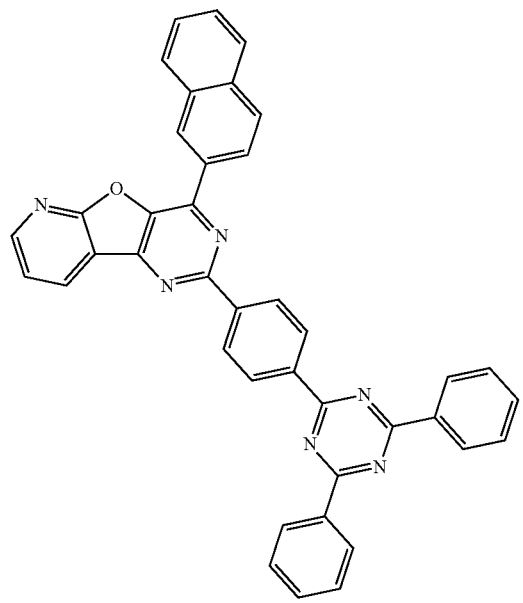
54
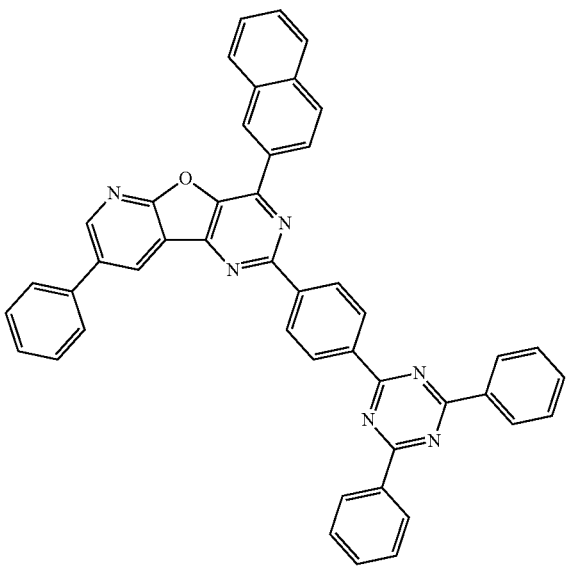
55
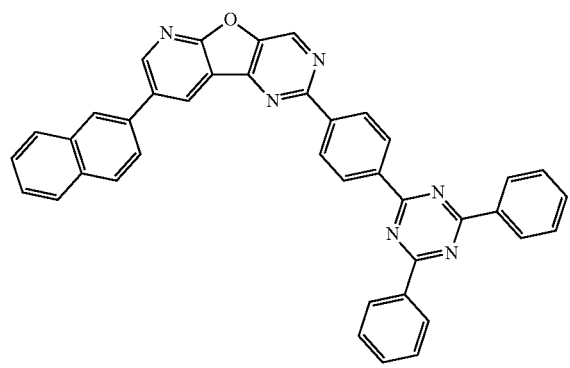
56
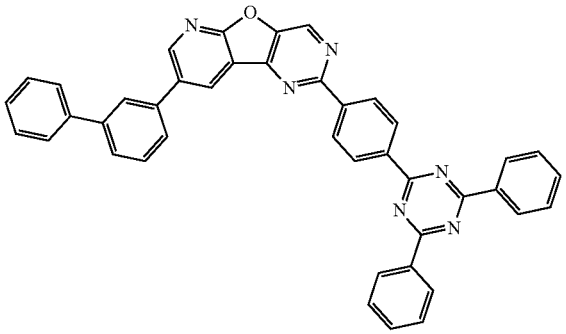
57
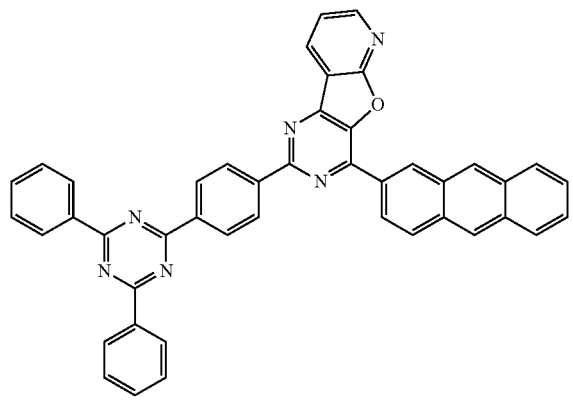
58
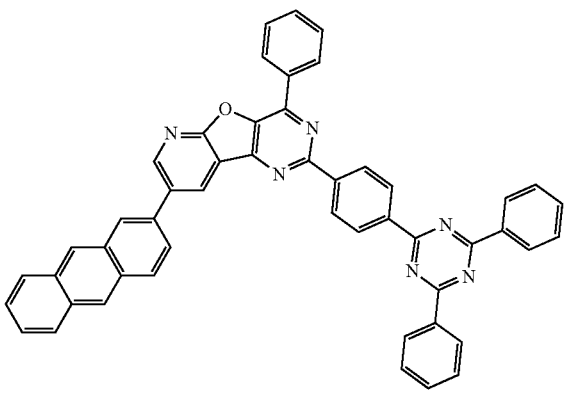

389
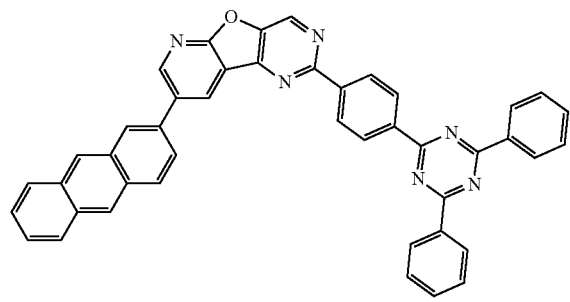
390
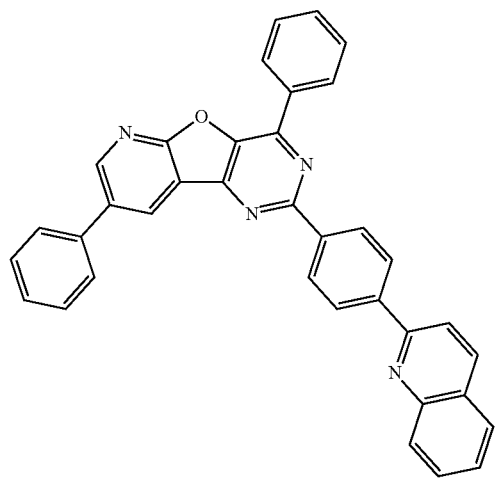
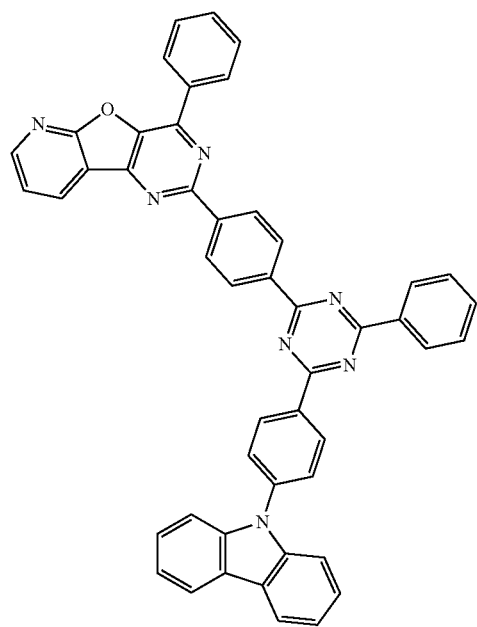
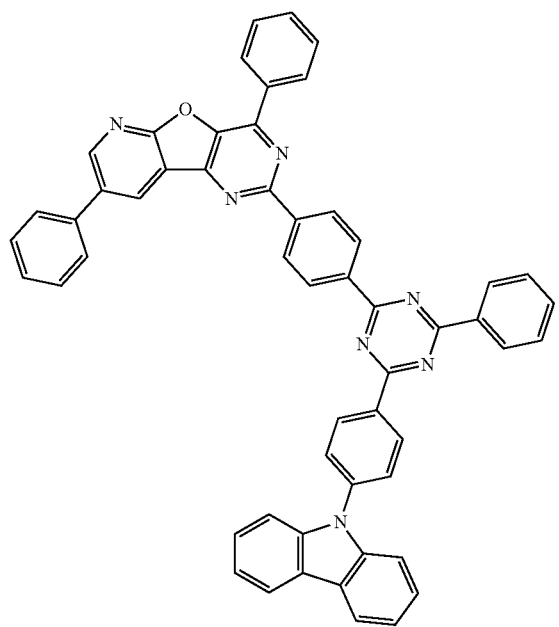

-continued
391
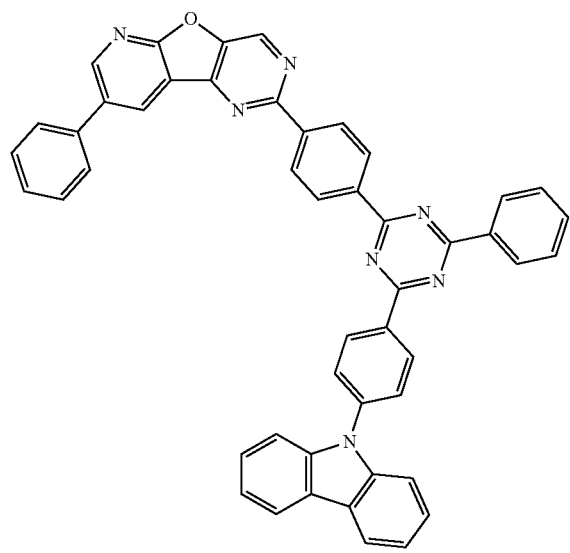
392
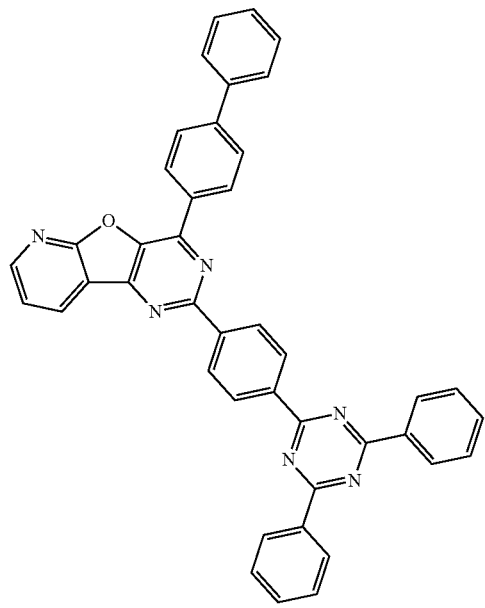
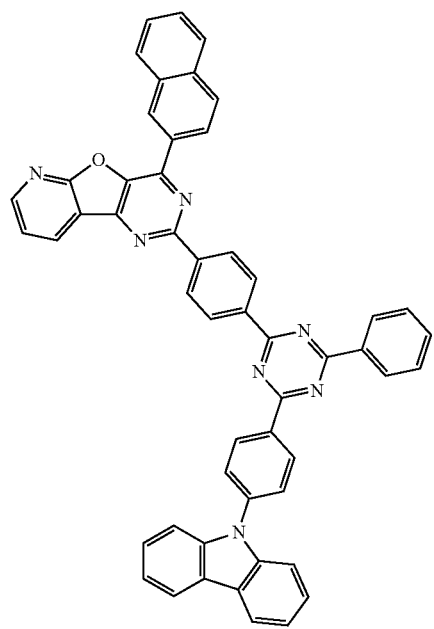
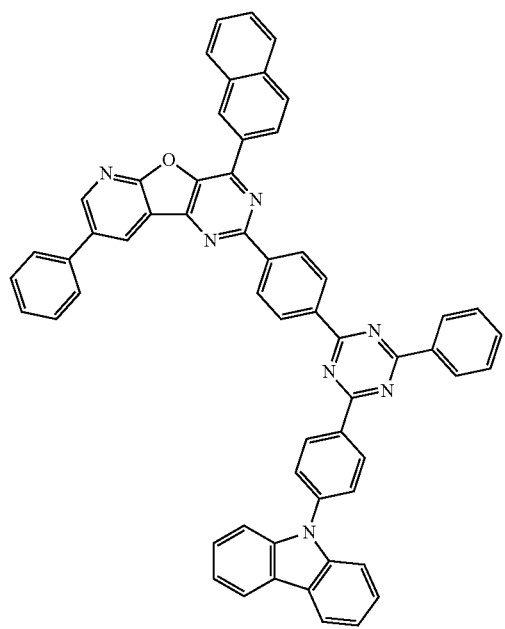

67
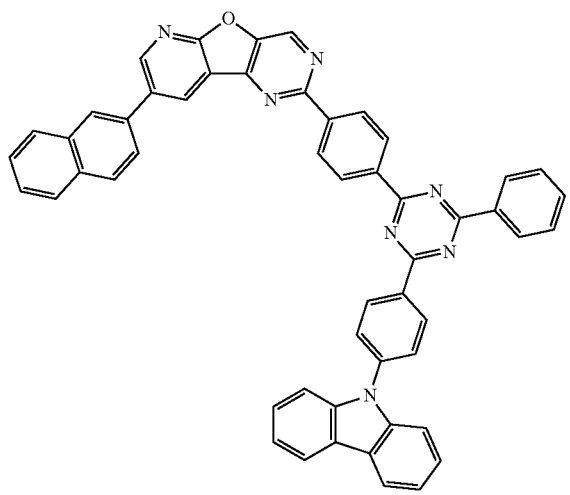
68
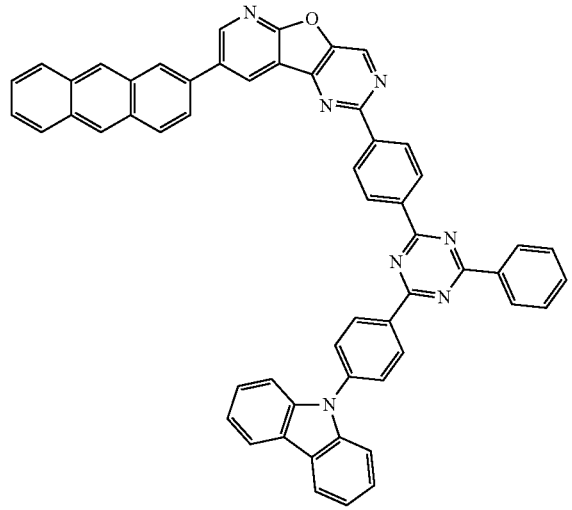
69
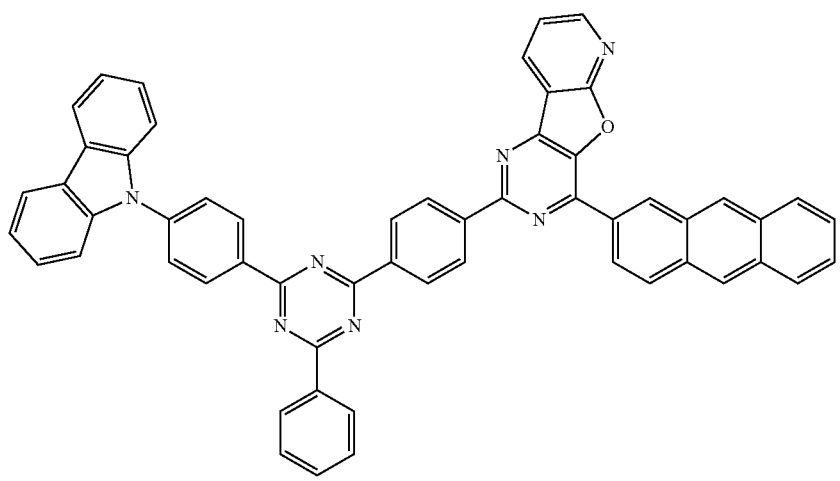
70
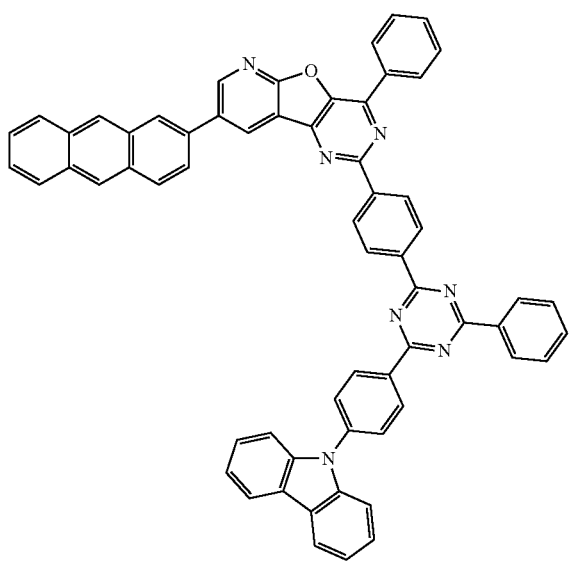
71
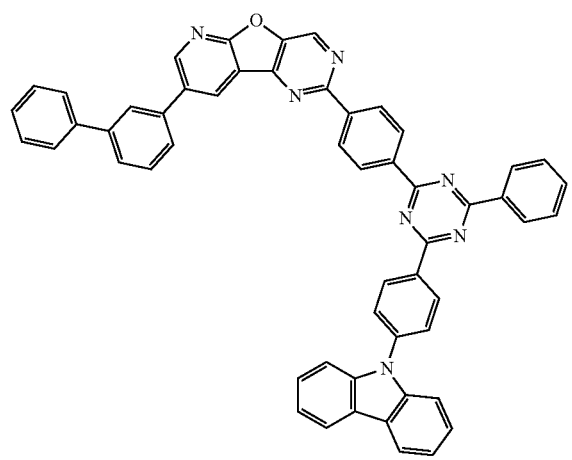

-continued
72
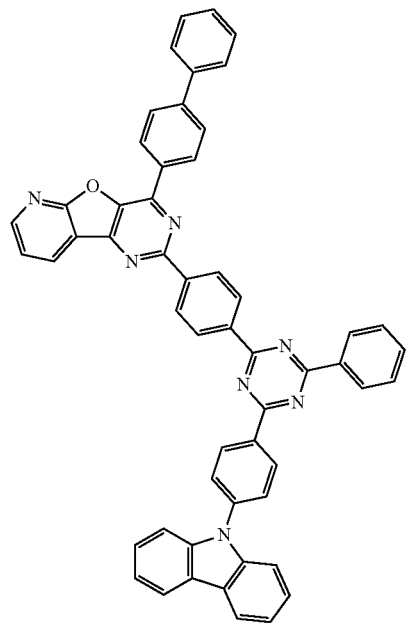
73
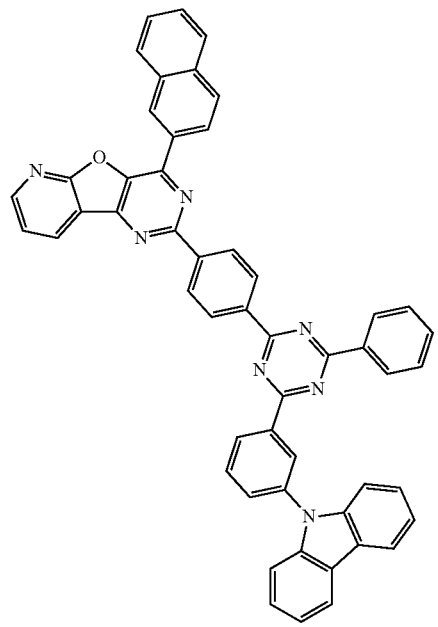
74
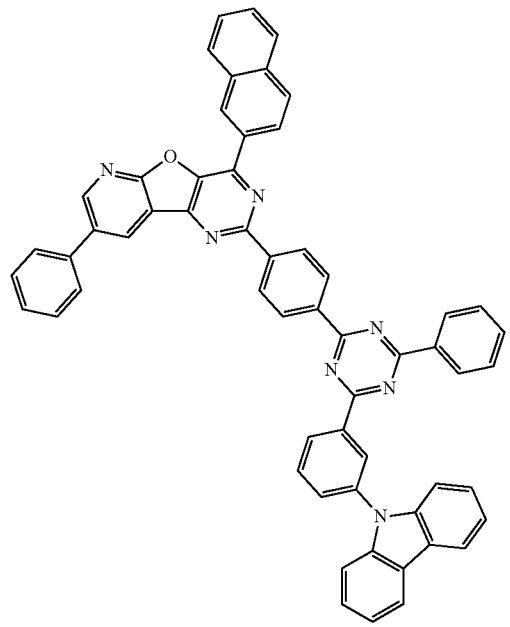
75
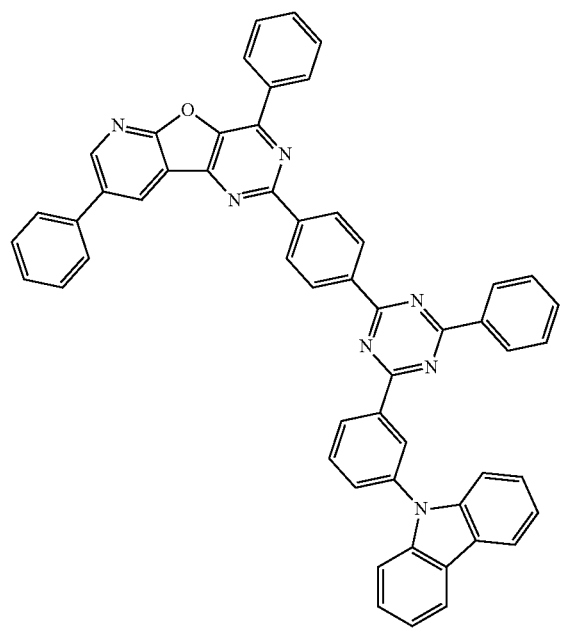

76
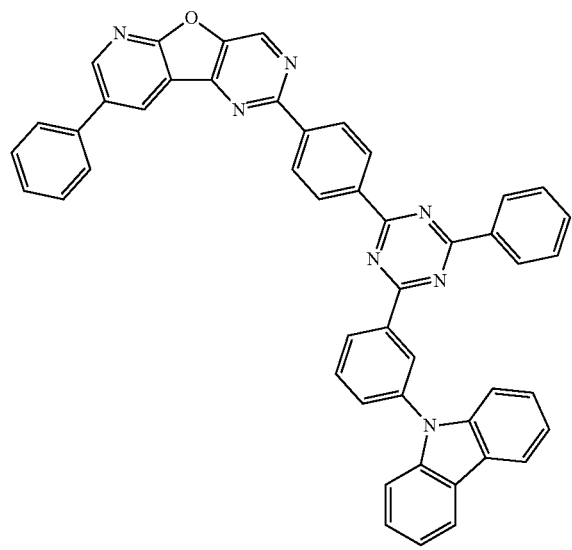
77
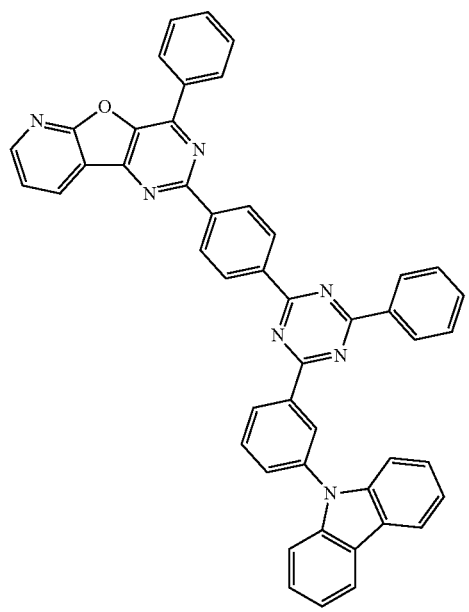
78
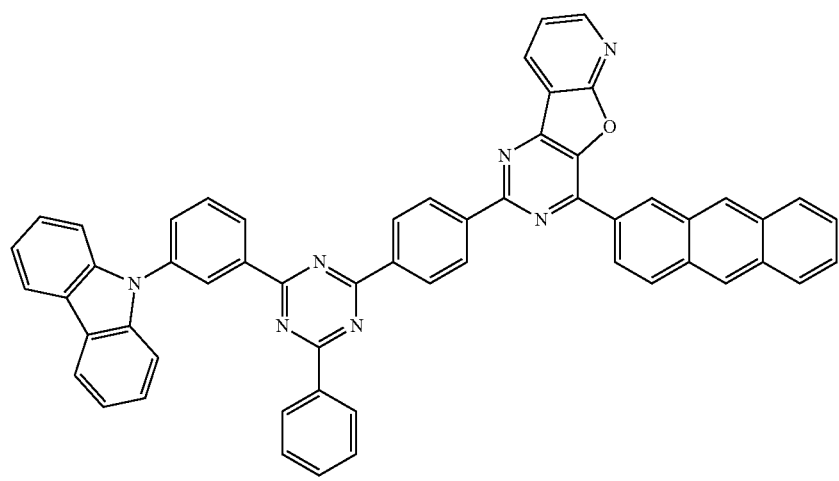
79
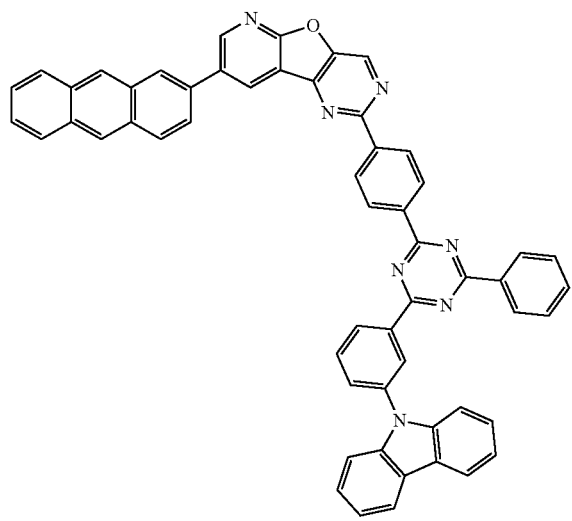
80
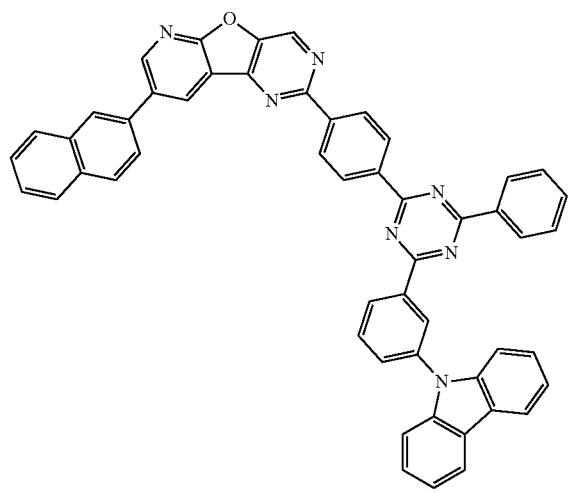

81
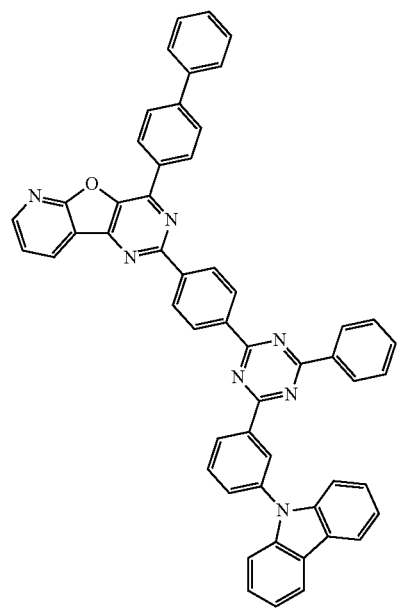
82
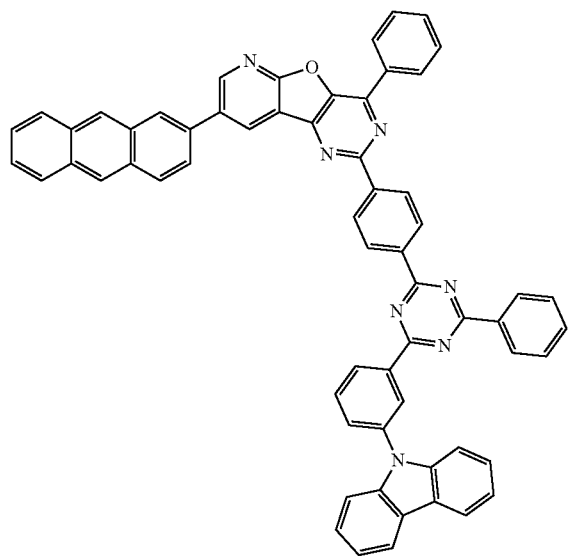
83
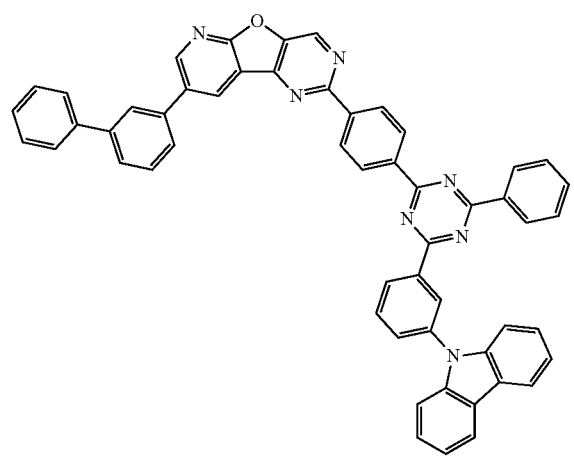
84
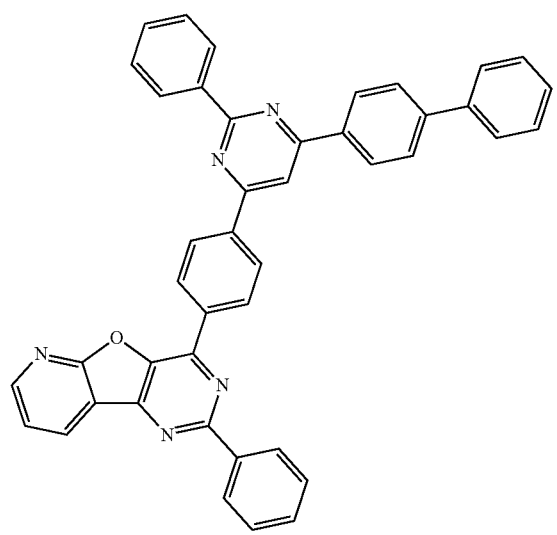
85
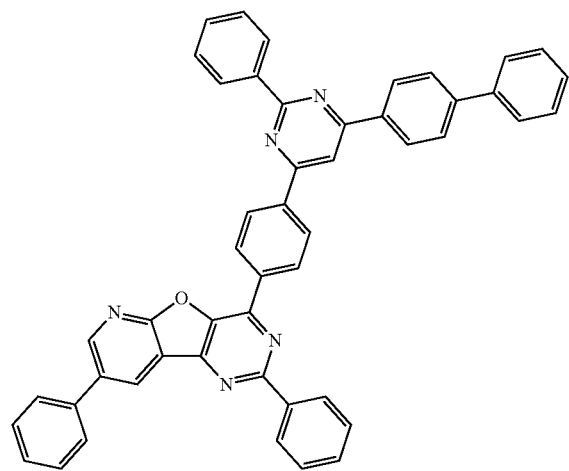
86
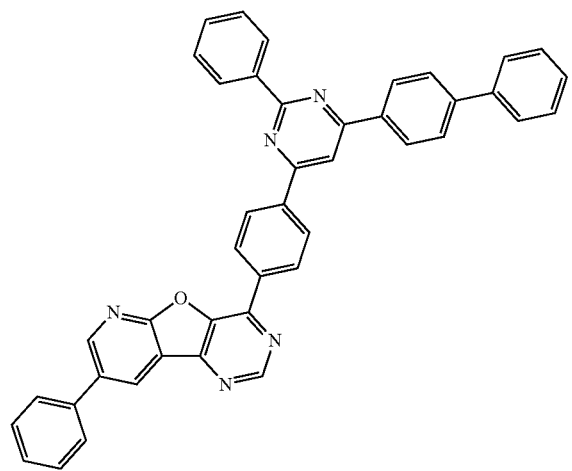

-continued
87
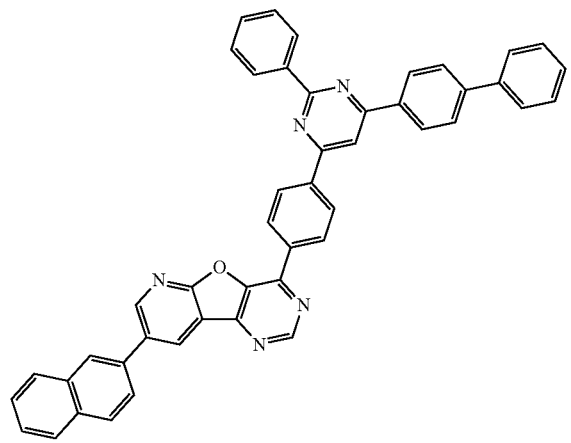
88
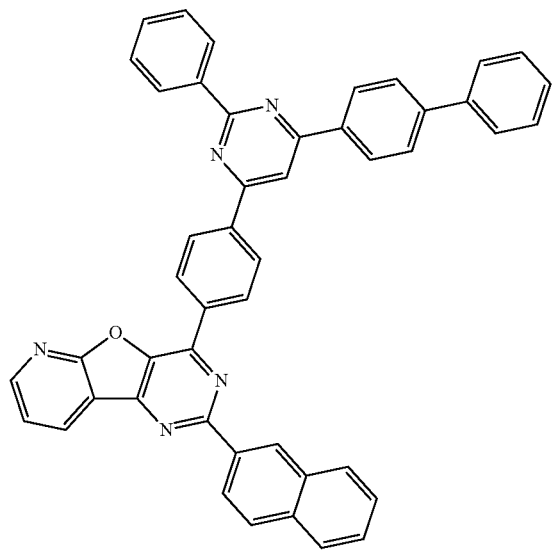
89
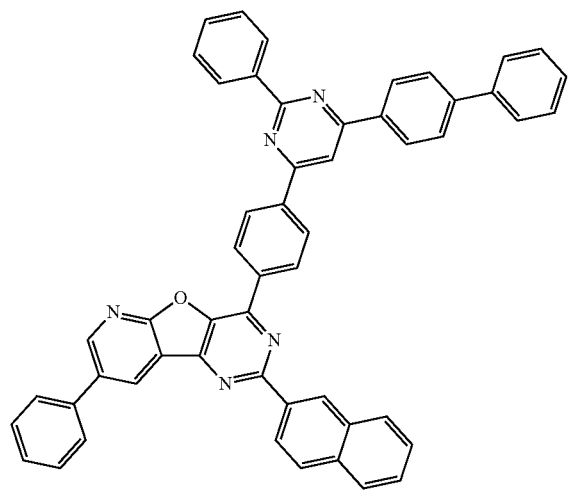
90
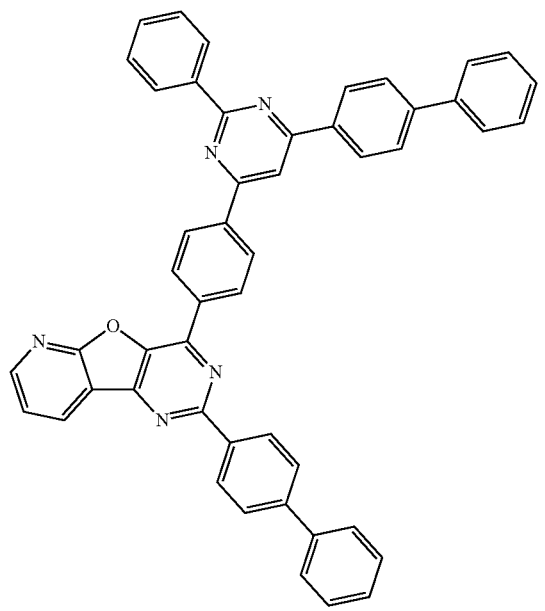

91
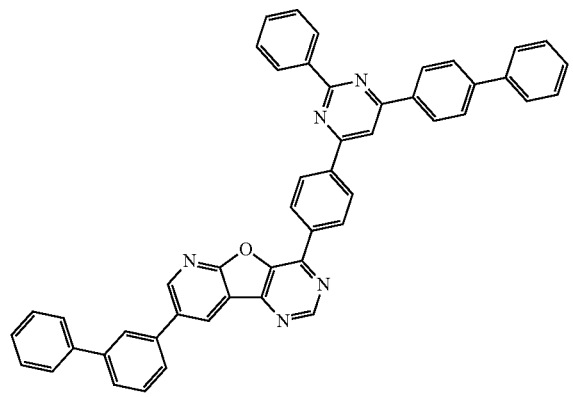
92
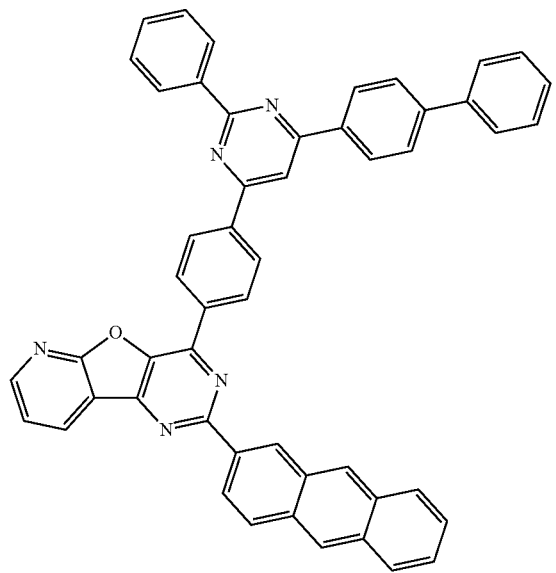
93
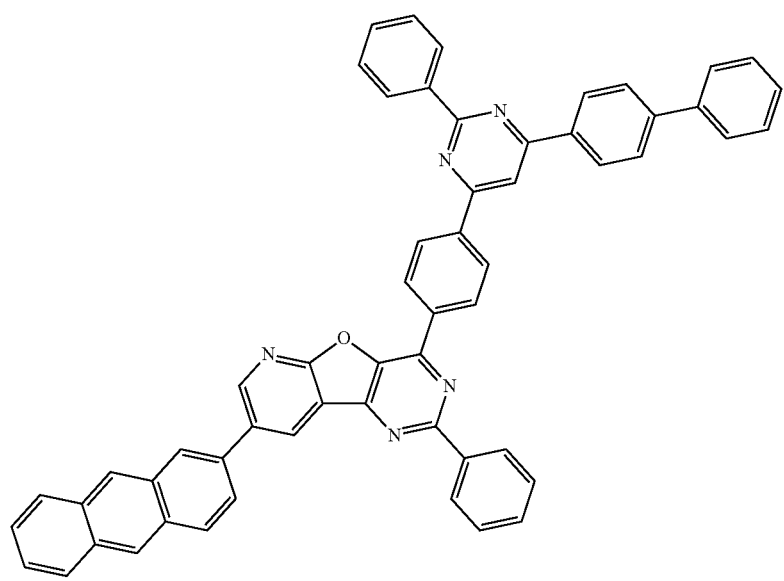

94
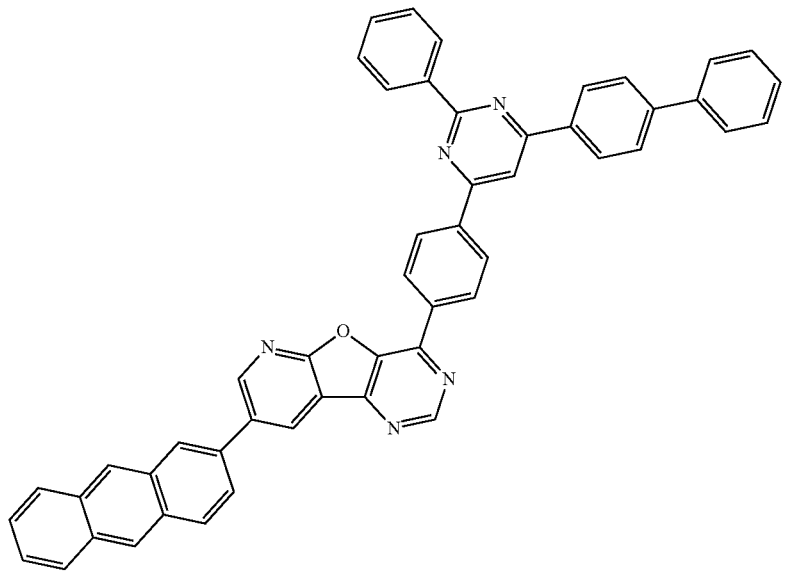
95
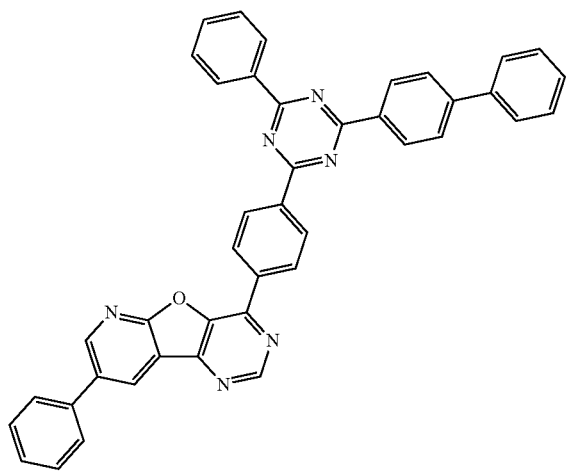
96
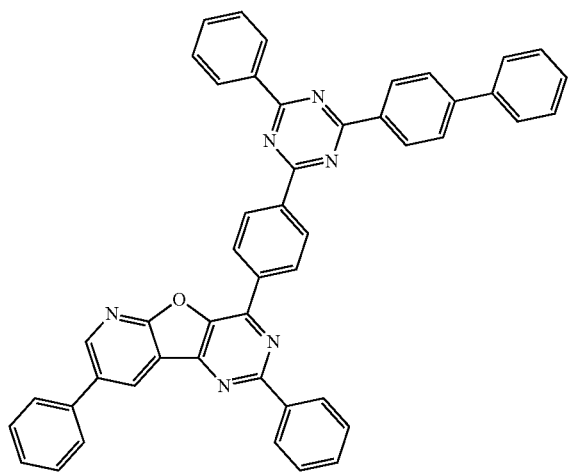
97
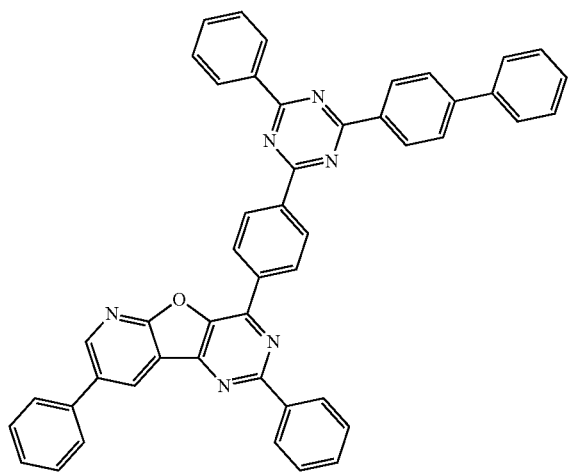
98
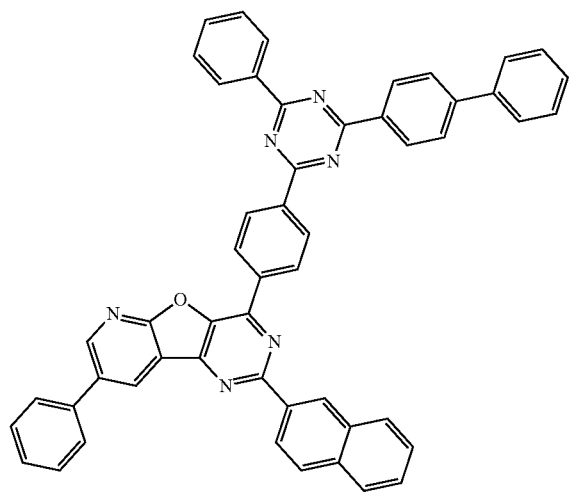

407
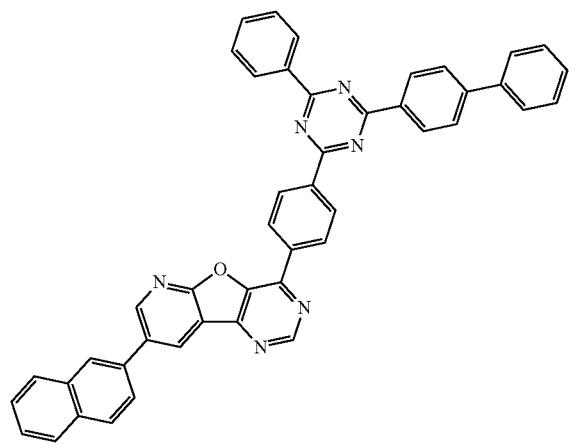
99
408
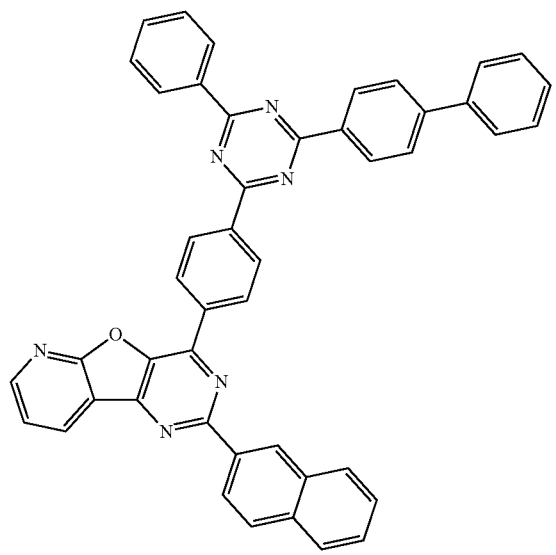
100
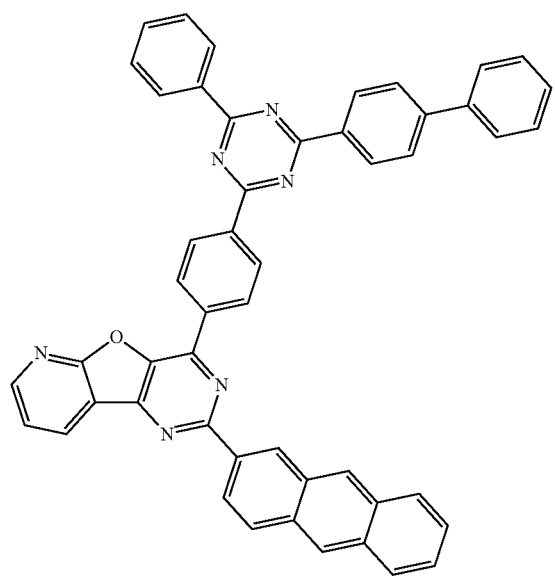
101

-continued
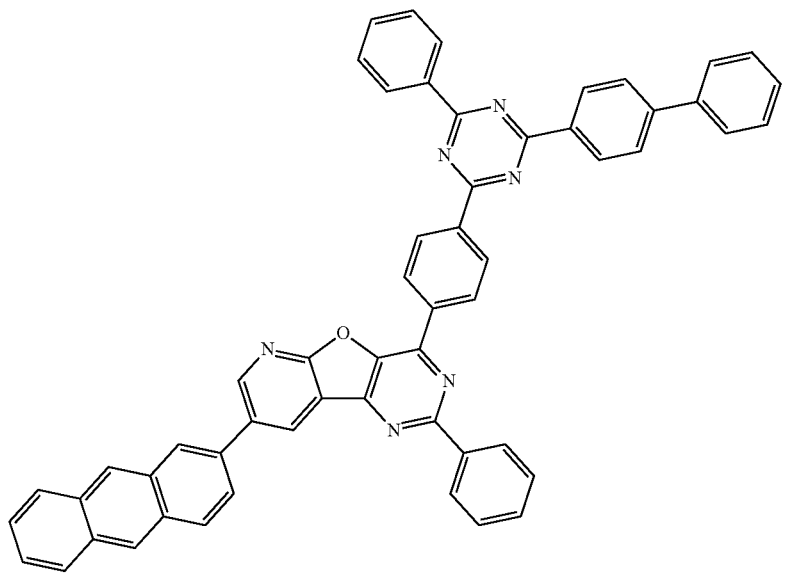
102
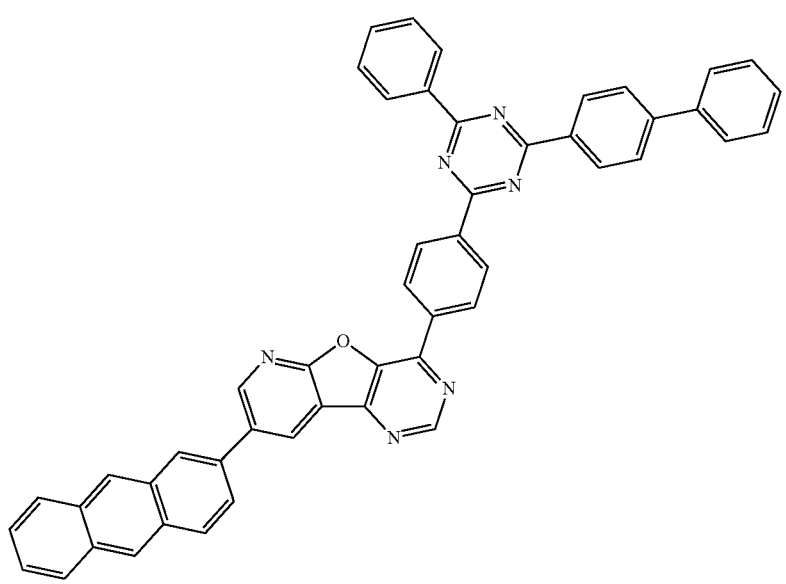
103

411
104
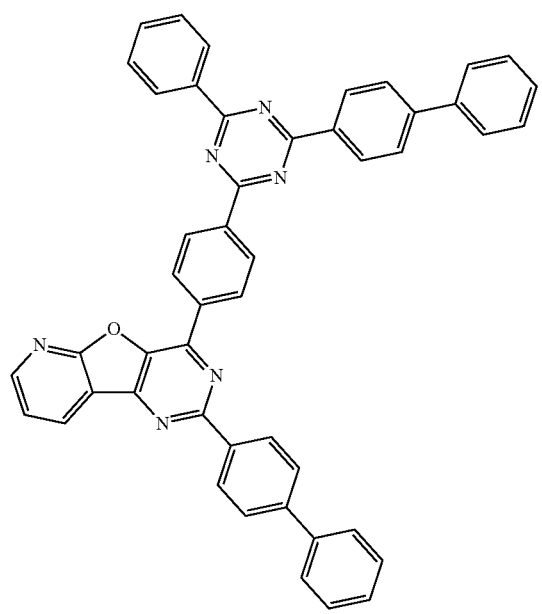
412
105
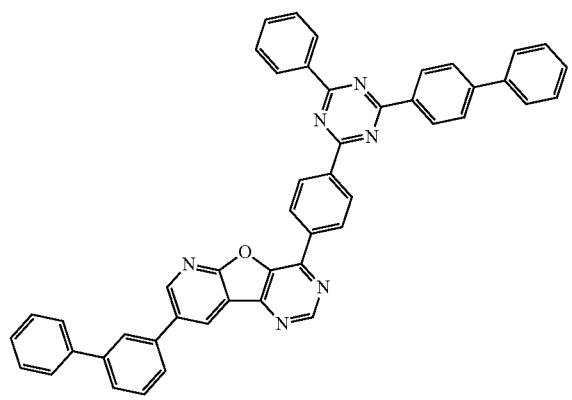
106
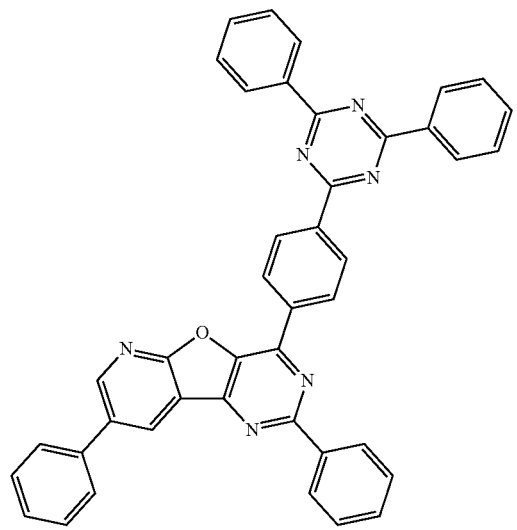
107
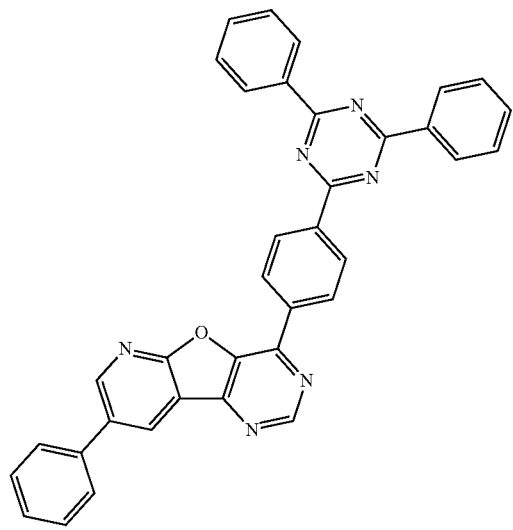

-continued
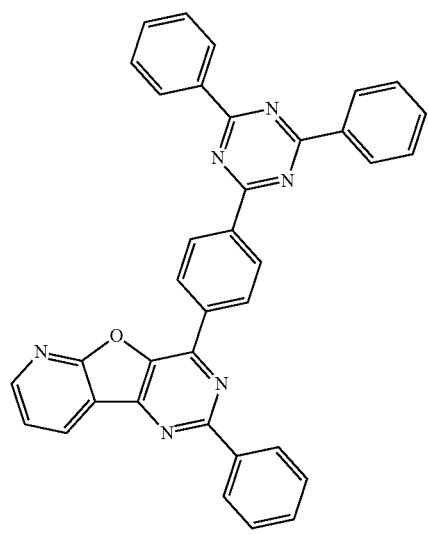
108
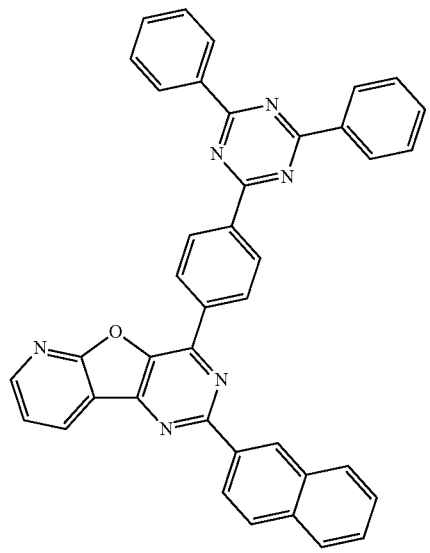
109
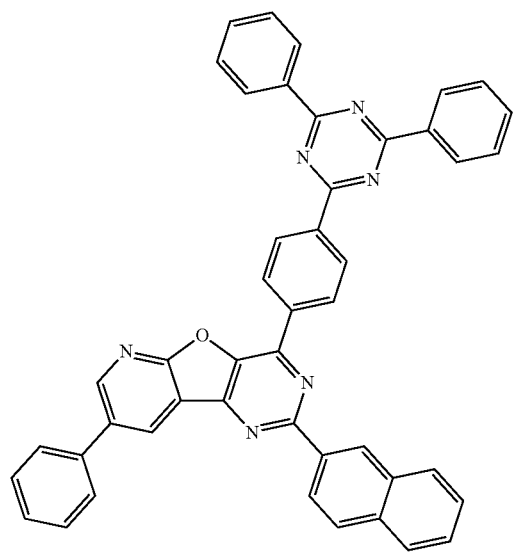
110
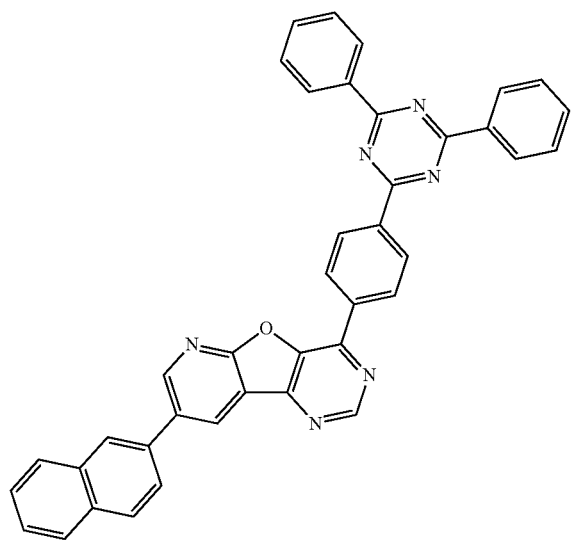
111

415 416
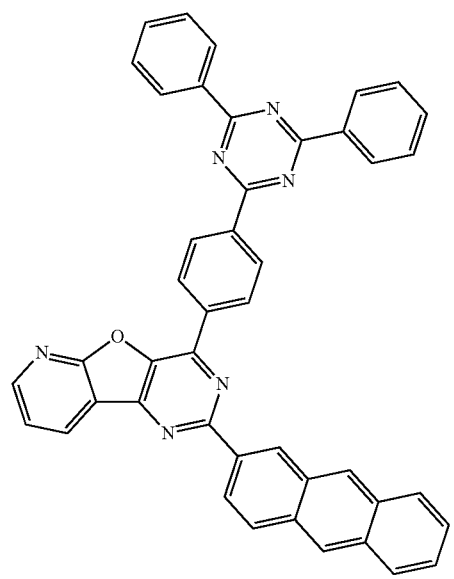
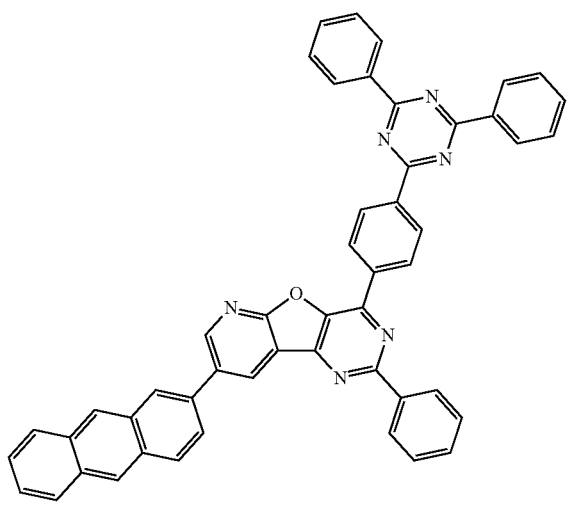
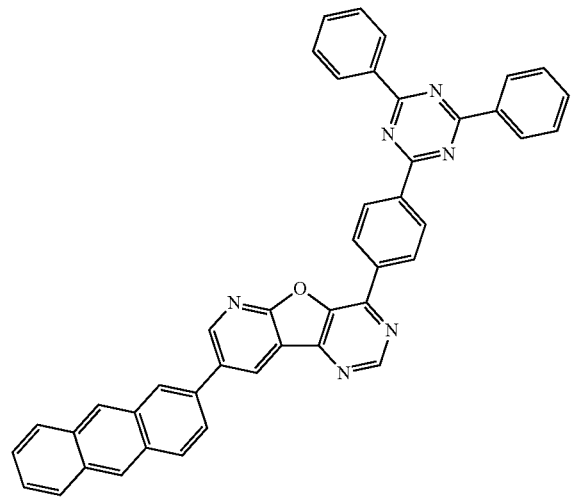
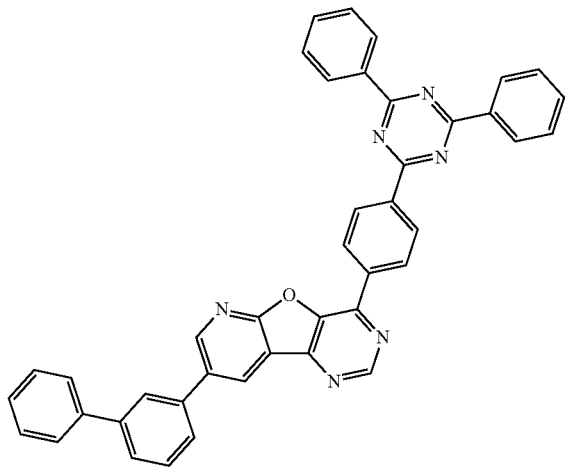

-continued
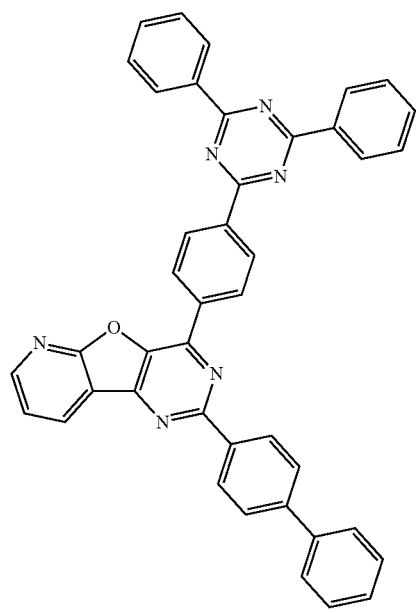
116
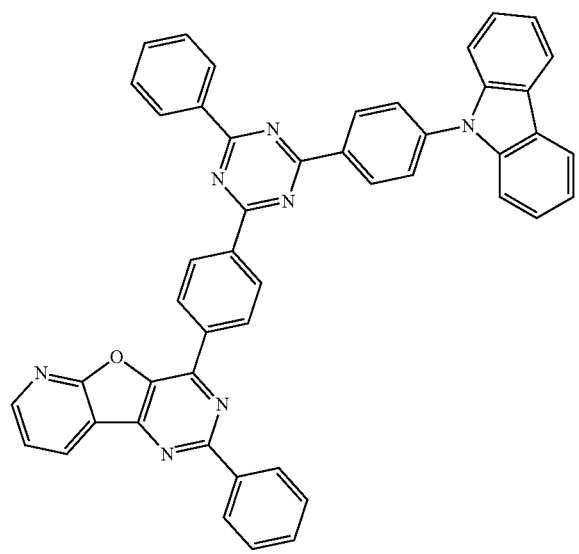
117
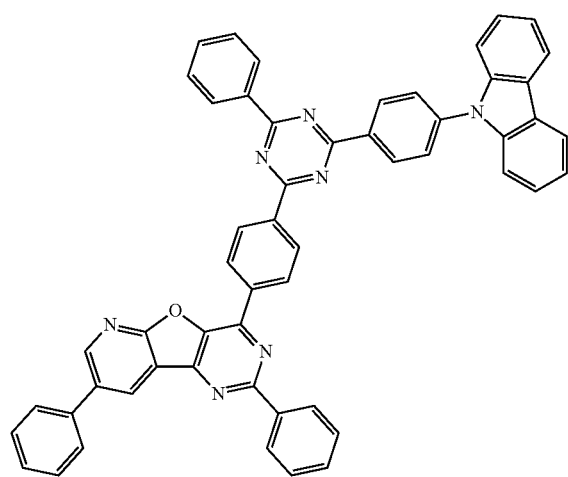
118
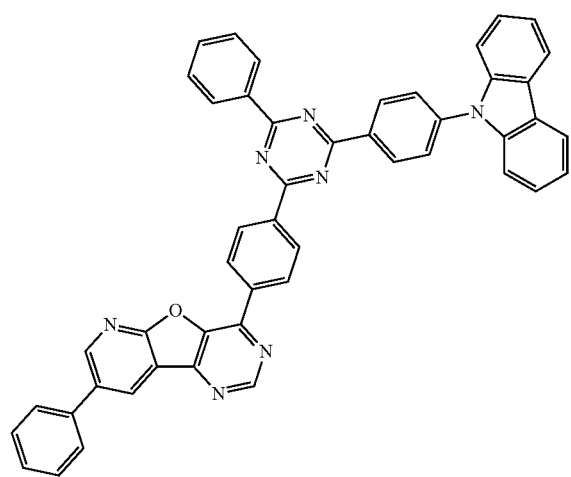
119

-continued
120
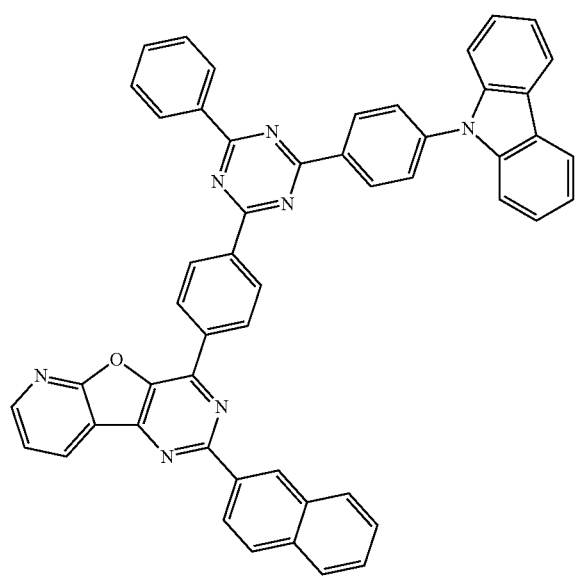
121
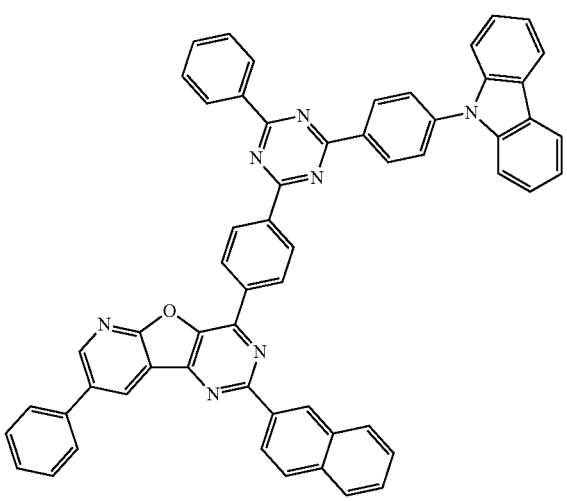
122
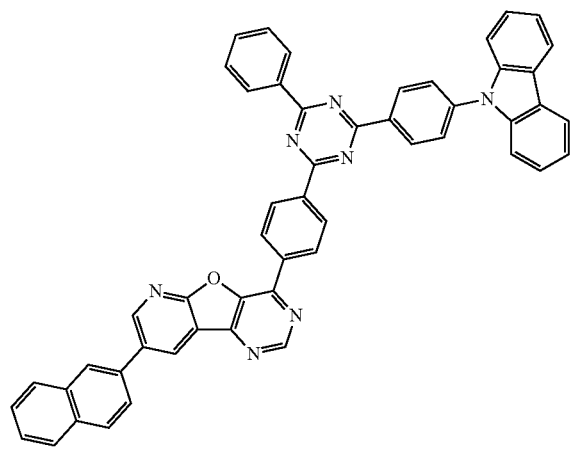
123
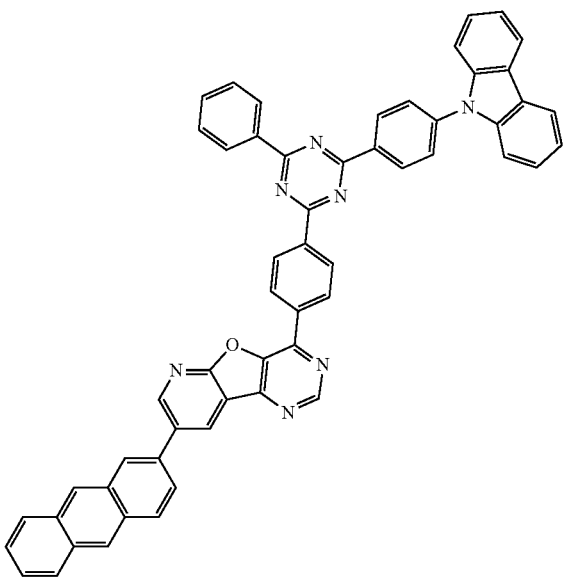

-continued
421
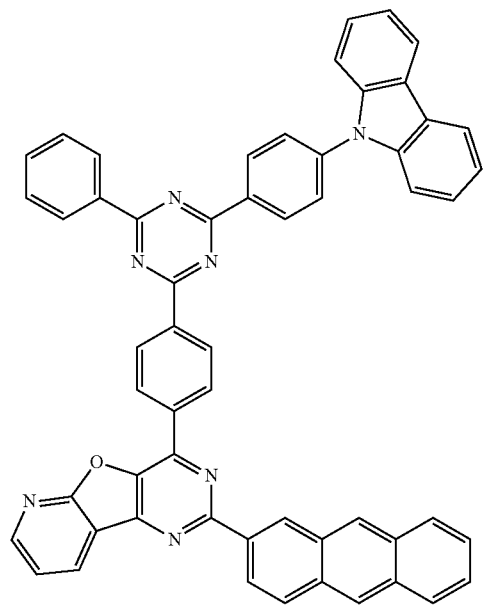
422
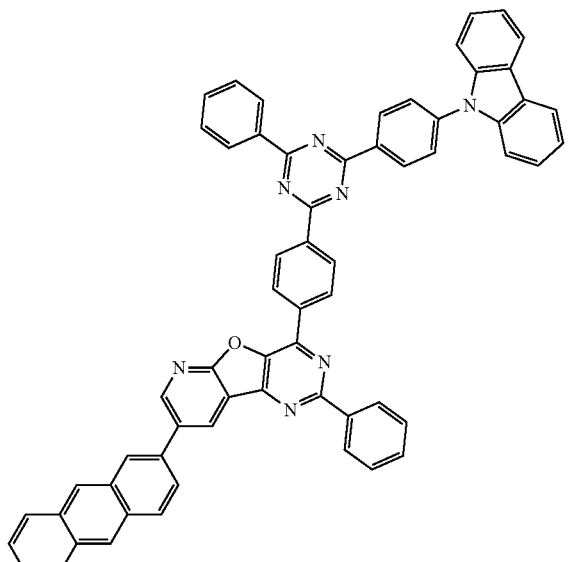
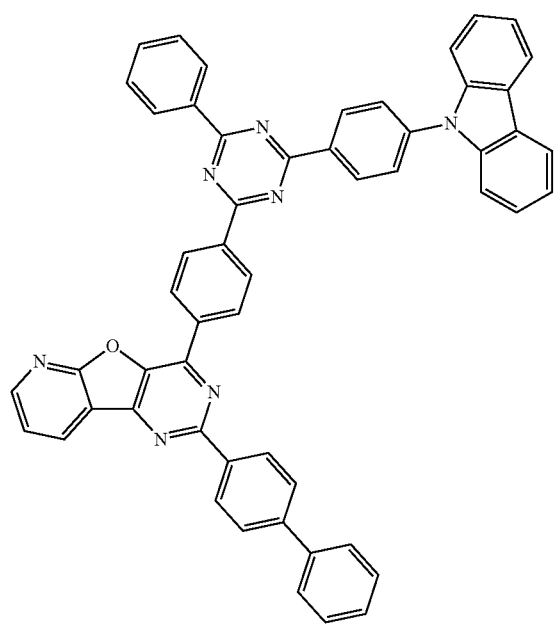

423
-continued
127
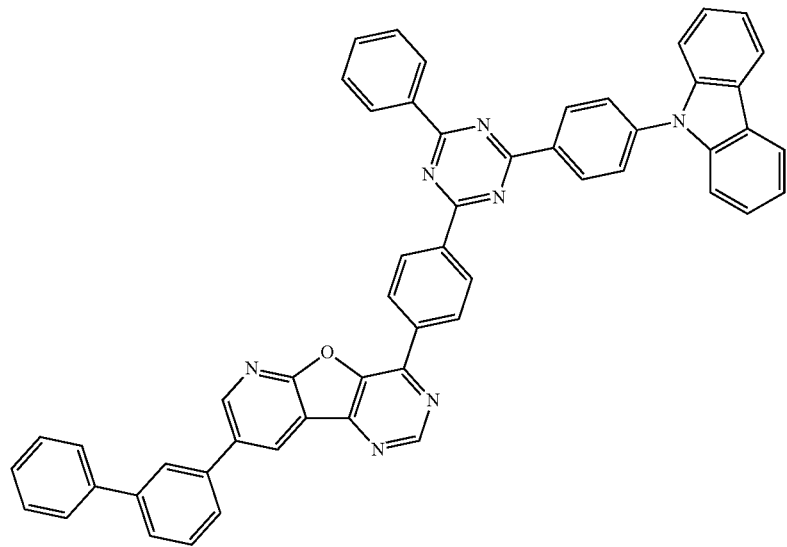
128
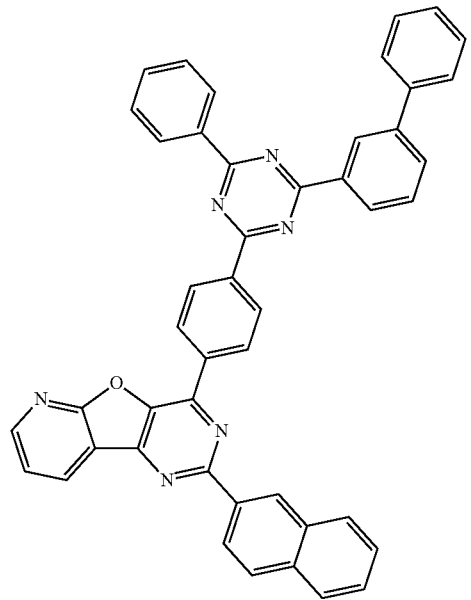
129
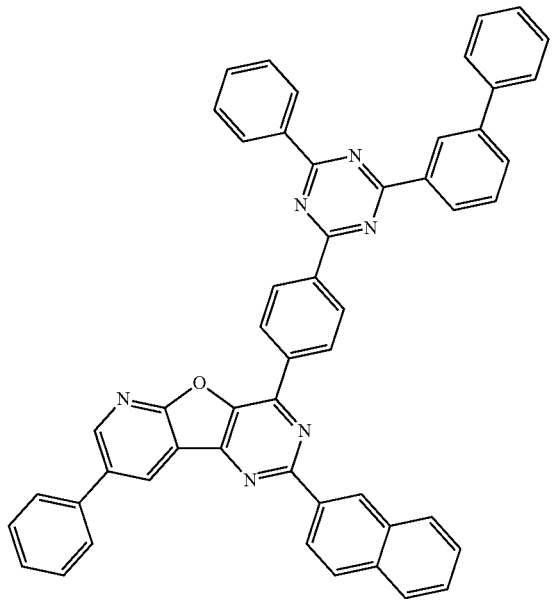
424

-continued
130
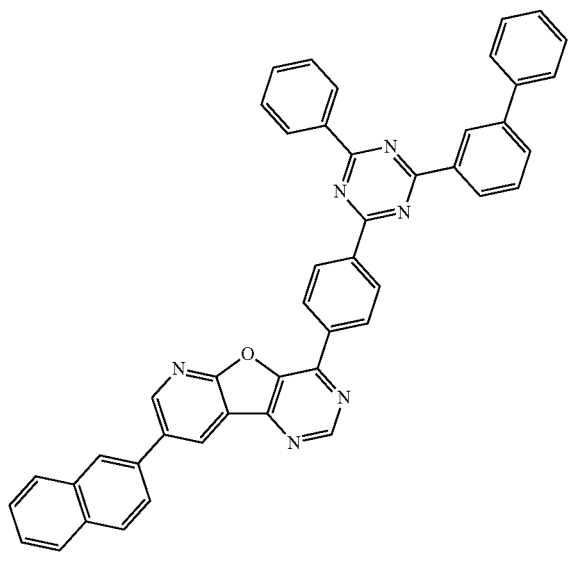
131
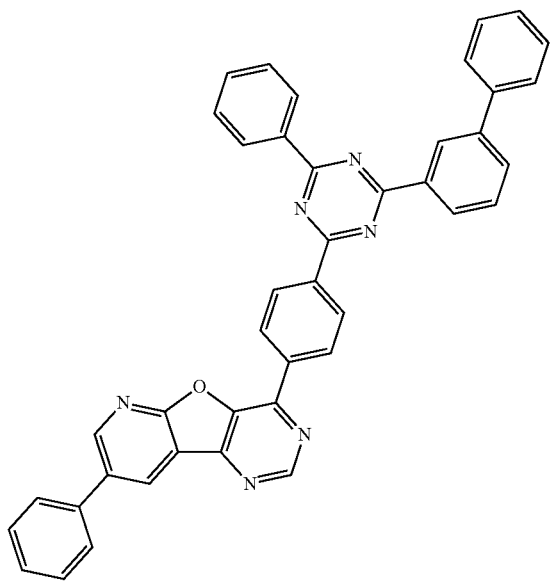
132
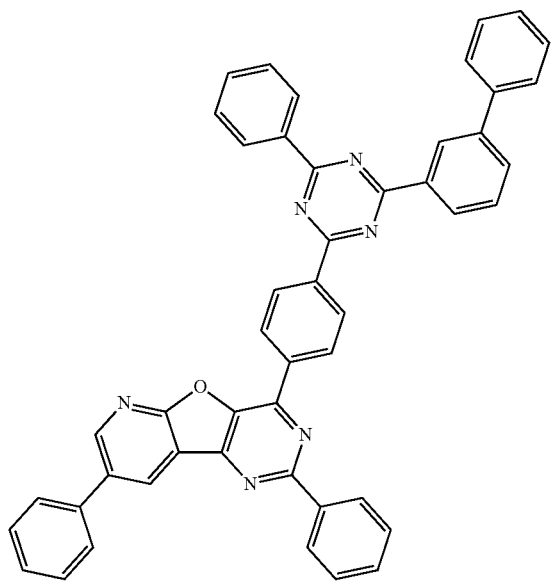
133
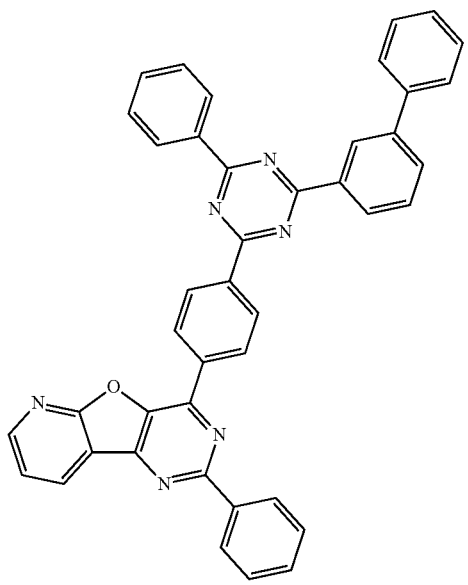

427
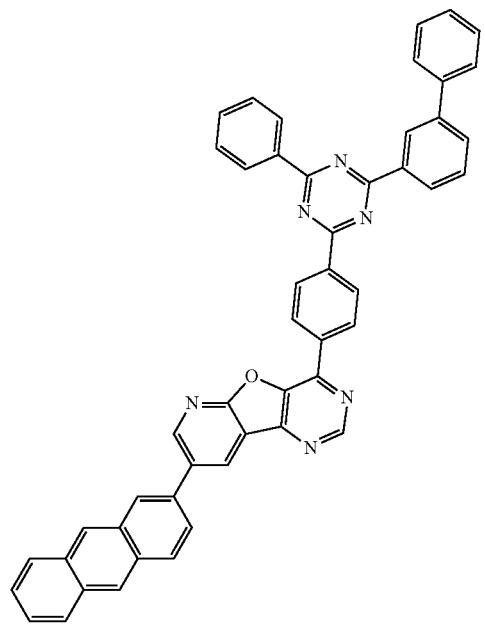
428
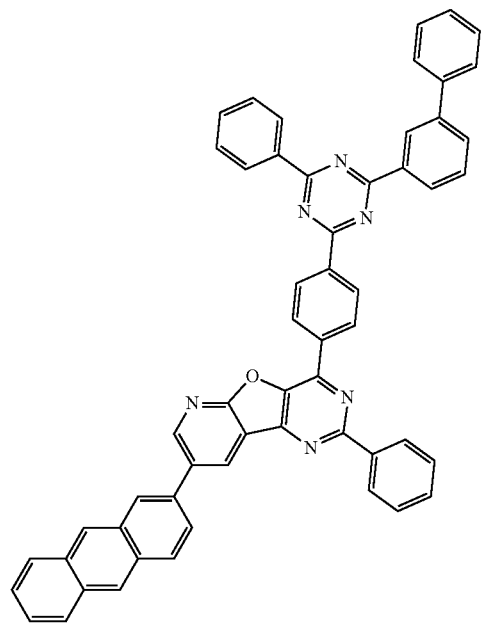
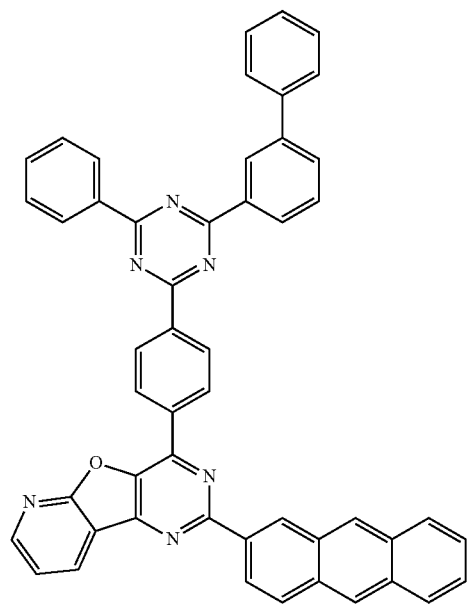
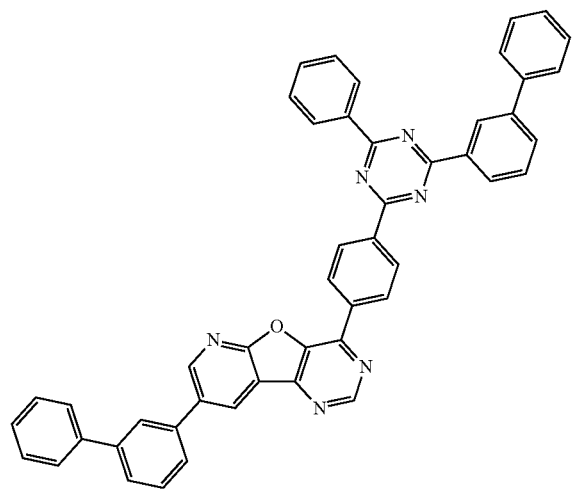

-continued
429
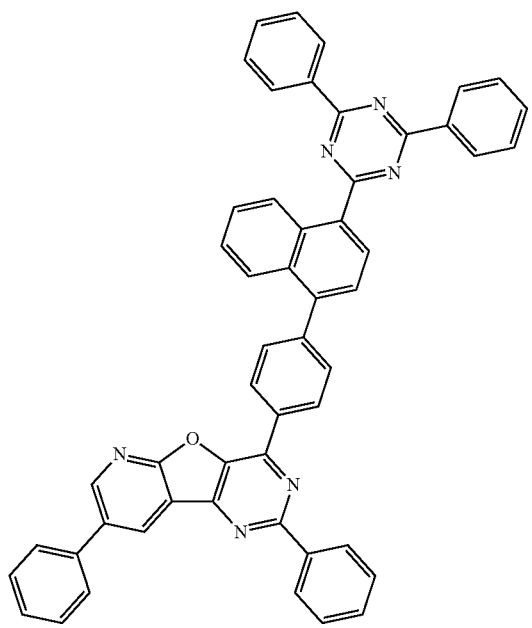
138
430
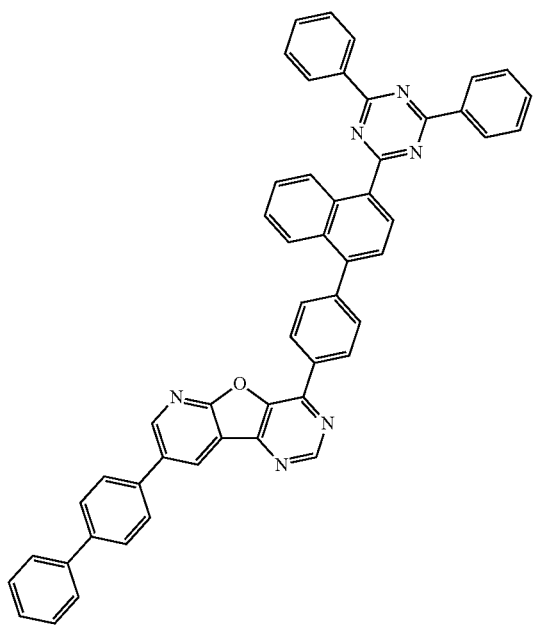
139
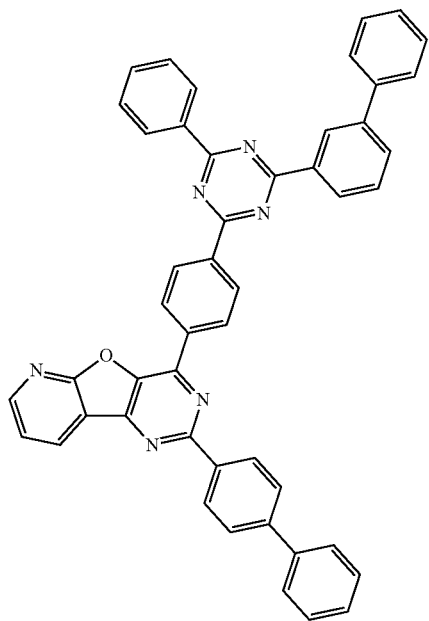
140
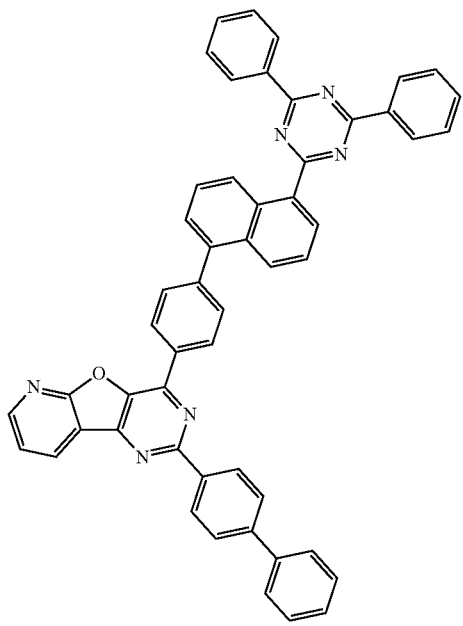
141

-continued
142
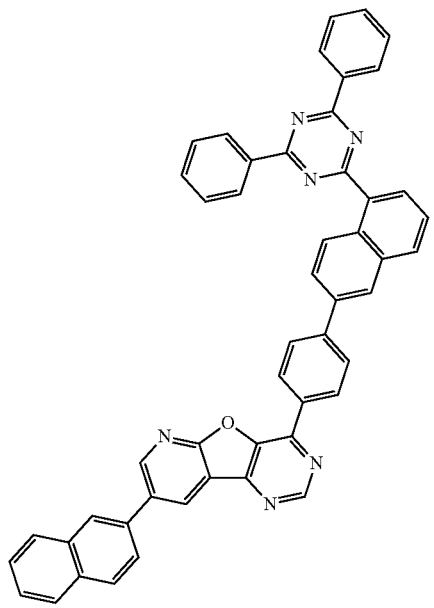
143
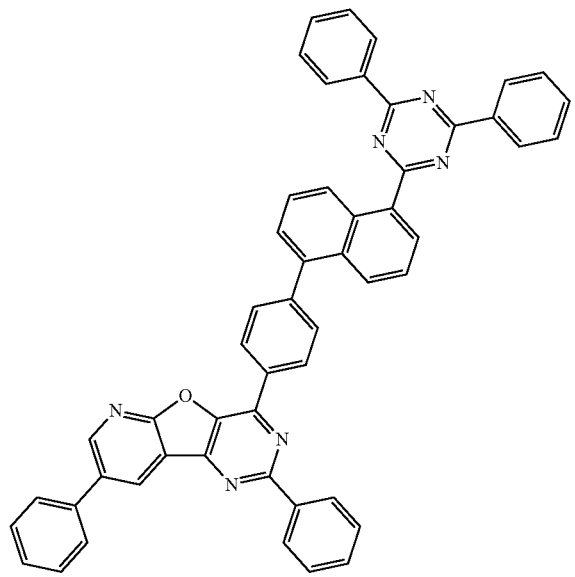
144
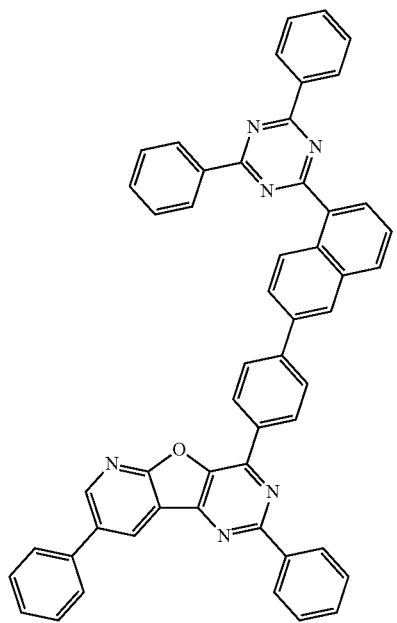
145
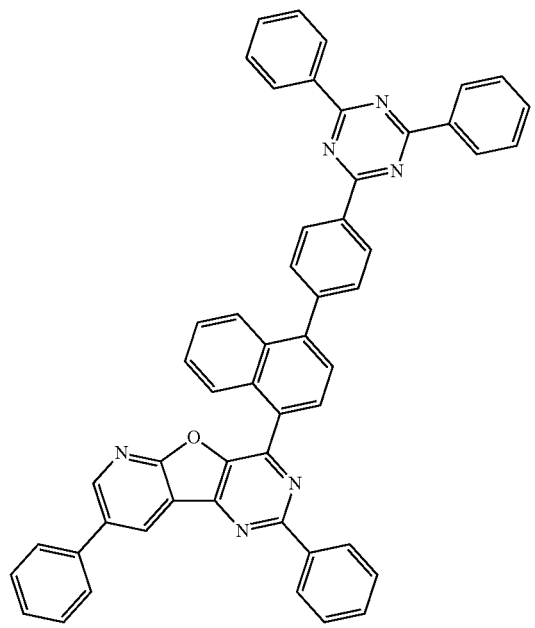

-continued
146
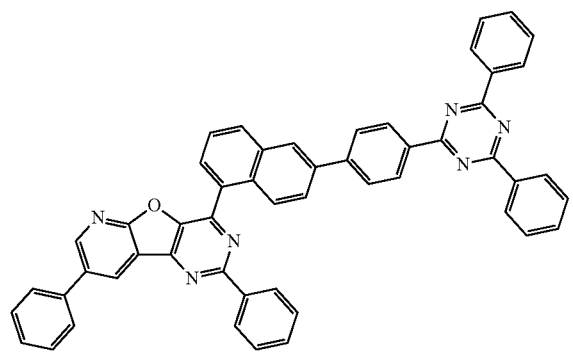
147
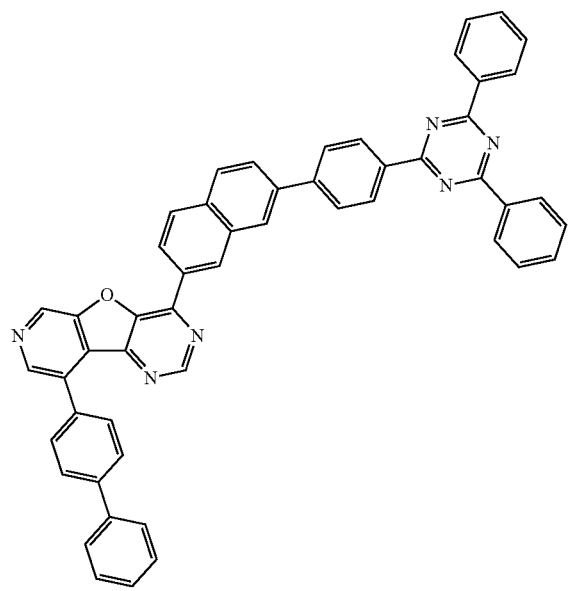
148
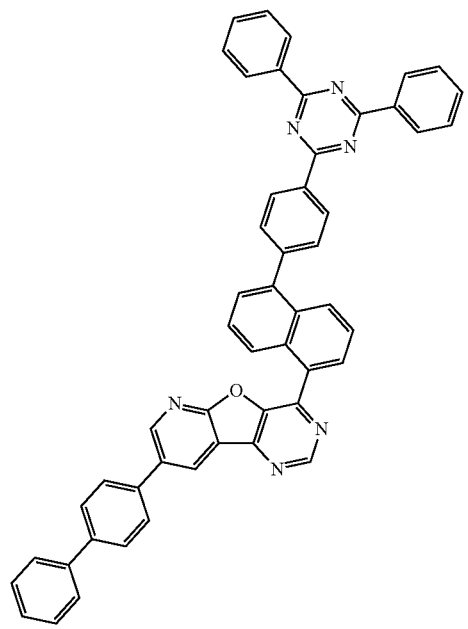
149
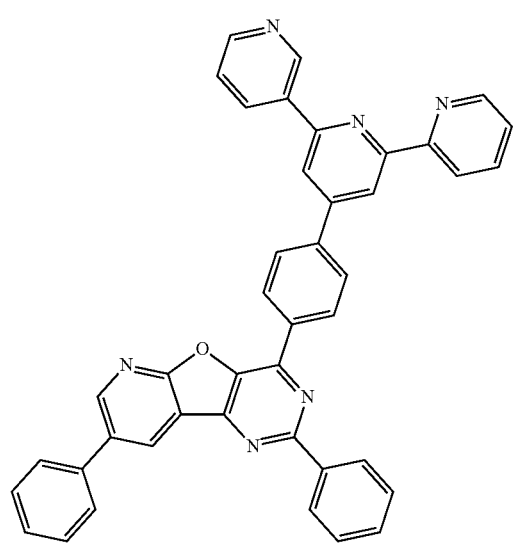

-continued
150
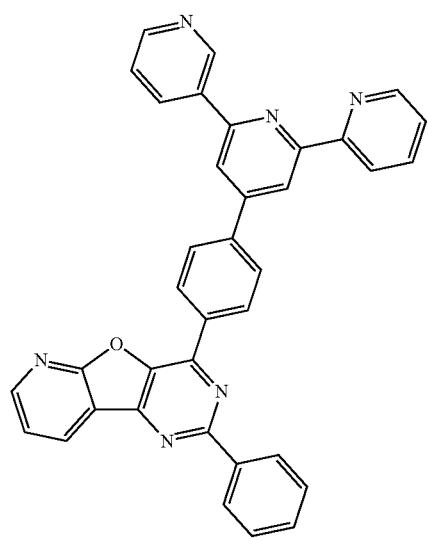
151
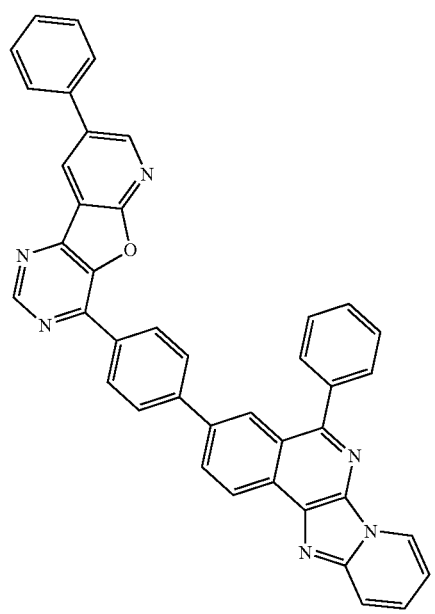
152
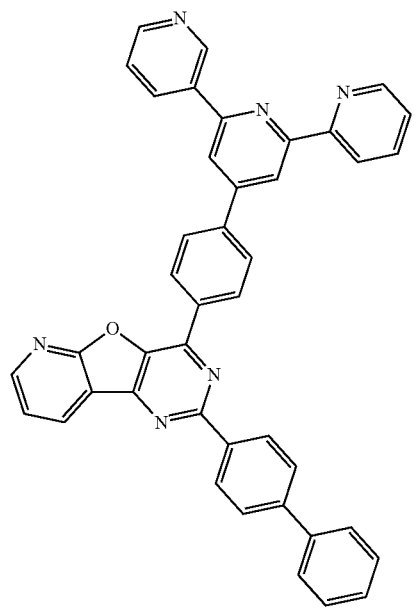
153
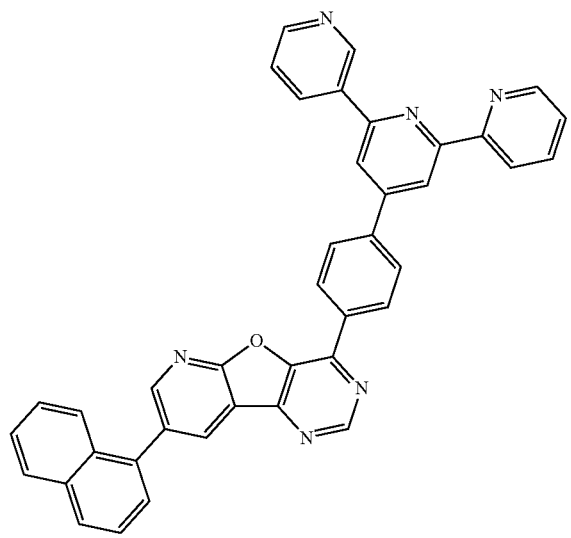

437 438
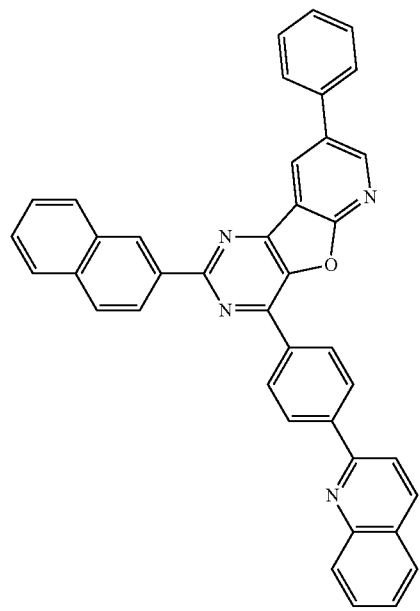 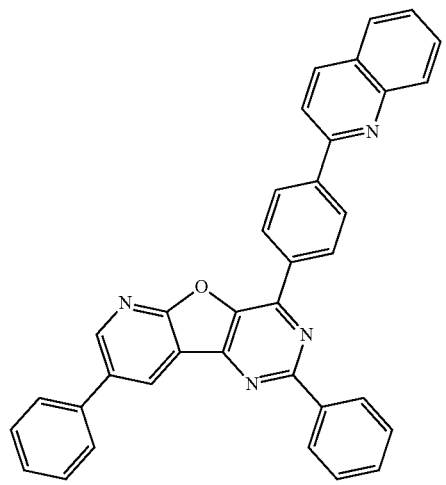
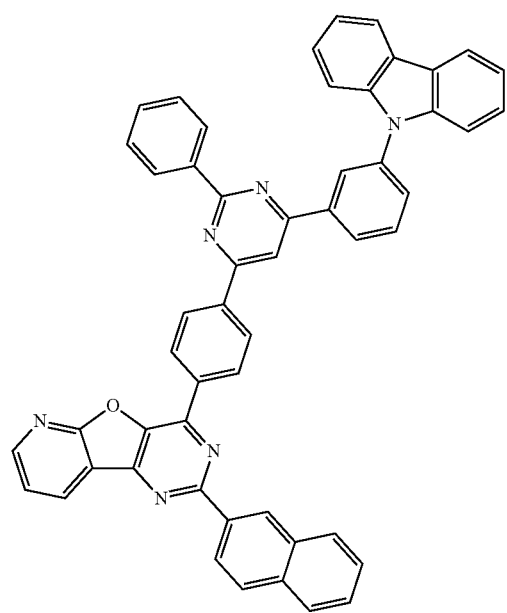

158
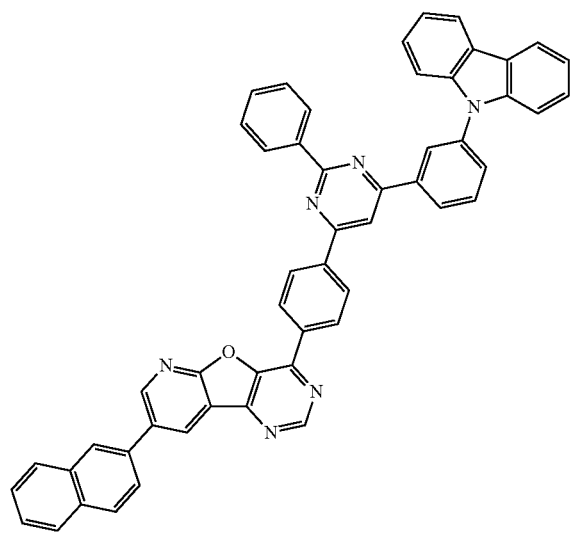
159
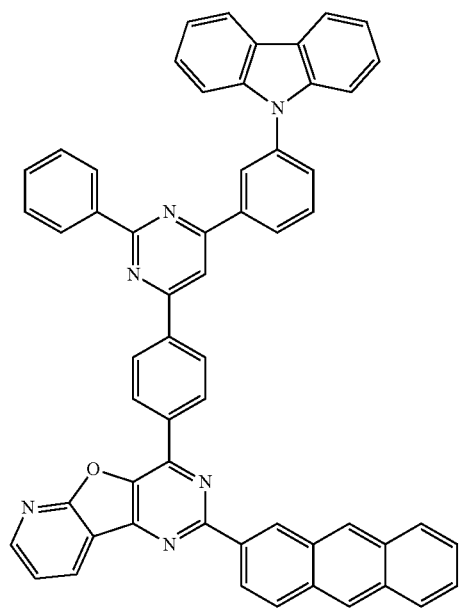
160
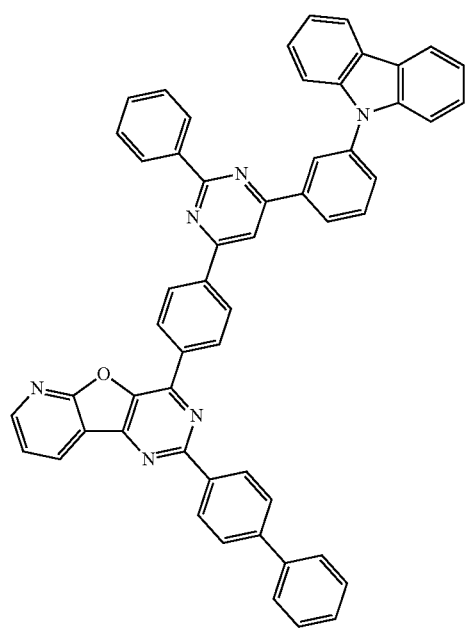

161
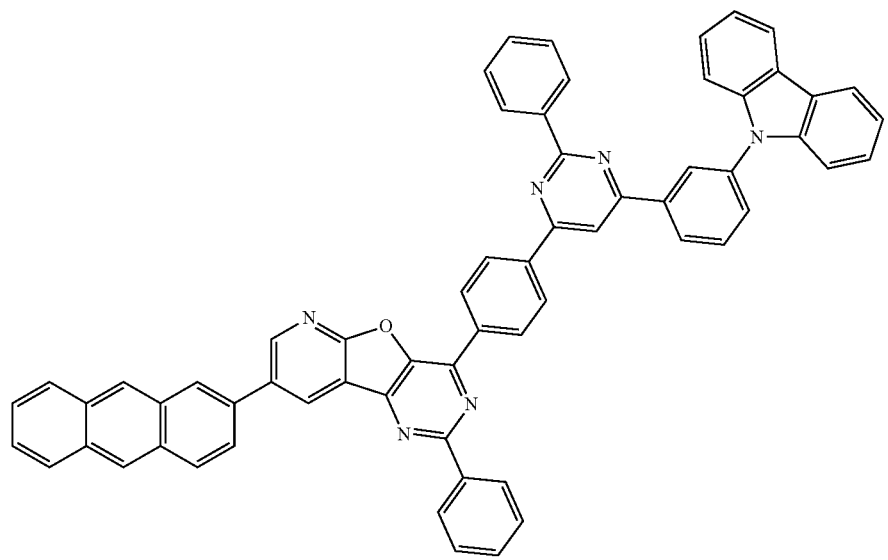
162
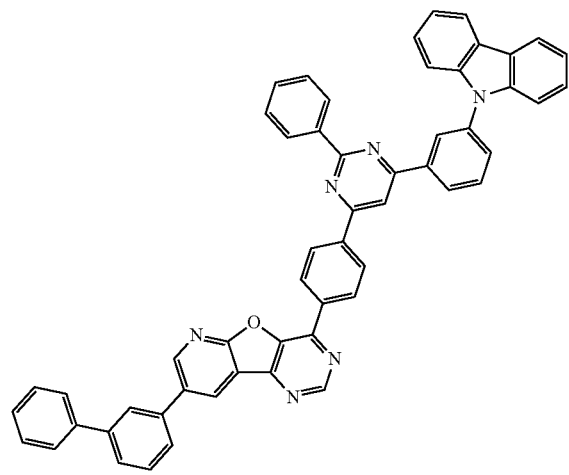
163
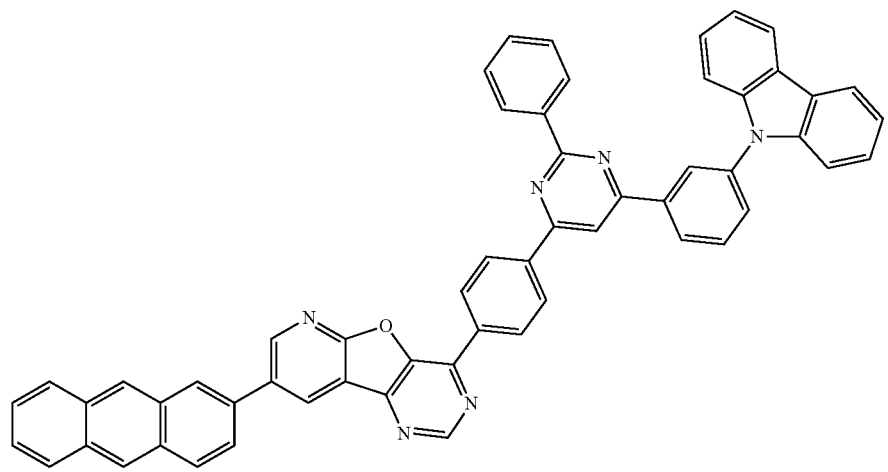

443
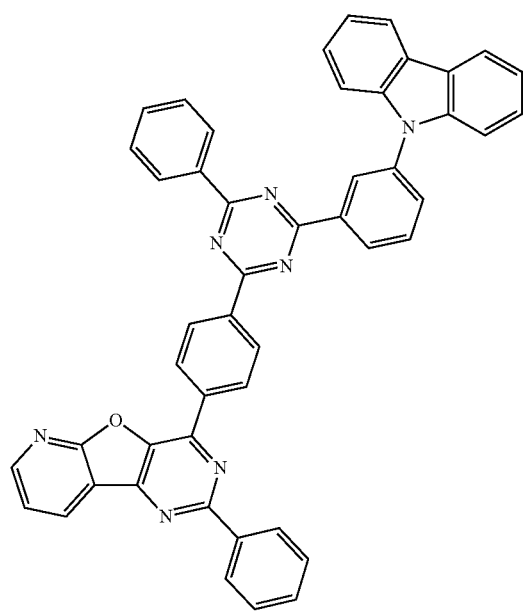
444
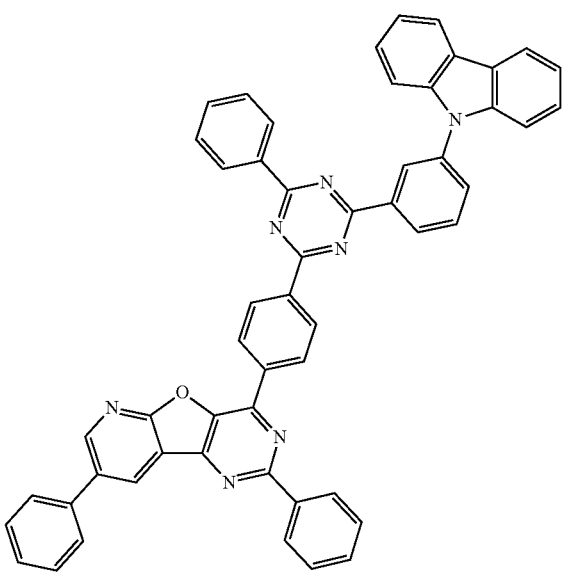
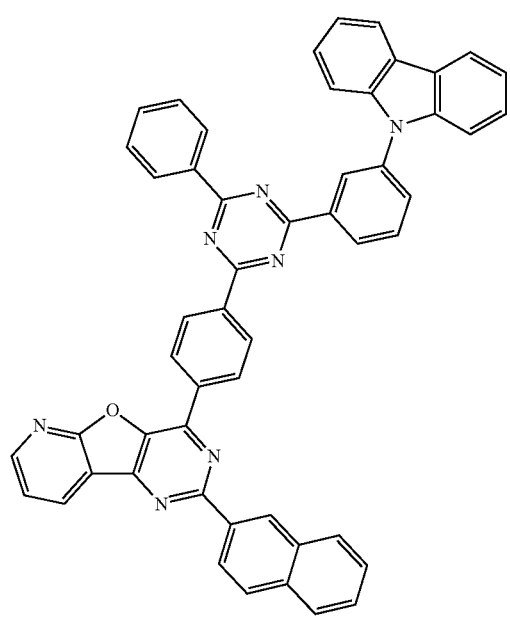
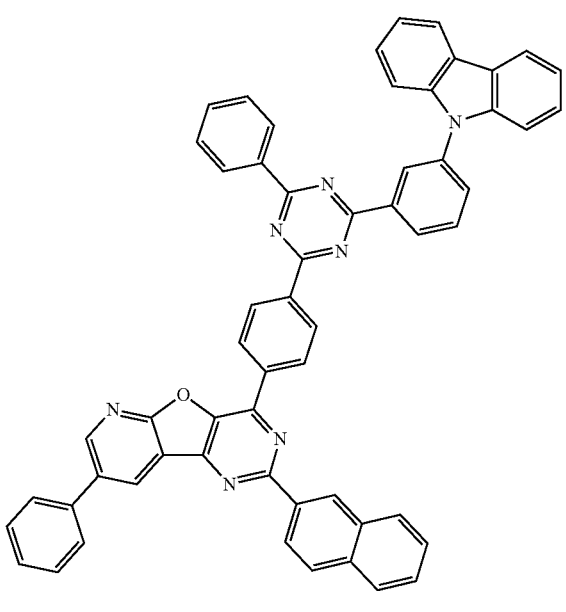

168
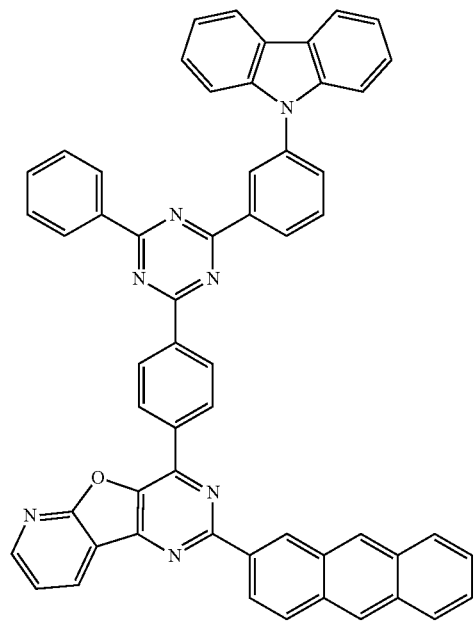
169
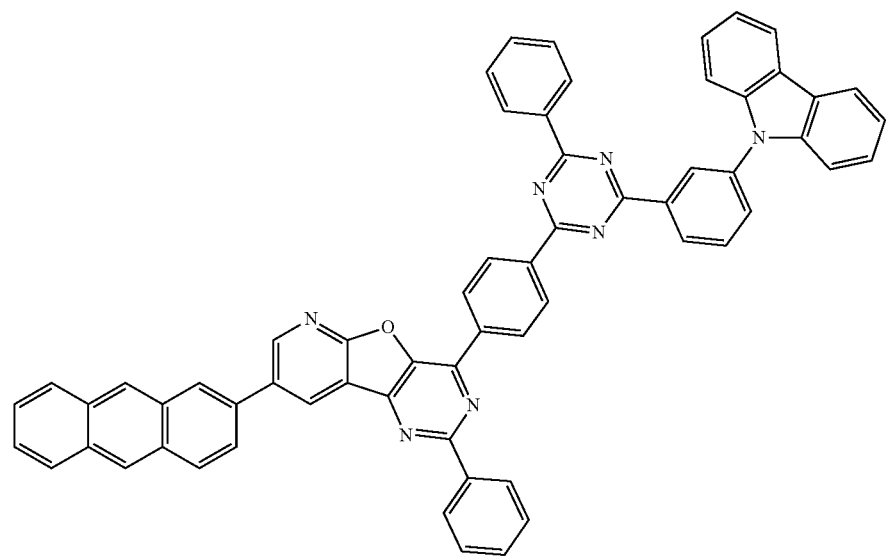

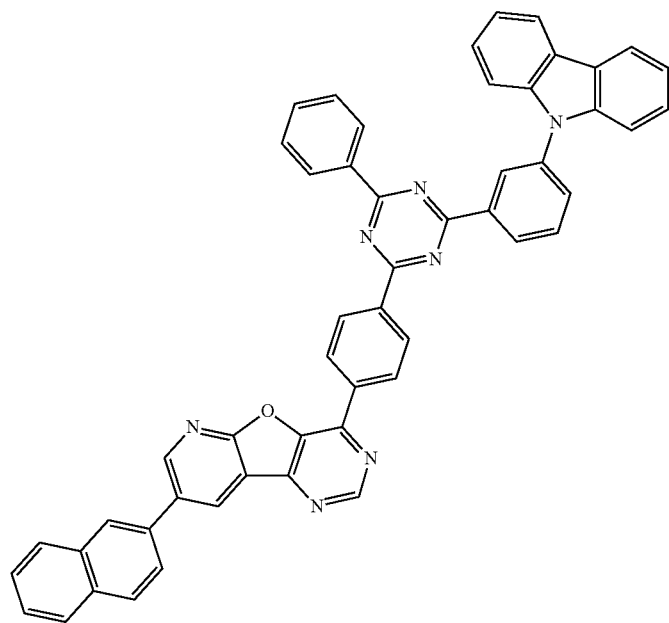
170
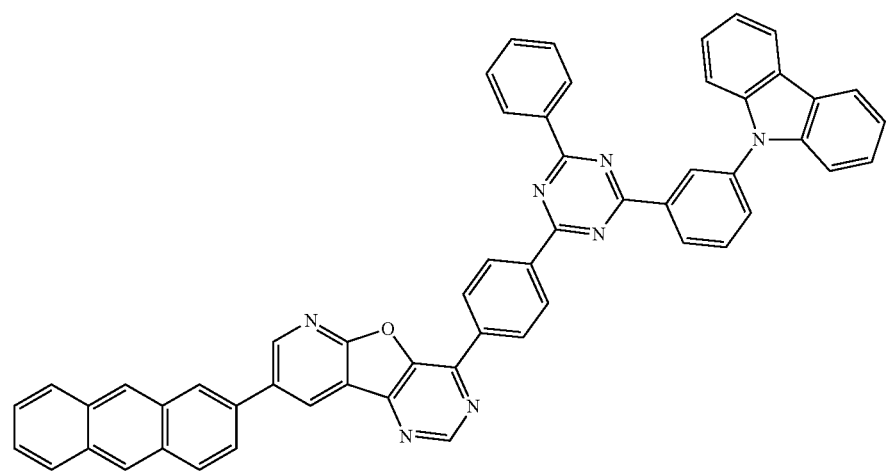
171

-continued
172 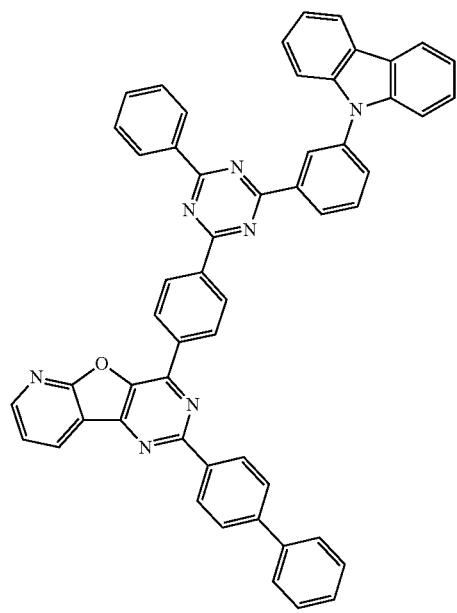
173 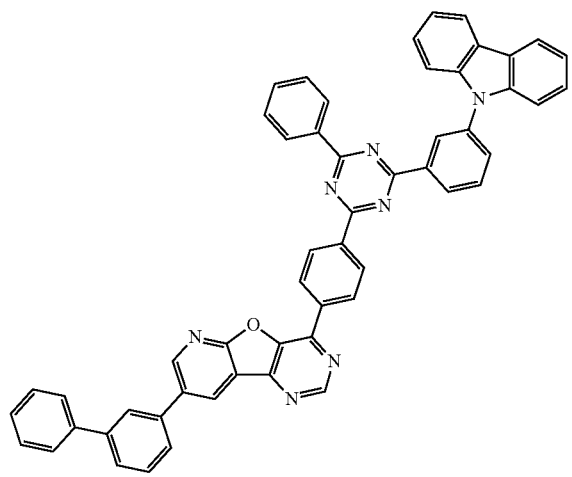
174 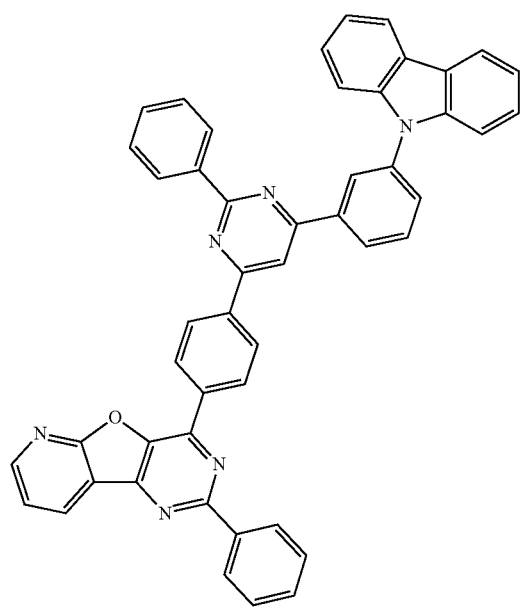
175 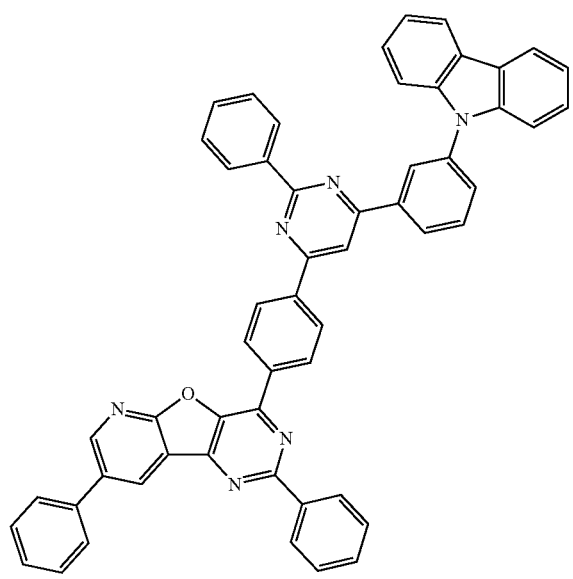

176
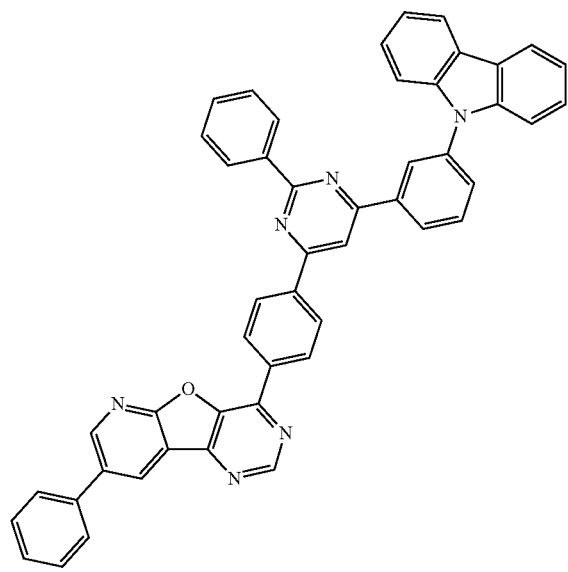
177
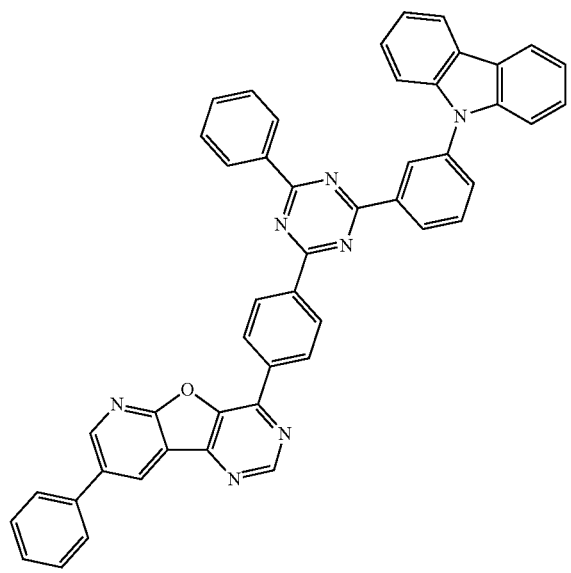
178
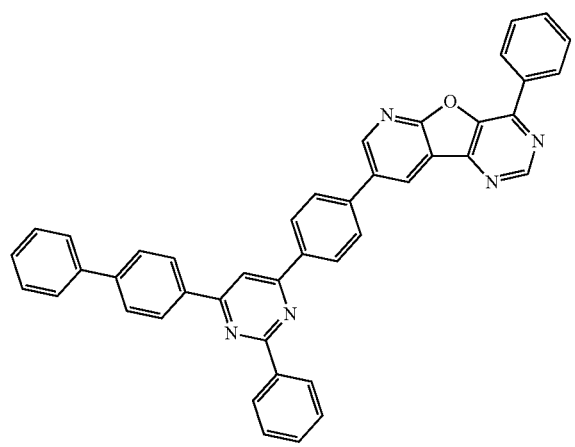
179
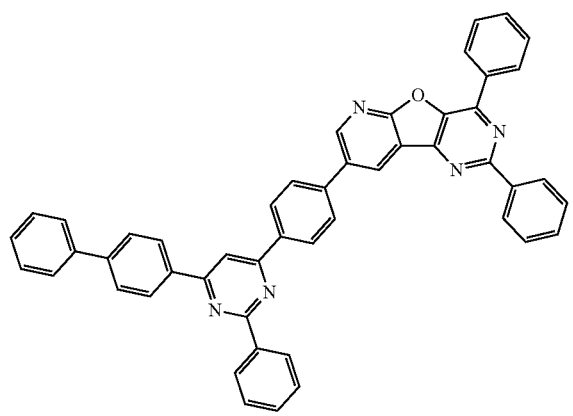
180
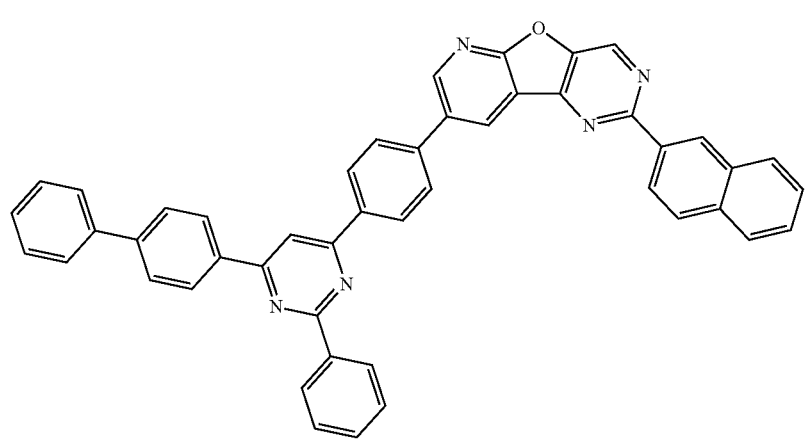

-continued
181
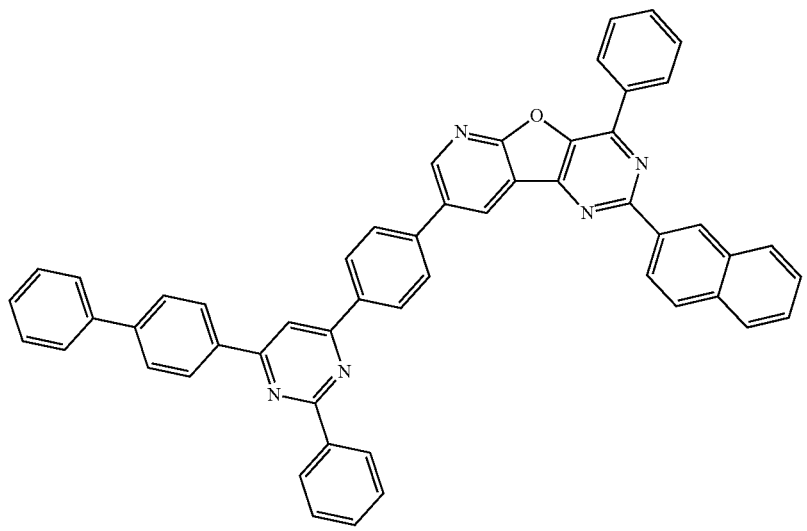
182
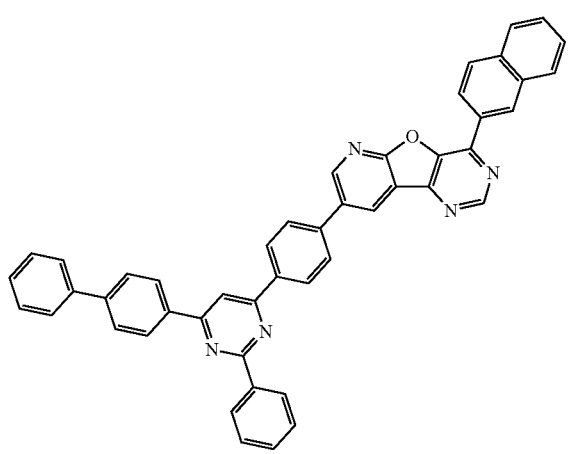
183
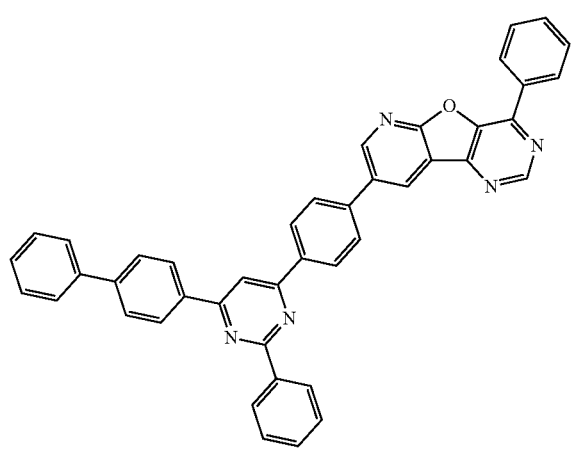
184
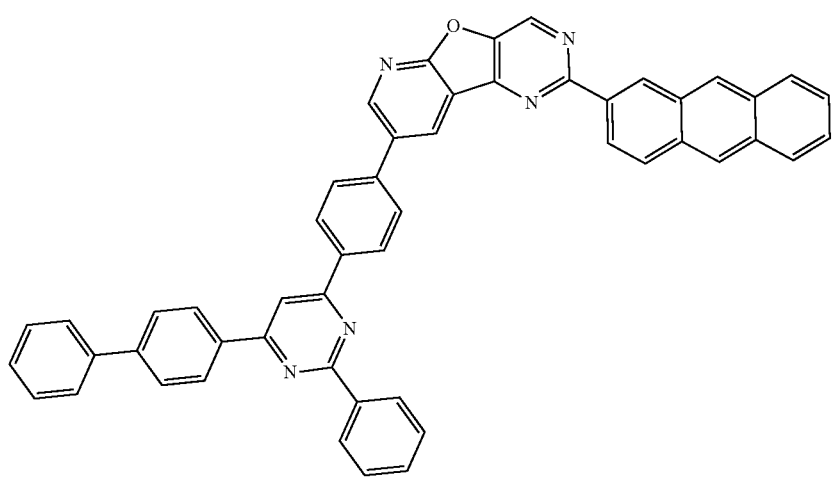

455 456
-continued
185
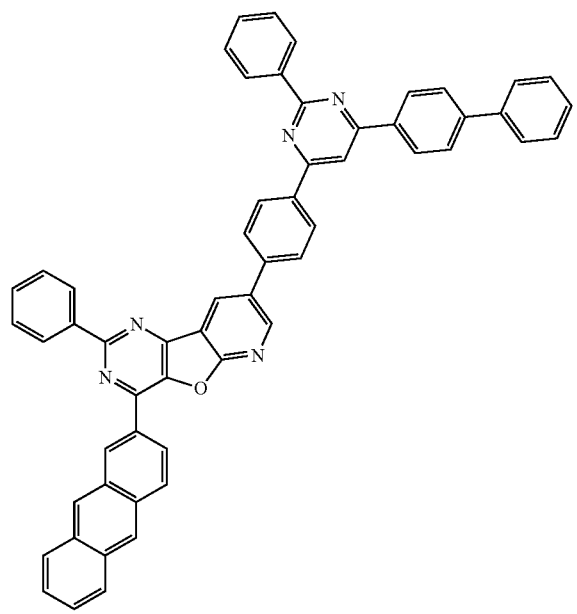
186
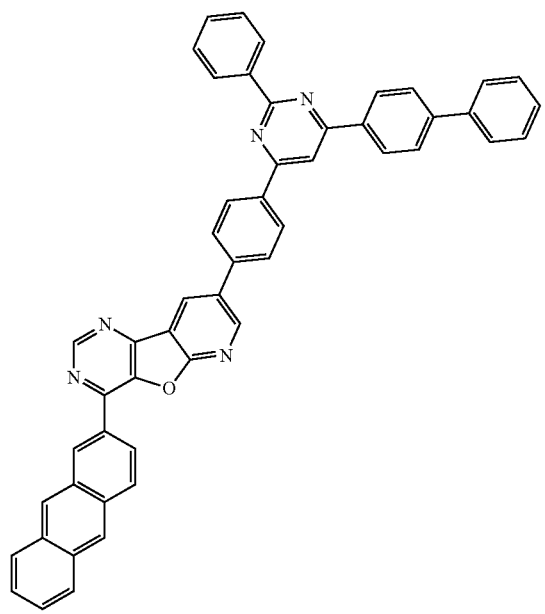
187
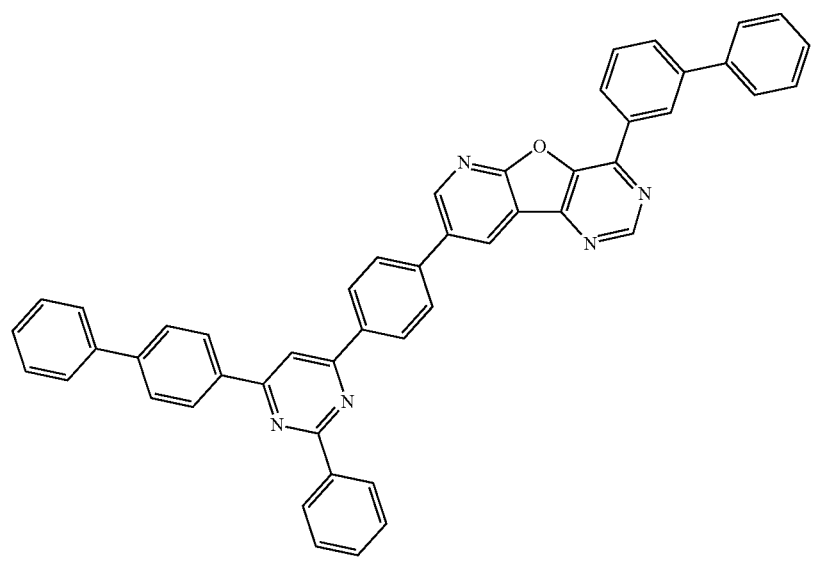
188
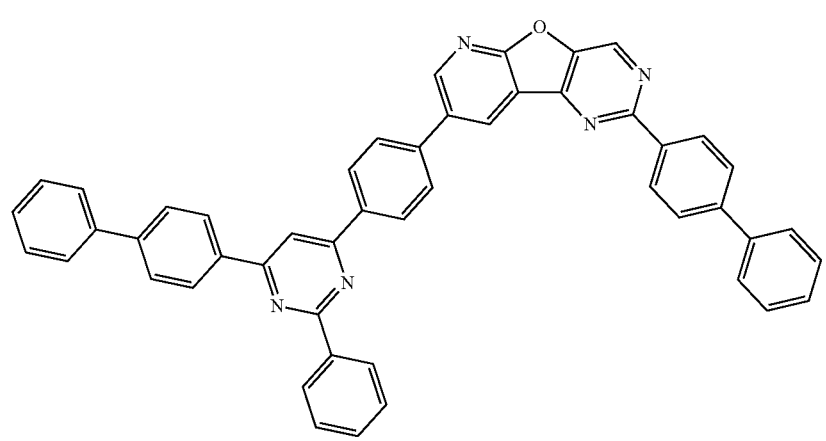

189
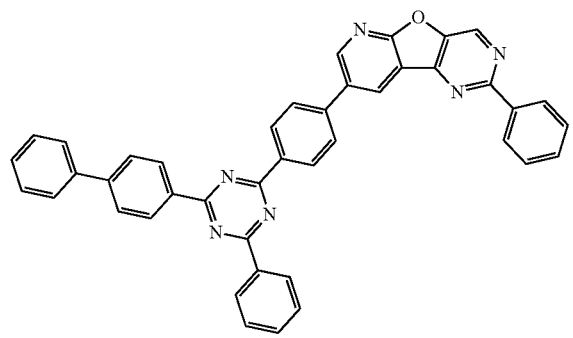
190
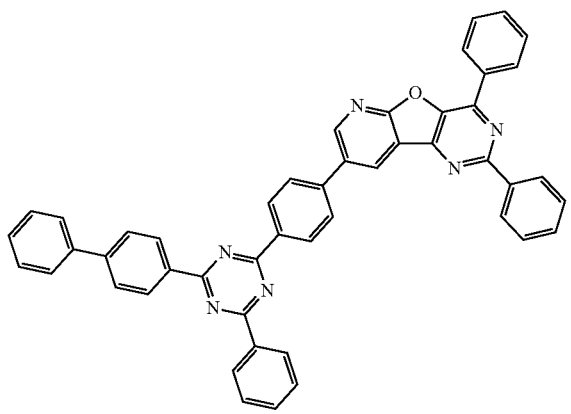
191
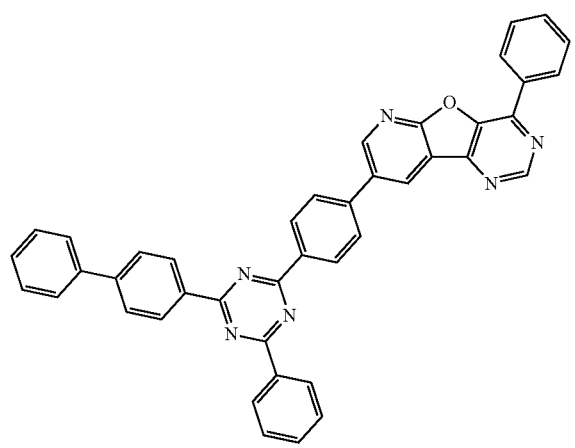
192
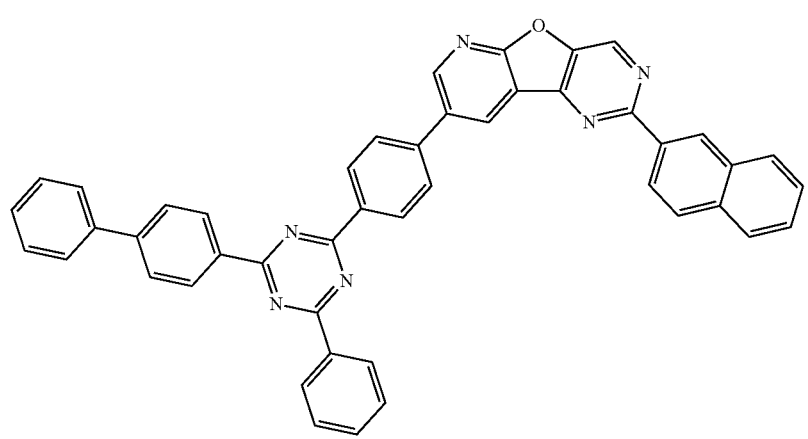

-continued
193
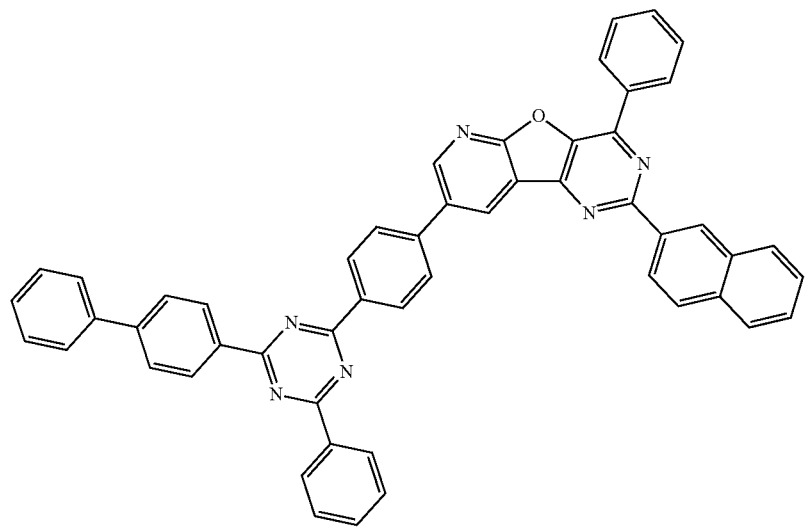
194
195
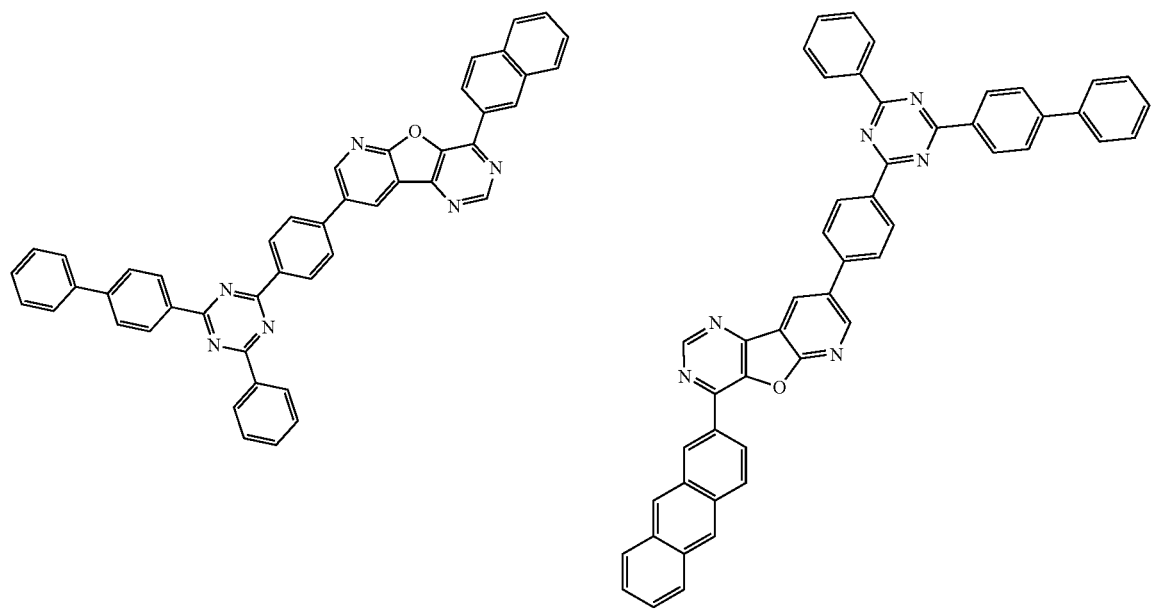
196
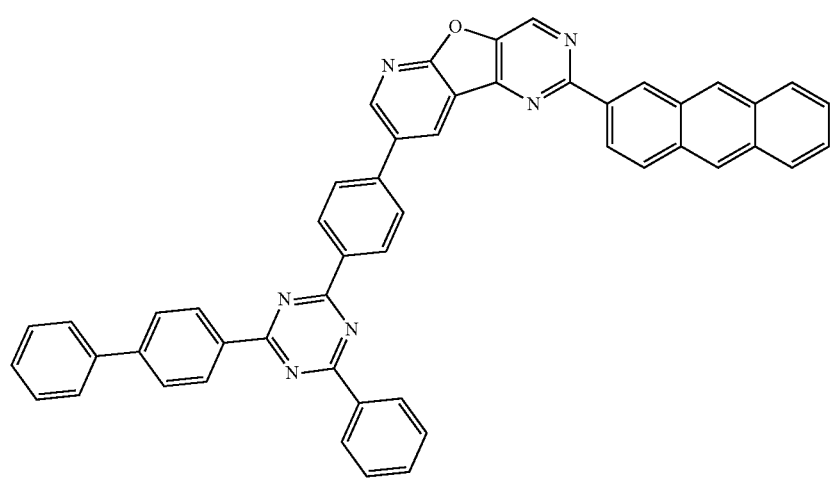

197
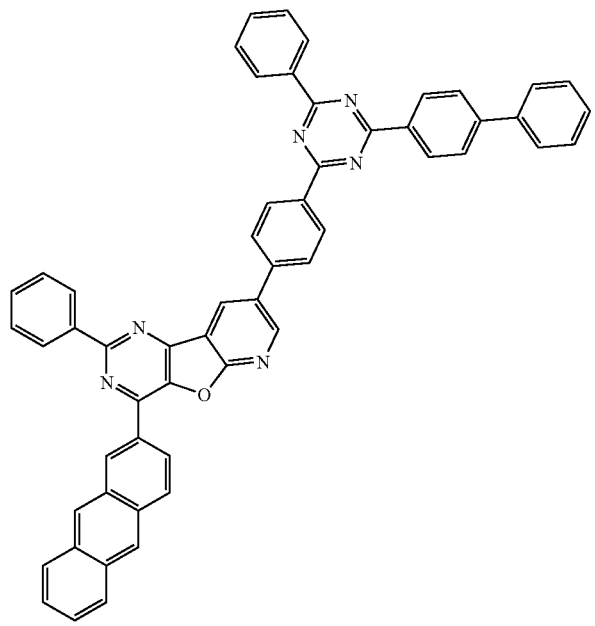
198
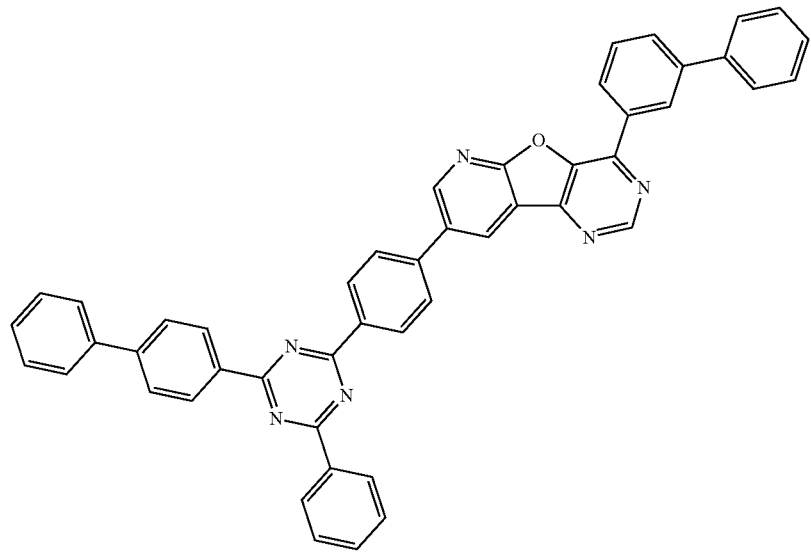
199
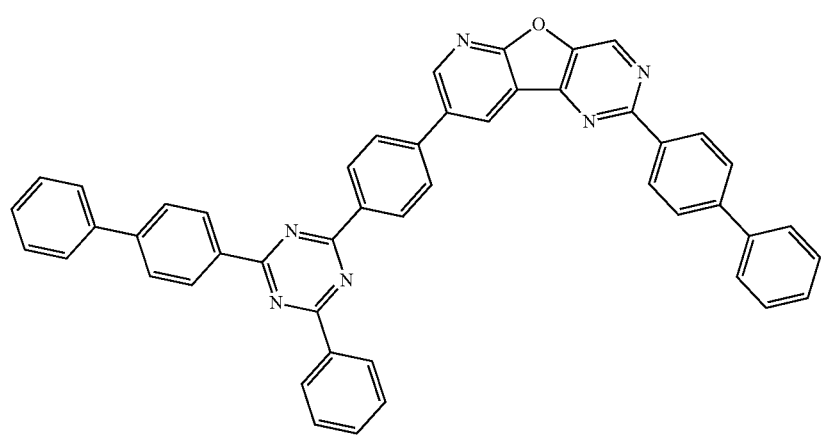

-continued
200
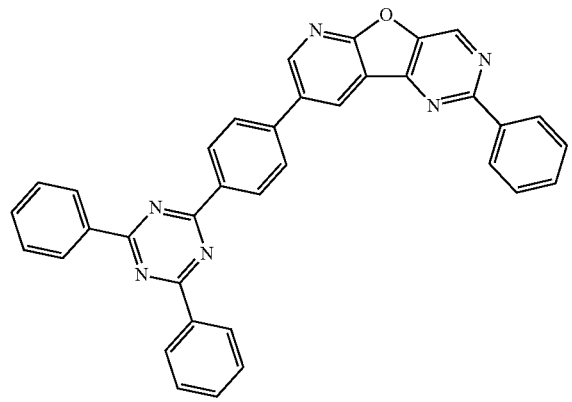
201
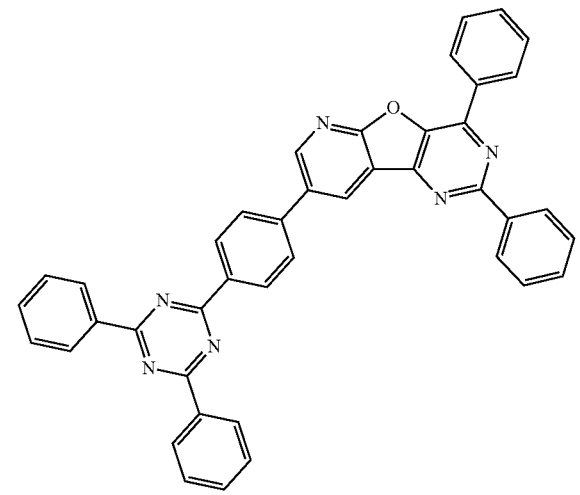
202
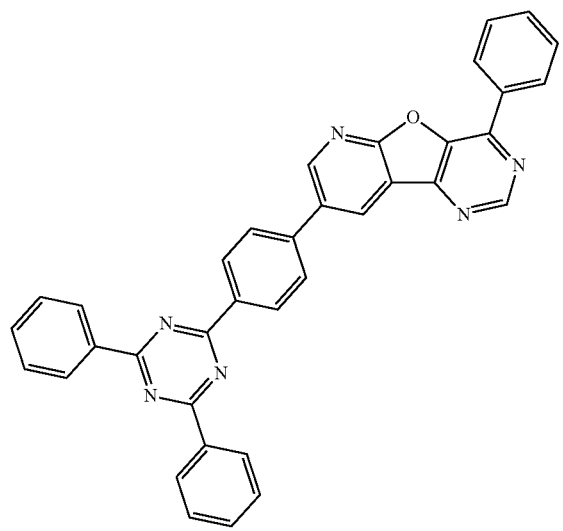
203
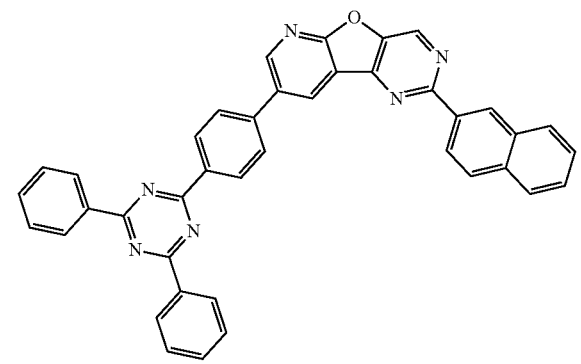
204
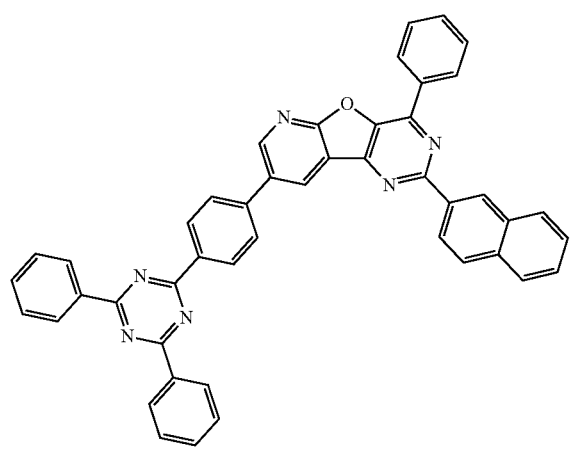
205
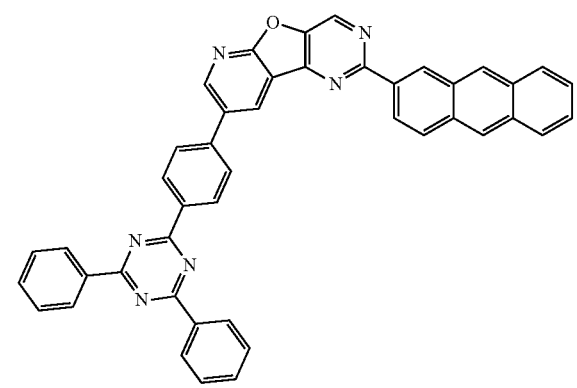

-continued
206 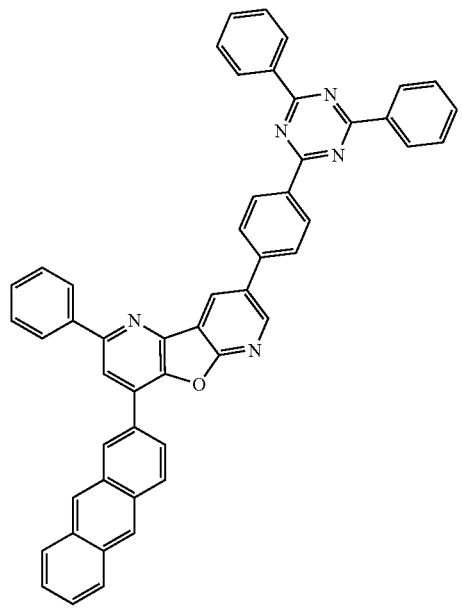
207 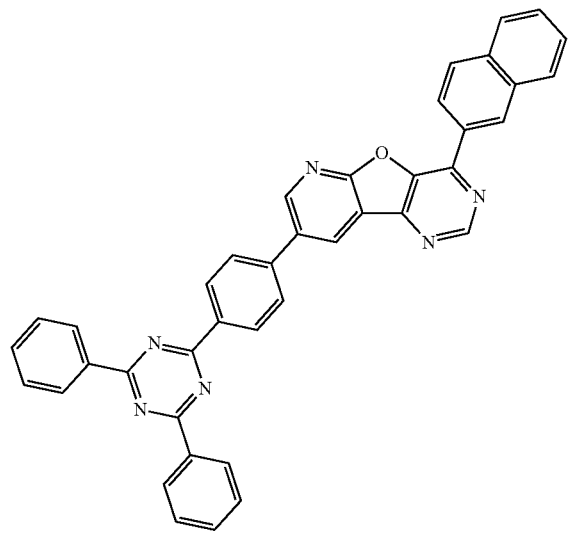
208 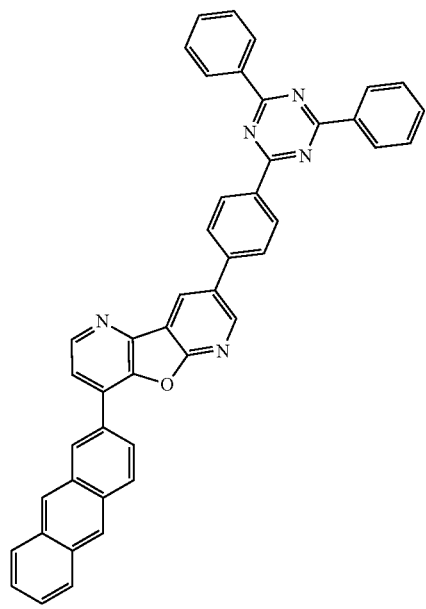
209 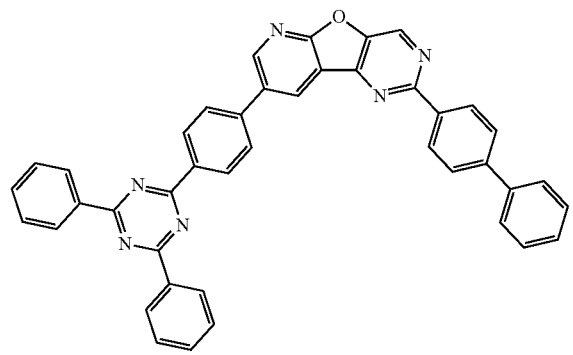

-continued
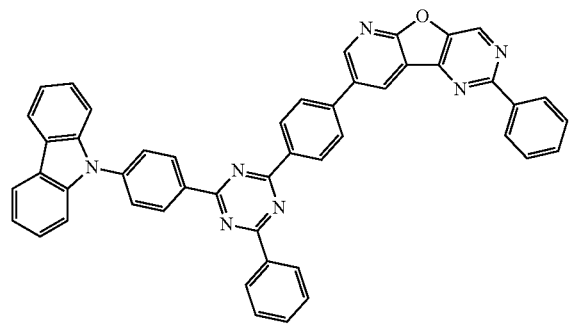
210
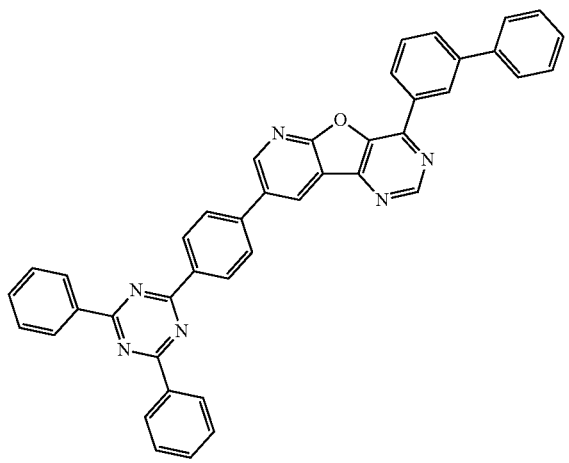
211
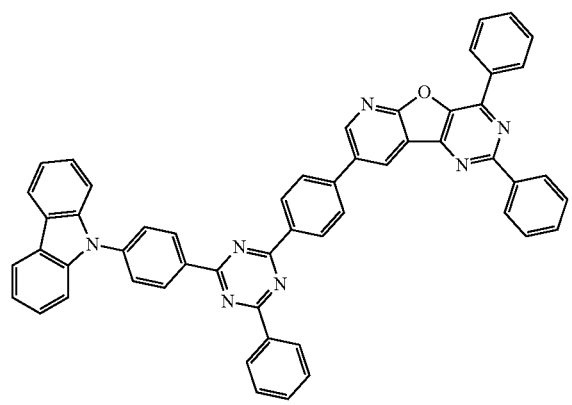
212
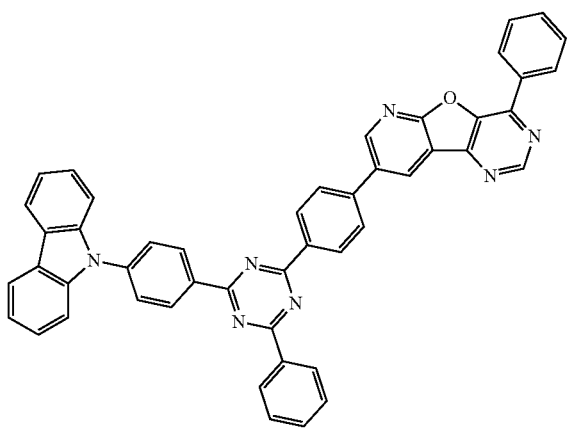
213
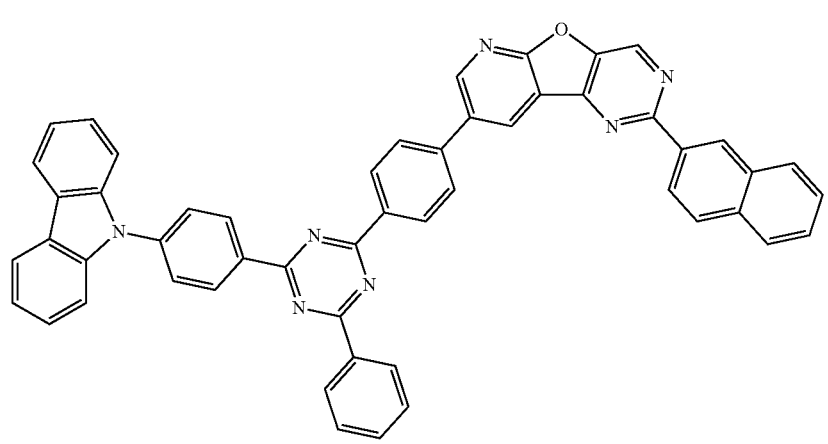
214

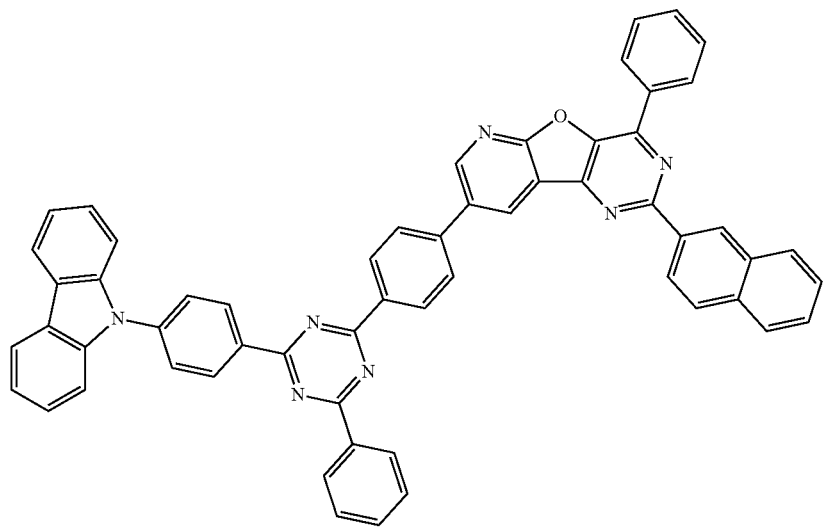
215
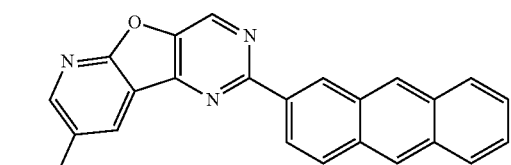
216
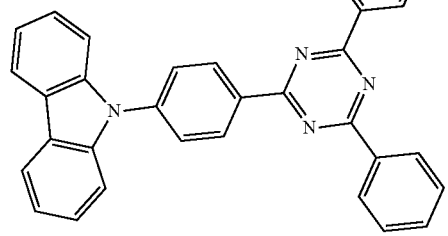
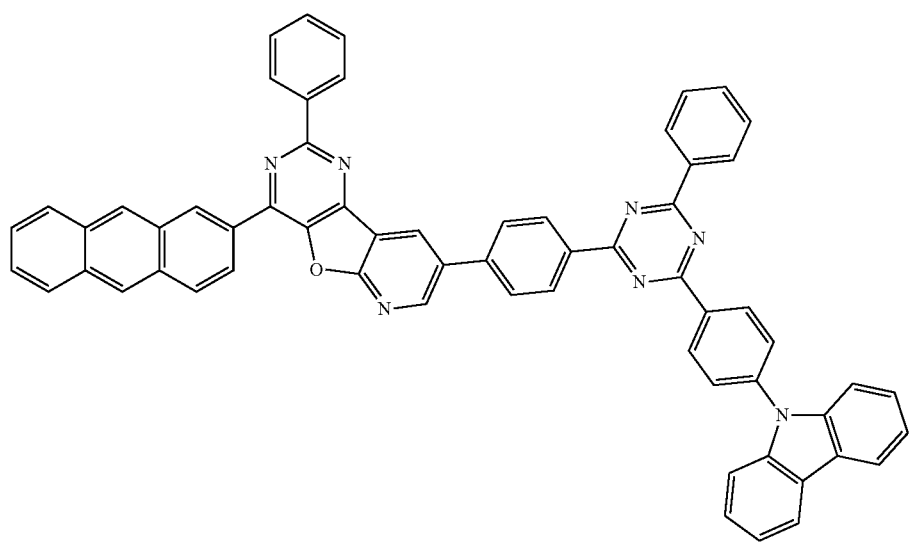
217

218
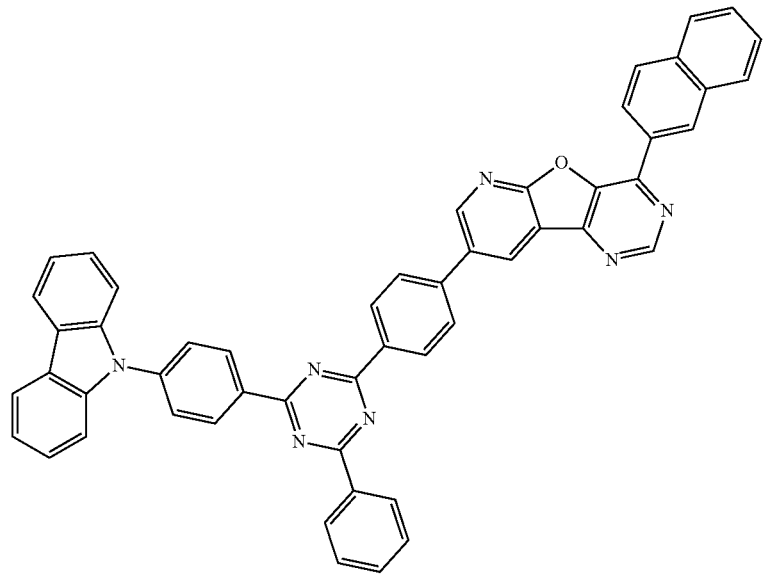
219
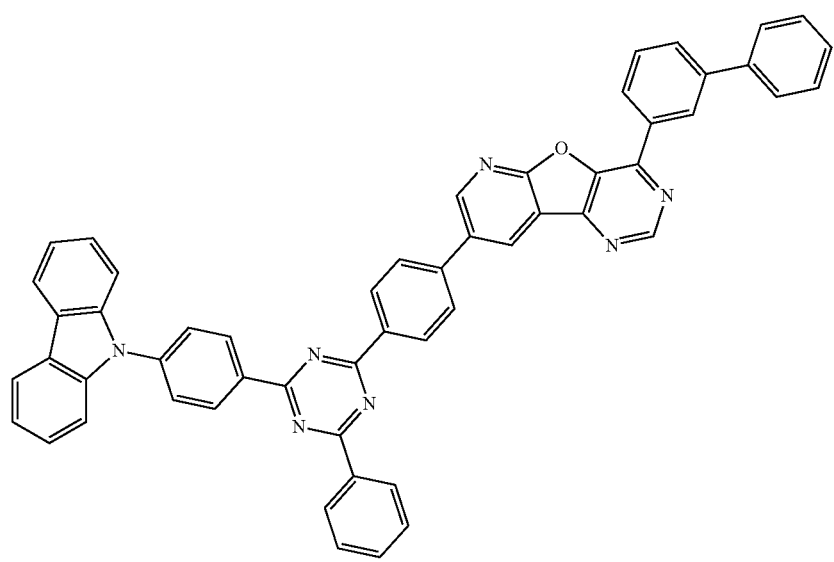
220
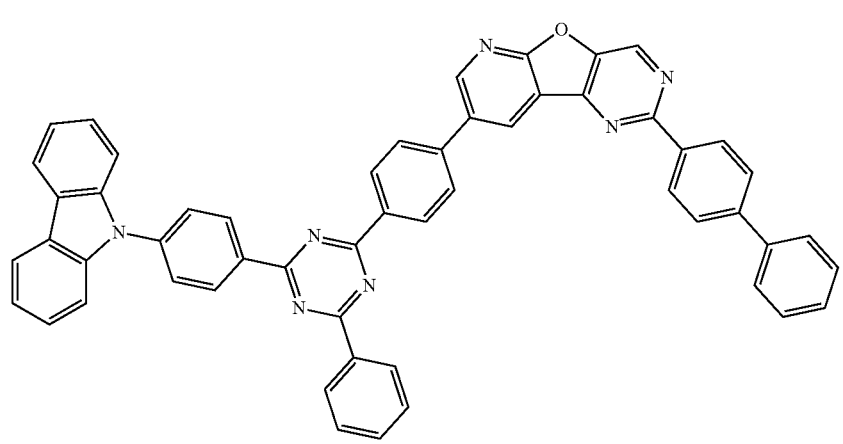

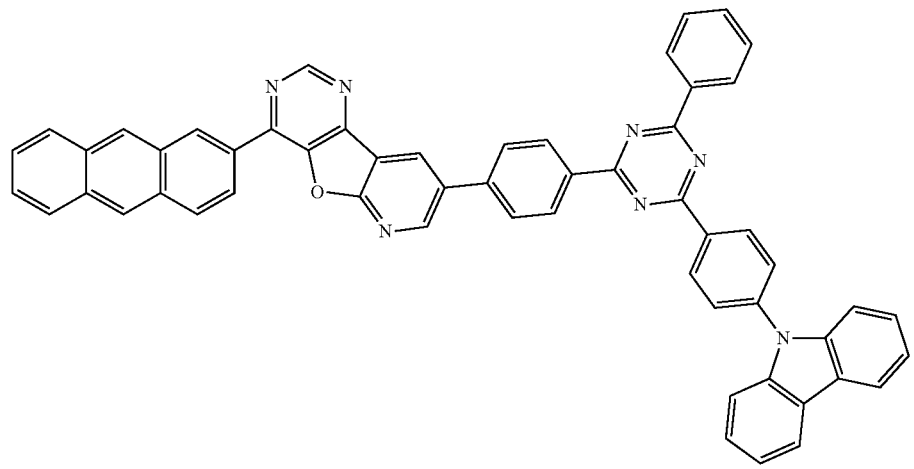
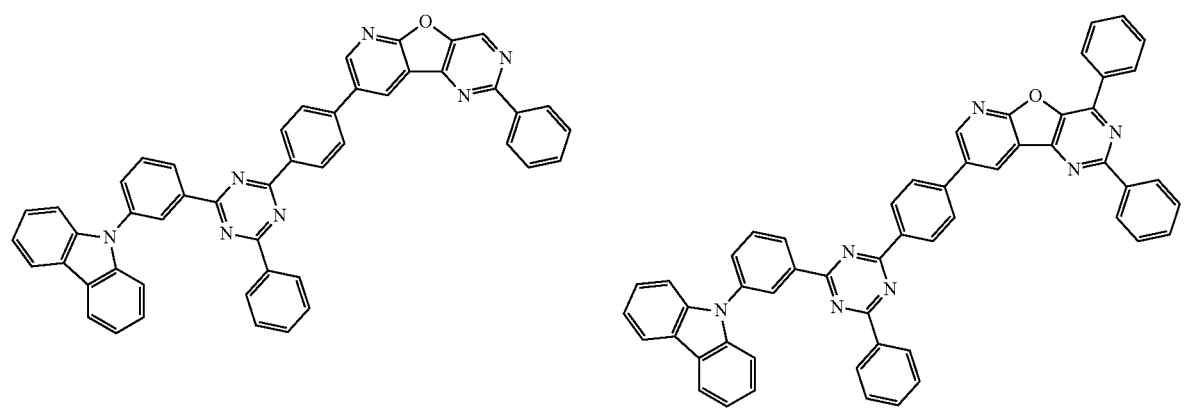
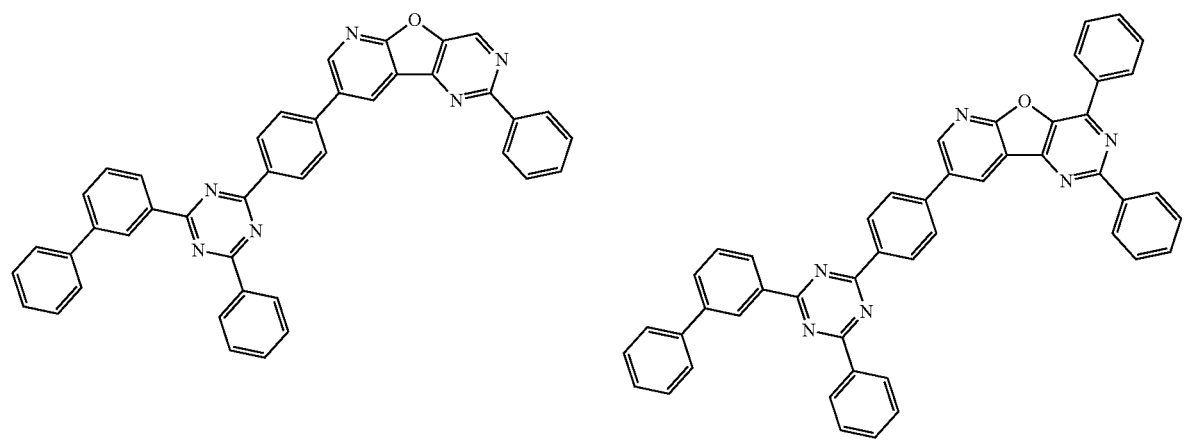

-continued
226
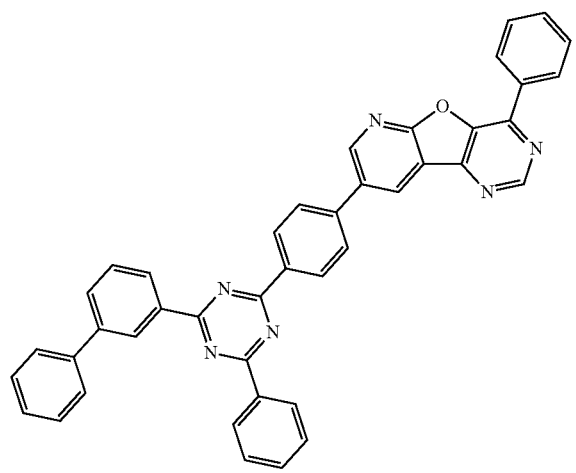
227
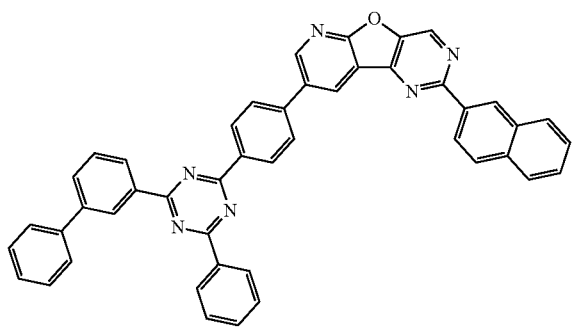
228
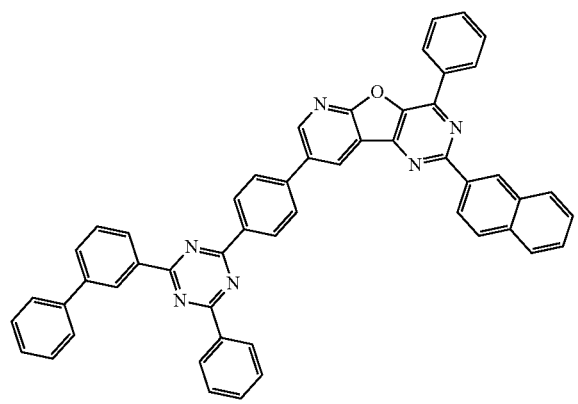
229
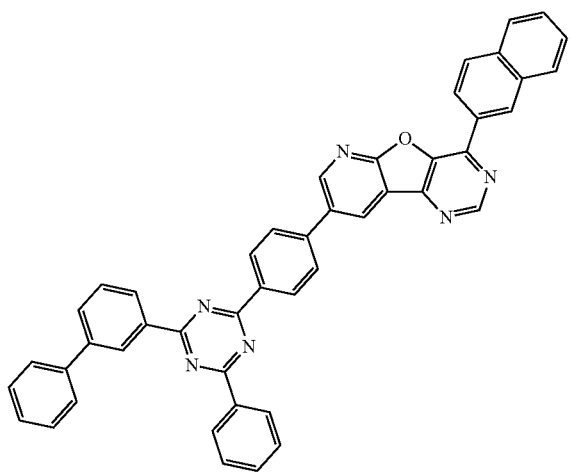
230
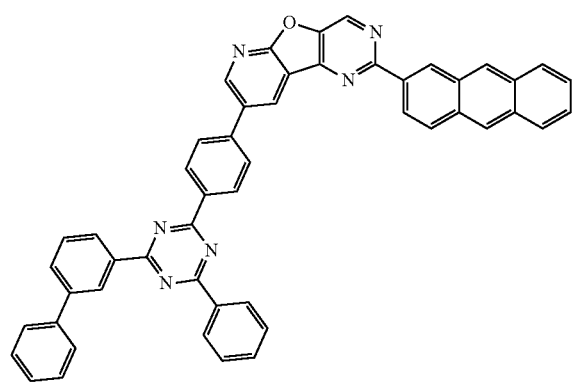
231
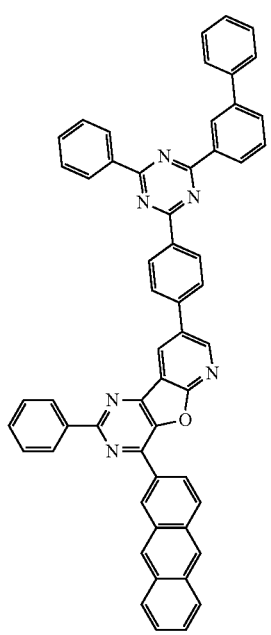

477 478
-continued
232 233
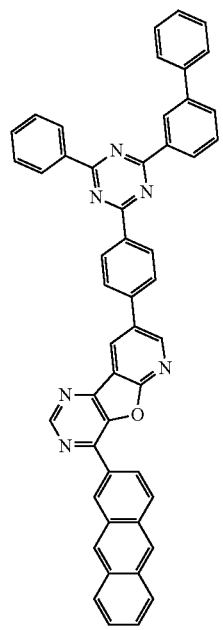
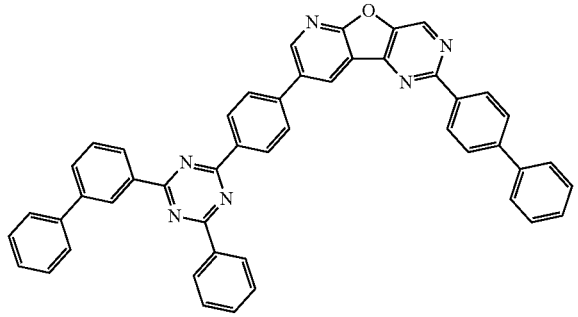
234 235
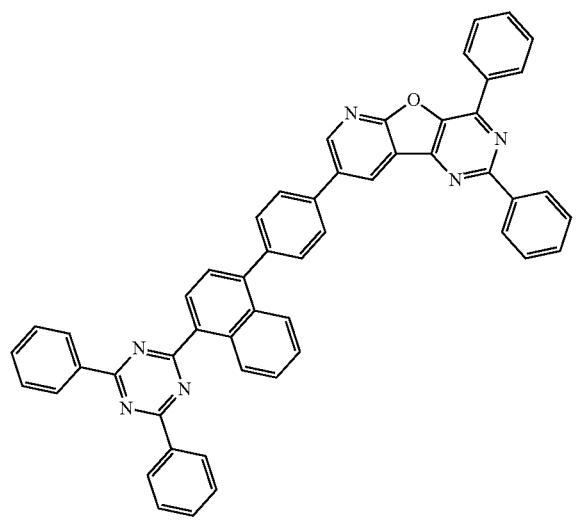
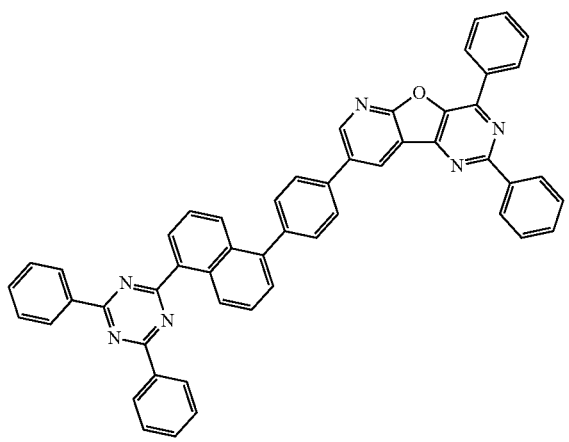

-continued
236
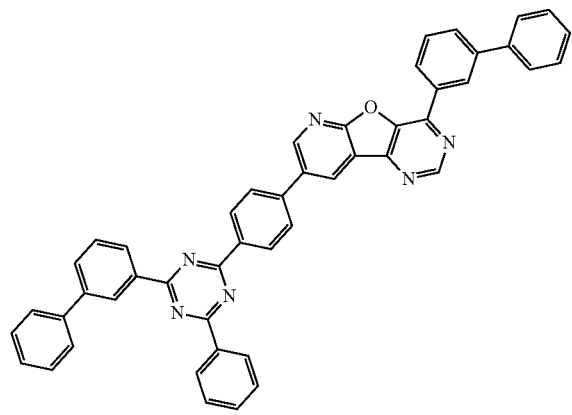
237
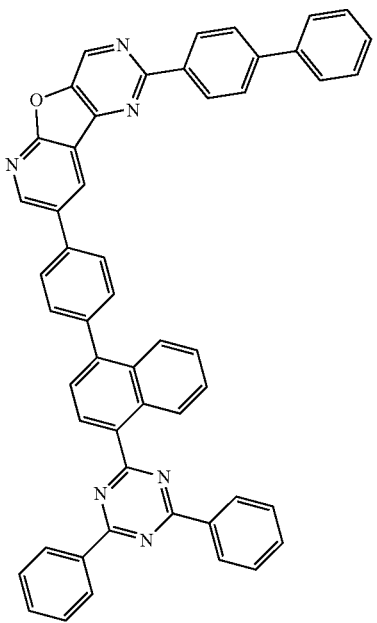
238
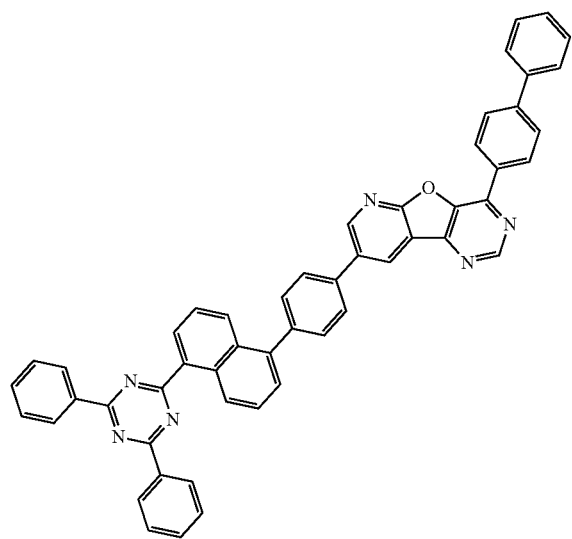
239
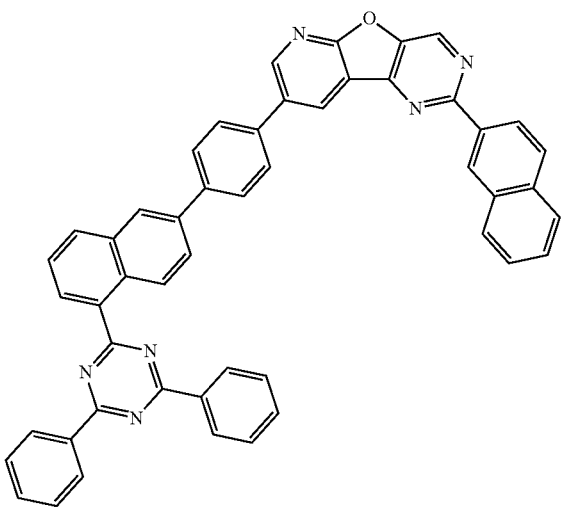

481 482
-continued
240 241
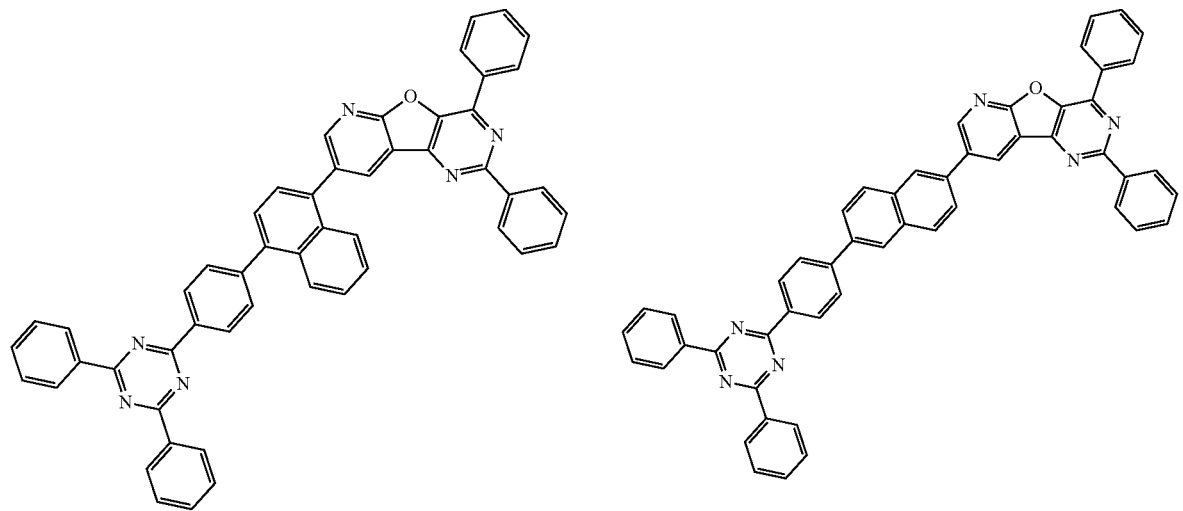
242
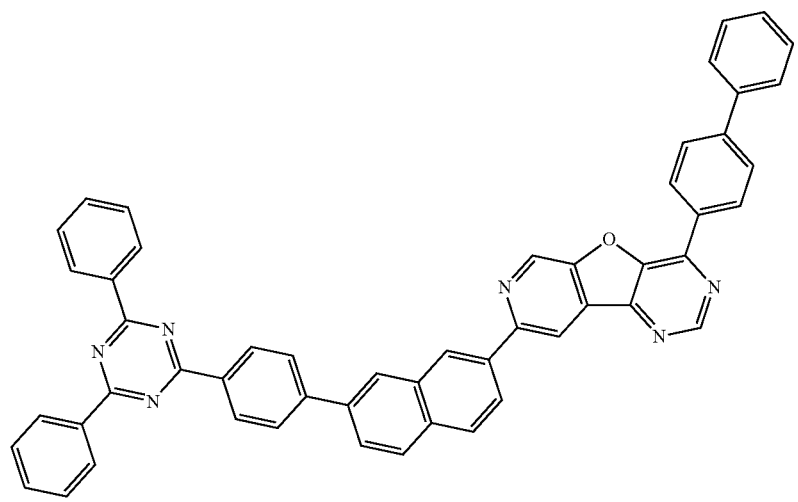

243
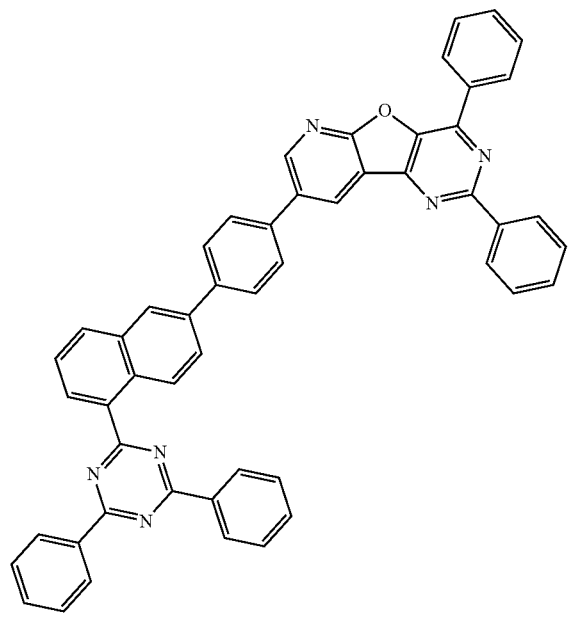
244
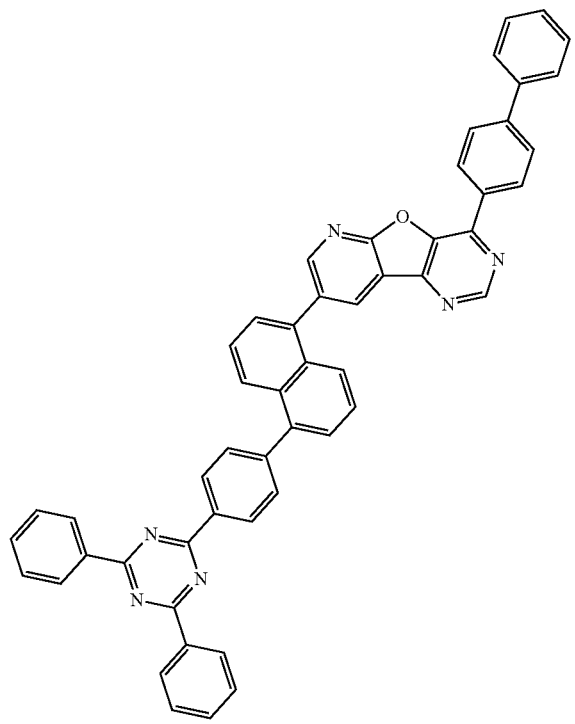
245
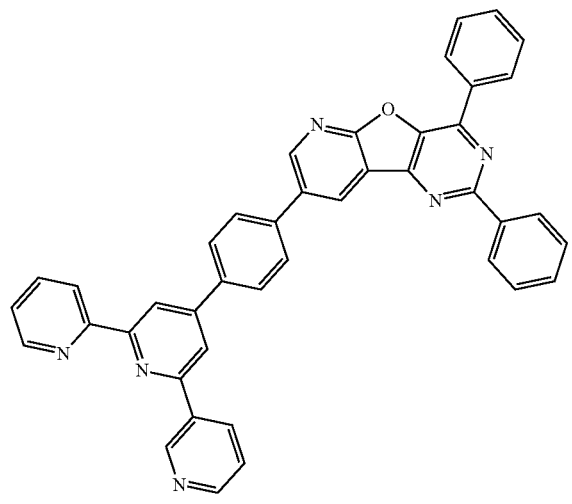
246
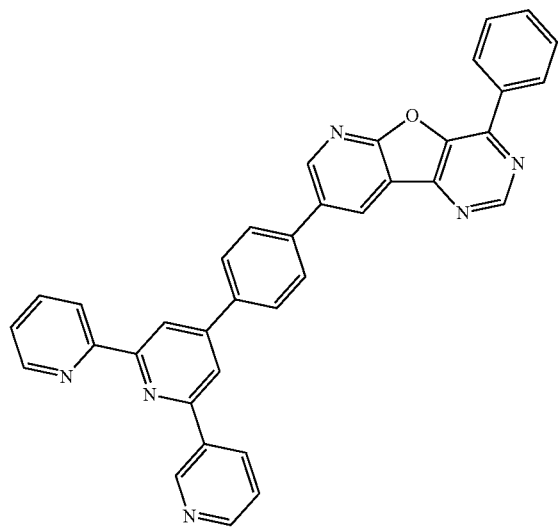

247
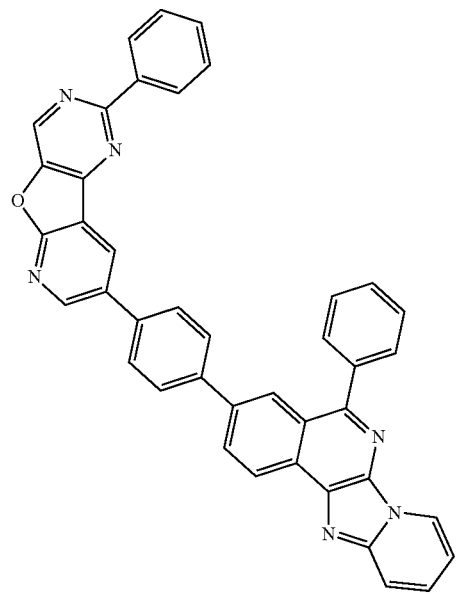
248
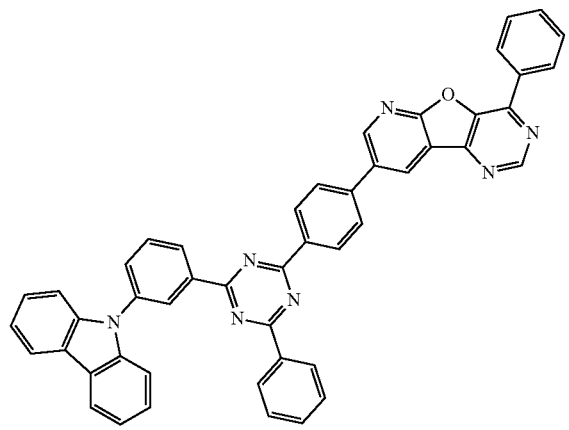
249
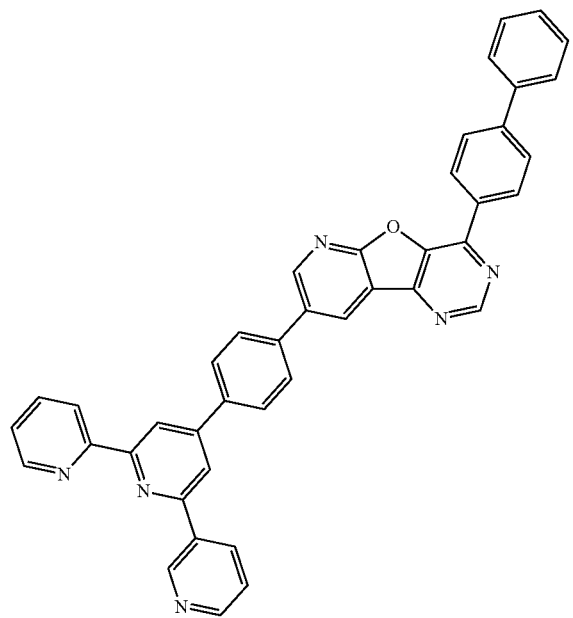
250
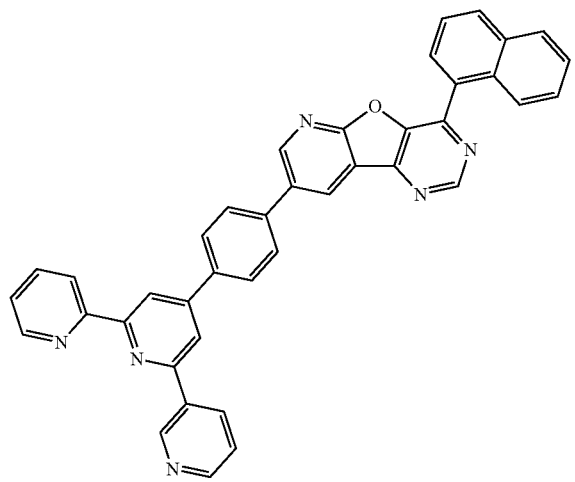

251
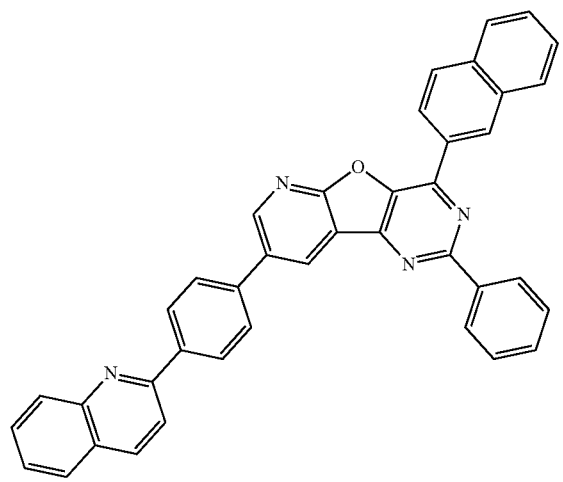
252
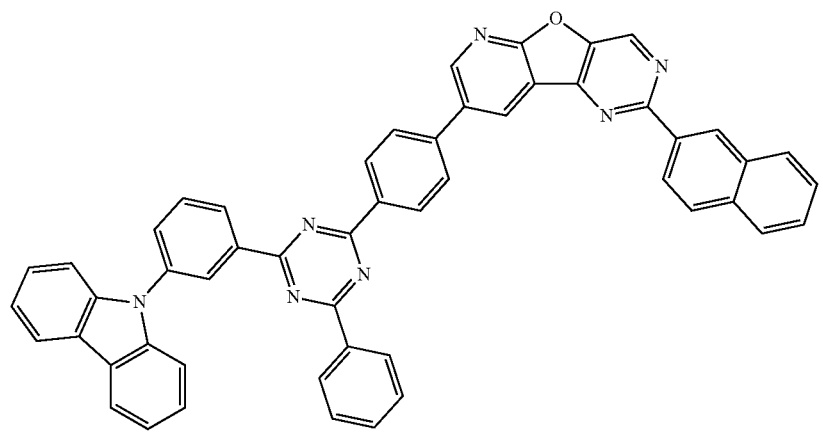
253
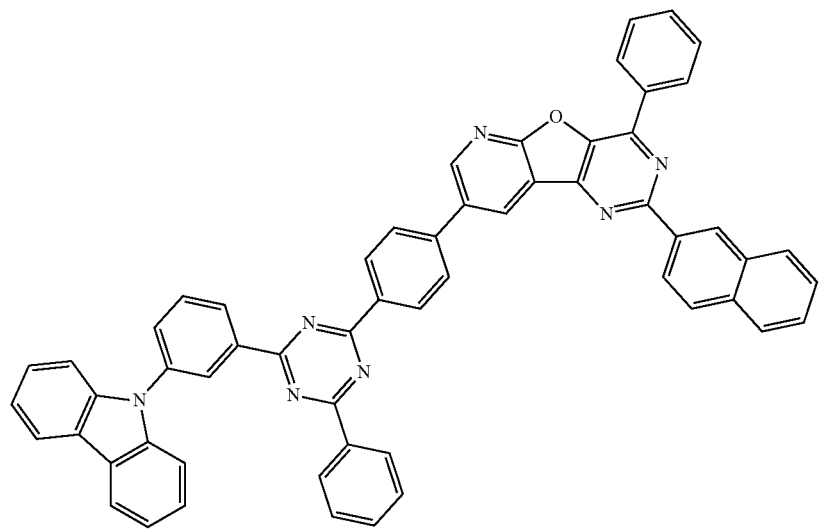

-continued
254
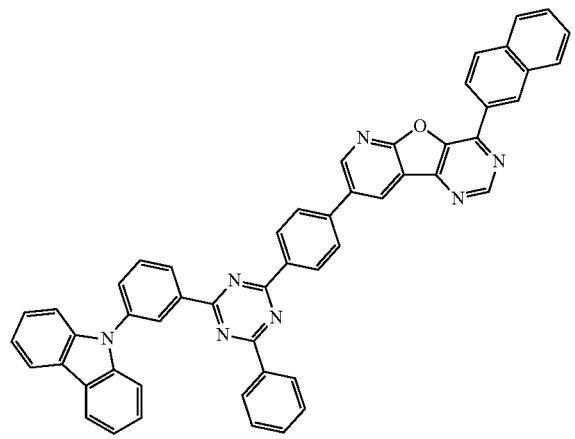
255
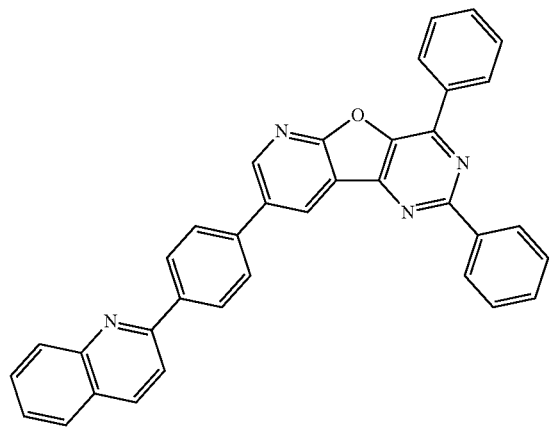
256
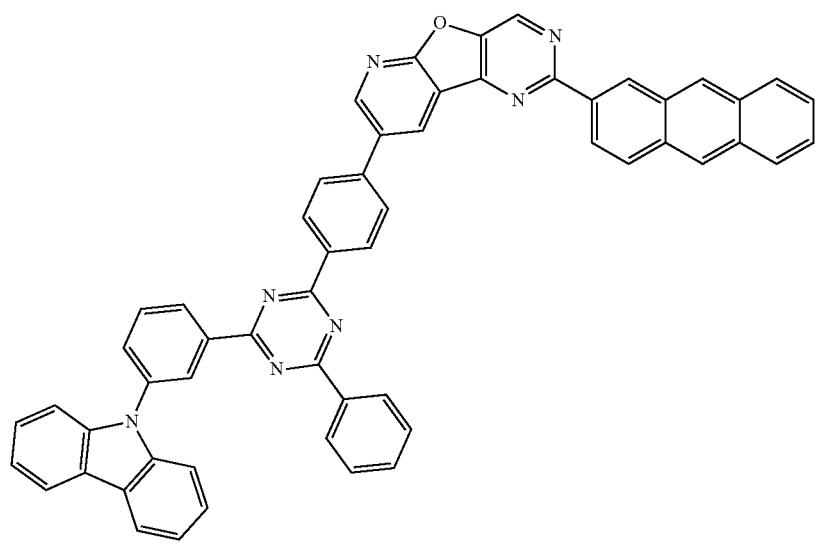
257
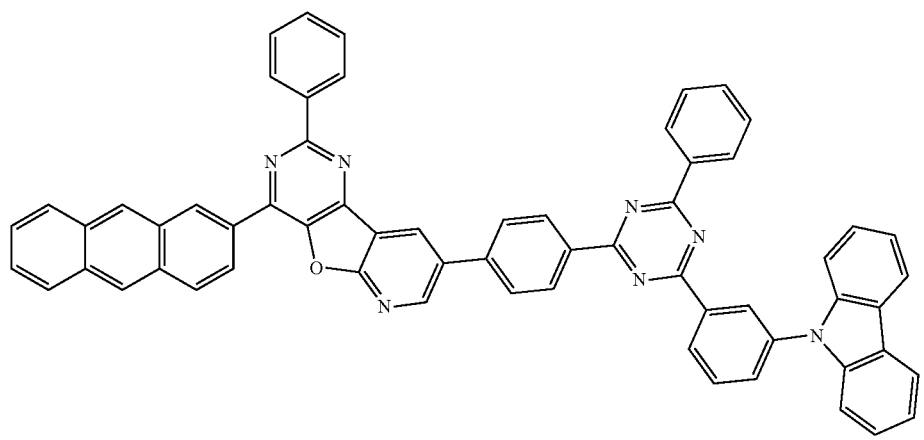

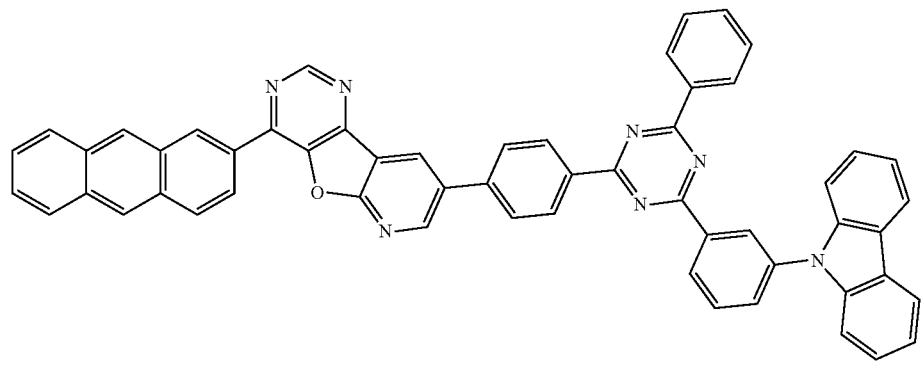
258
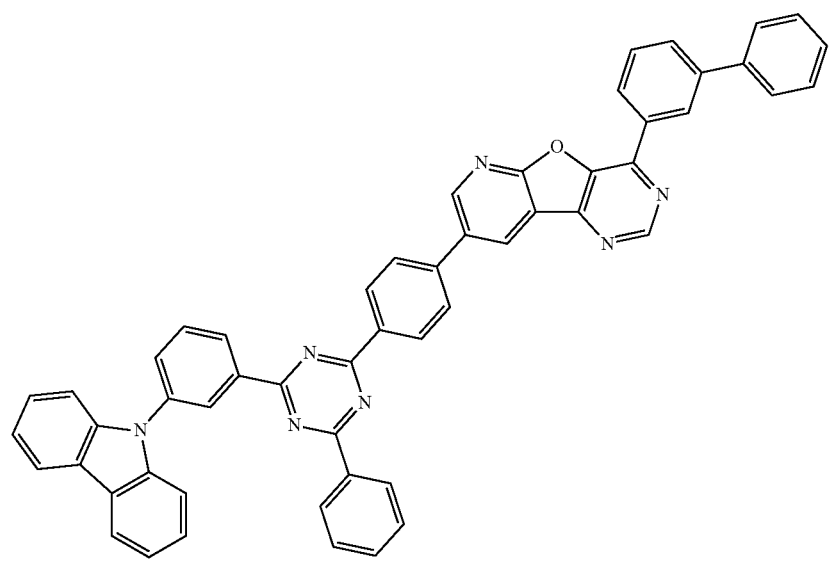
259
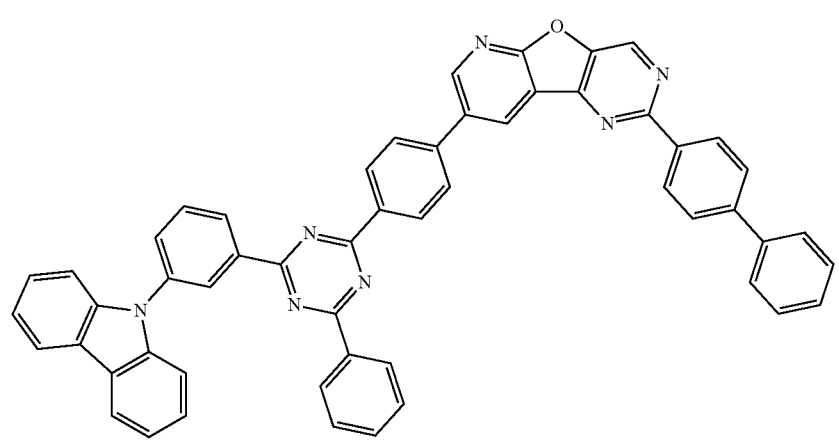
260

-continued
261
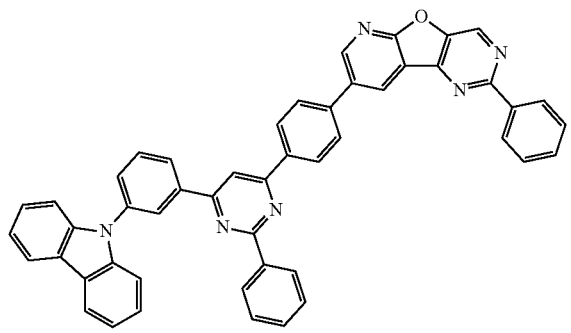
262
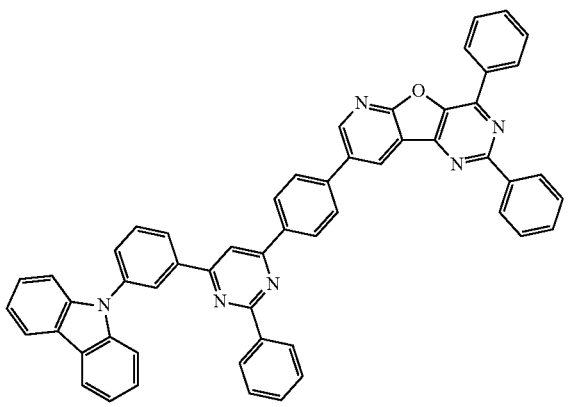
263
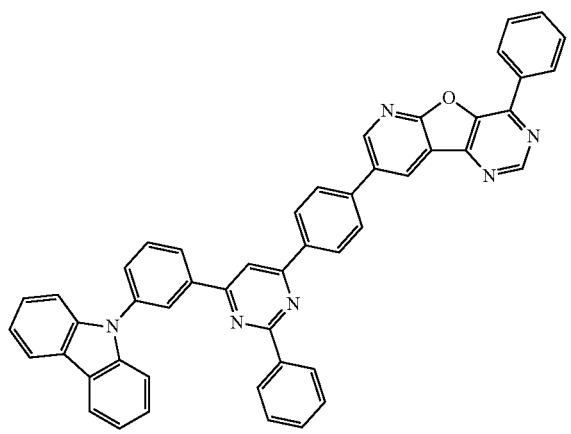
264
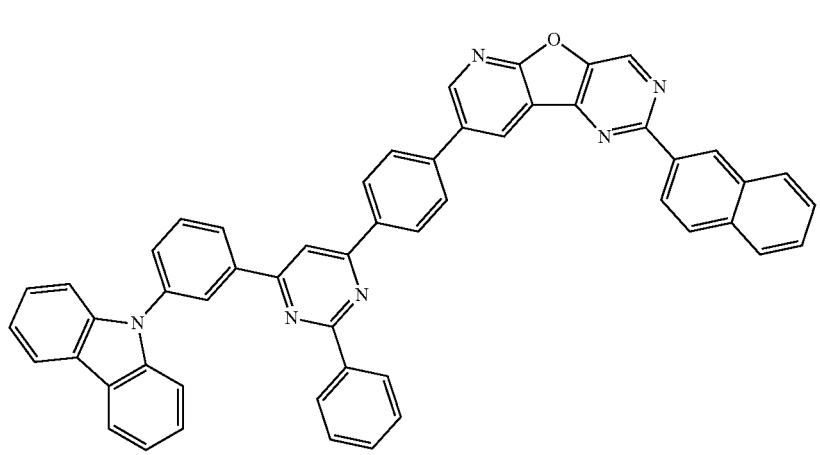

265
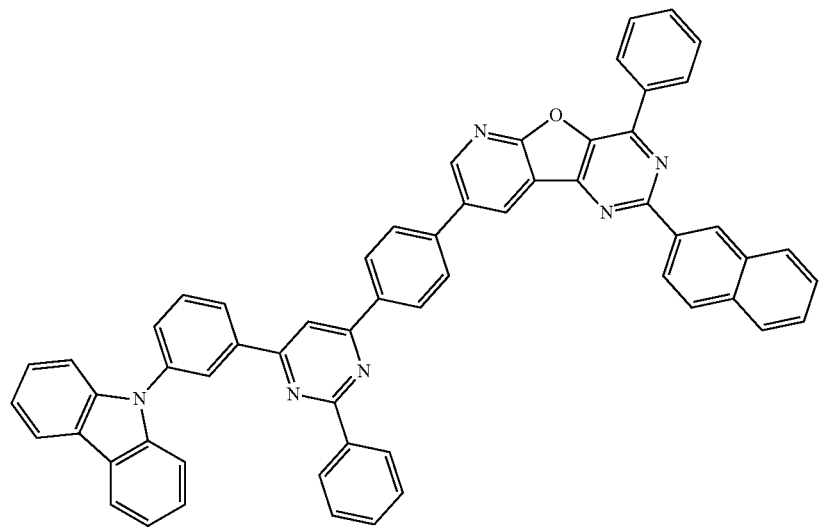
266
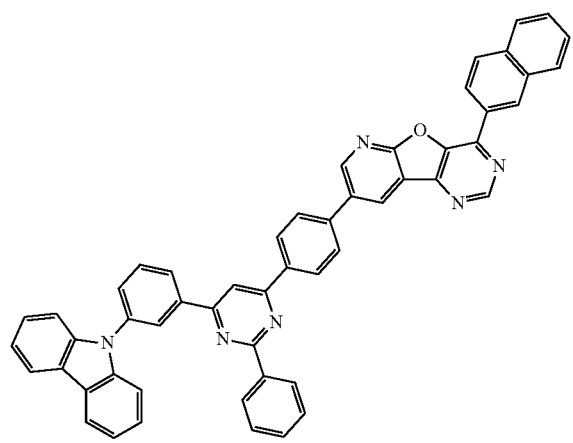
267
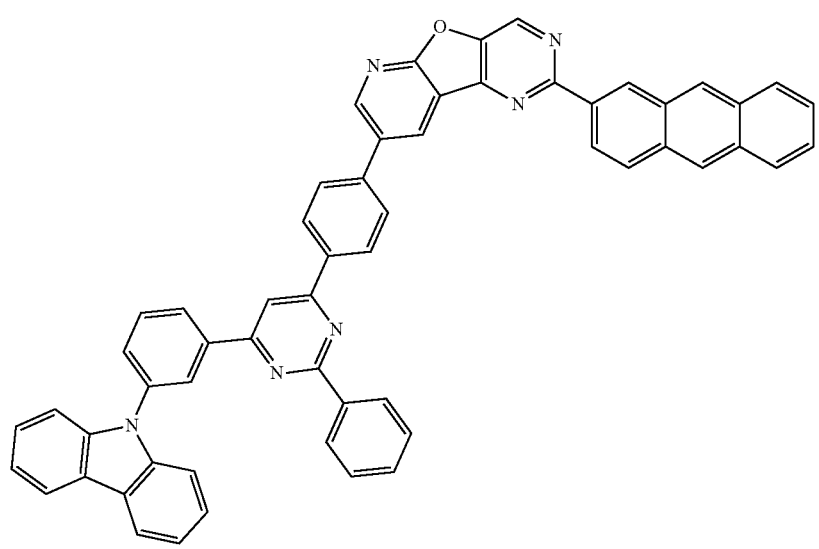

-continued
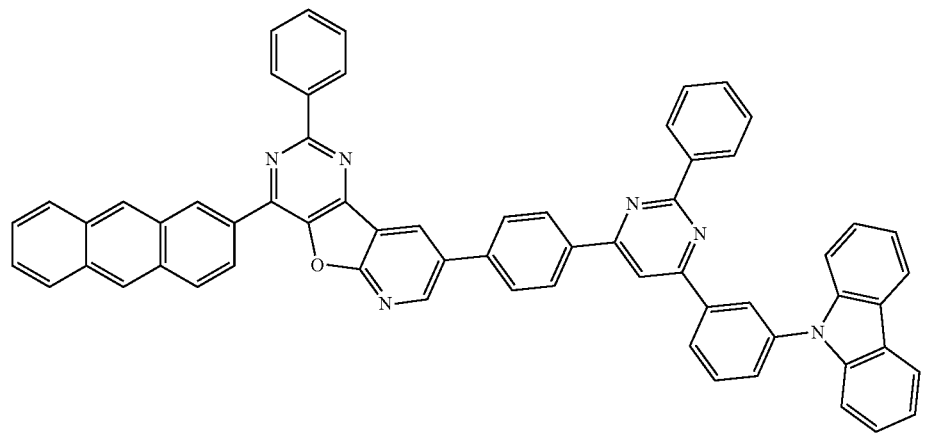
268
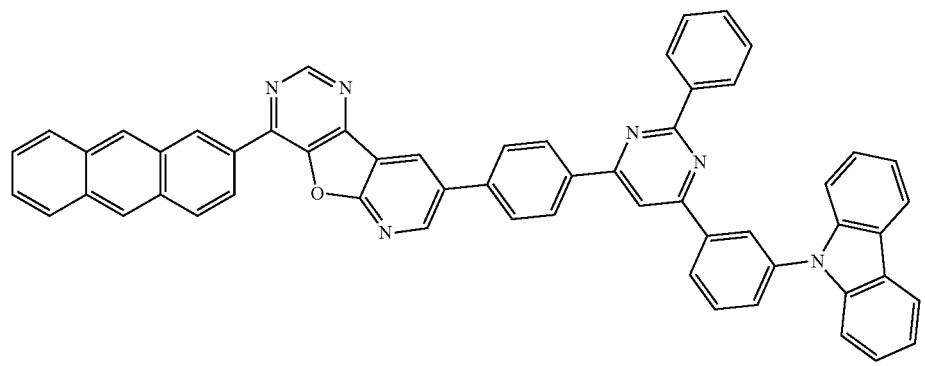
269
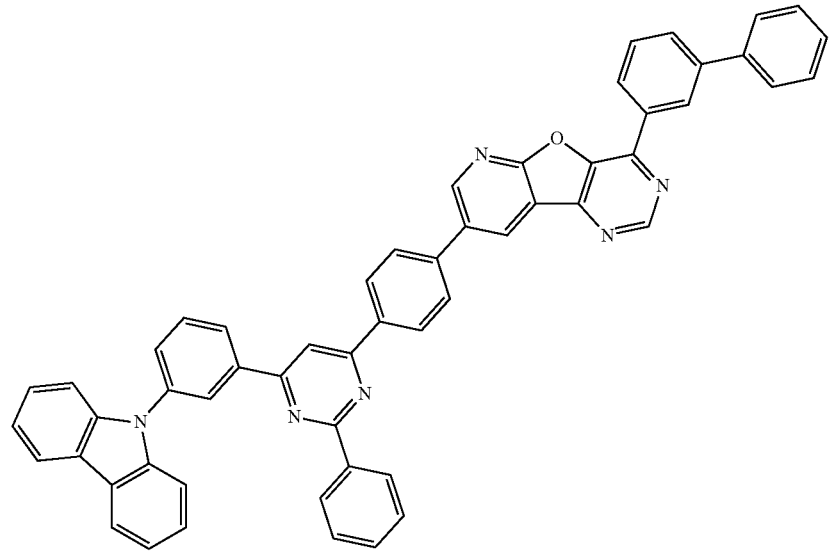
270

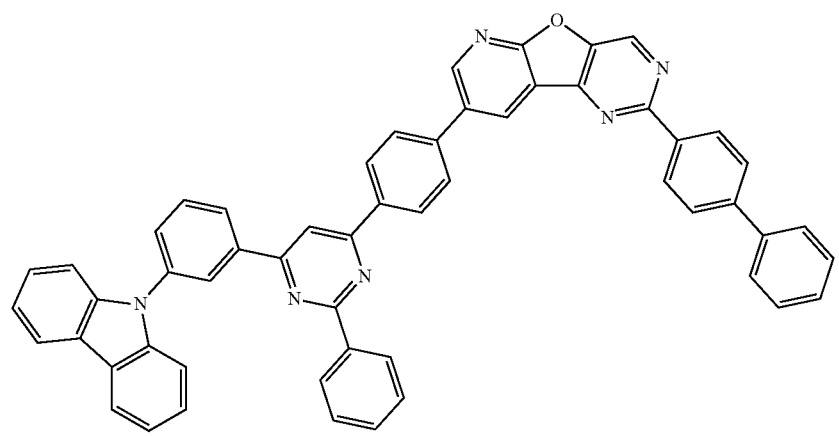
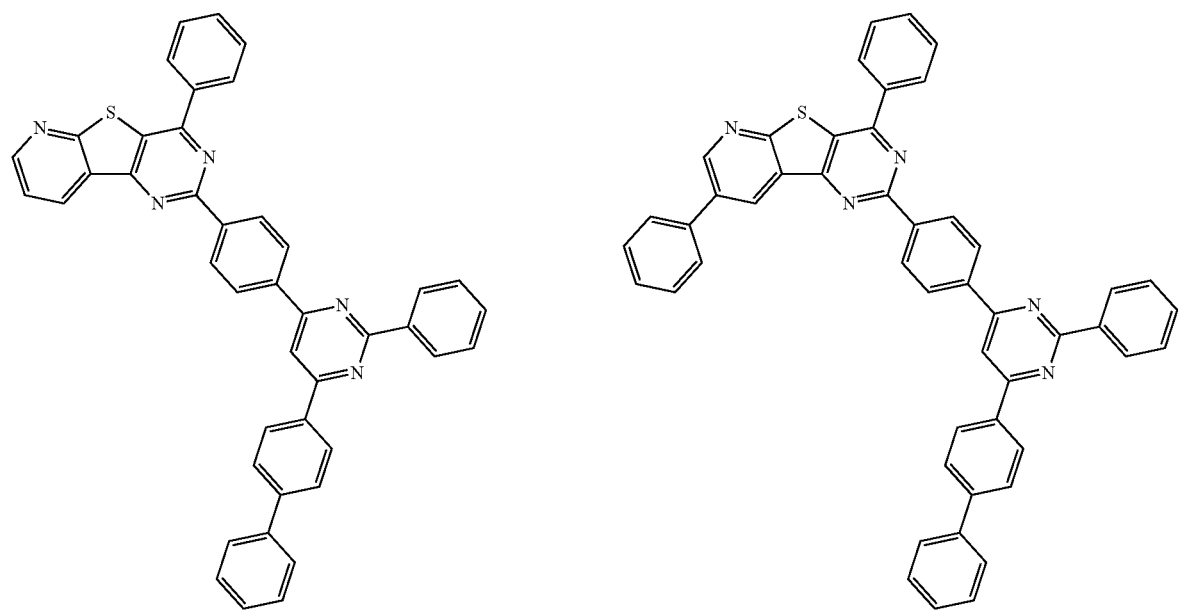

274
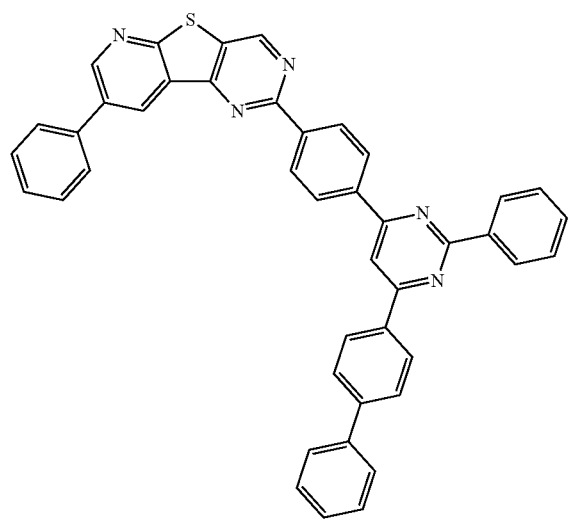
275
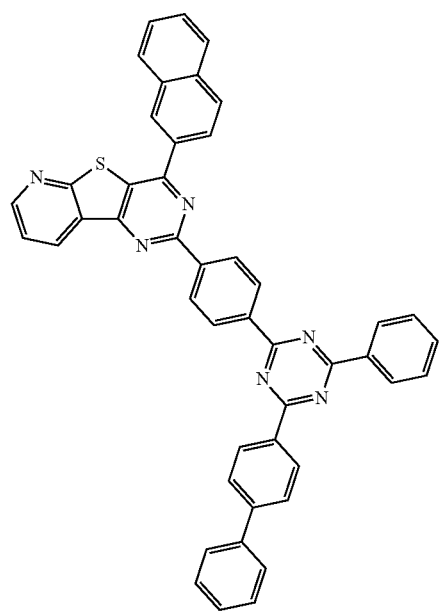
276
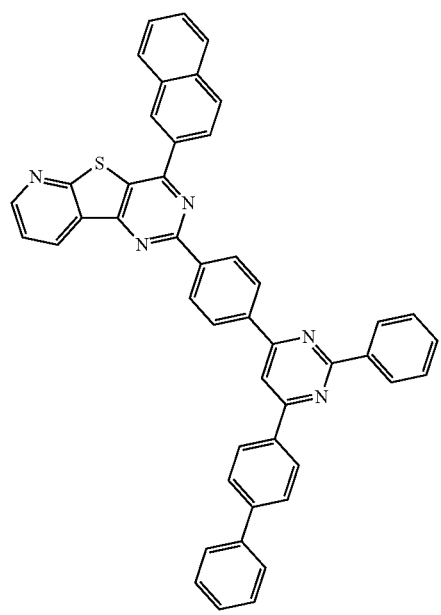
277
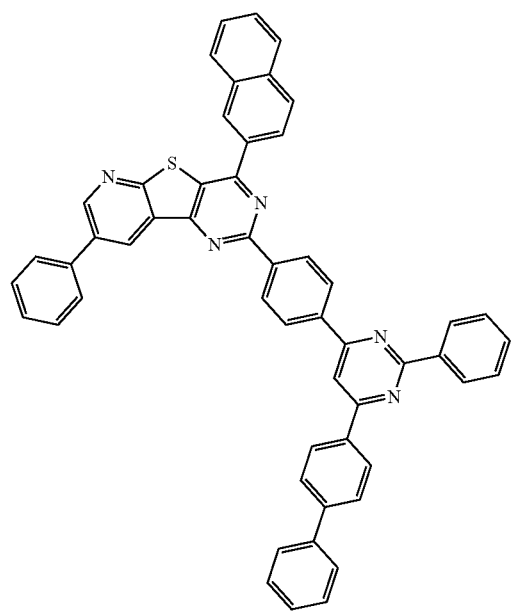

-continued
503
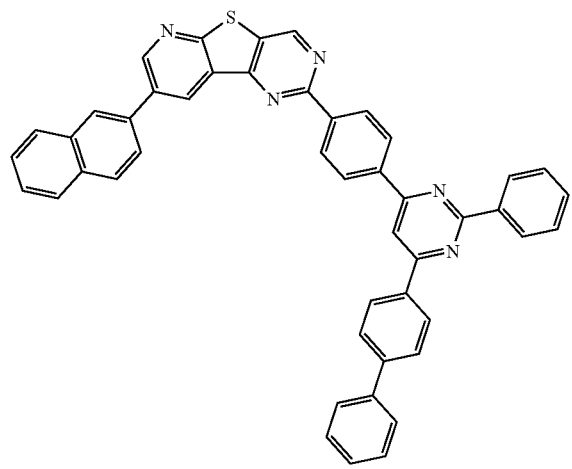
504
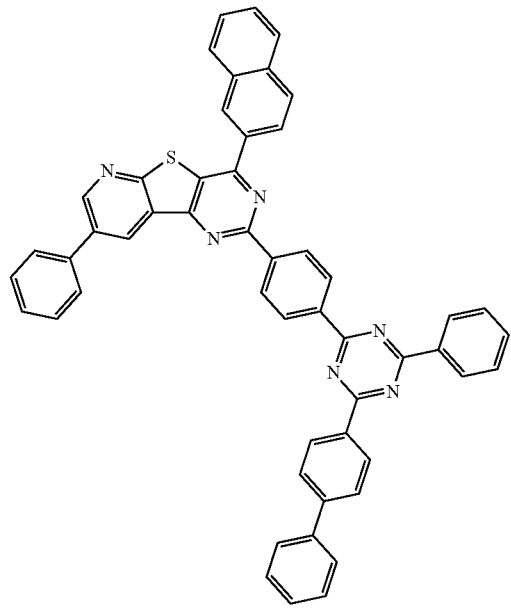
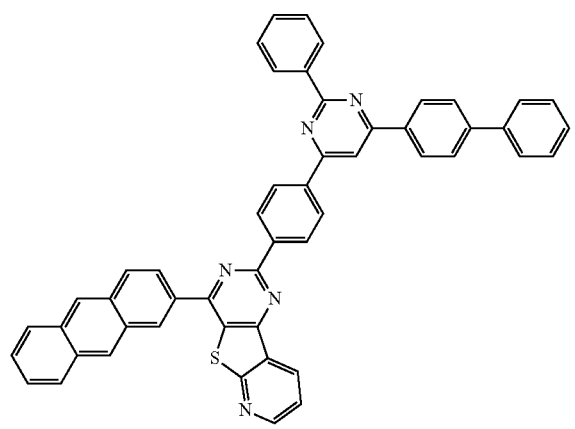
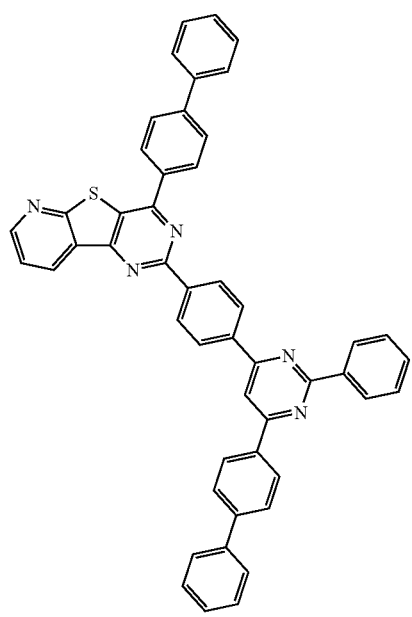

-continued
282
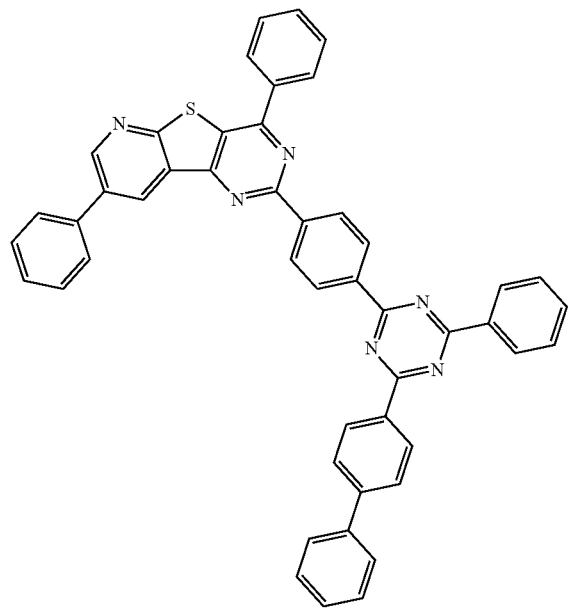
283
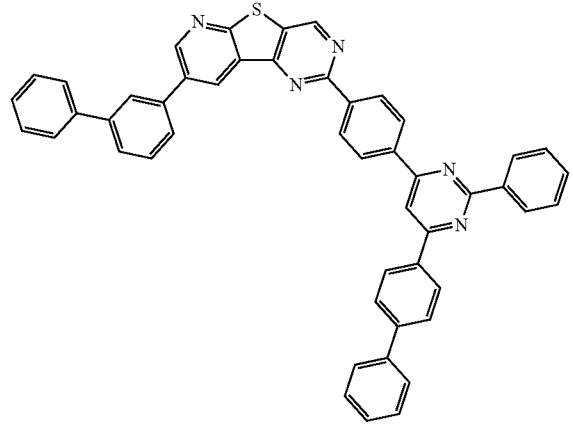
284
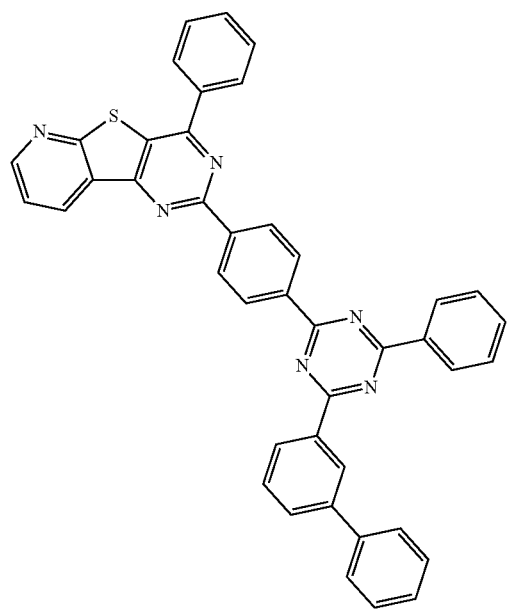
285
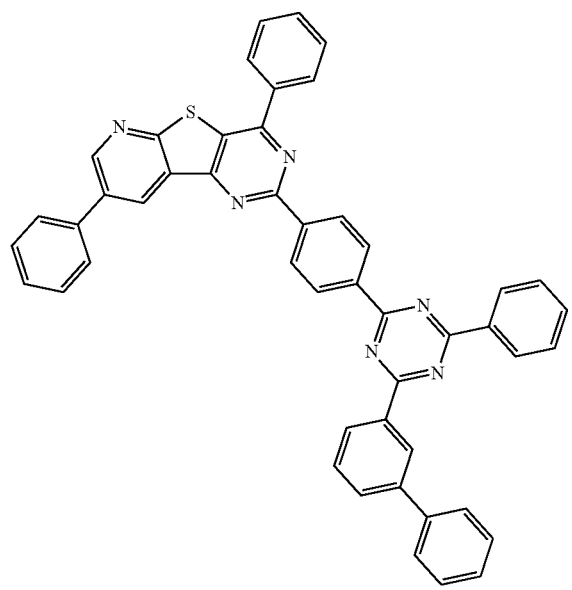

-continued
286
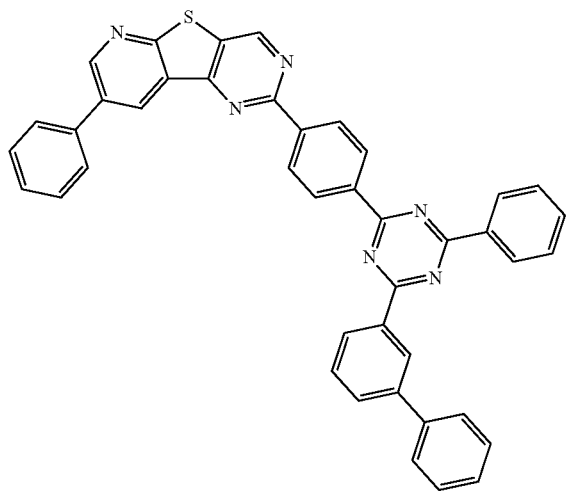
287
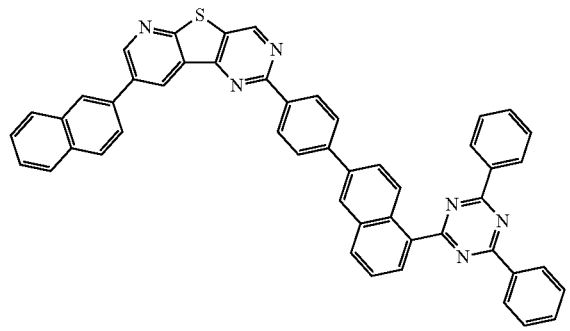
288
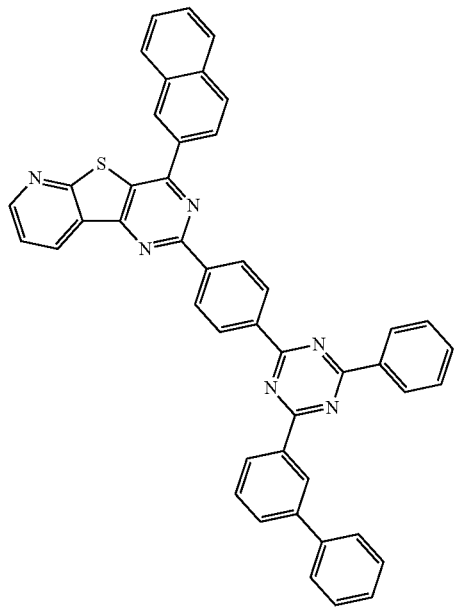
289
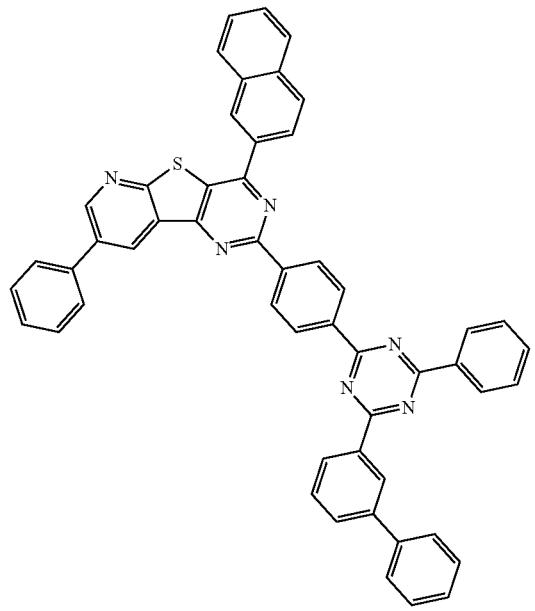
290
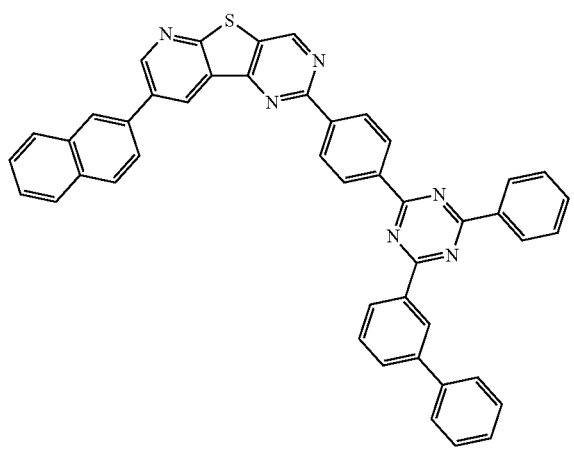
291
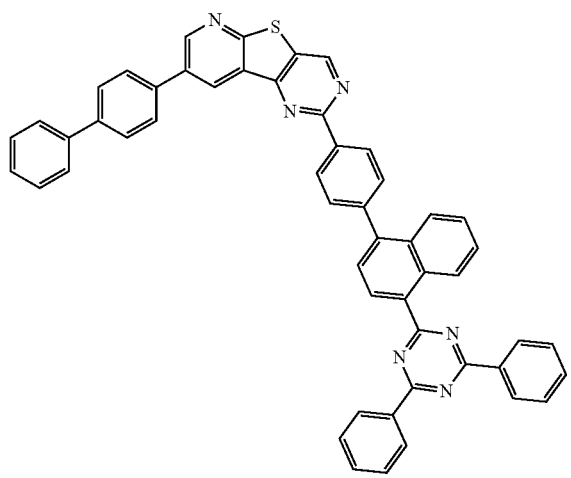

-continued
292
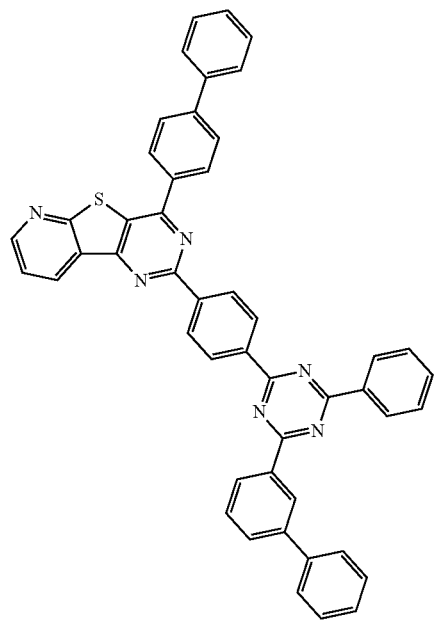
293
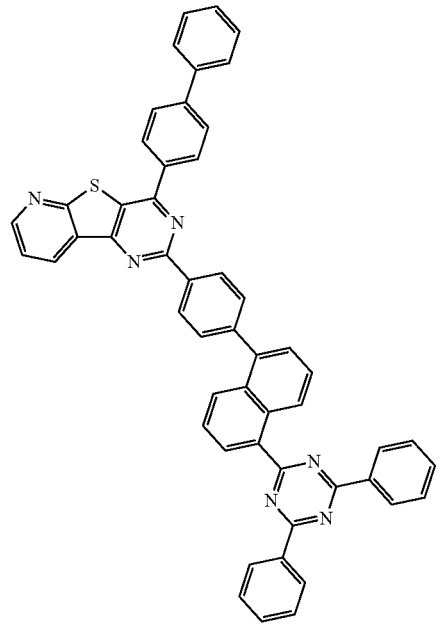
294
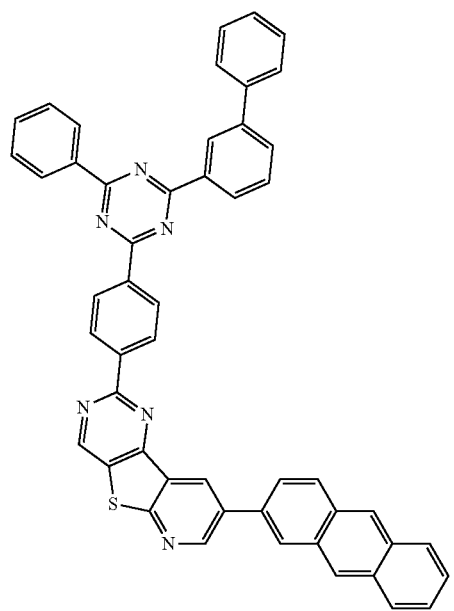
295
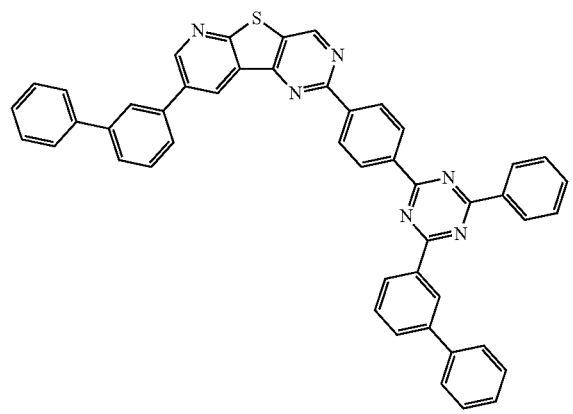

296
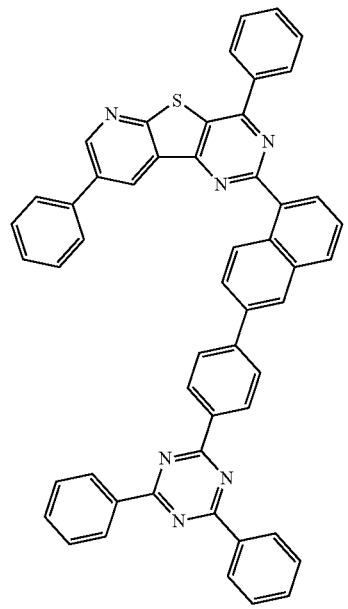
297
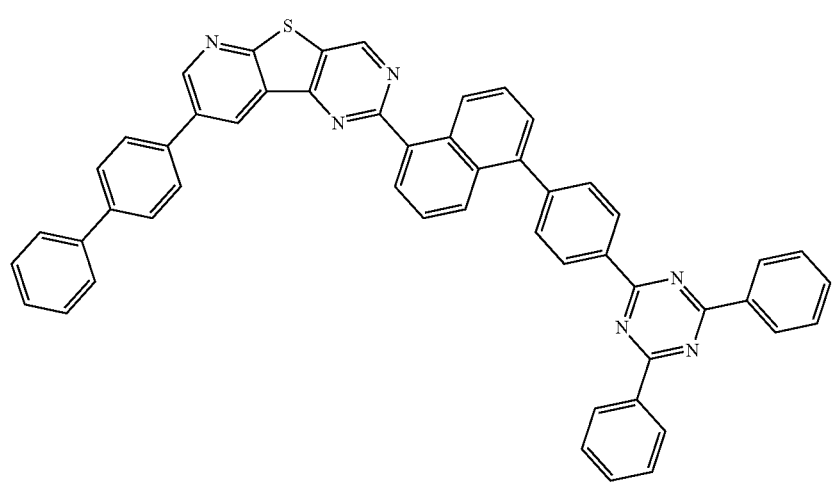
298
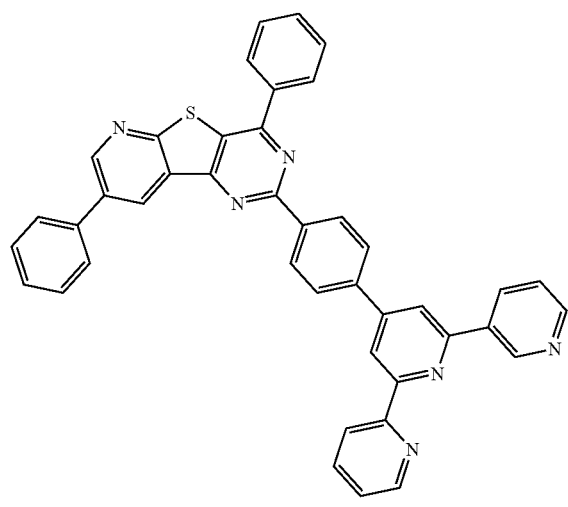
299
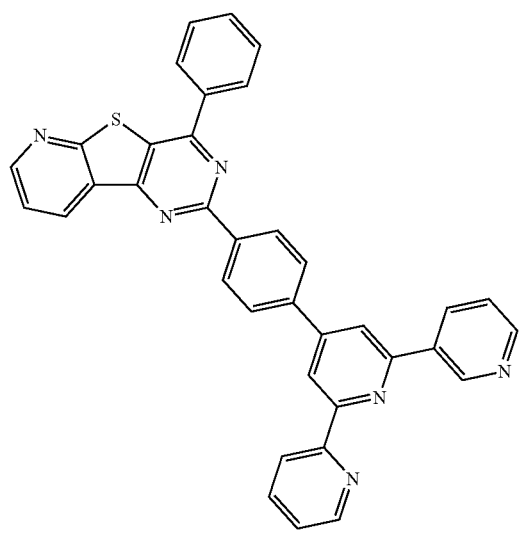

-continued
300
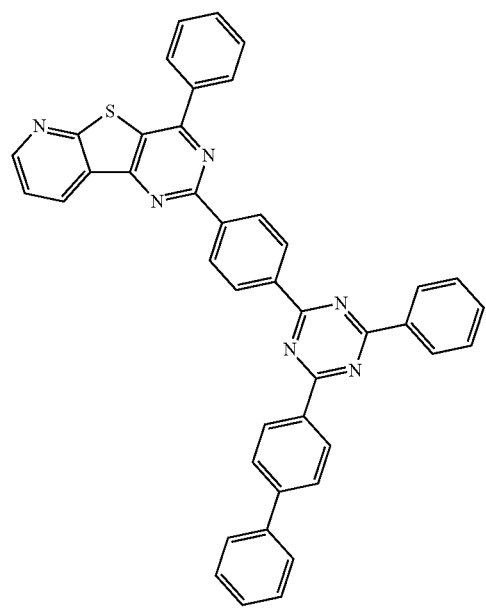
301
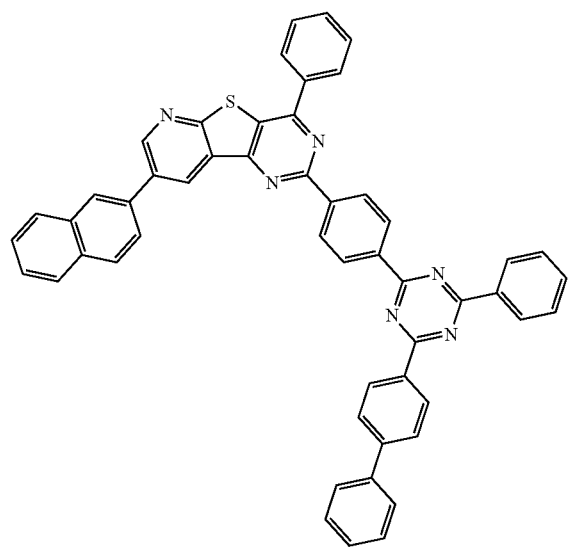
302
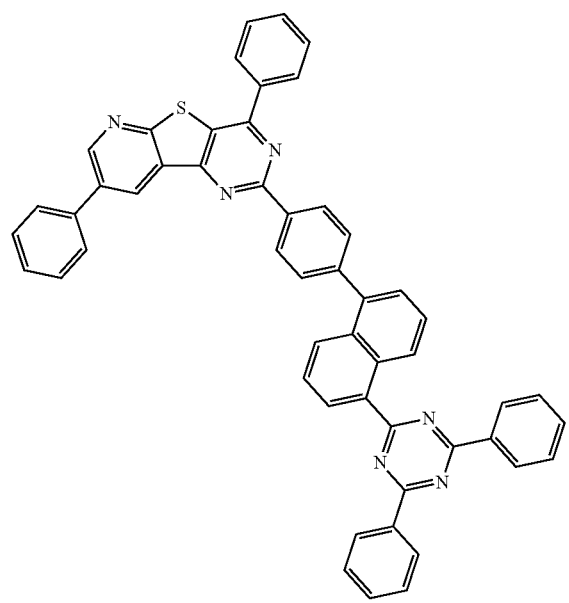
303
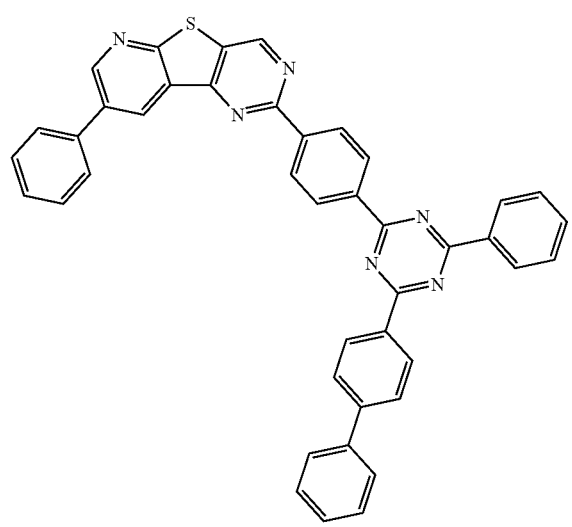

-continued
304
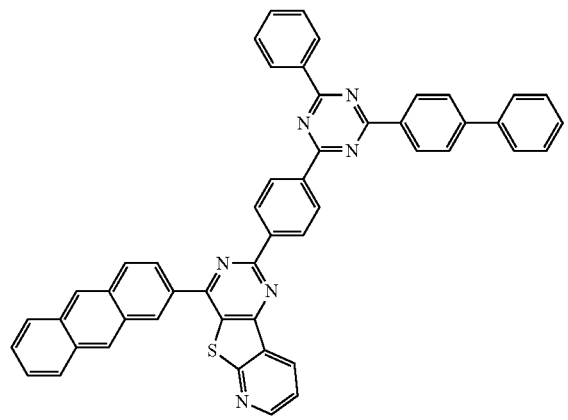
305
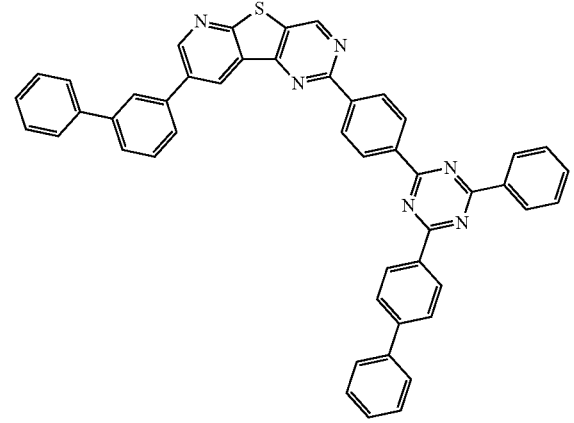
306
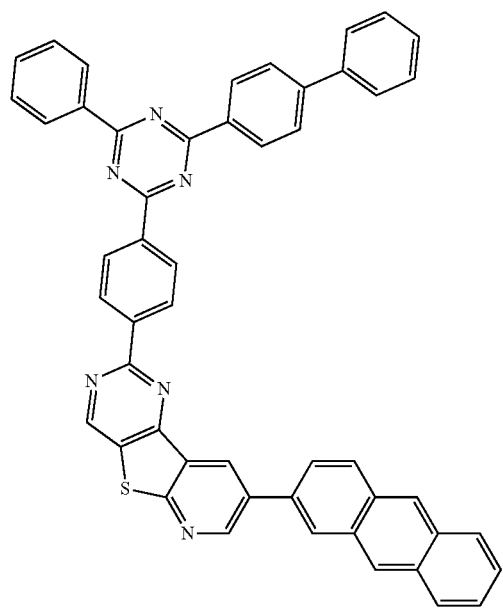
307
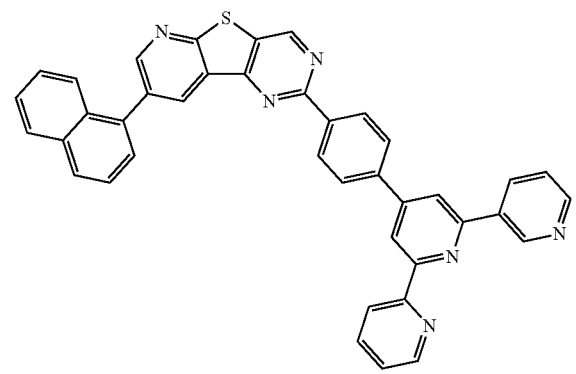

-continued
308
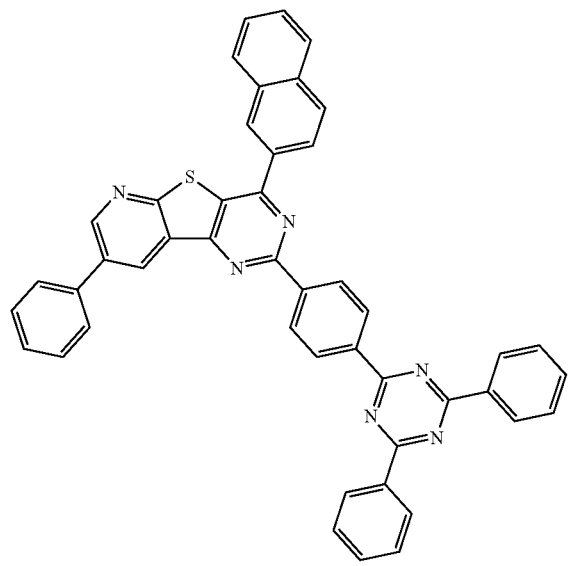
309
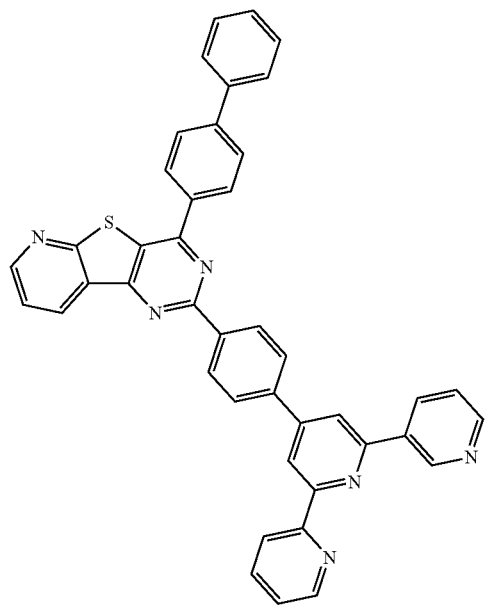
310
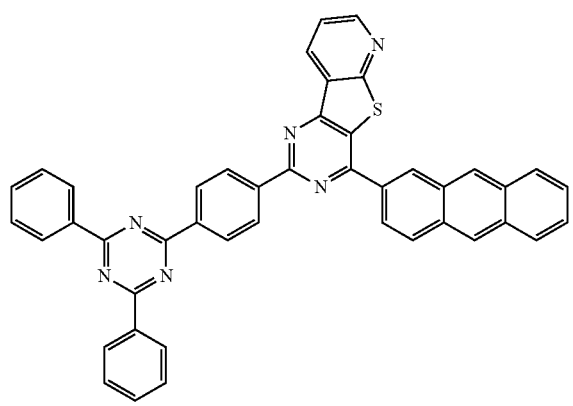
311
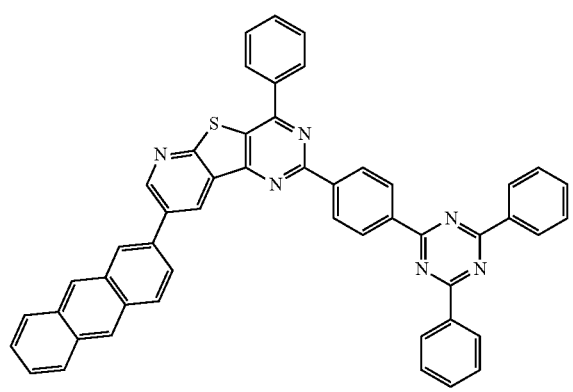
312
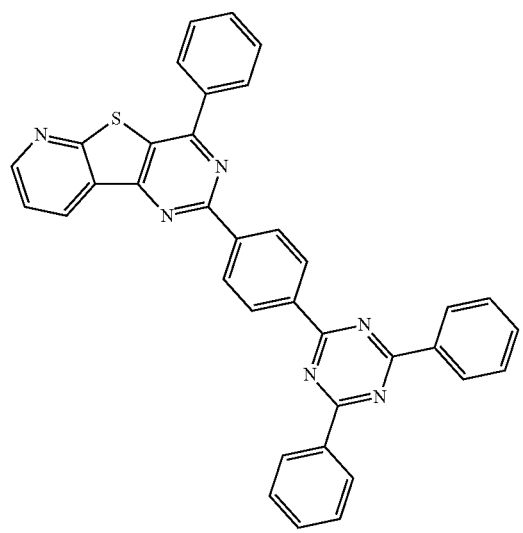
313
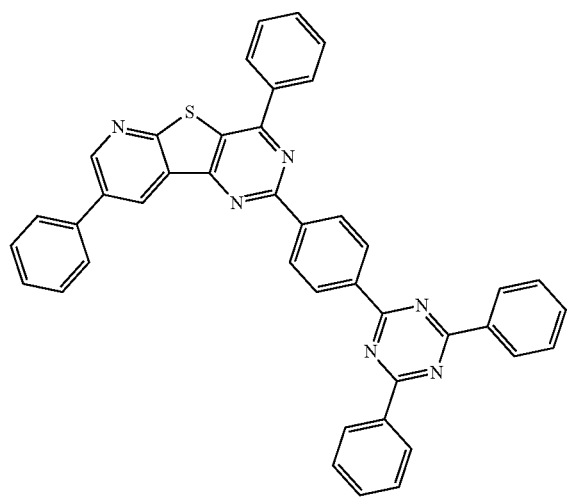

-continued
314
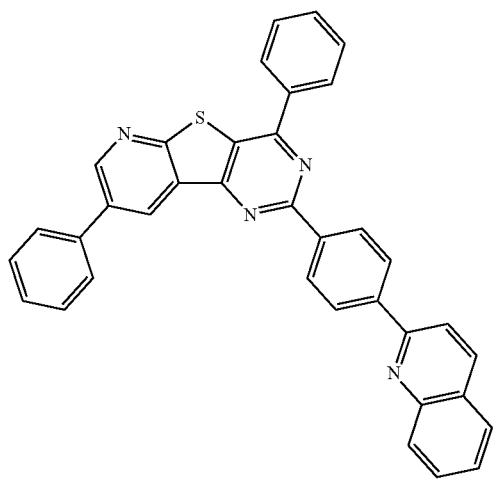
315
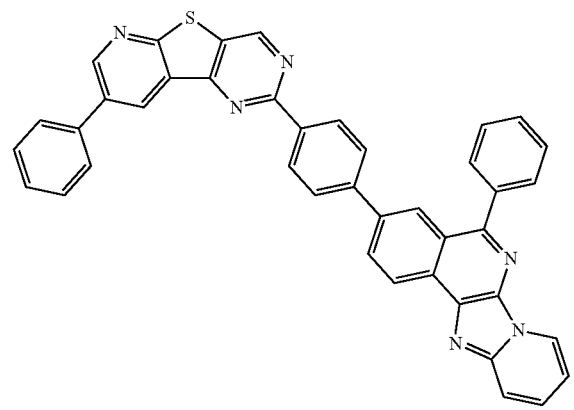
316
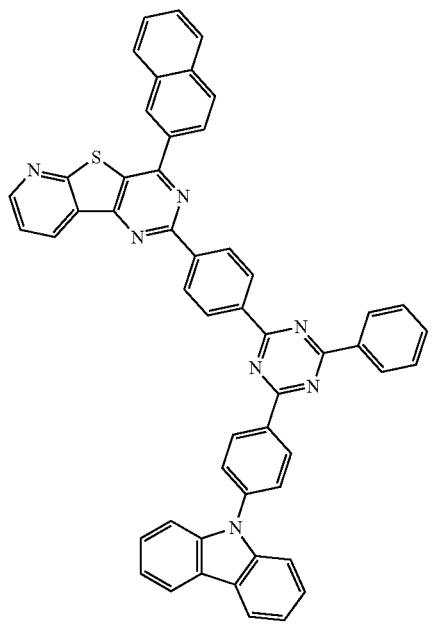
317
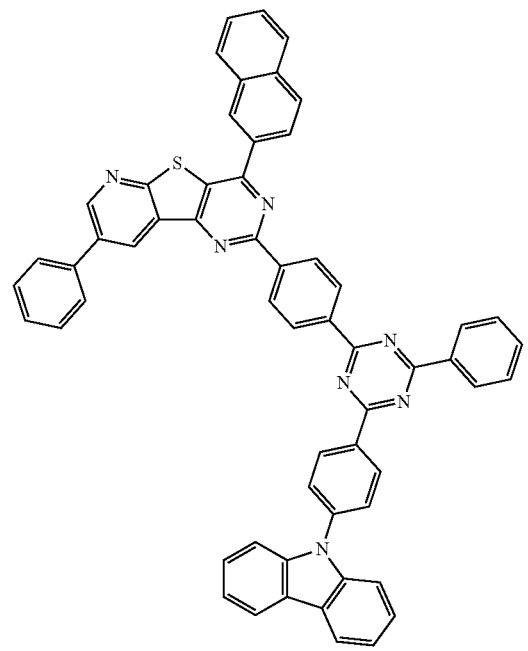
318
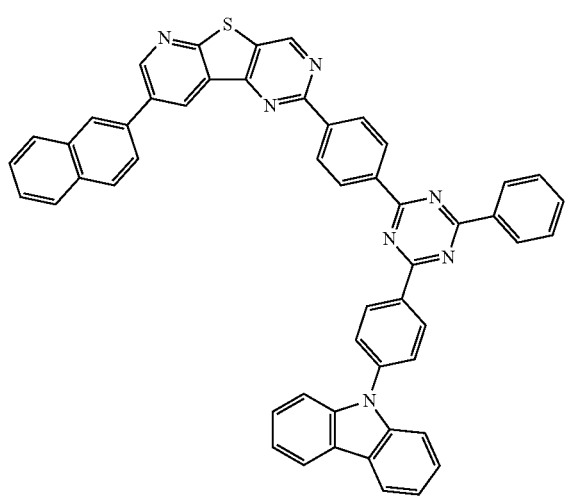
319
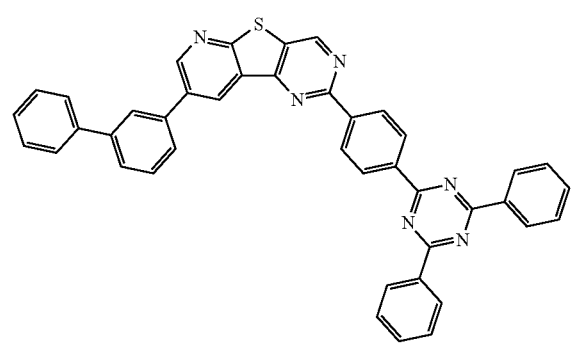

-continued
521
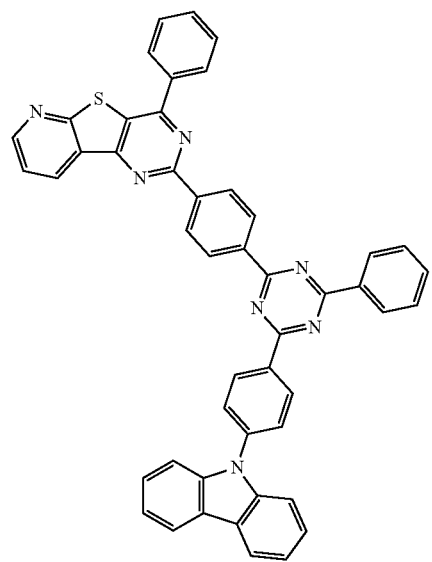
320
522
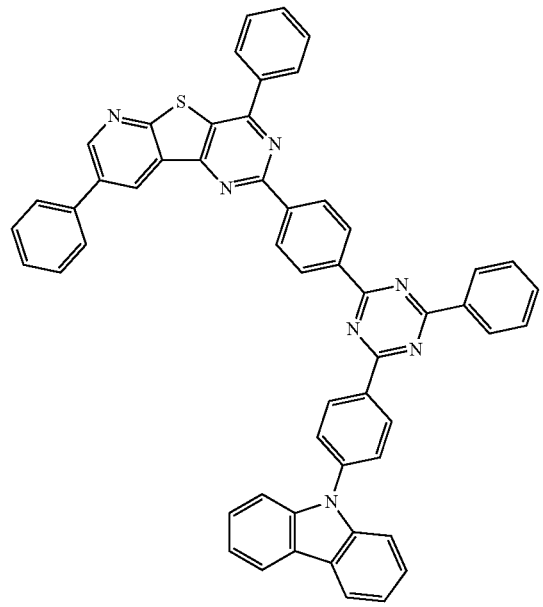
321
322
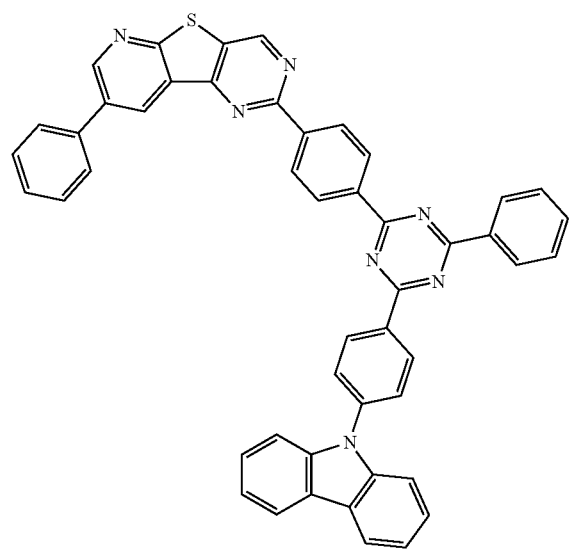
323
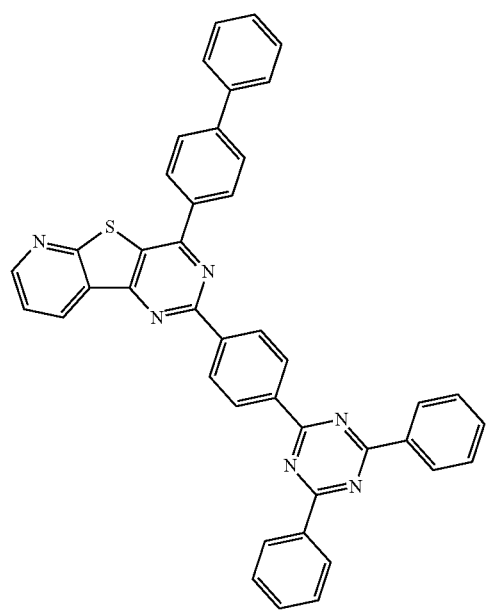

-continued
323
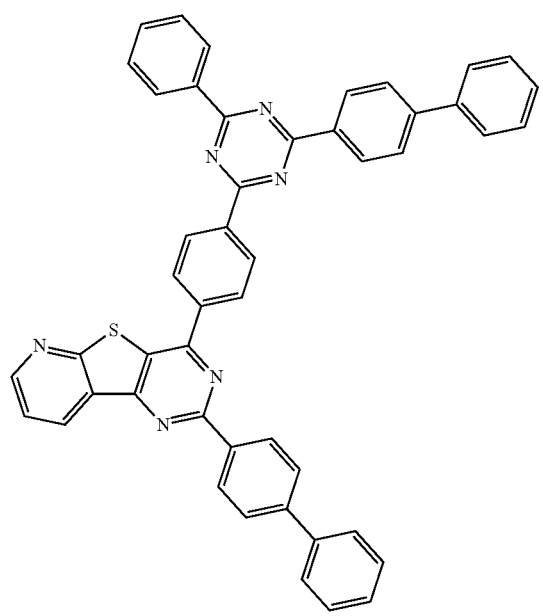
324
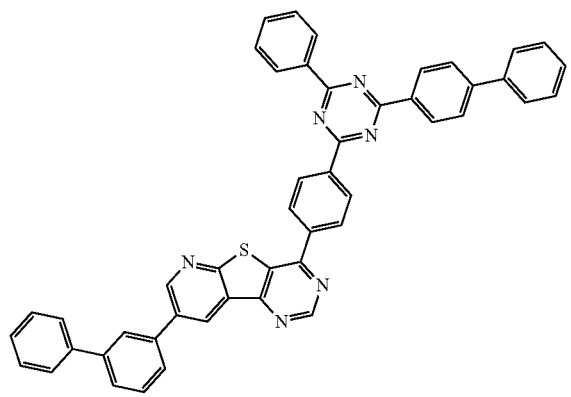
326
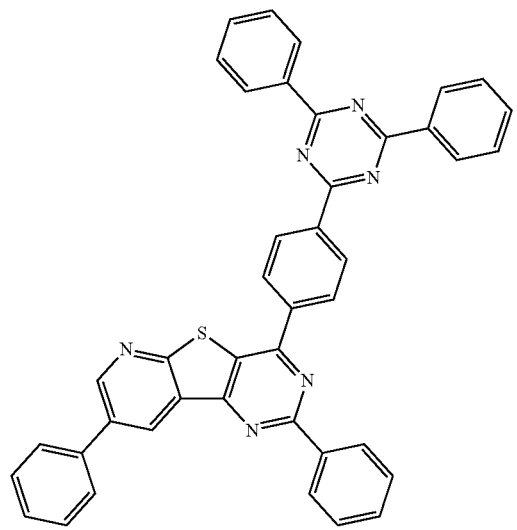
327
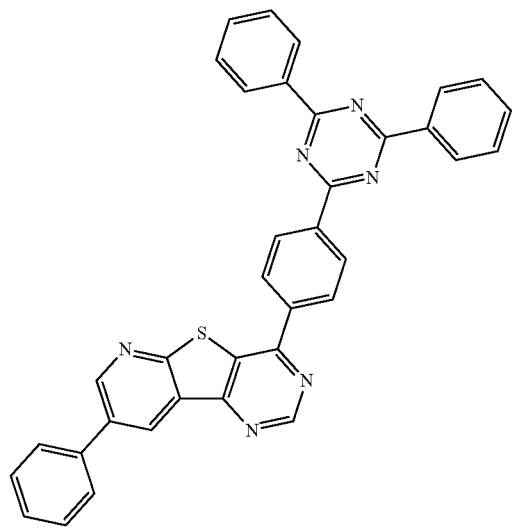

-continued
328
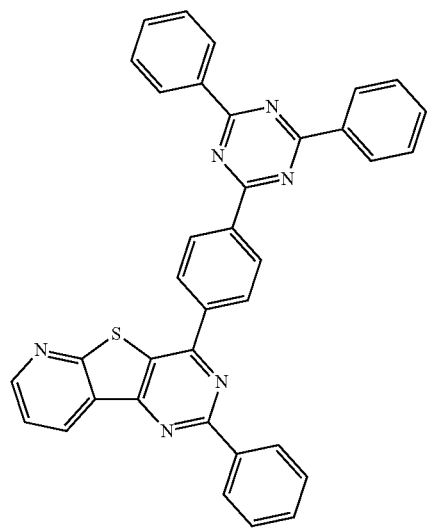
329
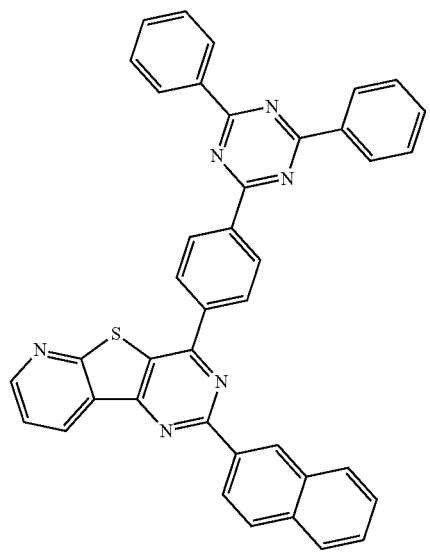
330
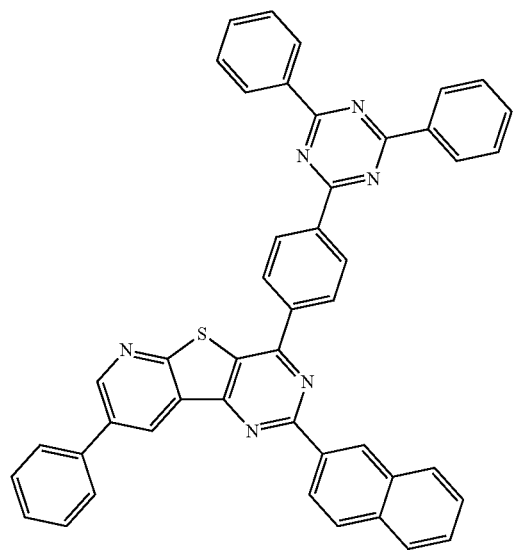
331
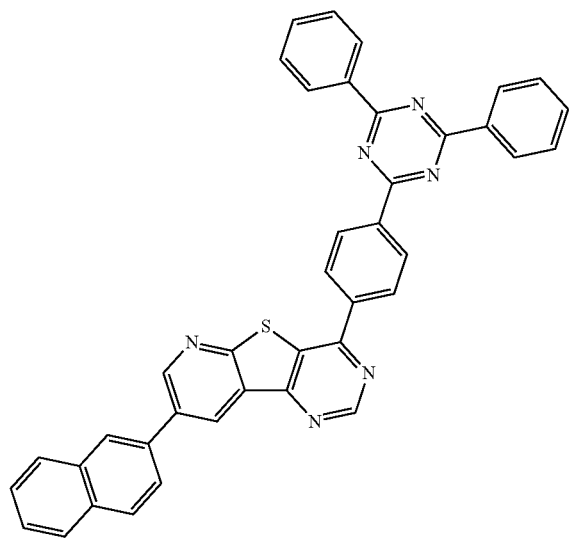

527 528
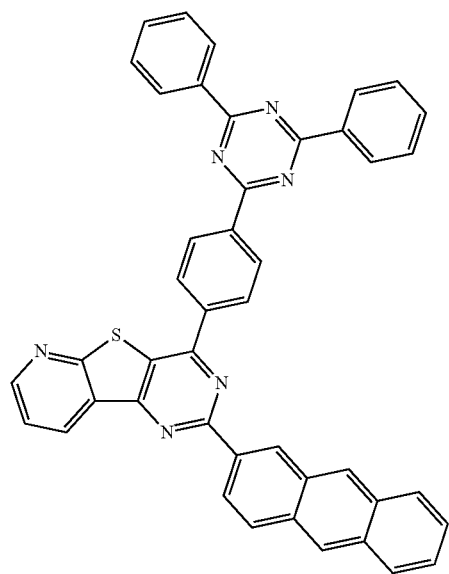
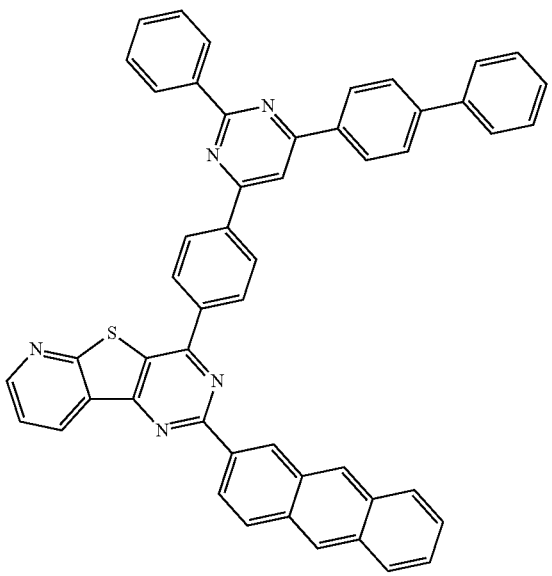
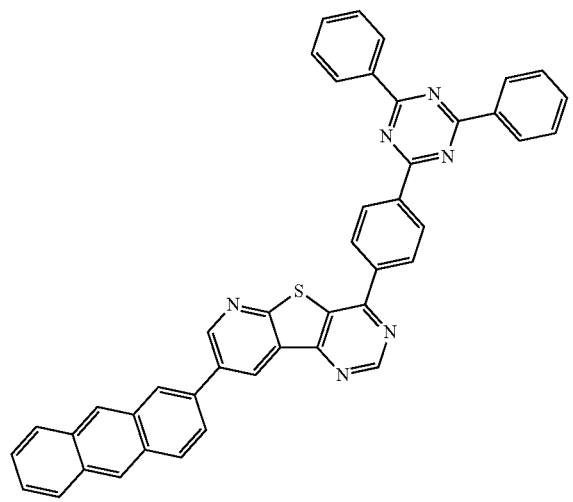
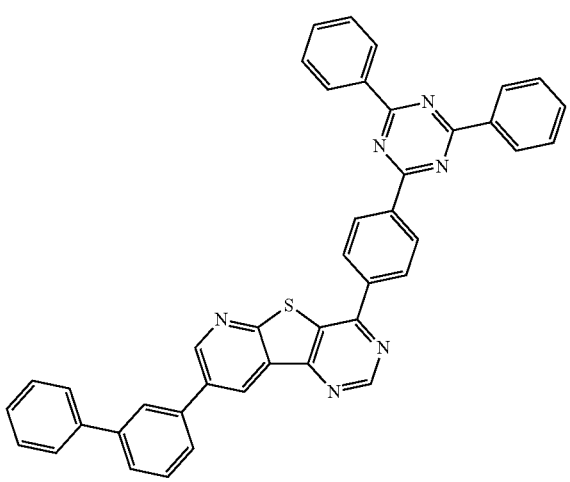

-continued
336
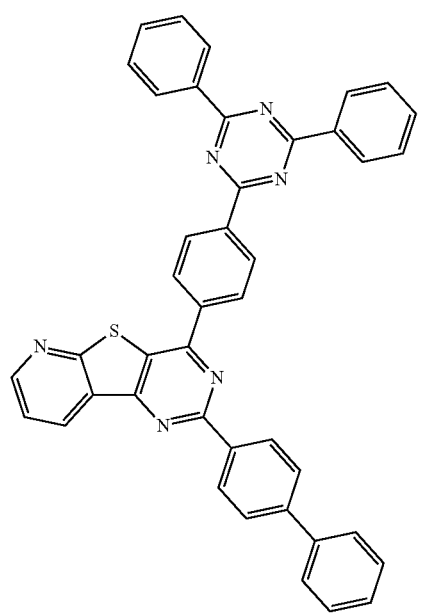
337
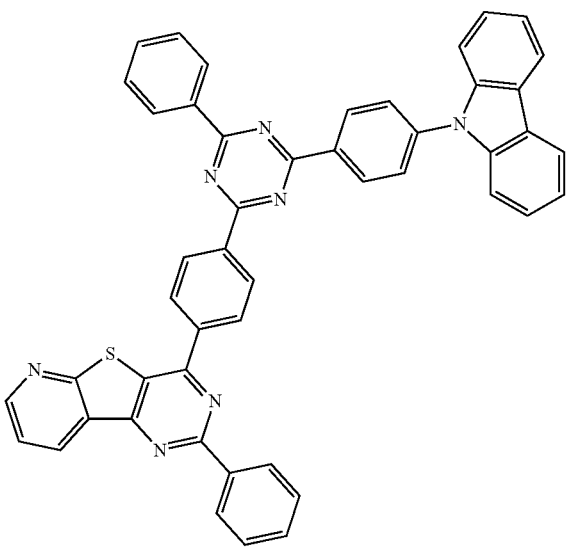
338
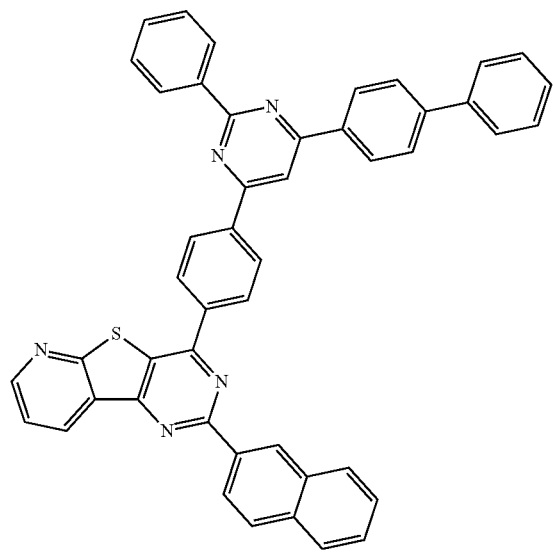
339
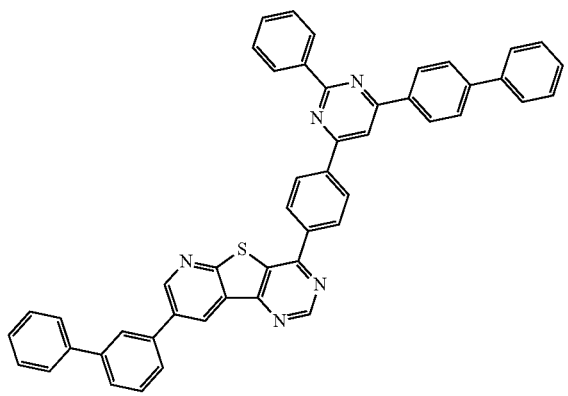

-continued
340
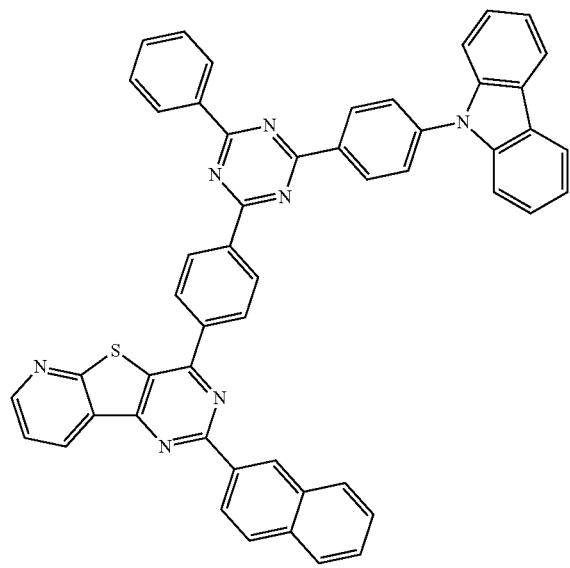
341
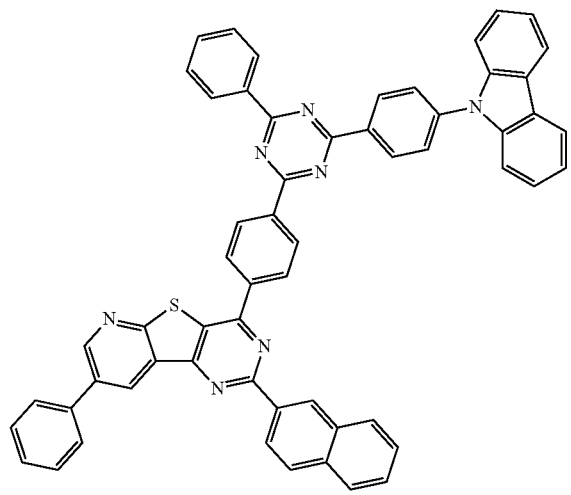
342
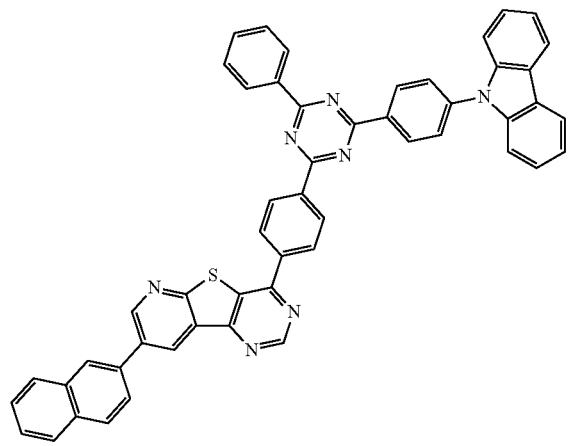
343
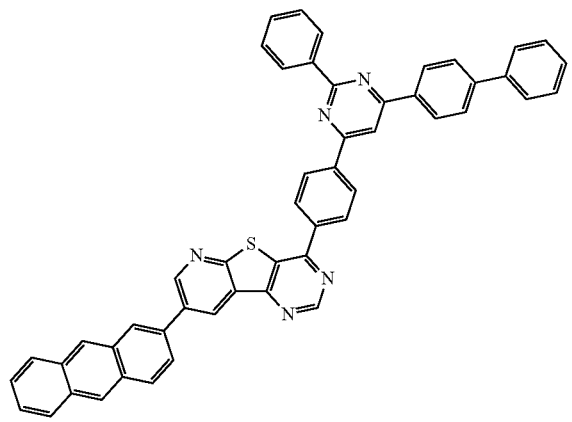
344
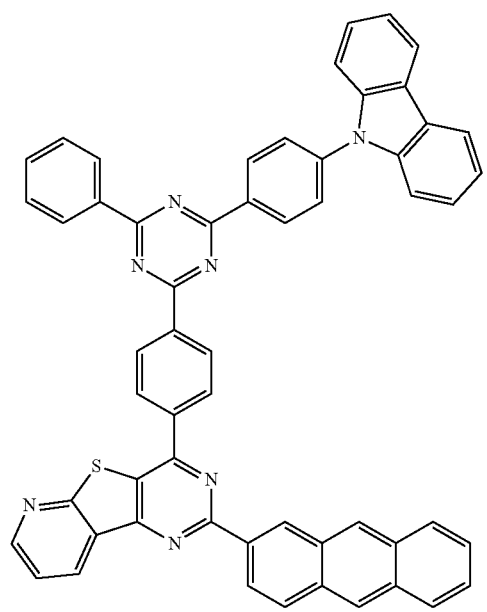
345
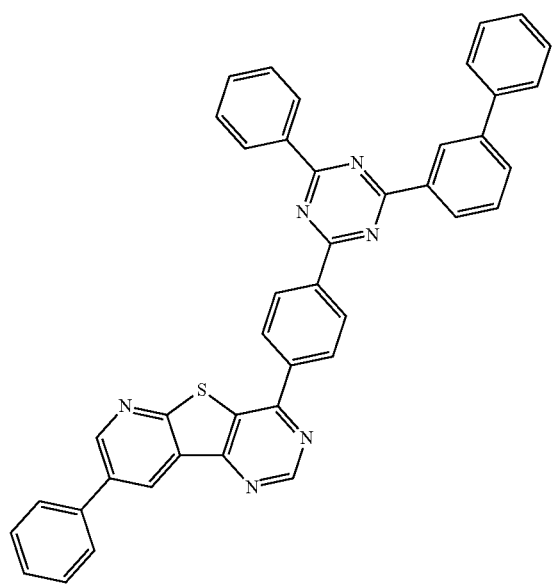

-continued
346
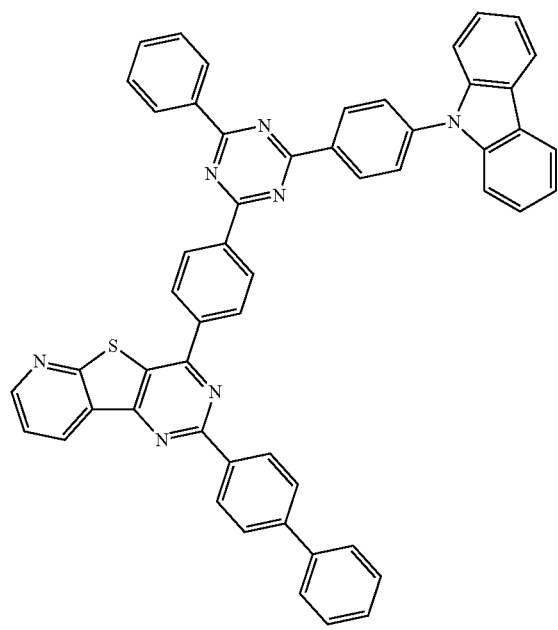
347
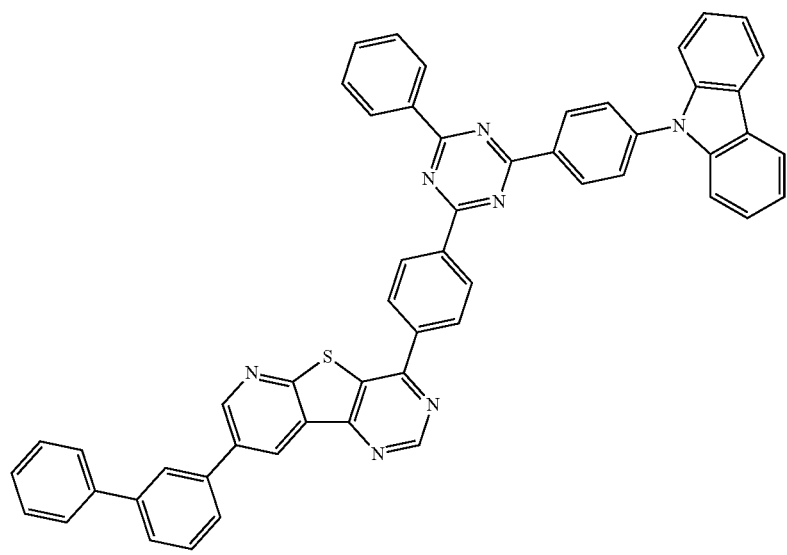

-continued
348
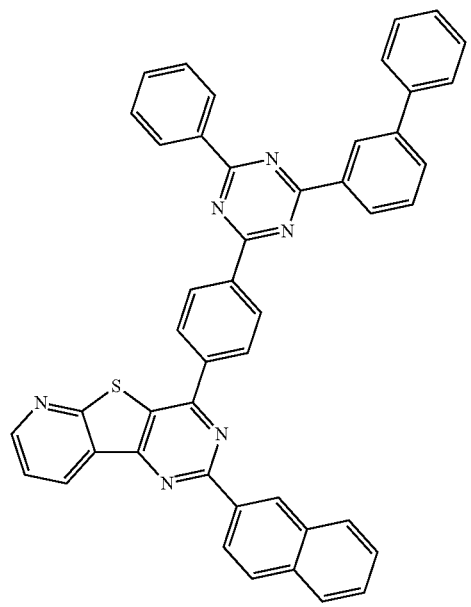
349
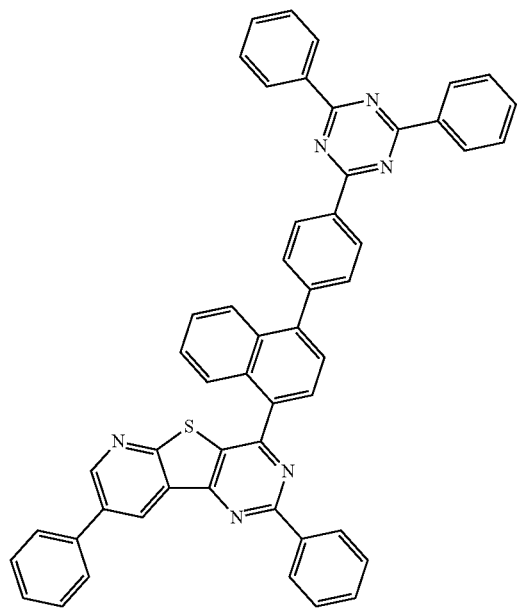
350
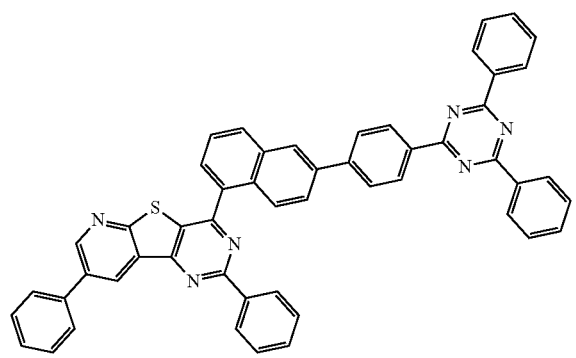
351
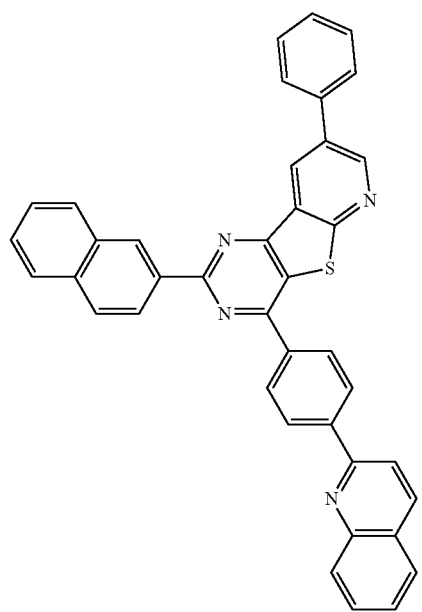

-continued
352
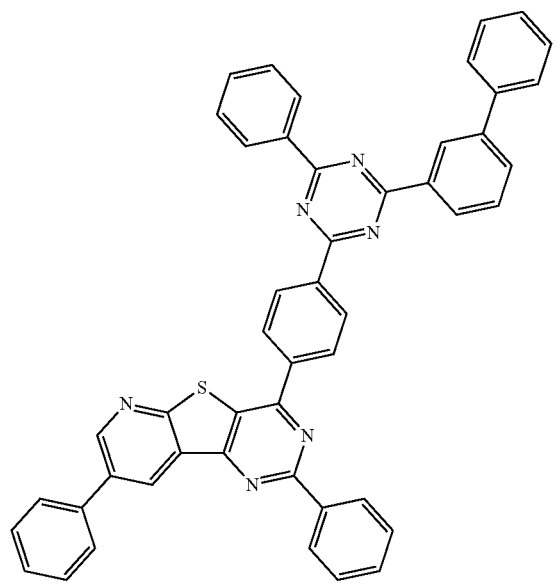
353
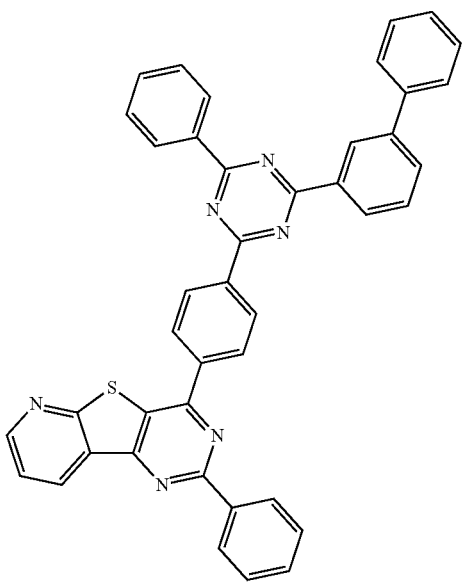
354
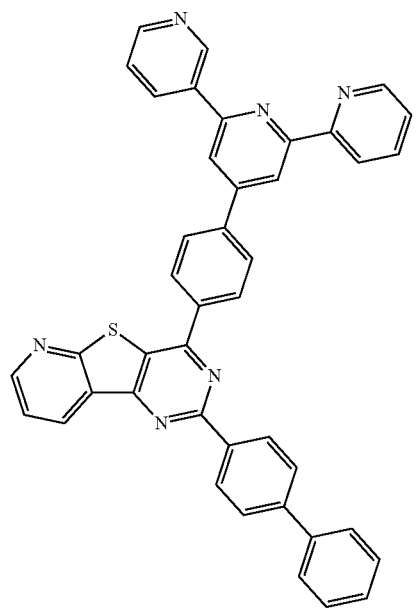
355
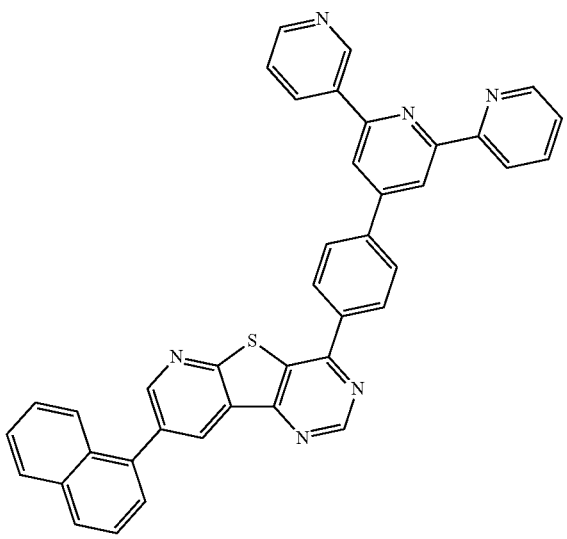

356
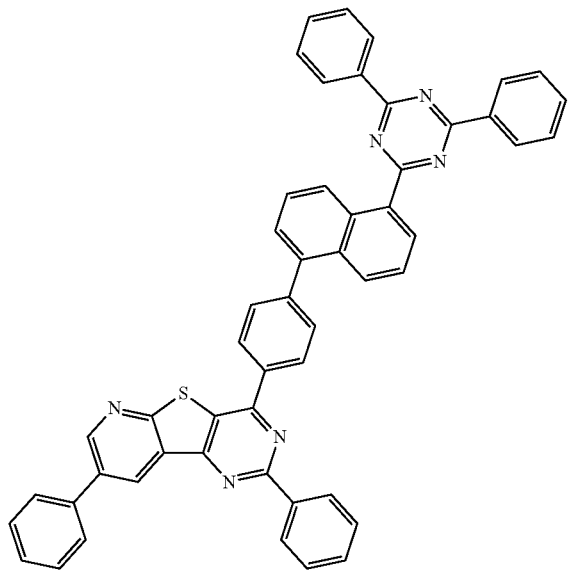
357
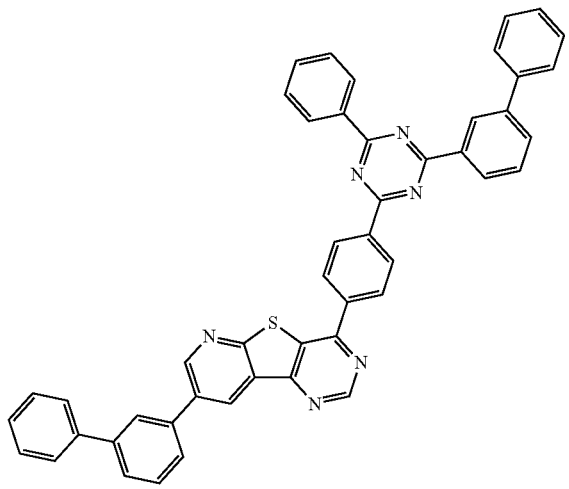
358
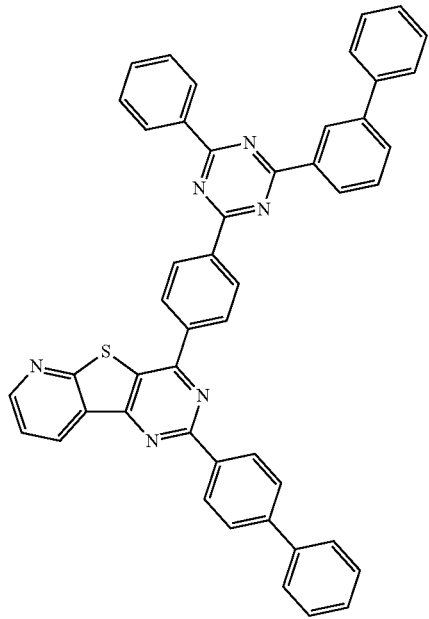
359
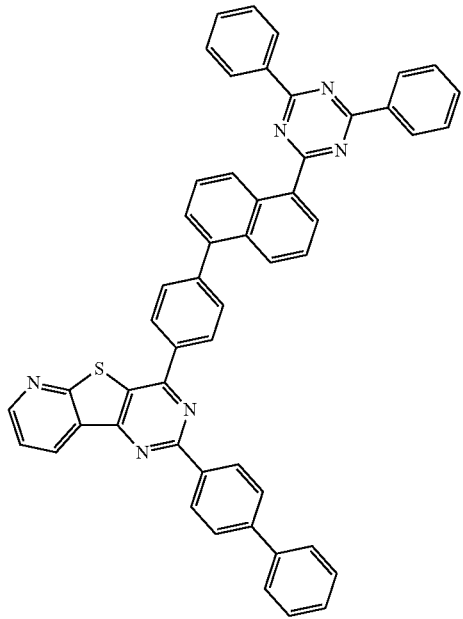

-continued
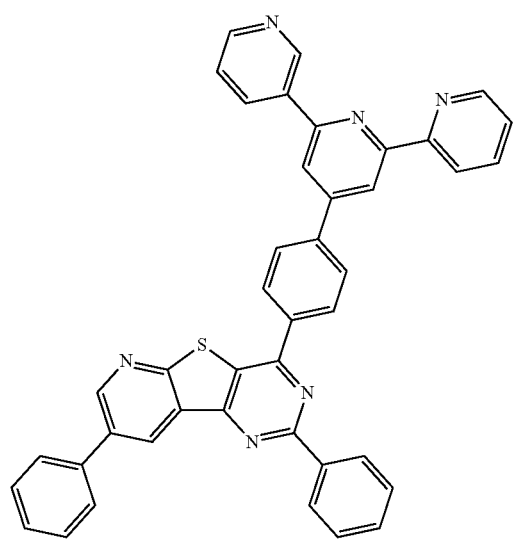
360
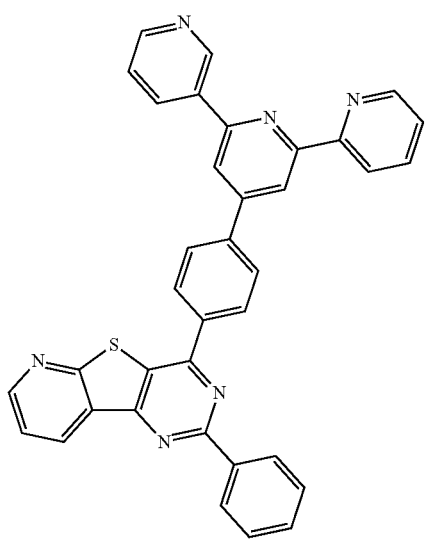
361
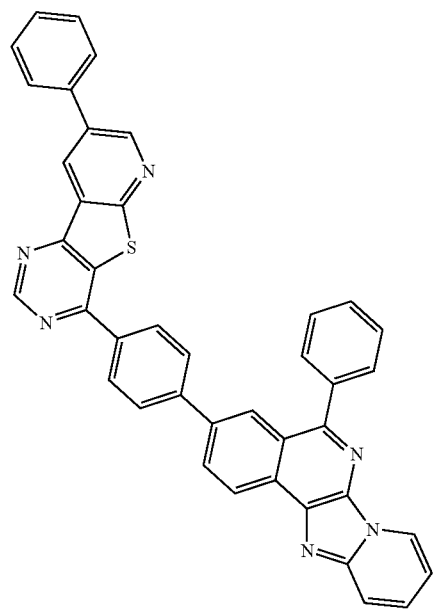
362
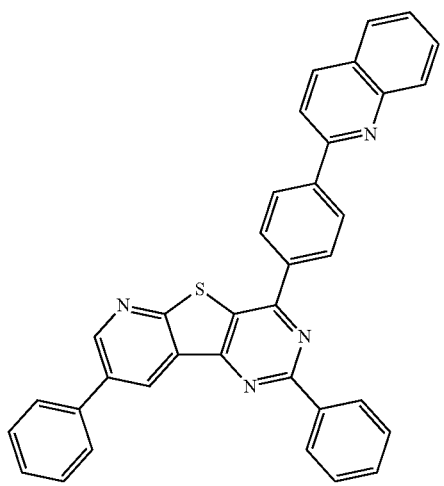
363

-continued
543
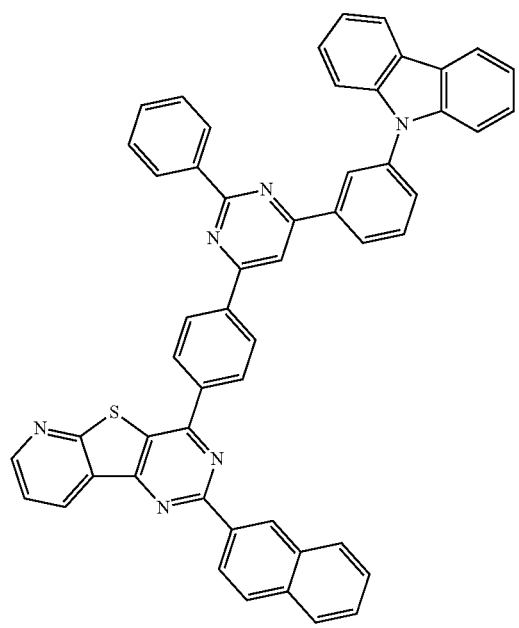
544
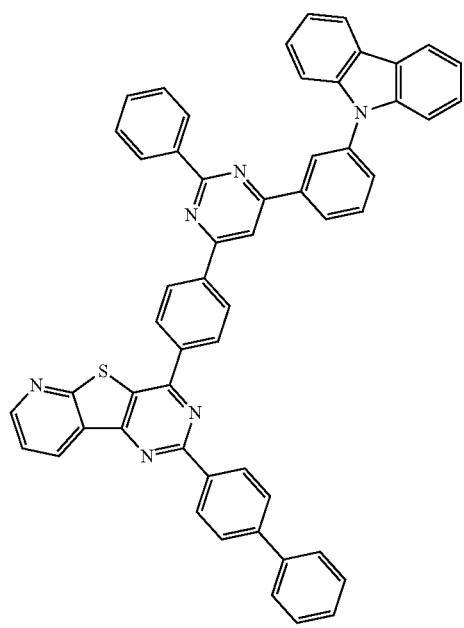
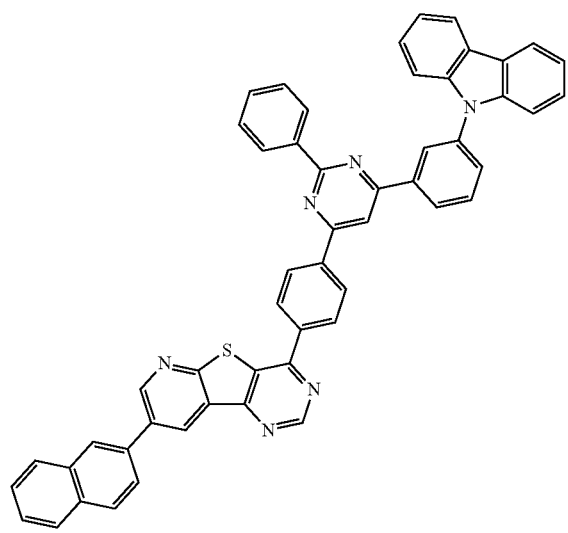
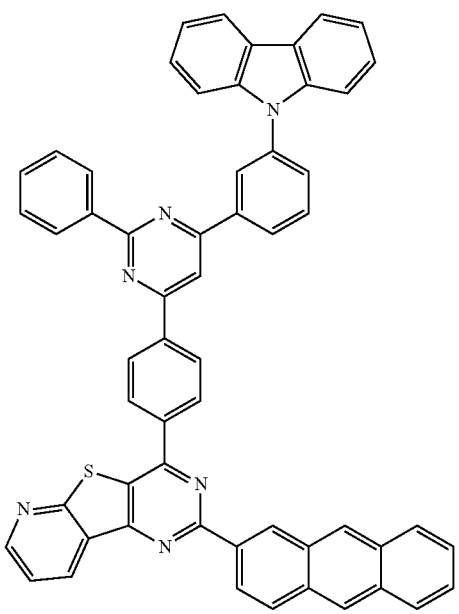

-continued
545
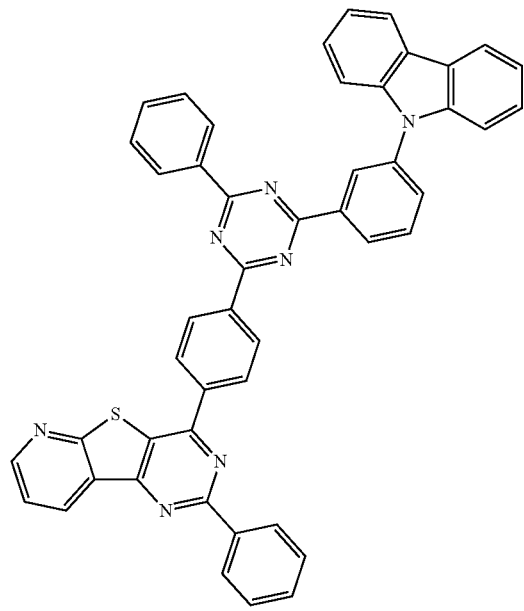
368
546
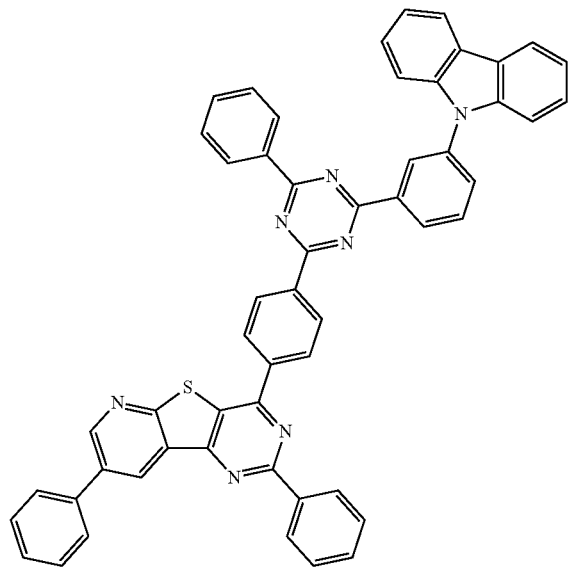
369
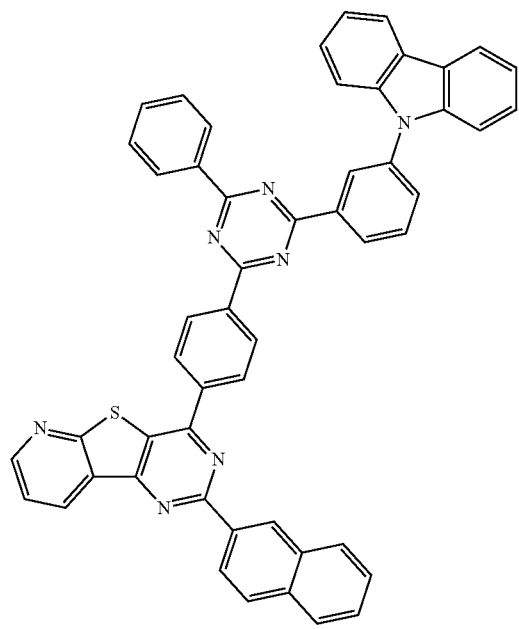
370
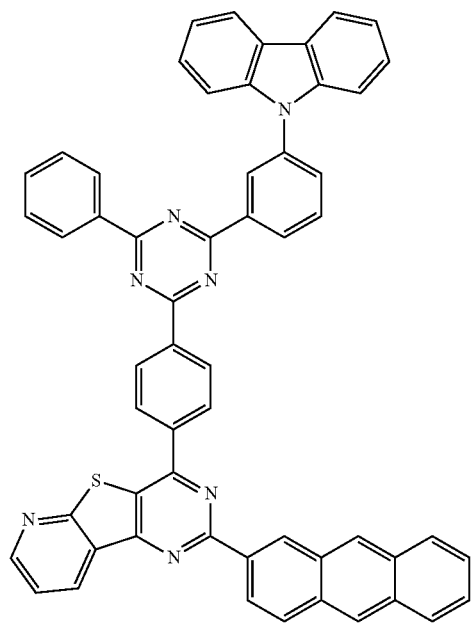
371

372
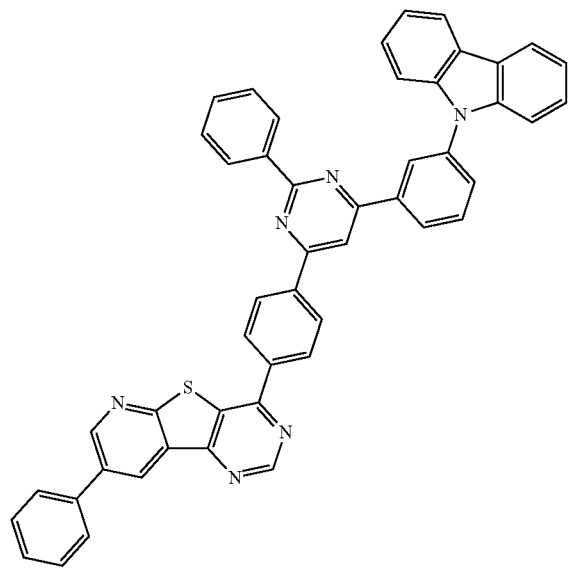
373
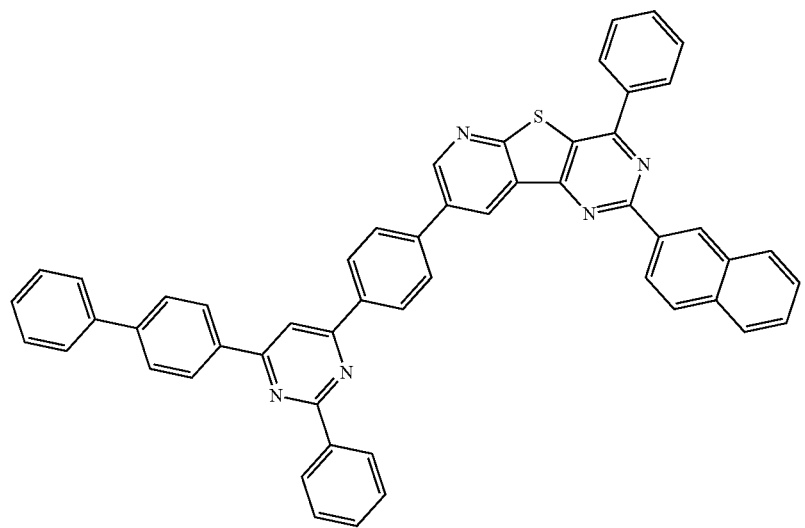
374
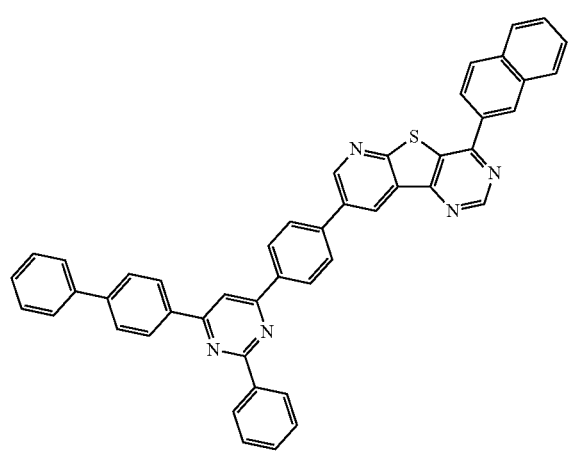
375
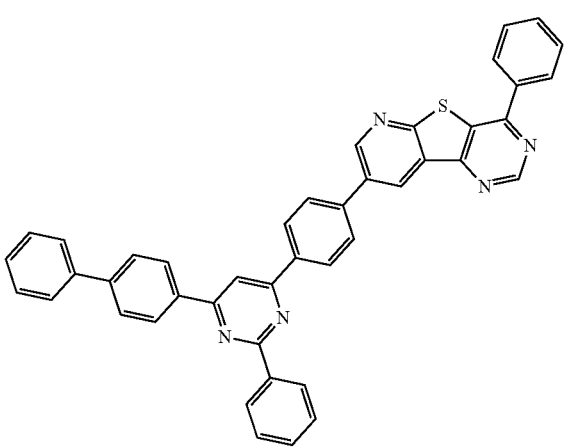

376
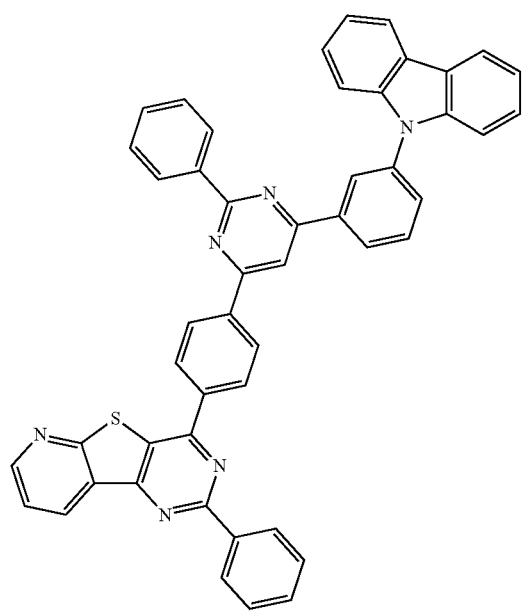
377
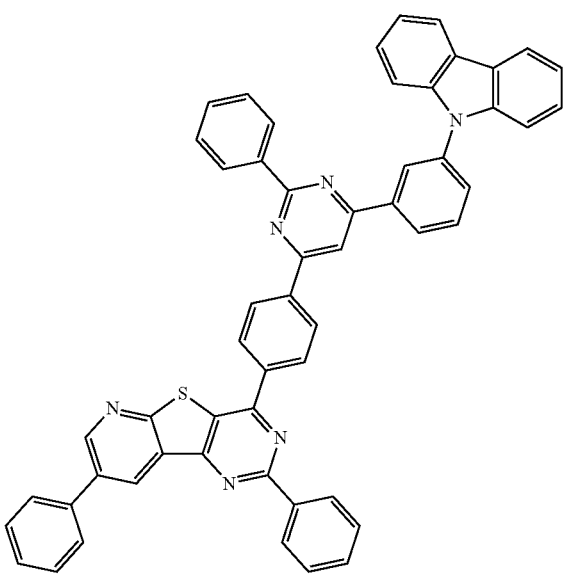
378
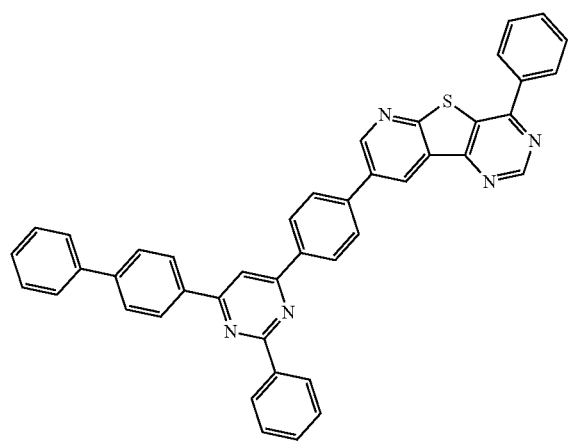
379
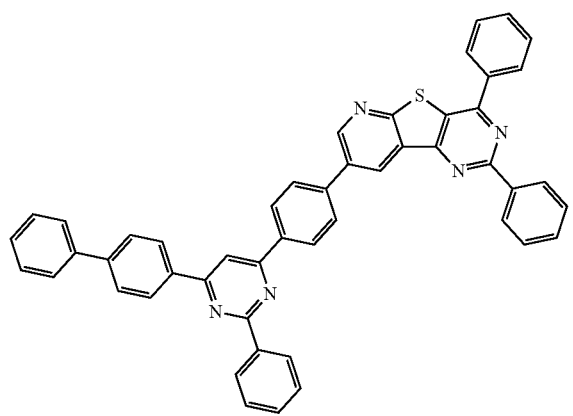

-continued
380
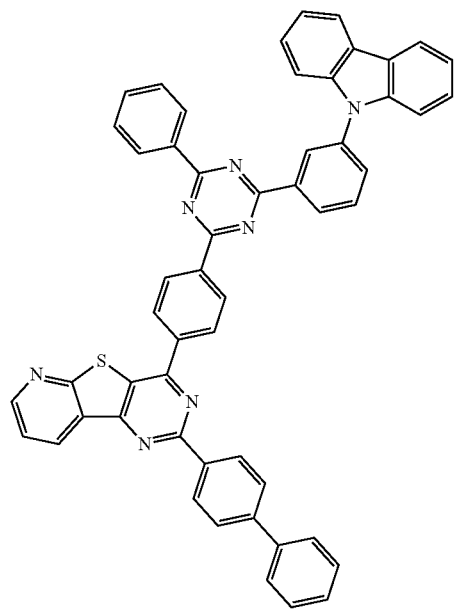
381
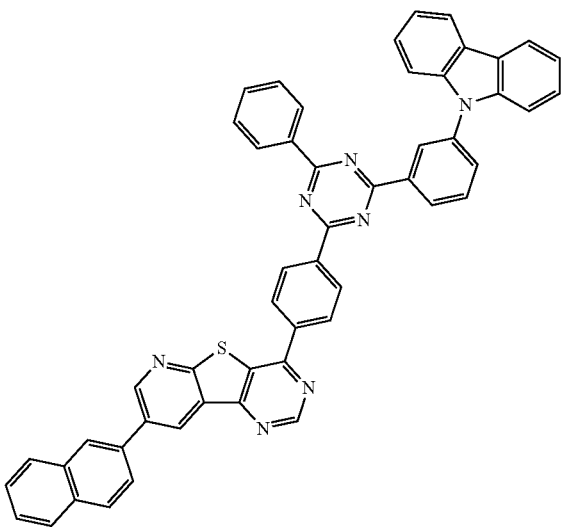
382
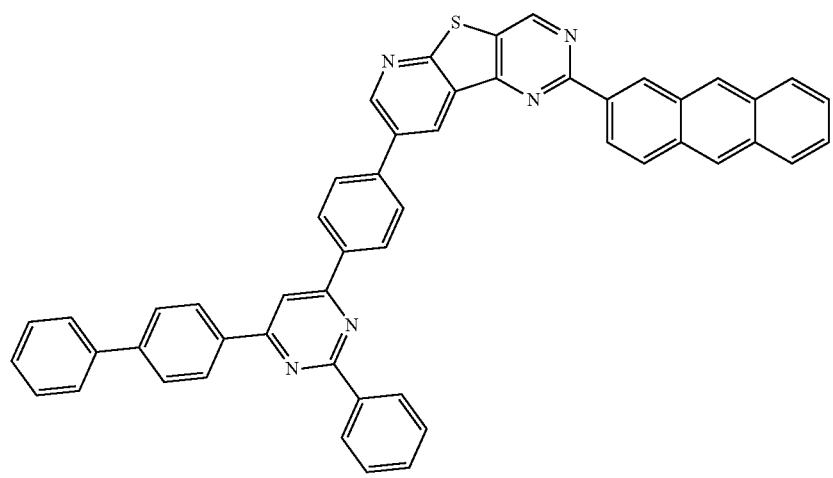
383
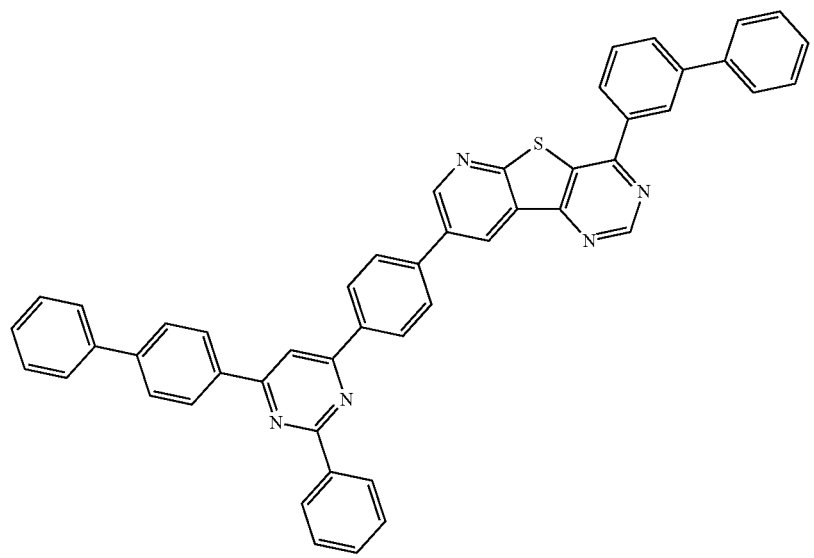

-continued
384
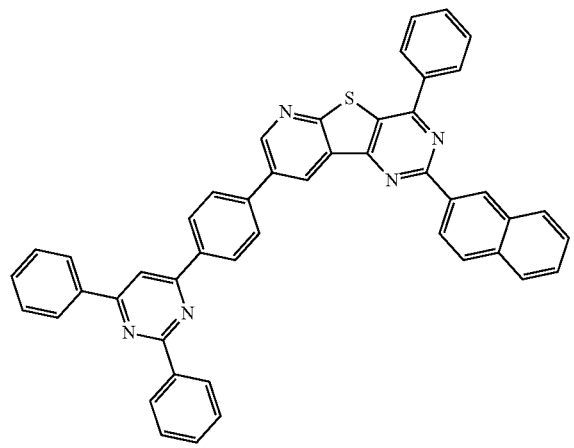
385
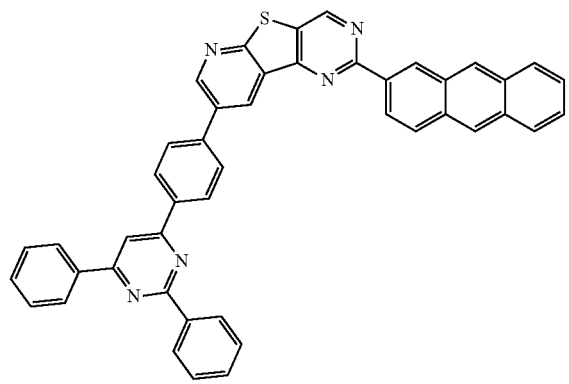
386
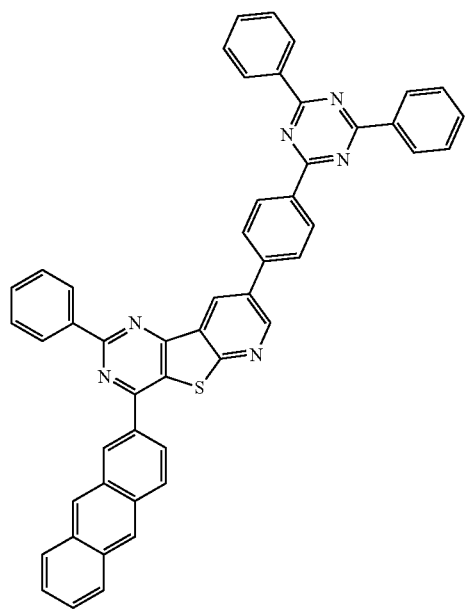
387
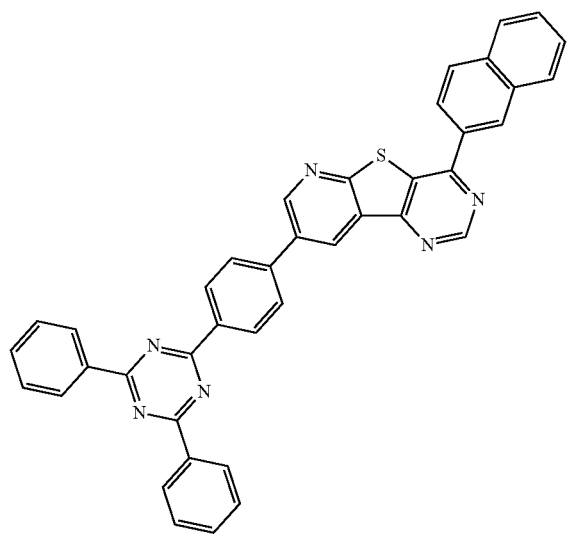
388
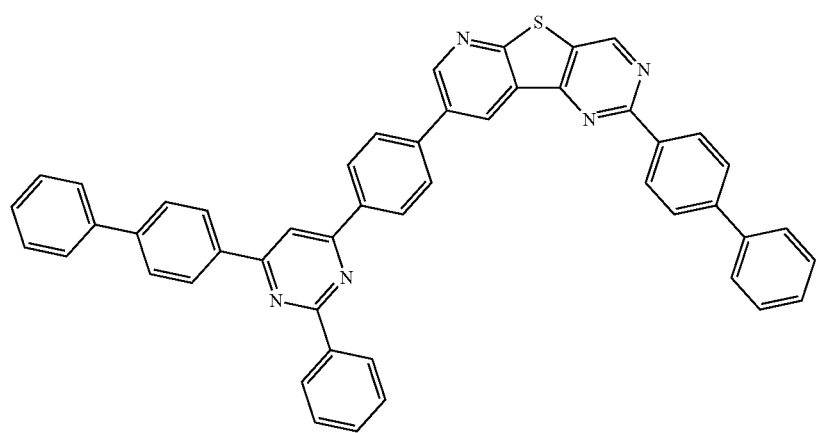

389 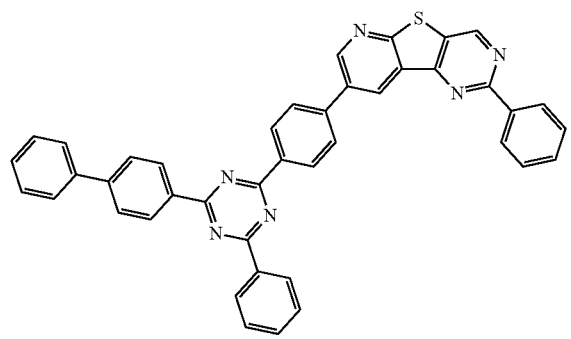
390 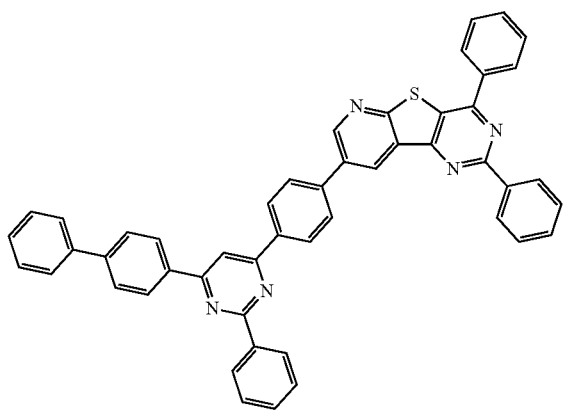
391 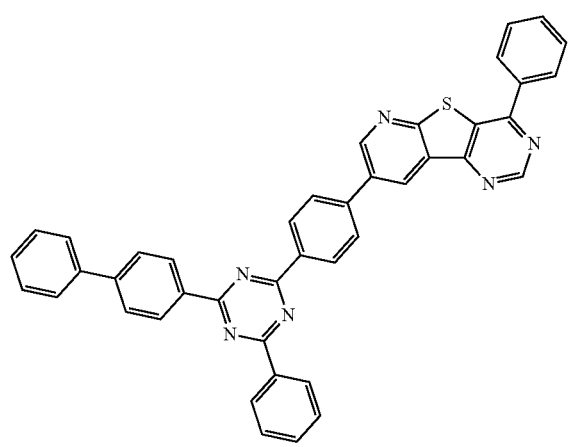
392 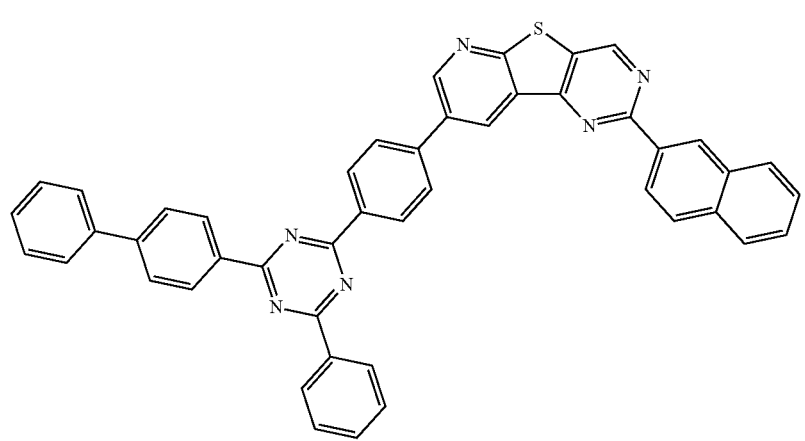

393
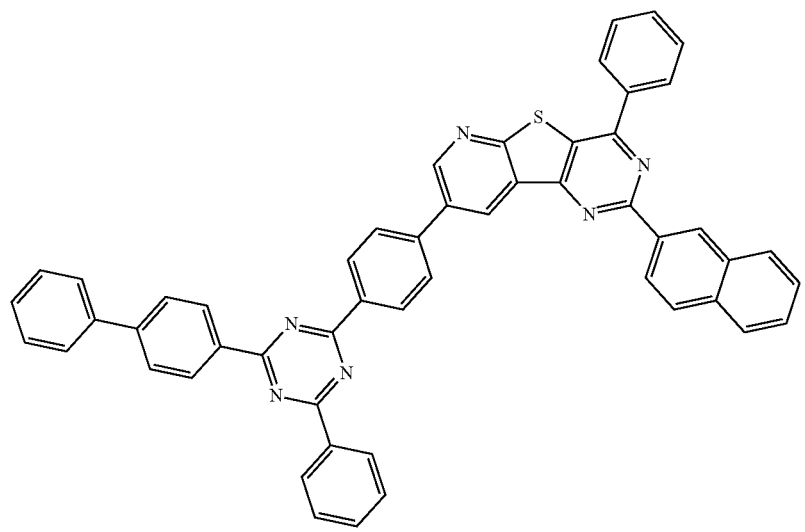
394
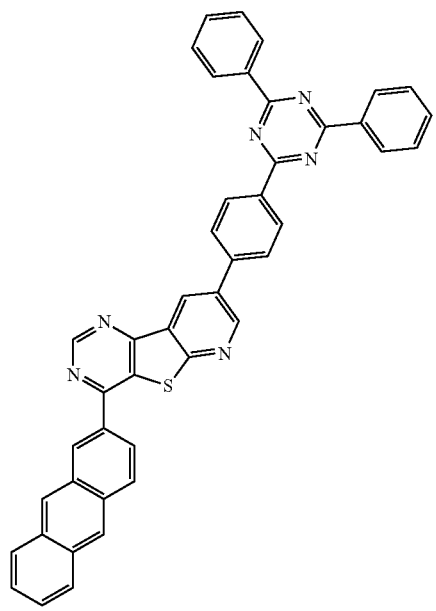
395
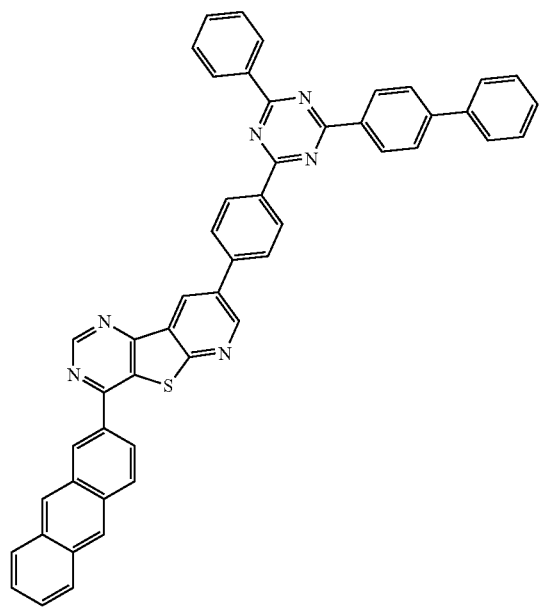

396
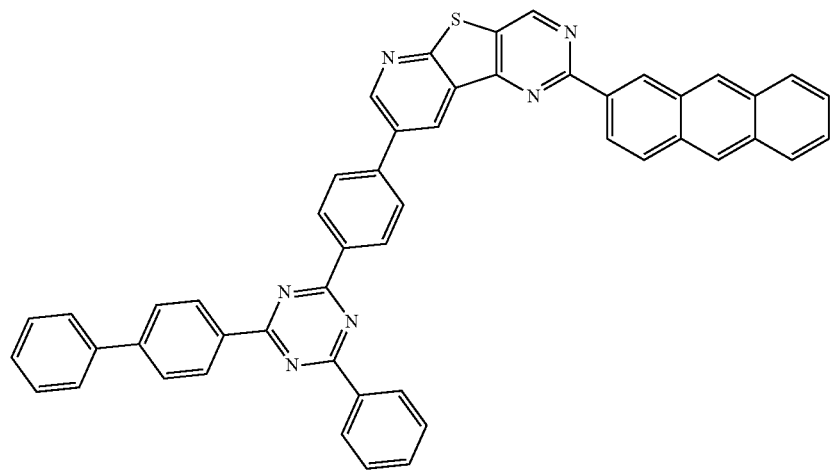
397
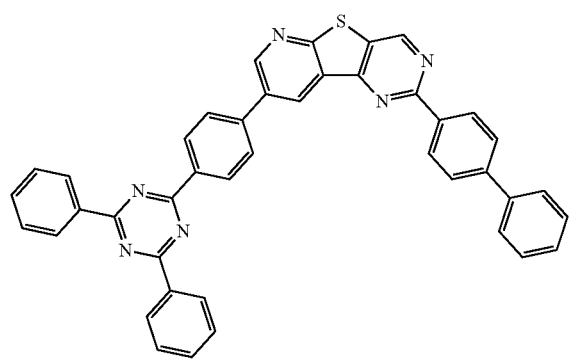
398
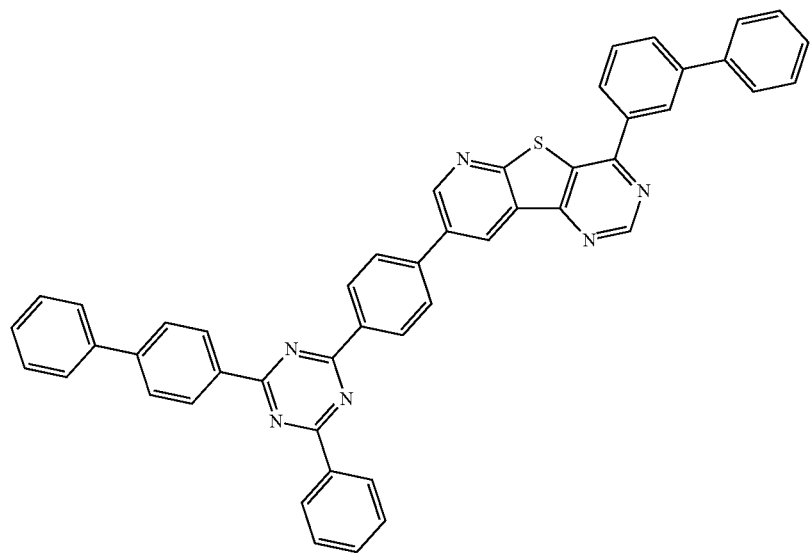

399
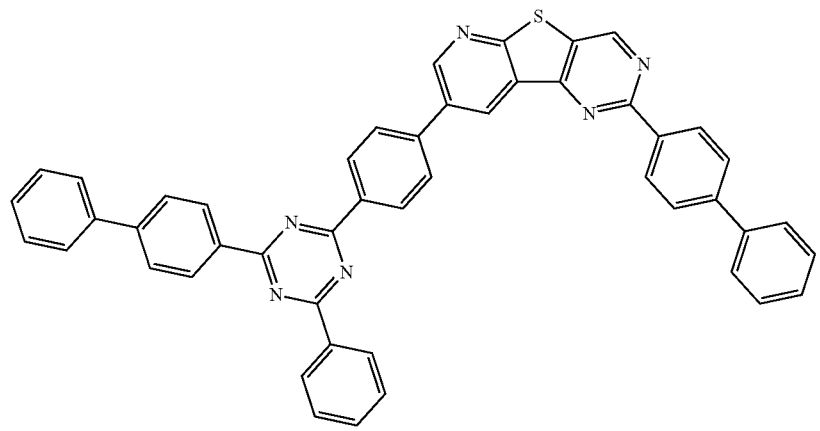
400
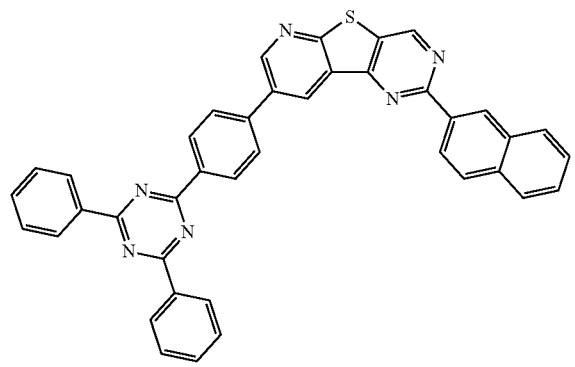
401
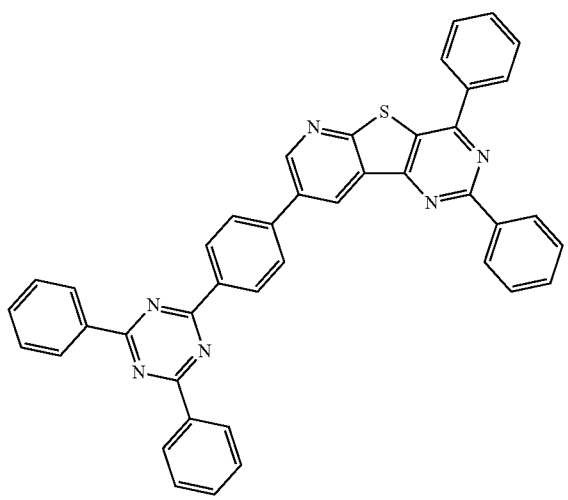
402
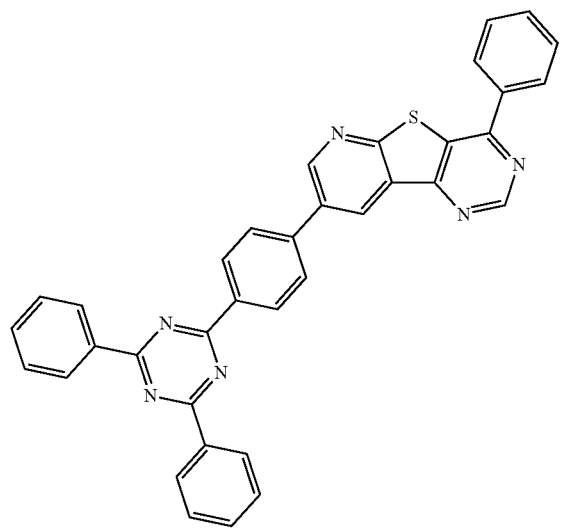
403
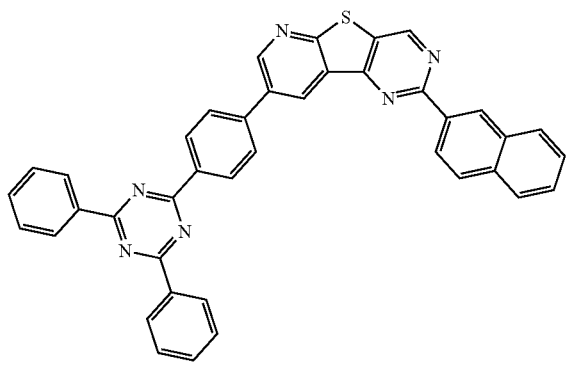

-continued
404
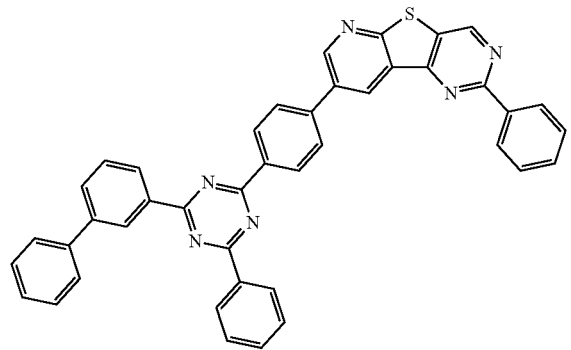
405
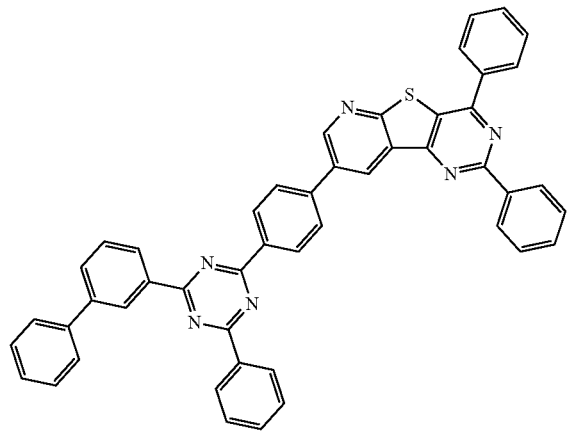
406
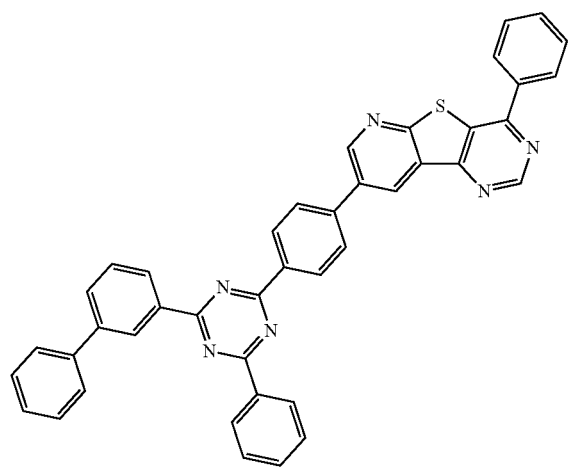
407
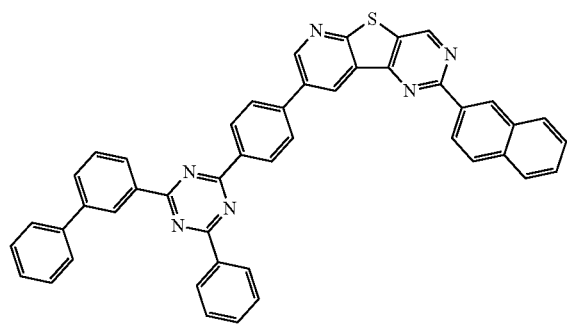
408
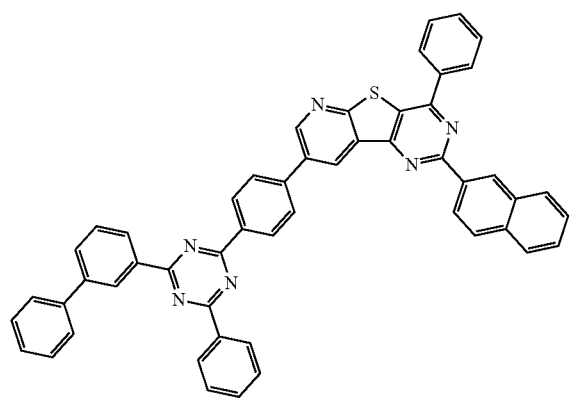
409
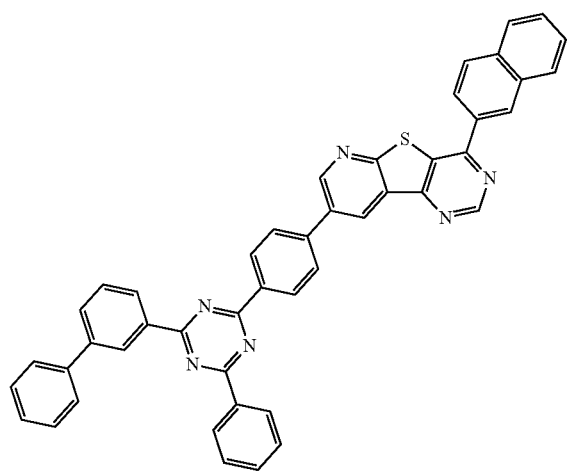

-continued
410
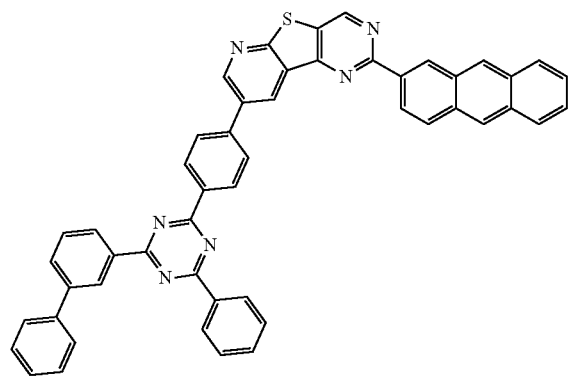
411
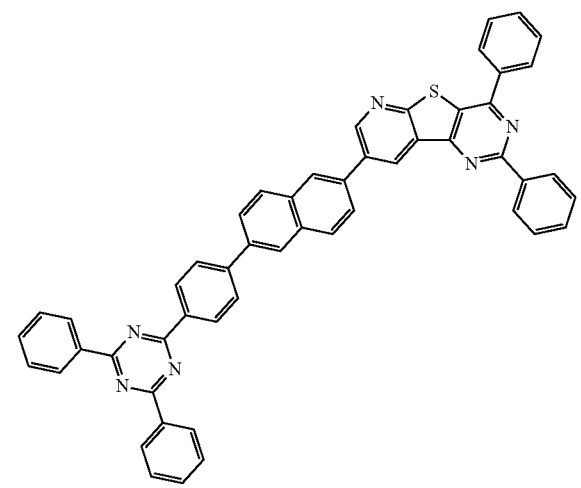
412
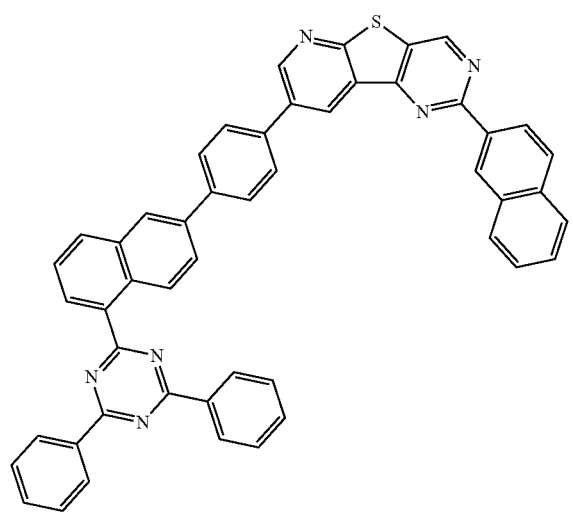
413
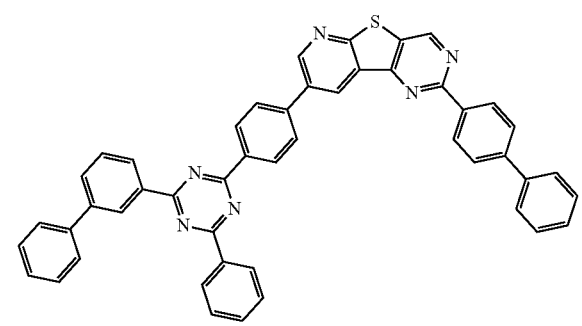
414
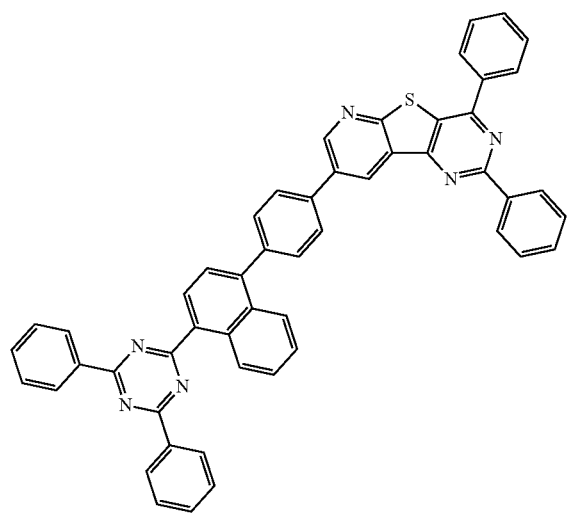
415
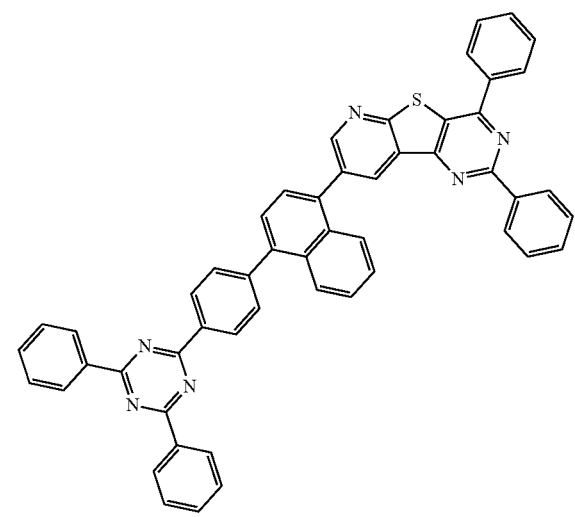

-continued
416
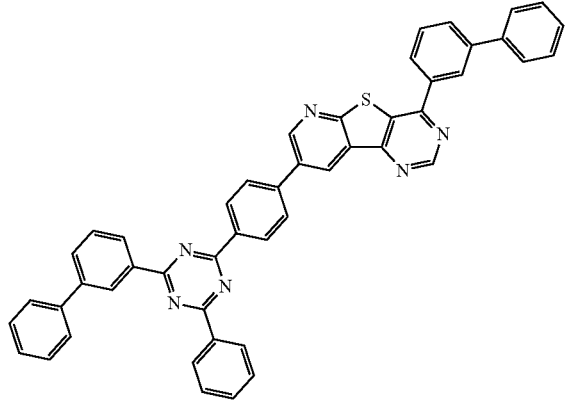
417
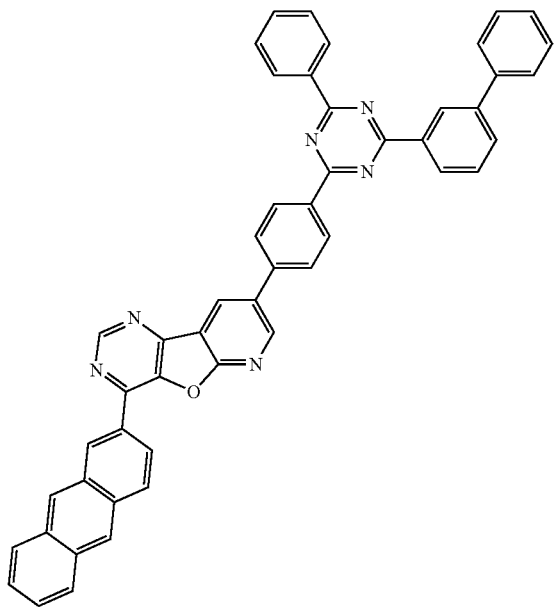
418
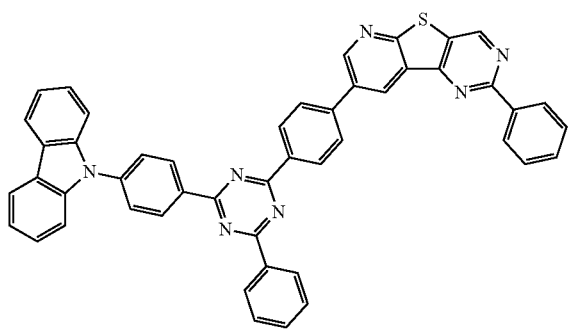
419
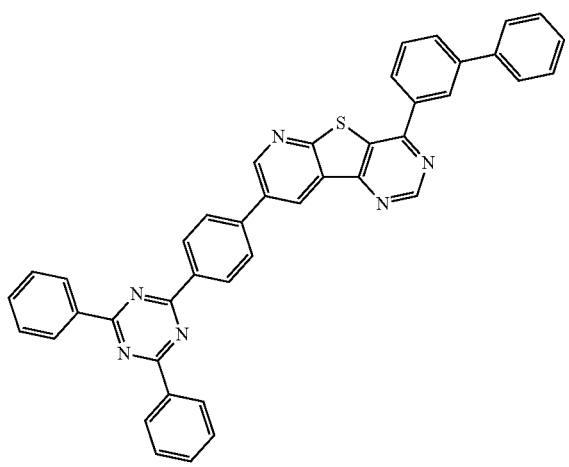
420
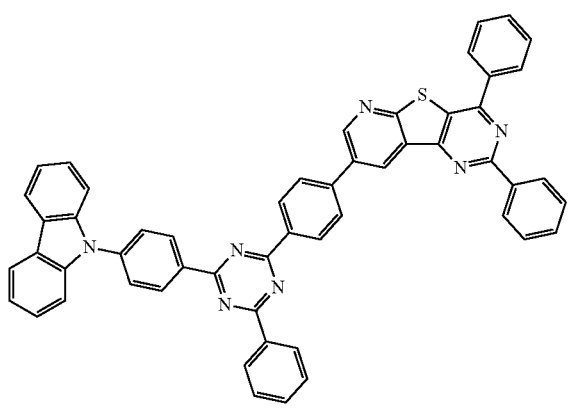
421
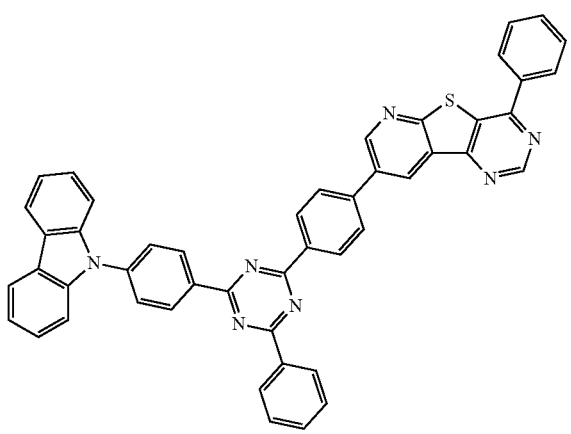

422
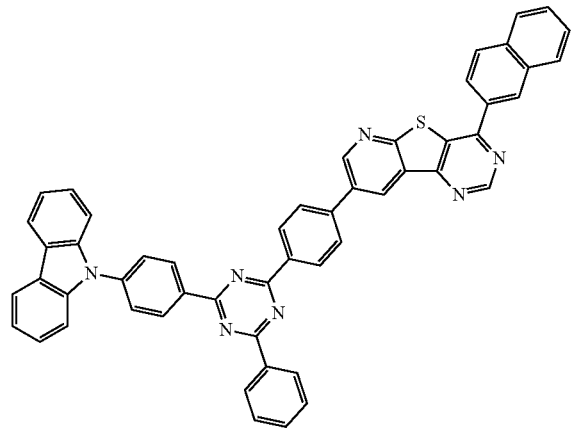
423
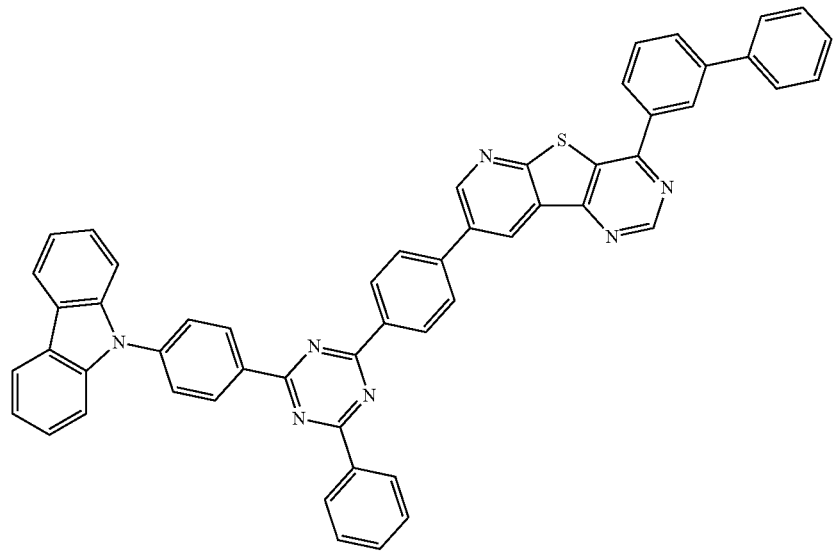
424
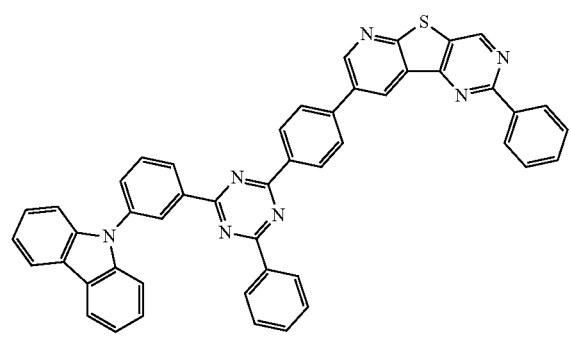
425
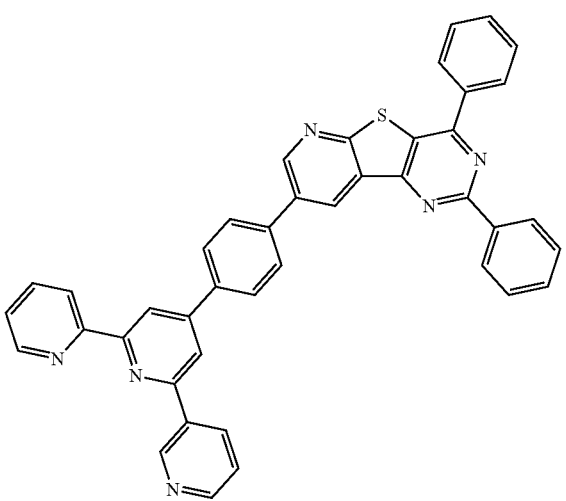

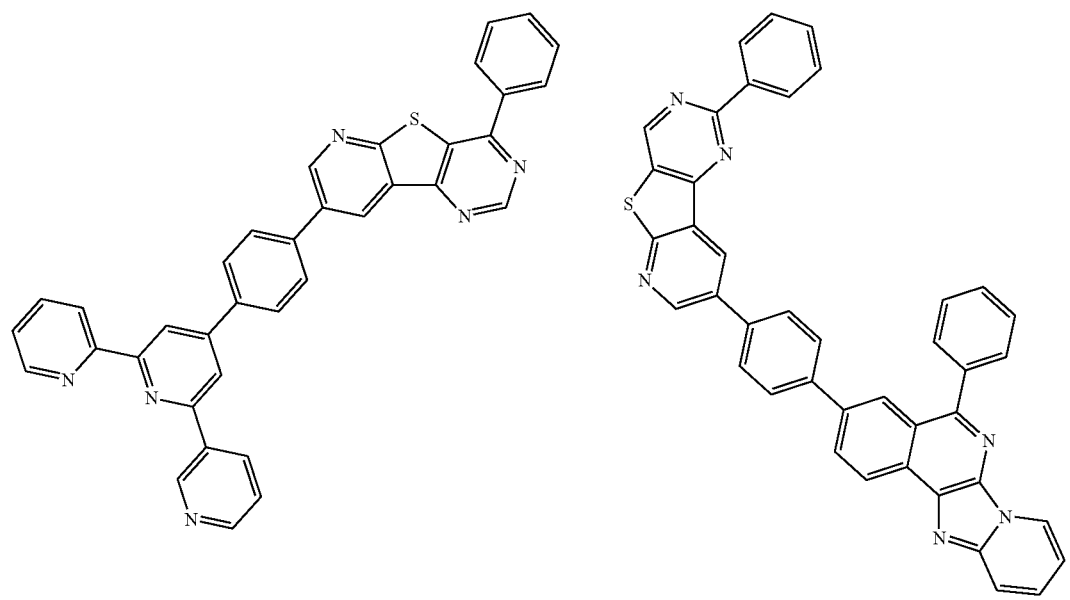
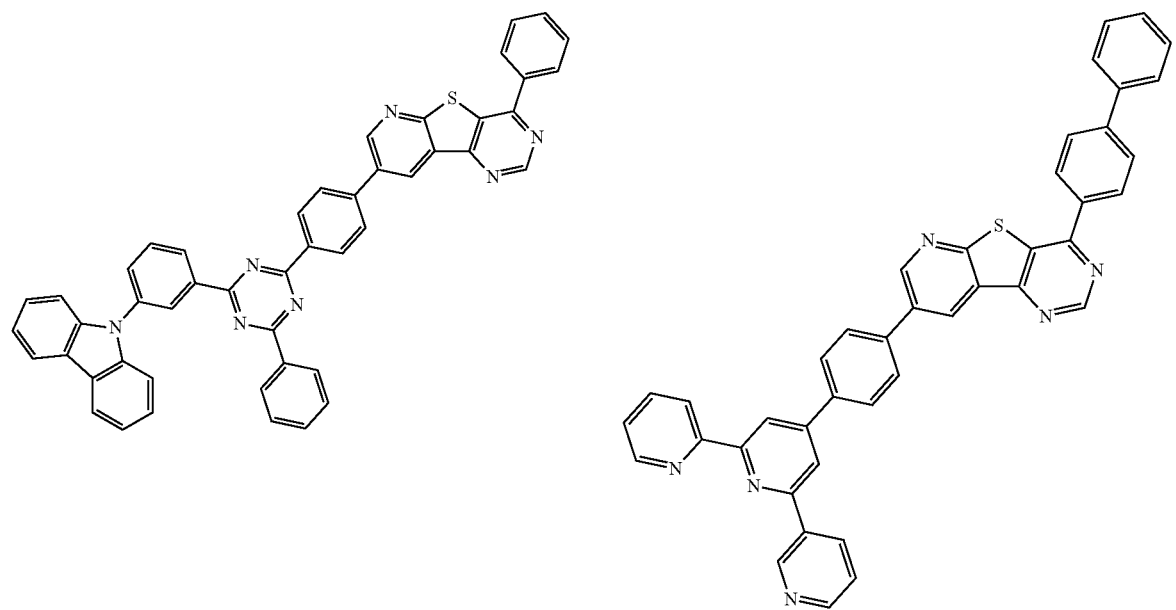

-continued
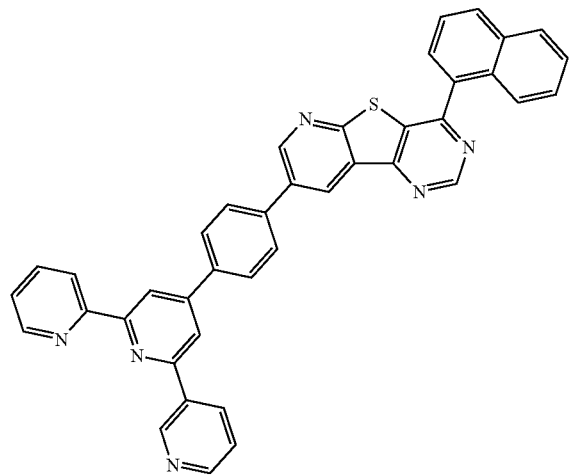
430
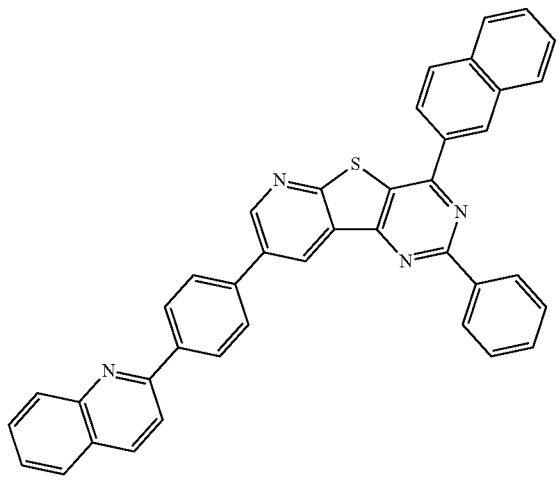
431
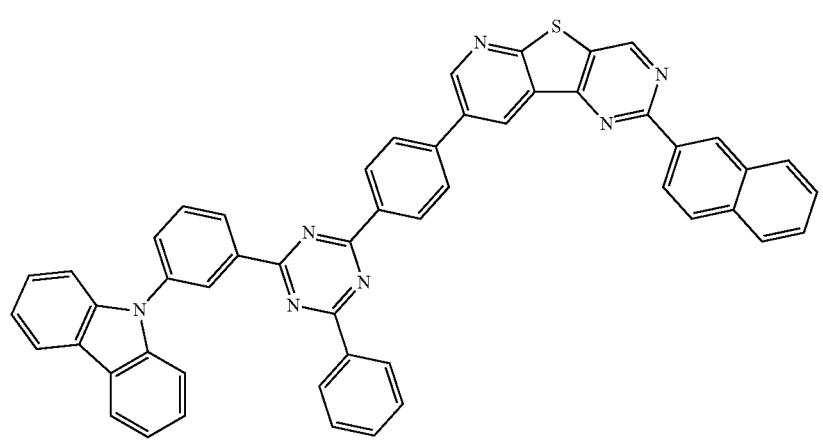
432
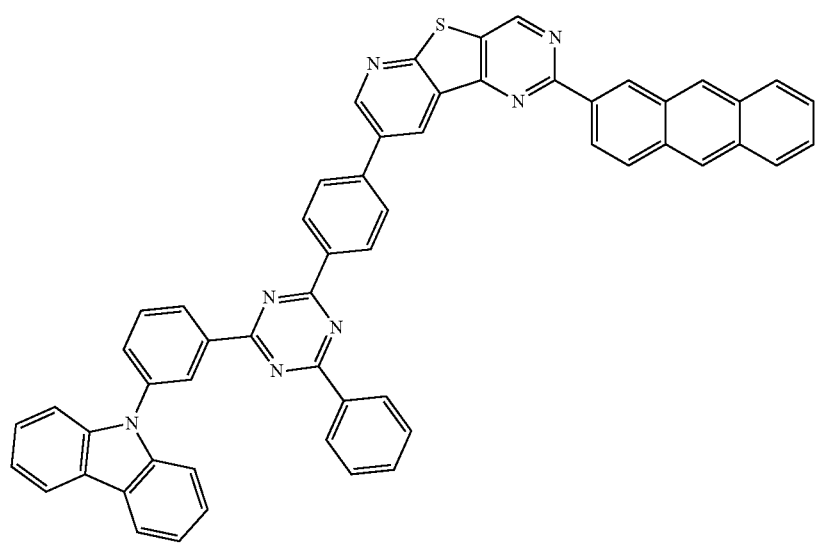
434

435
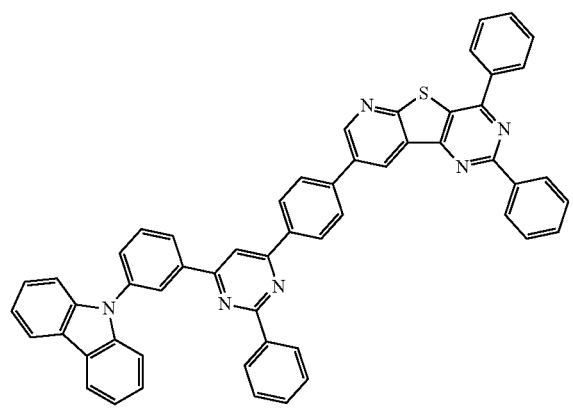
436
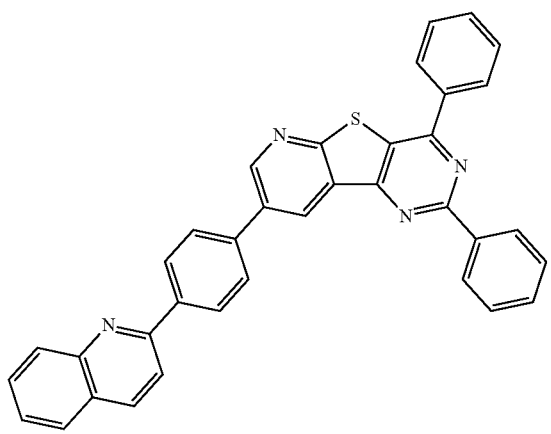
437
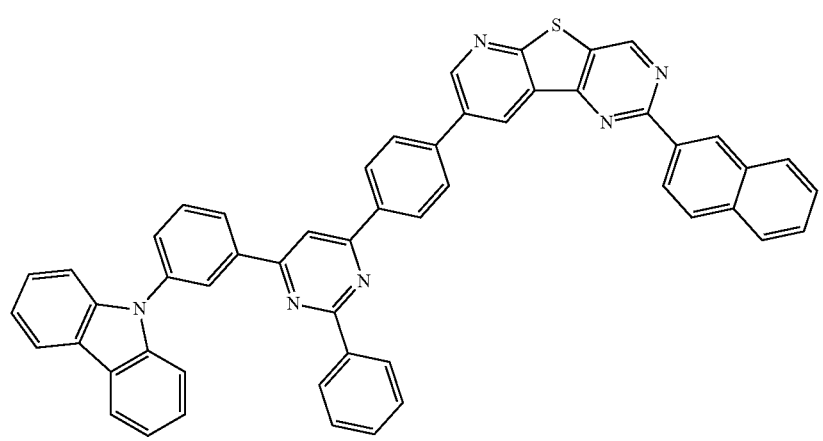
438
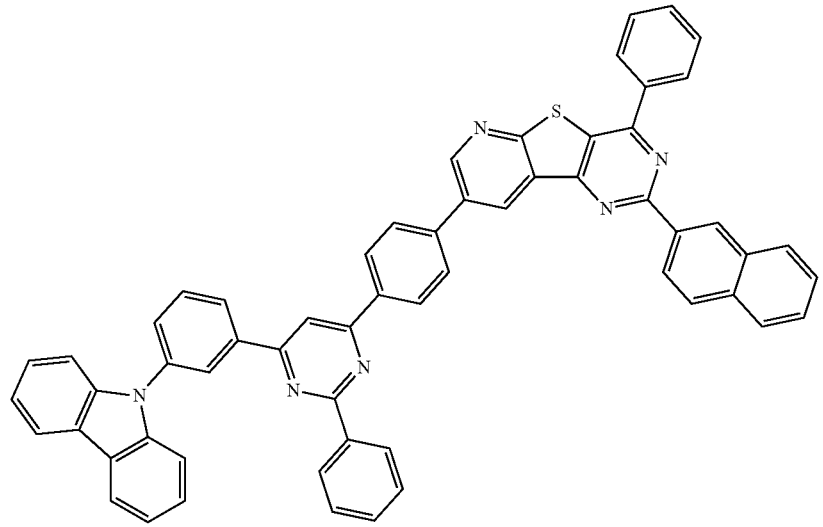

-continued
439
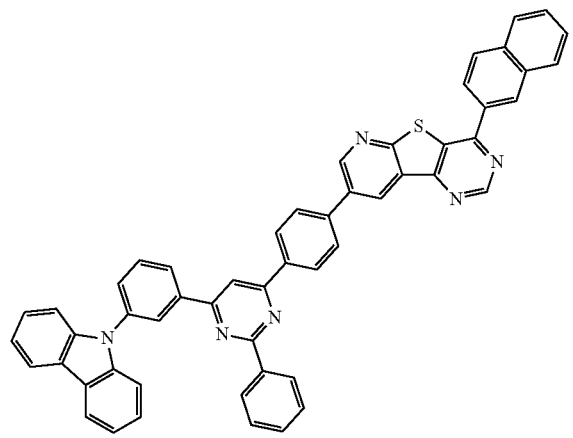
440
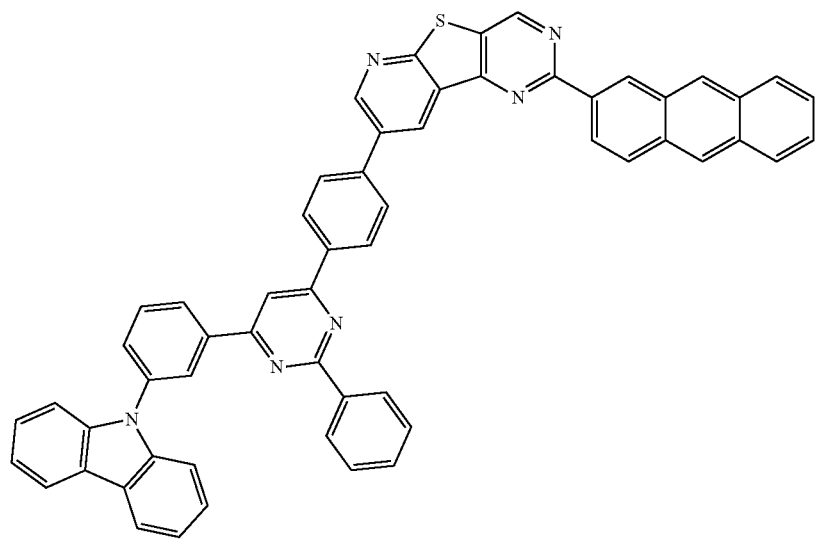
441
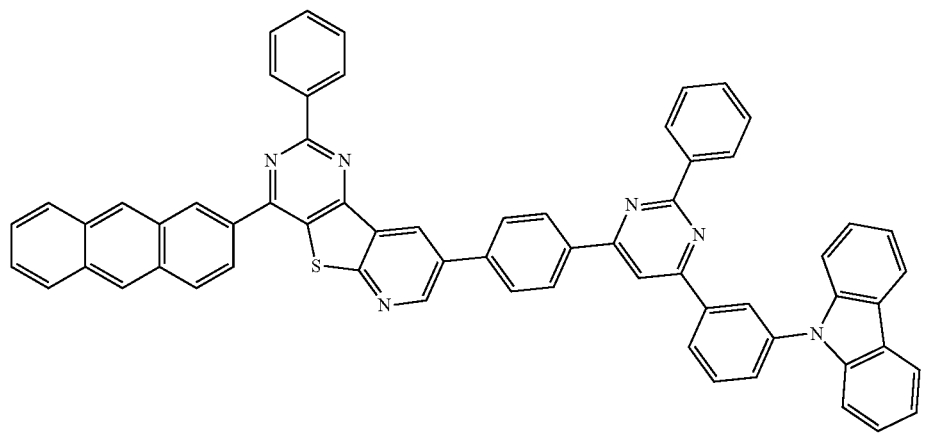

442
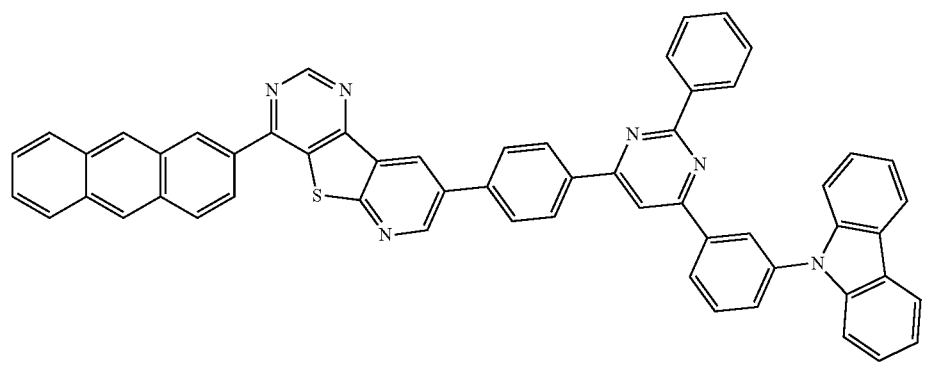
443
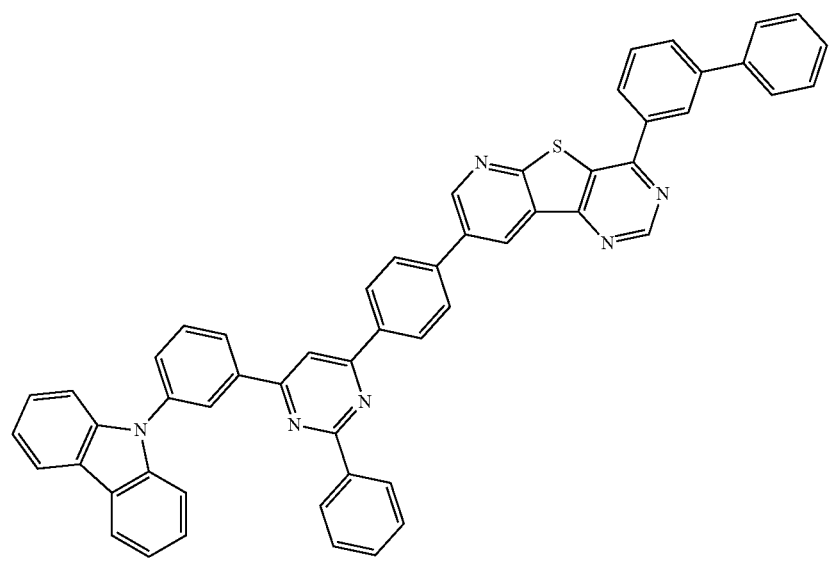
444
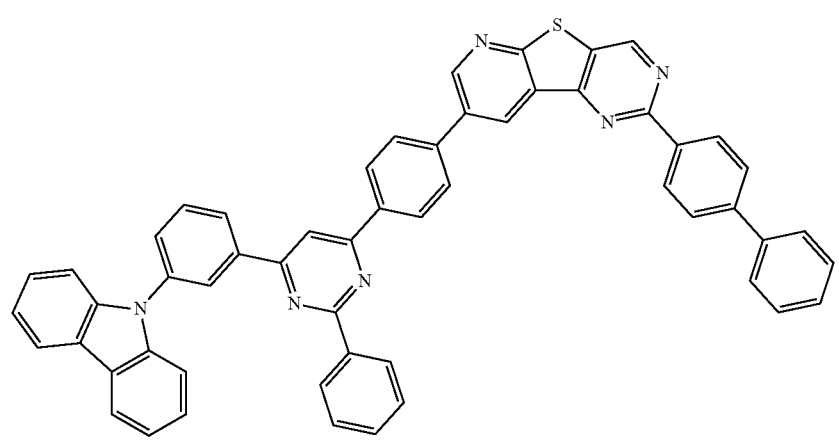

445
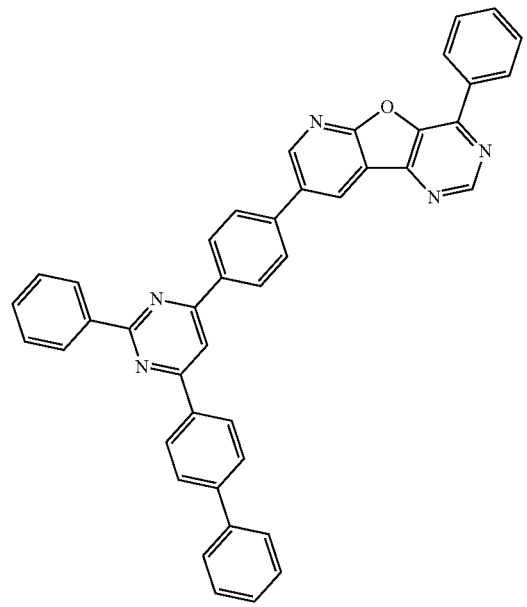
581
446
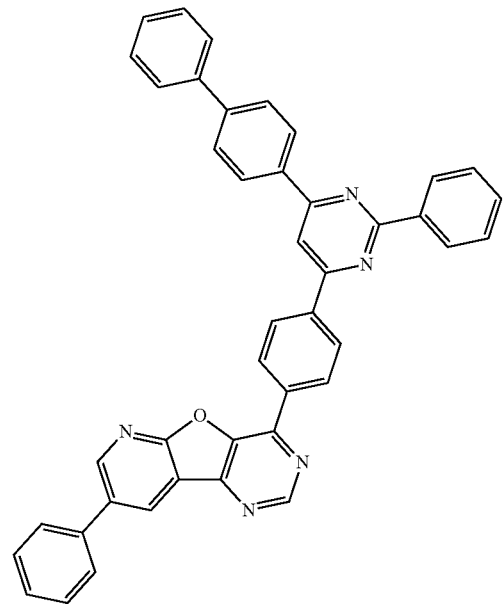
582
447
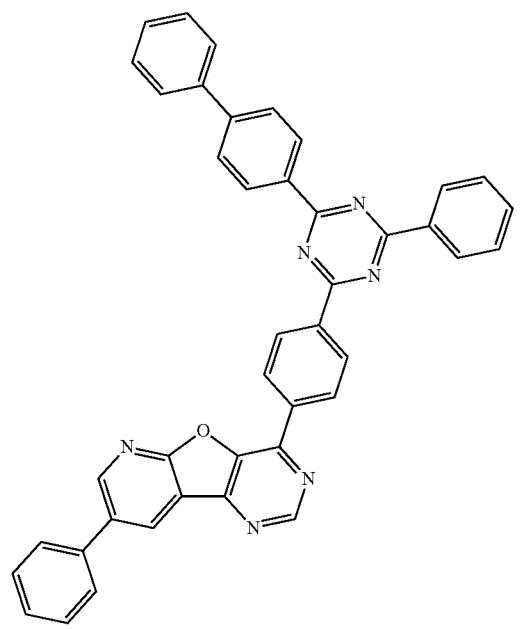
448
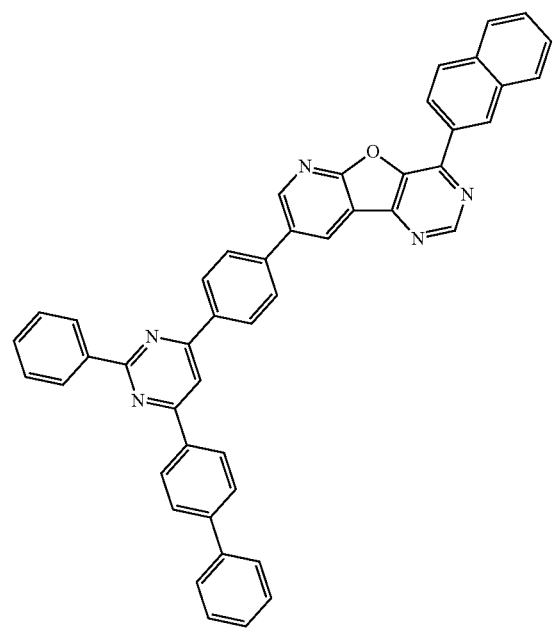

449
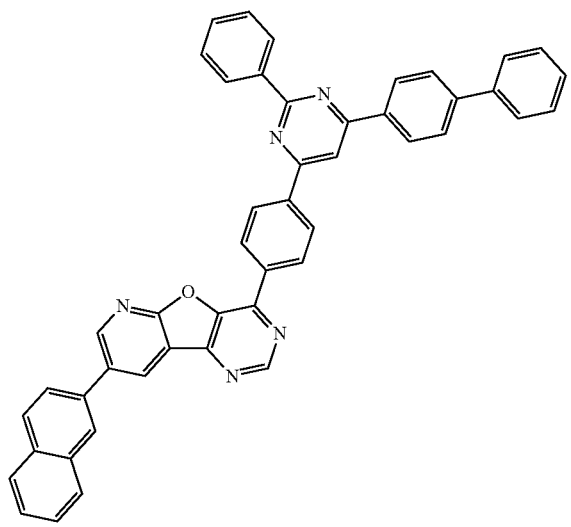
450
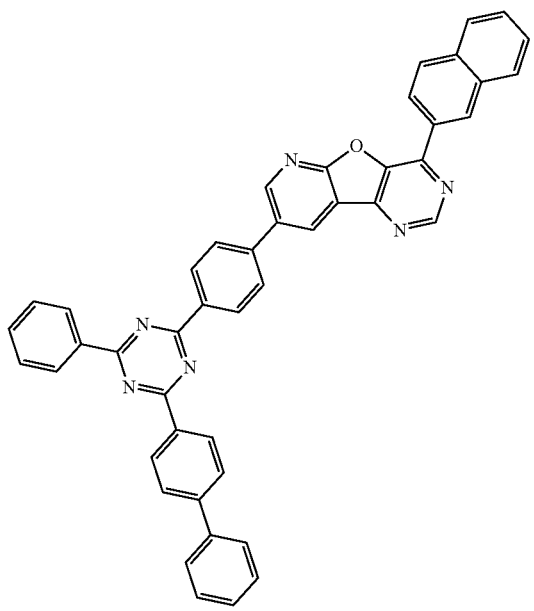
451
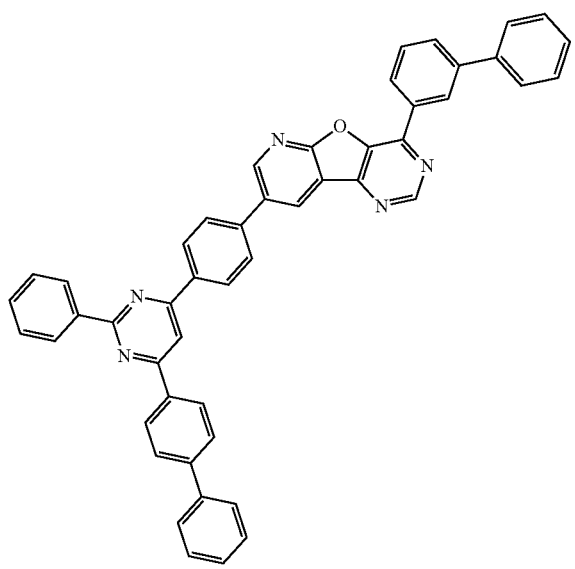
452
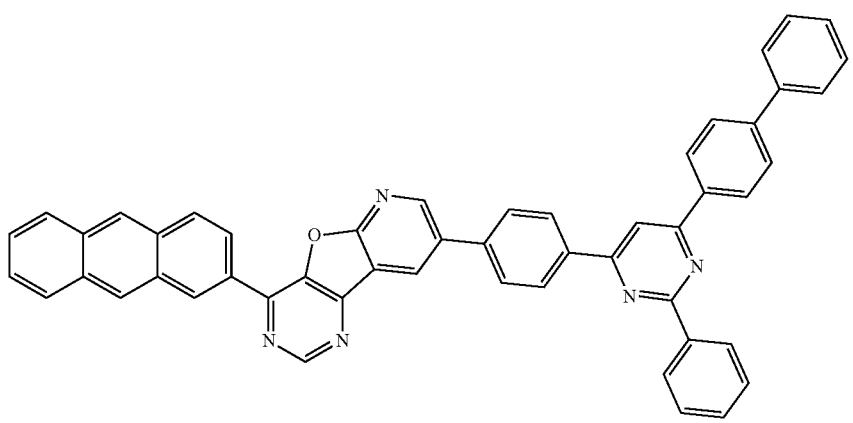

585 586
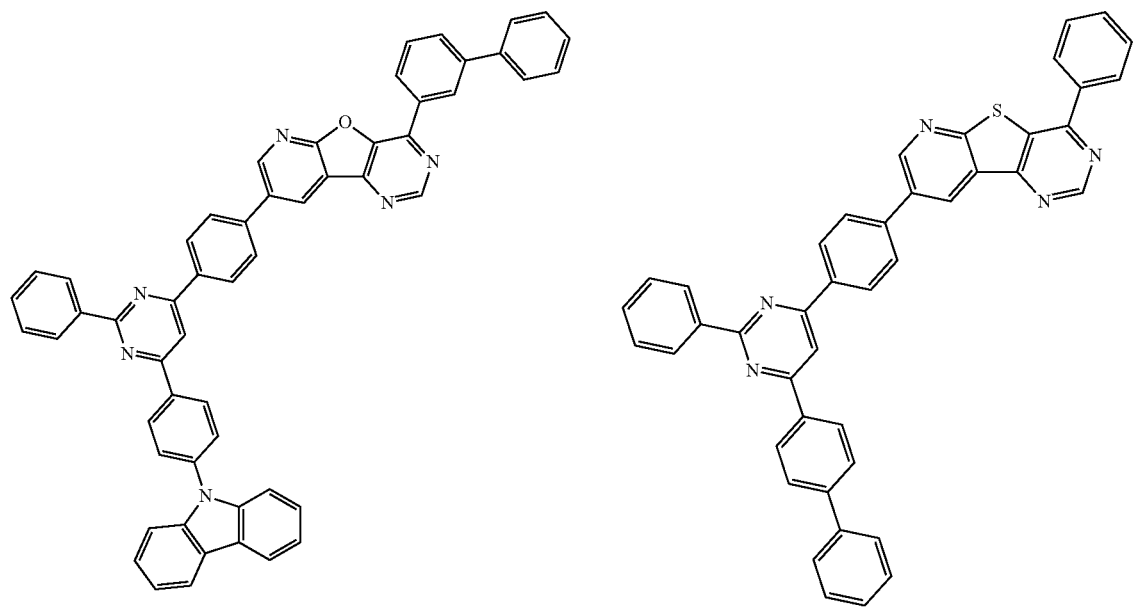
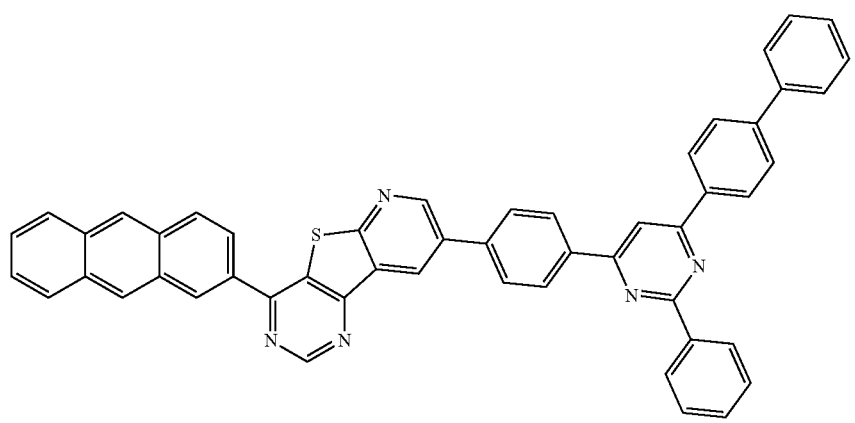
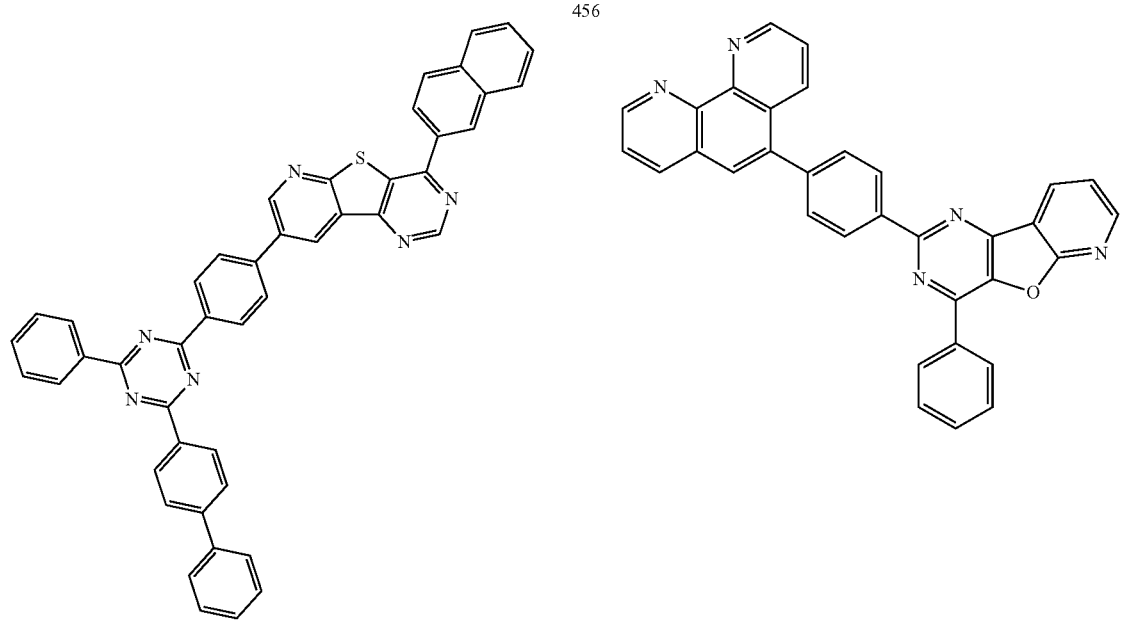

458
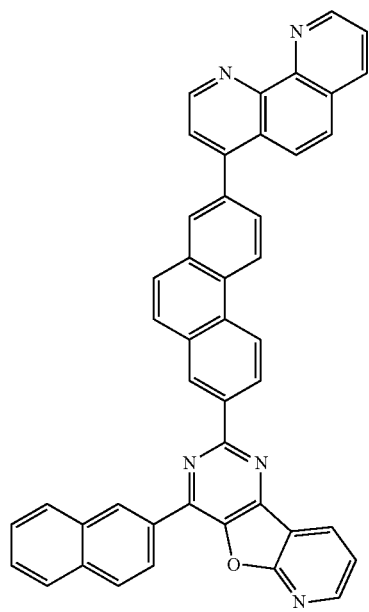
459
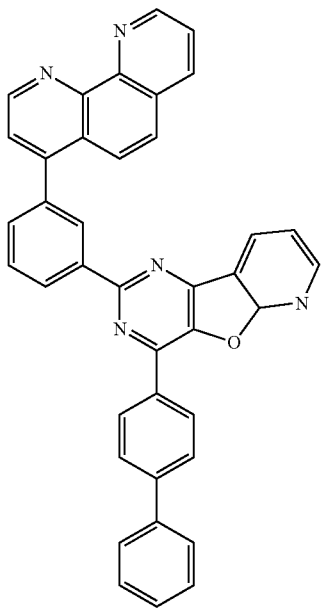
460
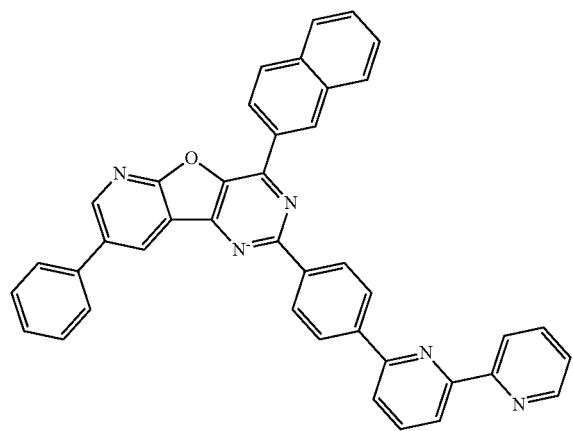
461
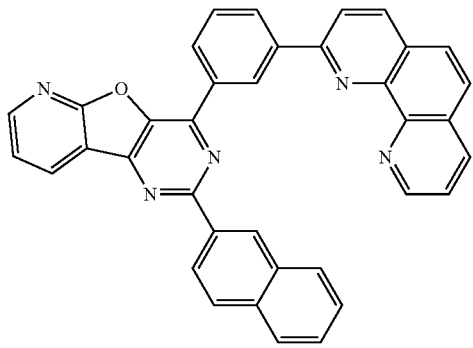
462
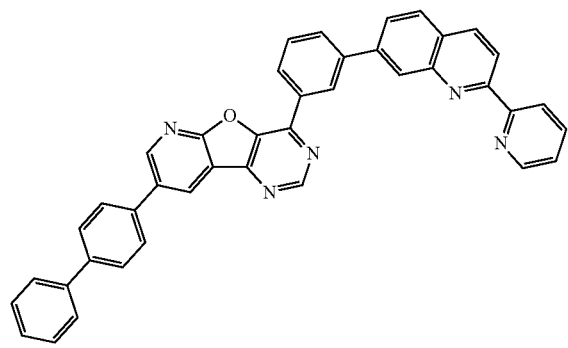
463
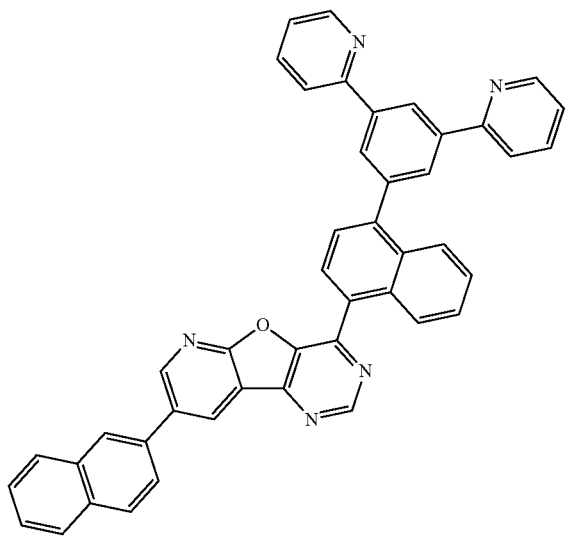

-continued
464
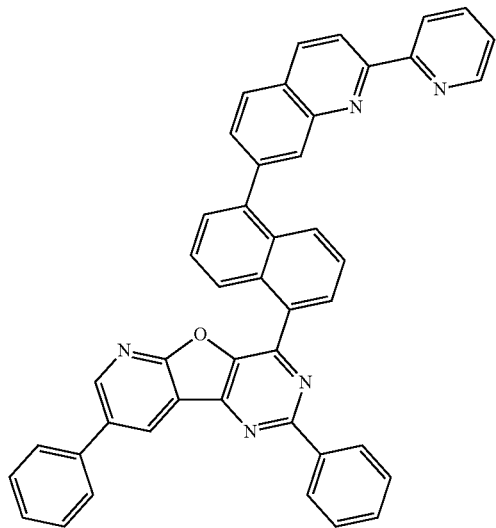
465
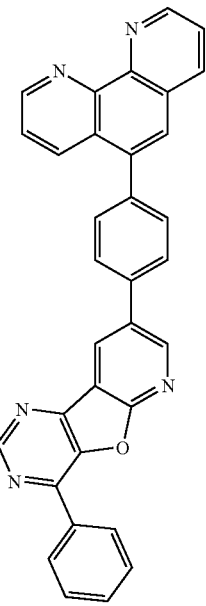
466
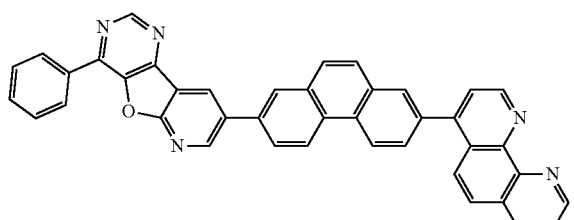
467
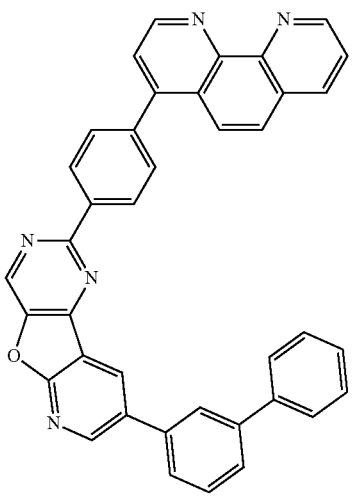
468
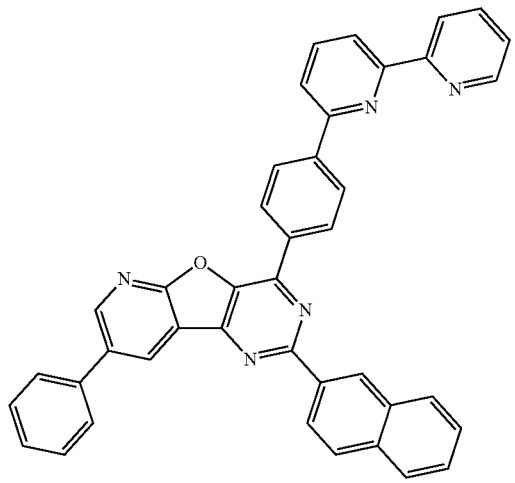
469
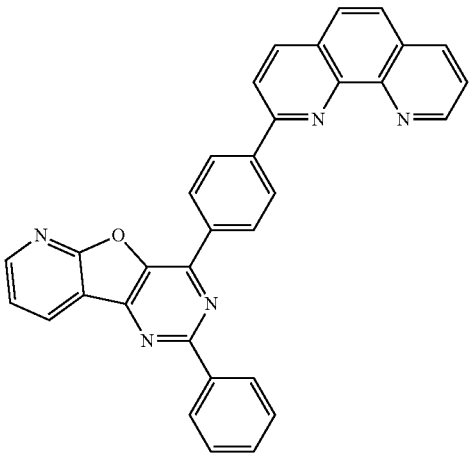

470

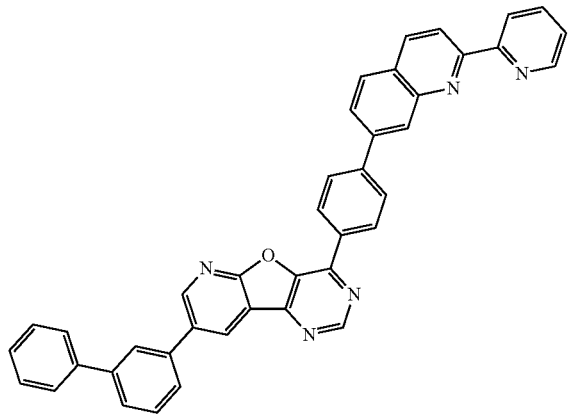

471

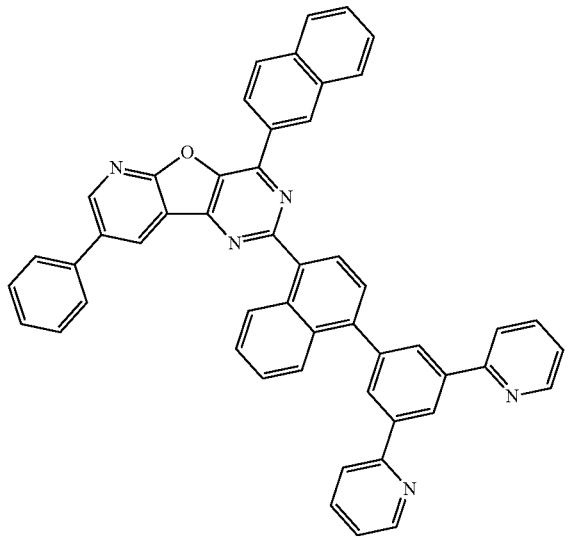

472

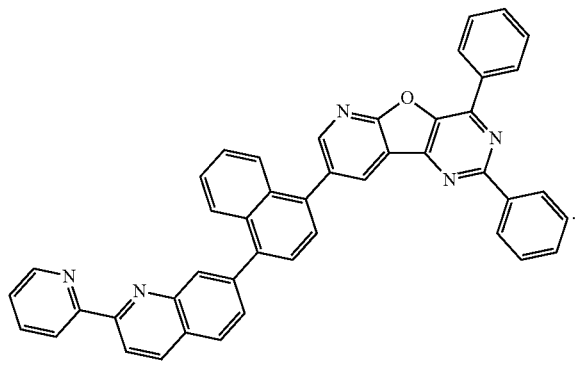

7. An organic light emitting device comprising:
a first electrode;
a second electrode provided opposite to the first electrode; and
one or more organic material layers provided between the first electrode and the second electrode,
wherein one or more layers of the organic material layers comprise the heterocyclic compound of claim 1.

8. The organic light emitting device of claim 7, wherein the organic material layer comprises a light emitting layer, and the light emitting layer comprises the heterocyclic compound.

9. The organic light emitting device of claim 7, wherein the organic material layer comprises an electron injection layer or an electron transfer layer, and the electron injection layer or the electron transfer layer comprises the heterocyclic compound.

10. The organic light emitting device of claim 7, wherein the organic material layer comprises an electron transfer layer, and the electron transfer layer comprises the heterocyclic compound.

11. The organic light emitting device of claim 7, wherein the organic material layer comprises an electron blocking layer or a hole blocking layer, and the electron blocking layer or the hole blocking layer comprises the heterocyclic compound.

12. The organic light emitting device of claim 7, further comprising one, two or more layers selected from the group consisting of a light emitting layer, a hole injection layer, a hole transfer layer, an electron injection layer, an electron transfer layer, an electron blocking layer and a hole blocking layer.

* * * * *